US012686876B2

(12) United States Patent
Chang et al.

(10) Patent No.: US 12,686,876 B2
(45) **Date of Patent: *Jul. 21, 2026**

(54) COMPOSITIONS AND METHODS COMPRISING A TTR GUIDE RNA AND A POLYNUCLEOTIDE ENCODING AN RNA-GUIDED DNA BINDING AGENT

(71) Applicant: Intellia Therapeutics, Inc., Cambridge, MA (US)

(72) Inventors: Yong Chang, Acton, MA (US); Seth C. Alexander, Medford, MA (US); Kristy M. Wood, Wellesley, MA (US); Arti Mahendra Prakash Kanjolia, Malden, MA (US); Shobu Odate, Arlington, MA (US); Jessica Lynn Seitzer, Windham, NH (US); Reynald Michael Lescarbeau, Medford, MA (US); Walter Strapps, Dedham, MA (US)

(73) Assignee: Intellia Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/362,867

(22) Filed: Jul. 31, 2023

(65) Prior Publication Data

US 2024/0124897 A1 Apr. 18, 2024

Related U.S. Application Data

(63) Continuation of application No. 17/486,735, filed on Sep. 27, 2021, now abandoned, which is a continuation of application No. PCT/US2020/025513, filed on Mar. 27, 2020.

(60) Provisional application No. 62/825,637, filed on Mar. 28, 2019.

(51) Int. Cl.

| | |
|---|---|
| ***C12N 9/22*** | (2006.01) |
| ***C12N 15/11*** | (2006.01) |
| ***C12N 15/90*** | (2006.01) |
| *A61K 38/00* | (2006.01) |

(52) U.S. Cl.

CPC ............. *C12N 15/907* (2013.01); *C12N 9/22* (2013.01); *C12N 15/11* (2013.01); *A61K 38/00* (2013.01); *C12N 2310/20* (2017.05); *C12N 2310/315* (2013.01); *C12N 2310/321* (2013.01); *C12N 2310/322* (2013.01); *C12N 2310/3515* (2013.01); *C12N 2320/30* (2013.01); *C12N 2800/80* (2013.01)

(58) Field of Classification Search

None

See application file for complete search history.

(56) References Cited

U.S. PATENT DOCUMENTS

| | | | | |
|---|---|---|---|---|
| 5,378,825 | A | 1/1995 | Cook et al. | |
| 5,585,481 | A | 12/1996 | Arnold, Jr. et al. | |
| 8,889,356 | B2 | 11/2014 | Zhang | |
| 9,023,649 | B2 | 5/2015 | Mali et al. | |
| 11,795,460 | B2 | 10/2023 | Kanjolia et al. | |
| 2005/0038117 | A1 | 2/2005 | Kong et al. | |
| 2005/0244869 | A1 | 11/2005 | Brown-Driver et al. | |
| 2012/0294905 | A1 | 11/2012 | Sah | |
| 2014/0186958 | A1 | 7/2014 | Zhang et al. | |
| 2015/0166980 | A1 | 6/2015 | Liu et al. | |
| 2016/0046960 | A1 | 2/2016 | Frendewey et al. | |
| 2016/0304846 | A1 | 10/2016 | Liu et al. | |
| 2016/0312198 | A1 | 10/2016 | Joung et al. | |
| 2016/0312199 | A1 | 10/2016 | Joung et al. | |
| 2017/0191123 | A1 | 7/2017 | Kim et al. | |
| 2018/0127786 | A1 | 5/2018 | Bouchon et al. | |
| 2019/0136231 | A1 | 5/2019 | Morrissey et al. | |
| 2020/0248180 | A1 * | 8/2020 | Kanjolia | C12N 15/102 |
| 2020/0354702 | A1 * | 11/2020 | Dombrowski | C12N 15/11 |
| 2023/0257747 | A1 | 8/2023 | Kanjolia et al. | |

FOREIGN PATENT DOCUMENTS

| | | | |
|---|---|---|---|
| CN | 105821072 | A | 8/2016 |
| WO | 9313121 | A1 | 7/1993 |
| WO | 9532305 | A1 | 11/1995 |
| WO | 2002029103 | A2 | 4/2002 |
| WO | 2006007712 | A1 | 1/2006 |
| WO | 2010017509 | A1 | 2/2010 |
| WO | 2010048228 | A2 | 4/2010 |
| WO | 2010105209 | A1 | 9/2010 |
| WO | 2011056883 | A1 | 5/2011 |
| WO | 2011139917 | A1 | 11/2011 |
| WO | 2013075035 | A1 | 5/2013 |
| WO | 2014065596 | A1 | 5/2014 |
| WO | 2014093622 | A2 | 6/2014 |
| WO | 2014093655 | A2 | 6/2014 |

(Continued)

OTHER PUBLICATIONS

Nakamura, Y., et al., "Codon Usage Tabulated from International DNA Sequence Databases: Status for the Year 2000," Nucleic Acids Research, vol. 28, No. 1, 1 page (2000).

Anders, C., et al., "In Vitro Enzymology of Cas9," Methods in Enzymology, vol. 546, pp. 1-20 (2014).

Anonymous: , "Intellia Therapeutics Company Overview" Jefferies Healthcare Conference, Jun. 6, 2017, XP55527492, New York, Retrieved from the Internet: URL:http://www.jefferies.com/CMSFiles/Jeff eries.com/files/Intellia%20Therapeutics%20 Inc(3).pdf, 24 pages.

Chang, Y., "Delivering on the therapeutic potential of CRISPR/Cas9: Development of an LNP-mediated genome editing therapeutic for the treatment of ATTR" 26th Annual Congress of the European Society of Gene and Cell Therapy, Oct. 18, 2018, 19 pages.

(Continued)

*Primary Examiner* — Brian Whiteman
*Assistant Examiner* — Khaleda B Hasan
(74) *Attorney, Agent, or Firm* — McNeill PLLC

(57) ABSTRACT

Compositions and methods for editing, e.g., introducing double-stranded breaks, within the TTR gene are provided. Compositions and methods for treating subjects having amyloidosis associated with transthyretin (ATTR), are provided.

30 Claims, 5 Drawing Sheets

Specification includes a Sequence Listing.

(56) References Cited

FOREIGN PATENT DOCUMENTS

| | | | | |
|---|---|---|---|---|
| WO | 2014136086 | A1 | 9/2014 | |
| WO | 2014172489 | A2 | 10/2014 | |
| WO | 2014179627 | A2 | 11/2014 | |
| WO | 2014204728 | A1 | 12/2014 | |
| WO | 2015089351 | A1 | 6/2015 | |
| WO | 2015089406 | A1 | 6/2015 | |
| WO | 2015089419 | A2 | 6/2015 | |
| WO | 2015095340 | A1 | 6/2015 | |
| WO | 2015183026 | A1 | 12/2015 | |
| WO | 2016010840 | A1 | 1/2016 | |
| WO | 2016186772 | A2 | 11/2016 | |
| WO | 2017019867 | A1 | 2/2017 | |
| WO | 2017053297 | A1 | 3/2017 | |
| WO | 2017053431 | A2 | 3/2017 | |
| WO | 2017077386 | A1 | 5/2017 | |
| WO | 2017093804 | A2 | 6/2017 | |
| WO | 2017158422 | A1 | 9/2017 | |
| WO | 2017165704 | A1 | 9/2017 | |
| WO | 2017185054 | A1 | 10/2017 | |
| WO | WO-2017173054 | A1 * | 10/2017 | ................ A61P 1/16 |
| WO | 2018007871 | A1 | 1/2018 | |
| WO | 2018067447 | A1 | 4/2018 | |
| WO | 2018107028 | A1 | 6/2018 | |
| WO | 2018183808 | A1 | 10/2018 | |
| WO | 2019067872 | A1 | 4/2019 | |
| WO | 2019067910 | A1 | 4/2019 | |
| WO | 2019067992 | A1 | 4/2019 | |
| WO | 2019237069 | A1 | 12/2019 | |
| WO | 2020069296 | A1 | 4/2020 | |

OTHER PUBLICATIONS

Coelho, T., et al., "Safety and Efficacy of RNAi Therapy for Transthyretin Amyloidosis," The New England Journal of Medicine, vol. 369:9, pp. 819-829 plus supplemental information (2013).

Cuomo, et al., Gen Bank Accession No. EZM83080, Submitted (Mar. 25, 2014) Broad Institute of MIT and Harvard, 7 Cambridge Center, Cambridge, MA 02142, USA, 2 pages.

Doench, et al. (2016), "Optimized sgRNA design to maximize activity and minimize off-target effects of CRISPR-Cas9", Nature Biotechnology, 34(2), pp. 184-191 & supplementary information.

Kerschen, P. et al: "Current and Future Treatment Approaches in Transthyretin Familial Amyloid Polyneuropathy", Current Treatment Options in Neurology, Springer US, Boston, vol. 18, No. 12, Nov. 21, 2016 (Nov. 21, 2016), pp. 1-13.

Kudla et al., "High Guanine and Cytosine Content Increases mRNA Levels in Mammalian Cells," PLoS Biology, vol. 4, Issue 6, pp. 0933-0942 (Jun. 2006) e180.

Morrissey, D., "Robust In Vivo Editing of Hepatocyte Target DNA Mediated by Lipid Nanoparticle Delivery of CRISPR/Cas9 Components," ASGCT 20th Annual Meeting, 30 pages (May 13, 2017).

Rejman et al., "Characterization and transfection properties of lipoplexes stabilized with novel exchangeable polyethylene glycol-lipid conjugates" Biochimica et Biophysica Acta 1660 (2004) pp. 41-52.

Saraiva, M. et al. "Rescue of Amyloid Deposition Phenotype after Single-Treatment CRISPR/Cas9 Gene Editing in a Humanized Mouse Model of TTR Amyloidosis" ASGCT 2018, May 14, 2018, abstract No. 276, 1 page.

Abbas, Yazan M et al. "Structure of human IFIT1 with capped RNA reveals adaptable mRNA binding and mechanisms for sensing N1 and N2 ribose 2'-O methylations." Proceedings of the National Academy of Sciences of the United States of America vol. 114,11 (2017): E2106-E2115.

Adams et al., "The Biochemistry of the Nucleic Acids", ed., 11th ed., 1992.

Beaudet, Arthur L, and Linyan Meng. "Gene-targeting pharmaceuticals for single-gene disorders." Human molecular genetics vol. 25,R1 (2016): R18-26.

Benson, Dennis A et al. "GenBank." Nucleic acids research vol. 34, Database issue (2006): D16-20.

Butler, James S et al. "Preclinical evaluation of RNAi as a treatment for transthyretin-mediated amyloidosis." Amyloid : the international journal of experimental and clinical investigation : the official journal of the International Society of Amyloidosis vol. 23,2 (2016): 109-18.

Dittmar, Kimberly A et al. "Tissue-specific differences in human transfer RNA expression." PLoS genetics vol. 2,12 (2006): e221.

Finn et al., "A Single Administration of CRISPR-Cas9 Lipid Nanoparticles Achieves Robust and Persistent In Vivo Genome Editing", Cell Reports, (2018), vol. 22, Issue 9, pp. 2227-2235.

Galant et al., "Transthyretin Amuloidosis: an Under Recognized Neuropathy and Cardiomyopathy", Clinical Science, 2017, 131 (5) 395-409.

Gilbert, Luke A et al. "CRISPR-mediated modular RNA-guided regulation of transcription in eukaryotes." Cell vol. 154,2 (2013): 442-51.

Gonçalves, Nádia Pereira et al. "Interleukin-1 signaling pathway as a therapeutic target in transthyretin amyloidosis." Amyloid : the international journal of experimental and clinical investigation : the official journal of the International Society of Amyloidosis vol. 21,3 (2014): 175-84.

Guo, P X, and B Moss., "Interaction and mutual stabilization of the two subunits of vaccinia virus mRNA capping enzyme coexpressed in *Escherichia coli*." Proceedings of the National Academy of Sciences of the United States of America vol. 87,11 (1990): 4023-7.

Harris, Milton J., "Poly(ethylene glycol) chemistry: bio-technical and biomedical applications", (1992).

Hoekstra et al., "Characterization and Transfection Properties of Lipoplexes Stabilized with Novel Exchangeable Polyethylene Glycol-lipid Conjugates", Biochimica et Biophysica Acta 1660 (2004) 41-52.

International Search Report corresponding to International Patent Application No. PCT/US2020/025513, mailed Jun. 30, 2020, 5 pages.

Ishikawa et al., "Preparation of eukaryotic mRNA having differently methylated adenosine at the 5-terminus and the effect of the methyl group in translation", Nucl. Acids. Symp. Ser. (2009) No. 53, 129-130.

Kariko, Katalin et al. "Generating the optimal mRNA for therapy: HPLC purification eliminates immune activation and improves translation of nucleoside-modified, protein-encoding mRNA." Nucleic acids research vol. 39,21 (2011): e142.

Katibah, George E et al. "Broad and adaptable RNA structure recognition by the human interferon-induced tetratricopeptide repeat protein IFIT5." Proceedings of the National Academy of Sciences of the United States of America vol. 111,33 (2014): 12025-30.

Maier, Martin A et al. "Biodegradable lipids enabling rapidly eliminated lipid nanoparticles for systemic delivery of RNAi therapeutics." Molecular therapy : the journal of the American Society of Gene Therapy vol. 21,8 (2013): 1570-8.

Makarova, Kira S et al. "Evolution and classification of the CRISPR-Cas systems." Nature reviews. Microbiology vol. 9,6 (2011): 467-77.

Makarova, Kira S, et al., "An updated evolutionary classification of CRISPR-Cas systems." Nature reviews. Microbiology vol. 13,11 (2015): 722-36.

Mali, Prashant et al. "CAS9 transcriptional activators for target specificity screening and paired nickases for cooperative genome engineering." Nature biotechnology vol. 31,9 (2013): 833-8.

Mao, X. and Shuman, S., "Intrinsic RNA (Guanine-7) Methyltransferase Activity of the Vaccinia Virus Capping Enzyme D1 Subunit Is Stimulated by the D12 Subunit", Journal of Biological Chemistry, 1994, 269, 24472-24479.

Mefferd et al., "Expression of CRISPR/Cas single guide RNAs using small tRNA promoters", RNA, (2015), 21:1683-9.

Nakamura, Y et al. "Codon usage tabulated from international DNA sequence databases: status for the year 2000." Nucleic acids research vol. 28,1 (2000): 292.

Perez-Pinera, Pablo et al. "RNA-guided gene activation by CRISPR-Cas9-based transcription factors." Nature methods vol. 10,10 (2013): 973-6.

(56) References Cited

OTHER PUBLICATIONS

Qi, Lei S et al. "Repurposing CRISPR as an RNA-guided platform for sequence-specific control of gene expression." Cell vol. 152,5 (2013): 1173-83.
Romberg et al., "Sheddable coatings for long-circulating nanoparticles" Pharmaceutical Research, vol. 25, No. 1, p. 55-71 (2008).
Santos et al., The Heat Shock Response Modulates Transthyretin Deposition in the Peripheral and Autonomic Nervous Systems, Neurobiol Aging. Feb. 2010;31(2):280-9.
Scherer, Lisa J et al. "Optimization and characterization of tRNA-shRNA expression constructs." Nucleic acids research vol. 35,8 (2007): 2620-8.
Schmidt, Manfred et al. "High-resolution insertion-site analysis by linear amplification-mediated PCR (LAM-PCR)." Nature methods vol. 4, 12 (2007): 1051-7.
Sekjima, "Recent Progress in the Understanding and Treatment of Transthyretin Amyloidosis", Journal of Clinical Pharmacy and Therapeutics, 2014, vol. 39, Issue 3, pp. 225-233.
Shendure, Jay, and Hanlee Ji. "Next-generation DNA sequencing." Nature biotechnology vol. 26,10 (2008): 1135-45.
Shmakov, Sergey et al. "Discovery and Functional Characterization of Diverse Class 2 CRISPR-Cas Systems." Molecular cell vol. 60,3 (2015): 385-97.
Stepinski et al., "Synthesis and Properties of mRNAs Containing the Novel (anti-reverse) Cap Analogs 7-methyl(3'-O-methyl)GpppG and 7-methyl(3'-deoxy)GpppG", RNA, (2001) 7:1486-1495.
Tsai, Shengdar Q et al. "GUIDE-seq enables genome-wide profiling of off-target cleavage by CRISPR-Cas nucleases." Nature biotechnology vol. 33,2 (2015): 187-197.
Vester and Wengel, "LNA (locked nucleic acid): high-affinity targeting of complementary RNA and DNA", Biochemistry, (2004), 43(42):13233-41.
Zetsche et al., "Cpf1 is a Single RNA-Guided Endonuclease of a Class 2 CRISPR-Cas System," Cell, (2015) 163, 3:759-771.
Anderson, E., et al., "Systematic analysis of CRISPR-Cas9 mismatch tolerance reveals low levels of off-target activity," Journal of Biotechnology, vol. 211, pp. 56-65 (2015).
Prosecution History of U.S. Appl. No. 19/295,369, inventors Yong Chang, et al., filed Aug. 8, 2025.
Anonymous, "Intellia Therapeutics, Corporate Overview," 33 pages (May 2025), Retrieved from the Internet: URL: https://ir.intelliatx.com/static-files/a57908a6-aaca-404d-9072-32471cd3d41e.
Cohen, N., et al., "GC Composition of the Human Genome: In Search of Isochores," Molecular Biology and Evolution, vol. 22, No. 5, pp. 1260-1272 (2005).
Dewitt, M., et al. "Genome Editing via Delivery of Cas9 Ribonucleoprotein," Methods, vol. 121-122, pp. 9-15, (2017).
Fontana, M., et al., "CRISPR-Cas9 Gene Editing with Nexiguran Ziclumeran for ATTR Cardiomyopathy," The New England Journal of Medicine, vol. 391, No. 23, 10 pages, (Nov. 16, 2024).
Fontana, M., et al., "Nexiguran Ziclumeran (nex-z, Also Known as NTLA-2001), an Investigational In Vivo CRISPR-Based Therapy for Patients With Transthyretin Amyloidosis With Cardiomyopathy (ATTR-CM): Interim Report of the Phase 1 Study," American Heart Association Scientific Sessions, 21 pages (Nov. 16, 2024).
Mallus, M., et al., "Treatment of Amyloidosis: Present and Future," European Heart Journal Supplements: Journal of the European Society of Cardiology, vol. 25, No. Suppl B, pp. B99-B103 (2023).
Nishimasu, H., et al. "Crystal Structure of Cas9 in Complex with Guide RNA and Target DNA," Cell, vol. 156, No. 5, 15 pages (2014).
Paine, R., Food and Drug Administration Center for Drug Evaluation and Research, Clinical Review Application No. NDA 210922, 485 pages (Published Aug. 6, 2018).
PCT International Search Report and Written Opinion issued Feb. 11, 2019, in PCT Application No. PCT/US2018/053382, 24 pages.
PCT International Search Report and Written Opinion issued Jun. 30, 2020, in PCT Application No. PCT/US2020/025513, 13 pages.
PCT International Search Report and Written Opinion issued Jun. 30, 2020, in PCT Application No. PCT/US2020/025533, 13 pages.
Peng, R., et al., "CRISPR/DCas9-Mediated Transcriptional Improvement of the Biosynthetic Gene Cluster for the Epothilone Production in Myxococcus Xanthus," Microbial Cell Factories, vol. 17, No. 15, 12 pages (2018).
Taubel, J., et al., "Activity of Follow-On Dosing for an Investigational In Vivo CRISPR-Based Lipid Nanoparticle Therapy in Transthyretin Amyloidosis," Peripheral Nerve Society Annual Meeting Presentation, 13 pages (Jun. 25, 2024).

* cited by examiner

COMPOSITIONS AND METHODS COMPRISING A TTR GUIDE RNA AND A POLYNUCLEOTIDE ENCODING AN RNA-GUIDED DNA BINDING AGENT

This patent application is a continuation application of U.S. non-provisional application Ser. No. 17/486,735, filed Sep. 27, 2021, which is a continuation application of International Application No. PCT/US2020/025513, filed on Mar. 27, 2020, which claims priority to U.S. provisional application 62/825,637 filed Mar. 28, 2019, the contents of which are incorporated herein by reference in their entirety for all purposes.

The instant application contains a Sequence Listing which has been submitted electronically in ASCII format and is hereby incorporated by reference in its entirety. Said ASCII copy, created on Aug. 10, 2023, is named 01155-0028-01US-T1.xml and is 633,446 bytes in size.

Transthyretin (TTR) is a protein produced by the TTR gene that normally functions to transport retinol and thyroxine throughout the body. TTR is predominantly synthesized in the liver, with small fractions being produced in the choroid plexus and retina. TTR normally circulates as a soluble tetrameric protein in the blood.

Pathogenic variants of TTR, which may disrupt tetramer stability, can be encoded by mutant alleles of the TTR gene. Mutant TTR may result in misfolded TTR, which may generate amyloids (i.e., aggregates of misfolded TTR protein). In some cases, pathogenic variants of TTR can lead to amyloidosis, or disease resulting from build-up of amyloids. For example, misfolded TTR monomers can polymerize into amyloid fibrils within tissues, such as the peripheral nerves, heart, and gastrointestinal tract. Amyloid plaques can also comprise wild-type TTR that has deposited on misfolded TTR.

Misfolding and deposition of wild-type TTR has also been observed in males aged 60 or more and is associated with heart rhythm problems, heart failure, and carpal tunnel.

Amyloidosis characterized by deposition of TTR may be referred to as "ATTR," "TTR-related amyloidosis," "TTR amyloidosis," or "ATTR amyloidosis," "ATTR familial amyloidosis" (when associated with a genetic mutation in a family), or "ATTRwt" or "wild-type ATTR" (when arising from misfolding and deposition of wild-type TTR).

ATTR can present with a wide spectrum of symptoms, and patients with different classes of ATTR may have different characteristics and prognoses. Some classes of ATTR include familial amyloid polyneuropathy (FAP), familial amyloid cardiomyopathy (FAC), and wild-type TTR amyloidosis (wt-TTR amyloidosis). FAP commonly presents with sensorimotor neuropathy, while FAC and wt-TTR amyloidosis commonly present with congestive heart failure. FAP and FAC are usually associated with a genetic mutation in the TTR gene, and more than 100 different mutations in the TTR gene have been associated with ATTR. In contrast, wt-TTR amyloidosis is associated with aging and not with a genetic mutation in TTR. It is estimated that approximately 50,000 patients worldwide may be affected by FAP and FAC.

While more than 100 mutations in TTR are associated with ATTR, certain mutations have been more closely associated with neuropathy and/or cardiomyopathy. For example, mutations at T60 of TTR are associated with both cardiomyopathy and neuropathy; mutations at V30 are more associated with neuropathy; and mutations at V122 are more associated with cardiomyopathy.

A range of treatment approaches have been studied for treatment of ATTR, but there are no approved drugs that stop disease progression and improve quality of life. While liver transplant has been studied for treatment of ATTR, its use is declining as it involves significant risk and disease progression sometimes continues after transplantation. Small molecule stabilizers, such as diflunisal and tafamidis, appear to slow ATTR progression, but these agents do not halt disease progression.

Approaches using small interfering RNA (siRNA) knockdown, antisense knockdown, or a monoclonal antibody targeting amyloid fibrils for destruction are also currently being investigated, but while results on short-term suppression of TTR expression show encouraging preliminary data, a need exists for treatments that can produce long-lasting suppression of TTR.

Accordingly, the following embodiments are provided. In some embodiments, the present invention provides compositions and methods using a guide RNA with an RNA-guided DNA binding agent such as the CRISPR/Cas system to substantially reduce or knockout expression of the TTR gene, thereby substantially reducing or eliminating the production of TTR protein associated with ATTR. The substantial reduction or elimination of the production of TTR protein associated with ATTR through alteration of the TTR gene can be a long-term reduction or elimination.

SUMMARY

The following embodiments are provided herein.

Embodiment 1 is a composition comprising:

(i) a nucleic acid comprising an open reading frame encoding an RNA-guided DNA binding agent, wherein:
  - a. the open reading frame comprises a sequence with at least 93% identity to SEQ ID NO: 311; and/or
  - b. the open reading frame has at least 93% identity to SEQ ID NO: 311 over at least its first 50, 200, 250, or 300 nucleotides, or at least 95% identity to SEQ ID NO: 311 over at least its first 30, 50, 70, 100, 150, 200, 250, or 300 nucleotides; and/or
  - c. the open reading frame consists of a set of codons of which at least 95%, 96%, 97%, 98%, 99%, 99.5%, or 100% of the codons are codons listed in Table 4, the low A set of Table 5, or the low A/U set of Table 5; and/or
  - d. the open reading frame has an adenine content ranging from its minimum adenine content to 123% of the minimum adenine content; and/or
  - e. the open reading frame has an adenine dinucleotide content ranging from its minimum adenine dinucleotide content to 150% of the minimum adenine dinucleotide content; and (ii) a guide RNA or a vector encoding a guide RNA, wherein the guide RNA comprises a guide sequence selected from SEQ ID NOs: 5-72, 74-78, and 80-82.

Embodiment 2 is a method of modifying the TTR gene and/or inducing a double-stranded break (DSB) within the TTR gene, comprising delivering a composition to a cell, wherein the composition comprises:

(i) a nucleic acid comprising an open reading frame encoding an RNA-guided DNA binding agent, wherein:
  - a. the open reading frame comprises a sequence with at least 93% identity to SEQ ID NO:311; and/or
  - b. the open reading frame has at least 93% identity to SEQ ID NO: 311 over at least its first 50, 200, 250, or 300 nucleotides, or at least 95% identity to SEQ ID NO: 311 over at least its first 30, 50, 70, 100, 150, 200, 250, or 300 nucleotides; and/or c. the open reading frame consists of a set of codons of which at least 95%, 96%, 97%, 98%, 99%, 99.5%, or 100% of the codons are codons listed in Table 4, the low A set of Table 5, or the low A/U set of Table 5; and/or d. the open reading frame has an adenine content ranging from its minimum adenine content to 123% of the minimum adenine content; and/or e. the open reading frame has an adenine dinucleotide content ranging from its minimum adenine dinucleotide content to 150% of the minimum adenine dinucleotide content; and (ii) a guide RNA or a vector encoding a guide RNA, wherein the guide RNA comprises a guide sequence selected from SEQ ID NOs: 5-72, 74-78, and 80-82.

Embodiment 3 is a method of reducing TTR serum concentration, treating amyloidosis associated with TTR (ATTR), and/or reducing or preventing the accumulation of amyloids or amyloid fibrils comprising TTR in a subject, comprising administering a composition to a subject in need thereof, wherein the composition comprises:

(i) a nucleic acid comprising an open reading frame encoding an RNA-guided DNA binding agent, wherein:

a. the open reading frame comprises a sequence with at least 95% identity to SEQ ID NO:311; and/or b. the open reading frame has at least 95% identity to SEQ ID NO: 311 over at least its first 30, 50, 70, 100, 150, 200, 250, or 300 nucleotides; and/or c. the open reading frame consists of a set of codons of which at least 95%, 96%, 97%, 98%, 99%, 99.5%, or 100% of the codons are codons listed in Table 4, the low A set of Table 5, or the low A/U set of Table 5; and/or d. the open reading frame has an adenine content ranging from its minimum adenine content to 150% of the minimum adenine content; and/or e. the open reading frame has an adenine dinucleotide content ranging from its minimum adenine dinucleotide content to 150% of the minimum adenine dinucleotide content; and (ii) a guide RNA or a vector encoding a guide RNA, wherein the guide RNA comprises a guide sequence selected from SEQ ID NOs: 5-72, 74-78, and 80-82, thereby reducing TTR serum concentration, treating amyloidosis associated with TTR (ATTR), and/or reducing or preventing the accumulation of amyloids or amyloid fibrils comprising TTR in the subject.

Embodiment 4 is the composition or method of any one of the preceding embodiments, wherein the guide RNA comprises a guide sequence selected from SEQ ID NOs: 5, 6, 7, 8, 9, 12, 13, 14, 15, 16, 17, 22, 23, 27, 29, 30, 35, 36, 37, 38, 55, 61, 63, 65, 66, 68, or 69.

Embodiment 5 is the composition of embodiment 1 or 4, for use in inducing a double-stranded break (DSB) within the TTR gene in a cell or subject.

Embodiment 6 is the composition of embodiment 1, 4, or 5 for use in modifying the TTR gene in a cell or subject.

Embodiment 7 is the composition of embodiment 1, 4, 5, or 6 for use in treating amyloidosis associated with TTR (ATTR) in a subject.

Embodiment 8 is the composition of embodiment 1, 4, 5, 6, or 7 for use in reducing TTR serum concentration in a subject.

Embodiment 9 is the composition of embodiment 1, 4, 5, 6, 7, or 8, for use in reducing or preventing the accumulation of amyloids or amyloid fibrils in a subject.

Embodiment 10 is the composition for use or method of any one of embodiments 2-9, wherein the method comprises administering the composition by infusion for more than 30 minutes.

Embodiment 11 is the method or composition for use of embodiment 10, wherein the composition is administered by infusion for about 45-75 minutes, 75-105 minutes, 105-135 minutes, 135-165 minutes, 165-195 minutes, 195-225 minutes, 225-255 minutes, 255-285 minutes, 285-315 minutes, 315-345 minutes, or 345-375 minutes.

Embodiment 12 is the method or composition for use of embodiment 10 or 11, wherein the composition is administered by infusion for about 1.5-6 hours.

Embodiment 13 is the method or composition for use of embodiment 10, wherein the composition is administered by infusion for about 60 minutes, about 90 minutes, about 120 minutes, about 150 minutes, about 180 minutes, or about 240 minutes.

Embodiment 14 is the method or composition for use of embodiment 10, wherein the composition is administered by infusion for about 120 minutes.

Embodiment 15 is the method or composition for use of any one of embodiments 2-14, wherein the composition reduces serum TTR levels.

Embodiment 16 is the method or composition for use of embodiment 15, wherein the serum TTR levels are reduced by at least 50% as compared to serum TTR levels before administration of the composition.

Embodiment 17 is the method or composition for use of embodiment 151, wherein the serum TTR levels are reduced by 50-60%, 60-70%, 70-80%, 80-90%, 90-95%, 95-98%, 98-99%, or 99-100% as compared to serum TTR levels before administration of the composition.

Embodiment 18 is the method or composition for use of any one of embodiments 2-17, wherein the composition results in editing of the TTR gene.

Embodiment 19 is the method or composition for use of embodiment 18, wherein the editing is calculated as a percentage of the population that is edited (percent editing).

Embodiment 20 is the method or composition for use of embodiment 19, wherein the percent editing is between 30 and 99% of the population.

Embodiment 21 is the method or composition for use of embodiment 19, wherein the percent editing is between 30 and 35%, 35 and 40%, 40 and 45%, 45 and 50%, 50 and 55%, 55 and 60%, 60 and 65%, 65 and 70%, 70 and 75%, 75 and 80%, 80 and 85%, 85 and 90%, 90 and 95%, or 95 and 99% of the population.

Embodiment 22 is the method or the composition for use of any one of embodiments of any one of embodiments 2-21, wherein the composition reduces amyloid deposition in at least one tissue.

Embodiment 23 is the method or composition for use of embodiment 22, wherein the at least one tissue comprises one or more of stomach, colon, sciatic nerve, or dorsal root ganglion.

Embodiment 24 is the method or composition for use of embodiment 22 or 23, wherein amyloid deposition is measured 8 weeks after administration of the composition.

Embodiment 25 is the method or composition for use of any one of embodiments 22-24, wherein amyloid deposition is compared to a negative control or a level measured before administration of the composition.

Embodiment 26 is the method or composition for use of any one of embodiments 22-25, wherein amyloid deposition is measured in a biopsy sample and/or by immunostaining.

Embodiment 27 is the method or composition for use of any one of embodiments 22-26, wherein amyloid deposition is reduced by between 30 and 35%, 35 and 40%, 40 and 45%, 45 and 50%, 50 and 55%, 55 and 60%, 60 and 65%, 65 and 70%, 70 and 75%, 75 and 80%, 80 and 85%, 85 and 90%, 90 and 95%, or 95 and 99% of the amyloid deposition seen in a negative control.

Embodiment 28 is the method or composition for use of any one of embodiments 22-27, wherein amyloid deposition is reduced by between 30 and 35%, 35 and 40%, 40 and 45%, 45 and 50%, 50 and 55%, 55 and 60%, 60 and 65%, 65 and 70%, 70 and 75%, 75 and 80%, 80 and 85%, 85 and 90%, 90 and 95%, or 95 and 99% of the amyloid deposition seen before administration of the composition.

Embodiment 29 is the method or composition for use of any one of embodiments 2-28, wherein the composition is administered or delivered at least two times.

Embodiment 30 is The method or composition for use of embodiment 29, wherein the composition is administered or delivered at least three times.

Embodiment 31 is the method or composition for use of embodiment 29, wherein the composition is administered or delivered at least four times.

Embodiment 32 is the method or composition for use of embodiment 29, wherein the composition is administered or delivered up to five, six, seven, eight, nine, or ten times.

Embodiment 33 is the method or composition for use of any one of embodiments 29-32, wherein the administration or delivery occurs at an interval of 1, 2, 3, 4, 5, 6, 7, 8, 9, 10, 11, 12, 13, 14, or 15 days.

Embodiment 34 is the method or composition for use of any one of embodiments 29-32, wherein the administration or delivery occurs at an interval of 1, 2, 3, 4, 5, 6, 7, 8, 9, 10, 11, 12, 13, 14, or 15 weeks.

Embodiment 35 is the method or composition for use of any one of embodiments 29-32, wherein the administration or delivery occurs at an interval of 1, 2, 3, 4, 5, 6, 7, 8, 9, 10, 11, 12, 13, 14, or 15 months.

Embodiment 36 is the method or composition of any one of the preceding embodiments, wherein the guide RNA comprises a crRNA that comprises the guide sequence and further comprises a nucleotide sequence of SEQ ID NO: 126, wherein the nucleotides of SEQ ID NO: 126 follow the guide sequence at its 3' end.

Embodiment 37 is the method or composition of any one of the preceding embodiments, wherein the guide RNA is a dual guide (dgRNA).

Embodiment 38 is the method or composition of embodiment 37, wherein the dual guide RNA comprises a crRNA comprising a nucleotide sequence of SEQ ID NO: 126, wherein the nucleotides of SEQ ID NO: 126 follow the guide sequence at its 3' end, and a trRNA.

Embodiment 39 is the method or composition of any one of embodiments 1-36, wherein the guide RNA is a single guide (sgRNA).

Embodiment 40 is the method or composition of embodiment 39, wherein the sgRNA comprises a guide sequence that has the pattern of SEQ ID NO: 3.

Embodiment 41 is the method or composition of embodiment 39, wherein the sgRNA comprises the sequence of SEQ ID NO: 3.

Embodiment 42 is the method or composition of any one of embodiments 39-41, wherein the sgRNA comprises any one of the guide sequences of SEQ ID NOs: 5-72, 74-78, and 80-82 and the nucleotides of SEQ ID NO: 126.

Embodiment 43 is the method or composition of any one of embodiments 39-42, wherein the sgRNA comprises a sequence that is at least 99%, 98%, 97%, 96%, 95%, 94%, 93%, 92%, 91%, or 90% identical to a sequence selected from SEQ ID Nos: 87-113, 115-120, and 122-124.

Embodiment 44 is the method or composition of embodiment 39, wherein the sgRNA comprises a sequence selected from SEQ ID Nos: 87-113, 115-120, and 122-124.

Embodiment 45 is the method or composition of any one of the preceding embodiments, wherein the guide RNA comprises at least one modification.

Embodiment 46 is the method or composition of embodiment 45, wherein the at least one modification includes a 2'-O-methyl (2'-O-Me) modified nucleotide.

Embodiment 47 is the method or composition of embodiment 45 or 46, wherein the at least one modification includes a phosphorothioate (PS) bond between nucleotides.

Embodiment 48 is the method or composition of any one of embodiments 45-47, wherein the at least one modification includes a 2'-fluoro (2'-F) modified nucleotide.

Embodiment 49 is the method or composition of any one of embodiments 45-48, wherein the at least one modification includes a modification at one or more of the first five nucleotides at the 5' end.

Embodiment 50 is the method or composition of any one of embodiments 45-49, wherein the at least one modification includes a modification at one or more of the last five nucleotides at the 3' end.

Embodiment 51 is the method or composition of any one of embodiments 45-50, wherein the at least one modification includes PS bonds between the first four nucleotides.

Embodiment 52 is the method or composition of any one of embodiments 45-51, wherein the at least one modification includes PS bonds between the last four nucleotides.

Embodiment 53 is the method or composition of any one of embodiments 45-52, wherein the at least one modification includes 2'-O-Me modified nucleotides at the first three nucleotides at the 5' end.

Embodiment 54 is The method or composition of any one of embodiments 45-53, wherein the at least one modification includes 2'-O-Me modified nucleotides at the last three nucleotides at the 3' end.

Embodiment 55 is the method or composition of any one of embodiments 45-54, wherein the guide RNA comprises the modified nucleotides of SEQ ID NO: 3.

Embodiment 56 is the method or composition of any one of embodiments 1-55, wherein the composition further comprises a pharmaceutically acceptable excipient.

Embodiment 57 is the method or composition of any one of embodiments 1-56, wherein the guide RNA and the nucleic acid comprising an open reading frame encoding an RNA-guided DNA binding agent are associated with a lipid nanoparticle (LNP).

Embodiment 58 is the method or composition of embodiment 57, wherein the LNP comprises a CCD lipid.

Embodiment 59 is the method or composition of embodiment 58, wherein the CCD lipid is Lipid A or Lipid B, optionally wherein the CCD lipid is lipid A.

Embodiment 60 is the method or composition of any one of embodiments 57-59, wherein the LNP comprises a helper lipid.

Embodiment 61 is the method or composition of embodiment 60, wherein the helper lipid is cholesterol.

Embodiment 62 is the method or composition of any one of embodiments 57-61, wherein the LNP comprises a stealth lipid (e.g., a PEG lipid).

Embodiment 63 is the method or composition of embodiment 62, wherein the stealth lipid is PEG2k-DMG.

Embodiment 64 is the method or composition of any one of embodiments 57-63, wherein:

(i) the LNP comprises a lipid component and the lipid component comprises: about 50-60 mol-% amine lipid such as Lipid A, about 8-10 mol-% neutral lipid; and about 2.5-4 mol-% stealth lipid (e.g., a PEG lipid), wherein the remainder of the lipid component is helper lipid, and wherein the N/P ratio of the LNP composition is about 6;

(ii) the LNP comprises about 50-60 mol-% amine lipid such as Lipid A; about 27-39.5 mol-% helper lipid; about 8-10 mol-% neutral lipid; and about 2.5-4 mol-% stealth lipid (e.g., a PEG lipid), wherein the N/P ratio of the LNP composition is about 5-7 (e.g., about 6); (iii) the LNP comprises a lipid component and the lipid component comprises: about 50-60 mol-% amine lipid such as Lipid A; about 5-15 mol-% neutral lipid; and about 2.5-4 mol-% Stealth lipid (e.g., a PEG lipid), wherein the remainder of the lipid component is helper lipid, and wherein the N/P ratio of the LNP composition is about 3-10;

(iv) the LNP comprises a lipid component and the lipid component comprises: about 40-60 mol-% amine lipid such as Lipid A; about 5-15 mol-% neutral lipid; and about 2.5-4 mol-% Stealth lipid (e.g., a PEG lipid), wherein the remainder of the lipid component is helper lipid, and wherein the N/P ratio of the LNP composition is about 6;

(v) the LNP comprises a lipid component and the lipid component comprises: about 50-60 mol-% amine lipid such as Lipid A; about 5-15 mol-% neutral lipid; and about 1.5-10 mol-% Stealth lipid (e.g., a PEG lipid), wherein the remainder of the lipid component is helper lipid, and wherein the N/P ratio of the LNP composition is about 6;

(vi) the LNP comprises a lipid component and the lipid component comprises: about 40-60 mol-% amine lipid such as Lipid A; about 0-10 mol-% neutral lipid; and about 1.5-10 mol-% Stealth lipid (e.g., a PEG lipid), wherein the remainder of the lipid component is helper lipid, and wherein the N/P ratio of the LNP composition is about 3-10;

(vii) the LNP comprises a lipid component and the lipid component comprises: about 40-60 mol-% amine lipid such as Lipid A; less than about 1 mol-% neutral lipid; and about 1.5-10 mol-% Stealth lipid (e.g., a PEG lipid), wherein the remainder of the lipid component is helper lipid, and wherein the N/P ratio of the LNP composition is about 3-10;

(viii) the LNP comprises a lipid component and the lipid component comprises: about 40-60 mol-% amine lipid such as Lipid A; and about 1.5-10 mol-% Stealth lipid (e.g., a PEG lipid), wherein the remainder of the lipid component is helper lipid, wherein the N/P ratio of the LNP composition is about 3-10, and wherein the LNP composition is essentially free of or free of neutral phospholipid; or (ix) the LNP comprises a lipid component and the lipid component comprises: about 50-60 mol-% amine lipid such as Lipid A; about 8-10 mol-% neutral lipid; and about 2.5-4 mol-% Stealth lipid (e.g., a PEG lipid), wherein the remainder of the lipid component is helper lipid, and wherein the N/P ratio of the LNP composition is about 3-7.

Embodiment 64a is the method or composition of embodiment 64, wherein the mol-% PEG lipid is about 3.

Embodiment 64b is the method or composition of embodiment 64 or 64a, wherein the mol-% amine lipid is about 50.

Embodiment 64c is the method or composition of any one of embodiments 64-64b, wherein the mol-% amine lipid is about 55.

Embodiment 64d is the method or composition of any one of embodiments 64-64c, wherein the mol-% amine lipid is ±3 mol-%.

Embodiment 64e is the method or composition of any one of embodiments 64-64d, wherein the mol-% amine lipid is ±2 mol-%.

Embodiment 64f is the method or composition of any one of embodiments 64-64e, wherein the mol-% amine lipid is 47-53 mol-%.

Embodiment 64g is the method or composition of any one of embodiments 64-64f, wherein the mol-% amine lipid is 48-53 mol-%.

Embodiment 64 h is the method or composition of any one of embodiments 64-64g, wherein the mol-% amine lipid is 53-57 mol-%.

Embodiment 64i is the method or composition of any one of embodiments 64-64h, wherein the N/P ratio is 6±1.

Embodiment 64j is the method or composition of any one of embodiments 64-64i, wherein the N/P ratio is 6±0.5.

Embodiment 64k is the method or composition of any one of embodiments 64-64j, wherein the amine lipid is Lipid A.

Embodiment 64l is the method or composition of any one of embodiments 64-64l, wherein the amine lipid is an analog of Lipid A.

Embodiment 64m is the method or composition of embodiment 641, wherein the analog is an acetal analog.

Embodiment 64n is the method or composition of embodiment 64m, wherein the acetal analog is a C4, and C12 analog.

Embodiment 64r is the method or composition of any one of embodiments 64-64q, wherein the helper lipid is cholesterol.

Embodiment 64s is the method or composition of any one of embodiments 64-64r, wherein the neutral lipid is DSPC.

Embodiment 64t is the method or composition of any one of embodiments 64-64s, wherein the neutral lipid is DPPC.

Embodiment 64u is the method or composition of any one of embodiments 64-64t, wherein the PEG lipid comprises dimyristoylglycerol (DMG).

Embodiment 64v is the method or composition of any one of embodiments 64-64u, wherein the PEG lipid comprises a PEG-2k.

Embodiment 64w is the method or composition of any one of embodiments 64-64v, wherein the PEG lipid is a PEG-DMG.

Embodiment 64x is the method or composition of embodiment 64w, wherein the PEG-DMG is a PEG2k-DMG.

Embodiment 64y is the method or composition of any one of embodiments 64-64x, wherein the LNP composition is essentially free of neutral lipid.

Embodiment 64z is the method or composition of embodiment 64y, wherein the neutral lipid is a phospholipid.

Embodiment 65 is the method or composition of any one of embodiments 57-64z, wherein the LNP comprises a neutral lipid, optionally wherein the neutral lipid is DSPC.

Embodiment 66 is the method or composition of any one of embodiments 64-65, wherein the amine lipid is present at about 50 mol-%.

Embodiment 67 is the method or composition of any one of embodiments 64-66, wherein the neutral lipid is present at about 9 mol-%.

Embodiment 68 is the method or composition of any one of embodiments 62-67, wherein the stealth lipid is present at about 3 mol-%.

Embodiment 69 is the method or composition of any one of embodiments 60-68, wherein the helper lipid is present at about 38 mol-%.

Embodiment 70 is the method or composition of any one of the preceding embodiments, wherein the LNP has an N/P ratio of about 6.

Embodiment 71 is the method or composition of embodiment 70, wherein the LNP comprises a lipid component and the lipid component comprises: about 50 mol-% amine lipid such as Lipid A; about 9 mol-% neutral lipd such as DSPC; about 3 mol-% of stealth lipid such as a PEG lipid, such as PEG2k-DMG, and the remainder of the lipid component is helper lipid such as cholesterol wherein the N/P ratio of the LNP composition is about 6.

Embodiment 72 is the method or composition of any one of embodiments 64-71, wherein the amine lipid is Lipid A.

Embodiment 73 is the method or composition of any one of embodiments 64-72, wherein the neutral lipid is DSPC.

Embodiment 74 is the method or composition of any one of embodiments 62-73, wherein the stealth lipid is PEG2k-DMG.

Embodiment 75 is the method or composition of any one of embodiments 60-74, wherein the helper lipid is cholesterol.

Embodiment 76 is the method or composition of any one of embodiments 70, wherein the LNP comprises a lipid component and the lipid component comprises: about 50 mol-% Lipid A; about 9 mol-% DSPC; about 3 mol-% of PEG2k-DMG, and the remainder of the lipid component is cholesterol wherein the N/P ratio of the LNP composition is about 6.

Embodiment 77 is the method or composition of any one of the preceding embodiments, wherein the RNA-guided DNA binding agent is a Cas cleavase.

Embodiment 78 is the method or composition of embodiment 77, wherein the RNA-guided DNA binding agent is Cas9.

Embodiment 79 is the method or composition of any one of the preceding embodiments, wherein the RNA-guided DNA binding agent is modified.

Embodiment 80 is the method or composition of embodiment 79, wherein the modified RNA-guided DNA binding agent comprises a nuclear localization signal (NLS).

Embodiment 81 is the method or composition of any one of the preceding embodiments, wherein the RNA-guided DNA binding agent is a Cas from a Type-II CRISPR/Cas system.

Embodiment 82 is the method or composition of any one of the preceding embodiments, wherein the composition is a pharmaceutical formulation and further comprises a pharmaceutically acceptable carrier.

Embodiment 83 is the method or composition for use of any one of embodiments 2-82, wherein the composition reduces or prevents amyloids or amyloid fibrils comprising TTR.

Embodiment 84 is the method or composition for use of embodiment 83, wherein the amyloids or amyloid fibrils are in the nerves, heart, or gastrointestinal track.

Embodiment 85 is the method or composition for use of any one of embodiments 2-84, wherein non-homologous ending joining (NHEJ) leads to a mutation during repair of a DSB in the TTR gene.

Embodiment 86 is the method or composition for use of embodiment 85, wherein NHEJ leads to a deletion or insertion of a nucleotide(s) during repair of a DSB in the TTR gene.

Embodiment 87 is the method or composition for use of embodiment 86, wherein the deletion or insertion of a nucleotide(s) induces a frame shift or nonsense mutation in the TTR gene.

Embodiment 88 is the method or composition for use of embodiment 86, wherein a frame shift or nonsense mutation is induced in the TTR gene of at least 50% of liver cells.

Embodiment 89 is the method or composition for use of embodiment 88, wherein a frame shift or nonsense mutation is induced in the TTR gene of 50%-60%, 60%-70%, 70% or 80%, 80%-90%, 90-95%, 95%-99%, or 99%-100% of liver cells.

Embodiment 90 is the method or composition for use of any one of embodiments 86-89, wherein a deletion or insertion of a nucleotide(s) occurs in the TTR gene at least 50-fold or more than in off-target sites.

Embodiment 91 is the method or composition for use of embodiment 90, wherein the deletion or insertion of a nucleotide(s) occurs in the TTR gene 50-fold to 150-fold, 150-fold to 500-fold, 500-fold to 1500-fold, 1500-fold to 5000-fold, 5000-fold to 15000-fold, 15000-fold to 30000-fold, or 30000-fold to 60000-fold more than in off-target sites.

Embodiment 92 is the method or composition for use of any one of embodiments 86-91, wherein the deletion or insertion of a nucleotide(s) occurs at less than or equal to 3, 2, 1, or 0 off-target site(s) in primary human hepatocytes, optionally wherein the off-target site(s) does (do) not occur in a protein coding region in the genome of the primary human hepatocytes.

Embodiment 93 is the method or composition for use of embodiment 92, wherein the deletion or insertion of a nucleotide(s) occurs at a number of off-target sites in primary human hepatocytes that is less than the number of off-target sites at which a deletion or insertion of a nucleotide(s) occurs in Cas9-overexpressing cells, optionally wherein the off-target site(s) does (do) not occur in a protein coding region in the genome of the primary human hepatocytes.

Embodiment 94 is the method or composition for use of embodiment 93, wherein the Cas9-overexpressing cells are HEK293 cells stably expressing Cas9.

Embodiment 95 is the method or composition for use of any one of embodiments 92-94, wherein the number of off-target sites in primary human hepatocytes is determined by analyzing genomic DNA from primary human hepatocytes transfected in vitro with Cas9 mRNA and the guide RNA, optionally wherein the off-target site(s) does (do) not occur in a protein coding region in the genome of the primary human hepatocytes.

Embodiment 96 is the method or composition for use of any one of embodiments 92-94, wherein the number of off-target sites in primary human hepatocytes is determined by an oligonucleotide insertion assay comprising analyzing genomic DNA from primary human hepatocytes transfected in vitro with Cas9 mRNA, the guide RNA, and a donor oligonucleotide, optionally wherein the off-target site(s) does (do) not occur in a protein coding region in the genome of the primary human hepatocytes.

Embodiment 97 is the method or composition of any one of embodiments 1-36 or 39-96, wherein the sequence of the guide RNA is:

a) SEQ ID NO: 92 or 104;
b) SEQ ID NO: 87, 89, 96, or 113;
c) SEQ ID NO: 100, 102, 106, 111, or 112; or
d) SEQ ID NO: 88, 90, 91, 93, 94, 95, 97, 101, 103, 108, or 109.

Embodiment 98 is the method or composition of embodiment 97, wherein the guide RNA does not produce indels at off-target site(s) that occur in a protein coding region in the genome of primary human hepatocytes.

Embodiment 99 is the method or composition for use of any one of embodiments 2-98, wherein administering the composition reduces levels of TTR in the subject.

Embodiment 100 is the method or composition for use of embodiment 99, wherein the levels of TTR are reduced by at least 50%.

Embodiment 101 is the method or composition for use of embodiment 100, wherein the levels of TTR are reduced by 50%-60%, 60%-70%, 70% or 80%, 80%-90%, 90-95%, 95%-99%, or 99%-100%.

Embodiment 102 is the method or composition for use of embodiment 100 or 101, wherein the levels of TTR are measured in serum, plasma, blood, cerebral spinal fluid, or sputum.

Embodiment 103 is the method or composition for use of embodiment 100 or 101, wherein the levels of TTR are measured in liver, choroid plexus, and/or retina.

Embodiment 104 is the method or composition for use of any one of embodiments 99-103, wherein the levels of TTR are measured via enzyme-linked immunosorbent assay (ELISA).

Embodiment 105 is the method or composition for use of any one of embodiments 2-104, wherein the subject has ATTR.

Embodiment 106 is the method or composition for use of any one of embodiments 2-105, wherein the subject is human.

Embodiment 107 is the method or composition for use of embodiment 105 or 106, wherein the subject has ATTRwt.

Embodiment 108 is the method or composition for use of embodiment 105 or 106, wherein the subject has hereditary ATTR.

Embodiment 109 is the method or composition for use of any one of embodiments 2-106 or 108, wherein the subject has a family history of ATTR.

Embodiment 110 is the method or composition for use of any one of embodiments 2-106 or 108-109, wherein the subject has familial amyloid polyneuropathy.

Embodiment 111 is the method or composition for use of any one of embodiments 2-110, wherein the subject has only or predominantly nerve symptoms of ATTR.

Embodiment 112 is the method or composition for use of any one of embodiments 2-111, wherein the subject has familial amyloid cardiomyopathy.

Embodiment 113 is the method or composition for use of any one of embodiments 2-110 or 112, wherein the subject has only or predominantly cardiac symptoms of ATTR.

Embodiment 114 is the method or composition for use of any one of embodiments 2-113, wherein the subject expresses TTR having a V30 mutation.

Embodiment 115 is the method or composition for use of embodiment 114, wherein the V30 mutation is V30A, V30G, V30L, or V30M.

Embodiment 116 is the method or composition for use of embodiment any one of embodiments 2-113, wherein the subject expresses TTR having a T60 mutation.

Embodiment 117 is the method or composition for use of embodiment 116, wherein the T60 mutation is T60A.

Embodiment 118 is the method or composition for use of embodiment any one of embodiments 2-113, wherein the subject expresses TTR having a V122 mutation.

Embodiment 119 is the method or composition for use of embodiment 118, wherein the V122 mutation is V122A, V122I, or V122(-).

Embodiment 120 is the method or composition for use of any one of embodiments 2-113, wherein the subject expresses wild-type TTR.

Embodiment 121 is the method or composition for use of any one of embodiments 2-107, or 120, wherein the subject does not express TTR having a V30, T60, or V122 mutation.

Embodiment 122 is the method or composition for use of any one of embodiments 2-107, or 120-121, wherein the subject does not express TTR having a pathological mutation.

Embodiment 123 is the method or composition for use of embodiment 122, wherein the subject is homozygous for wild-type TTR.

Embodiment 124 is the method or composition for use of any one of embodiments 2-123, wherein after administration the subject has an improvement, stabilization, or slowing of change in symptoms of sensorimotor neuropathy.

Embodiment 125 is the method or composition for use of embodiment 124, wherein the improvement, stabilization, or slowing of change in sensory neuropathy is measured using electromyogram, nerve conduction tests, or patient-reported outcomes.

Embodiment 126 is the method or composition for use of any one of embodiments 2-125, wherein the subject has an improvement, stabilization, or slowing of change in symptoms of congestive heart failure.

Embodiment 127 is the method or composition for use of embodiment 126, wherein the improvement, stabilization, or slowing of change in congestive heart failure is measured using cardiac biomarker tests, lung function tests, chest x-rays, or electrocardiography.

Embodiment 128 is the method or composition for use of any one of embodiments 2-127, wherein the composition or pharmaceutical formulation is administered via a viral vector.

Embodiment 129 is the method or composition for use of any one of embodiments 2-127, wherein the composition or pharmaceutical formulation is administered via lipid nanoparticles.

Embodiment 130 is the method or composition for use of any one of embodiments 2-129, wherein the subject is tested for specific mutations in the TTR gene before administering the composition or formulation.

Embodiment 131 is the method or composition of any one of the preceding embodiments, wherein the sequence selected from SEQ ID NOs: 5-72, 74-78, and 80-82 is SEQ ID NO: 5, 6, 9, 13, 14, 15, 16, 17, 22, 23, 27, 30, 35, 36, 37, 38, 55, 63, 65, 66, 68, or 69.

Embodiment 132 is the method or composition of any one of embodiments 1-130, wherein the sequence selected from SEQ ID NOs: 5-72, 74-78, and 80-82 is SEQ ID NO: 5.

Embodiment 133 is the method or composition of any one of embodiments 1-130, wherein the sequence selected from SEQ ID NOs: 5-72, 74-78, and 80-82 is SEQ ID NO: 6.

Embodiment 134 is the method or composition of any one of embodiments 1-130, wherein the sequence selected from SEQ ID NOs: 5-72, 74-78, and 80-82 is SEQ ID NO: 7.

Embodiment 135 is the method or composition of any one of embodiments 1-130, wherein the sequence selected from SEQ ID NOs: 5-72, 74-78, and 80-82 is SEQ ID NO: 8.

Embodiment 136 is the method or composition of any one of embodiments 1-130, wherein the sequence selected from SEQ ID NOs: 5-72, 74-78, and 80-82 is SEQ ID NO: 9.

Embodiment 137 is the method or composition of any one of embodiments 1-130, wherein the sequence selected from SEQ ID NOs: 5-72, 74-78, and 80-82 is SEQ ID NO: 10.

Embodiment 138 is the method or composition of any one of embodiments 1-130, wherein the sequence selected from SEQ ID NOs: 5-72, 74-78, and 80-82 is SEQ ID NO: 11.

Embodiment 139 is the method or composition of-any one of embodiments 1-130, wherein the sequence selected from SEQ ID NOs: 5-72, 74-78, and 80-82 is SEQ ID NO: 12.

Embodiment 140 is the method or composition of any one of embodiments 1-130, wherein the sequence selected from SEQ ID NOs: 5-72, 74-78, and 80-82 is SEQ ID NO: 13.

Embodiment 141 is the method or composition of any one of embodiments 1-130, wherein the sequence selected from SEQ ID NOs: 5-72, 74-78, and 80-82 is SEQ ID NO: 14.

Embodiment 142 is the method or composition of any one of embodiments 1-130, wherein the sequence selected from SEQ ID NOs: 5-72, 74-78, and 80-82 is SEQ ID NO: 15.

Embodiment 143 is the method or composition of any one of embodiments 1-130, wherein the sequence selected from SEQ ID NOs: 5-72, 74-78, and 80-82 is SEQ ID NO: 16.

Embodiment 144 is the method or composition of any one of embodiments 1-130, wherein the sequence selected from SEQ ID NOs: 5-72, 74-78, and 80-82 is SEQ ID NO: 17.

Embodiment 145 is the method or composition of any one of embodiments 1-130, wherein the sequence selected from SEQ ID NOs: 5-72, 74-78, and 80-82 is SEQ ID NO: 18.

Embodiment 146 is the method or composition of any one of embodiments 1-130, wherein the sequence selected from SEQ ID NOs: 5-72, 74-78, and 80-82 is SEQ ID NO: 19.

Embodiment 147 is the method or composition of any one of embodiments 1-130, wherein the sequence selected from SEQ ID NOs: 5-72, 74-78, and 80-82 is SEQ ID NO: 20.

Embodiment 148 is the method or composition of any one of embodiments 1-130, wherein the sequence selected from SEQ ID NOs: 5-72, 74-78, and 80-82 is SEQ ID NO: 21.

Embodiment 149 is the method or composition of any one of embodiments 1-130, wherein the sequence selected from SEQ ID NOs: 5-72, 74-78, and 80-82 is SEQ ID NO: 22.

Embodiment 150 is the method or composition of any one of embodiments 1-130, wherein the sequence selected from SEQ ID NOs: 5-72, 74-78, and 80-82 is SEQ ID NO: 23.

Embodiment 151 is the method or composition of any one of embodiments 1-130, wherein the sequence selected from SEQ ID NOs: 5-72, 74-78, and 80-82 is SEQ ID NO: 24.

Embodiment 152 is the method or composition of any one of embodiments 1-130, wherein the sequence selected from SEQ ID NOs: 5-72, 74-78, and 80-82 is SEQ ID NO: 25.

Embodiment 153 is the method or composition of any one of embodiments 1-130, wherein the sequence selected from SEQ ID NOs: 5-72, 74-78, and 80-82 is SEQ ID NO: 26.

Embodiment 154 is the method or composition of any one of embodiments 1-130, wherein the sequence selected from SEQ ID NOs: 5-72, 74-78, and 80-82 is SEQ ID NO: 27.

Embodiment 155 is the method or composition of any one of embodiments 1-130, wherein the sequence selected from SEQ ID NOs: 5-72, 74-78, and 80-82 is SEQ ID NO: 28.

Embodiment 156 is the method or composition of any one of embodiments 1-130, wherein the sequence selected from SEQ ID NOs: 5-72, 74-78, and 80-82 is SEQ ID NO: 29.

Embodiment 157 is the method or composition of any one of embodiments 1-130, wherein the sequence selected from SEQ ID NOs: 5-72, 74-78, and 80-82 is SEQ ID NO: 30.

Embodiment 158 is the method or composition of any one of embodiments 1-130, wherein the sequence selected from SEQ ID NOs: 5-72, 74-78, and 80-82 is SEQ ID NO: 31.

Embodiment 159 is the method or composition of any one of embodiments 1-130, wherein the sequence selected from SEQ ID NOs: 5-72, 74-78, and 80-82 is SEQ ID NO: 32.

Embodiment 160 is the method or composition of any one of embodiments 1-130, wherein the sequence selected from SEQ ID NOs: 5-72, 74-78, and 80-82 is SEQ ID NO: 33.

Embodiment 161 is the method or composition of any one of embodiments 1-130, wherein the sequence selected from SEQ ID NOs: 5-72, 74-78, and 80-82 is SEQ ID NO: 34.

Embodiment 162 is the method or composition of any one of embodiments 1-130, wherein the sequence selected from SEQ ID NOs: 5-72, 74-78, and 80-82 is SEQ ID NO: 35.

Embodiment 163 is the method or composition of any one of embodiments 1-130, wherein the sequence selected from SEQ ID NOs: 5-72, 74-78, and 80-82 is SEQ ID NO: 36.

Embodiment 164 is the method or composition of any one of embodiments 1-130, wherein the sequence selected from SEQ ID NOs: 5-72, 74-78, and 80-82 is SEQ ID NO: 37.

Embodiment 165 is the method or composition of any one of embodiments 1-130, wherein the sequence selected from SEQ ID NOs: 5-72, 74-78, and 80-82 is SEQ ID NO: 38.

Embodiment 166 is the method or composition of any one of embodiments 1-130, wherein the sequence selected from SEQ ID NOs: 5-72, 74-78, and 80-82 is SEQ ID NO: 39.

Embodiment 167 is the method or composition of any one of embodiments 1-130, wherein the sequence selected from SEQ ID NOs: 5-72, 74-78, and 80-82 is SEQ ID NO: 40.

Embodiment 168 is the method or composition of any one of embodiments 1-130, wherein the sequence selected from SEQ ID NOs: 5-72, 74-78, and 80-82 is SEQ ID NO: 41.

Embodiment 169 is the method or composition of any one of embodiments 1-130, wherein the sequence selected from SEQ ID NOs: 5-72, 74-78, and 80-82 is SEQ ID NO: 42.

Embodiment 170 is the method or composition of any one of embodiments 1-130, wherein the sequence selected from SEQ ID NOs: 5-72, 74-78, and 80-82 is SEQ ID NO: 43.

Embodiment 171 is the method or composition of any one of embodiments 1-130, wherein the sequence selected from SEQ ID NOs: 5-72, 74-78, and 80-82 is SEQ ID NO: 44.

Embodiment 172 is the method or composition of any one of embodiments 1-130, wherein the sequence selected from SEQ ID NOs: 5-72, 74-78, and 80-82 is SEQ ID NO: 45.

Embodiment 173 is the method or composition of any one of embodiments 1-130, wherein the sequence selected from SEQ ID NOs: 5-72, 74-78, and 80-82 is SEQ ID NO: 46.

Embodiment 174 is the method or composition of any one of embodiments 1-130, wherein the sequence selected from SEQ ID NOs: 5-72, 74-78, and 80-82 is SEQ ID NO: 47.

Embodiment 175 is the method or composition of any one of embodiments 1-130, wherein the sequence selected from SEQ ID NOs: 5-72, 74-78, and 80-82 is SEQ ID NO: 48.

Embodiment 176 is the method or composition of any one of embodiments 1-130, wherein the sequence selected from SEQ ID NOs: 5-72, 74-78, and 80-82 is SEQ ID NO: 49.

Embodiment 177 is the method or composition of any one of embodiments 1-130, wherein the sequence selected from SEQ ID NOs: 5-72, 74-78, and 80-82 is SEQ ID NO: 50.

Embodiment 178 is the method or composition of any one of embodiments 1-130, wherein the sequence selected from SEQ ID NOs: 5-72, 74-78, and 80-82 is SEQ ID NO: 51.

Embodiment 179 is the method or composition of any one of embodiments 1-130, wherein the sequence selected from SEQ ID NOs: 5-72, 74-78, and 80-82 is SEQ ID NO: 52.

Embodiment 180 is the method or composition of any one of embodiments 1-130, wherein the sequence selected from SEQ ID NOs: 5-72, 74-78, and 80-82 is SEQ ID NO: 53.

Embodiment 181 is the method or composition of any one of embodiments 1-130, wherein the sequence selected from SEQ ID NOs: 5-72, 74-78, and 80-82 is SEQ ID NO: 54.

Embodiment 182 is the method or composition of any one of embodiments 1-130, wherein the sequence selected from SEQ ID NOs: 5-72, 74-78, and 80-82 is SEQ ID NO: 55.

Embodiment 183 is the method or composition of any one of embodiments 1-130, wherein the sequence selected from SEQ ID NOs: 5-72, 74-78, and 80-82 is SEQ ID NO: 56.

Embodiment 184 is the method or composition of any one of embodiments 1-130, wherein the sequence selected from SEQ ID NOs: 5-72, 74-78, and 80-82 is SEQ ID NO: 57.

Embodiment 185 is the method or composition of any one of embodiments 1-130, wherein the sequence selected from SEQ ID NOs: 5-72, 74-78, and 80-82 is SEQ ID NO: 58.

Embodiment 186 is the method or composition of any one of embodiments 1-130, wherein the sequence selected from SEQ ID NOs: 5-72, 74-78, and 80-82 is SEQ ID NO: 59.

Embodiment 187 is the method or composition of any one of embodiments 1-130, wherein the sequence selected from SEQ ID NOs: 5-72, 74-78, and 80-82 is SEQ ID NO: 60.

Embodiment 188 is the method or composition of any one of embodiments 1-130, wherein the sequence selected from SEQ ID NOs: 5-72, 74-78, and 80-82 is SEQ ID NO: 61.

Embodiment 189 is the method or composition of any one of embodiments 1-130, wherein the sequence selected from SEQ ID NOs: 5-72, 74-78, and 80-82 is SEQ ID NO: 62.

Embodiment 190 is the method or composition of any one of embodiments 1-130, wherein the sequence selected from SEQ ID NOs: 5-72, 74-78, and 80-82 is SEQ ID NO: 63.

Embodiment 191 is the method or composition of any one of embodiments 1-130, wherein the sequence selected from SEQ ID NOs: 5-72, 74-78, and 80-82 is SEQ ID NO: 64.

Embodiment 192 is the method or composition of any one of embodiments 1-130, wherein the sequence selected from SEQ ID NOs: 5-72, 74-78, and 80-82 is SEQ ID NO: 65.

Embodiment 193 is the method or composition of any one of embodiments 1-130, wherein the sequence selected from SEQ ID NOs: 5-72, 74-78, and 80-82 is SEQ ID NO: 66.

Embodiment 194 is the method or composition of any one of embodiments 1-130, wherein the sequence selected from SEQ ID NOs: 5-72, 74-78, and 80-82 is SEQ ID NO: 67.

Embodiment 195 is the method or composition of any one of embodiments 1-130, wherein the sequence selected from SEQ ID NOs: 5-72, 74-78, and 80-82 is SEQ ID NO: 68.

Embodiment 196 is the method or composition of any one of embodiments 1-130, wherein the sequence selected from SEQ ID NOs: 5-72, 74-78, and 80-82 is SEQ ID NO: 69.

Embodiment 197 is the method or composition of any one of embodiments 1-130, wherein the sequence selected from SEQ ID NOs: 5-72, 74-78, and 80-82 is SEQ ID NO: 70.

Embodiment 198 is the method or composition of any one of embodiments 1-130, wherein the sequence selected from SEQ ID NOs: 5-72, 74-78, and 80-82 is SEQ ID NO: 71.

Embodiment 199 is the method or composition of any one of embodiments 1-130, wherein the sequence selected from SEQ ID NOs: 5-72, 74-78, and 80-82 is SEQ ID NO: 72.

Embodiment 200 is the method or composition of any one of embodiments 1-130, wherein the sequence selected from SEQ ID NOs: 5-72, 74-78, and 80-82 is SEQ ID NO: 74.

Embodiment 201 is the method or composition of any one of embodiments 1-130, wherein the sequence selected from SEQ ID NOs: 5-72, 74-78, and 80-82 is SEQ ID NO: 75.

Embodiment 202 is the method or composition of any one of embodiments 1-130, wherein the sequence selected from SEQ ID NOs: 5-72, 74-78, and 80-82 is SEQ ID NO: 76.

Embodiment 203 is the method or composition of any one of embodiments 1-130, wherein the sequence selected from SEQ ID NOs: 5-72, 74-78, and 80-82 is SEQ ID NO: 77.

Embodiment 204 is the method or composition of any one of embodiments 1-130, wherein the sequence selected from SEQ ID NOs: 5-72, 74-78, and 80-82 is SEQ ID NO: 78.

Embodiment 205 is the method or composition of any one of embodiments 1-130, wherein the sequence selected from SEQ ID NOs: 5-72, 74-78, and 80-82 is SEQ ID NO: 80.

Embodiment 206 is the method or composition of any one of embodiments 1-130, wherein the sequence selected from SEQ ID NOs: 5-72, 74-78, and 80-82 is SEQ ID NO: 81.

Embodiment 207 is the method or composition of any one of embodiments 1-130, wherein the sequence selected from SEQ ID NOs: 5-72, 74-78, and 80-82 is SEQ ID NO: 82.

Embodiment 208 is the composition or method of any one of the preceding embodiments, wherein the open reading frame has at least 95% identity to SEQ ID NO: 311 over at least its first 10%, 12%, 15%, 20%, 25%, 30%, or 35% of its sequence.

Embodiment 209 is the composition or method of any one of the preceding embodiments, wherein the open reading frame comprises a sequence with at least 94%, 95%, 96%, 97%, 98%, 99%, 99.5%, or 100% identity to SEQ ID NO: 311.

Embodiment 210 is the composition or method of any one of the preceding embodiments, wherein at least 95%, 96%, 97%, 98%, 99%, 99.5%, or 100% of the codons of the open reading frame are codons listed in Table 4, Table 5, or Table 7.

Embodiment 211 is the composition or method of embodiment 210, wherein the codons listed in Table 4, Table 5, or Table 7 are codons listed in Table 4.

Embodiment 212 is the composition or method of embodiment 210, wherein the codons listed in Table 4, Table 5, or Table 7 are codons of the Low U codon set of Table 5.

Embodiment 213 is the composition or method of embodiment 210, wherein the codons listed in Table 4, Table 5, or Table 7 are codons of the Low A codon set of Table 5.

Embodiment 214 is the composition or method of embodiment 210, wherein the codons listed in Table 4, Table 5, or Table 7 are codons of the Low A/U codon set of Table 5.

Embodiment 215 is the composition or method of embodiment 210, wherein the codons listed in Table 4, Table 5, or Table 7 are codons listed in Table 7.

Embodiment 216 is the composition or method of any one of the preceding embodiments, wherein the open reading frame has an adenine content ranging from its minimum adenine content to 101%, 102%, 103%, 105%, 110%, 115%, 120%, or 123% of the minimum adenine content.

Embodiment 217 is the composition or method of any one of the preceding embodiments, wherein the open reading frame has an adenine dinucleotide content ranging from its minimum adenine dinucleotide content to 101%, 102%, 103%, 105%, 110%, 115%, 120%, 125%, 130%, 135%, 140%, 145%, or 150% of the minimum adenine dinucleotide content.

Embodiment 218 is the composition or method of any one of the preceding embodiments, wherein the nucleic acid comprises a 5' UTR with at least 90% identity to any one of SEQ ID NOs: 232, 234, 236, 238, 241, or 275-277.

Embodiment 219 is the composition or method of any one of the preceding embodiments, wherein the nucleic acid comprises a 3' UTR with at least 90% identity to any one of SEQ ID NOs: 233, 235, 237, 239, or 240.

Embodiment 220 is the composition or method of any one of the preceding embodiments, wherein the nucleic acid comprises a 5' UTR and a 3' UTR from the same source.

Embodiment 221 is the composition or method of any one of the preceding embodiments, wherein the nucleic acid is an mRNA comprising a 5' cap selected from Cap0, Cap1, and Cap2.

Embodiment 222 is the composition or method of any one of the preceding embodiments, wherein the open reading frame comprises a sequence with at least 95%, 96%, 97%, 98%, 99%, 99.5%, or 100% identity to SEQ ID NO: 377.

Embodiment 223 is the composition or method of any of the preceding embodiments, wherein the nucleic acid is an mRNA in which at least 10% of the uridine is substituted with a modified uridine.

Embodiment 224 is the composition or method of embodiment 223, wherein the modified uridine is one or more of N1-methyl-pseudouridine, pseudouridine, 5-methoxyuridine, or 5-iodouridine.

Embodiment 225 is the composition or method of embodiment 223, wherein the modified uridine is one or both of N1-methyl-pseudouridine or 5-methoxyuridine.

Embodiment 226 is the composition or method of embodiment 223, wherein the modified uridine is N1-methyl-pseudouridine.

Embodiment 227 is the composition or method of embodiment 223, wherein the modified uridine is 5-methoxyuridine.

Embodiment 228 is the composition or method of any one of embodiments 223-210, wherein 15% to 45% of the uridine in the mRNA is substituted with the modified uridine.

Embodiment 229 is the composition or method of any one of embodiments 223-211, wherein at least 20% or at least 30% of the uridine in the mRNA is substituted with the modified uridine.

Embodiment 230 is the composition or method of embodiment 229, wherein at least 80% or at least 90% of the uridine in the mRNA is substituted with the modified uridine.

Embodiment 231 is the composition or method of embodiment 229, wherein 100% of the uridine in the mRNA is substituted with the modified uridine.

Embodiment 232 is a use of a composition or formulation of any of embodiments 1 or 4-231 for the preparation of a medicament for treating a human subject having ATTR.

DETAILED DESCRIPTION

Figure 1A:
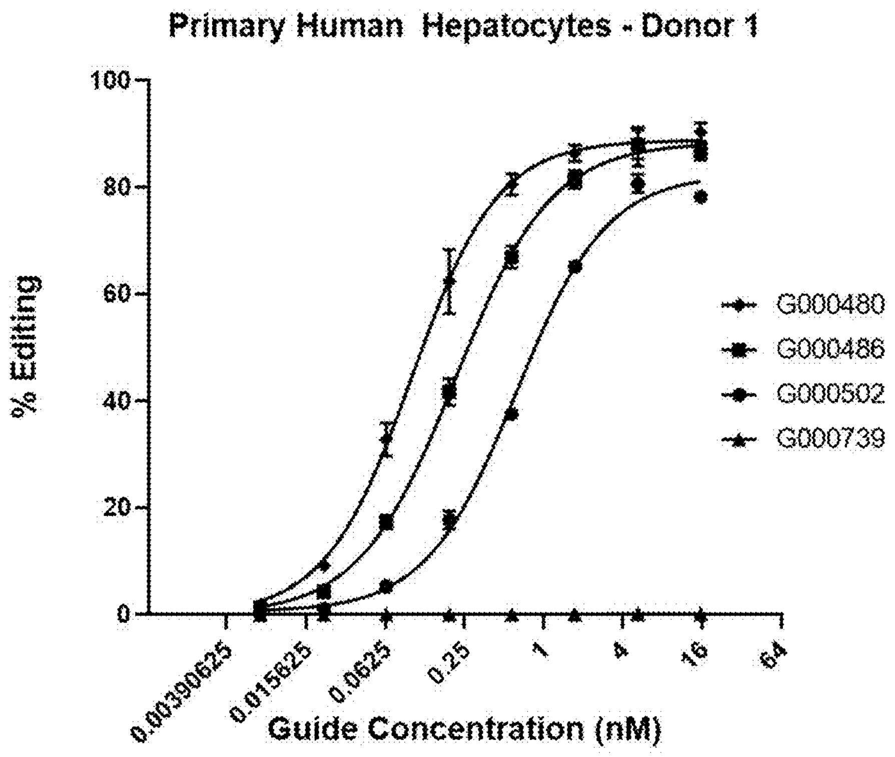
FIGS. 1A-1B show % Editing in primary human hepatocytes from two donors as described in Example 2.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

Before describing the present teachings in detail, it is to be understood that the disclosure is not limited to specific compositions or process steps, as such may vary. It should be noted that, as used in this specification and the appended claims, the singular form "a", "an" and "the" include plural references unless the context clearly dictates otherwise. Thus, for example, reference to "a conjugate" includes a plurality of conjugates and reference to "a cell" includes a plurality of cells and the like.

Numeric ranges are inclusive of the numbers defining the range. Measured and measureable values are understood to be approximate, taking into account significant digits and the error associated with the measurement. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings.

Unless specifically noted in the above specification, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims). The term "or" is used in an inclusive sense, i.e., equivalent to "and/or," unless the context clearly indicates otherwise.

The section headings used herein are for organizational purposes only and are not to be construed as limiting the desired subject matter in any way. In the event that any material incorporated by reference contradicts any term defined in this specification or any other express content of this specification, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

I. Definitions

Unless stated otherwise, the following terms and phrases as used herein are intended to have the following meanings:

"Polynucleotide" and "nucleic acid" are used herein to refer to a multimeric compound comprising nucleosides or nucleoside analogs which have nitrogenous heterocyclic bases or base analogs linked together along a backbone, including conventional RNA, DNA, mixed RNA-DNA, and polymers that are analogs thereof. A nucleic acid "backbone" can be made up of a variety of linkages, including one or more of sugar-phosphodiester linkages, peptide-nucleic acid bonds ("peptide nucleic acids" or PNA; PCT No. WO 95/32305), phosphorothioate linkages, methylphosphonate linkages, or combinations thereof. Sugar moieties of a nucleic acid can be ribose, deoxyribose, or similar compounds with substitutions, e.g., 2' methoxy or 2' halide substitutions. Nitrogenous bases can be conventional bases (A, G, C, T, U), analogs thereof (e.g., modified uridines such as 5-methoxyuridine, pseudouridine, or N1-methylpseudouridine, or others); inosine; derivatives of purines or pyrimidines (e.g., $N^4$-methyl deoxyguanosine, deaza- or aza-purines, deaza- or aza-pyrimidines, pyrimidine bases with substituent groups at the 5 or 6 position (e.g., 5-methylcytosine), purine bases with a substituent at the 2, 6, or 8 positions, 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines; U.S. Pat. No. 5,378,825 and PCT No. WO 93/13121). For general discussion see *The Biochemistry of the Nucleic Acids* 5-36, Adams et al., ed., $11^{th}$ ed., 1992). Nucleic acids can include one or more "abasic" residues where the backbone includes no nitrogenous base for position(s) of the polymer (U.S. Pat. No. 5,585,481). A nucleic acid can comprise only conventional RNA or DNA sugars, bases and linkages, or can include both conventional components and substitutions (e.g., conventional bases with 2' methoxy linkages, or polymers containing both conventional bases and one or more base analogs). Nucleic acid includes "locked nucleic acid" (LNA), an analogue containing one or more LNA nucleotide monomers with a bicyclic furanose unit locked in an RNA mimicking sugar conformation, which enhance hybridization affinity toward complementary RNA and DNA sequences (Vester and Wengel, 2004, Biochemistry 43(42): 13233-41). RNA and DNA have different sugar moieties and can differ by the presence of uracil or analogs thereof in RNA and thymine or analogs thereof in DNA.

"Polypeptide" as used herein refers to a multimeric compound comprising amino acid residues that can adopt a three-dimensional conformation. Polypeptides include but are not limited to enzymes, enzyme precursor proteins, regulatory proteins, structural proteins, receptors, nucleic acid binding proteins, antibodies, etc. Polypeptides may, but do not necessarily, comprise post-translational modifications, non-natural amino acids, prosthetic groups, and the like.

"Guide RNA", "gRNA", and "guide" are used herein interchangeably to refer to either a crRNA (also known as CRISPR RNA), or the combination of a crRNA and a trRNA (also known as tracrRNA). The crRNA and trRNA may be associated as a single RNA molecule (single guide RNA, sgRNA) or in two separate RNA molecules (dual guide RNA, dgRNA). "Guide RNA" or "gRNA" refers to each type. The trRNA may be a naturally-occurring sequence, or a trRNA sequence with modifications or variations compared to naturally-occurring sequences. Guide RNAs can include modified RNAs as described herein.

As used herein, a "guide sequence" refers to a sequence within a guide RNA that is complementary to a target sequence and functions to direct a guide RNA to a target sequence for binding or modification (e.g., cleavage) by an RNA-guided DNA binding agent. A "guide sequence" may also be referred to as a "targeting sequence," or a "spacer sequence." A guide sequence can be 20 base pairs in length, e.g., in the case of *Streptococcus pyogenes* (i.e., Spy Cas9) and related Cas9 homologs/orthologs. Shorter or longer sequences can also be used as guides, e.g., 15-, 16-, 17-, 18-, 19-, 21-, 22-, 23-, 24-, or 25-nucleotides in length. In some embodiments, the guide sequence and the target region may be 100% complementary or identical. In other embodiments, the guide sequence and the target region may contain at least one mismatch. For example, the guide sequence and the target sequence may contain 1, 2, 3, or 4 mismatches, where the total length of the target sequence is at least 17, 18, 19, 20 or more base pairs. In some embodiments, the guide sequence and the target region may contain 1-4 mismatches where the guide sequence comprises at least 17, 18, 19, 20 or more nucleotides. In some embodiments, the guide sequence and the target region may contain 1, 2, 3, or 4 mismatches where the guide sequence comprises 20 nucleotides.

Target sequences for Cas proteins include both the positive and negative strands of genomic DNA (i.e., the sequence given and the sequence's reverse compliment), as a nucleic acid substrate for a Cas protein is a double stranded nucleic acid. Accordingly, where a guide sequence is said to be "complementary to a target sequence", it is to be understood that the guide sequence may direct a guide RNA to bind to the reverse complement of a target sequence. Thus, in some embodiments, where the guide sequence binds the reverse complement of a target sequence, the guide sequence is identical to certain nucleotides of the target sequence (e.g., the target sequence not including the PAM) except for the substitution of U for T in the guide sequence.

As used herein, an "RNA-guided DNA binding agent" means a polypeptide or complex of polypeptides having RNA and DNA binding activity, or a DNA-binding subunit of such a complex, wherein the DNA binding activity is sequence-specific and depends on the sequence of the RNA. Exemplary RNA-guided DNA binding agents include Cas cleavases/nickases and inactivated forms thereof ("dCas DNA binding agents"). "Cas nuclease", also called "Cas protein", as used herein, encompasses Cas cleavases, Cas nickases, and dCas DNA binding agents. Cas cleavases/nickases and dCas DNA binding agents include a Csm or Cmr complex of a type III CRISPR system, the Cas10, Csm1, or Cmr2 subunit thereof, a Cascade complex of a type I CRISPR system, the Cas3 subunit thereof, and Class 2 Cas nucleases. As used herein, a "Class 2 Cas nuclease" is a single-chain polypeptide with RNA-guided DNA binding activity, such as a Cas9 nuclease or a Cpf1 nuclease. Class 2 Cas nucleases include Class 2 Cas cleavases and Class 2 Cas nickases (e.g., H840A, D10A, or N863A variants), which further have RNA-guided DNA cleavases or nickase activity, and Class 2 dCas DNA binding agents, in which cleavase/nickase activity is inactivated. Class 2 Cas nucleases include, for example, Cas9, Cpf1, C2c1, C2c2, C2c3, HF Cas9 (e.g., N497A, R661A, Q695A, Q926A variants), HypaCas9 (e.g., N692A, M694A, Q695A, H698A variants), eSPCas9(1.0) (e.g, K810A, K1003A, R1060A variants), and eSPCas9(1.1) (e.g., K848A, K1003A, R1060A variants) proteins and modifications thereof. Cpf1 protein, Zetsche et al., *Cell,* 163: 1-13 (2015), is homologous to Cas9, and contains a RuvC-like nuclease domain. Cpf1 sequences of Zetsche are incorporated by reference in their entirety. See, e.g., Zetsche, Tables S1 and S3. "Cas9" encompasses Spy Cas9, the variants of Cas9 listed herein, and equivalents thereof. See, e.g., Makarova et al., *Nat Rev Microbiol,* 13(11): 722-36 (2015); Shmakov et al., *Molecular Cell,* 60:385-397 (2015).

"Modified uridine" is used herein to refer to a nucleoside other than thymidine with the same hydrogen bond acceptors as uridine and one or more structural differences from uridine. In some embodiments, a modified uridine is a substituted uridine, i.e., a uridine in which one or more non-proton substituents (e.g., alkoxy, such as methoxy) takes the place of a proton. In some embodiments, a modified uridine is pseudouridine. In some embodiments, a modified uridine is a substituted pseudouridine, i.e., a pseudouridine in which one or more non-proton substituents (e.g., alkyl, such as methyl) takes the place of a proton, e.g., N1-methyl pseudouridine. In some embodiments, a modified uridine is any of a substituted uridine, pseudouridine, or a substituted pseudouridine.

"Uridine position" as used herein refers to a position in a polynucleotide occupied by a uridine or a modified uridine. Thus, for example, a polynucleotide in which "100% of the uridine positions are modified uridines" contains a modified uridine at every position that would be a uridine in a conventional RNA (where all bases are standard A, U, C, or G bases) of the same sequence. Unless otherwise indicated, a U in a polynucleotide sequence of a sequence table or sequence listing in, or accompanying, this disclosure can be a uridine or a modified uridine.

As used herein, a first sequence is considered to "comprise a sequence with at least X % identity to" a second sequence if an alignment of the first sequence to the second sequence shows that X % or more of the positions of the second sequence in its entirety are matched by the first sequence. For example, the sequence AAGA comprises a sequence with 100% identity to the sequence AAG because an alignment would give 100% identity in that there are matches to all three positions of the second sequence. The differences between RNA and DNA (generally the exchange of uridine for thymidine or vice versa) and the presence of nucleoside analogs such as modified uridines do not contribute to differences in identity or complementarity among polynucleotides as long as the relevant nucleotides. (such as thymidine, uridine, or modified uridine) have the same complement (e.g., adenosine for all of thymidine, uridine, or modified uridine; another example is cytosine and 5-methylcytosine, both of which have guanosine or modified guanosine as a complement). Thus, for example, the sequence 5'-AXG where X is any modified uridine, such as pseudouridine, N1-methyl pseudouridine, or 5-methoxyuridine, is considered 100% identical to AUG in that both are perfectly complementary to the same sequence (5'-CAU). Exemplary alignment algorithms are the Smith-Waterman and Needleman-Wunsch algorithms, which are well-known in the art. One skilled in the art will understand what choice of algorithm and parameter settings are appropriate for a given pair of sequences to be aligned; for sequences of generally similar length and expected identity >50% for amino acids or >75% for nucleotides, the Needleman-Wunsch algorithm with default settings of the Needleman-Wunsch algorithm interface provided by the EBI at the www.ebi.ac.uk web server is generally appropriate.

"mRNA" is used herein to refer to a polynucleotide that is RNA or modified RNA and comprises an open reading frame that can be translated into a polypeptide (i.e., can serve as a substrate for translation by a ribosome and amino-acylated tRNAs). mRNA can comprise a phosphate-sugar backbone including ribose residues or analogs thereof, e.g., 2'-methoxy ribose residues. In some embodiments, the sugars of a nucleic acid phosphate-sugar backbone consist essentially of ribose residues, 2'-methoxy ribose residues, or a combination thereof. In general, mRNAs do not contain a substantial quantity of thymidine residues (e.g., 0 residues or fewer than 30, 20, 10, 5, 4, 3, or 2 thymidine residues; or less than 10%, 9%, 8%, 7%, 6%, 5%, 4%, 4%, 3%, 2%, 1%, 0.5%, 0.2%, or 0.1% thymidine content). An mRNA can contain modified uridines at some or all of its uridine positions.

As used herein, the "minimum uridine content" of a given ORF is the uridine content of an ORF that (a) uses a minimal uridine codon at every position and (b) encodes the same amino acid sequence as the given ORF. The minimal uridine codon(s) for a given amino acid is the codon(s) with the fewest uridines (usually 0 or 1 except for a codon for phenylalanine, where the minimal uridine codon has 2 uridines). Modified uridine residues are considered equivalent to uridines for the purpose of evaluating minimum uridine content.

As used herein, the "minimum uridine dinucleotide content" of a given ORF is the lowest possible uridine dinucleotide (UU) content of an ORF that (a) uses a minimal uridine codon (as discussed above) at every position and (b) encodes the same amino acid sequence as the given ORF. The uridine dinucleotide (UU) content can be expressed in absolute terms as the enumeration of UU dinucleotides in an ORF or on a rate basis as the percentage of positions occupied by the uridines of uridine dinucleotides (for example, AUUAU would have a uridine dinucleotide content of 40% because 2 of 5 positions are occupied by the uridines of a uridine dinucleotide). Modified uridine residues are considered equivalent to uridines for the purpose of evaluating minimum uridine dinucleotide content. As used herein, the "minimum adenine content" of a given open reading frame (ORF) is the adenine content of an ORF that (a) uses a minimal adenine codon at every position and (b) encodes the same amino acid sequence as the given ORF. The minimal adenine codon(s) for a given amino acid is the codon(s) with the fewest adenines (usually 0 or 1 except for a codon for lysine and asparagine, where the minimal adenine codon has 2 adenines). Modified adenine residues are considered equivalent to adenines for the purpose of evaluating minimum adenine content.

As used herein, the "minimum adenine dinucleotide content" of a given open reading frame (ORF) is the lowest possible adenine dinucleotide (AA) content of an ORF that (a) uses a minimal adenine codon (as discussed above) at every position and (b) encodes the same amino acid sequence as the given ORF. The adenine dinucleotide (AA) content can be expressed in absolute terms as the enumeration of AA dinucleotides in an ORF or on a rate basis as the percentage of positions occupied by the adenines of adenine dinucleotides (for example, UAAUA would have an adenine dinucleotide content of 40% because 2 of 5 positions are occupied by the adenines of an adenine dinucleotide). Modified adenine residues are considered equivalent to adenines for the purpose of evaluating minimum adenine dinucleotide content.

As used herein, "TTR" refers to transthyretin, which is the gene product of a TTR gene.

As used herein, "amyloid" refers to abnormal aggregates of proteins or peptides that are normally soluble. Amyloids are insoluble, and amyloids can create proteinaceous deposits in organs and tissues. Proteins or peptides in amyloids may be misfolded into a form that allows many copies of the protein to stick together to form fibrils. While some forms of amyloid may have normal functions in the human body, "amyloids" as used herein refers to abnormal or pathologic aggregates of protein. Amyloids may comprise a single protein or peptide, such as TTR, or they may comprise multiple proteins or peptides, such as TTR and additional proteins.

As used herein, "amyloid fibrils" refers to insoluble fibers of amyloid that are resistant to degradation. Amyloid fibrils can produce symptoms based on the specific protein or peptide and the tissue and cell type in which it has aggregated.

As used herein, "amyloidosis" refers to a disease characterized by symptoms caused by deposition of amyloid or amyloid fibrils. Amyloidosis can affect numerous organs including the heart, kidney, liver, spleen, nervous system, and digestive track.

As used herein, "ATTR," "TTR-related amyloidosis," "TTR amyloidosis," "ATTR amyloidosis," or "amyloidosis associated with TTR" refers to amyloidosis associated with deposition of TTR.

As used herein, "familial amyloid cardiomyopathy" or "FAC" refers to a hereditary transthyretin amyloidosis (ATTR) characterized primarily by restrictive cardiomyopathy. Congestive heart failure is common in FAC. Average age of onset is approximately 60-70 years of age, with an estimated life expectancy of 4-5 years after diagnosis.

As used herein, "familial amyloid polyneuropathy" or "FAP" refers to a hereditary transthyretin amyloidosis (ATTR) characterized primarily by sensorimotor neuropathy. Autonomic neuropathy is common in FAP. While neuropathy is a primary feature, symptoms of FAP may also include cachexia, renal failure, and cardiac disease. Average age of onset of FAP is approximately 30-50 years of age, with an estimated life expectancy of 5-15 after diagnosis.

As used herein, "wild-type ATTR" and "ATTRwt" refer to ATTR not associated with a pathological TTR mutation such as T60A, V30M, V30A, V30G, V30L, V122I, V122A, or V122(-). ATTRwt has also been referred to as senile systemic amyloidosis. Onset typically occurs in men aged 60 or higher with the most common symptoms being congestive heart failure and abnormal heart rhythm such as atrial fibrillation. Additional symptoms include consequences of poor heart function such as shortness of breath, fatigue, dizziness, swelling (especially in the legs), nausea, angina, disrupted sleep, and weight loss. A history of carpal tunnel syndrome indicates increased risk for ATTRwt and may in some cases be indicative of early-stage disease. ATTRwt generally leads to decreasing heart function over time but can have a better prognosis than hereditary ATTR because wild-type TTR deposits accumulate more slowly. Existing treatments are similar to other forms of ATTR (other than liver transplantation) and are generally directed to supporting or improving heart function, ranging from diuretics and limited fluid and salt intake to anticoagulants, and in severe cases, heart transplants. Nonetheless, like FAC, ATTRwt can result in death from heart failure, sometimes within 3-5 years of diagnosis.

Guide sequences useful in the guide RNA compositions and methods described herein are shown in Table 1 and throughout the application.

As used herein, "hereditary ATTR" refers to ATTR that is associated with a mutation in the sequence of the TTR gene. Known mutations in the TTR gene associated with ATTR include those resulting in TTR with substitutions of T60A, V30M, V30A, V30G, V30L, V122I, V122A, or V122(-).

As used herein, "indels" refer to insertion/deletion mutations consisting of a number of nucleotides that are either inserted or deleted at the site of double-stranded breaks (DSBs) in a target nucleic acid.

As used herein, "knockdown" refers to a decrease in expression of a particular gene product (e.g., protein, mRNA, or both). Knockdown of a protein can be measured either by detecting protein secreted by tissue or population of cells (e.g., in serum or cell media) or by detecting total cellular amount of the protein from a tissue or cell population of interest. Methods for measuring knockdown of mRNA are known, and include sequencing of mRNA isolated from a tissue or cell population of interest. In some embodiments, "knockdown" may refer to some loss of expression of a particular gene product, for example a decrease in the amount of mRNA transcribed or a decrease in the amount of protein expressed or secreted by a population of cells (including in vivo populations such as those found in tissues).

As used herein, "mutant TTR" refers to a gene product of TTR (i.e., the TTR protein) having a change in the amino acid sequence of TTR compared to the wildtype amino acid sequence of TTR. The human wild-type TTR sequence is available at NCBI Gene ID: 7276; Ensembl: Ensembl: ENSG00000118271. Mutants forms of TTR associated with ATTR, e.g., in humans, include T60A, V30M, V30A, V30G, V30L, V122I, V122A, or V122(-).

As used herein, "ribonucleoprotein" (RNP) or "RNP complex" refers to a guide RNA together with an RNA-guided DNA binding agent, such as a Cas nuclease, e.g., a Cas cleavase, Cas nickase, or dCas DNA binding agent (e.g., Cas9). In some embodiments, the guide RNA guides the RNA-guided DNA binding agent such as Cas9 to a target sequence, and the guide RNA hybridizes with and the agent binds to the target sequence; in cases where the agent is a cleavase or nickase, binding can be followed by cleaving or nicking.

As used herein, a "target sequence" refers to a sequence of nucleic acid in a target gene that has complementarity to the guide sequence of the gRNA. The interaction of the target sequence and the guide sequence directs an RNA-guided DNA binding agent to bind, and potentially nick or cleave (depending on the activity of the agent), within the target sequence.

As used herein, "treatment" refers to any administration or application of a therapeutic for disease or disorder in a subject, and includes inhibiting the disease, arresting its development, relieving one or more symptoms of the disease, curing the disease, or preventing reoccurrence of one or more symptoms of the disease. For example, treatment of ATTR may comprise alleviating symptoms of ATTR.

As used herein, the term "pathological mutation" refers to a mutation that renders a gene product, such as TTR, more likely to cause, promote, contribute to, or fail to inhibit the development of a disease, such as ATTR.

As used herein, the term "lipid nanoparticle" (LNP) refers to a particle that comprises a plurality of (i.e., more than one) lipid molecules physically associated with each other by intermolecular forces. The LNPs may be, e.g., microspheres (including unilamellar and multilamellar vesicles, e.g., "liposomes"—lamellar phase lipid bilayers that, in some embodiments, are substantially spherical—and, in more particular embodiments, can comprise an aqueous core, e.g., comprising a substantial portion of RNA molecules), a dispersed phase in an emulsion, micelles, or an internal phase in a suspension. See also, e.g., WO2017173054A1 and WO2019067992A1, the contents of which are hereby incorporated by reference in their entirety. Any LNP known to those of skill in the art to be capable of delivering nucleotides to subjects may be utilized with the guide RNAs and the nucleic acid encoding an RNA-guided DNA binding agent described herein.

As used herein, the terms "donor oligonucleotide" or "donor template" refers to a oligonucleotide that includes a desired nucleic acid sequence to be inserted into a target site (e.g., a target sit of a genomic DNA). A donor oligonucleotide may be a single-strand oligonucleotide or a double-strand oligonucleotide. In some embodiments, a donor oligonucleotide may be delivered with a guide RNA and a nucleic acid sequence encoding an RNA-guided DNA binding agent (e.g., Cas9) via use of LNP or transfection.

As used herein, the terms "nuclear localization signal" (NLS) or "nuclear localization sequence" refers to an amino acid sequence which induces transport of molecules comprising such sequences or linked to such sequences into the nucleus of eukaryotic cells. The nuclear localization signal may form part of the molecule to be transported. In some embodiments, the NLS may be linked to the remaining parts of the molecule by covalent bonds, hydrogen bonds or ionic interactions.

As used herein, the phrase "pharmaceutically acceptable" means that which is useful in preparing a pharmaceutical composition that is generally non-toxic and is not biologically undesirable and that are not otherwise unacceptable for pharmaceutical use.

As used herein, "infusion" refers to an active administration of one or more agents with an infusion time of, for example, between approximately 30 minutes and 12 hours. In some embodiments, the one or more agents comprise an LNP, e.g., comprising an mRNA encoding an RNA-guided DNA binding agent (such as Cas9) described herein and a gRNA described herein.

As used herein, "infusion prophylaxis" refers to a regimen administered to a subject before treatment (e.g., comprising administration of an LNP) comprising one or more, or all, of an intravenous corticosteroid (e.g., dexamethasone 10 mg or equivalent), an antipyretic (e.g. oral acetaminophen or paracetamol 500 mg), an intravenous H1 blocker (e.g., diphenhydramine 50 mg or equivalent), and an intravenous H2 blocker (e.g., ranitidine 50 mg or equivalent). Infusion prophylaxis is optionally combined with advance administration of an oral corticosteroid (e.g., dexamethasone 8 mg or equivalent). In some embodiments, the oral corticosteroid is administered 8-24 hours prior to treatment. In some embodiments, one or more, or all, of an intravenous corticosteroid (e.g., dexamethasone 10 mg or equivalent), oral acetaminophen 500 mg, an intravenous H1 blocker (e.g., diphenhydramine 50 mg or equivalent), an intravenous H2 blocker (e.g., ranitidine 50 mg or equivalent) are administered 1-2 hours before treatment. In some embodiments, an H1 blocker and/or an H2 blocker are administered orally.

The term "about" or "approximately" means an acceptable error for a particular value as determined by one of ordinary skill in the art, which depends in part on how the value is measured or determined.

II. Methods and Compositions Targeting the TTR Gene

Disclosed herein are methods for inducing a double-stranded break (DSB) within the TTR gene in a subject, modifying the TTR gene in a cell or subject, treating amyloidosis associated with TTR (ATTR) in a subject, reducing TTR serum concentration in a subject, and/or reducing or preventing the accumulation of amyloids or amyloid fibrils in a subject, and related compositions, including compositions for use in such methods. In general, the disclosed compositions comprise a guide RNA targeting TTR and a nucleic acid comprising an open reading frame encoding an RNA-guided DNA binding agent (e.g., a CRISPR/Cas system). The subjects treated with such methods and compositions may have wild-type or non-wild type TTR gene sequences, such as, for example, subjects with ATTR, which may be ATTR wt or a hereditary or familial form of ATTR.

In some embodiments, the composition is administered by infusion for longer than 30 minutes. In some embodiments, the composition is administered by 30 minute infusion. In some embodiments, the composition is administered by infusion for longer than 60 minutes. In some embodiments, the composition is administered by infusion for longer than 90 minutes. In some embodiments, the composition is administered by infusion for longer than 120 minutes, longer than 150 minutes, longer than 180 minutes, longer than 240 minutes, longer than 300 minutes, or longer than 360 minutes. In some embodiments, the composition is administered by infusion for at least 1 hour, at least 2 hours, at least 4 hours, at least 6 hours, at least 7 hours, at least 8 hours, at least 9 hours, at least 10 hours, at least 11 hours or at least 12 hours. In some embodiments, the composition is administered by infusion for 0.5-1.5 hours, 1.5-2.5 hours, 2.5-3.5 hours, 3.5-4.5 hours, 4.5-5.5 hours, 5.5-6.5 hours, 6.5-7.5 hours, 7.5-8.5 hours, 8.5-9.5 hours, 9.5-10.5 hours, 10.5-11.5 hours, or 11.5-12.5 hours. In some embodiments, the composition is administered by infusion for about 60 minutes, about 90 minutes, about 120 minutes, about 150 minutes, about 180 minutes, about 240 minutes, about 300 minutes, or about 360 minutes. In some embodiments, the composition is administered by infusion for about 45-75 minutes, 75-105 minutes, 105-135 minutes, 135-165 minutes, 165-195 minutes, 195-225 minutes, 225-255 minutes, 255-285 minutes, 285-315 minutes, 315-345 minutes, or 345-375 minutes. In some embodiments, the composition is administered by infusion for about 1.5-6 hours.

A. Guide RNA (gRNAs)

The guide RNA used in the disclosed methods and compositions comprises a guide sequence targeting the TTR gene. Exemplary guide sequences targeting the TTR gene are shown in Table 1 at SEQ ID Nos: 5-82.

TABLE 1

TTR targeted guide sequences, nomenclature, chromosomal coordinates, and sequence.

| SEQ ID No. | Guide ID | Description | Species | Chromosomal Location | Guide Sequences* |
|---|---|---|---|---|---|
| 5 | CR003335 | TTR (Exon 1) | Human | chr18:31591917-31591937 | CUGCUCCUCCUCUGCCUUGC |
| 6 | CR003336 | TTR (Exon 1) | Human | chr18:31591922-31591942 | CCUCCUCUGCCUUGCUGGAC |
| 7 | CR003337 | TTR (Exon 1) | Human | chr18:31591925-31591945 | CCAGUCCAGCAAGGCAGAGG |

TABLE 1-continued

TTR targeted guide sequences, nomenclature, chromosomal coordinates, and sequence.

| SEQ ID No. | Guide ID | Description | Species | Chromosomal Location | Guide Sequences* |
|---|---|---|---|---|---|
| 8 | CR003338 | TTR (Exon 1) | Human | chr18:31591928-31591948 | AUACCAGUCCAGCAAGGCAG |
| 9 | CR003339 | TTR (Exon 1) | Human | chr18:31591934-31591954 | ACACAAAUACCAGUCCAGCA |
| 10 | CR003340 | TTR (Exon 1) | Human | chr18:31591937-31591957 | UGGACUGGUAUUUGUGUCUG |
| 11 | CR003341 | TTR (Exon 1) | Human | chr18:31591941-31591961 | CUGGUAUUUGUGUCUGAGGC |
| 12 | CR003342 | TTR (Exon 2) | Human | chr18:31592880-31592900 | CUUCUCUACACCCAGGGCAC |
| 13 | CR003343 | TTR (Exon 2) | Human | chr18:31592902-31592922 | CAGAGGACACUUGGAUUCAC |
| 14 | CR003344 | TTR (Exon 2) | Human | chr18:31592911-31592931 | UUUGACCAUCAGAGGACACU |
| 15 | CR003345 | TTR (Exon 2) | Human | chr18:31592919-31592939 | UCUAGAACUUUGACCAUCAG |
| 16 | CR003346 | TTR (Exon 2) | Human | chr18:31592928-31592948 | AAAGUUCUAGAUGCUGUCCG |
| 17 | CR003347 | TTR (Exon 2) | Human | chr18:31592948-31592968 | CAUUGAUGGCAGGACUGCCU |
| 18 | CR003348 | TTR (Exon 2) | Human | chr18:31592948-31592968 | AGGCAGUCCUGCCAUCAAUG |
| 19 | CR003349 | TTR (Exon 2) | Human | chr18:31592958-31592978 | UGCACGGCCACAUUGAUGGC |
| 20 | CR003350 | TTR (Exon 2) | Human | chr18:31592962-31592982 | CACAUGCACGGCCACAUUGA |
| 21 | CR003351 | TTR (Exon 2) | Human | chr18:31592974-31592994 | AGCCUUUCUGAACACAUGCA |
| 22 | CR003352 | TTR (Exon 2) | Human | chr18:31592986-31593006 | GAAAGGCUGCUGAUGACACC |
| 23 | CR003353 | TTR (Exon 2) | Human | chr18:31592987-31593007 | AAAGGCUGCUGAUGACACCU |
| 24 | CR003354 | TTR (Exon 2) | Human | chr18:31593003-31593023 | ACCUGGGAGCCAUUUGCCUC |
| 25 | CR003355 | TTR (Exon 2) | Human | chr18:31593007-31593027 | CCCAGAGGCAAAUGGCUCCC |
| 26 | CR003356 | TTR (Exon 2) | Human | chr18:31593015-31593035 | GCAACUUACCCAGAGGCAAA |
| 27 | CR003357 | TTR (Exon 2) | Human | chr18:31593022-31593042 | UUCUUUGGCAACUUACCCAG |
| 28 | CR003358 | TTR (Exon 3) | Human | chr18:31595127-31595147 | AUGCAGCUCUCCAGACUCAC |
| 29 | CR003359 | TTR (Exon 3) | Human | chr18:31595126-31595146 | AGUGAGUCUGGAGAGCUGCA |
| 30 | CR003360 | TTR (Exon 3) | Human | chr18:31595127-31595147 | GUGAGUCUGGAGAGCUGCAU |
| 31 | CR003361 | TTR (Exon 3) | Human | chr18:31595140-31595160 | GCUGCAUGGGCUCACAACUG |

TABLE 1-continued

TTR targeted guide sequences, nomenclature, chromosomal coordinates, and sequence.

| SEQ ID No. | Guide ID | Description | Species | Chromosomal Location | Guide Sequences* |
|---|---|---|---|---|---|
| 32 | CR003362 | TTR (Exon 3) | Human | chr18:31595143-31595163 | GCAUGGGCUCACAACUGAGG |
| 33 | CR003363 | TTR (Exon 3) | Human | chr18:31595156-31595176 | ACUGAGGAGGAAUUUGUAGA |
| 34 | CR003364 | TTR (Exon 3) | Human | chr18:31595157-31595177 | CUGAGGAGGAAUUUGUAGAA |
| 35 | CR003365 | TTR (Exon 3) | Human | chr18:31595170-31595190 | UGUAGAAGGGAUAUACAAAG |
| 36 | CR003366 | TTR (Exon 3) | Human | chr18:31595193-31595213 | AAAUAGACACCAAAUCUUAC |
| 37 | CR003367 | TTR (Exon 3) | Human | chr18:31595197-31595217 | AGACACCAAAUCUUACUGGA |
| 38 | CR003368 | TTR (Exon 3) | Human | chr18:31595205-31595225 | AAGUGCCUUCCAGUAAGAUU |
| 39 | CR003369 | TTR (Exon 3) | Human | chr18:31595235-31595255 | CUCUGCAUGCUCAUGGAAUG |
| 40 | CR003370 | TTR (Exon 3) | Human | chr18:31595236-31595256 | CCUCUGCAUGCUCAUGGAAU |
| 41 | CR003371 | TTR (Exon 3) | Human | chr18:31595237-31595257 | ACCUCUGCAUGCUCAUGGAA |
| 42 | CR003372 | TTR (Exon 3) | Human | chr18:31595242-31595262 | UACUCACCUCUGCAUGCUCA |
| 43 | CR003373 | TTR (Exon 4) | Human | chr18:31598570-31598590 | GUAUUCACAGCCAACGACUC |
| 44 | CR003374 | TTR (Exon 4) | Human | chr18:31598583-31598603 | GCGGCGGGGGCCGGAGUCGU |
| 45 | CR003375 | TTR (Exon 4) | Human | chr18:31598592-31598612 | AAUGGUGUAGCGGCGGGGGC |
| 46 | CR003376 | TTR (Exon 4) | Human | chr18:31598596-31598616 | CGGCAAUGGUGUAGCGGCGG |
| 47 | CR003377 | TTR (Exon 4) | Human | chr18:31598597-31598617 | GCGGCAAUGGUGUAGCGGCG |
| 48 | CR003378 | TTR (Exon 4) | Human | chr18:31598598-31598618 | GGCGGCAAUGGUGUAGCGGC |
| 49 | CR003379 | TTR (Exon 4) | Human | chr18:31598599-31598619 | GGGCGGCAAUGGUGUAGCGG |
| 50 | CR003380 | TTR (Exon 4) | Human | chr18:31598602-31598622 | GCAGGGCGGCAAUGGUGUAG |
| 51 | CR003381 | TTR (Exon 4) | Human | chr18:31598610-31598630 | GGGGCUCAGCAGGGCGGCAA |
| 52 | CR003382 | TTR (Exon 4) | Human | chr18:31598616-31598636 | GGAGUAGGGGCUCAGCAGGG |
| 53 | CR003383 | TTR (Exon 4) | Human | chr18:31598619-31598639 | AUAGGAGUAGGGGCUCAGCA |
| 54 | CR003384 | TTR (Exon 4) | Human | chr18:31598620-31598640 | AAUAGGAGUAGGGGCUCAGC |
| 55 | CR003385 | TTR (Exon 4) | Human | chr18:31598626-31598646 | CCCCUACUCCUAUUCCACCA |

TABLE 1-continued

TTR targeted guide sequences, nomenclature, chromosomal coordinates, and sequence.

| SEQ ID No. | Guide ID | Description | Species | Chromosomal Location | Guide Sequences* |
|---|---|---|---|---|---|
| 56 | CR003386 | TTR (Exon 4) | Human | chr18:31598629-31598649 | CCGUGGUGGAAUAGGAGUAG |
| 57 | CR003387 | TTR (Exon 4) | Human | chr18:31598630-31598650 | GCCGUGGUGGAAUAGGAGUA |
| 58 | CR003388 | TTR (Exon 4) | Human | chr18:31598637-31598657 | GACGACAGCCGUGGUGGAAU |
| 59 | CR003389 | TTR (Exon 4) | Human | chr18:31598643-31598663 | AUUGGUGACGACAGCCGUGG |
| 60 | CR003390 | TTR (Exon 4) | Human | chr18:31598646-31598666 | GGGAUUGGUGACGACAGCCG |
| 61 | CR003391 | TTR (Exon 4) | Human | chr18:31598647-31598667 | GGCUGUCGUCACCAAUCCCA |
| 62 | CR003392 | TTR (Exon 4) | Human | chr18:31598661-31598681 | AGUCCCUCAUUCCUUGGGAU |
| 63 | CR005298 | TTR (Exon 1) | Human | chr18:31591883-31591903 | UCCACUCAUUCUUGGCAGGA |
| 64 | CR005299 | TTR (Exon 4) | Human | chr18:31598631-31598651 | AGCCGUGGUGGAAUAGGAGU |
| 65 | CR005300 | TTR (Exon 1) | Human | chr18:31591967-31591987 | UCACAGAAACACUCACCGUA |
| 66 | CR005301 | TTR (Exon 1) | Human | chr18:31591968-31591988 | GUCACAGAAACACUCACCGU |
| 67 | CR005302 | TTR (Exon 2) | Human | chr18:31592874-31592894 | ACGUGUCUUCUCUACACCCA |
| 68 | CR005303 | TTR (Exon 2) | Human | chr18:31592903-31592923 | UGAAUCCAAGUGUCCUCUGA |
| 69 | CR005304 | TTR (Exon 2) | Human | chr18:31592969-31592989 | GGCCGUGCAUGUGUUCAGAA |
| 70 | CR005305 | TTR (Exon 3) | Human | chr18:31595114-31595134 | UAUAGGAAAACCAGUGAGUC |
| 71 | CR005306 | TTR (Exon 3) | Human | chr18:31595204-31595224 | AAAUCUUACUGGAAGGCACU |
| 72 | CR005307 | TTR (Exon 4) | Human | chr18:31598548-31598568 | UGUCUGUCUUCUCUCAUAGG |
| 73 | CR000689 | TTR | Cyno | chr18:50681533-50681553 | ACACAAAUACCAGUCCAGCG |
| 74 | CR005364 | TTR | Cyno | chr18:50680481-50680501 | AAAGGCUGCUGAUGAGACCU |
| 75 | CR005365 | TTR | Cyno | chr18:50680520-50680540 | CAUUGACAGCAGGACUGCCU |
| 76 | CR005366 | TTR | Cyno | chr18:50681539-50681559 | AUACCAGUCCAGCGAGGCAG |
| 77 | CR005367 | TTR | Cyno | chr18:50681542-50681562 | CCAGUCCAGCGAGGCAGAGG |
| 78 | CR005368 | TTR | Cyno | chr18:50681545-50681565 | CCUCCUCUGCCUCGCUGGAC |
| 79 | CR005369 | TTR | Cyno | chr18:50680540-50680560 | AAAGUUCUAGAUGCCGUCCG |
| 80 | CR005370 | TTR | Cyno | chr18:50680594-50680614 | ACUUGUCUUCUCUAUACCCA |
| 81 | CR005371 | TTR | Cyno | chr18:50678216-50678236 | AAGUGACUUCCAGUAAGAUU |
| 82 | CR005372 | TTR | Cyno | chr18:50680482-50680502 | AAAAGGCUGCUGAUGAGACC |

Each of the Guide Sequences above may further comprise additional nucleotides to form a crRNA, e.g., with the following exemplary nucleotide sequence following the Guide Sequence at its 3' end: GUUUUAGAGCUAUGCU-GUUUUG (SEQ ID NO: 126). In the case of a sgRNA, the above Guide Sequences may further comprise additional nucleotides to form a sgRNA, e.g., with the following exemplary nucleotide sequence following the 3' end of the Guide Sequence: GUUUUAGAGCUA-GAAAUAGCAAGUUAAAAUAAGGCUAGU-CCGUUAUCAACUUGA AAAAGUGGCACCGAGUCG-GUGCUUUU (SEQ ID NO: 125) in 5' to 3' orientation.

In some embodiments, the sgRNA is modified. In some embodiments, the sgRNA comprises the modification pattern shown below in SEQ ID NO: 3, where N is any natural or non-natural nucleotide, and where the totality of the N's comprise a guide sequence as described herein and the modified sgRNA comprises the following sequence: mN*mN*mN*NNNNNNNNNNNNNGUUUUAGAmGmCmUmAmGmAmAmAmUmA mGmCAAGUUAAAAUAAGGCUAGUCCGUUAU-CAmAmCmUmUmGmAmAmAmAmAm GmUmGmGmCmAmCmCmGmAmGmUmCmGm GmUmGmCmU*mU*mU*mU (SEQ ID NO: 3), where "N" may be any natural or non-natural nucleotide. For example, encompassed herein is SEQ ID NO: 3, where the N's are replaced with any of the guide sequences disclosed herein. The modifications remain as shown in SEQ ID NO: 3 despite the substitution of N's for the nucleotides of a guide. That is, although the nucleotides of the guide replace the "N's", the first three nucleotides are 2'OMe modified and there are phosphorothioate linkages between the first and second nucleotides, the second and third nucleotides and the third and fourth nucleotides.

In some embodiments, any one of the sequences recited in Table 2 is encompassed.

TABLE 2

TTR targeted sgRNA sequences

| SEQ ID No. | Guide ID | Target and Description | Species | Sequence |
|---|---|---|---|---|
| 87 | G000480 | TTR sgRNA modified sequence | Human | mA*mA*mA*GGCUGCUGAUGACACCUGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 88 | G000481 | TTR sgRNA modified sequence | Human | mU*mC*mU*AGAACUUUGACCAUCAGGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 89 | G000482 | TTR sgRNA modified sequence | Human | mU*mG*mU*AGAAGGGAUAUACAAAGG UUUUAGAmGmCmUmAmGmAmAmAmUm AmGmCAAGUUAAAAUAAGGCUAGUCCG UUAUCAmAmCmUmUmGmAmAmAmAmA mGmUmGmGmCmAmCmCmGmAmGmUmC mGmGmUmGmCmU*mU*mU*mU |
| 90 | G000483 | TTR sgRNA modified sequence | Human | mU*mC*mC*ACUCAUUCUUGGCAGGAGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 91 | G000484 | TTR sgRNA modified sequence | Human | mA*mG*mA*CACCAAAUCUUACUGGAGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 92 | G000485 | TTR sgRNA modified sequence | Human | mC*mC*mU*CCUCUGCCUUGCUGGACGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 93 | G000486 | TTR sgRNA modified sequence | Human | mA*mC*mA*CAAAUACCAGUCCAGCAGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |

TABLE 2-continued

TTR targeted sgRNA sequences

| SEQ ID No. | Guide ID | Target and Description | Species | Sequence |
|---|---|---|---|---|
| 94 | G000487 | TTR sgRNA modified sequence | Human | mU*mU*mC*UUUGGCAACUUACCCAGGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 95 | G000488 | TTR sgRNA modified sequence | Human | mA*mA*mA*GUUCUAGAUGCUGUCCGGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 96 | G000489 | TTR sgRNA modified sequence | Human | mU*mU*mU*GACCAUCAGAGGACACUGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 97 | G000490 | TTR sgRNA modified sequence | Human | mA*mA*mA*UAGACACCAAAUCUUACGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 98 | G000491 | TTR sgRNA modified sequence | Human | mA*mU*mA*CCAGUCCAGCAAGGCAGGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 99 | G000492 | TTR sgRNA modified sequence | Human | mC*mU*mU*CUCUACACCCAGGGCACGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 100 | G000493 | TTR sgRNA modified sequence | Human | mA*mA*mG*UGCCUUCCAGUAAGAUUGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 101 | G000494 | TTR sgRNA modified sequence | Human | mG*mU*mG*AGUCUGGAGAGCUGCAUGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 102 | G000495 | TTR sgRNA modified sequence | Human | mC*mA*mG*AGGACACUUGGAUUCACGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 103 | G000496 | TTR sgRNA modified sequence | Human | mG*mG*mC*CGUGCAUGUGUUCAGAAGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 104 | G000497 | TTR sgRNA modified | Human | mC*mU*mG*CUCCUCCUCUGCCUUGCGU UUUAGAmGmCmUmAmGmAmAmAmUmA mGmCAAGUUAAAAUAAGGCUAGUCCGU |

TABLE 2-continued

| TTR targeted sgRNA sequences | | | | |
|---|---|---|---|---|
| SEQ ID No. | Guide ID | Target and Description | Species | Sequence |
| | | sequence | | UAUCAmAmCmUmUmGmAmAmAmAmAm GmUmGmGmCmAmCmCmGmAmGmUmCm GmGmUmGmCmU*mU*mU*mU |
| 105 | G000498 | TTR sgRNA modified sequence | Human | mA*mG*mU*GAGUCUGGAGAGCUGCAGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 106 | G000499 | TTR sgRNA modified sequence | Human | mU*mG*mA*AUCCAAGUGUCCUCUGAGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 107 | G000500 | TTR sgRNA modified sequence | Human | mC*mC*mA*GUCCAGCAAGGCAGAGGGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 108 | G000501 | TTR sgRNA modified sequence | Human | mU*mC*mA*CAGAAACACUCACCGUAGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 109 | G000567 | TTR sgRNA modified sequence | Human | mG*mA*mA*AGGCUGCUGAUGACACCGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 110 | G000568 | TTR sgRNA modified sequence | Human | mG*mG*mC*UGUCGUCACCAAUCCCAGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 111 | G000570 | TTR sgRNA modified sequence | Human | mC*mA*mU*UGAUGGCAGGACUGCCUGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 112 | G000571 | TTR sgRNA modified sequence | Human | mG*mU*mC*ACAGAAACACUCACCGUGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 113 | G000572 | TTR sgRNA modified sequence | Human | mC*mC*mC*CUACUCCUAUUCCACCAGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |
| 114 | G000502 | TTR Cyno specific sgRNA modified sequence | Cyno | mA*mC*mA*CAAAUACCAGUCCAGCGGU UUUAGAmGmCmUmAmGmAmAmAmUmA mGmCAAGUUAAAAUAAGGCUAGUCCGU UAUCAmAmCmUmUmGmAmAmAmAmAm GmUmGmGmCmAmCmCmGmAmGmUmCm GmGmUmGmCmU*mU*mU*mU |

TABLE 2-continued

| TTR targeted sgRNA sequences | | | | |
|---|---|---|---|---|
| SEQ ID No. | Guide ID | Target and Description | Species | Sequence |
| 115 | G000503 | TTR Cyno specific sgRNA modified sequence | Cyno | mA*mA*mA*AGGCUGCUGAUGAGACCGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 116 | G000504 | TTR Cyno specific sgRNA modified sequence | Cyno | mA*mA*mA*GGCUGCUGAUGAGACCUGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 117 | G000505 | TTR Cyno specific sgRNA modified sequence | Cyno | mC*mA*mU*UGACAGCAGGACUGCCUGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 118 | G000506 | TTR Cyno specific sgRNA modified sequence | Cyno | mA*mU*mA*CCAGUCCAGCGAGGCAGGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 119 | G000507 | TTR Cyno specific sgRNA modified sequence | Cyno | mC*mC*mA*GUCCAGCGAGGCAGAGGGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 120 | G000508 | TTR Cyno specific sgRNA modified sequence | Cyno | mC*mC*mU*CCUCUGCCUCGCUGGACGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 121 | G000509 | TTR Cyno specific sgRNA modified sequence | Cyno | mA*mA*mA*GUUCUAGAUGCCGUCCGGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 122 | G000510 | TTR Cyno specific sgRNA modified sequence | Cyno | mA*mC*mU*UGUCUUCUCUAUACCCAGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 123 | G000511 | TTR Cyno specific sgRNA modified sequence | Cyno | mA*mA*mG*UGACUUCCAGUAAGAUUGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |
| 124 | G000282 | TTR | Mouse | mU*mU*mA*CAGCCACGUCUACAGCAGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU |

* = PS linkage;
'm' = 2'-O-Menucleotide

An alignment mapping of the Guide IDs with the corresponding sgRNA IDs as well as homology to the cyno genome and cyno matched guide IDs are provided in Table 3.

TABLE 3

TTR targeted guide sequence ID mapping and Cyno Homology

| Description | Human Dual Guide ID | Human Single Guide ID | Number Mismatches to Cyno Genome | Cyno Matched dgRNA ID | Cyno Matched sgRNA ID |
|---|---|---|---|---|---|
| TTR | CR003335 | G000497 | 1 | | |
| TTR | CR003336 | G000485 | 1 | CR005368 | G000508 |
| TTR | CR003337 | G000500 | 1 | CR005367 | G000507 |
| TTR | CR003338 | G000491 | 1 | CR005366 | G000506 |
| TTR | CR003339 | G000486 | 1 | CR000689 | G000502 |
| TTR | CR003340 | | 0 | | |
| TTR | CR003341 | | 0 | | |
| TTR | CR003342 | G000492 | no PAM in cyno | | |
| TTR | CR003343 | G000495 | no PAM in cyno | | |
| TTR | CR003344 | G000489 | 0 | | |
| TTR | CR003345 | G000481 | 0 | | |
| TTR | CR003346 | G000488 | 1 | CR005369 | G000509 |
| TTR | CR003347 | G000570 | 2 | CR005365 | G000505 |
| TTR | CR003348 | | 2 | | |
| TTR | CR003349 | | >3 | | |
| TTR | CR003350 | | no PAM in cyno | | |
| TTR | CR003351 | | no PAM in cyno | | |
| TTR | CR003352 | G000567 | 2 | CR005372 | G000503 |
| TTR | CR003353 | G000480 | 1 | CR005364 | G000504 |
| TTR | CR003354 | | 1 | | |
| TTR | CR003355 | | 1 | | |
| TTR | CR003356 | | 3 | | |
| TTR | CR003357 | G000487 | >3 | | |
| TTR | CR003358 | | 0 | | |
| TTR | CR003359 | G000498 | 0 | | |
| TTR | CR003360 | G000494 | 0 | | |
| TTR | CR003361 | | 0 | | |
| TTR | CR003362 | | 0 | | |
| TTR | CR003363 | | 0 | | |
| TTR | CR003364 | | 0 | | |
| TTR | CR003365 | G000482 | 0 | | |
| TTR | CR003366 | G000490 | 0 | | |
| TTR | CR003367 | G000484 | no PAM in cyno | | |
| TTR | CR003368 | G000493 | 1 | CR005371 | G000511 |
| TTR | CR003369 | | 0 | | |
| TTR | CR003370 | | 0 | | |
| TTR | CR003371 | | 0 | | |
| TTR | CR003372 | | 0 | | |
| TTR | CR003373 | | 1 | | |
| TTR | CR003374 | | 2 | | |
| TTR | CR003375 | | 2 | | |
| TTR | CR003376 | | 2 | | |
| TTR | CR003377 | | 2 | | |
| TTR | CR003378 | | 2 | | |
| TTR | CR003379 | | 2 | | |
| TTR | CR003380 | | 1 | | |
| TTR | CR003381 | | 1 | | |
| TTR | CR003382 | | 0 | | |
| TTR | CR003383 | | 0 | | |
| TTR | CR003384 | | 0 | | |
| TTR | CR003385 | G000572 | 0 | | |
| TTR | CR003386 | | 0 | | |
| TTR | CR003387 | | 0 | | |
| TTR | CR003388 | | 0 | | |
| TTR | CR003389 | G000569 | 0 | | |
| TTR | CR003390 | | 0 | | |
| TTR | CR003391 | G000568 | 0 | | |
| TTR | CR003392 | | 0 | | |
| TTR | CR005298 | G000483 | 1 | | |
| TTR | CR005299 | | 0 | | |
| TTR | CR005300 | G000501 | no PAM in cyno | | |
| TTR | CR005301 | G000571 | 0 | | |
| TTR | CR005302 | | 2 | CR005370 | G000510 |
| TTR | CR005303 | G000499 | 0 | | |
| TTR | CR005304 | G000496 | >3 | | |
| TTR | CR005305 | | 0 | | |

TABLE 3-continued

TTR targeted guide sequence ID mapping and Cyno Homology

| Description | Human Dual Guide ID | Human Single Guide ID | Number Mismatches to Cyno Genome | Cyno Matched dgRNA ID | Cyno Matched sgRNA ID |
|---|---|---|---|---|---|
| TTR | CR005306 | | 1 | | |
| TTR | CR005307 | | 0 | | |

In some embodiments, the gRNA comprises a guide sequence that direct an RNA-guided DNA binding agent, which can be a nuclease (e.g., a Cas nuclease such as Cas9), to a target DNA sequence in TTR. The gRNA may comprise a crRNA comprising a guide sequence shown in Table 1. The gRNA may comprise a crRNA comprising 17, 18, 19, or 20 contiguous nucleotides of a guide sequence shown in Table 1. In some embodiments, the gRNA comprises a crRNA comprising a sequence with about 75%, 80%, 85%, 90%, 95%, 96%, 97%, 98%, 99%, or 100% identity to at least 17, 18, 19, or 20 contiguous nucleotides of a guide sequence shown in Table 1. In some embodiments, the gRNA comprises a crRNA comprising a sequence with about 75%, 80%, 85%, 90%, 95%, 96%, 97%, 98%, 99%, or 100% identity to a guide sequence shown in Table 1. The gRNA may further comprise a trRNA. In each composition and method embodiment described herein, the crRNA and trRNA may be associated as a single RNA (sgRNA), or may be on separate RNAs (dgRNA). In the context of sgRNAs, the crRNA and trRNA components may be covalently linked, e.g., via a phosphodiester bond or other covalent bond.

In each of the composition, use, and method embodiments described herein, the guide RNA may comprise two RNA molecules as a "dual guide RNA" or "dgRNA". The dgRNA comprises a first RNA molecule comprising a crRNA comprising, e.g., a guide sequence shown in Table 1, and a second RNA molecule comprising a trRNA. The first and second RNA molecules may not be covalently linked, but may form a RNA duplex via the base pairing between portions of the crRNA and the trRNA.

In each of the composition, use, and method embodiments described herein, the guide RNA may comprise a single RNA molecule as a "single guide RNA" or "sgRNA". The sgRNA may comprise a crRNA (or a portion thereof) comprising a guide sequence shown in Table 1 covalently linked to a trRNA. The sgRNA may comprise 17, 18, 19, or 20 contiguous nucleotides of a guide sequence shown in Table 1. In some embodiments, the crRNA and the trRNA are covalently linked via a linker. In some embodiments, the sgRNA forms a stem-loop structure via the base pairing between portions of the crRNA and the trRNA. In some embodiments, the crRNA and the trRNA are covalently linked via one or more bonds that are not a phosphodiester bond.

In some embodiments, the trRNA may comprise all or a portion of a trRNA sequence derived from a naturally-occurring CRISPR/Cas system. In some embodiments, the trRNA comprises a truncated or modified wild type trRNA. The length of the trRNA depends on the CRISPR/Cas system used. In some embodiments, the trRNA comprises or consists of 5, 6, 7, 8, 9, 10, 11, 12, 13, 14, 15, 16, 17, 18, 19, 20, 25, 30, 40, 50, 60, 70, 80, 90, 100, or more than 100 nucleotides. In some embodiments, the trRNA may comprise certain secondary structures, such as, for example, one or more hairpin or stem-loop structures, or one or more bulge structures.

In some embodiments, the composition comprises one or more guide RNAs comprising a guide sequence selected from SEQ ID NOs: 5-82.

In some embodiments, the composition comprises a gRNA that comprises a guide sequence that is at least 99%, 98%, 97%, 96%, 95%, 94%, 93%, 92%, 91%, or 90% identical to a sequence selected from SEQ ID NOs: 5-82.

In some embodiments, the composition comprises one or more guide RNAs comprising a guide sequence selected from SEQ ID NOs: 5-72, 74-78, and 80-82. In some embodiments, the composition comprises a gRNA that comprises a guide sequence that is at least 99%, 98%, 97%, 96%, 95%, 94%, 93%, 92%, 91%, or 90% identical to a sequence selected from SEQ ID NOs: 5-72, 74-78, and 80-82. In some embodiments, the sequence selected from SEQ ID NOs: 5-72, 74-78, and 80-82 is SEQ ID NOs: 5, 6, 7, 8, 9, 12, 13, 14, 15, 16, 17, 22, 23, 27, 29, 30, 35, 36, 37, 38, 55, 61, 63, 65, 66, 68, or 69. In some embodiments, the sequence selected from SEQ ID NOs: 5-72, 74-78, and 80-82 is SEQ ID NO: 5, 6, 9, 13, 14, 15, 16, 17, 22, 23, 27, 30, 35, 36, 37, 38, 55, 63, 65, 66, 68, or 69. In particular, the guide RNA comprising a guide sequence selected from SEQ ID NOs: 5-72, 74-78, and 80-82 may be an sgRNA. The guide RNA comprising a guide sequence selected from SEQ ID NOs: 5-72, 74-78, and 80-82 may be a chemically modified sgRNA, such as an end modified RNA. The guide RNA comprising a guide sequence selected from SEQ ID NOs: 5-72, 74-78, and 80-82 may be dgRNA, such as a chemically modified dgRNA.

In other embodiments, the composition comprises at least one, e.g., at least two gRNAs comprising guide sequences selected from any two or more of the guide sequences of SEQ ID NOs: 5-82. In some embodiments, the composition comprises at least two gRNAs that each comprise a guide sequence at least 99%, 98%, 97%, 96%, 95%, 94%, 93%, 92%, 91%, or 90% identical to any of the nucleic acids of SEQ ID NOs: 5-82.

In other embodiments, the composition comprises at least one, e.g., at least two gRNAs comprising guide sequences selected from any two or more of the guide sequences selected from SEQ ID NOs: 5-72, 74-78, and 80-82. In some embodiments, the composition comprises at least two gRNAs that each comprise a guide sequence at least 99%, 98%, 97%, 96%, 95%, 94%, 93%, 92%, 91%, or 90% identical to any of the sequences selected from SEQ ID NOs: 5-72, 74-78, and 80-82. In some embodiments, the sequences selected from SEQ ID NOs: 5-72, 74-78, and 80-82 comprise a sequence, or two sequences, selected from SEQ ID NOs: 5, 6, 7, 8, 9, 12, 13, 14, 15, 16, 17, 22, 23, 27, 29, 30, 35, 36, 37, 38, 55, 61, 63, 65, 66, 68, or 69. In some embodiments, the sequence selected from SEQ ID NOs: 5-72, 74-78, and 80-82 comprise a sequence, or two sequences, selected from SEQ ID NO: 5, 6, 9, 13, 14, 15, 16, 17, 22, 23, 27, 30, 35, 36, 37, 38, 55, 63, 65, 66, 68, or 69.

In some embodiments, the gRNA is a sgRNA comprising any one of the sequences shown in Table 2 (SEQ ID Nos. 87-124). In some embodiments, the gRNA is a sgRNA comprising any one of the sequences shown in Table 2 (SEQ ID Nos. 87-124, but without the modifications as shown (i.e., unmodified SEQ ID Nos. 87-124). In some embodiments, the sgRNA comprises a sequence that is at least 99%, 98%, 97%, 96%, 95%, 94%, 93%, 92%, 91%, or 90% identical to any of the nucleic acids of SEQ ID Nos. 87-124. In some embodiments, the sgRNA comprises a sequence that is at least 99%, 98%, 97%, 96%, 95%, 94%, 93%, 92%, 91%, or 90% identical to any of the nucleic acids of SEQ ID Nos, 87-124, but without the modifications as shown (i.e., unmodified SEQ ID Nos. 87-124). In some embodiments; the sgRNA comprises any one of the guide sequences shown in Table 1 in place of the guide sequences shown in the sgRNA sequences of Table 2 at SEQ ID Nos: 87-124, with or without the modifications.

In some embodiments, the gRNA is a sgRNA comprising any one of SEQ ID Nos. 87-113, 115-120, or 122-124. In some embodiments, the gRNA is a sgRNA comprising any one of SEQ ID Nos. 87-113, 115-120, or 122-124, but without the modifications as shown in Table 2 (i.e., unmodified SEQ ID Nos. 87-113, 115-120, or 122-124). In some embodiments, the gRNA is a sgRNA comprising any one of SEQ ID Nos. 87-113, 115-120, or 122-124, but with at least one chemical modification and without the modification pattern as shown in Table 2 (i.e., chemically modified SEQ ID Nos. 87-113, 115-120, or 122-124). The chemically modified guide RNAs may comprise one or more of the modifications as shown in Table 2. In some embodiments, the chemically modified SEQ ID Nos. 87-113, 115-120, or 122-124 without the modification pattern as shown in Table 2 comprise 5' and/or 3' end modifications. In some embodiments, the sgRNA comprises a sequence that is at least 99%, 98%, 97%; 96%, 95%, 94%, 93%, 92%, 91%, or 90% identical to any of the nucleic acids of SEQ ID Nos. 87-113, 115-120, or 122-124. In some embodiments, the sgRNA comprises a sequence that is at least 99%, 98%, 97%, 96%, 95%, 94%, 93%, 92%, 91%, or 90% identical to any of the nucleic acids of SEQ ID Nos. 87-113, 115-120, or 122-124, but without the modifications as shown (i.e., unmodified SEQ ID Nos. 87-113, 115-120, or 122-124). In some embodiments, the sgRNA comprises any one of the guide sequences shown in Table 1 in place of the guide sequences shown in the sgRNA sequences of Table 2 at SEQ ID Nos: 87-113, 115-120, or 122-124, with or without the modifications.

The guide RNAs provided herein can be useful for recognizing (e.g., hybridizing to) a target sequence in the TTR gene. For example, the TTR target sequence may be recognized and cleaved by a provided Cas cleavase comprising a guide RNA. Thus, an RNA-guided DNA binding agent, such as a Cas cleavase, may be directed by a guide RNA to a target sequence of the TTR gene, where the guide sequence of the guide RNA hybridizes with the target sequence and the RNA-guided DNA binding agent, such as a Cas cleavase, cleaves the target sequence.

In some embodiments, the selection of the one or more guide RNAs is determined based on target sequences within the TTR gene.

Without being bound by any particular theory, mutations (e.g., frameshift mutations resulting from indels occurring as a result of a nuclease-mediated DSB) in certain regions of the gene may be less tolerable than mutations in other regions of the gene, thus the location of a DSB is an important factor in the amount or type of protein knockdown that may result. In some embodiments, a gRNA complementary or having complementarity to a target sequence within TTR is used to direct the RNA-guided DNA binding agent to a particular location in the TTR gene. In some embodiments, gRNAs are designed to have guide sequences that are complementary or have complementarity to target sequences in exon 1, exon 2, exon 3, or exon 4 of TTR.

B. Modifications of gRNAs

In some embodiments, the gRNA is chemically modified. A gRNA comprising one or more modified nucleosides or nucleotides is called a "modified" gRNA or "chemically modified" gRNA, to describe the presence of one or more non-naturally and/or naturally occurring components or configurations that are used instead of or in addition to the canonical A, G, C, and U residues. In some embodiments, a modified gRNA is synthesized with a non-canonical nucleoside or nucleotide, is here called "modified." Modified nucleosides and nucleotides can include one or more of: (i) alteration, e.g., replacement, of one or both of the non-linking phosphate oxygens and/or of one or more of the linking phosphate oxygens in the phosphodiester backbone linkage (an exemplary backbone modification); (ii) alteration, e.g., replacement, of a constituent of the ribose sugar, e.g., of the 2' hydroxyl on the ribose sugar (an exemplary sugar modification); (iii) wholesale replacement of the phosphate moiety with "dephospho" linkers (an exemplary backbone modification); (iv) modification or replacement of a naturally occurring nucleobase, including with a non-canonical nucleobase (an exemplary base modification); (v) replacement or modification of the ribose-phosphate backbone (an exemplary backbone modification); (vi) modification of the 3' end or 5' end of the oligonucleotide, e.g., removal, modification or replacement of a terminal phosphate group or conjugation of a moiety, cap or linker (such 3' or 5' cap modifications may comprise a sugar and/or backbone modification); and (vii) modification or replacement of the sugar (an exemplary sugar modification).

Chemical modifications such as those listed above can be combined to provide modified gRNAs comprising nucleosides and nucleotides (collectively "residues") that can have two, three, four, or more modifications. For example, a modified residue can have a modified sugar and a modified nucleobase. In some embodiments, every base of a gRNA is modified, e.g., all bases have a modified phosphate group, such as a phosphorothioate group. In certain embodiments, all, or substantially all, of the phosphate groups of an gRNA molecule are replaced with phosphorothioate groups. In some embodiments, modified gRNAs comprise at least one modified residue at or near the 5' end of the RNA. In some embodiments, modified gRNAs comprise at least one modified residue at or near the 3' end of the RNA.

In some embodiments, the gRNA comprises one, two, three or more modified residues. In some embodiments, at least 5% (e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%) of the positions in a modified gRNA are modified nucleosides or nucleotides.

Unmodified nucleic acids can be prone to degradation by, e.g., intracellular nucleases or those found in serum. For example, nucleases can hydrolyze nucleic acid phosphodiester bonds. Accordingly, in one aspect the gRNAs described herein can contain one or more modified nucleosides or nucleotides, e.g., to introduce stability toward intracellular or serum-based nucleases. In some embodiments, the modified gRNA molecules described herein can exhibit a reduced innate immune response when introduced into a population of cells, both in vivo and ex vivo. The term "innate immune response" includes a cellular response to exogenous nucleic acids, including single stranded nucleic acids, which involves the induction of cytokine expression and release, particularly the interferons, and cell death.

In some embodiments of a backbone modification, the phosphate group of a modified residue can be modified by replacing one or more of the oxygens with a different substituent. Further, the modified residue, e.g., modified residue present in a modified nucleic acid, can include the wholesale replacement of an unmodified phosphate moiety with a modified phosphate group as described herein. In some embodiments, the backbone modification of the phosphate backbone can include alterations that result in either an uncharged linker or a charged linker with unsymmetrical charge distribution.

Examples of modified phosphate groups include, phosphorothioate, phosphoroselenates, borano phosphates, borano phosphate esters, hydrogen phosphonates, phosphoroamidates, alkyl or aryl phosphonates and phosphotriesters. The phosphorous atom in an unmodified phosphate group is achiral. However, replacement of one of the non-bridging oxygens with one of the above atoms or groups of atoms can render the phosphorous atom chiral. The stereogenic phosphorous atom can possess either the "R" configuration (herein Rp) or the "S" configuration (herein Sp). The backbone can also be modified by replacement of a bridging oxygen, (i.e., the oxygen that links the phosphate to the nucleoside), with nitrogen (bridged phosphoroamidates), sulfur (bridged phosphorothioates) and carbon (bridged methylenephosphonates). The replacement can occur at either linking oxygen or at both of the linking oxygens.

The phosphate group can be replaced by non-phosphorus containing connectors in certain backbone modifications. In some embodiments, the charged phosphate group can be replaced by a neutral moiety. Examples of moieties which can replace the phosphate group can include, without limitation, e.g., methyl phosphonate, hydroxylamino, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino.

Scaffolds that can mimic nucleic acids can also be constructed wherein the phosphate linker and ribose sugar are replaced by nuclease resistant nucleoside or nucleotide surrogates. Such modifications may comprise backbone and sugar modifications. In some embodiments, the nucleobases can be tethered by a surrogate backbone. Examples can include, without limitation, the morpholino, cyclobutyl, pyrrolidine and peptide nucleic acid (PNA) nucleoside surrogates.

The modified nucleosides and modified nucleotides can include one or more modifications to the sugar group, i.e. at sugar modification. For example, the 2' hydroxyl group (OH) can be modified, e.g. replaced with a number of different "oxy" or "deoxy" substituents. In some embodiments, modifications to the 2' hydroxyl group can enhance the stability of the nucleic acid since the hydroxyl can no longer be deprotonated to form a 2'-alkoxide ion.

Examples of 2' hydroxyl group modifications can include alkoxy or aryloxy (OR, wherein "R" can be, e.g., alkyl, cycloalkyl, aryl, aralkyl, heteroaryl or a sugar); polyethyleneglycols (PEG), $O(CH_2CH_2O)_nCH_2CH_2OR$ wherein R can be, e.g., H or optionally substituted alkyl, and n can be an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4- to 20). In some embodiments, the 2' hydroxyl group modification can be 2'-O-Me. In some embodiments, the 2' hydroxyl group modification can be a 2'-fluoro modification, which replaces the 2' hydroxyl group with a fluoride. In some embodiments, the 2' hydroxyl group modification can include "locked" nucleic acids (LNA) in which the 2' hydroxyl can be connected, e.g., by a $C_{1-6}$ alkylene or $C_{1-6}$ heteroalkylene bridge, to the 4' carbon of the same ribose sugar, where exemplary bridges can include methylene, propylene, ether, or amino bridges; O-amino (wherein amino can be, e.g., $NH_2$; alkylamino, dialkylamino, heterocyclyl, arylamino, diarylamino, heteroarylamino, or diheteroarylamino, ethylenediamine, or polyamino) and aminoalkoxy, $O(CH_2)_n$-amino, (wherein amino can be, e.g., $NH_2$; alkylamino, dialkylamino, heterocyclyl, arylamino, diarylamino, heteroarylamino, or diheteroarylamino, ethylenediamine, or polyamino). In some embodiments, the 2' hydroxyl group modification can included "unlocked" nucleic acids (UNA) in which the ribose ring lacks the C2'-C3' bond. In some embodiments, the 2' hydroxyl group modification can include the methoxyethyl group (MOE), ($OCH_2CH_2OCH_3$, e.g., a PEG derivative).

"Deoxy" 2' modifications can include hydrogen (i.e. deoxyribose sugars, e.g., at the overhang portions of partially dsRNA); halo (e.g., bromo, chloro, fluoro, or iodo); amino (wherein amino can be, e.g., $NH_2$; alkylamino, dialkylamino, heterocyclyl, arylamino, diarylamino, heteroarylamino, diheteroarylamino, or amino acid); $NH(CH_2CH_2NH)_nCH2CH_2$-amino (wherein amino can be, e.g., as described herein), —NHC(O)R (wherein R can be, e.g., alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino as described herein.

The sugar modification can comprise a sugar group which may also contain one or more carbons that possess the opposite stereochemical configuration than that of the corresponding carbon in ribose. Thus, a modified nucleic acid can include nucleotides containing e.g., arabinose, as the sugar. The modified nucleic acids can also include abasic sugars. These abasic sugars can also be further modified at one or more of the constituent sugar atoms. The modified nucleic acids can also include one or more sugars that are in the L form, e.g. L-nucleosides.

The modified nucleosides and modified nucleotides described herein, which can be incorporated into a modified nucleic acid, can include a modified base, also called a nucleobase. Examples of nucleobases include, but are not limited to, adenine (A), guanine (G), cytosine (C), and uracil (U). These nucleobases can be modified or wholly replaced to provide modified residues that can be incorporated into modified nucleic acids. The nucleobase of the nucleotide can be independently selected from a purine, a pyrimidine, a purine analog, or pyrimidine analog. In some embodiments, the nucleobase can include, for example, naturally-occurring and synthetic derivatives of a base.

In embodiments employing a dual guide RNA, each of the crRNA and the tracr RNA can contain modifications. Such modifications may be at one or both ends of the crRNA and/or tracr RNA. In embodiments comprising an sgRNA, one or more residues at one or both ends of the sgRNA may be chemically modified, or the entire sgRNA may be chemically modified. Certain embodiments comprise a 5' end modification. Certain embodiments comprise a 3' end modification. In certain embodiments, one or more or all of the nucleotides in single stranded overhang of a guide RNA molecule are deoxynucleotides.

In some embodiments, the guide RNAs disclosed herein comprise one of the modification patterns disclosed in U.S. 62/431,756, filed Dec. 8, 2016, titled "Chemically Modified Guide RNAs," the contents of which are hereby incorporated by reference in their entirety.

In some embodiments, the invention comprises a gRNA comprising one or more modifications. In some embodiments, the modification comprises a 2'-O-methyl (2'-O-Me) modified nucleotide. In some embodiments, the modification comprises a phosphorothioate (PS) bond between nucleotides.

The terms "mA," "mC," "mU," or "mG" may be used to denote a nucleotide that has been modified with 2'-O-Me.

Modification of 2'-O-methyl can be depicted as follows:

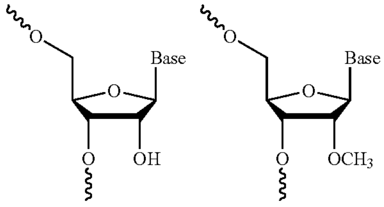

RNA 2'-O—Me

Another chemical modification that has been shown to influence nucleotide sugar rings is halogen substitution. For example, 2'-fluoro (2'-F) substitution on nucleotide sugar rings can increase oligonucleotide binding affinity and nuclease stability.

In this application, the terms "fA," "fC," "fU," or "fG" may be used to denote a nucleotide that has been substituted with 2'-F.

Substitution of 2'-F can be depicted as follows:

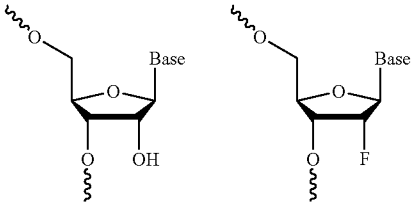

RNA
Natural composition of RNA

2'F—RNA
2'F substitution

Phosphorothioate (PS) linkage or bond refers to a bond where a sulfur is substituted for one nonbridging phosphate oxygen in a phosphodiester linkage, for example in the bonds between nucleotides bases. When phosphorothioates are used to generate oligonucleotides, the modified oligonucleotides may also be referred to as S-oligos.

A "*" may be used to depict a PS modification. In this application, the terms A*, C*, U*, or G* may be used to denote a nucleotide that is linked to the next (e.g., 3') nucleotide with a PS bond.

In this application, the terms "mA*," "mC*," "mU*," or "mG*" may be used to denote a nucleotide that has been substituted with 2'-O-Me and that is linked to the next (e.g., 3') nucleotide with a PS bond.

The diagram below shows the substitution of S— into a nonbridging phosphate oxygen, generating a PS bond in lieu of a phosphodiester bond:

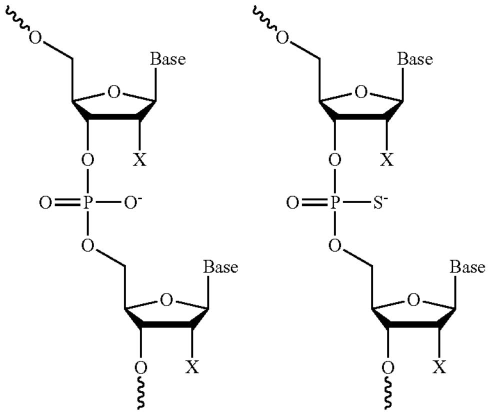

Phosphodiester
Natural phosphodiester
linkage of RNA

Phosphorothioate (PS)
Modified phosphorothioate
(PS) bond

Abasic nucleotides refer to those which lack nitrogenous bases. The figure below depicts an oligonucleotide with an abasic (also known as apurinic) site that lacks a base:

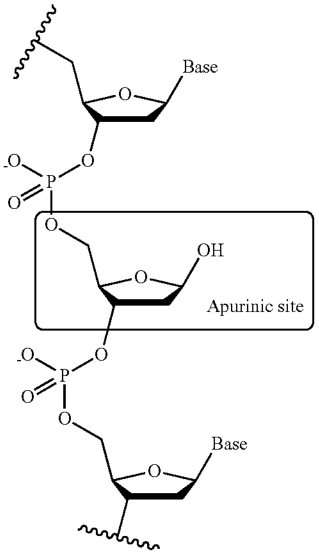

Inverted bases refer to those with linkages that are inverted from the normal 5' to 3' linkage (i.e., either a 5' to 5' linkage or a 3' to 3' linkage). For example:

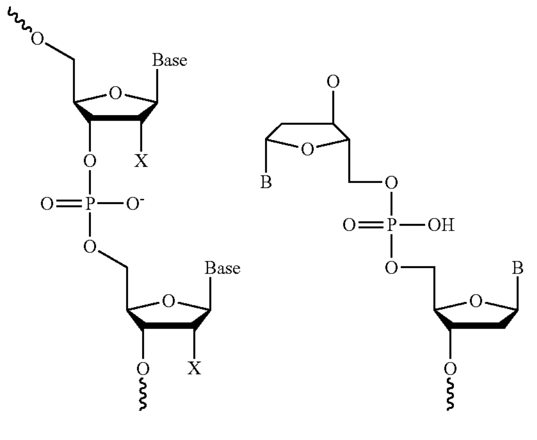

Normal oligonucleotide linkage

Inverted oligonucleotide linkage

An abasic nucleotide can be attached with an inverted linkage. For example, an abasic nucleotide may be attached to the terminal 5' nucleotide via a 5' to 5' linkage, or an abasic nucleotide may be attached to the terminal 3' nucleotide via a 3' to 3' linkage. An inverted abasic nucleotide at either the terminal 5' or 3'-nucleotide may also be called an inverted abasic end cap.

In some embodiments, one or more of the first three, four, or five nucleotides at the 5' terminus, and one or more of the last three, four, or five nucleotides at the 3' terminus are modified. In some embodiments, the modification is a 2'-O-Me, 2'-F, inverted abasic nucleotide, PS bond, or other nucleotide modification well known in the art to increase stability and/or performance.

In some embodiments, the first four nucleotides at the 5' terminus, and the last four nucleotides at the 3' terminus are linked with phosphorothioate (PS) bonds.

In some embodiments, the first three nucleotides at the 5' terminus, and the last three nucleotides at the 3' terminus comprise a 2'-O-methyl (2'-O-Me) modified nucleotide. In some embodiments, the first three nucleotides at the 5' terminus, and the last three nucleotides at the 3' terminus comprise a 2'-fluoro (2'-F) modified nucleotide. In some embodiments, the first three nucleotides at the 5' terminus, and the last three nucleotides at the 3' terminus comprise an inverted abasic nucleotide.

In some embodiments, the guide RNA comprises a modified sgRNA. In some embodiments, the sgRNA comprises the modification pattern shown in SEQ ID No: 3, where N is any natural or non-natural nucleotide, and where the totality of the N's comprise a guide sequence that directs a nuclease to a target sequence.

In some embodiments, the guide RNA comprises a sgRNA shown in any one of SEQ ID No: 87-124. In some embodiments, the guide RNA comprises a sgRNA comprising any one of the guide sequences of SEQ ID No: 5-82 and the nucleotides of SEQ ID No: 125, wherein the nucleotides of SEQ ID No: 125 are on the 3' end of the guide sequence, and wherein the guide sequence may be modified as shown in SEQ ID No: 3.

In some embodiments, the guide RNA comprises a sgRNA comprising a guide sequence selected from SEQ ID Nos: 5-72, 74-78, and 80-82 and the nucleotides of SEQ ID No: 125, wherein the nucleotides of SEQ ID No: 125 are on the 3' end of the guide sequence, and wherein the guide sequence may be modified as shown in SEQ ID No: 3.

C. Nucleic Acid Comprising an Open Reading Frame Encoding an RNA-Guided DNA Binding Agent Any nucleic acid comprising an ORF encoding an RNA-guided DNA binding agent, e.g. a Cas9 nuclease such as an *S. pyogenes* Cas9, disclosed herein may be combined in a composition or method with any of the gRNAs disclosed herein. In any of the embodiments set forth herein, the nucleic acid comprising an open reading frame encoding an RNA-guided DNA binding agent may be an mRNA.

1. ORFs with Low Adenine Content

In some embodiments, the ORF encoding the RNA-guided DNA-binding agent, e.g. a Cas9 nuclease such as an *S. pyogenes* Cas9, has an adenine content ranging from its minimum adenine content to about 150% of its minimum adenine content. In some embodiments, the adenine content of the ORF is less than or equal to about 145%, 140%, 135%, 130%, 125%, 120%, 115%, 110%, 105%, 104%, 103%, 102%, or 101% of its minimum adenine content. In some embodiments, the ORF has an adenine content equal to its minimum adenine content. In some embodiments, the ORF has an adenine content less than or equal to about 150% of its minimum adenine content. In some embodiments, the ORF has an adenine content less than or equal to about 145% of its minimum adenine content. In some embodiments, the ORF has an adenine content less than or equal to about 140% of its minimum adenine content. In some embodiments, the ORF has an adenine content less than or equal to about 135% of its minimum adenine content. In some embodiments, the ORF has an adenine content less than or equal to about 130% of its minimum adenine content. In some embodiments, the ORF has an adenine content less than or equal to about 125% of its minimum adenine content. In some embodiments, the ORF has an adenine content less than or equal to about 120% of its minimum adenine content. In some embodiments, the ORF has an adenine content less than or equal to about 115% of its minimum adenine content. In some embodiments, the ORF has an adenine content less than or equal to about 110% of its minimum adenine content. In some embodiments, the ORF has an adenine content less than or equal to about 105% of its minimum adenine content. In some embodiments, the ORF has an adenine content less than or equal to about 104% of its minimum adenine content. In some embodiments, the ORF has an adenine content less than or equal to about 103% of its minimum adenine content. In some embodiments, the ORF has an adenine content less than or equal to about 102% of its minimum adenine content. In some embodiments, the ORF has an adenine content less than or equal to about 101% of its minimum adenine content.

In some embodiments, the ORF has an adenine dinucleotide content ranging from its minimum adenine dinucleotide content to 200% of its minimum adenine dinucleotide content. In some embodiments, the adenine dinucleotide content of the ORF is less than or equal to about 195%, 190%, 185%, 180%, 175%, 170%, 165%, 160%, 155%, 150%, 145%, 140%, 135%, 130%, 125%, 120%, 115%, 110%, 105%, 104%, 103%, 102%, or 101% of its minimum adenine dinucleotide content. In some embodiments, the ORF has an adenine dinucleotide content equal to its minimum adenine dinucleotide content. In some embodiments, the ORF has an adenine dinucleotide content less than or equal to about 200% of its minimum adenine dinucleotide content. In some embodiments, the ORF has an adenine dinucleotide content less than or equal to about 195% of its minimum adenine dinucleotide content. In some embodiments, the ORF has an adenine dinucleotide content less than or equal to about 190% of its minimum adenine dinucleotide content. In some embodiments, the ORF has an adenine dinucleotide content less than or equal to about 185% of its minimum adenine dinucleotide content. In some embodiments, the ORF has an adenine dinucleotide content less than or equal to about 180% of its minimum adenine dinucleotide content. In some embodiments, the ORF has an adenine dinucleotide content less than or equal to about 175% of its minimum adenine dinucleotide content. In some embodiments, the ORF has an adenine dinucleotide content less than or equal to about 170% of its minimum adenine dinucleotide content. In some embodiments, the ORF has an adenine dinucleotide content less than or equal to about 165% of its minimum adenine dinucleotide content. In some embodiments, the ORF has an adenine dinucleotide content less than or equal to about 160% of its minimum adenine dinucleotide content. In some embodiments, the ORF has an adenine dinucleotide content less than or equal to about 155% of its minimum adenine dinucleotide content. In some embodiments, the ORF has an adenine dinucleotide content equal to its minimum adenine dinucleotide content. In some embodiments, the ORF has an adenine dinucleotide content less than or equal to about 150% of its minimum adenine dinucleotide content. In some embodiments, the ORF has an adenine dinucleotide content less than or equal to about 145% of its minimum adenine dinucleotide content. In some embodiments, the ORF has an adenine dinucleotide content less than or equal to about 140% of its minimum adenine dinucleotide content. In some embodiments, the ORF has an adenine dinucleotide content less than or equal to about 135% of its minimum adenine dinucleotide content. In some embodiments, the ORF has an adenine dinucleotide content less than or equal to about 130% of its minimum adenine dinucleotide content. In some embodiments, the ORF has an adenine dinucleotide content less than or equal to about 125% of its minimum adenine dinucleotide content. In some embodiments, the ORF has an adenine dinucleotide content less than or equal to about 120% of its minimum adenine dinucleotide content. In some embodiments, the ORF has an adenine dinucleotide content less than or equal to about 115% of its minimum adenine dinucleotide content. In some embodiments, the ORF has an adenine dinucleotide content less than or equal to about 110% of its minimum adenine dinucleotide content. In some embodiments, the ORF has an adenine dinucleotide content less than or equal to about 105% of its minimum adenine dinucleotide content. In some embodiments, the ORF has an adenine dinucleotide content less than or equal to about 104% of its minimum adenine dinucleotide content. In some embodiments, the ORF has an adenine dinucleotide content less than or equal to about 103% of its minimum adenine dinucleotide content. In some embodiments, the ORF has an adenine dinucleotide content less than or equal to about 102% of its minimum adenine dinucleotide content. In some embodiments, the ORF has an adenine dinucleotide content less than or equal to about 101% of its minimum adenine dinucleotide content.

In some embodiments, the ORF has an adenine dinucleotide content ranging from its minimum adenine dinucleotide content to the adenine dinucleotide content that is 90% or lower of the maximum adenine dinucleotide content of a reference sequence that encodes the same protein as the mRNA in question. In some embodiments, the adenine dinucleotide content of the ORF is less than or equal to about 85%, 80%, 75%, 70%, 65%, 60%, 55%, 50%, 45%, 40%, 35%, 30%, 25%, 20%, 15%, 10%, or 5% of the maximum adenine dinucleotide content of a reference sequence that encodes the same protein as the mRNA in question.

In some embodiments, the ORF has an adenine trinucleotide content ranging from 0 adenine trinucleotides to 1, 2, 3, 4, 5, 6, 7, 8, 9, 10, 20, 30, 40, or 50 adenine trinucleotides (where a longer run of adenines counts as the number of unique three-adenine segments within it, e.g., an adenine tetranucleotide contains two adenine trinucleotides, an adenine pentanucleotide contains three adenine trinucleotides, etc.). In some embodiments, the ORF has an adenine trinucleotide content ranging from 0% adenine trinucleotides to 0.1%, 0.2%, 0.3%, 0.4%, 0.5%, 0.6%, 0.7%, 0.8%, 0.9%, 1%, 1.5%, or 2% adenine trinucleotides, where the percentage content of adenine trinucleotides is calculated as the percentage of positions in a sequence that are occupied by adenines that form part of an adenine trinucleotide (or longer run of adenines), such that the sequences UUUAAA and UUUUAAAA would each have an adenine trinucleotide content of 50%. For example, in some embodiments, the ORF has an adenine trinucleotide content less than or equal to 2%. For example, in some embodiments, the ORF has an adenine trinucleotide content less than or equal to 1.5%. In some embodiments, the ORF has an adenine trinucleotide content less than or equal to 1%. In some embodiments, the ORF has an adenine trinucleotide content less than or equal to 0.9%. In some embodiments, the ORF has an adenine trinucleotide content less than or equal to 0.8%. In some embodiments, the ORF has an adenine trinucleotide content less than or equal to 0.7%. In some embodiments, the ORF has an adenine trinucleotide content less than or equal to 0.6%. In some embodiments, the ORF has an adenine trinucleotide content less than or equal to 0.5%. In some embodiments, the ORF has an adenine trinucleotide content less than or equal to 0.4%. In some embodiments, the ORF has an adenine trinucleotide content less than or equal to 0.3%. In some embodiments, the ORF has an adenine trinucleotide content less than or equal to 0.2%. In some embodiments, the ORF has an adenine trinucleotide content less than or equal to 0.1%. In some embodiments, a nucleic acid is provided that encodes an RNA-guided DNA-binding agent comprising an ORF containing no adenine trinucleotides.

In some embodiments, the ORF has an adenine trinucleotide content ranging from its minimum adenine trinucleotide content to the adenine trinucleotide content that is 90% or lower of the maximum adenine trinucleotide content of a reference sequence that encodes the same protein as the mRNA in question. In some embodiments, the adenine trinucleotide content of the ORF is less than or equal to about 85%, 80%, 75%, 70%, 65%, 60%, 55%, 50%, 45%, 40%, 35%, 30%, 25%, 20%, 15%, 10%, or 5% of the maximum adenine trinucleotide content of a reference sequence that encodes the same protein as the mRNA in question.

A given ORF can be reduced in adenine content or adenine dinucleotide content or adenine trinucleotide content, for example, by using minimal adenine codons in a sufficient fraction of the ORF. For example, an amino acid sequence for an RNA-guided DNA-binding agent can be back-translated into an ORF sequence by converting amino acids to codons, wherein some or all of the ORF uses the exemplary minimal adenine codons shown below. In some embodiments, at least about 50%, 55%, 60%, 65%, 70%, 75%, 80%, 85%, 90%, 95%, 98%, 99%, or 100% of the codons in the ORF are codons listed in Table 4.

TABLE 4

| Exemplary minimal adenine codons | | |
|---|---|---|
| | Amino Acid | Minimal adenine codon |
| A | Alanine | GCU or GCC or GCG |
| G | Glycine | GGU or GGC or GGG |
| V | Valine | GUC or GUU or GUG |
| D | Aspartic acid | GAC or GAU |
| E | Glutamic acid | GAG |
| I | Isoleucine | AUC or AUU |
| T | Threonine | ACU or ACC or ACG |
| N | Asparagine | AAC or AAU |
| K | Lysine | AAG |
| S | Serine | UCU or UCC or UCG |
| R | Arginine | CGU or CGC or CGG |
| L | Leucine | CUG or CUC or CUU |
| P | Proline | CCG or CCU or CCC |
| H | Histidine | CAC or CAU |
| Q | Glutamine | CAG |
| F | Phenylalanine | UUC or UUU |
| Y | Tyrosine | UAC or UAU |
| C | Cysteine | UGC or UGU |
| W | Tryptophan | UGG |
| M | Methionine | AUG |

In some embodiments, a nucleic acid is provided that encodes an RNA-guided DNA-binding agent, e.g. a Cas9 nuclease such as an *S. pyogenes* Cas9, comprising an ORF consisting of a set of codons of which at least about 75%, 80%, 85%, 90%, 95%, 98%, 99%, or 100% of the codons are codons listed in Table 4. In some embodiments, the ORF has minimal nucleotide homopolymers, e.g., repetitive strings of the same nucleotides. For example, in some embodiments, when selecting a minimal uridine codon from the codons listed in Table 4, a nucleic acid is constructed by selecting the minimal adenine codons that reduce the number and length of nucleotide homopolymers, e.g., selecting GCG instead of GCC for alanine or selecting GGC instead of GGG for glycine.

In any of the foregoing embodiments, the nucleic acid may be an mRNA.

2. Codons that Increase Translation and/or that Correspond to Highly Expressed tRNAs; Exemplary Codon Sets In some embodiments, the nucleic acid comprises an ORF having codons that increase translation in a mammal, such as a human. In further embodiments, the nucleic acid comprises an ORF having codons that increase translation in an organ, such as the liver, of the mammal, e.g., a human. In further embodiments, the nucleic acid comprises an ORF having codons that increase translation in a cell type, such as a hepatocyte, of the mammal, e.g., a human. An increase in translation in a mammal, cell type, organ of a mammal, human, organ of a human, etc., can be determined relative to the extent of translation wild-type sequence of the ORF, or relative to an ORF having a codon distribution matching the codon distribution of the organism from which the ORF was derived or the organism that contains the most similar ORF at the amino acid level, such as *S. pyogenes, S. aureus*, or another prokaryote as the case may be for prokaryotically-derived Cas nucleases, such as the Cas nucleases from other prokaryotes described below. Alternatively, in some embodiments, an increase in translation for a Cas9 sequence in a mammal, cell type, organ of a mammal, human, organ of a human, etc., is determined relative to translation of an ORF with the sequence of SEQ ID NO: 205 with all else equal, including any applicable point mutations, heterologous domains, and the like. Codons useful for increasing expression in a human, including the human liver and human hepatocytes, can be codons corresponding to highly expressed tRNAs in the human liver/hepatocytes, which are discussed in Dittmar K A, *PLos Genetics* 2(12): e221 (2006). In some embodiments, at least about 75%, 80%, 85%, 90%, 95%, 96%, 97%, 98%, 99%, or 100% of the codons in an ORF are codons corresponding to highly expressed tRNAs (e.g., the highest-expressed tRNA for each amino acid) in a mammal, such as a human. In some embodiments, at least 75%, 80%, 85%, 90%, 95%, 96%, 97%, 98%, 99%, or 100% of the codons in an ORF are codons corresponding to highly expressed tRNAs (e.g., the highest-expressed tRNA for each amino acid) in a mammalian organ, such as a human organ. In some embodiments, at least 75%, 80%, 85%, 90%, 95%, 96%, 97%, 98%, 99%, or 100% of the codons in an ORF are codons corresponding to highly expressed tRNAs (e.g., the highest-expressed tRNA for each amino acid) in a mammalian liver, such as a human liver. In some embodiments, at least 75%, 80%, 85%, 90%, 95%, 96%, 97%, 98%, 99%, or 100% of the codons in an ORF are codons corresponding to highly expressed tRNAs (e.g., the highest-expressed tRNA for each amino acid) in a mammalian hepatocyte, such as a human hepatocyte.

Alternatively, codons corresponding to highly expressed tRNAs in an organism (e.g., human) in general may be used.

Any of the foregoing approaches to codon selection can be combined with the minimal adenine codons shown above, e.g., by starting with the codons of Table 4, and then where more than one option is available, using the codon that corresponds to a more highly-expressed tRNA, either in the organism (e.g., human) in general, or in an organ or cell type of interest, such as the liver or hepatocytes (e.g., human liver or human hepatocytes).

In some embodiments, at least 75%, 80%, 85%, 90%, 95%, 96%, 97%, 98%, 99%, or 100% of the codons in an ORF are codons from a codon set shown in Table 5 (e.g., the low U, low A, or low A/U codon set). The codons in the low A and low A/U sets use codons that minimize the indicated nucleotides while also using codons corresponding to highly expressed tRNAs where more than one option is available. In some embodiments, at least 75%, 80%, 85%, 90%, 95%, 96%, 97%, 98%, 99%, or 100% of the codons in an ORF are codons from the low U codon set shown in Table 5. In some embodiments, at least 75%, 80%, 85%, 90%, 95%, 96%, 97%, 98%, 99%, or 100% of the codons in an ORF are codons from the low A codon set shown in Table 5. In some embodiments, at least 75%, 80%, 85%, 90%, 95%, 96%, 97%, 98%, 99%, or 100% of the codons in an ORF are codons from the low A/U codon set shown in Table 5.

TABLE 5

| Exemplary Codon Sets. | | | |
|---|---|---|---|
| Amino Acid | Low U | Low A | Low A/U |
| Gly | GGC | GGC | GGC |
| Glu | GAG | GAG | GAG |
| Asp | GAC | GAC | GAC |
| Val | GTG | GTG | GTG |
| Ala | GCC | GCC | GCC |
| Arg | AGA | CGG | CGG |
| Ser | AGC | TCC | AGC |
| Lys | AAG | AAG | AAG |
| Asn | AAC | AAC | AAC |
| Met | ATG | ATG | ATG |
| Ile | ATC | ATC | ATC |
| Thr | ACC | ACC | ACC |
| Trp | TGG | TGG | TGG |
| Cys | TGC | TGC | TGC |
| Tyr | TAC | TAC | TAC |
| Leu | CTG | CTG | CTG |

TABLE 5-continued

| Exemplary Codon Sets. | | | |
|---|---|---|---|
| Amino Acid | Low U | Low A | Low A/U |
| Phe | TTC | TTC | TTC |
| Gln | CAG | CAG | CAG |
| His | CAC | CAC | CAC |

3. Exemplary Sequences

In some embodiments, the ORF encoding the RNA-guided DNA binding agent comprises a sequence with at least 93% identity to SEQ ID NO: 311; and/or the ORF has at least 93% identity to SEQ ID NO: 311 over at least its first 50, 200, 250, or 300 nucleotides, or at least 95% identity to SEQ ID NO: 311 over at least its first 30, 50, 70, 100, 150, 200, 250, or 300 nucleotides; and/or the ORF consists of a set of codons of which at least 95%, 96%, 97%, 98%, 99%, 99.5%, or 100% of the codons are codons listed in Table 4 or 5; and/or the ORF has an adenine content ranging from its minimum adenine content to 123% of the minimum adenine content; and/or the ORF has an adenine dinucleotide content ranging from its minimum adenine dinucleotide content to 150% of the minimum adenine dinucleotide content.

In some embodiments, the ORF encoding the RNA-guided DNA binding agent comprises a sequence with at least 95%, 96%, 97%, 98%, 99%, 99.5%, or 100% identity to SEQ ID NO: 377.

In some embodiments, the ORF encoding the RNA-guided DNA binding agent comprises a sequence with at least 90% identity to any one of SEQ ID NOs: 311-313, 328, 329, 346-348, 355, 356, 363, or 364. In some embodiments, the mRNA comprises an ORF encoding an RNA-guided DNA binding agent, wherein the RNA-guided DNA binding agent comprises an amino acid sequence with at least 90% identity to any one of SEQ ID NOs: 203, 213, 268, or 386-396, wherein the ORF has an adenine content ranging from its minimum adenine content to 150% of the minimum adenine content, and/or has a adenine dinucleotide content ranging from its minimum adenine dinucleotide content to 150% of the minimum adenine dinucleotide content. In some embodiments, the encoded RNA-guided DNA binding agent comprises an amino acid sequence with at least 90% identity to any one of SEQ ID NOs: 203, 213, 268, or 386-396, wherein the ORF has a uridine content ranging from its minimum uridine content to 150% of the minimum uridine content, and/or has a uridine dinucleotide content ranging from its minimum uridine dinucleotide content to 150% of the minimum uridine dinucleotide content. In some such embodiments, both the adenine and uridine nucleotide contents are less than or equal to 150% of their respective minima. In some embodiments, both the adenine and uridine dinucleotide contents are less than or equal to 150% of their respective minima. In some embodiments, any of the foregoing levels of identity is at least 95%, at least 98%, at least 99%, or 100%.

In some embodiments, the ORF encoding an RNA-guided DNA binding agent has at least 90% identity to any one of SEQ ID NO: 311-313, 328, 329, 346-348, 355, 356, 363, or 364 over at least its first 30, 50, 70, 100, 150, 200, 250, or 300 nucleotides. The first 30, 50, 70, 100, 150, 200, 250, or 300 nucleotides are measured from the first nucleotide of the start codon (typically ATG), such that the A is nucleotide 1, the T is nucleotide 2, etc. In some embodiments, the open reading frame has at least 90% identity to any one of SEQ ID NO: 311-313, 328, 329, 346-348, 355, 356, 363, or 364 over at least its first 10%, 12%, 15%, 20%, 25%, 30%, or 35% of its sequence. The length of the sequence of the ORF is the number of nucleotides from the beginning of the start codon to the end of the stop codon, and the first 10%, 12%, 15%, 20%, 25%, 30%, or 35% of its sequence corresponds to the number of nucleotides starting from the first nucleotide of the start codon that make up the indicated percentage of the length of the total sequence.

In some embodiments, the nucleic acid comprising an ORF encoding an RNA-guided DNA binding agent comprises a sequence having at least 90% identity to SEQ ID NO: 243 in which the ORF of SEQ ID NO: 243 (i.e., SEQ ID NO: 204) is substituted with the ORF of any one of SEQ ID NO: 311-313, 328, 329, 346-348, 355, 356, 363, or 364.

In some embodiments, the nucleic acid comprising an ORF encoding an RNA-guided DNA binding agent comprises a sequence having at least 90% identity to SEQ ID NO: 244 in which the ORF of SEQ ID NO: 244 (i.e., SEQ ID NO: 204) is substituted with the ORF of any one of SEQ ID NO: 311-313, 328, 329, 346-348, 355, 356, 363, or 364.

In some embodiments, the nucleic acid comprising an ORF encoding an RNA-guided DNA binding agent comprises a sequence having at least 90% identity to SEQ ID NO: 256 in which the ORF of SEQ ID NO: 256 (i.e., SEQ ID NO: 204) is substituted with the ORF of any one of SEQ ID NO: 311-313, 328, 329, 346-348, 355, 356, 363, or 364.

In some embodiments, the nucleic acid comprising an ORF encoding an RNA-guided DNA binding agent comprises a sequence having at least 90% identity to SEQ ID NO: 257 in which the ORF of SEQ ID NO: 257 (i.e., SEQ ID NO: 204) is substituted with the ORF of any one of SEQ ID NO: 311-313, 328, 329, 346-348, 355, 356, 363, or 364.

In some embodiments, the nucleic acid comprising an ORF encoding an RNA-guided DNA binding agent comprises a sequence having at least 90% identity to SEQ ID NO: 258 in which the ORF of SEQ ID NO: 258 (i.e., SEQ ID NO: 204) is substituted with the ORF of any one of SEQ ID NO: 311-313, 328, 329, 346-348, 355, 356, 363, or 364.

In some embodiments, the nucleic acid comprising an ORF encoding an RNA-guided DNA binding agent comprises a sequence having at least 90% identity to SEQ ID NO: 259 in which the ORF of SEQ ID NO: 259 (i.e., SEQ ID NO: 204) is substituted with the ORF of any one of SEQ ID NO: 311-313, 328, 329, 346-348, 355, 356, 363, or 364.

In some embodiments, the nucleic acid comprising an ORF encoding an RNA-guided DNA binding agent comprises a sequence having at least 90% identity to SEQ ID NO: 260 in which the ORF of SEQ ID NO: 260 (i.e., SEQ ID NO: 204) is substituted with the ORF of any one of SEQ ID NO: 311-313, 328, 329, 346-348, 355, 356, 363, or 364.

In some embodiments, the nucleic acid comprising an ORF encoding an RNA-guided DNA binding agent comprises a sequence having at least 90% identity to SEQ ID NO: 261 in which the ORF of SEQ ID NO: 261 (i.e., SEQ ID NO: 204) is substituted with the ORF of any one of SEQ ID NO: 311-313, 328, 329, 346-348, 355, 356, 363, or 364.

In some embodiments, the nucleic acid comprising an ORF encoding an RNA-guided DNA binding agent comprises a sequence having at least 90% identity to SEQ ID NO: 376, optionally wherein the ORF of SEQ ID NO: 376 is substituted with an alternative ORF of any one of SEQ ID NO: 311-313, 328, 329, 346-348, 355, 356, 363, or 364.

In some embodiments, the nucleic acid comprising an ORF encoding an RNA-guided DNA binding agent comprises a sequence having at least 90% identity to SEQ ID NO: 377, optionally wherein the ORF of SEQ ID NO: 377 is substituted with an alternative ORF of any one of SEQ ID NO: 311-313, 328, 329, 346-348, 355, 356, 363, or 364.

In some embodiments, the nucleic acid comprising an ORF encoding an RNA-guided DNA binding agent comprises a sequence having at least 90% identity to SEQ ID NO: 378, optionally wherein the ORF of SEQ ID NO: 378 is substituted with an alternative ORF of any one of SEQ ID NO: 311-313, 328, 329, 346-348, 355, 356, 363, or 364.

In some embodiments, the nucleic acid comprising an ORF encoding an RNA-guided DNA binding agent comprises a sequence having at least 90% identity to SEQ ID NO: 379 in which the ORF of SEQ ID NO: 379 is substituted with the ORF of any one of SEQ ID NO: 311-313, 328, 329, 346-348, 355, 356, 363, or 364.

In some embodiments, the nucleic acid comprising an ORF encoding an RNA-guided DNA binding agent comprises a sequence having at least 90% identity to SEQ ID NO: 380 in which the ORF of SEQ ID NO: 380 is substituted with the ORF of any one of SEQ ID NO: 311-313, 328, 329, 346-348, 355, 356, 363, or 364.

In some embodiments, the nucleic acid comprising an ORF encoding an RNA-guided DNA binding agent comprises a sequence having at least 90% identity to SEQ ID NO: 381 in which the ORF of SEQ ID NO: 381 is substituted with the ORF of any one of SEQ ID NO: 311-313, 328, 329, 346-348, 355, 356, 363, or 364.

In some embodiments, the nucleic acid comprising an ORF encoding an RNA-guided DNA binding agent comprises a sequence having at least 90% identity to SEQ ID NO: 382 in which the ORF of SEQ ID NO: 382 is substituted with the ORF of any one of SEQ ID NO: 311-313, 328, 329, 346-348, 355, 356, 363, or 364.

In some embodiments, the nucleic acid comprising an ORF encoding an RNA-guided DNA binding agent comprises a sequence having at least 90% identity to SEQ ID NO: 383 in which the ORF of SEQ ID NO: 383 is substituted with the ORF of any one of SEQ ID NO: 311-313, 328, 329, 346-348, 355, 356, 363, or 364.

In some embodiments, the nucleic acid comprising an ORF encoding an RNA-guided DNA binding agent comprises a sequence having at least 90% identity to SEQ ID NO: 384 in which the ORF of SEQ ID NO: 384 is substituted with the ORF of any one of SEQ ID NO: 311-313, 328, 329, 346-348, 355, 356, 363, or 364.

In some embodiments, the nucleic acid comprising an ORF encoding an RNA-guided DNA binding agent comprises a sequence having at least 90% identity to SEQ ID NO: 385 in. which the ORF of SEQ ID NO: 385 is substituted with the ORF of any one of SEQ ID NO: 311-313, 328, 329, 346-348, 355, 356, 363, or 364.

In some embodiments, the degree of identity to the optionally substituted sequences of SEQ ID NOs 243, 244, 256-261, or 376-385 is at least 95%. In some embodiments, the degree of identity to the optionally substituted sequences of SEQ ID NOs 243, 244, 256-261, or 376-385 is at least 98%. In some embodiments, the degree of identity to the optionally substituted sequences of SEQ ID NOs 243, 244, 256-261, or 176-385 is at least 99%. In some embodiments, the degree of identity to the optionally substituted sequences of SEQ ID NOs 243, 244, 256-261, or 376-385 is 100%.

4. Additional Features of Nucleic Acids, mRNAs, and ORFs

Any of the additional features described herein may be combined to the extent feasible with any of the embodiments described above.

a) Low Uridine Content

In some embodiments, the ORF encoding the RNA-guided DNA-binding agent, e.g. a Cas9 nuclease such as an *S. pyogenes* Cas9, has a uridine content ranging from its minimum uridine content to about 150% of its minimum uridine content. In some embodiments, the uridine content of the ORF is less than or equal to about 145%, 140%, 135%, 130%, 125%, 120%, 115%, 110%, 105%, 104%, 103%, 102%, or 101% of its minimum uridine content. In some embodiments, the ORF has a uridine content equal to its minimum uridine content. In some embodiments, the ORF has a uridine content less than or equal to about 150% of its minimum uridine content. In some embodiments, the ORF has a uridine content less than or equal to about 145% of its minimum uridine content. In some embodiments, the ORF has a uridine content less than or equal to about 140% of its minimum uridine content. In some embodiments, the ORF has a uridine content less than or equal to about 135% of its minimum uridine content. In some embodiments, the ORF has a uridine content less than or equal to about 130% of its minimum uridine content. In some embodiments, the ORF has a uridine content less than or equal to about 125% of its minimum uridine content. In some embodiments, the ORF has a uridine content less than or equal to about 120% of its minimum uridine content. In some embodiments, the ORF has a uridine content less than or equal to about 115% of its minimum uridine content. In some embodiments, the ORF has a uridine content less than or equal to about 110% of its minimum uridine content. In some embodiments, the ORF has a uridine content less than or equal to about 105% of its minimum uridine content. In some embodiments, the ORF has a uridine content less than or equal to about 104% of its minimum uridine content. In some embodiments, the ORF has a uridine content less than or equal to about 103% of its minimum uridine content. In some embodiments, the ORF has a uridine content less than or equal to about 102% of its minimum uridine content. In some embodiments, the ORF has a uridine content less than or equal to about 101% of its minimum uridine content.

In some embodiments, the ORF has a uridine dinucleotide content ranging from its minimum uridine dinucleotide content to 200% of its minimum uridine dinucleotide content. In some embodiments, the uridine dinucleotide content of the ORF is less than or equal to about 195%, 190%, 185%, 180%, 175%, 170%, 165%, 160%, 155%, 150%, 145%, 140%, 135%, 130%, 125%, 120%, 115%, 110%, 105%, 104%, 103%, 102%, or 101% of its minimum uridine dinucleotide content. In some embodiments, the ORF has a uridine dinucleotide content equal to its minimum uridine dinucleotide content. In some embodiments, the ORF has a uridine dinucleotide content less than or equal to about 200% of its minimum uridine dinucleotide content. In some embodiments, the ORF has a uridine dinucleotide content less than or equal to about 195% of its minimum uridine dinucleotide content. In some embodiments, the ORF has a uridine dinucleotide content less than or equal to about 190% of its minimum uridine dinucleotide content. In some embodiments, the ORF has a uridine dinucleotide content less than or equal to about 185% of its minimum uridine dinucleotide content. In some embodiments, the ORF has a uridine dinucleotide content less than or equal to about 180% of its minimum uridine dinucleotide content. In some embodiments, the ORF has a uridine dinucleotide content less than or equal to about 175% of its minimum uridine dinucleotide content. In some embodiments, the ORF has a uridine dinucleotide content less than or equal to about 170% of its minimum uridine dinucleotide content. In some embodiments, the ORF has a uridine dinucleotide content less than or equal to about 165% of its minimum uridine dinucleotide content. In some embodiments, the ORF has a uridine dinucleotide content less than or equal to about 160% of its minimum uridine dinucleotide content. In some embodiments, the ORF has a uridine dinucleotide content less than or equal to about 155% of its minimum uridine dinucleotide content. In some embodiments, the ORF has a uridine dinucleotide content equal to its minimum uridine dinucleotide content. In some embodiments, the ORF has a uridine dinucleotide content less than or equal to about 150% of its minimum uridine dinucleotide content. In some embodiments, the ORF has a uridine dinucleotide content less than or equal to about 145% of its minimum uridine dinucleotide content. In some embodiments, the ORF has a uridine dinucleotide content less than or equal to about 140% of its minimum uridine dinucleotide content. In some embodiments, the ORF has a uridine dinucleotide content less than or equal to about 135% of its minimum uridine dinucleotide content. In some embodiments, the ORF has a uridine dinucleotide content less than or equal to about 130% of its minimum uridine dinucleotide content. In some embodiments, the ORF has a uridine dinucleotide content less than or equal to about 125% of its minimum uridine dinucleotide content. In some embodiments, the ORF has a uridine dinucleotide content less than or equal to about 120% of its minimum uridine dinucleotide content. In some embodiments, the ORF has a uridine dinucleotide content less than or equal to about 115% of its minimum uridine dinucleotide content. In some embodiments, the ORF has a uridine dinucleotide content less than or equal to about 110% of its minimum uridine dinucleotide content. In some embodiments, the ORF has a uridine dinucleotide content less than or equal to about 105% of its minimum uridine dinucleotide content. In some embodiments, the ORF has a uridine dinucleotide content less than or equal to about 104% of its minimum uridine dinucleotide content. In some embodiments, the ORF has a uridine dinucleotide content less than or equal to about 103% of its minimum uridine dinucleotide content. In some embodiments, the ORF has a uridine dinucleotide content less than or equal to about 102% of its minimum uridine dinucleotide content. In some embodiments, the ORF has a uridine dinucleotide content less than or equal to about 101% of its minimum uridine dinucleotide content.

In some embodiments, the ORF has a uridine dinucleotide content ranging from its minimum uridine dinucleotide content to the uridine dinucleotide content that is 90% or lower of the maximum uridine dinucleotide content of a reference sequence that encodes the same protein as the mRNA in question. In some embodiments, the uridine dinucleotide content of the ORF is less than or equal to about 85%, 80%, 75%, 70%, 65%, 60%, 55%, 50%, 45%, 40%, 35%, 30%, 25%, 20%, 15%, 10%, or 5% of the maximum uridine dinucleotide content of a reference sequence that encodes the same protein as the mRNA in question.

In some embodiments, the ORF has a uridine trinucleotide content ranging from 0 uridine trinucleotides to 1, 2, 3, 4, 5, 6, 7, 8, 9, 10, 20, 30, 40, or 50 uridine trinucleotides (where a longer run of uridines counts as the number of unique three-uridine segments within it, e.g., a uridine tetranucleotide contains two uridine trinucleotides, a uridine pentanucleotide contains three uridine trinucleotides, etc.). In some embodiments, the ORF has a uridine trinucleotide content ranging from 0% uridine trinucleotides to 0.1%, 0.2%, 0.3%, 0.4%, 0.5%, 0.6%, 0.7%, 0.8%, 0.9%, 1%, 1.5%, or 2% uridine trinucleotides, where the percentage content of uridine trinucleotides is calculated as the percentage of positions in a sequence that are occupied by uridines that form part of a uridine trinucleotide (or longer run of uridines), such that the sequences UUUAAA and UUUUAAAA would each have a uridine trinucleotide content of 50%. For example, in some embodiments, the ORF has a uridine trinucleotide content less than or equal to 2%. For example, in some embodiments, the ORF has a uridine trinucleotide content less than or equal to 1.5%. In some embodiments, the ORF has a uridine trinucleotide content less than or equal to 1%. In some embodiments, the ORF has a uridine trinucleotide content less than or equal to 0.9%. In some embodiments, the ORF has a uridine trinucleotide content less than or equal to 0.8%. In some embodiments, the ORF has a uridine trinucleotide content less than or equal to 0.7%. In some embodiments, the ORF has a uridine trinucleotide content less than or equal to 0.6%. In some embodiments, the ORF has a uridine trinucleotide content less than or equal to 0.5%. In some embodiments, the ORF has a uridine trinucleotide content less than or equal to 0.4%. In some embodiments, the ORF has a uridine trinucleotide content less than or equal to 0.3%. In some embodiments, the ORF has a uridine trinucleotide content less than or equal to 0.2%. In some embodiments, the ORF has a uridine trinucleotide content less than or equal to 0.1%. In some embodiments, the ORF has no uridine trinucleotides.

In some embodiments, the ORF has a uridine trinucleotide content ranging from its minimum uridine trinucleotide content to the uridine trinucleotide content that is 90% or lower of the maximum uridine trinucleotide content of a reference sequence that encodes the same protein as the mRNA in question. In some embodiments, the uridine trinucleotide content of the ORF is less than or equal to about 85%, 80%, 75%, 70%, 65%, 60%, 55%, 50%, 45%, 40%, 35%, 30%, 25%, 20%, 15%, 10%, or 5% of the maximum uridine trinucleotide content of a reference sequence that encodes the same protein as the mRNA in question.

A given ORF can be reduced in uridine content or uridine dinucleotide content or uridine trinucleotide content, for example, by using minimal uridine codons in a sufficient fraction of the ORF. For example, an amino acid sequence for an RNA-guided DNA-binding agent can be back-translated into an ORF sequence by converting amino acids to codons, wherein some or all of the ORF uses the exemplary minimal uridine codons shown below. In some embodiments, at least about 50%, 55%, 60%, 65%, 70%, 75%, 80%, 85%, 90%, 95%, 98%, 99%, or 100% of the codons in the ORF are codons listed in Table 6.

TABLE 6

Exemplary minimal uridine codons

| | Amino Acid | Minimal uridine codon |
|---|---|---|
| A | Alanine | GCA or GCC or GCG |
| G | Glycine | GGA or GGC or GGG |
| V | Valine | GUC or GUA or GUG |
| D | Aspartic acid | GAC |
| E | Glutamic acid | GAA or GAG |
| I | Isoleucine | AUC or AUA |
| T | Threonine | ACA or ACC or ACG |
| N | Asparagine | AAC |
| K | Lysine | AAG or AAA |
| S | Serine | AGC |
| R | Arginine | AGA or AGG |
| L | Leucine | CUG or CUA or CUC |
| P | Proline | CCG or CCA or CCC |
| H | Histidine | CAC |
| Q | Glutamine | CAG or CAA |
| F | Phenylalanine | UUC |
| Y | Tyrosine | UAC |
| C | Cysteine | UGC |
| W | Tryptophan | UGG |
| M | Methionine | AUG |

In some embodiments, the ORF consists of a set of codons of which at least about 75%, 80%, 85%, 90%, 95%, 98%, 99%, or 100% of the codons are codons listed in Table 6.

b) Low Adenine and Uridine Content

To the extent feasible, any of the features described herein with respect to low adenine content can be combined with any of the features described herein with respect to low uridine content. For example, a nucleic acid (e.g., mRNA) may be provided that encodes an RNA-guided DNA-binding agent, e.g. a Cas9 nuclease such as an *S. pyogenes* Cas9, comprising an ORF having a uridine content ranging from its minimum uridine content to about 150% of its minimum uridine content (e.g., a uridine content of the ORF is less than or equal to about 145%, 140%, 135%, 130%, 125%, 120%, 115%, 110%, 105%, 104%, 103%, 102%, or 101% of its minimum uridine content) and an adenine content ranging from its minimum adenine content to about 150% of its minimum adenine content (e.g., less than or equal to about 145%, 140%, 135%, 130%, 125%, 120%, 115%, 110%, 105%, 104%, 103%, 102%, or 101% of its minimum adenine content). So too for uridine and adenine dinucleotides. Similarly, the content of uridine nucleotides and adenine dinucleotides in the ORF may be as set forth above. Similarly, the content of uridine dinucleotides and adenine nucleotides in the ORF may be as set forth above.

A given ORF can be reduced in uridine and adenine nucleotide and/or dinucleotide content, for example, by using minimal uridine and adenine codons in a sufficient fraction of the ORF. For example, an amino acid sequence for an RNA-guided DNA-binding agent can be back-translated into an ORF sequence by converting amino acids to codons, wherein some or all of the ORF uses the exemplary minimal uridine and adenine codons shown below. In some embodiments, at least about 50%, 55%, 60%, 65%, 70%, 75%, 80%, 85%, 90%, 95%, 98%, 99%, or 100% of the codons in the ORF are codons listed in Table 7.

TABLE 7

Exemplary minimal uridine and adenine codons

| | Amino Acid | Minimal uridine codon |
|---|---|---|
| A | Alanine | GCC or GCG |
| G | Glycine | GGC or GGG |
| V | Valine | GUC or GUG |
| D | Aspartic acid | GAC |
| E | Glutamic acid | GAG |
| I | Isoleucine | AUC |
| T | Threonine | ACC or ACG |
| N | Asparagine | AAC |
| K | Lysine | AAG |
| S | Serine | AGC or UCC or UCG |
| R | Arginine | CGC or CGG |
| L | Leucine | CUG or CUC |
| P | Proline | CCG or CCC |
| H | Histidine | CAC |
| Q | Glutamine | CAG |
| F | Phenylalanine | UUC |
| Y | Tyrosine | UAC |
| C | Cysteine | UGC |
| W | Tryptophan | UGG |
| M | Methionine | AUG |

In some embodiments, the ORF consists of a set of codons of which at least about 75%, 80%, 85%, 90%, 95%, 98%, 99%, or 100% of the codons are codons listed in Table 7. As can be seen in Table 7, each of the three listed serine codons contains either one A or one U. In some embodiments, uridine minimization is prioritized by using AGC codons for serine. In some embodiments, adenine minimization is prioritized by using UCC and/or UCG codons for serine.

c) Encoded RNA-Guided DNA Binding Agent

In some embodiments, the RNA-guided DNA-binding agent is a Class 2 Cas nuclease. In some embodiments, the RNA-guided DNA-binding agent has cleavase activity, which can also be referred to as double-strand endonuclease activity. In some embodiments, the RNA-guided DNA-binding agent comprises a Cas nuclease, such as a Class 2 Cas nuclease (which may be, e.g., a Cas nuclease of Type II, V, or VI). Class 2 Cas nucleases include, for example, Cas9, Cpf1, C2c1, C2c2, and C2c3 proteins and modifications thereof. Examples of Cas9 nucleases include those of the type II CRISPR systems of *S. pyogenes, S. aureus*, and other prokaryotes (see, e.g., the list in the next paragraph), and modified (e.g., engineered or mutant) versions thereof. See, e.g., US2016/0312198 A1; US 2016/0312199 A1. Other examples of Cas nucleases include a Csm or Cmr complex of a type III CRISPR system or the Cas10, Csm1, or Cmr2 subunit thereof; and a Cascade complex of a type I CRISPR system, or the Cas3 subunit thereof. In some embodiments, the Cas nuclease may be from a Type-IIA, Type-IIB, or Type-IIC system. For discussion of various CRISPR systems and Cas nucleases see, e.g., Makarova et al., Nat. Rev. Microbiol. 9:467-477 (2011); Makarova et al., Nat. Rev. Microbiol, 13: 722-36 (2015); Shmakov et al., Molecular Cell, 60:385-397 (2015). In some embodiments, the RNA-guided DNA building agent is a Cas cleavase, e.g. a Cas9 cleavagse. In some embodiments, the RNA-guided DNA binding agent is a Cas nickase, e.g. a Cas9 nickase. In some embodiments, the RNA-guided DNA binding agent is an *S. pyogenes* Cas9 nuclease, e.g. a cleavase.

Non-limiting exemplary species that the Cas nuclease can be derived from include *Streptococcus pyogenes, Streptococcus thermophilus, Streptococcus* sp., *Staphylococcus aureus, Listeria innocua, Lactobacillus gasseri, Francisella novicida, Wolinella succinogenes, Sutterella wadsworthensis*, Gammaproteobacterium, *Neisseria meningitidis, Campylobacter jejuni, Pasteurella multocida, Fibrobacter succinogene, Rhodospirillum rubrum, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Lactobacillus buchneri, Treponema denticola, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus, Streptococcus pasteurianus, Neisseria cinerea, Campylobacter lari, Parvibaculum lavamentivorans, Corynebacterium diphtheria, Acidaminococcus* sp., Lachnospiraceae bacterium ND2006, and *Acaryochloris marina.*

In some embodiments, the Cas nuclease is the Cas9 nuclease from *Streptococcus pyogenes*. In some embodiments, the Cas nuclease is the Cas9 nuclease from *Streptococcus thermophilus*. In some embodiments, the Cas nuclease is the Cas9 nuclease from *Neisseria meningitidis*. In some embodiments, the Cas nuclease is the Cas9 nuclease is from *Staphylococcus aureus*. In some embodiments, the Cas nuclease is the Cpf1 nuclease from *Francisella novicida*. In some embodiments, the Cas nuclease is the Cpf1 nuclease from *Acidaminococcus* sp. In some embodiments, the Cas nuclease is the Cpf1 nuclease from Lachnospiraceae bacterium ND2006. In further embodiments, the Cas nuclease is the Cpf1 nuclease from *Francisella tularensis, Lachnospiraceae bacterium, Butyrivibrio proteoclasticus, Peregrinibacteria bacterium, Parcubacteria bacterium, Smithella, Acidaminococcus, Candidatus Methanoplasma termitum, Eubacterium eligens, Moraxella bovoculi, Leptospira inadai, Porphyromonas crevioricanis, Prevotella disiens*, or *Porphyromonas macacae*. In certain embodiments, the Cas nuclease is a Cpf1 nuclease from an *Acidaminococcus* or Lachnospiraceae.

Wild type Cas9 has two nuclease domains: RuvC and HNH. The RuvC domain cleaves the non-target DNA strand, and the HNH domain cleaves the target strand of DNA. In some embodiments, the Cas9 nuclease comprises more than one RuvC domain and/or more than one HNH domain. In some embodiments, the Cas9 nuclease is a wild type Cas9. In some embodiments, the Cas9 is capable of inducing a double strand break in target DNA. In certain embodiments, the Cas nuclease may cleave dsDNA, it may cleave one strand of dsDNA, or it may not have DNA cleavase or nickase activity. An exemplary Cas9 amino acid sequence is provided as SEQ ID NO: 203. An exemplary Cas9 mRNA ORF sequence, which includes start and stop codons, is provided as SEQ ID NO: 311. An exemplary Cas9 mRNA coding sequence, suitable for inclusion in a fusion protein, is provided as SEQ ID NO: 346.

In some embodiments, chimeric Cas nucleases are used, where one domain or region of the protein is replaced by a portion of a different protein. In some embodiments, a Cas nuclease domain may be replaced with a domain from a different nuclease such as Fok1. In some embodiments, a Cas nuclease may be a modified nuclease.

In other embodiments, the Cas nuclease may be from a Type-I CRISPR/Cas system. In some embodiments, the Cas nuclease may be a component of the Cascade complex of a Type-I CRISPR/Cas system. In some embodiments, the Cas nuclease may be a Cas3 protein. In some embodiments, the Cas nuclease may be from a Type-III CRISPR/Cas system. In some embodiments, the Cas nuclease may have an RNA cleavage activity.

d) Heterologous Functional Domains; Nuclear Localization Signals

In some embodiments, the RNA-guided DNA-binding agent, e.g. a Cas9 nuclease such as an *S. pyogenes* Cas9, comprises one or more heterologous functional domains (e.g., is or comprises a fusion polypeptide).

In some embodiments, the heterologous functional domain may facilitate transport of the RNA-guided DNA-binding agent, e.g. a Cas9 nuclease such as an *S. pyogenes* Cas9, into the nucleus of a cell. For example, the heterologous functional domain may be a nuclear localization signal (NLS). In some embodiments, the RNA-guided DNA-binding agent may be fused with 1-10 NLS(s). In some embodiments, the RNA-guided DNA-binding agent may be fused with 1-5 NLS(s). In some embodiments, the RNA-guided DNA-binding agent may be fused with one NLS. Where one NLS is used, the NLS may be linked at the N-terminus or the C-terminus of the RNA-guided DNA-binding agent sequence. In some embodiments, the RNA-guided DNA-binding agent may be fused C-terminally to at least one NLS. An NLS may also be inserted within the RNA-guided DNA binding agent sequence. In other embodiments, the RNA-guided DNA-binding agent may be fused with more than one NLS. In some embodiments, the RNA-guided DNA-binding agent may be fused with 2, 3, 4, or 5 NLSs. In some embodiments, the RNA-guided DNA-binding agent may be fused with two NLSs. In certain circumstances, the two NLSs may be the same (e.g., two SV40 NLSs) or different. In some embodiments, the RNA-guided DNA-binding agent is fused to two SV40 NLS sequences linked at the carboxy terminus. In some embodiments, the RNA-guided DNA-binding agent may be fused with two NLSs, one linked at the N-terminus and one at the C-terminus. In some embodiments, the RNA-guided DNA-binding agent may be fused with 3 NLSs. In some embodiments, the RNA-guided DNA-binding agent may be fused with no NLS. In some embodiments, the NLS may be a monopartite sequence, such as, e.g., the SV40 NLS, PKKKRKV (SEQ ID NO: 278) or PKKKRRV (SEQ ID NO: 290). In some embodiments, the NLS may be a bipartite sequence, such as the NLS of nucleoplasmin, KRPAATKKAGQAKKKK (SEQ ID NO: 291). In some embodiments, the NLS sequence may comprise LAAKRSRTT (SEQ ID NO: 279), QAAKRSRTT (SEQ ID NO: 280), PAPAKRERTT (SEQ ID NO: 281), QAAKRPRTT (SEQ ID NO: 282), RAAKRPRTT (SEQ ID NO: 283), AAAKRSWSMAA (SEQ ID NO: 284), AAAKRVWSMAF (SEQ ID NO: 285), AAAKRSWSMAF (SEQ ID NO: 286), AAAKRKYFAA (SEQ ID NO: 287), RAAKRKAFAA (SEQ ID NO: 288), or RAAKRKYFAV (SEQ ID NO: 289). In a specific embodiment, a single PKKKRKV (SEQ ID NO: 278) NLS may be linked at the C-terminus of the RNA-guided DNA-binding agent. One or more linkers are optionally included at the fusion site. In some embodiments, one or more NLS(s) according to any of the foregoing embodiments are present in the RNA-guided DNA-binding agent in combination with one or more additional heterologous functional domains, such as any of the heterologous functional domains described below. Exemplary coding sequences for NLSs are provided as SEQ ID NOs: 292-304.

In some embodiments, the heterologous functional domain may be capable of modifying the intracellular half-life of the RNA-guided DNA binding agent, e.g. a Cas9 nuclease such as an *S. pyogenes* Cas9. In some embodiments, the half-life of the RNA-guided DNA binding agent may be increased. In some embodiments, the half-life of the RNA-guided DNA-binding agent may be reduced. In some embodiments, the heterologous functional domain may be capable of increasing the stability of the RNA-guided DNA-binding agent. In some embodiments, the heterologous functional domain may be capable of reducing the stability of the RNA-guided DNA-binding agent. In some embodiments, the heterologous functional domain may act as a signal peptide for protein degradation. In some embodiments, the protein degradation may be mediated by proteolytic enzymes, such as, for example, proteasomes, lysosomal proteases, or calpain proteases. In some embodiments, the heterologous functional domain may comprise a PEST sequence. In some embodiments, the RNA-guided DNA-binding agent may be modified by addition of ubiquitin or a polyubiquitin chain. In some embodiments, the ubiquitin may be a ubiquitin-like protein (UBL). Non-limiting examples of ubiquitin-like proteins include small ubiquitin-like modifier (SUMO), ubiquitin cross-reactive protein (UCRP, also known as interferon-stimulated gene-15 (ISG15)), ubiquitin-related modifier-1 (URM1), neuronal-precursor-cell-expressed developmentally down-regulated protein-8 (NEDD8, also called Rub1 in *S. cerevisiae*), human leukocyte antigen F-associated (FAT10), autophagy-8 (ATG8) and -12 (ATG12), Fau ubiquitin-like protein (FUB1), membrane-anchored UBL (MUB), ubiquitin fold-modifier-1 (UFM1), and ubiquitin-like protein-5 (UBL5).

In some embodiments, the heterologous functional domain may be a marker domain. Non-limiting examples of marker domains include fluorescent proteins, purification tags, epitope tags, and reporter gene sequences. In some embodiments, the marker domain may be a fluorescent protein. Non-limiting examples of suitable fluorescent proteins include green fluorescent proteins (e.g., GFP, GFP-2, tagGFP, turboGFP, sfGFP, EGFP, Emerald, Azami Green, Monomeric Azami Green, CopGFP, AceGFP, ZsGreen1), yellow fluorescent proteins (e.g., YFP, EYFP, Citrine, Venus, YPet, PhiYFP, ZsYellow1), blue fluorescent proteins (e.g., EBFP, EBFP2, Azurite, mKalamal, GFPuv, Sapphire, T-sapphire,), cyan fluorescent proteins (e.g., ECFP, Cerulean, CyPet, AmCyan1, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRed1, AsRed2, eqFP611, mRasberry, mStrawberry, Jred), and orange fluorescent proteins (mOrange, mKO, Kusabira-Orange, Monomeric Kusabira-Orange, mTangerine, tdTomato) or any other suitable fluorescent protein. In other embodiments, the marker domain may be a purification tag and/or an epitope tag. Non-limiting exemplary tags include glutathione-S-transferase (GST), chitin binding protein (CBP), maltose binding protein (MBP), thioredoxin (TRX), poly(NANP), tandem affinity purification (TAP) tag, myc, AcV5, AU1, AU5, E, ECS, E2, FLAG, HA, nus, Softag 1, Softag 3, Strep, SBP, Glu-Glu, HSV, KT3, S, S1, T7, V5, VSV-G, 6×His, 8×His, biotin carboxyl carrier protein (BCCP), poly-His, and calmodulin. Non-limiting exemplary reporter genes include glutathione-S-transferase (GST), horseradish peroxidase (HRP), chloramphenicol acetyltransferase (CAT), beta-galactosidase, beta-glucuronidase, luciferase, or fluorescent proteins.

In additional embodiments, the heterologous functional domain may target the RNA-guided DNA-binding agent, e.g. a Cas9 nuclease such as an *S. pyogenes* Cas9, to a specific organelle, cell type, tissue, or organ. In some embodiments, the heterologous functional domain may target the RNA-guided DNA-binding agent to mitochondria.

In further embodiments, the heterologous functional domain may be an effector domain. When the RNA-guided DNA-binding agent is directed to its target sequence, e.g., when a Cas nuclease is directed to a target sequence by a gRNA, the effector domain may modify or affect the target sequence. In some embodiments, the effector domain may be chosen from a nucleic acid binding domain, a nuclease domain (e.g., a non-Cas nuclease domain), an epigenetic modification domain, a transcriptional activation domain, or a transcriptional repressor domain. In some embodiments, the heterologous functional domain is a nuclease, such as a FokI nuclease. See, e.g., U.S. Pat. No. 9,023,649. In some embodiments, the heterologous functional domain is a transcriptional activator or repressor. See, e.g., Qi et al., "Repurposing CRISPR as an RNA-guided platform for sequence-specific control of gene expression," *Cell* 152:1173-83 (2013); Perez-Pinera et al., "RNA-guided gene activation by CRISPR-Cas9-based transcription factors," *Nat. Methods* 10:973-6 (2013); Mali et al., "CAS9 transcriptional activators for target specificity screening and paired nickases for cooperative genome engineering," *Nat. Biotechnol.* 31:833-8 (2013); Gilbert et al., "CRISPR-mediated modular RNA-guided regulation of transcription in eukaryotes," *Cell* 154:442-51 (2013). As such, the RNA-guided DNA-binding agent essentially becomes a transcription factor that can be directed to bind a desired target sequence using a guide RNA. In certain embodiments, the DNA modification domain is a methylation domain, such as a demethylation or methyltransferase domain. In certain embodiments, the effector domain is a DNA modification domain, such as a base-editing domain. In particular embodiments, the DNA modification domain is a nucleic acid editing domain that introduces a specific modification into the DNA, such as a deaminase domain. See, e.g., WO 2015/089406; US 2016/0304846. The nucleic acid editing domains, deaminase domains, and Cas9 variants described in WO 2015/089406 and US 2016/0304846 are hereby incorporated by reference.

e) UTRs; Kozak Sequences

In some embodiments, the polynucleotide (e.g. mRNA) comprises a 5' UTR, a 3' UTR, or 5' and 3' UTRs. In some embodiments, the polynucleotide (e.g. mRNA) comprises at least one UTR from Hydroxysteroid 17-Beta Dehydrogenase 4 (HSD17B4 or HSD), e.g., a 5' UTR from HSD. In some embodiments, the polynucleotide (e.g. mRNA) comprises at least one UTR from a globin mRNA, for example, human alpha globin (HBA) mRNA, human beta globin (HBB) mRNA, or *Xenopus laevis* beta globin (XBG) mRNA. In some embodiments, the polynucleotide (e.g. mRNA) comprises a 5' UTR, 3' UTR, or 5' and 3' UTRs from a globin mRNA, such as HBA, HBB, or XBG. In some embodiments, the polynucleotide (e.g. mRNA) comprises a 5' UTR from bovine growth hormone, cytomegalovirus (CMV), mouse Hba-a1, HSD, an albumin gene, HBA, HBB, or XBG. In some embodiments, the polynucleotide (e.g. mRNA) comprises a 3' UTR from bovine growth hormone, cytomegalovirus, mouse Hba-a1, HSD, an albumin gene, HBA, HBB, or XBG. In some embodiments, the polynucleotide (e.g. mRNA) comprises 5' and 3' UTRs from bovine growth hormone, cytomegalovirus, mouse Hba-a1, HSD, an albumin gene, HBA, HBB, XBG, heat shock protein 90 (Hsp90), glyceraldehyde 3-phosphate dehydrogenase (GAPDH), beta-actin, alpha-tubulin, tumor protein (p53), or epidermal growth factor receptor (EGFR).

In some embodiments, the polynucleotide (e.g. mRNA) comprises 5' and 3' UTRs that are from the same source, e.g., a constitutively expressed mRNA such as actin, albumin, or a globin such as HBA, HBB, or XBG.

In some embodiments, a nucleic acid disclosed herein comprises a 5' UTR with at least 90% identity to any one of SEQ ID NOs: 232, 234, 236, 238, 241, or 275-277. In some embodiments, a nucleic acid disclosed herein comprises a 3' UTR with at least 90% identity to any one of SEQ ID NOs: 233, 235, 237, 239, or 240. In some embodiments, any of the foregoing levels of identity is at least 95%, at least 98%, at least 99%, or 100%. In some embodiments, a nucleic acid disclosed herein comprises a 5' UTR having the sequence of any one of SEQ ID NOs: 232, 234, 236, 238, or 241. In some embodiments, a nucleic acid disclosed herein comprises a 3' UTR having the sequence of any one of SEQ ID NOs: 233, 235, 237, 239, or 240.

In some embodiments, the polynucleotide (e.g. mRNA) does not comprise a 5' UTR, e.g., there are no additional nucleotides between the 5' cap and the start codon. In some embodiments, the polynucleotide (e.g. mRNA) comprises a Kozak sequence (described below) between the 5' cap and the start codon, but does not have any additional 5' UTR. In some embodiments, the polynucleotide (e.g. mRNA) does not comprise a 3' UTR, e.g., there are no additional nucleotides between the stop codon and the poly-A tail.

In some embodiments, the polynucleotide (e.g. mRNA) comprises a Kozak sequence. The Kozak sequence can affect translation initiation and the overall yield of a polypeptide translated from a nucleic acid. A Kozak sequence includes a methionine codon that can function as the start codon. A minimal Kozak sequence is NNNRUGN wherein at least one of the following is true: the first N is A or G and the second N is G. In the context of a nucleotide sequence, R means a purine (A or G). In some embodiments, the Kozak sequence is RNNRUGN, NNNRUGG, RNNRUGG, RNNAUGN, NNNAUGG, or RNNAUGG. In some embodiments, the Kozak sequence is rccRUGg with zero mismatches or with up to one or two mismatches to positions in lowercase. In some embodiments, the Kozak sequence is rccAUGg with zero mismatches or with up to one or two mismatches to positions in lowercase. In some embodiments, the Kozak sequence is gccRccAUGG (nucleotides 4-13 of SEQ ID NO: 305) with zero mismatches or with up to one, two, or three mismatches to positions in lowercase. In some embodiments, the Kozak sequence is gccAccAUG with zero mismatches or with up to one, two, three, or four mismatches to positions in lowercase. In some embodiments, the Kozak sequence is GCCACCAUG. In some embodiments, the Kozak sequence is gccgccRccAUGG (SEQ ID NO: 305) with zero mismatches or with up to one, two, three, or four mismatches to positions in lowercase.

f) Poly-A Tail

In some embodiments, the polynucleotide (e.g. mRNA) further comprises a polyadenylated (poly-A) tail. In some instances, the poly-A tail is "interrupted" with one or more non-adenine nucleotide "anchors" at one or more locations within the poly-A tail. The poly-A tails may comprise at least 8 consecutive adenine nucleotides, but also comprise one or more non-adenine nucleotide. As used herein, "non-adenine nucleotides" refer to any natural or non-natural nucleotides that do not comprise adenine. Guanine, thymine, and cytosine nucleotides are exemplary non-adenine nucleotides. Thus, the poly-A tails on the polynucleotide (e.g. mRNA) described herein may comprise consecutive adenine nucleotides located 3' to nucleotides encoding an RNA-guided DNA-binding agent or a sequence of interest. In some instances, the poly-A tails on mRNA comprise non-consecutive adenine nucleotides located 3' to nucleotides encoding an RNA-guided DNA-binding agent or a sequence of interest, wherein non-adenine nucleotides interrupt the adenine nucleotides at regular or irregularly spaced intervals.

In some embodiments, the poly-A tail is encoded in the plasmid used for in vitro transcription of mRNA and becomes part of the transcript. The poly-A sequence encoded in the plasmid, i.e., the number of consecutive adenine nucleotides in the poly-A sequence, may not be exact, e.g., a 100 poly-A sequence in the plasmid may not result in a precisely 100 poly-A sequence in the transcribed mRNA. In some embodiments, the poly-A tail is not encoded in the plasmid, and is added by PCR tailing or enzymatic tailing, e.g., using *E. coli* poly(A) polymerase.

In some embodiments, the one or more non-adenine nucleotides are positioned to interrupt the consecutive adenine nucleotides so that a poly(A) binding protein can bind to a stretch of consecutive adenine nucleotides. In some embodiments, one or more non-adenine nucleotide(s) is located after at least 8, 9, 10, 11, or 12 consecutive adenine nucleotides. In some embodiments, the one or more non-adenine nucleotide is located after at least 8-50 consecutive adenine nucleotides. In some embodiments, the one or more non-adenine nucleotide is located after at least 8-100 consecutive adenine nucleotides. In some embodiments, the non-adenine nucleotide is after one, two, three, four, five, six, or seven adenine nucleotides and is followed by at least 8 consecutive adenine nucleotides.

The poly-A tail of the present disclosure may comprise one sequence of consecutive adenine nucleotides followed by one or more non-adenine nucleotides, optionally followed by additional adenine nucleotides.

In some embodiments, the poly-A tail comprises or contains one non-adenine nucleotide or one consecutive stretch of 2-10 non-adenine nucleotides. In some embodiments, the non-adenine nucleotide(s) is located after at least 8, 9, 10, 11, or 12 consecutive adenine nucleotides. In some instances, the one or more non-adenine nucleotides are located after at least 8-50 consecutive adenine nucleotides. In some embodiments, the one or more non-adenine nucleotides are located after at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive adenine nucleotides.

In some embodiments, the non-adenine nucleotide is guanine, cytosine, or thymine. In some instances, the non-adenine nucleotide is a guanine nucleotide. In some embodiments, the non-adenine nucleotide is a cytosine nucleotide. In some embodiments, the non-adenine nucleotide is a thymine nucleotide. In some instances, where more than one non-adenine nucleotide is present, the non-adenine nucleotide may be selected from: a) guanine and thymine nucleotides; b) guanine and cytosine nucleotides; c) thymine and cytosine nucleotides; or d) guanine, thymine and cytosine nucleotides. An exemplary poly-A tail comprising non-adenine nucleotides is provided as SEQ ID NO: 262.

g) Modified Nucleotides

In some embodiments, the nucleic acid comprising an ORF encoding an RNA-guided DNA-binding agent comprises a modified uridine at some or all uridine positions. In some embodiments, the modified uridine is a uridine modified at the 5 position, e.g., with a halogen or C1-C3 alkoxy. In some embodiments, the modified uridine is a pseudouridine modified at the 1 position, e.g., with a C1-C3 alkyl. The modified uridine can be, for example, pseudouridine, N1-methyl-pseudouridine, 5-methoxyuridine, 5-iodouridine, or a combination thereof. In some embodiments the modified uridine is 5-methoxyuridine. In some embodiments the modified uridine is 5-iodouridine. In some embodiments the modified uridine is pseudouridine. In some embodiments the modified uridine is N1-methyl-pseudouridine. In some embodiments, the modified uridine is a combination of pseudouridine and N1-methyl-pseudouridine. In some embodiments, the modified uridine is a combination of pseudouridine and 5-methoxyuridine. In some embodiments, the modified uridine is a combination of N1-methyl pseudouridine and 5-methoxyuridine. In some embodiments, the modified uridine is a combination of 5-iodouridine and N1-methyl-pseudouridine. In some embodiments, the modified uridine is a combination of pseudouridine and 5-iodouridine. In some embodiments, the modified uridine is a combination of 5-iodouridine and 5-methoxyuridine.

In some embodiments, at least 10%, 15%, 20%, 25%, 30%, 35%, 40%, 45%, 50%, 55%, 60%, 65%, 70%, 75%, 80%, 85%, 90%, 95%, 98%, 99%, or 100% of the uridine positions in the nucleic acid are modified uridines. In some embodiments, 10%-25%, 15-25%, 25-35%, 35-45%, 45-55%, 55-65%, 65-75%, 75-85%, 85-95%, or 90-100% of the uridine positions in the nucleic acid are modified uridines, e.g., 5-methoxyuridine, 5-iodouridine, N1-methyl pseudouridine, pseudouridine, or a combination thereof. In some embodiments, 10%-25%, 15-25%, 25-35%, 35-45%, 45-55%, 55-65%, 65-75%, 75-85%, 85-95%, or 90-100% of the uridine positions in the nucleic acid are 5-methoxyuridine. In some embodiments, 10%-25%, 15-25%, 25-35%, 35-45%, 45-55%, 55-65%, 65-75%, 75-85%, 85-95%, or 90-100% of the uridine positions in the nucleic acid are pseudouridine. In some embodiments, 10%-25%, 15-25%, 25-35%, 35-45%, 45-55%, 55-65%, 65-75%, 75-85%, 85-95%, or 90-100% of the uridine positions in the nucleic acid are N1-methyl pseudouridine. In some embodiments, 10%-25%, 15-25%, 25-35%, 35-45%, 45-55%, 55-65%, 65-75%, 75-85%, 85-95%, or 90-100% of the uridine positions in the nucleic acid are 5-iodouridine. In some embodiments, 10%-25%, 15-25%, 25-35%, 35-45%, 45-55%, 55-65%, 65-75%, 75-85%, 85-95%, or 90-100% of the uridine positions in the nucleic acid are 5-methoxyuridine, and the remainder are N1-methyl pseudouridine. In some embodiments, 10%-25%, 15-25%, 25-35%, 35-45%, 45-55%, 55-65%, 65-75%, 75-85%, 85-95%, or 90-100% of the uridine positions in the nucleic acid are 5-iodouridine, and the remainder are N1-methyl pseudouridine.

h) 5' Cap

In some embodiments, the nucleic acid (e.g., mRNA) comprising an ORF encoding an RNA-guided DNA-binding agent comprises a 5' cap, such as a Cap0, Cap1, or Cap2. A 5' cap is generally a 7-methylguanine ribonucleotide (which may be further modified, as discussed below e.g. with respect to ARCA) linked through a 5'-triphosphate to the 5' position of the first nucleotide of the 5'-to-3' chain of the nucleic acid, i.e., the first cap-proximal nucleotide. In Cap0, the riboses of the first and second cap-proximal nucleotides of the mRNA both comprise a 2'-hydroxyl. In Cap1, the riboses of the first and second transcribed nucleotides of the mRNA comprise a 2'-methoxy and a 2'-hydroxyl, respectively. In Cap2, the riboses of the first and second cap-proximal nucleotides of the mRNA both comprise a 2'-methoxy. See, e.g., Katibah et al. (2014) *Proc Natl Acad Sci USA* 111(33):12025-30; Abbas et al. (2017) *Proc Natl Acad Sci USA* 114(11):E2106-E2115. Most endogenous higher eukaryotic mRNAs, including mammalian nucleic acids such as human nucleic acids, comprise Cap1 or Cap2. Cap0 and other cap structures differing from Cap1 and Cap2 may be immunogenic in mammals, such as humans, due to recognition as "non-self" by components of the innate immune system such as IFIT-1 and IFIT-5, which can result in elevated cytokine levels including type I interferon. Components of the innate immune system such as IFIT-1 and IFIT-5 may also compete with eIF4E for binding of a nucleic acid with a cap other than Cap1 or Cap2, potentially inhibiting translation of the mRNA.

A cap can be included in an RNA co-transcriptionally. For example, ARCA (anti-reverse cap analog; Thermo Fisher Scientific Cat. No. AM8045) is a cap analog comprising a 7-methylguanine 3'-methoxy-5'-triphosphate linked to the 5' position of a guanine ribonucleotide which can be incorporated in vitro into a transcript at initiation. ARCA results in a Cap0 cap in which the 2' position of the first cap-proximal nucleotide is hydroxyl. See, e.g., Stepinski et al., (2001) "Synthesis and properties of mRNAs containing the novel 'anti-reverse' cap analogs 7-methyl(3'-O-methyl)GpppG and 7-methyl(3'deoxy)GpppG," RNA 7:1486-1495. The ARCA structure is shown below.

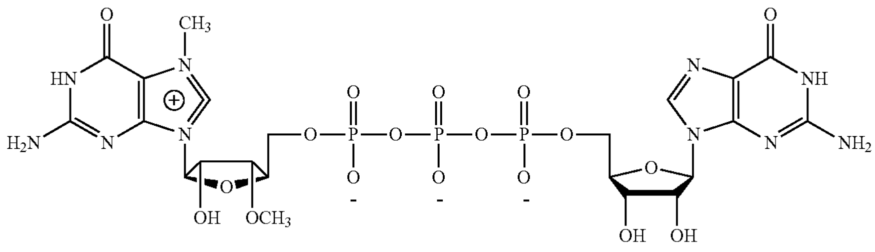

CleanCap™ AG (m7G(5')ppp(5')(2'OMeA)pG; TriLink Biotechnologies Cat. No. N-7113) or CleanCap™ GG (m7G(5')ppp(5')(2'OMeG)pG; TriLink Biotechnologies Cat. No. N-7133) can be used to provide a Cap1 structure co-transcriptionally. 3'-O-methylated versions of CleanCap™ AG and CleanCap™ GG are also available from TriLink Biotechnologies as Cat. Nos. N-7413 and N-7433, respectively. The CleanCap™ AG structure is shown below. CleanCap™ structures are sometimes referred to herein using the last three digits of the catalog numbers listed above (e.g., "CleanCap™ 113" for TriLink Biotechnologies Cat. No. N-7113).

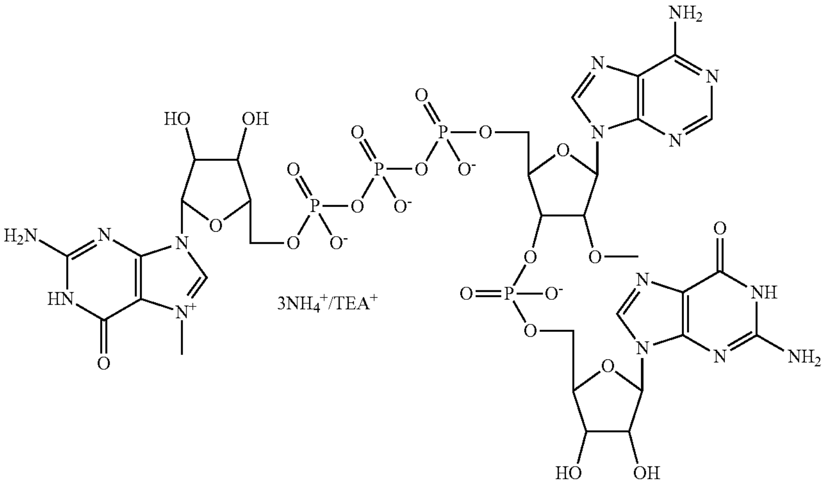 [SMILES: COC1C(OP(=O)([O-])OCC2OC(n3cnc4c(=O)[nH]c(N)nc43)C(O)C2O)C(COP(=O)([O-])OP(=O)([O-])OP(=O)([O-])OCC2OC(n3c[n+](C)c4c(=O)[nH]c(N)nc43)C(O)C2O)OC1n1cnc2c(N)ncnc21]

Alternatively, a cap can be added to an RNA post-transcriptionally. For example, Vaccinia capping enzyme is commercially available (New England Biolabs Cat. No. M2080S) and has RNA triphosphatase and guanylyltransferase activities, provided by its D1 subunit, and guanine methyltransferase, provided by its D12 subunit. As such, it can add a 7-methylguanine to an RNA, so as to give Cap0, in the presence of S-adenosyl methionine and GTP. See, e.g., Guo, P. and Moss, B. (1990) *Proc. Natl. Acad. Sci. USA* 87, 4023-4027; Mao, X. and Shuman, S. (1994) *J. Biol. Chem.* 269, 24472-24479. For additional discussion of caps and capping approaches, see, e.g., WO2017/053297 and Ishikawa et al., *Nucl. Acids. Symp. Ser.* (2009) No. 53, 129-130.

D. Determination of Efficacy of RNAs

In some embodiments, the efficacy of a gRNA is determined when delivered together with other components, e.g., a nucleic acid encoding an RNA-guided DNA binding agent such as any of those described herein. In some embodiments, the efficacy of a combination of a gRNA and a nucleic acid encoding an RNA-guided DNA binding agent is determined.

As described herein, use of an RNA-guided DNA nuclease and a guide RNA disclosed herein can lead to double-stranded breaks in the DNA which can produce errors in the form of insertion/deletion (indel) mutations upon repair by cellular machinery. Many mutations due to indels alter the reading frame or introduce premature stop codons and, therefore, produce a non-functional protein.

In some embodiments, the efficacy of particular gRNAs or combinations is determined based on in vitro models. In some embodiments, the in vitro model is HEK293 cells. In some embodiments, the in vitro model is HUH7 human hepatocarcinoma cells. In some embodiments, the in vitro model is HepG2 cells. In some embodiments, the in vitro model is primary human hepatocytes. In some embodiments, the in vitro model is primary cynomolgus hepatocytes. With respect to using primary human hepatocytes, commercially available primary human hepatocytes can be used to provide greater consistency between experiments. In some embodiments, the number of off-target sites at which a deletion or insertion occurs in an in vitro model (e.g., in primary human hepatocytes) is determined, e.g., by analyzing genomic DNA from primary human hepatocytes transfected in vitro with Cas9 mRNA and the guide RNA. In some embodiments, such a determination comprises analyzing genomic DNA from primary human hepatocytes transfected in vitro with Cas9 mRNA, the guide RNA, and a donor oligonucleotide. Exemplary procedures for such determinations are provided in the working examples below.

In some embodiments, the efficacy of particular gRNAs or combinations is determined across multiple in vitro cell models for a gRNA selection process. In some embodiments, a cell line comparison of data with selected gRNAs is performed. In some embodiments, cross screening in multiple cell models is performed.

In some embodiments, the efficacy of particular gRNAs or combinations is determined based on in vivo models. In some embodiments, the in vivo model is a rodent model. In some embodiments, the rodent model is a mouse which expresses a human TTR gene, which may be a mutant human TTR gene. In some embodiments, the in vivo model is a non-human primate, for example cynomolgus monkey.

In some embodiments, the efficacy of a guide RNA or combination is measured by percent editing of TTR. In some embodiments, the percent editing of TTR is compared to the percent editing necessary to achieve knockdown of TTR protein, e.g., in the cell culture media in the case of an in vitro model or in serum or tissue in the case of an in vivo model.

In some embodiments, the efficacy of a guide RNA or combination is measured by the number and/or frequency of indels at off-target sequences within the genome of the target cell type. In some embodiments, efficacious guide RNAs and combinations are provided which produce indels at off target sites at very low frequencies (e.g., <5%) in a cell population and/or relative to the frequency of indel creation at the target site. Thus, the disclosure provides for guide RNAs which do not exhibit off-target indel formation in the target cell type (e.g., a hepatocyte), or which produce a frequency of off-target indel formation of <5% in a cell population and/or relative to the frequency of indel creation at the target site. In some embodiments, the disclosure provides guide RNAs and combinations which do not exhibit any off target indel formation in the target cell type (e.g., hepatocyte). In some embodiments, guide RNAs and combinations are provided which produce indels at less than 5 off-target sites, e.g., as evaluated by one or more methods described herein. In some embodiments, guide RNAs and combinations are provided which produce indels at less than or equal to 4, 3, 2, or 1 off-target site(s) e.g., as evaluated by one or more methods described herein. In some embodiments, the off-target site(s) does not occur in a protein coding region in the target cell (e.g., hepatocyte) genome.

In some embodiments, detecting gene editing events, such as the formation of insertion/deletion ("indel") mutations and homology directed repair (HDR) events in target DNA utilize linear amplification with a tagged primer and isolating the tagged amplification products (herein after referred to as "LAM-PCR," or "Linear Amplification (LA)" method), as described in WO2018/067447 or Schmidt et al., Nature Methods 4:1051-1057 (2007).

In some embodiments, detecting gene editing events, such as the formation of insertion/deletion ("indel") mutations and homology directed repair (HDR) events in target DNA, further comprises sequencing the linear amplified products or the further amplified products. Sequencing may comprise any method known to those of skill in the art, including, next generation sequencing, and cloning the linear amplification products or further amplified products into a plasmid and sequencing the plasmid or a portion of the plasmid. Exemplary next generation sequencing methods are discussed, e.g., in Shendure et al., Nature 26:1135-1145 (2008). In other aspects, detecting gene editing events, such as the formation of insertion/deletion ("indel") mutations and homology directed repair (HDR) events in target DNA, further comprises performing digital PCR (dPCR) or droplet digital PCR (ddPCR) on the linear amplified products or the further amplified products, or contacting the linear amplified products or the further amplified products with a nucleic acid probe designed to identify DNA comprising HDR template sequence and detecting the probes that have bound to the linear amplified product(s) or further amplified product(s). In some embodiments, the method further comprises determining the location of the HDR template in the target DNA.

In certain embodiments, the method further comprises determining the sequence of an insertion site in the target DNA, wherein the insertion site is the location where the HDR template incorporates into the target DNA, and wherein the insertion site may include some target DNA sequence and some HDR template sequence.

In some embodiments, the efficacy of a guide RNA or combination is measured by secretion of TTR. In some embodiments, secretion of TTR is measured using an enzyme-linked immunosorbent assay (ELISA) assay with cell culture media or serum. In some embodiments, secretion of TTR is measured in the same in vitro or in vivo systems or models used to measure editing. In some embodiments, secretion of TTR is measured in primary human hepatocytes. In some embodiments, secretion of TTR is measured in HUH7 cells. In some embodiments, secretion of TTR is measured in HepG2 cells.

ELISA assays are generally known to the skilled artisan and can be designed to determine serum TTR levels. In one exemplary embodiment, blood is collected and the serum is isolated. The total TTR serum levels may be determined using a Mouse Prealbumin (Transthyretin) ELISA Kit (Aviva Systems Biology, Cat. OKIA00111) or similar kit for measuring human TTR. If no kit is available, an ELISA can be developed using plates that are pre-coated with capture antibody specific for the TTR one is measuring. The plate is next incubated at room temperature for a period of time before washing. Enzyme-anti-TTR antibody conjugate is added and incubated. Unbound antibody conjugate is removed and the plate washed before the addition of the chromogenic substrate solution that reactes with the enzyme. The plate is read on an appropriate plate reader at an absorbance specific for the enzyme and substrate used.

In some embodiments, the amount of TTR in cells (including those from tissue) measures efficacy of a gRNA or combination. In some embodiments, the amount of TTR in cells is measured using western blot. In some embodiments, the cell used is HUH7 cells. In some embodiments, the cell used is a primary human hepatocyte. In some embodiments, the cell used is a primar cell obtained from an animal. In some embodiments, the amount of TTR is compared to the amount of glyceraldehyde 3-phosphate dehydrogenase GAPDH (a housekeeping gene) to control for changes in cell number.

III. LNP formulations and Treatment of ATTR

In some embodiments, a method of inducing a double-stranded break (DSB) within the 7TR gene is provided comprising administering a composition comprising a guide RNA as described herein, e.g. comprising any one or more guide sequences of SEQ ID Nos: 5-82, or any one or more of the sgRNAs of SEQ ID Nos: 87-124. In some embodiments, gRNAs comprising any one or more of the guide sequences of SEQ ID Nos: 5-82 are administered to induce a DSB in the TTR gene. The guide RNA is administered together with a nucleic acid (e.g., mRNA) or vector described herein encoding an RNA-guided DNA nuclease such as a Cas nuclease (e.g., Cas9). The RNA-guided DNA nuclease may be an *S. pyogenes* Cas9. In particular embodiments, the guide RNA is chemically modified. In some embodiments, the guide RNA and the nucleic acid encoding an RNA-guided DNA nuclease are administered in an LNP described herein, such as an LNP comprising a CCD lipid (e.g., an amine lipid, such as lipid A), a helper lipid (e.g., cholesterol), a stealth lipid (e.g., a PEG lipid, such as PEG2k-DMG), and optionally a neutral lipid (e.g., DSPC).

In some embodiments, a method of inducing a double-stranded break (DSB) within the TTR gene is provided comprising administering a composition comprising a guide RNA, such as a chemically modified guide RNA, comprising any one or more guide sequences of SEQ ID NOs: 5-72, 74-78, and 80-82, or any one or more of the sgRNAs of SEQ ID Nos: 87-113, 115-120, and 122-124. In some embodiments, any one or more of the sgRNAs of SEQ ID Nos: 87-113, 115-120, and 122-124 or gRNAs comprising any one or more of the guide sequences of SEQ ID NOs: 5-72, 74-78, and 80-82 are administered to induce a DSB in the TTR gene. The guide RNA is administered together with a nucleic acid or vector described herein encoding an RNA-guided DNA nuclease such as a Cas nuclease (e.g., Cas9). The RNA-guided DNA nuclease may be an *S. pyogenes* Cas9. In particular embodiments, the guide RNA is chemically modified. In some embodiments, the guide RNA and the nucleic acid encoding an RNA-guided DNA nuclease are administered in an LNP described herein, such as an LNP comprising a CCD lipid (e.g., an amine lipid, such as lipid A), a helper lipid (e.g., cholesterol), a stealth lipid (e.g., a PEG lipid, such as PEG2k-DMG), and optionally a neutral lipid (e.g., DSPC).

In some embodiments, a method of modifying the TTR gene is provided comprising administering a composition comprising a guide RNA as described herein, e.g. comprising any one or more of the guide sequences of SEQ ID Nos: 5-82, or any one or more of the sgRNAs of SEQ ID Nos: 87-124. In some embodiments, gRNAs comprising any-one or more of the guide sequences of SEQ ID Nos: 5-82, or any one or more of the sgRNAs of SEQ ID Nos: 87-124, are administered to modify the TTR gene. The guide RNA is administered together with a nucleic acid or vector described herein encoding an RNA-guided DNA nuclease such as a Cas nuclease (e.g., Cas9). The RNA-guided DNA nuclease may be an *S. pyogenes* Cas9. In particular embodiments, the guide RNA is chemically modified. In some embodiments, the guide RNA and the nucleic acid encoding an RNA-guided DNA nuclease are administered in an LNP described herein, such as an LNP comprising a CCD lipid (e.g., an amine lipid, such as lipid A), a helper lipid (e.g., cholesterol), a stealth lipid (e.g., a PEG lipid, such as PEG2k-DMG), and optionally a neutral lipid (e.g., DSPC).

In some embodiments, a method of modifying the TTR gene is provided comprising administering a composition comprising a guide RNA comprising any one or more of the guide sequences of SEQ ID NOs: 5-72, 74-78, and 80-82, or any one or more of the sgRNAs of SEQ ID Nos: 87-113, 115-120, and 122-124. In some embodiments, gRNAs comprising any one or more of the guide sequences of SEQ ID NOs: 5-72, 74-78, and 80-82, or any one or more of the sgRNAs of SEQ ID Nos: 87-113, 115-120, and 122-124, are administered to modify the TTR gene. The guide RNA is administered together with a nucleic acid or vector described herein encoding an RNA-guided DNA nuclease such as a Cas nuclease (e.g., Cas9). The RNA-guided DNA nuclease may be an *S. pyogenes* Cas9. In particular embodiments, the guide RNA is chemically modified. In some embodiments, the guide RNA and the nucleic acid encoding an RNA-guided DNA nuclease are administered in an LNP described herein, such as an LNP comprising a CCD lipid (e.g., an amine lipid, such as lipid A), a helper lipid (e.g., cholesterol), a stealth lipid (e.g., a PEG lipid, such as PEG2k-DMG), and optionally a neutral lipid (e.g., DSPC).

In some embodiments, a method of treating ATTR is provided comprising administering a composition comprising a guide RNA as described herein, e.g. comprising any one or more of the guide sequences of SEQ ID NOs: 5-82, or any one or more of the sgRNAs of SEQ ID Nos: 87-124. In some embodiments, gRNAs comprising any one or more of the guide sequences of SEQ ID NOs: 5-82, or any one or more of the sgRNAs of SEQ ID Nos: 87-124 are administered to treat ATTR. The guide RNA is administered together with a nucleic acid or vector described herein encoding an RNA-guided DNA nuclease such as a Cas nuclease (e.g., Cas9). The RNA-guided DNA nuclease may be an *S. pyogenes* Cas9. In particular embodiments, the guide RNA is chemically modified. In some embodiments, the guide RNA and the nucleic acid encoding an RNA-guided DNA nuclease are administered in an LNP described herein, such as an LNP comprising a CCD lipid (e.g., an amine lipid, such as lipid A), a helper lipid (e.g., cholesterol), a stealth lipid (e.g., a PEG lipid, such as PEG2k-DMG), and optionally a neutral lipid (e.g., DSPC).

In some embodiments, a method of treating ATTR is provided comprising administering a composition comprising a guide RNA comprising any one or more of the guide sequences of SEQ ID NOs: 5-72, 74-78, and 80-82, or any one or more of the sgRNAs of SEQ ID Nos: 87-113, 115-120, and 122-124. In some embodiments, gRNAs comprising any one or more of the guide sequences of SEQ ID NOs: 5-72, 74-78, and 80-82, or any one or more of the sgRNAs of SEQ ID Nos: 87-113, 115-120, and 122-124 are administered to treat ATTR. The guide RNA is administered together with a nucleic acid or vector described herein encoding an RNA-guided DNA nuclease such as a Cas nuclease (e.g., Cas9). The RNA-guided DNA nuclease may be an *S. pyogenes* Cas9. In particular embodiments, the guide RNA is chemically modified. In some embodiments, the guide RNA and the nucleic acid encoding an RNA-guided DNA nuclease are administered in an LNP described herein, such as an LNP comprising a CCD lipid (e.g., an amine lipid, such as lipid A), a helper lipid (e.g., cholesterol), a stealth lipid (e.g., a PEG lipid, such as PEG2k-DMG), and optionally a neutral lipid (e.g., DSPC).

In some embodiments, a method of reducing TTR serum concentration is provided comprising administering a guide RNA as described herein, e.g. comprising any one or more of the guide sequences of SEQ ID NOs: 5-82, or any one or more of the sgRNAs of SEQ ID Nos: 87-124. In some embodiments, gRNAs comprising any one or more of the guide sequences of SEQ ID NOs: 5-82 or any one or more of the sgRNAs of SEQ ID Nos: 87-124 are administered to reduce or prevent the accumulation of TTR in amyloids or amyloid fibrils. The gRNA is administered together with a nucleic acid or vector described herein encoding an RNA-guided DNA nuclease such as a Cas nuclease (e.g., Cas9). The RNA-guided DNA nuclease may be an *S. pyogenes* Cas9. In particular embodiments, the guide RNA is chemically modified. In some embodiments, the guide RNA and the nucleic acid encoding an RNA-guided DNA nuclease are administered in an LNP described herein, such as an LNP comprising a CCD lipid (e.g., an amine lipid, such as lipid A), a helper lipid (e.g., cholesterol), a stealth lipid (e.g., a PEG lipid, such as PEG2k-DMG), and optionally a neutral lipid (e.g., DSPC).

In some embodiments, a method of reducing TTR serum concentration is provided comprising administering a guide RNA as described herein, e.g., comprising any one or more of the guide sequences of SEQ ID NOs: 5-72, 74-78, and 80-82, or any one or more of the sgRNAs of SEQ ID Nos: 87-113, 115-120, and 122-124. In some embodiments, gRNAs comprising any one or more of the guide sequences of SEQ ID NOs: 5-72, 74-78, and 80-82, or any one or more of the sgRNAs of SEQ ID Nos: 87-113, 115-120, and 122-124 are administered to reduce or prevent the accumulation of TTR in amyloids or amyloid fibrils. The gRNA is administered together with a nucleic acid or vector described herein encoding an RNA-guided DNA nuclease such as a Cas nuclease (e.g., Cas9). The RNA-guided DNA nuclease may be an *S. pyogenes* Cas9. In particular embodiments, the guide RNA is chemically modified. In some embodiments, the guide RNA and the nucleic acid encoding an RNA-guided DNA nuclease are administered in an LNP described herein, such as an LNP comprising a CCD lipid (e.g., an amine lipid, such as lipid A), a helper lipid (e.g., cholesterol), a stealth lipid (e.g., a PEG lipid, such as PEG2k-DMG), and optionally a neutral lipid (e.g., DSPC).

In some embodiments, a method of reducing or preventing the accumulation of TTR in amyloids or amyloid fibrils of a subject is provided comprising administering a composition comprising a guide RNA as described herein, e.g. comprising any one or more of the guide sequences of SEQ ID NOs: 5-82, or any one or more of the sgRNAs of SEQ ID Nos: 87-124. In some embodiments, a method of reducing or preventing the accumulation of TTR in amyloids or amyloid fibrils of a subject is provided comprising administering a composition comprising any one or more of the sgRNAs of SEQ ID Nos: 87-113. In some embodiments, gRNAs comprising any one or more of the guide sequences of SEQ ID NOs: 5-82 or any one or more of the sgRNAs of SEQ ID Nos: 87-124 are administered to reduce or prevent the accumulation of TTR in amyloids or amyloid fibrils. The gRNA is administered together with a nucleic acid or vector described herein encoding an RNA-guided DNA nuclease such as a Cas nuclease (e.g., Cas9). The RNA-guided DNA nuclease may be an *S. pyogenes* Cas9. In particular embodiments, the guide RNA is chemically modified. In some embodiments, the guide RNA and the nucleic acid encoding an RNA-guided DNA nuclease are administered in an LNP described herein, such as an LNP comprising a CCD lipid (e.g., an amine lipid, such as lipid A), a helper lipid (e.g., cholesterol), a stealth lipid (e.g., a PEG lipid, such as PEG2k-DMG), and optionally a neutral lipid (e.g., DSPC).

In some embodiments, a method of reducing or preventing the accumulation of TTR in amyloids or amyloid fibrils of a subject is provided comprising administering a composition comprising a guide RNA as described herein, e.g. comprising any one or more of the guide sequences of SEQ ID NOs: 5-72, 74-78, and 80-82, or any one or more of the sgRNAs of SEQ ID Nos: 87-124. In some embodiments, a method of reducing or preventing the accumulation of TTR in amyloids or amyloid fibrils of a subject is provided comprising administering a composition comprising any one or more of the sgRNAs of SEQ ID Nos: 87-113, 115-120, and 122-124. In some embodiments, gRNAs comprising any one or more of the guide sequences of SEQ ID NOs: 5-72, 74-78, and 80-82 or any one or more of the sgRNAs of SEQ ID Nos: 87-113, 115-120, and 122-124 are administered to reduce or prevent the accumulation of TTR in amyloids or amyloid fibrils. The gRNA is administered together with a nucleic acid or vector described herein encoding an RNA-guided DNA nuclease such as a Cas nuclease (e.g., Cas9). The RNA-guided DNA nuclease may be an *S. pyogenes* Cas9. In particular embodiments, the guide RNA is chemically modified. In some embodiments, the guide RNA and the nucleic acid encoding an RNA-guided DNA nuclease are administered in an LNP described herein, such as an LNP comprising a CCD lipid (e.g., an amine lipid, such as lipid A), a helper lipid (e.g., cholesterol), a stealth lipid (e.g., a PEG lipid, such as PEG2k-DMG), and optionally a neutral lipid (e.g., DSPC).

In some embodiments, the gRNA comprising a guide sequence of Table 1 or one or more sgRNAs from Table 2 together with an RNA-guided DNA nuclease such as a Cas nuclease translated from the nucleic acid induce DSBs, and non-homologous ending joining (NHEJ) during repair leads to a mutation in the TTR gene. In some embodiments, NHEJ leads to a deletion or insertion of a nucleotide(s), which induces a frame shift or nonsense mutation in the TTR gene.

In some embodiments, administering the guide RNA and nucleic acid encoding an RNA-guided DNA binding agent (e.g., in a composition provided herein) reduces levels (e.g., serum levels) of TTR in the subject, and therefore prevents accumulation and aggregation of TTR in amyloids or amyloid fibrils.

In some embodiments, reducing or preventing the accumulation of TTR in amyloids or amyloid fibrils of a subject comprises reducing or preventing TTR deposition in one or more tissues of the subject, such as stomach, colon, or nervous tissue. In some embodiments, the nervous tissue comprises sciatic nerve or dorsal root ganglion. In some embodiments, TTR deposition is reduced in two, three, or four of the stomach, colon, dorsal root ganglion, and sciatic nerve. The level of deposition in a given tissue can be determined using a biopsy sample, e.g., using immunostaining. In some embodiments, reducing or preventing the accumulation of TTR in amyloids or amyloid fibrils of a subject and/or reducing or preventing TTR deposition is inferred based on reducing serum TTR levels for a period of time. As discussed in the examples, it has been found that reducing serum TTR levels in accordance with methods and uses provided herein can result in clearance of deposited TTR from tissues such as those discussed above and in the examples, e.g., as measured 8 weeks after administration of the composition.

In some embodiments, the subject is mammalian. In some embodiments, the subject is human. In some embodiments, the subject is cow, pig, monkey, sheep, dog, cat, fish, or poultry.

In some embodiments, the use of one or more guide RNAs as described herein, e.g. comprising any one or more of the guide sequences in Table 1 or one or more sgRNAs from Table 2 (e.g., in a composition provided herein) and of a nucleic acid (e.g. mRNA) described herein encoding an RNA-guided DNA-binding agent is provided for the preparation of a medicament for treating a human subject having ATTR. The RNA-guided DNA-binding agent may be a Cas9, e.g. an *S. pyogenes* Cas9. In particular embodiments, the guide RNA is chemically modified.

In some embodiments, the composition comprising the guide RNA and nucleic acid is administered intravenously. In some embodiments, the composition comprising the guide RNA and nucleic acid is administered into the hepatic circulation.

In some embodiments, a single administration of a composition comprising a guide RNA and nucleic acid provided herein is sufficient to knock down expression of the mutant protein. In some embodiments, a single administration of a composition comprising a guide RNA and nucleic acid provided herein is sufficient to knock out expression of the mutant protein in a population of cells. In other embodiments, more than one administration of a composition comprising a guide RNA and nucleic acid provided herein may be beneficial to maximize editing via cumulative effects. For example, a composition provided herein can be administered 2, 3, 4, 5, or more times, such as 2 times. Administrations can be separated by a period of time ranging from, e.g., 1 day to 2 years, such as 1 to 7 days, 7 to 14 days, 14 days to 30 days, 30 days to 60 days, 60 days to 120 days, 120 days to 183 days, 183 days to 274 days, 274 days to 366 days, or 366 days to 2 years.

In some embodiments, a composition is administered in an effective amount in the range of 0.01 to 10 mg/kg (mpk), e.g., 0.01 to 0.1 mpk, 0.1 to 0.3 mpk, 0.3 to 0.5 mpk, 0.5 to 1 mpk, 1 to 2 mpk, 2 to 3 mpk, 3 to 5 mpk, 5 to 10 mpk, or 0.1, 0.2, 0.3, 0.5, 1, 2, 3, 5, or 10 mpk. In some embodiments, a composition is administered in the amount of 2-4 mg/kg, such as 2.5-3.5 mg/kg. In some embodiments, a composition is administered in the amount of about 3 mg/kg.

In some embodiments, the efficacy of treatment with the compositions of the invention is seen at 1 year, 2 years, 3 years, 4 years, 5 years, or 10 years after delivery. In some embodiments, efficacy of treatment with the compositions of the invention is assessed by measuring serum levels of TTR before and after treatment. In some embodiments, efficacy of treatment with the compositions assessed via a reduction of serum levels of TTR is seen at 1 week, 2 weeks, 3 weeks, 4 weeks, 2 months, 3 months, 4 months, 5 months, 6 months, 7 months, 8 months, 9 months, 10 months, or at 11 months.

In some embodiments, treatment slows or halts disease progression.

In some embodiments, treatment slows or halts progression of FAP. In some embodiments, treatment results in improvement, stabilization, or slowing of change in symptoms of sensorimotor neuropathy or autonomic neuropathy.

In some embodiments, treatment results in improvement, stabilization, or slowing of change in symptoms of FAC. In some embodiments, treatment results in improvement, stabilization, or slowing of change symptoms of restrictive cardiomyopathy or congestive heart failure.

In some embodiments, efficacy of treatment is measured by increased survival time of the subject.

In some embodiments, efficacy of treatment is measured by improvement or slowing of progression in symptoms of sensorimotor or autonomic neuropathy. In some embodiments, efficacy of treatment is measured by an increase or a slowing of decrease in ability to move an area of the body or to feel in any area of the body. In some embodiments, efficacy of treatment is measured by improvement or a slowing of decrease in the ability to swallow; breath; use arms, hands, legs, or feet; or walk. In some embodiments, efficacy of treatment is measured by improvement or a slowing of progression of neuralgia. In some embodiments, the neuralgia is characterized by pain, burning, tingling, or abnormal feeling. In some embodiments, efficacy of treatment is measured by improvement or a slowing of increase in postural hypotension, dizziness, gastrointestinal dysmotility, bladder dysfunction, or sexual dysfunction. In some embodiments, efficacy of treatment is measured by improvement or a slowing of progression of weakness. In some embodiments, efficacy of treatment is measured using electromyogram, nerve conduction tests, or patient-reported outcomes.

In some embodiments, efficacy of treatment is measured by improvement or slowing of progression of symptoms of congestive heart failure or CHF. In some embodiments, efficacy of treatment is measured by an decrease or a slowing of increase in shortness of breath, trouble breathing, fatigue, or swelling in the ankles, feet, legs, abdomen, or veins in the neck. In some embodiments, efficacy of treatment is measured by improvement or a slowing of progression of fluid buildup in the body, which may be assessed by measures such as weight gain, frequent urination, or nighttime cough. In some embodiments, efficacy of treatment is measured using cardiac biomarker tests (such as B-type natriuretic peptide [BNP] or N-terminal pro b-type natriuretic peptide [NT-proBNP]), lung function tests, chest x-rays, or electrocardiography.

A. Combination Therapy

In some embodiments, the invention comprises combination therapies comprising administering any one of the gRNAs as described herein, e.g., comprising any one or more of the guide sequences disclosed in Table 1 or any one or more of the sgRNAs in Table 2 and a nucleic acid encoding an RNA-guided DNA-binding agent (e.g., in a composition provided herein) as described herein, such as a nucleic acid (e.g. mRNA) or vector described herein encoding an *S. pyogenes* Cas9, together with an additional therapy suitable for alleviating symptoms of ATTR. In particular embodiments, the guide RNA is chemically modified. In some embodiments, the guide RNA and the nucleic acid encoding an RNA-guided DNA nuclease are administered in an LNP described herein, such as an LNP comprising a CCD lipid (e.g., an amine lipid, such as lipid A), a helper lipid (e.g., cholesterol), a stealth lipid (e.g., a PEG lipid, such as PEG2k-DMG), and optionally a neutral lipid (e.g., DSPC).

In some embodiments, the additional therapy for ATTR is a treatment for sensorimotor or autonomic neuropathy. In some embodiments, the treatment for sensorimotor or autonomic neuropathy is a nonsteroidal anti-inflammatory drug, antidepressant, anticonvulsant medication, antiarrythmic medication, or narcotic agent. In some embodiments, the antidepressant is a tricylic agent or a serotonin-norepinephrine reuptake inhibitor. In some embodiments, the antidepressant is amitriptyline, duloxetine, or venlafaxine. In some embodiments, the anticonvulsant agent is gabapentin, pregabalin, topiramate, or carbamazepine. In some embodiments, the additional therapy for sensorimotor neuropathy is transcutaneous electrical nerve stimulation.

In some embodiments, the additional therapy for ATTR is a treatment for restrictive cardiomyopathy or congestive heart failure (CHF). In some embodiments, the treatment for CHF is a ACE inhibitor, aldosterone antagonist, angiotensin receptor blocker, beta blocker, digoxin, diuretic, or isosorbide dinitrate/hydralazine hydrochloride. In some embodiments, the ACE inhibitor is enalapril, captopril, ramipril, perindopril, imidapril, or quinapril. In some embodiments, the aldosterone antagonist is eplerenone or spironolactone. In some embodiments, the angiotensin receptor blocker is azilsartan, cadesartan, eprosartan, irbesartan, losartan, olmesartan, telmisartan, or valsartan. In some embodiments, the beta blocker is acebutolol, atenolol, bisoprolol, metoprolol, nadolol, nebivolol, or propranolol. In some embodiments, the diuretic is chlorothiazide, chlorthalidone, hydrochlorothiazide, indapamide, metolazone, bumetanide, furosemide, torsemide, amiloride, or triameterene.

In some embodiments, the combination therapy comprises administering any one of the gRNAs comprising any one or more of the guide sequences disclosed in Table 1 or any one or more of the sgRNAs in Table 2 and a nucleic acid encoding an RNA-guided DNA-binding agent (e.g., in a composition provided herein) together with a siRNA that targets TTR or mutant TTR. In some embodiments, the siRNA is any siRNA capable of further reducing or eliminating the expression of wild type or mutant TTR. In some embodiments, the siRNA is the drug Patisiran (ALN-TTR02) or ALN-TTRsc02. In some embodiments, the siRNA is administered after any one of the gRNAs comprising any one or more of the guide sequences disclosed in Table 1 or any one or more of the sgRNAs in Table 2 (e.g., in a composition provided herein). In some embodiments, the siRNA is administered on a regular basis following treatment with any of the gRNA compositions provided herein.

In some embodiments, the combination therapy comprises administering any one of the gRNAs comprising any one or more of the guide sequences described herein, e.g., disclosed in Table 1 or any one or more of the sgRNAs in Table 2 and a nucleic acid encoding an RNA-guided DNA-binding agent described herein (e.g., in a composition provided herein) together with antisense nucleotide that targets TTR or mutant TTR. In some embodiments, the antisense nucleotide is any antisense nucleotide capable of further reducing or eliminating the expression of wild type or mutant TTR. In some embodiments, the antisense nucleotide is the drug Inotersen (IONS-$TTR_{Rx}$). In some embodiments, the antisense nucleotide is administered after any one of the gRNAs comprising any one or more of the guide sequences disclosed in Table 1 or any one or more of the sgRNAs in Table 2 and a nucleic acid encoding an RNA-guided DNA-binding agent (e.g., in a composition provided herein). In some embodiments, the antisense nucleotide is administered on a regular basis following treatment with any of the gRNA compositions provided herein.

In some embodiments, the combination therapy comprises administering any one of the gRNAs comprising any one or more of the guide sequences disclosed in Table 1 or any one or more of the sgRNAs in Table 2 and a nucleic acid encoding an RNA-guided DNA-binding agent (e.g., in a composition provided herein) together with a small molecule stabilizer that promotes kinetic stabilization of the correctly folded tetrameric form of TTR. In some embodiments, the small molecule stabilizer is the drug tafamidis (Vyndagel®) or diflunisal. In some embodiments, the small molecule stabilizer is administered after any one of the gRNAs comprising any one or more of the guide sequences disclosed in Table 1 or any one or more of the sgRNAs in Table 2 (e.g., in a composition provided herein). In some embodiments, the small molecule stabilizer is administered on a regular basis following treatment with any of the compositions provided herein.

In any of the foregoing embodiments, the guide sequences disclosed in Table 1 may be selected from SEQ ID NOs: 5-72, 74-78, and 80-82, and/or the sgRNAs in Table 2 may be selected from SEQ ID Nos: 87-113, 115-120, and 122-124, and/or the guide RNA may be a chemically modified guide RNA.

In some embodiments, a method described herein comprises infusion prophylaxis. In some embodiments, an infusion prophylaxis is administered to a subject before the gene editing composition. In some embodiments, an infusion prophylaxis is administered to a subject 8-24 hours or 1-2 hours prior to the administration of the nucleic acid composition. In some embodiments, an infusion prophylaxis comprises corticosteroid. In some embodiments, the infusion prophylaxis comprises one or more, or all, of corticosteroid, an antipyretic (e.g. oral acetaminophen (also called paracetamol), which may reduce pain and fever and/or inhibit COX enzymes and/or prostaglandins), H1 blocker, or H2 blocker. In some embodiments, the infusion prophylaxis comprises an intravenous corticosteroid (e.g., dexamethasone 8-12 mg, such as 10 mg or equivalent) and an antipyretic (e.g. oral acetaminophen or paracetamol 500 mg). In some embodiments, the H1 blocker (e.g., diphenhydramine 50 mg or equivalent) and/or H2 blocker (e.g., ranitidine 50 mg or equivalent) are administered orally. In some embodiments, the H1 blocker (e.g., diphenhydramine 50 mg or equivalent) and/or H2 blocker (e.g., ranitidine 50 mg or equivalent) are administered intravenously. In some embodiments, an infusion prophylaxis is administered intravenously 1-2 hour before infusion of the nucleic acid composition. In some embodiments an intravenous H1 blocker and/or an intravenous H2 blocker is substituted with an oral equivalent. The infusion prophylaxis may function to reduce adverse reactions associated with administering the nucleic acid composition. In some embodiments, the infusion prophylaxis is administered as a required premedication prior to administering the nucleic acid composition. The dosage, frequency and mode of administration of the corticosteroid; infusion prophylaxis, and the guide-RNA containing composition described herein can be controlled independently.

The corticosteroid used in the disclosed methods may be administered according to regimens known in the art, e.g., US FDA-approved regimens. In some embodiments, e.g., comprising administration to or for use in a human subject, the corticosteroid can be administered in an amount that ranges from about 0.75 mg to about 25 mg. In some embodiments, e.g., comprising administration to or for use in a human subject, the corticosteroid can be administered in an amount that ranges from about 0.01-0.5 mg/kg, such as 0.1-0.40 mg/kg or 0.25-0.40 mg/kg.

In some embodiments, the corticosteroid is administered before the guide RNA-containing composition described herein. In some embodiments, the corticosteroid is administered after the guide RNA-containing composition described herein. In some embodiments, the corticosteroid is administered simultaneously with the guide RNA-containing composition described herein. In some embodiments, multiple doses of the corticosteroid are administered before or after the administration of the guide RNA-containing composition. In some embodiments, multiple doses of the guide RNA-containing composition are administered before or after the administration of the corticosteroid. In some embodiments, multiple doses of the corticosteroid and multiple doses of the guide RNA-containing composition are administered.

If appropriate, a dose of corticosteroid may be administered as at least two sub-doses administered separately at appropriate intervals. In some embodiments, the corticosteroid is administered at least two times before the administration of the guide RNA-containing composition described herein. In some embodiments, a dose of corticosteroid is administered at least two times after the administration of the guide RNA-containing composition described herein. In some embodiments, the corticosteroid is administered (e.g., before, with, and/or after the administration of the guide RNA-containing composition described herein) at an interval of 1 hour, 2 hours, 3 hours, 4 hours, 6 hours, 12 hours, 18 hours; 1, 2, 3, 4, 5, 6, 7, 8, 9, 10, 11, 12, 13, 14, or 15 days; 3, 4, 5, 6, 7, 8, 9, 10, 11, 12, 13, 14, or 15 weeks; or an amount of time in a range bounded by any two of the preceding values. In some embodiments; the corticosteroid is administered before the administration of the guide RNA-containing composition described herein at an interval of 1 hour, 2 hours, 3 hours, 4 hours, 6 hours, 12 hours, 18 hours; 1, 2, 3, 4, 5, 6, 7, 8, 9, 10, 11, 12, 13, 14, 15 days; 3, 4, 5, 6, 7, 8, 9, 10, 11, 12, 13, 14, or 15 weeks; or an amount of time in a range bounded by any two of the preceding values. In some embodiments, the corticosteroid is administered after the administration of the guide RNA-containing composition described herein at an interval of 1 hour, 2 hours, 3 hours, 4 hours, 6 hours, 12 hours, 18 hours; 1, 2, 3, 4, 5, 6, 7, 8, 9, 10, 11, 12, 13, 14, 15 days; 3, 4, 5, 6, 7, 8, 9, 10, 11, 12, 13, 14, or 15 weeks; or an amount of time in a range bounded by any two of the preceding values.

In some embodiments, the corticosteroid is administered at least two times. In some embodiments, the corticosteroid is administered is administered at least three times. In some embodiments, the corticosteroid is administered at least four times. In some embodiments, the corticosteroid is administered is up to five, six, seven, eight, nine, or ten times. A first dose may be oral and a second or subsequent dose may be by parenteral administration, e.g. infusion. Alternatively, a first dose may be perenteral and a second or subsequent dose may be by oral administration.

In some embodiments, the corticosteroid is administered orally before intravenous administration of a guide RNA-containing composition described herein. In some embodiments, the corticosteroid is administered orally at or after intravenous administration of a guide RNA-containing composition described herein.

In some embodiments, corticosteroid is dexamethasone. In some embodiments, dexamethasone is administered intravenously 1-2 hour before infusion of the nucleic acid composition. In some embodiments, dexamethasone is administered intravenously in the amount of 8-12 mg, such as 10 mg, 1-2 hour before infusion of the nucleic acid composition. In some embodiments, dexamethasone is administered orally 8 to 24 hours before infusion of the nucleic acid composition. In some embodiments, dexamethasone is administered orally in the amount of 8-12 mg, such as 8 mg, 8 to 24 hours before infusion of the nucleic acid composition. In some embodiments, dexamethasone is administered orally in the amount of 8-12 mg, such as 8 mg, 8 to 24 hours before infusion of the nucleic acid composition and dexamethasone is administered intravenously in the amount of 8-12 mg, such as 10 mg, 1-2 hour before infusion of the nucleic acid composition.

B. Delivery of Nucleic Acid Compositions

In some embodiments, the nucleic acid compositions described herein, comprising a gRNA and a nucleic acid described herein encoding an RNA-guided DNA-binding agent as RNA or encoded on one or more vectors, are formulated in or administered via a lipid nanoparticle; see e.g., WO2017173054A1 entitled "LIPID NANOPARTICLE FORMULATIONS FOR CRISPR/CAS COMPONENTS," and WO2019067992A1 entitled "FORMULATIONS," the contents of which are hereby incorporated by reference in their entirety. Any lipid nanoparticle (LNP) known to those of skill in the art to be capable of delivering nucleotides to subjects may be utilized with the guide RNAs described herein and the nucleic acid encoding an RNA-guided DNA nuclease.

Disclosed herein are various embodiments of LNP formulations for RNAs, including CRISPR/Cas cargoes. Such LNP formulations may include (i) a CCD lipid, such as an amine lipid, (ii) a neutral lipid, (iii) a helper lipid, and (iv) a stealth lipid, such as a PEG lipid. Some embodiments of the LNP formulations include an "amine lipid", along with a helper lipid, a neutral lipid, and a stealth lipid such as a PEG lipid. In some embodiments, the LNP formulations include less than 1 percent neutral phospholipid. In some embodiments, the LNP formulations include less than 0.5 percent neutral phospholipid. By "lipid nanoparticle" is meant a particle that comprises a plurality of (i.e. more than one) lipid molecules physically associated with each other by intermolecular forces.

CCD Lipids

Lipid compositions for delivery of CRISPR/Cas mRNA and guide RNA components to a liver cell comprise a CCD Lipid.

In some embodiments, the CCD lipid is Lipid A, which is (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z,12Z)-octadeca-9,12-dienoate. Lipid A can be depicted as:

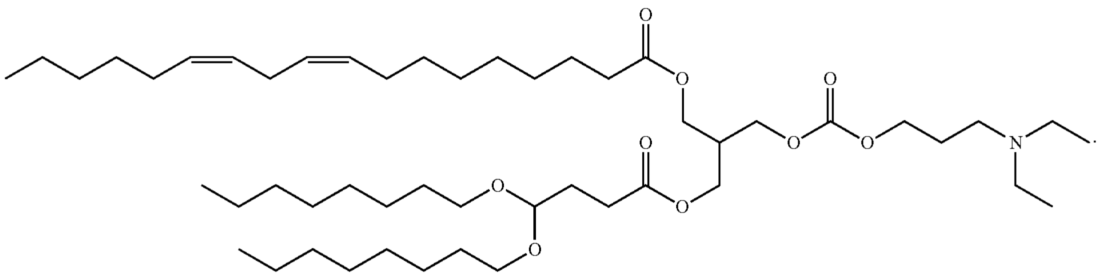 [SMILES: CCCCC/C=C\C/C=C\CCCCCCCC(=O)OCC(COC(=O)CCC(OCCCCCCCC)OCCCCCCCC)COC(=O)OCCCN(CC)CC]

Lipid A may be synthesized according to WO2015/095340 (e.g., pp. 84-86).

In some embodiments, the CCD lipid is Lipid B, which is ((5-((dimethylamino)methyl)-1,3-phenylene)bis(oxy))bis(octane-8,1-diyl)bis(decanoate), also called ((5-((dimethylamino)methyl)-1,3-phenylene)bis(oxy))bis(octane-8,1-diyl) bis(decanoate). Lipid B can be depicted as:

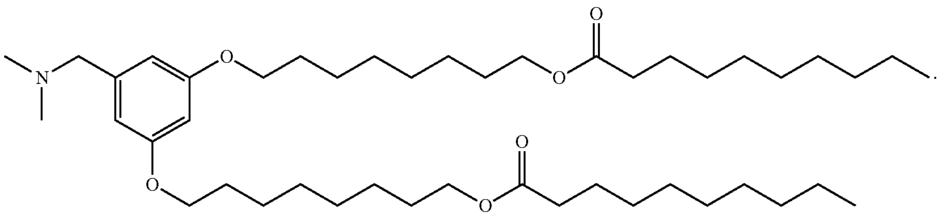 [SMILES: CCCCCCCCCC(=O)OCCCCCCCCOc1cc(CN(C)C)cc(OCCCCCCCCOC(=O)CCCCCCCCC)c1]

Lipid B may be synthesized according to WO2014/136086 (e.g., pp. 107-09).

In some embodiments, the CCD lipid is Lipid C, which is 2-((4-(((3-(dimethylamino)propoxy)carbonyl)oxy)hexadecanoyl)oxy)propane-1,3-diyl (9Z,9'Z,12Z,12'Z)-bis(octadeca-9,12-dienoate). Lipid C can be depicted as:

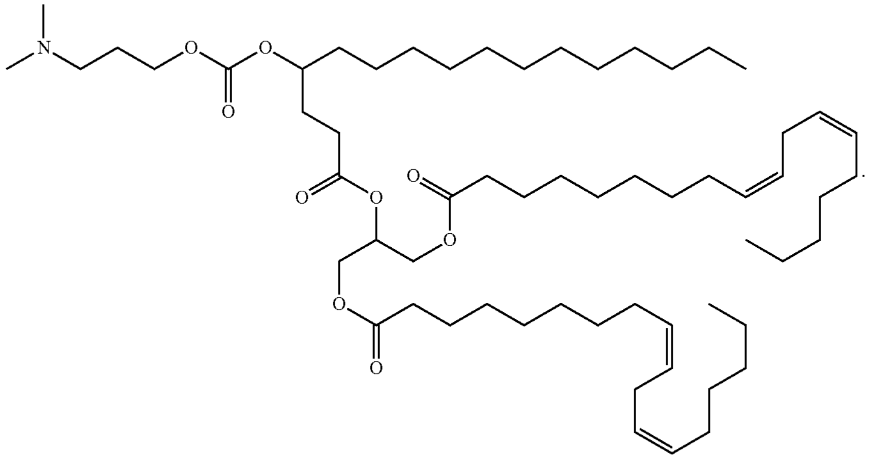 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(C)C]

In some embodiments, the CCD lipid is Lipid D, which is 3-(((3-(dimethylamino)propoxy)carbonyl)oxy)-13-(octanoyloxy)tridecyl 3-octylundecanoate.

Lipid D can be depicted as:

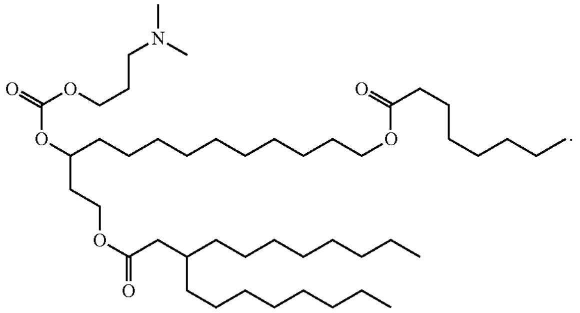 [SMILES: CCCCCCCCC(CCCCCCCC)CC(=O)OCCC(CCCCCCCCCCOC(=O)CCCCCCC)OC(=O)OCCCN(C)C]

Lipid C and Lipid D may be synthesized according to WO2015/095340.

The CCD lipid can also be an equivalent to Lipid A, Lipid B, Lipid C, or Lipid D. In certain embodiments, the CCD lipid is an equivalent to Lipid A, an equivalent to Lipid B, an equivalent to Lipid C, or an equivalent to Lipid D.

Amine Lipids

In some embodiments, the LNP compositions for the delivery of biologically active agents comprise an "amine lipid", which is defined as Lipid A, Lipid B, Lipid C, Lipid D or equivalents of Lipid A (including acetal analogs of Lipid A), equivalents of Lipid B, equivalents of Lipid C, and equivalents of Lipid D.

In some embodiments, the amine lipid is Lipid A, which is (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z,12Z)-octadeca-9,12-dienoate. Lipid A can be depicted as:

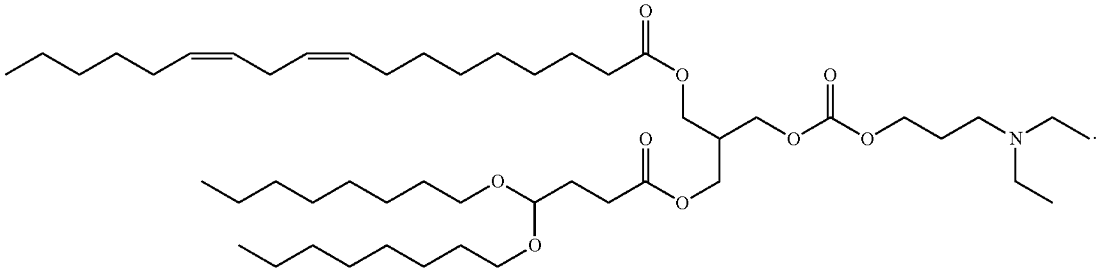 [SMILES: CCCCC/C=C\C/C=C\CCCCCCCC(=O)OCC(COC(=O)CCC(OCCCCCCCC)OCCCCCCCC)COC(=O)OCCCN(CC)CC]

Lipid A may be synthesized according to WO2015/095340 (e.g., pp. 84-86). In certain embodiments, the amine lipid is an equivalent to Lipid A.

In certain embodiments, an amine lipid is an analog of Lipid A. In certain embodiments, a Lipid A analog is an acetal analog of Lipid A. In particular LNP compositions, the acetal analog is a C4-C12 acetal analog. In some embodiments, the acetal analog is a C5-C12 acetal analog. In additional embodiments, the acetal analog is a C5-C10 acetal analog. In further embodiments, the acetal analog is chosen from a C4, C5, C6, C7, C9, C10, C11, and C12 acetal analog.

Amine lipids suitable for use in the LNPs described herein are biodegradable in vivo and suitable for delivering a biologically active agent, such as an RNA to a cell. The amine lipids have low toxicity (e.g., are tolerated in an animal model without adverse effect in amounts of greater than or equal to 10 mg/kg of RNA cargo). In certain embodiments, LNPs comprising an amine lipid include those where at least 75% of the amine lipid is cleared from the plasma within 8, 10, 12, 24, or 48 hours, or 3, 4, 5, 6, 7, or 10 days. In certain embodiments, LNPs comprising an amine lipid include those where at least 50% of the mRNA or gRNA is cleared from the plasma within 8, 10, 12, 24, or 48 hours, or 3, 4, 5, 6, 7, or 10 days. In certain embodiments, LNPs comprising an amine lipid include those where at least 50% of the LNP is cleared from the plasma within 8, 0.10, 12, 24, or 48 hours, or 3, 4, 5, 6, 7, or 10 days, for example by measuring a lipid (e.g., an amine lipid), RNA (e.g., mRNA), or another component. In certain embodiments, lipid-encapsulated versus free lipid, RNA, or nucleic acid component of the LNP is measured.

Lipid clearance may be measured as described in literature. See Maier, M. A., et al. "Biodegradable Lipids Enabling Rapidly Eliminated Lipid Nanoparticles for Systemic Delivery of RNAi Therapeutics," *Mol. Ther.* 2013, 21(8), 1570-78 ("Maier"). For example, in Maier, LNP-siRNA systems containing luciferases-targeting siRNA were administered to six- to eight-week old male C57Bl/6 mice at 0.3 mg/kg by intravenous bolus injection via the lateral tail vein. Blood, liver, and spleen samples were collected at 0.083, 0.25, 0.5, 1, 2, 4, 8, 24, 48, 96, and 168 hours post-dose. Mice were perfused with saline before tissue collection and blood samples were processed to obtain plasma. All samples were processed and analyzed by LC-MS. Further, Maier describes a procedure for assessing toxicity after administration of LNP-siRNA formulations. For example, a luciferase-targeting siRNA was administered at 0, 1, 3, 5, and 10 mg/kg (5 animals/group) via single intravenous bolus injection at a dose volume of 5 mL/kg to male Sprague-Dawley rats. After 24 hours, about 1 mL of blood was obtained from the jugular vein of conscious animals and the serum was isolated. At 72 hours post-dose, all animals were euthanized for necropsy. Assessments of clinical signs, body weight, serum chemistry, organ weights and histopathology were performed. Although Maier describes methods for assessing siRNA-LNP formulations, these methods may be applied to assess clearance, pharmacokinetics, and toxicity of administration of LNP compositions of the present disclosure.

The amine lipids may lead to an increased clearance rate. In some embodiments, the clearance rate is a lipid clearance rate, for example the rate at which a lipid is cleared from the blood, serum, or plasma. In some embodiments, the clearance rate is an RNA clearance rate, for example the rate at which an mRNA or a gRNA is cleared from the blood, serum, or plasma. In some embodiments, the clearance rate is the rate at which LNP is cleared from the blood, serum, or plasma. In some embodiments, the clearance rate is the rate at which LNP is cleared from a tissue, such as liver tissue or spleen tissue. In certain embodiments, a high clearance rate leads to a safety profile with no substantial adverse effects. The amine lipids may reduce LNP accumulation in circulation and in tissues. In some embodiments, a reduction in LNP accumulation in circulation and in tissues leads to a safety profile with no substantial adverse effects.

The amine lipids of the present disclosure are ionizable (e.g., may form a salt) depending upon the pH of the medium they are in. For example, in a slightly acidic medium, the amine lipids may be protonated and thus bear a positive charge. Conversely, in a slightly basic medium, such as, for example, blood, where pH is approximately 7.35, the amine lipids may not be protonated and thus bear no charge. In some embodiments, the amine lipids of the present disclosure may be protonated at a pH of at least about 9. In some embodiments, the amine lipids of the present disclosure may be protonated at a pH of at least about 9. In some embodiments, the amine lipids of the present disclosure may be protonated at a pH of at least about 10.

The pH at which an amine lipid is predominantly protonated is related to its intrinsic pKa. In some embodiments, the amine lipids of the present disclosure may each, independently, have a pKa in the range of from about 5.1 to about 7.4. In some embodiments, the amine lipids of the present disclosure may each, independently, have a pKa in the range of from about 5.5 to about 6.6. In some embodiments, the amine lipids of the present disclosure may each, independently, have a pKa in the range of from about 5.6 to about 6.4. In some embodiments, the amine lipids of the present disclosure may each, independently, have a pKa in the range of from about 5.8 to about 6.2. For example, the amine lipids of the present disclosure may each, independently, have a pKa in the range of from about 5.8 to about 6.5. The pKa of an amine lipid can be an important consideration in formulating LNPs as it has been found that cationic lipids with a pKa ranging from about 5.1 to about 7.4 are effective for delivery of cargo in vivo, e.g., to the liver. Furthermore, it has been found that cationic lipids with a pKa ranging from about 5.3 to about 6.4 are effective for delivery in vivo, e.g., to tumors. See, e.g., WO 2014/136086.

Additional Lipids

"Neutral lipids" suitable for use in a lipid composition of the disclosure include, for example, a variety of neutral, uncharged or zwitterionic lipids. Examples of neutral phospholipids suitable for use in the present disclosure include, but are not limited to, 5-heptadecylbenzene-1,3-diol (resorcinol), dipalmitoylphosphatidylcholine (DPPC), distearoylphosphatidylcholine (DSPC), pohsphocholine (DOPC), dimyristoylphosphatidylcholine (DMPC), phosphatidylcholine (PLPC), 1,2-distearoyl-sn-glycero-3-phosphocholine (DAPC), phosphatidylethanolamine (PE), egg phosphatidylcholine (EPC), dilauryloylphosphatidylcholine (DLPC), dimyristoylphosphatidylcholine (DMPC), 1-myristoyl-2-palmitoyl phosphatidylcholine (MPPC), 1-palmitoyl-2-myristoyl phosphatidylcholine (PMPC), 1-palmitoyl-2-stearoyl phosphatidylcholine (PSPC), 1,2-diarachidoyl-sn-glycero-3-phosphocholine (DBPC), 1-stearoyl-2-palmitoyl phosphatidylcholine (SPPC), 1,2-dieicosenoyl-sn-glycero-3-phosphocholine (DEPC), palmitoyloleoyl phosphatidylcholine (POPC), lysophosphatidyl choline, dioleoyl phosphatidylethanolamine (DOPE), dilinoleoylphosphatidylcholine distearoylphosphatidylethanolamine (DSPE), dimyristoyl phosphatidylethanolamine (DMPE), dipalmitoyl phosphatidylethanolamine (DPPE), palmitoyloleoyl phosphatidylethanolamine (POPE), lysophosphatidylethanolamine and combinations thereof. In one embodiment, the neutral phospholipid may be selected from the group consisting of distearoylphosphatidylcholine (DSPC) and dimyristoyl phosphatidyl ethanolamine (DMPE). In another embodiment, the neutral phospholipid may be distearoylphosphatidylcholine (DSPC). In another embodiment, the neutral phospholipid may be dipalmitoylphosphatidylcholine (DPPC).

"Helper lipids" include steroids, sterols, and alkyl resorcinols. Helper lipids suitable for use in the present disclosure include, but are not limited to, cholesterol, 5-heptadecylresorcinol, and cholesterol hemisuccinate. In one embodiment, the helper lipid may be cholesterol. In one embodiment, the helper lipid may be cholesterol hemisuccinate.

"Stealth lipids" are lipids that alter the length of time the nanoparticles can exist in vivo (e.g., in the blood). Stealth lipids may assist in the formulation process by, for example, reducing particle aggregation and controlling particle size. Stealth lipids used herein may modulate pharmacokinetic properties of the LNP. Stealth lipids suitable for use in a lipid composition of the disclosure include, but are not limited to, stealth lipids having a hydrophilic head group linked to a lipid moiety. Stealth lipids suitable for use in a lipid composition of the present disclosure and information about the biochemistry of such lipids can be found in Romberg et al., Pharmaceutical Research, Vol. 25, No. 1, 2008, pg. 55-71 and Hoekstra et al., Biochimica et Biophysica Acta 1660 (2004) 41-52. Additional suitable PEG lipids are disclosed, e.g., in WO 2006/007712.

In one embodiment, the hydrophilic head group of stealth lipid comprises a polymer moiety selected from polymers based on PEG. Stealth lipids may comprise a lipid moiety. In some embodiments, the stealth lipid is a PEG lipid. PEG lipids may assist in the formulation process by, for example, reducing particle aggregation and controlling particle size. PEG lipids used herein may modulate pharmacokinetic properties of the LNPs. Typically, the PEG lipid comprises a lipid moiety and a polymer moiety based on PEG.

In one embodiment, a stealth lipid comprises a polymer moiety selected from polymers based on PEG (sometimes referred to as poly(ethylene oxide)), poly(oxazoline), poly (vinyl alcohol), poly(glycerol), poly(N-vinylpyrrolidone), polyaminoacids and poly[N-(2-hydroxypropyl)methacrylamide].

In one embodiment, the PEG lipid comprises a polymer moiety based on PEG (sometimes referred to as poly(ethylene oxide)).

The PEG lipid further comprises a lipid moiety. In some embodiments, the lipid moiety may be derived from diacylglycerol or diacylglycamide, including those comprising a dialkylglycerol or dialkylglycamide group having alkyl chain length independently comprising from about C4 to about C40 saturated or unsaturated carbon atoms, wherein the chain may comprise one or more functional groups such as, for example, an amide or ester. In some embodiments, the alkyl chain length comprises about C10 to C20. The dialkylglycerol or dialkylglycamide group can further comprise one or more substituted alkyl groups. The chain lengths may be symmetrical or assymetric.

Unless otherwise indicated, the term "PEG" as used herein means any polyethylene glycol or other polyalkylene ether polymer. In one embodiment, PEG is an optionally substituted linear or branched polymer of ethylene glycol or ethylene oxide. In one embodiment, PEG is unsubstituted. In one embodiment, the PEG is substituted, e.g., by one or more alkyl, alkoxy, acyl, hydroxy, or aryl groups. In one embodiment, the term includes PEG copolymers such as PEG-polyurethane or PEG-polypropylene (see, e.g., J. Milton Harris, Poly(ethylene glycol) chemistry: biotechnical and biomedical applications (1992)); in another embodiment, the term does not include PEG copolymers. In one embodiment, the PEG has a molecular weight of from about 130 to about 50,000, in a sub-embodiment, about 150 to about 30,000, in a sub-embodiment, about 150 to about 20,000, in a sub-embodiment about 150 to about 15,000, in a sub-embodiment, about 150 to about 10,000, in a sub-embodiment, about 150 to about 6,000, in a sub-embodiment, about 150 to about 5,000, in a sub-embodiment, about 150 to about 4,000, in a sub-embodiment, about 150 to about 3,000, in a sub-embodiment, about 300 to about 3,000, in a sub-embodiment, about 1,000 to about 3,000, and in a sub-embodiment, about 1,500 to about 2,500.

In certain embodiments, the PEG (e.g., conjugated to a lipid moiety or lipid, such as a stealth lipid), is a "PEG-2K," also termed "PEG 2000," which has an average molecular weight of about 2,000 daltons. PEG-2K is represented herein by the following formula (I), wherein n is 45, meaning that the number averaged degree of polymerization comprises about 45 subunits

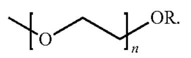

(I)

However, other PEG embodiments known in the art may be used, including, e.g., those where the number-averaged degree of polymerization comprises about 23 subunits (n=23), and/or 68 subunits (n=68). In some embodiments, n may range from about 30 to about 60. In some embodiments, n may range from about 35 to about 55. In some embodiments, n may range from about 40 to about 50. In some embodiments, n may range from about 42 to about 48. In some embodiments, n may be 45. In some embodiments, R may be selected from H, substituted alkyl, and unsubstituted alkyl. In some embodiments, R may be unsubstituted alkyl. In some embodiments, R may be methyl.

In any of the embodiments described herein, the PEG lipid may be selected from PEG-dilauroylglycerol, PEG-dimyristoylglycerol (PEG-DMG) (catalog #GM-020 from NOF, Tokyo, Japan), PEG-dipalmitoylglycerol, PEG-distearoylglycerol (PEG-DSPE) (catalog #DSPE-020CN, NOF, Tokyo, Japan), PEG-dilaurylglycamide, PEG-dimyristylglycamide, PEG-dipalmitoylglycamide, and PEG-distearoylglycamide, PEG-cholesterol (1-[8'-(Cholest-5-en-3 [beta]-oxy)carboxamido-3',6'-dioxaoctanyl]carbamoyl-[omega]-methyl-poly(ethylene glycol), PEG-DMB (3,4-ditetradecoxylbenzyl-[omega]-methyl-poly(ethylene glycol)ether), 1,2-dimyristoyl-sn-glycero-3-phosphoethanolamine-N-[methoxy(polyethylene glycol)-2000](PEG2k-DMG), 1,2-distearoyl-sn-glycero-3-phosphoethanolamine-N-[methoxy(polyethylene glycol)-2000](PEG2k-DSPE) (cat. #880120C from Avanti Polar Lipids, Alabaster, Alabama, USA), 1,2-distearoyl-sn-glycerol, methoxypolyethylene glycol (PEG2k-DSG; GS-020, NOF Tokyo, Japan), poly(ethylene glycol)-2000-dimethacrylate (PEG2k-DMA), and 1,2-distearyloxypropyl-3-amine-N-[methoxy(polyethylene glycol)-2000](PEG2k-DSA). In one embodiment, the PEG lipid may be PEG2k-DMG. In some embodiments, the PEG lipid may be PEG2k-DSG. In one embodiment, the PEG lipid may be PEG2k-DSPE. In one embodiment, the PEG lipid may be PEG2k-DMA. In one embodiment, the PEG lipid may be PEG2k-C-DMA. In one embodiment, the PEG lipid may be compound S027, disclosed in WO2016/010840 (paragraphs [00240] to [00244]). In one embodiment, the PEG lipid may be PEG2k-DSA. In one embodiment, the PEG lipid may be PEG2k-C11. In some embodiments, the PEG lipid may be PEG2k-C14. In some embodiments, the PEG lipid may be PEG2k-C16. In some embodiments, the PEG lipid may be PEG2k-C18.

LNP Formulations

The LNP may contain (i) an amine lipid for encapsulation and for endosomal escape, (ii) a neutral lipid for stabilization, (iii) a helper lipid, also for stabilization, and (iv) a stealth lipid, such as a PEG lipid. The neutral lipid may be omitted.

In some embodiments, an LNP composition may comprise an RNA component that includes one or more of an RNA-guided DNA-binding agent, a Cas nuclease mRNA, a Class 2 Cas nuclease mRNA, a Cas9 mRNA, and a gRNA. In some embodiments, an LNP composition includes an mRNA encoding a Class 2 Cas nuclease and a gRNA as the RNA component. In certain embodiments, an LNP composition may comprise the RNA component, an amine lipid, a helper lipid, a neutral lipid, and a stealth lipid. In certain LNP compositions, the helper lipid is cholesterol. In other compositions, the neutral lipid is DSPC. In additional embodiments, the stealth lipid is PEG2k-DMG or PEG2k-C11. In certain embodiments, the LNP composition comprises Lipid A or an equivalent of Lipid A; a helper lipid; a neutral lipid; a stealth lipid; and a guide RNA. In certain compositions, the amine lipid is Lipid A. In certain compositions, the amine lipid is Lipid A or an acetal analog thereof; the helper lipid is cholesterol; the neutral lipid is DSPC; and the stealth lipid is PEG2k-DMG.

In certain embodiments, lipid compositions are described according to the respective molar ratios of the component lipids in the formulation. Embodiments of the present disclosure provide lipid compositions described according to the respective molar ratios of the component lipids in the formulation. In one embodiment, the mol-% of the amine lipid may be from about 30 mol-% to about 60 mol-%. In one embodiment, the mol-% of the amine lipid may be from about 40 mol-% to about 60 mol-%. In one embodiment, the mol-% of the amine lipid may be from about 45 mol-% to about 60 mol-%. In one embodiment, the mol-% of the amine lipid may be from about 50 mol-% to about 60 mol-%. In one embodiment, the mol-% of the amine lipid may be from about 55 mol-% to about 60 mol-%. In one embodiment, the mol-% of the amine lipid may be from about 50 mol-% to about 55 mol-%. In one embodiment, the mol-% of the amine lipid may be about 50 mol-%. In one embodiment, the mol-% of the amine lipid may be about 55 mol-%. In some embodiments, the amine lipid mol-% of the LNP batch will be ±30%, ±25%, ±20%, ±15%, ±10%, ±5%, or ±2.5% of the target mol-%. In some embodiments, the amine lipid mol-% of the LNP batch will be ±4 mol-%, ±3 mol-%, ±2 mol-%, ±1.5 mol-%, 1 mol-%, ±0.5 mol-%, or ±0.25 mol-% of the target mol-%. All mol-% numbers are given as a fraction of the lipid component of the LNP compositions. In certain embodiments, LNP inter-lot variability of the amine lipid mol-% will be less than 15%, less than 10% or less than 5%.

In one embodiment, the mol-% of the neutral lipid, e.g., neutral phospholipid, may be from about 5 mol-% to about 15 mol-%. In one embodiment, the mol-% of the neutral lipid, e.g., neutral phospholipid, may be from about 7 mol-% to about 12 mol-%. In one embodiment, the mol-% of the neutral lipid, e.g., neutral phospholipid, may be from about 0 mol-% to about 5 mol-%. In one embodiment, the mol-% of the neutral lipid, e.g., neutral phospholipid, may be from about 0 mol-% to about 10 mol-%. In one embodiment, the mol-% of the neutral lipid, e.g., neutral phospholipid, may be from about 5 mol-% to about 10 mol-%. In one embodiment, the mol-% of the neutral lipid, e.g., neutral phospholipid, may be from about 8 mol-% to about 10 mol-%.

In one embodiment, the mol-% of the neutral lipid, e.g., neutral phospholipid, may be about 5 mol-%, about 6 mol-%, about 7 mol-%, about 8 mol-%, about 9 mol-%, about 10 mol-%, about 11 mol-%, about 12 mol-%, about 13 mol-%, about 14 mol-%, or about 15 mol-%. In one embodiment, the mol-% of the neutral lipid, e.g., neutral phospholipid, may be about 9 mol-%.

In one embodiment, the mol-% of the neutral lipid, e.g., neutral phospholipid, may be from about 1 mol-% to about 5 mol-%. In one embodiment, the mol-% of the neutral lipid may be from about 0.1 mol-% to about 1 mol-%. In one embodiment, the mol-% of the neutral lipid such as neutral phospholipid may be about 0.1 mol-%, about 0.2 mol-%, about 0.5 mol-%, 1 mol-%, about 1.5 mol-%, about 2 mol-%, about 2.5 mol-%, about 3 mol-%, about 3.5 mol-%, about 4 mol-%, about 4.5 mol-%, or about 5 mol-%.

In one embodiment, the mol-% of the neutral lipid, e.g., neutral phospholipid, may be less than about 1 mol-%. In one embodiment, the mol-% of the neutral lipid, e.g., neutral phospholipid, may be less than about 0.5 mol-%. In one embodiment, the mol-% of the neutral lipid, e.g., neutral phospholipid, may be about 0 mol-%, about 0.1 mol-%, about 0.2 mol-%, about 0.3 mol-%, about 0.4 mol-%, about 0.5 mol-%, about 0.6 mol-%, about 0.7 mol-%, about 0.8 mol-%, about 0.9 mol-%, or about 1 mol-%. In some embodiments, the formulations disclosed herein are free of neutral lipid (i.e., 0 mol-% neutral lipid). In some embodiments, the formulations disclosed herein are essentially free of neutral lipid (i.e., about 0 mol-% neutral lipid). In some embodiments, the formulations disclosed herein are free of neutral phospholipid (i.e., 0 mol-% neutral phospholipid). In some embodiments, the formulations disclosed herein are essentially free of neutral phospholipid (i.e., about 0 mol-% neutral phospholipid).

In some embodiments, the neutral lipid mol-% of the LNP batch will be ±30%, ±25%, ±20%, ±15%, ±10%, ±5%, or ±2.5% of the target neutral lipid mol-%. In certain embodiments, LNP inter-lot variability will be less than 15%, less than 10% or less than 5%.

In one embodiment, the mol-% of the helper lipid may be from about 20 mol-% to about 60 mol-%. In one embodiment, the mol-% of the helper lipid may be from about 25 mol-% to about 55 mol-%. In one embodiment, the mol-% of the helper lipid may be from about 25 mol-% to about 50 mol-%. In one embodiment, the mol-% of the helper lipid may be from about 25 mol-% to about 40 mol-%. In one embodiment, the mol-% of the helper lipid may be from about 30 mol-% to about 50 mol-%. In one embodiment, the mol-% of the helper lipid may be from about 30 mol-% to about 40 mol-%. In one embodiment, the mol-% of the helper lipid is adjusted based on amine lipid, neutral lipid, and PEG lipid concentrations to bring the lipid component to 100 mol-%. In one embodiment, the mol-% of the helper lipid is adjusted based on amine lipid and PEG lipid concentrations to bring the lipid component to 100 mol-%. In one embodiment, the mol-% of the helper lipid is adjusted based on amine lipid and PEG lipid concentrations to bring the lipid component to at least 99 mol-%. In some embodiments, the helper mol-% of the LNP batch will be ±30%, ±25%, ±20%, 15%, ±10%, ±5%, or ±2.5% of the target mol-%. In certain embodiments, LNP inter-lot variability will be less than 15%, less than 10% or less than 5%.

In one embodiment, the mol-% of the PEG lipid may be from about 1 mol-% to about 10 mol-%. In one embodiment, the mol-% of the PEG lipid may be from about 2 mol-% to about 10 mol-%. In one embodiment, the mol-% of the PEG lipid may be from about 2 mol-% to about 8 mol-%. In one embodiment, the mol-% of the PEG lipid may be from about 2 mol-% to about 4 mol-%. In one embodiment, the mol-% of the PEG lipid may be from about 2.5 mol-% to about 4 mol-%. In one embodiment, the mol-% of the PEG lipid may be about 3 mol-%. In one embodiment, the mol-% of the PEG lipid may be about 2.5 mol-%. In some embodiments, the PEG lipid mol-% of the LNP batch will be ±30%, ±25%, ±20%, ±15%, ±10%, ±5%, or ±2.5% of the target PEG lipid mol-%. In certain embodiments, LNP inter-lot variability will be less than 15%, less than 10% or less than 5%.

In certain embodiments, the cargo includes a nucleic acid encoding an RNA-guided DNA-binding agent (e.g. a Cas nuclease, a Class 2 Cas nuclease, or Cas9), and a gRNA or a nucleic acid encoding a gRNA, or a combination of mRNA and gRNA. In one embodiment, an LNP composition may comprise a Lipid A or its equivalents. In some aspects, the amine lipid is Lipid A. In some aspects, the amine lipid is a Lipid A equivalent, e.g. an analog of Lipid A. In certain aspects, the amine lipid is an acetal analog of Lipid A. In various embodiments, an LNP composition comprises an amine lipid, a neutral lipid, a helper lipid, and a PEG lipid. In certain embodiments, the helper lipid is cholesterol. In certain embodiments, the neutral lipid is DSPC. In specific embodiments, PEG lipid is PEG2k-DMG. In some embodiments, an LNP composition may comprise a Lipid A, a helper lipid, a neutral lipid, and a PEG lipid. In some embodiments, an LNP composition comprises an amine lipid, DSPC, cholesterol, and a PEG lipid. In some embodiments, the LNP composition comprises a PEG lipid comprising DMG. In certain embodiments, the amine lipid is selected from Lipid A, and an equivalent of Lipid A, including an acetal analog of Lipid A. In additional embodiments, an LNP composition comprises Lipid A, cholesterol, DSPC, and PEG2k-DMG.

In various embodiments, an LNP composition comprises an amine lipid, a helper lipid, a neutral lipid, and a PEG lipid. In various embodiments, an LNP composition comprises an amine lipid, a helper lipid, a neutral phospholipid, and a PEG lipid. In various embodiments, an LNP composition comprises a lipid component that consists of an amine lipid, a helper lipid, a neutral lipid, and a PEG lipid. In various embodiments, an LNP composition comprises an amine lipid, a helper lipid, and a PEG lipid. In certain embodiments, an LNP composition does not comprise a neutral lipid, such as a neutral phospholipid. In various embodiments, an LNP composition comprises a lipid component that consists of an amine lipid, a helper lipid, and a PEG lipid. In certain embodiments, the neutral lipid is chosen from one or more of DSPC, DPPC, DAPC, DMPC, DOPC, DOPE, and DSPE. In certain embodiments, the neutral lipid is DSPC. In certain embodiments, the neutral lipid is DPPC. In certain embodiments, the neutral lipid is DAPC. In certain embodiments, the neutral lipid is DMPC. In certain embodiments, the neutral lipid is DOPC. In certain embodiments, the neutral lipid is DOPE. In certain embodiments, the neutral lipid is DSPE. In certain embodiments, the helper lipid is cholesterol. In specific embodiments, the PEG lipid is PEG2k-DMG. In some embodiments, an LNP composition may comprise a Lipid A, a helper lipid, and a PEG lipid. In some embodiments, an LNP composition may comprise a lipid component that consists of Lipid A, a helper lipid, and a PEG lipid. In some embodiments, an LNP composition comprises an amine lipid, cholesterol, and a PEG lipid. In some embodiments, an LNP composition comprises a lipid component that consists of an amine lipid, cholesterol, and a PEG lipid. In some embodiments, the LNP composition comprises a PEG lipid comprising DMG. In certain embodiments, the amine lipid is selected from Lipid A and an equivalent of Lipid A, including an acetal analog of Lipid A. In certain embodiments, the amine lipid is a C5-C12 or a C4-C12 acetal analog of Lipid A. In additional embodiments, an LNP composition comprises Lipid A, cholesterol, and PEG2k-DMG.

Embodiments of the present disclosure also provide lipid compositions described according to the molar ratio between the positively charged amine groups of the amine lipid (N) and the negatively charged phosphate groups (P) of the nucleic acid to be encapsulated. This may be mathematically represented by the equation N/P. In some embodiments, an LNP composition may comprise a lipid component that comprises an amine lipid, a helper lipid, a neutral lipid, and a PEG lipid; and a nucleic acid component, wherein the NIP ratio is about 3 to 10. In some embodiments, an LNP composition may comprise a lipid component that comprises an amine lipid, a helper lipid, and a PEG lipid; and a nucleic acid component, wherein the N/P ratio is about 3 to 10. In some embodiments, an LNP composition may comprise a lipid component that comprises an amine lipid, a helper lipid, a neutral lipid, and a helper lipid; and an RNA component, wherein the N/P ratio is about 3 to 10. In some embodiments, an LNP composition may comprise a lipid component that comprises an amine lipid, a helper lipid, and a PEG lipid; and an RNA component, wherein the N/P ratio is about 3 to 10. In one embodiment, the N/P ratio may be about 5 to 7. In one embodiment, the N/P ration may be about 3 to 7. In one embodiment, the N/P ratio may be about 4.5 to 8. In one embodiment, the N/P ratio may be about 6. In one embodiment, the N/P ratio may be 6±1. In one embodiment, the N/P ratio may be 6±0.5. In some embodiments, the N/P ratio will be ±30%, 25%, ±20%, ±15%, ±10%, ±5%, or ±2.5% of the target N/P ratio. In certain embodiments, LNP inter-lot variability will be less than 15%, less than 10% or less than 5%.

In some embodiments, the RNA component may comprise a nucleic acid, such as a nucleic acid disclosed herein, e.g., encoding a Cas nuclease described herein (such as a Cas9 mRNA described herein), and a gRNA described herein. In some embodiments, the RNA component comprises a Cas nuclease mRNA described herein and a gRNA described herein. In some embodiments, the RNA component comprises a Class 2 Cas nuclease mRNA described herein and a gRNA described herein. In any of the foregoing embodiments, the gRNA may be an sgRNA described herein, such as a chemically modified sgRNA described herein.

In certain embodiments, an LNP composition may comprise an RNA component as discussed above, an amine lipid, a helper lipid, a neutral lipid, and a PEG lipid. In certain LNP compositions, the helper lipid is cholesterol; the neutral lipid is DSPC; and/or the PEG lipid is PEG2k-DMG or PEG2k-C11. In specific compositions, the amine lipid is selected from Lipid A and its equivalents, such as an acetal analog of Lipid A. In one embodiment, the lipid component of the LNP composition consists of an amine lipid, a helper lipid, a neutral lipid, and a PEG lipid. In one embodiment, the lipid component of the LNP composition consists of an amine lipid, a helper lipid, and a PEG lipid. In certain compositions comprising an mRNA encoding a Cas nuclease and a gRNA, the helper lipid is cholesterol. In some compositions comprising an mRNA encoding a Cas nuclease and a gRNA, the neutral lipid is DSPC. Certain compositions comprising an mRNA encoding a Cas nuclease and a gRNA comprise less than about 1 mol-% neutral lipid, e.g. neutral phospholipid. Certain compositions comprising an mRNA encoding a Cas nuclease and a gRNA comprise less than about 0.5 mol-% neutral lipid, e.g. neutral phospholipid. In certain compositions, the LNP does not comprise a neutral lipid, e.g., neutral phospholipid. In additional embodiments comprising an mRNA encoding a Cas nuclease and a gRNA, the PEG lipid is PEG2k-DMG or PEG2k-C11. In certain embodiments, the amine lipid is selected from Lipid A and its equivalents, such as acetal analogs of Lipid A.

In certain embodiments, the LNP compositions include a Cas nuclease mRNA (such as a Class 2 Cas mRNA) described herein and at least one gRNA described herein. In certain embodiments, the LNP composition includes a ratio of gRNA to Cas nuclease mRNA, such as Class 2 Cas nuclease mRNA from about 25:1 to about 1:25. In certain embodiments, the LNP formulation includes a ratio of gRNA to Cas nuclease mRNA, such as Class 2 Cas nuclease mRNA from about 10:1 to about 1:10. In certain embodiments, the LNP formulation includes a ratio of gRNA to Cas nuclease mRNA, such as Class 2 Cas nuclease mRNA from about 8:1 to about 1:8. As measured herein, the ratios are by weight. In some embodiments, the LNP formulation includes a ratio of gRNA to Cas nuclease mRNA, such as Class 2 Cas mRNA from about 5:1 to about 1:5. In some embodiments, ratio range is about 3:1 to 1:3, about 2:1 to 1:2, about 5:1 to 1:2, about 5:1 to 1:1, about 3:1 to 1:2, about 3:1 to 1:1, about 3:1, about 2:1 to 1:1. In some embodiments, the gRNA to mRNA ratio is about 3:1 or about 2:1 In some embodiments the ratio of gRNA to Cas nuclease mRNA, such as Class 2 Cas nuclease is about 1:1. The ratio may be about 25:1, 10:1, 5:1, 3:1, 1:1, 1:3, 1:5, 1:10, or 1:25.

In some embodiments, LNPs are formed by mixing an aqueous RNA solution with an organic solvent-based lipid solution, e.g., 100% ethanol. Suitable solutions or solvents include or may contain: water, PBS, Tris buffer, NaCl, citrate buffer, ethanol, chloroform, diethylether, cyclohexane, tetrahydrofuran, methanol, isopropanol. A pharmaceutically acceptable buffer, e.g., for in vivo administration of LNPs, may be used. In certain embodiments, a buffer is used to maintain the pH of the composition comprising LNPs at or above pH 6.5. In certain embodiments, a buffer is used to maintain the pH of the composition comprising LNPs at or above pH 7.0. In certain embodiments, the composition has a pH ranging from about 7.2 to about 7.7. In additional embodiments, the composition has a pH ranging from about 7.3 to about 7.7 or ranging from about 7.4 to about 7.6. In further embodiments, the composition has a pH of about 7.2, 7.3, 7.4, 7.5, 7.6, or 7.7. The pH of a composition may be measured with a micro pH probe. In certain embodiments, a cryoprotectant is included in the composition. Non-limiting examples of cryoprotectants include sucrose, trehalose, glycerol, DMSO, and ethylene glycol. Exemplary compositions may include up to 10% cryoprotectant, such as, for example, sucrose. In certain embodiments, the LNP composition may include about 1, 2, 3, 4, 5, 6, 7, 8, 9, or 10% cryoprotectant. In certain embodiments, the LNP composition may include about 1, 2, 3, 4, 5, 6, 7, 8, 9, or 10% sucrose. In some embodiments, the LNP composition may include a buffer. In some embodiments, the buffer may comprise a phosphate buffer (PBS), a Tris buffer, a citrate buffer, and mixtures thereof. In certain exemplary embodiments, the buffer comprises NaCl. In certain embodiments, NaCl is omitted. Exemplary amounts of NaCl may range from about 20 mM to about 45 mM. Exemplary amounts of NaCl may range from about 40 mM to about 50 mM. In some embodiments, the amount of NaCl is about 45 mM. In some embodiments, the buffer is a Tris buffer. Exemplary amounts of Tris may range from about 20 mM to about 60 mM. Exemplary amounts of Tris may range from about 40 mM to about 60 mM. In some embodiments, the amount of Tris is about 50 mM. In some embodiments, the buffer comprises NaCl and Tris. Certain exemplary embodiments of the LNP compositions contain 5% sucrose and 45 mM NaCl in Tris buffer. In other exemplary embodiments, compositions contain sucrose in an amount of about 5% w/v, about 45 mM NaCl, and about 50 mM Tris at pH 7.5. The salt, buffer, and cryoprotectant amounts may be varied such that the osmolality of the overall formulation is maintained. For example, the final osmolality may be maintained at less than 450 mOsm/L. In further embodiments, the osmolality is between 350 and 250 mOsm/L. Certain embodiments have a final osmolality of 300+/−20 mOsm/L.

In some embodiments, microfluidic mixing, T-mixing, or cross-mixing is used. In certain aspects, flow rates, junction size, junction geometry, junction shape, tube diameter, solutions, and/or RNA and lipid concentrations may be varied. LNPs or LNP compositions may be concentrated or purified, e.g., via dialysis, tangential flow filtration, or chromatography. The LNPs may be stored as a suspension, an emulsion, or a lyophilized powder, for example. In some embodiments, an LNP composition is stored at 2-8° C., in certain aspects, the LNP compositions are stored at room temperature. In additional embodiments, an LNP composition is stored frozen, for example at −20° C. or −80° C. In other embodiments, an LNP composition is stored at a temperature ranging from about 0° C. to about −80° C. Frozen LNP compositions may be thawed before use, for example on ice, at room temperature, or at 25° C.

The LNPs may be, e.g., microspheres (including unilamellar and multilamellar vesicles, e.g., "liposomes"—lamellar phase lipid bilayers that, in some embodiments, are substantially spherical—and, in more particular embodiments, can comprise an aqueous core, e.g., comprising a substantial portion of RNA molecules), a dispersed phase in an emulsion, micelles, or an internal phase in a suspension.

Moreover, the LNP compositions are biodegradable, in that they do not accumulate to cytotoxic levels in vivo at a therapeutically effective dose. In some embodiments, the LNP compositions do not cause an innate immune response that leads to substantial adverse effects at a therapeutic dose level. In some embodiments, the LNP compositions provided herein do not cause toxicity at a therapeutic dose level.

In some embodiments, the pdi may range from about 0.005 to about 0.75. In some embodiments, the pdi may range from about 0.01 to about 0.5. In some embodiments, the pdi may range from about zero to about 0.4. In some embodiments, the pdi may range from about zero to about 0.35. In some embodiments, the pdi may range from about zero to about 0.35. In some embodiments, the pdi may range from about zero to about 0.3. In some embodiments, the pdi may range from about zero to about 0.25. In some embodiments, the pdi may range from about zero to about 0.2. In some embodiments, the pdi may be less than about 0.08, 0.1, 0.15, 0.2, or 0.4.

The LNPs disclosed herein have a size (e.g., Z-average diameter) of about 1 to about 250 nm. In some embodiments, the LNPs have a size of about 10 to about 200 nm. In further embodiments, the LNPs have a size of about 20 to about 150 nm. In some embodiments, the LNPs have a size of about 50 to about 150 nm. In some embodiments, the LNPs have a size of about 50 to about 100 nm. In some embodiments, the LNPs have a size of about 50 to about 120 nm. In some embodiments, the LNPs have a size of about 60 to about 100 nm. In some embodiments, the LNPs have a size of about 75 to about 150 nm. In some embodiments, the LNPs have a size of about 75 to about 120 nm. In some embodiments, the LNPs have a size of about 75 to about 100 nm. Unless indicated otherwise, all sizes referred to herein are the average sizes (diameters) of the fully formed nanoparticles, as measured by dynamic light scattering on a dynamic light scattering measurement system (Malvern Zetasizer®). The nanoparticle sample is diluted in phosphate buffered saline (PBS) so that the count rate is approximately 200-400 kcps. The data is presented as a weighted-average of the intensity measure (Z-average diameter).

In some embodiments, the LNPs are formed with an average encapsulation efficiency ranging from about 50% to about 100%. In some embodiments, the LNPs are formed with an average encapsulation efficiency ranging from about 50% to about 70%. In some embodiments, the LNPs are formed with an average encapsulation efficiency ranging from about 70% to about 90%. In some embodiments, the LNPs are formed with an average encapsulation efficiency ranging from about 90% to about 100%. In some embodiments, the LNPs are formed with an average encapsulation efficiency ranging from about 75% to about 95%.

In some embodiments, the LNPs are formed with an average molecular weight ranging from about 1.00E+05 g/mol to about 1.00E+10 g/mol. In some embodiments, the LNPs are formed with an average molecular weight ranging from about 5.00E+05 g/mol to about 7.00E+07 g/mol. In some embodiments, the LNPs are formed with an average molecular weight ranging from about 1.00E+06 g/mol to about 1.00E+10 g/mol. In some embodiments, the LNPs are formed with an average molecular weight ranging from about 1.00E+07 g/mol to about 1.00E+09 g/mol. In some embodiments, the LNPs are formed with an average molecular weight ranging from about 5.00E+06 g/mol to about 5.00E+09 g/mol.

In some embodiments, the polydispersity (Mw/Mn; the ratio of the weight averaged molar mass (Mw) to the number averaged molar mass (Mn)) may range from about 1.000 to about 2.000. In some embodiments, the Mw/Mn may range from about 1.00 to about 1.500. In some embodiments, the Mw/Mn may range from about 1.020 to about 1.400. In some embodiments, the Mw/Mn may range from about 1.010 to about 1.100. In some embodiments, the Mw/Mn may range from about 1.100 to about 1.350.

Dynamic Light Scattering ("DLS") can be used to characterize the polydispersity index ("pdi") and size of the LNPs of the present disclosure. DLS measures the scattering of light that results from subjecting a sample to a light source. PDI, as determined from DLS measurements, represents the distribution of particle size (around the mean particle size) in a population, with a perfectly uniform population having a PDI of zero. In some embodiments, the pdi may range from 0.005 to 0.75. In some embodiments, the pdi may range from 0.01 to 0.5. In some embodiments, the pdi may range from 0.02 to 0.4. In some embodiments, the pdi may range from 0.03 to 0.35. In some embodiments, the pdi may range from 0.1 to 0.35.

In some embodiments, LNPs disclosed herein have a size of 1 to 250 nm. In some embodiments, the LNPs have a size of 10 to 200 nm. In further embodiments, the LNPs have a size of 20 to 150 nm. In some embodiments, the LNPs have a size of 50 to 150 nm. In some embodiments, the LNPs have a size of 50 to 100 nm. In some embodiments, the LNPs have a size of 50 to 120 nm. In some embodiments, the LNPs have a size of 75 to 150 nm. In some embodiments, the LNPs have a size of 30 to 200 nm. Unless indicated otherwise, all sizes referred to herein are the average sizes (diameters) of the fully formed nanoparticles, as measured by dynamic light scattering on a dynamic light scattering measurement system (Malvern Zetasizer®). The nanoparticle sample is diluted in phosphate buffered saline (PBS) so that the count rate is approximately 200-400 kcts. The data is presented as a weighted-average of the intensity measure. In some embodiments, the LNPs are formed with an average encapsulation efficiency ranging from 50% to 100%. In some embodiments, the LNPs are formed with an average encapsulation efficiency ranging from 50% to 70%. In some embodiments, the LNPs are formed with an average encapsulation efficiency ranging from 70% to 90%. In some embodiments, the LNPs are formed with an average encapsulation efficiency ranging from 90% to 100%. In some embodiments, the LNPs are formed with an average encapsulation efficiency ranging from 75% to 95%.

In some embodiments, LNPs associated with the gRNAs disclosed herein and nucleic acids (e.g., mRNA) encoding an RNA-guided DNA binding agent (e.g. Cas9, Spy Cas9) disclosed herein are for use in preparing a medicament for treating ATTR. In some embodiments, LNPs associated with the gRNAs disclosed herein and nucleic acids (e.g., mRNA) encoding an RNA-guided DNA binding agent (e.g. Cas9, Spy Cas9) disclosed herein are for use in preparing a medicament for reducing or preventing accumulation and aggregation of TTR in amyloids or amyloid fibrils in subjects having ATTR. In some embodiments, LNPs associated with the gRNAs disclosed herein and nucleic acids (e.g., mRNA) encoding an RNA-guided DNA binding agent (e.g. Cas9, Spy Cas9) disclosed herein are for use in preparing a medicament for reducing serum TTR concentration. In some embodiments, LNPs associated with the gRNAs disclosed herein and nucleic acids (e.g., mRNA) encoding an RNA-guided DNA binding agent (e.g. Cas9, Spy Cas9) disclosed herein are for use in treating ATTR in a subject, such as a mammal, e.g., a primate such as a human. In some embodiments, LNPs associated with the gRNAs disclosed herein and nucleic acids (e.g., mRNA) encoding an RNA-guided DNA binding agent (e.g. Cas9, Spy Cas9) disclosed herein are for use in reducing or preventing accumulation and aggregation of TTR in amyloids or amyloid fibrils in subjects having ATTR, such as a mammal, e.g., a primate such as a human. In some embodiments, LNPs associated with the gRNAs disclosed herein and nucleic acids (e.g., mRNA) encoding an RNA-guided DNA binding agent (e.g. Cas9, Spy Cas9) disclosed herein are for use in reducing serum TTR concentration in a subject, such as a mammal, e.g., a primate such as a human.

Electroporation is also a well-known means for delivery of cargo, and any electroporation methodology may be used for delivery of any one of the gRNAs disclosed herein. In some embodiments, electroporation may be used to deliver any one of the gRNAs disclosed herein and an RNA-guided DNA nuclease such as Cas9 or a nucleic acid encoding an RNA-guided DNA nuclease such as Cas9.

In some embodiments, the invention comprises a method for delivering any one of the gRNAs disclosed herein and nucleic acids (e.g., mRNA) encoding an RNA-guided DNA binding agent (e.g. Cas9, Spy Cas9) disclosed herein to an ex vivo cell, wherein the gRNA and nucleic acid are associated with an LNP.

In certain embodiments, the invention comprises DNA or RNA vectors encoding any of the guide RNAs comprising any one or more of the guide sequences described herein. In some embodiments, in addition to guide RNA sequences, the vectors further comprise nucleic acids that do not encode guide RNAs. Nucleic acids that do not encode guide RNA include, but are not limited to, promoters, enhancers, regulatory sequences, and nucleic acids encoding an RNA-guided DNA nuclease, which can be a nuclease such as Cas9. In some embodiments, the vector comprises one or more nucleotide sequence(s) encoding a crRNA, a trRNA, or a crRNA and trRNA. In some embodiments, the vector comprises one or more nucleotide sequence(s) encoding a sgRNA and a nucleic acid encoding an RNA-guided DNA nuclease, which can be a Cas nuclease, such as Cas9 or Cpf1. In some embodiments, the vector comprises one or more nucleotide sequence(s) encoding a crRNA, a trRNA, and a nucleic acid encoding an RNA-guided DNA nuclease, which can be a Cas protein, such as, Cas9. In one embodiment, the Cas9 is from *Streptococcus pyogenes* (i.e., Spy Cas9). In some embodiments, the nucleotide sequence encoding the crRNA, trRNA, or crRNA and trRNA (which may be a sgRNA) comprises or consists of a guide sequence flanked by all or a portion of a repeat sequence from a naturally-occurring CRISPR/Cas system. The nucleic acid comprising or consisting of the crRNA, trRNA, or crRNA and trRNA may further comprise a vector sequence wherein the vector sequence comprises or consists of nucleic acids that are not naturally found together with the crRNA, trRNA, or crRNA and trRNA.

In some embodiments, the crRNA and the trRNA are encoded by non-contiguous nucleic acids within one vector. In other embodiments, the crRNA and the trRNA may be encoded by a contiguous nucleic acid. In some embodiments, the crRNA and the trRNA are encoded by opposite strands of a single nucleic acid. In other embodiments, the crRNA and the trRNA are encoded by the same strand of a single nucleic acid.

In some embodiments, the vector may be circular. In other embodiments, the vector may be linear. In some embodiments, the vector may be enclosed in a lipid nanoparticle, liposome, non-lipid nanoparticle, or viral capsid. Non-limiting exemplary vectors include plasmids, phagemids, cosmids, artificial chromosomes, minichromosomes, transposons, viral vectors, and expression vectors.

In some embodiments, the vector may be a viral vector. In some embodiments, the viral vector may be genetically modified from its wild type counterpart. For example, the viral vector may comprise an insertion, deletion, or substitution of one or more nucleotides to facilitate cloning or such that one or more properties of the vector is changed. Such properties may include packaging capacity, transduction efficiency, immunogenicity, genome integration, replication, transcription, and translation. In some embodiments, a portion of the viral genome may be deleted such that the virus is capable of packaging exogenous sequences having a larger size. In some embodiments, the viral vector may have an enhanced transduction efficiency. In some embodiments, the immune response induced by the virus in a host may be reduced. In some embodiments, viral genes (such as, e.g., integrase) that promote integration of the viral sequence into a host genome may be mutated such that the virus becomes non-integrating. In some embodiments, the viral vector may be replication defective. In some embodiments, the viral vector may comprise exogenous transcriptional or translational control sequences to drive expression of coding sequences on the vector. In some embodiments, the virus may be helper-dependent. For example, the virus may need one or more helper virus to supply viral components (such as, e.g., viral proteins) required to amplify and package the vectors into viral particles. In such a case, one or more helper components, including one or more vectors encoding the viral components, may be introduced into a host cell along with the vector system described herein. In other embodiments, the virus may be helper-free. For example, the virus may be capable of amplifying and packaging the vectors without any helper virus. In some embodiments, the vector system described herein may also encode the viral components required for virus amplification and packaging.

Non-limiting exemplary viral vectors include adeno-associated virus (AAV) vector, lentivirus vectors, adenovirus vectors, helper dependent adenoviral vectors (HDAd), herpes simplex virus (HSV-1) vectors, bacteriophage T4, baculovirus vectors, and retrovirus vectors. In some embodiments, the viral vector may be an AAV vector. In some embodiments, the viral vector is AAV2, AAV3, AAV3B, AAV5, AAV6, AAV6.2, AAV7, AAVrh. 64R1, AAVhu. 37, AAVrh. 8, AAVrh. 32.33, AAV8, AAV9, AAVrh10, or AAVLK03. In other embodiments, the viral vector may a lentivirus vector.

In some embodiments, the lentivirus may be non-integrating. In some embodiments, the viral vector may be an adenovirus vector. In some embodiments, the adenovirus may be a high-cloning capacity or "gutless" adenovirus, where all coding viral regions apart from the 5' and 3' inverted terminal repeats (ITRs) and the packaging signal (T) are deleted from the virus to increase its packaging capacity. In yet other embodiments, the viral vector may be an HSV-1 vector. In some embodiments, the HSV-1-based vector is helper dependent, and in other embodiments it is helper independent. For example, an amplicon vector that retains only the packaging sequence requires a helper virus with structural components for packaging, while a 30 kb-deleted HSV-1 vector that removes non-essential viral functions does not require helper virus. In additional embodiments, the viral vector may be bacteriophage T4. In some embodiments, the bacteriophage T4 may be able to package any linear or circular DNA or RNA molecules when the head of the virus is emptied. In further embodiments, the viral vector may be a baculovirus vector. In yet further embodiments, the viral vector may be a retrovirus vector. In embodiments using AAV or lentiviral vectors, which have smaller cloning capacity, it may be necessary to use more than one vector to deliver all the components of a vector system as disclosed herein. For example, one AAV vector may contain sequences encoding an RNA-guided DNA nuclease such as a Cas nuclease, while a second AAV vector may contain one or more guide sequences.

In some embodiments, the vector may be capable of driving expression of one or more coding sequences in a cell. In some embodiments, the cell may be a prokaryotic cell, such as, e.g., a bacterial cell. In some embodiments, the cell may be a eukaryotic cell, such as, e.g., a yeast, plant, insect, or mammalian cell. In some embodiments, the eukaryotic cell may be a mammalian cell. In some embodiments, the eukaryotic cell may be a rodent cell. In some embodiments, the eukaryotic cell may be a human cell. Suitable promoters to drive expression in different types of cells are known in the art. In some embodiments, the promoter may be wild type. In other embodiments, the promoter may be modified for more efficient or efficacious expression. In yet other embodiments, the promoter may be truncated yet retain its function. For example, the promoter may have a normal size or a reduced size that is suitable for proper packaging of the vector into a virus.

In some embodiments, the vector may comprise a nucleotide sequence encoding an RNA-guided DNA nuclease such as a nuclease described herein. In some embodiments, the nuclease encoded by the vector may be a Cas protein. In some embodiments, the vector system may comprise one copy of the nucleotide sequence encoding the nuclease. In other embodiments, the vector system may comprise more than one copy of the nucleotide sequence encoding the nuclease. In some embodiments, the nucleotide sequence encoding the nuclease may be operably linked to at least one transcriptional or translational control sequence. In some embodiments, the nucleotide sequence encoding the nuclease may be operably linked to at least one promoter.

In some embodiments, the promoter may be constitutive, inducible, or tissue-specific. In some embodiments, the promoter may be a constitutive promoter. Non-limiting exemplary constitutive promoters include cytomegalovirus immediate early promoter (CMV), simian virus (SV40) promoter, adenovirus major late (MLP) promoter, Rous sarcoma virus (RSV) promoter, mouse mammary tumor virus (MMTV) promoter, phosphoglycerate kinase (PGK) promoter, elongation factor-alpha (EF1a) promoter, ubiquitin promoters, actin promoters, tubulin promoters, immunoglobulin promoters, a functional fragment thereof, or a combination of any of the foregoing. In some embodiments, the promoter may be a CMV promoter. In some embodiments, the promoter may be a truncated CMV promoter. In other embodiments, the promoter may be an EF1a promoter. In some embodiments, the promoter may be an inducible promoter. Non-limiting exemplary inducible promoters include those inducible by heat shock, light, chemicals, peptides, metals, steroids, antibiotics, or alcohol. In some embodiments, the inducible promoter may be one that has a low basal (non-induced) expression level, such as, e.g., the Tet-On® promoter (Clontech).

In some embodiments, the promoter may be a tissue-specific promoter, e.g., a promoter specific for expression in the liver.

The vector may further comprise a nucleotide sequence encoding the guide RNA described herein. In some embodiments, the vector comprises one copy of the guide RNA. In other embodiments, the vector comprises more than one copy of the guide RNA. In embodiments with more than one guide RNA, the guide RNAs may be non-identical such that they target different target sequences, or may be identical in that they target the same target sequence. In some embodiments where the vectors comprise more than one guide RNA, each guide RNA may have other different properties, such as activity or stability within a complex with an RNA-guided DNA nuclease, such as a Cas RNP complex. In some embodiments, the nucleotide sequence encoding the guide RNA may be operably linked to at least one transcriptional or translational control sequence, such as a promoter, a 3' UTR, or a 5' UTR. In one embodiment, the promoter may be a tRNA promoter, e.g., tRNALys3, or a tRNA chimera. See Mefferd et al., RNA. 2015 21:1683-9; Scherer et al., Nucleic Acids Res. 2007 35: 2620-2628. In some embodiments, the promoter may be recognized by RNA polymerase III (Pol III). Non-limiting examples of Pol III promoters include U6 and H1 promoters. In some embodiments, the nucleotide sequence encoding the guide RNA may be operably linked to a mouse or human U6 promoter. In other embodiments, the nucleotide sequence encoding the guide RNA may be operably linked to a mouse or human H1 promoter. In embodiments with more than one guide RNA, the promoters used to drive expression may be the same or different. In some embodiments, the nucleotide encoding the crRNA of the guide RNA and the nucleotide encoding the trRNA of the guide RNA may be provided on the same vector. In some embodiments, the nucleotide encoding the crRNA and the nucleotide encoding the trRNA may be driven by the same promoter. In some embodiments, the crRNA and trRNA may be transcribed into a single transcript. For example, the crRNA and trRNA may be processed from the single transcript to form a double-molecule guide RNA. Alternatively, the crRNA and trRNA may be transcribed into a single-molecule guide RNA (sgRNA). In other embodiments, the crRNA and the trRNA may be driven by their corresponding promoters on the same vector. In yet other embodiments, the crRNA and the trRNA may be encoded by different vectors.

In some embodiments, the nucleotide sequence encoding the guide RNA may be located on the same vector comprising the nucleotide sequence encoding an RNA-guided DNA nuclease such as a Cas nuclease. In some embodiments, expression of the guide RNA and of the RNA-guided DNA nuclease such as a Cas protein may be driven by their own corresponding promoters. In some embodiments, expression of the guide RNA may be driven by the same promoter that drives expression of the RNA-guided DNA nuclease such as a Cas protein. In some embodiments, the guide RNA and the RNA-guided DNA nuclease such as a Cas protein transcript may be contained within a single transcript. For example, the guide RNA may be within an untranslated region (UTR) of the RNA-guided DNA nuclease such as a Cas protein transcript. In some embodiments, the guide RNA may be within the 5' UTR of the transcript. In other embodiments, the guide RNA may be within the 3' UTR of the transcript. In some embodiments, the intracellular half-life of the transcript may be reduced by containing the guide RNA within its 3' UTR and thereby shortening the length of its 3' UTR. In additional embodiments, the guide RNA may be within an intron of the transcript. In some embodiments, suitable splice sites may be added at the intron within which the guide RNA is located such that the guide RNA is properly spliced out of the transcript. In some embodiments, expression of the RNA-guided DNA nuclease such as a Cas protein and the guide RNA from the same vector in close temporal proximity may facilitate more efficient formation of the CRISPR RNP complex.

In some embodiments, the compositions comprise a vector system. In some embodiments, the vector system may comprise one single vector. In other embodiments, the vector system may comprise two vectors. In additional embodiments, the vector system may comprise three vectors. When different guide RNAs are used for multiplexing, or when multiple copies of the guide RNA are used, the vector system may comprise more than three vectors.

In some embodiments, the vector system may comprise inducible promoters to start expression only after it is delivered to a target cell. Non-limiting exemplary inducible promoters include those inducible by heat shock, light, chemicals, peptides, metals, steroids, antibiotics, or alcohol. In some embodiments, the inducible promoter may be one that has a low basal (non-induced) expression level, such as, e.g., the Tet-On® promoter (Clontech).

In additional embodiments, the vector system may comprise tissue-specific promoters to start expression only after it is delivered into a specific tissue.

The vector may be delivered by liposome, a nanoparticle, an exosome, or a microvesicle. The vector may also be delivered by a lipid nanoparticle (LNP); see e.g., WO2017/173054, published Oct. 5, 2017, and entitled "LIPID NANOPARTICLE FORMULATIONS FOR CRISPR/CAS COMPONENTS," and WO2019067992A1 published Apr. 4, 2019, entitled "FORMULATIONS," the contents of each of which are hereby incorporated by reference in their entirety. Any of the LNPs and LNP formulations described herein are suitable for delivery of the guides alone or together a cas nuclease or a nucleic acid encoding a cas nuclease. In some embodiments, an LNP composition is encompassed comprising: an RNA component and a lipid component, wherein the lipid component comprises an amine lipid, a neutral lipid, a helper lipid, and a stealth lipid; and wherein the N/P ratio is about 1-10.

In some instances, the lipid component comprises Lipid A or its acetal analog, cholesterol, DSPC, and PEG-DMG; and wherein the N/P ratio is about 1-10. In some embodiments, the lipid component comprises: about 40-60 mol-% amine lipid; about 5-15 mol-% neutral lipid; and about 1.5-10 mol-% PEG lipid, wherein the remainder of the lipid component is helper lipid, and wherein the N/P ratio of the LNP composition is about 3-10. In some embodiments, the lipid component comprises about 50-60 mol-% amine lipid; about 8-10 mol-% neutral lipid; and about 2.5-4 mol-% PEG lipid, wherein the remainder of the lipid component is helper lipid, and wherein the N/P ratio of the LNP composition is about 3-8. In some instances, the lipid component comprises: about 50-60 mol-% amine lipid; about 5-15 mol-% DSPC; and about 2.5-4 mol-% PEG lipid, wherein the remainder of the lipid component is cholesterol, and wherein the N/P ratio of the LNP composition is about 3-8. In some instances, the lipid component comprises: 48-53 mol-% Lipid A; about 8-10 mol-% DSPC; and 1.5-10 mol-% PEG lipid, wherein the remainder of the lipid component is cholesterol, and wherein the N/P ratio of the LNP composition is 3-8±0.2.

In some embodiments, the LNP comprises a lipid component and the lipid component comprises, consists essentially of, or consists of: about 50 mol-% amine lipid such as Lipid A; about 9 mol-% neutral lipid such as DSPC; about 3 mol-% of a stealth lipid such as a PEG lipid, such as PEG2k-DMG, and the remainder of the lipid component is helper lipid such as cholesterol, wherein the N/P ratio of the LNP composition is about 6. In some embodiments, the amine lipid is Lipid A. In some embodiments, the neutral lipid is DSPC. In some embodiments, the stealth lipid is a PEG lipid. In some embodiments, the stealth lipid is a PEG2k-DMG. In some embodiments, the helper lipid is cholesterol. In some embodiments, the LNP comprises a lipid component and the lipid component comprises: about 50 mol-% Lipid A; about 9 mol-% DSPC; about 3 mol-% of PEG2k-DMG, and the remainder of the lipid component is cholesterol wherein the N/P ratio of the LNP composition is about 6.

In some embodiments, the vector may be delivered systemically. In some embodiments, the vector may be delivered into the hepatic circulation.

This description and exemplary embodiments should not be taken as limiting. For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

EXAMPLES

The following examples are provided to illustrate certain disclosed embodiments and are not to be construed as limiting the scope of this disclosure in any way.

General Reagents and Methods

Unless otherwise indicated, mRNA was synthesized by in vitro transcription (IVT) using a linearized plasmid DNA template and T7 RNA polymerase. Transcription was generally performed from constructs comprising a T7 Promoter, a transcript sequence disclosed herein such as SEQ ID NO: 243 (which encodes the RNA ORF of SEQ ID NO: 204) and a poly-A tail (SEQ ID NO: 263) encoded in the plasmid.

For all methods, the transcript concentration was determined by measuring the light absorbance at 260 nm (Nanodrop), and the transcript was analyzed by capillary electrophoresis by Bioanlayzer (Agilent).

LNP Formulation

The lipid components were dissolved in 100% ethanol with the lipid component molar ratios described below. The chemically modified sgRNA and Cas9 mRNA were combined and dissolved in 25 mM citrate, 100 mM NaCl, pH 5.0, resulting in a concentration of total RNA cargo of approximately 0.45 mg/mL. The LNPs were formulated with an N/P ratio of about 6, with the ratio of chemically modified sgRNA:Cas9 mRNA at a 1:2 w/w ratio as described below. Unless otherwise indicated, LNPs were formulated with 50% Lipid A, 9% DSPC, 38% cholesterol, and 3% PEG2k-DMG.

The LNPs were formed by an impinging jet mixing of the lipid in ethanol with two volumes of RNA solution and one volume of water. The lipid in ethanol is mixed through a mixing cross with the two volumes of RNA solution. A fourth stream of water is mixed with the outlet stream of the cross through an inline tee. (See, e.g., WO2016010840, FIG. 2.) A 2:1 ratio of aqueous to organic solvent was maintained during mixing using differential flow rates. The LNPs were held for 1 hour at room temperature, and further diluted with water (approximately 1:1 v/v). Diluted LNPs were concentrated using tangential flow filtration on a flat sheet cartridge (Sartorius, 100 kD MWCO) and then buffer exchanged by diafiltration into 50 mM Tris, 45 mM NaCl, 5% (w/v) sucrose, pH 7.5 (TSS). The resulting mixture was then filtered using a 0.2 μm sterile filter. The final LNP was stored at 4° C. or −80° C. until further use.

LNP Composition Analytics

Dynamic Light Scattering ("DLS") is used to characterize the polydispersity index ("pdi") and size of the LNPs of the present disclosure. DLS measures the scattering of light that results from subjecting a sample to a light source. PDI, as determined from DLS measurements, represents the distribution of particle size (around the mean particle size) in a population, with a perfectly uniform population having a PDI of zero.

Electropheretic light scattering is used to characterize the surface charge of the LNP at a specified pH. The surface charge, or the zeta potential, is a measure of the magnitude of electrostatic repulsion/attraction between particles in the LNP suspension.

Assymetric-Flow Field Flow Fractionation-Multi-Angle Light Scattering (AF4-MALS) is used to separate particles in the composition by hydrodynamic radius and then measure the molecular weights, hydrodynamic radii and root mean square radii of the fractionated particles. This allows the ability to assess molecular weight and size distributions as well as secondary characteristics such as the Burchard-Stockmeyer Plot (ratio of root mean square ("rms") radius to hydrodynamic radius over time suggesting the internal core density of a particle) and the rms conformation plot (log of rms radius vs log of molecular weight where the slope of the resulting linear fit gives a degree of compactness vs elongation).

Nanoparticle tracking analysis (NTA, Malvern Nanosight®) can be used to determine particle size distribution as well as particle concentration. LNP samples are diluted appropriately and injected onto a microscope slide. A camera records the scattered light as the particles are slowly infused through field of view. After the movie is captured, the Nanoparticle Tracking Analysis processes the movie by tracking pixels and calculating a diffusion coefficient. This diffusion coefficient can be translated into the hydrodynamic radius of the particle. The instrument also counts the number of individual particles counted in the analysis to give particle concentration.

Cryo-electron microscopy ("cryo-EM") can be used to determine the particle size, morphology, and structural characteristics of an LNP.

Lipid compositional analysis of the LNPs can be determined from liquid chromatography followed by charged aerosol detection (LC-CAD). This analysis can provide a comparison of the actual lipid content versus the theoretical lipid content.

LNP compositions are analyzed for average particle size, polydispersity index (pdi), total RNA content, encapsulation efficiency of RNA, and zeta potential. LNP compositions may be further characterized by lipid analysis, AF4-MALS, NTA, and/or cryo-EM. Average particle size and polydispersity are measured by dynamic light scattering (DLS) using a dynamic light scattering measurement system (Malvern Zetasizer® DLS instrument). LNP samples were diluted with PBS buffer prior to being measured by DLS. Z-average diameter which is an intensity-based measurement of average particle size is reported along with number average diameter and pdi. A dynamic light scattering measurement system (Malvern Zetasizer®) instrument is also used to measure the zeta potential of the LNP. Samples are diluted 1:17 (50 μL into 800 μL) in 0.1×PBS, pH 7.4 prior to measurement.

A fluorescence-based assay (Ribogreen®, ThermoFisher Scientific) is used to determine total RNA concentration and free RNA. Encapsulation efficiency is calculated as (Total RNA−Free RNA)/Total RNA. LNP samples are diluted appropriately with 1×TE buffer containing 0.2% Triton-X 100 to determine total RNA or 1×TE buffer to determine free RNA. Standard curves are prepared by utilizing the starting RNA solution used to make the compositions and diluted in 1×TE buffer+/−0.2% Triton-X 100. Diluted RiboGreen® dye (according to the manufacturer's instructions) is then added to each of the standards and samples and allowed to incubate for approximately 10 minutes at room temperature, in the absence of light. A SpectraMax M5 Microplate Reader (Molecular Devices) is used to read the samples with excitation, auto cutoff and emission wavelengths set to 488 nm, 515 nm, and 525 nm respectively. Total RNA and free RNA are determined from the appropriate standard curves.

Encapsulation efficiency is calculated as (Total RNA−Free RNA)/Total RNA. The same procedure may be used for determining the encapsulation efficiency of a DNA-based cargo component. In a fluorescence-based assay, for single-strand DNA Oligreen Dye may be used, and for double-strand DNA, Picogreen Dye. Alternatively, the total RNA concentration can be determined by a reverse-phase ion-pairing (RP-IP) HPLC method. Triton X-100 is used to disrupt the LNPs, releasing the RNA. The RNA is then separated from the lipid components chromatographically by RP-IP HPLC and quantified against a standard curve using UV absorbance at 260 nm.

AF4-MALS is used to look at molecular weight and size distributions as well as secondary statistics from those calculations. LNPs are diluted as appropriate and injected into a AF4 separation channel using an HPLC autosampler where they are focused and then eluted with an exponential gradient in cross flow across the channel. All fluid is driven by an HPLC pump and Wyatt Eclipse Instrument. Particles eluting from the AF4 channel flow through a UV detector, multi-angle light scattering detector, quasi-elastic light scattering detector and differential refractive index detector. Raw data is processed by using a Debeye model to determine molecular weight and rms radius from the detector signals.

Lipid components in LNPs are analyzed quantitatively by HPLC coupled to a charged aerosol detector (CAD). Chromatographic separation of 4 lipid components is achieved by reverse phase HPLC. CAD is a destructive mass-based detector which detects all non-volatile compounds and the signal is consistent regardless of analyte structure.

Cas9 mRNA and gRNA Cargos

The Cas9 mRNA cargo was prepared by in vitro transcription. Capped and polyadenylated Cas9 mRNA was generated by in vitro transcription using a linearized plasmid DNA template and T7 RNA polymerase using a method as follows. Plasmid DNA containing a T7 promoter and a 90-100 nt poly(A/T) region is linearized by incubating at 37° C. for 2 hours with XbaI with the following conditions: 200 ng/μL plasmid, 2 U/μL XbaI (NEB), and 1× reaction buffer. The XbaI is inactivated by heating the reaction at 65° C. for 20 min. The linearized plasmid is purified from enzyme and buffer. The IVT reaction to generate Cas9 modified mRNA is performed by incubating at 37° C. for 1.5-4 hours in the following conditions: 50 ng/μL linearized plasmid; 2-5 mM each of GTP, ATP, CTP, and N1-methyl pseudo-UTP (Trilink); 10-25 mM ARCA (Trilink); 5 U/μL T7 RNA polymerase (NEB); 1 U/μL Murine RNase inhibitor (NEB); 0.004 U/μL Inorganic *E. coli* pyrophosphatase (NEB); and 1× reaction buffer. TURBO DNase (ThermoFisher) is added to a final concentration of 0.01 U/μL, and the reaction is incubated for an additional 30 minutes to remove the DNA template. The Cas9 mRNA was purified with TFF and/or an LiCl precipitation-containing method.

The sgRNAs in the following examples were chemically synthesized by known methods using phosphoramidites.

Cas9 mRNA and Guide RNA Delivery In Vitro by LNP

Primary human liver hepatocytes (PHH) (Gibco) and primary cynomolgus liver hepatocytes (PCH) (InVitro Admet Laborotories) were thawed and resuspended in hepatocyte thawing medium with supplements (Gibco, Cat. CM7500) followed by centrifugation. The supernatant was discarded and the pelleted cells resuspended in hepatocyte plating medium plus supplement pack (Invitrogen, Cat. A1217601 and CM3000). Cells were counted and plated on Bio-coat collagen I coated 96-well plates (ThermoFisher, Cat. 877272) at a density of 33,000 cells/well for PHH and 50,000 cells/well for PCH. Plated cells were allowed to settle and adhere for 5 hours in a tissue culture incubator at 37° C. and 5% $CO_2$ atmosphere. After incubation cells were checked for monolayer formation and were washed once with hepatocyte culture medium (Invitrogen, Cat. A1217601 and CM4000).

PHH and PCH were treated with LNPs as further described below. Cells were incubated at 37° C., 5% $CO_2$ for 24 hours prior to treatment with LNPs. LNPs were incubated in media containing 3% cynomolgus serum or 3% fetal bovine serum at 37° C. for 5 minutes and administered to cells in amounts as further provided herein.

Genomic DNA Isolation

Treated cells were harvested post-treatment at 72 hours. The cells were lysed from each well of a 96-well plate using 50 μL/well Quick Extract DNA Extraction solution (Epicentre, Cat. QE09050) according to manufacturer's protocol. All DNA samples were subjected to PCR and subsequent NGS analysis, as described herein.

NGS Sequencing

In brief, to quantitatively determine the efficiency of editing at the target location in the genome, genomic DNA was isolated and deep sequencing was utilized to identify the presence of insertions and deletions introduced by gene editing.

PCR primers were designed around the target site (e.g., TTR), and the genomic area of interest was amplified. Additional PCR was performed according to the manufacturer's protocols (Illumina) to add the necessary chemistry for sequencing. The amplicons were sequenced on an Illumina MiSeq instrument. The reads were aligned to the appropriate reference genome (e.g., hg38, macFas5) after eliminating those having low quality scores. The resulting files containing the reads were mapped to the reference genome (BAM files), where reads that overlapped the target region of interest were selected and the number of wild-type reads versus the number of reads which contain an insertion, substitution, or deletion was calculated.

The editing percentage (e.g., the "editing efficiency" or "percent editing") is defined as the total number of sequence reads with insertions or deletions over the total number of sequence reads, including wild type.

Example 1—Dose Response with LNP Delivery of Cas9 mRNAs in Primary Hepatocytes The efficacy of various guide and mRNA combinations was evaluated in vitro in primary cyno hepatocytes (PCH) and primary human hepatocytes (PHH). PHH and PCH cells were plated as described above and then treated with various doses of LNP as described in Tables 8 and 9, respectively. The LNPs contained G000502 (SEQ ID No: 114) and either mRNA000001 (SEQ ID No: 1) or mRNA000042 (SEQ ID No: 377) as mRNA. Cells were lysed after 72 hrs and % editing was determined by NGS. Each condition was assayed in triplicate and Tables 8 and 9 show the mean and standard deviation for % Edit.

TABLE 8

In vitro editing using LNP delivery in PHHs

| Guide ID | mRNA ID | Dose Cas9 mRNA (ng) | Mean % Edit | SD |
|---|---|---|---|---|
| G000502 | mRNA01 | 50 | 46.1 | 3.97 |
| G000502 | mRNA01 | 10 | 32.37 | 2.64 |
| G000502 | mRNA01 | 5 | 24.87 | 0.06 |
| G000502 | mRNA01 | 1 | 5.2 | 0.75 |
| G000502 | mRNA01 | 0.01 | 0.43 | 0.12 |
| G000502 | mRNA01 | 0 | 0.23 | 0.15 |

TABLE 8-continued

In vitro editing using LNP delivery in PHHs

| Guide ID | mRNA ID | Dose Cas9 mRNA (ng) | Mean % Edit | SD |
|---|---|---|---|---|
| G000502 | mRNA42 | 50 | 42.27 | 1.8 |
| G000502 | mRNA42 | 10 | 41.67 | 0.81 |
| G000502 | mRNA42 | 5 | 32.7 | 2.93 |
| G000502 | mRNA42 | 1 | 10.13 | 1.62 |
| G000502 | mRNA42 | 0.01 | 0.8 | 0 |
| G000502 | mRNA42 | 0 | 0.13 | 0.06 |

TABLE 9

In vitro editing using LNP delivery in PCHs

| Guide ID | mRNA ID | Dose Cas9 mRNA (ng) | Mean % Indel | SD |
|---|---|---|---|---|
| G000502 | mRNA01 | 50 | 71.8 | 1.99 |
| G000502 | mRNA01 | 10 | 33.23 | 2.32 |
| G000502 | mRNA01 | 5 | 15.23 | 1.36 |
| G000502 | mRNA01 | 1 | 1.27 | 0.12 |
| G000502 | mRNA01 | 0.01 | 0.1 | 0 |
| G000502 | mRNA01 | 0 | 0.1 | 0 |
| G000502 | mRNA42 | 50 | 82.8 | 1.77 |
| G000502 | mRNA42 | 10 | 59.5 | 1.1 |
| G000502 | mRNA42 | 5 | 38.37 | 1 |
| G000502 | mRNA42 | 1 | 5.6 | 0.4 |
| G000502 | mRNA42 | 0.01 | 0.3 | 0.1 |
| G000502 | mRNA42 | 0 | 0.1 | 0 |

Figure 1B:
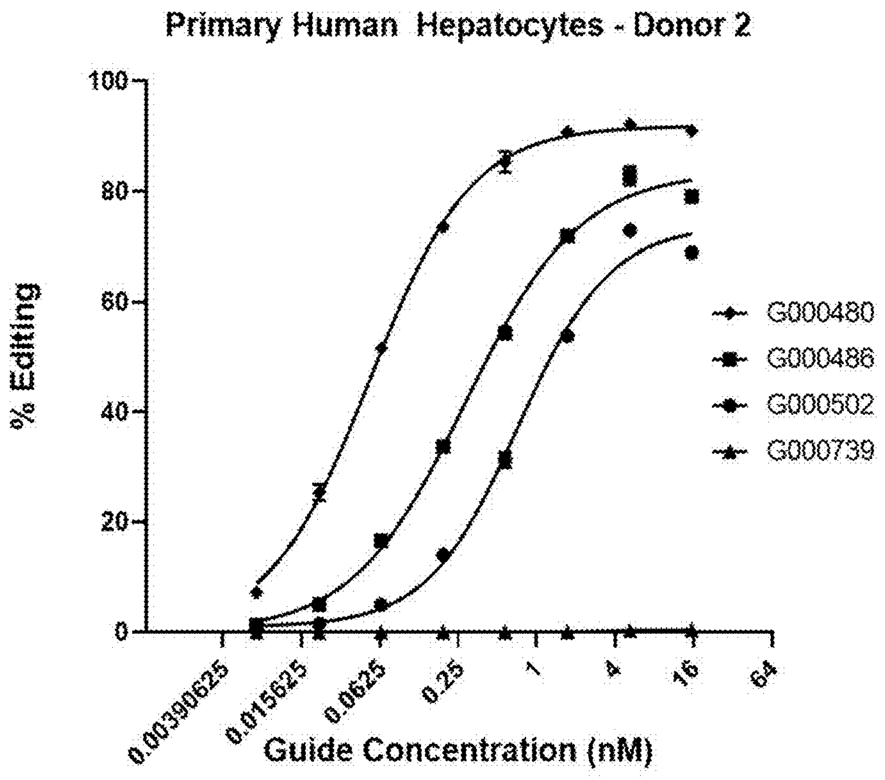
Figure 2:
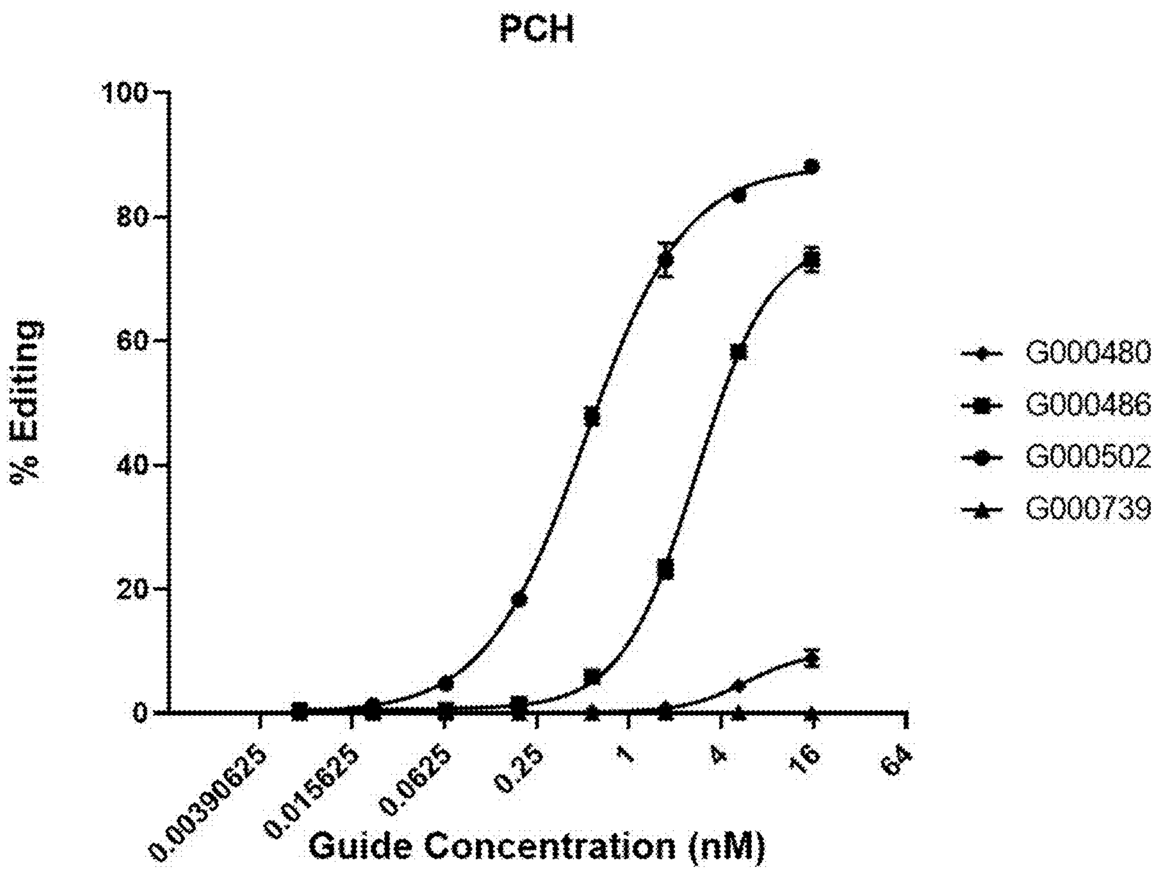
FIG. 2 shows % Editing in primary cyno hepatocytes as described in Example 2.

Example 2—Dose Response with LNP Delivery of Cas9 mRNAs in Primary Hepatocytes Various guide and mRNA combinations were evaluated in vitro in PCH and PHH cells. PHH cells from two donors and PCH cells were plated as described above and treated with doses of LNP as described in Tables 10 and 11, respectively. The LNPs contained Cas9 mRNA000042 (SEQ ID No: 377) and one of 4 single guide RNAs. Guides G000480 and G000486 (SEQ ID Nos: 87 and 93) perfectly target to the human TTR gene. Guide G000502 (SEQ ID No: 114) targets the human TTR gene with a single mismatch in the targeting region. G000739 (SEQ ID No: 2) is a negative control. Cells were lysed after 72 hrs and % editing was determined by NGS. Each condition was assayed in triplicate. Table 10 and FIG. 1 show % Editing results in PHH cells. Table 11 and FIG. 2 show % Editing results in PCH cells.

TABLE 10

In vitro editing in PHH cells

| Guide | Guide concentration (nM) | PHH - Donor 1 Mean % Editing | PHH - Donor 1 Std. Dev | PHH - Donor 2 Mean % Editing | PHH - Donor 2 Std. Dev |
|---|---|---|---|---|---|
| G000480 | 15.51724 | 90.97 | 0.91 | 90.33 | 1.71 |
| G000480 | 5.172414 | 92.23 | 0.85 | 87.57 | 3.63 |
| G000480 | 1.724138 | 90.83 | 0.68 | 86.37 | 1.50 |
| G000480 | 0.574713 | 85.37 | 1.86 | 80.53 | 1.97 |
| G000480 | 0.191571 | 73.53 | 0.91 | 62.37 | 5.98 |
| G000480 | 0.063857 | 51.57 | 0.40 | 32.80 | 3.10 |
| G000480 | 0.021286 | 25.37 | 1.48 | 9.07 | 0.67 |
| G000480 | 0.007095 | 7.23 | 0.40 | 1.97 | 0.57 |
| G000486 | 15.51724 | 79.07 | 0.74 | 86.73 | 1.63 |
| G000486 | 5.172414 | 82.83 | 1.69 | 88.03 | 2.69 |
| G000486 | 1.724138 | 71.87 | 0.67 | 81.43 | 1.68 |
| G000486 | 0.574713 | 54.33 | 0.32 | 66.90 | 2.10 |

TABLE 10-continued

In vitro editing in PHH cells

| Guide | Guide concentration (nM) | PHH - Donor 1 Mean % Editing | PHH - Donor 1 Std. Dev | PHH - Donor 2 Mean % Editing | PHH - Donor 2 Std. Dev |
|---|---|---|---|---|---|
| G000486 | 0.191571 | 33.70 | 1.06 | 41.70 | 2.52 |
| G000486 | 0.063857 | 16.67 | 0.67 | 17.33 | 1.29 |
| G000486 | 0.021286 | 5.10 | 0.26 | 4.27 | 0.76 |
| G000486 | 0.007095 | 1.33 | 0.06 | 1.37 | 0.15 |
| G000502 | 15.51724 | 68.93 | 0.90 | 78.20 | 0.17 |
| G000502 | 5.172414 | 72.90 | 0.53 | 80.73 | 1.70 |
| G000502 | 1.724138 | 53.83 | 0.71 | 65.13 | 0.71 |
| G000502 | 0.574713 | 31.23 | 1.33 | 37.53 | 0.84 |
| G000502 | 0.191571 | 14.17 | 0.98 | 17.70 | 1.71 |
| G000502 | 0.063857 | 5.03 | 0.32 | 5.27 | 0.12 |
| G000502 | 0.021286 | 1.57 | 0.31 | 1.13 | 0.35 |
| G000502 | 0.007095 | 0.33 | 0.06 | 0.33 | 0.06 |
| G000739 | 15.51724 | 0.47 | 0.06 | 0.20 | 0.10 |
| G000739 | 5.172414 | 0.40 | 0.10 | 0.20 | 0.10 |
| G000739 | 1.724138 | 0.13 | 0.06 | 0.07 | 0.06 |
| G000739 | 0.574713 | 0.10 | 0.00 | 0.07 | 0.06 |
| G000739 | 0.191571 | 0.07 | 0.06 | 0.10 | 0.00 |
| G000739 | 0.063857 | 0.07 | 0.06 | 0.07 | 0.06 |
| G000739 | 0.021286 | 0.03 | 0.06 | 0.07 | 0.06 |
| G000739 | 0.007095 | 0.10 | 0.00 | 0.03 | 0.06 |

TABLE 11

In vitro editing in PCH cells

| Guide | Guide concentration (nM) | Mean % Editing | Std. Dev |
|---|---|---|---|
| G000480 | 15.51724 | 8.87 | 1.29 |
| G000480 | 5.172414 | 4.43 | 0.71 |
| G000480 | 1.724138 | 0.80 | 0.20 |
| G000480 | 0.574713 | 0.23 | 0.12 |
| G000480 | 0.191571 | 0.23 | 0.06 |
| G000480 | 0.063857 | 0.10 | 0.00 |
| G000480 | 0.021286 | 0.10 | 0.00 |
| G000480 | 0.007095 | 0.10 | 0.00 |
| G000486 | 15.51724 | 73.10 | 2.00 |
| G000486 | 5.172414 | 58.27 | 0.47 |
| G000486 | 1.724138 | 23.23 | 1.40 |
| G000486 | 0.574713 | 5.93 | 0.25 |
| G000486 | 0.191571 | 1.43 | 0.21 |
| G000486 | 0.063857 | 0.53 | 0.15 |
| G000486 | 0.021286 | 0.40 | 0.17 |
| G000486 | 0.007095 | 0.47 | 0.12 |
| G000502 | 15.51724 | 88.10 | 0.53 |
| G000502 | 5.172414 | 83.53 | 0.55 |
| G000502 | 1.724138 | 73.07 | 2.68 |
| G000502 | 0.574713 | 47.87 | 1.38 |
| G000502 | 0.191571 | 18.37 | 0.86 |
| G000502 | 0.063857 | 4.80 | 0.26 |
| G000502 | 0.021286 | 1.27 | 0.50 |
| G000502 | 0.007095 | 0.57 | 0.12 |
| G000739 | 15.51724 | 0.10 | 0.00 |
| G000739 | 5.172414 | 0.13 | 0.06 |
| G000739 | 1.724138 | 0.13 | 0.06 |
| G000739 | 0.574713 | 0.10 | 0.00 |
| G000739 | 0.191571 | 0.10 | 0.00 |
| G000739 | 0.063857 | 0.10 | 0.00 |
| G000739 | 0.021286 | 0.10 | 0.00 |
| G000739 | 0.007095 | 0.10 | 0.00 |

Example 3—Characterization of Additional mRNAs

Materials and methods for this example were as described in International Patent Application No. PCT/US2018/053439, filed Sep. 28, 2018. Cas9 sequences using different codon schemes were designed to test for improved protein expression. Each sequence was designed to encode the Cas9 amino acid of SEQ ID No: 203 using a distinct set of codons. In each open reading frame sequence, a single codon was used to encode each amino acid. Sequences vary based on the frequency with which codons occur in complete protein coding genes in *Homo sapiens* based on the NCBI-GenBank Flat File Release 160.0 (Nakamura et al. (2000) *Nucl. Acids Res.* 28, 292; Benson et al. (2006) *Nucleic Acids Res.* 34(Database issue), D16-20) and the abundance of a particular nucleotide among the codons. Based on the codon schemes shown in Table 5, several different open reading frames for Cas9 (SEQ ID No: 252, 311, and 312) were constructed that encode Cas9 protein of SEQ ID NO: 203. These were incorporated into constructs also containing the HSD 5' UTR (SEQ ID NO: 241), an albumin 3' UTR, a T7 promoter and a polyA tail. An exemplary sequence containing the albumin 3' UTR and polyA tail is SEQ ID NO: 253, in which the 3' UTR and polyA tail follow the HSD 5' UTR and the ORF of SEQ ID NO: 252.

Messenger RNA was produced for each construct by IVT using 100% N1-methyl pseudouridine in place of uridine. HepG2 cells were transfected with 800 ng of each Cas9 mRNA using Lipofectamine™ MessengerMAX™ Transfection Reagent (ThermoFisher). Six hours post transfection, cells were lysed by freeze thaw and cleared by centrifugation. Cas9 protein levels were determined by ELISA assay. Briefly, total protein concentration was determined by bicinchoninic acid assay. An MSD GOLD 96-well Streptavidin SECTOR Plate (Meso Scale Diagnostics, Cat. L15SA-1) was prepared according to manufacturer's protocol using Cas9 mouse antibody (Origene, Cat. CF811179) as the capture antibody and Cas9 (7A9-3A3) Mouse mAb (Cell Signaling Technology, Cat. 14697) as the detection antibody. Recombinant Cas9 protein was used as a calibration standard in Diluent 39 (Meso Scale Diagnostics) with 1× Halt™ Protease Inhibitor Cocktail, EDTA-Free (ThermoFisher, Cat. 78437). ELISA plates were read using the Meso Quickplex SQ120 instrument (Meso Scale Discovery) and data was analyzed with Discovery Workbench 4.0 software package (Meso Scale Discovery).

Editing efficiency was assessed in vitro by transfecting mRNA together with a guide (G502; SEQ ID NO: 114) targeting transthyretin (TTR) into HepG2 cells and measuring percentage editing. Cas9 mRNAs comprising SEQ ID Nos indicated in Table 12 were assessed at concentrations of mRNA from 3 ng-100 ng. Untreated cells did not show measurable editing. Table 12 shows the effects of the different codon sets on Cas9 protein expression and editing in vitro.

TABLE 12

In vitro editing and expression of ORFs with different codon sets

| ORF (codon set) | ng Cas9/mg total protein | ng Cas9/mg total protein Standard Deviation | % Editing (30 ng mRNA transfected) | Editing Standard Deviation |
|---|---|---|---|---|
| SEQ ID No: 252 (Table 4 low U 1) | 31.23 | 4.47 | 22.2 | 2.83 |
| SEQ ID No: 311 (Table 4 low A) | 74.62 | 15.53 | 41.3 | 3.56 |
| SEQ ID No: 312 (Table 4 low A/U) | 77.32 | 10.60 | 34.8 | 7.32 |

To determine the effectiveness of the codon schemes in vivo, Cas9 protein expression was measured when expressed in vivo from mRNAs encoding Cas9 using codon schemes described in Table 4. Messenger RNAs as indicated in Table 26 were formulated as LNPs with a guide RNA targeting TTR (G282; SEQ ID NO: 242). The LNPs were assembled using the cross flow procedure and contained 50% Lipid A, 9% DSPC, 38% cholesterol, and 3% PEG2k-DMG in a 50:38:9:3 molar ratio, respectively, and had a N:P ratio of 6.0. LNPs were purified using Amicon PD-10 filters (GE Healthcare) and used at a concentration of 0.32 mg/ml (LNP concentration). CD-1 female mice (n=5 per group) were dosed i.v. at 1 mpk. At 3 hours post-dose, animals were sacrificed, the liver was collected and Cas9 expression in liver were measured. Cas9 protein expression was measured in the liver using the Meso Scale Discovery ELISA assay described above. Approximately 40-50 mg liver tissue was homogenized by bead mill in RIPA Buffer (Boston Bioproducts BP-115) with 1× Complete Protease Inhibitor Tablet (Roche, Cat. 11836170001). Table 13 shows Cas9 expression results in liver. mRNAs for the low A and low A/U codon schemes (ORFs of SEQ ID NOs: 311 and 312) showed the highest Cas9 expression of the tested ORFs. Cas9 protein expression of the negative control was below the lower limit of quantitation (LLOQ).

TABLE 13

| ORF | Average Cas9 (ng/g liver) | Standard Deviation |
|---|---|---|
| TSS | <LLOQ | 0.0 |
| SEQ ID No: 204 | 1644 | 1172 |
| SEQ ID NO: 252 | 1562 | 951 |
| SEQ ID NO: 311 | 2630 | 730 |
| SEQ ID NO: 312 | 2134 | 362 |

To determine the effectiveness of the codon schemes in vivo, genome editing was measured in vivo from mRNAs encoding Cas9 using different codon schemes. Messenger RNAs as indicated in Table 27 were formulated as LNPs with a guide RNA targeting TTR (G282; SEQ ID NO: 242). The LNPs were assembled using the cross flow procedure and contained 50% Lipid A, 9% DSPC, 38% cholesterol, and 3% PEG2k-DMG in a 50:38:9:3 molar ratio, respectively, and had a N:P ratio of 6.0. LNPs were purified using Amicon PD-10 filters (GE Healthcare), and used at a concentration of 0.05 mg/ml (LNP concentration). CD-1 female mice (n=5 per group, except n=4 for the group treated with SEQ ID NO: 252) were dosed i.v. at 0.1 mpk. At 6 days post-dose, animals were sacrificed, blood and the liver were collected, and serum TTR and liver editing were measured. Table 14 shows in vivo editing results and serum TTR levels.

TABLE 14

| ORF | Avg % Editing | Editing Standard Deviation | Serum TTR (μg/ml) | Serum TTR Standard Deviation | n |
|---|---|---|---|---|---|
| TSS | 0.06 | 0.05 | 856 | 68 | 5 |
| SEQ ID No: 204 | 40.96 | 8.41 | 329 | 143 | 5 |
| SEQ ID No: 252 | 60.10 | 8.07 | 143 | 78 | 4 |
| SEQ ID No: 311 | 57.26 | 4.15 | 216 | 62 | 5 |
| SEQ ID No: 312 | 61.44 | 4.50 | 100 | 79 | 5 |

To determine the efficacy of the codon schemes at different mRNA concentrations, an in vivo dose response experiment was performed. Messenger RNAs as indicated in Table 15 were formulated as LNPs with a guide RNA targeting TTR (G282; SEQ ID NO: 242). The LNPs were assembled using the cross flow method and contained 50% Lipid A, 9% DSPC, 38% cholesterol, and 3% PEG2k-DMG. LNPs were purified using Amicon PD-10 filters (GE Healthcare and used at a concentration of 0.7 mg/ml (LNP concentration). CD-1 female mice (n=5 per group) were dosed i.v. at 0.03, 0.1, or 0.3 mpk. At 7 days post-dose, animals were sacrificed, blood and the liver were collected, and serum TTR and liver editing were measured. Table 14 shows in vivo editing results and serum TTR levels.

TABLE 15

| ORF | Dose (mpk) | Liver editing (%) | Serum TTR (ug/mL) | Serum TTR (% KD) |
|---|---|---|---|---|
| TSS | n/a | 0.1 | 576.8 | 0.0 |
| SEQ ID | 0.3 | 51.3 | 165.6 | 71.3 |
| No: 204 | 0.1 | 17.3 | 540.7 | 6.3 |
| | 0.03 | 1.9 | 761.4 | −32.0 |
| SEQ ID | 0.3 | 57.0 | 100.8 | 82.5 |
| No: 252 | 0.1 | 29.6 | 336.1 | 41.7 |
| | 0.03 | 5.0 | 636.4 | −10.3 |
| SEQ ID | 0.3 | 59.4 | 93.8 | 83.7 |
| NO: 311 | 0.1 | 30.6 | 373.5 | 35.2 |
| | 0.03 | 5.9 | 559.6 | 3.0 |
| SEQ ID | 0.3 | 60.6 | 92.0 | 87.2 |
| NO: 312 | 0.1 | 25.5 | 397.5 | 31.1 |
| | 0.03 | 7.8 | 555.3 | 3.7 |

To determine the effectiveness of the codon schemes with different UTRs, genome editing was measured in vivo following administration of mRNAs encoding Cas9. Messenger RNAs as indicated in Table 15 were formulated as LNPs with a guide RNA targeting TTR (G282; SEQ ID NO: 242). The LNPs were assembled using the cross flow procedure and contained 50% Lipid A, 9% DSPC, 38% cholesterol, and 3% PEG2k-DMG in a 50:38:9:3 molar ratio, respectively, and had a N:P ratio of 6.0. LNPs were purified using Amicon PD-10 filters (GE Healthcare) and used at a concentration of 0.05 mg/ml (LNP concentration). CD-1 female mice (n=5 per group; n=4 for SEQ ID No: 243 editing) were dosed i.v. at 0.1 mpk. At 6 days post-dose, animals were sacrificed, blood and the liver were collected, and serum TTR and liver editing were measured. Table 16 shows in vivo editing and serum TTR results.

TABLE 16

| mRNA construct | % Editing | Standard Deviation | Serum TTR (μg/ml) | Standard Deviation |
|---|---|---|---|---|
| TSS | 0 | 0 | 1274 | 214 |
| SEQ ID No: 243 | 28 | 4 | 630 | 152 |
| SEQ ID No: 376 | 35 | 8 | 482 | 138 |
| SEQ ID No: 377 | 37 | 9 | 316 | 143 |
| SEQ ID No: 378 | 42 | 6 | 524 | 192 |

Example 4—Multiple Dose LNP Study Administered Via 30 Minute and 2 Hour IV Infusion in Cynomolgus Monkeys Male cynomolgus monkeys in cohorts of n=3 were administered dexamethasone (Dex) via IV bolus injection at 2 mg/kg a minimum of 1 hour prior to LNP or vehicle control administration. Each cohort received varying doses of LNP to provide 3 mg/kg, or 6 mg/kg (RNA) per NHP. Dosing groups are shown in Table 17. Two cohorts received an LNP dose of 3 mg/kg in order to compare infusion time. Formulations contained a Cas9 mRNA comprising SEQ ID No. 377) and guide RNA (gRNA) G000502 (SEQ ID No. 114) in a gRNA:mRNA ratio of 1:2 by weight. The cohorts receiving an LNP dose of 3 mg/kg (total RNA content), were administered by 30-minute or 120-minute IV infusion. All other cohorts with various doses of LNP (in mg/kg, total RNA content), were administered by 120-minute IV infusion.

TABLE 17

Infusion Study Dosing Groups

| Group Number | Test Material | Dose Level (mg/kg) | Infusion Time(min) | # of Animals |
|---|---|---|---|---|
| 1 | TSS | 0 | 120 | 3 |
| 2 | Cyn- | 3.0 | 120 | 3 |
| 3 | Cyn- | 3.0 | 30 | 3 |
| 4 | Cyn- | 6.0 | 120 | 3 |

TABLE 18

% Editing and Serum TTR

| Group Number | Liver Editing (%) | TTR % Reduction |
|---|---|---|
| 1 | 0.0 (0.0, 0.0, 0.0) | −28 (−34, −23, - |
| 2 | 63.3 (50.8, 69.0, 69.9) | 85 (66, 95, 94) |
| 3 | 63.3 (65.0, 66.0, 58.8) | 88 (90, 89, 86) |
| 4 | 74.5 (75.3, 74.6, 73.6) | 96 (97, 96, 95) |

At day 29 post-dose, liver specimens were collected through single ultrasound-guided percutaneous biopsy targeting the right lobe/side of the liver, using a 16-gauge SuperCore biopsy needle under an intramuscular injection of ketamine/xylazine. A sample between 1.0 $cm^3$ and 1.5 $cm^3$ of total liver biopsy were collected per animal. Each biopsy specimen was flash frozen in liquid nitrogen and stored at −80° C. Editing analysis of the liver specimens was performed through NGS sequencing as previously described. Results for the liver editing demonstrated up to about 70% editing. Corticosteroid pre-treatment with the described LNP treatment was well tolerated.

TABLE 19

Alanine Transaminase (ALT) Levels

| | Pre-Bleed | | 6 Hour | | 24 Hour | | 48 Hour | | Day 7 | | Day 29 | |
|---|---|---|---|---|---|---|---|---|---|---|---|---|
| | Avg | St Dev | Avg | St Dev | Avg | St Dev | Avg | St Dev | Avg | St Dev | Avg | St Dev |
| Grp1-TSS | 49.0 | 11.1 | 173.6 | 30.2 | 175.3 | 29.1 | 155.6 | 21.7 | 76.0 | 4.5 | 49.0 | 8.8 |
| Grp2-3 mpk, 2 hr infusion | 40.3 | 9.0 | 77.6 | 18.4 | 74.0 | 19.3 | 56.0 | 16.3 | 44.0 | 7.5 | 37.3 | 7.0 |
| Grp3-3 mpk, 30 min infusion | 50.3 | 7.5 | 149.0 | 130.0 | 285.3 | 352.2 | 236.3 | 294.1 | 88.3 | 88.1 | 35.6 | 6.3 |
| Grp4-6 mpk, 2 hr infusion | 30.6 | 12.5 | 108.3 | 48.4 | 162.0 | 87.1 | 209.0 | 174.6 | 65.0 | 32.0 | 27.0 | 7.5 |

Figure 3A:
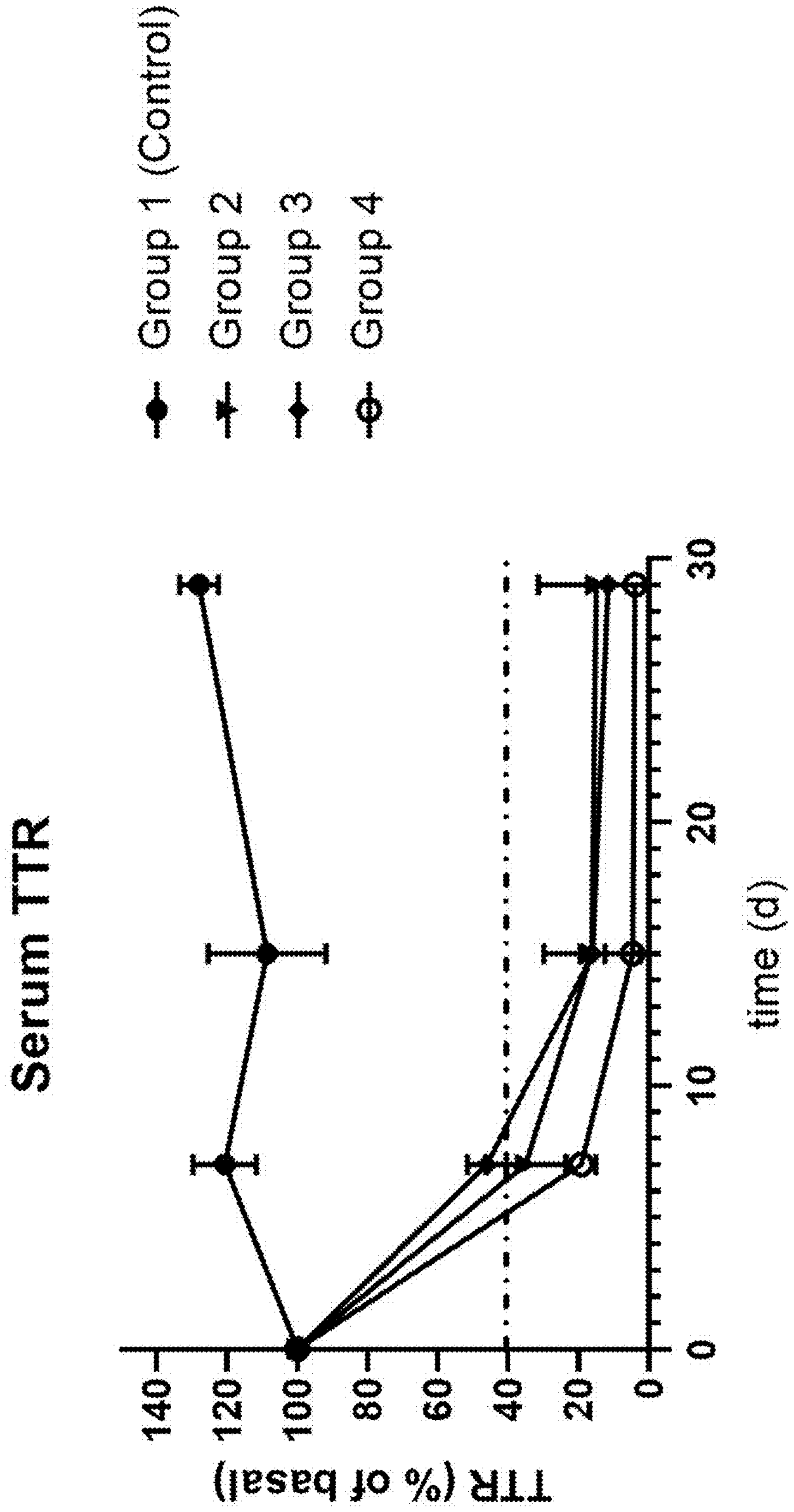
FIGS. 3A-C show serum TTR levels (FIG. 3A), liver TTR editing (FIG. 3B), and circulating ALT levels (FIG. 3C) in an in vivo study in nonhuman primates comparing 30' administration of LNPs to a long dosing protocol.
Figure 3B:
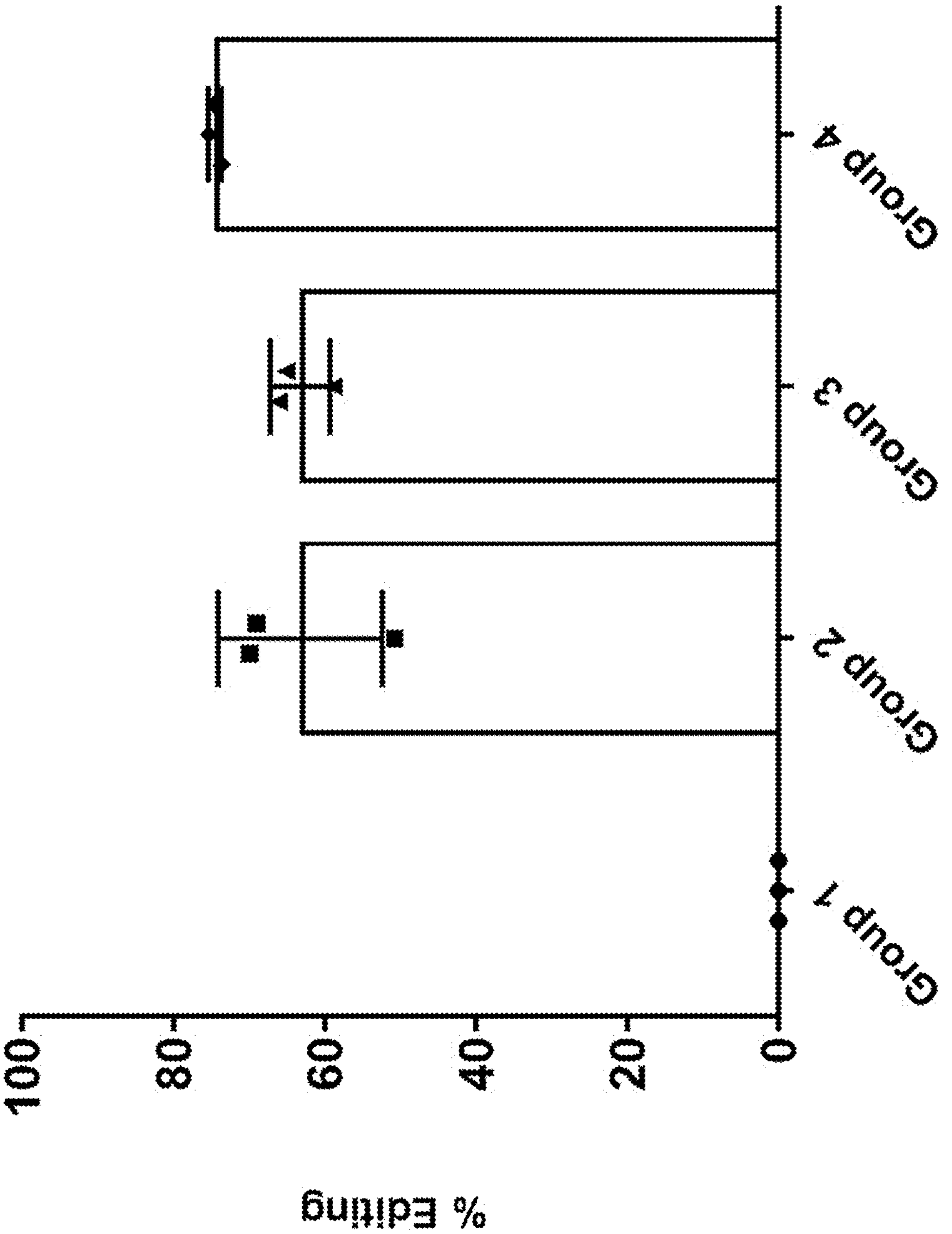
Figure 3C:
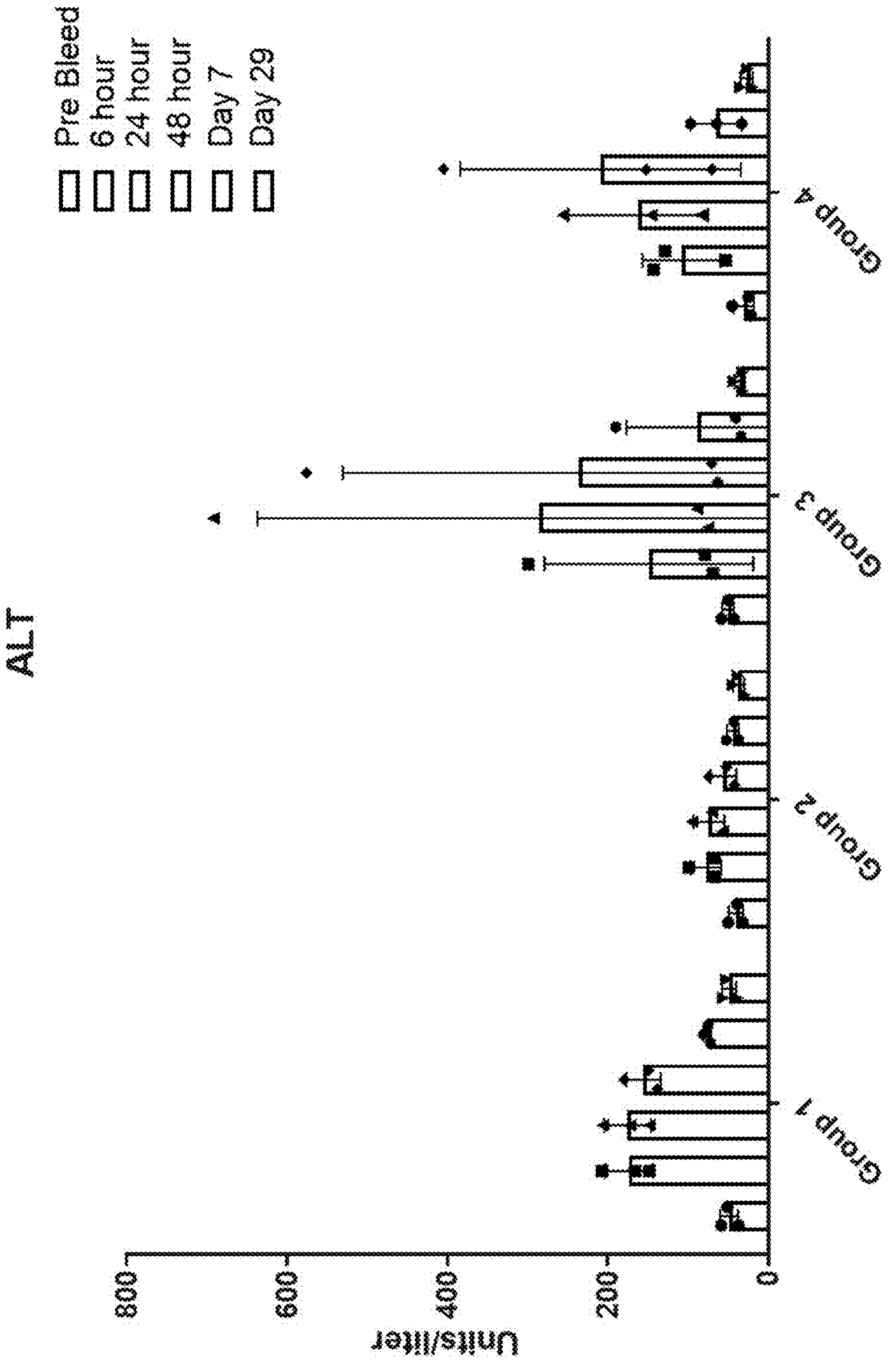

Liver samples were biopsied and analyzed for percent editing data, serum TTR data, and Alanine Transaminase (ALT) levels as seen in Table 18 and FIGS. 3A-B and Table 19 and FIG. 3C, respectively. Results for the liver editing and Serum TTR data demonstrate that there is no significant difference in efficacy between the 3 mg/kg dose with a 30 minute infusion time and a 3 mg/kg dose with a 120 minute infusion time. The greater than 30' infusion time administrations, however, demonstrate lower levels of ALT, a liver injury biomarker. ALT levels were observed to be higher in the 3 mg/kg dose with a 30 minute infusion time which indicated potential liver stress.

Materials and Methods for Example 4. mRNA was synthesized by in vitro transcription (IVT) using a linearized plasmid DNA template and T7 RNA polymerase. Transcription was generally performed from constructs comprising a T7 Promoter (SEQ ID NO: 231), a transcript sequence disclosed herein such as SEQ ID NO: 377 (which encodes the RNA ORF of SEQ ID NO: 311), and a poly-A tail (SEQ ID NO: 263) encoded in the plasmid.

For all methods, the transcript concentration was determined by measuring the light absorbance at 260 nm (Nanodrop), and the transcript was analyzed by capillary electrophoresis by Bioanalyzer (Agilent).

LNP Formulation

The lipid components were dissolved in 100% ethanol with the lipid component molar ratios described below. The chemically modified sgRNA and Cas9 mRNA were combined and dissolved in 25 mM citrate, 100 mM NaCl, pH 5.0, resulting in a concentration of total RNA cargo of approximately 1.5 mg/mL. The LNPs were formulated with an N/P ratio of about 6, with the ratio of chemically modified sgRNA:Cas9 mRNA at a 1:2 w/w ratio as described below. LNPs were formulated with 50% Lipid A, 9% DSPC, 38% cholesterol, and 3% PEG2k-DMG, and LNPs were formed by cross-flow technique as described in Example 1. During mixing, a 2:1 ratio of aqueous to organic solvent was maintained using differential flow rates. Diluted LNPs were concentrated using tangential flow filtration and then buffer exchanged by diafiltration prior to filtering and storage.

Cas9 mRNA and gRNA Cargos

Capped and polyadenylated Cas9 mRNA was generated by in vitro transcription using a linearized plasmid DNA template and T7 RNA polymerase using the method described in Example 1.

Genomic DNA Isolation

Genomic DNA was extracted from liver samples using 50 μL/well BuccalAmp™ DNA Extraction solution (Epicentre, Cat. QE09050) according to manufacturer's protocol. All DNA samples were subjected to PCR and subsequent NGS analysis, as described herein.

In brief, to quantitatively determine the efficiency of editing at the target location in the genome, genomic DNA was isolated and deep sequencing was utilized to identify the presence of insertions and deletions introduced by gene editing.

PCR primers were designed around the target site (e.g., TTR), and the genomic area of interest was amplified. Primer sequences are provided below. Additional PCR was performed according to the manufacturer's protocols (Illumina) to add the necessary chemistry for sequencing. The amplicons were sequenced on an Illumina MiSeq instrument. The reads were aligned to a cyno reference genome (e.g., macFas5) after eliminating those having low quality scores. The resulting files containing the reads were mapped to the reference genome (BAM files), where reads that overlapped the target region of interest were selected and the number of wild type reads versus the number of reads which contain an insertion, substitution, or deletion was calculated.

The editing percentage (e.g., the "editing efficiency" or "percent editing") is defined as the total number of sequence reads with insertions or deletions over the total number of sequence reads, including wild type.

Sequence Table

The following sequence table provides a listing of sequences disclosed herein. It is understood that if a DNA sequence (comprising Ts) is referenced with respect to an RNA, then Ts should be replaced with Us (which may be modified or unmodified depending on the context), and vice versa.

Sequence Table

| Description | Sequence | SEQ ID No. |
| --- | --- | --- |
| Cas9 transcript with 5' UTR of HSD, ORF corresponding to SEQ ID NO: 204, Kozak sequence, and 3' UTR of ALB | GGGTCCCGCAGTCGGCGTCCAGCGGCTCTGCTTGTTCGTGTGTGTGTCGTTGCAGGCCTTATTCGGATCCGCCACCATGGACAAGAA<br>GTACAGCATCGGACTGGACATCGGAACAAACAGCGTCGGATGGGCAGTCATCACAGACGAATACAAGGTCCCGAGCAAGAAGTTCAA<br>GGTCCTGGGAAACACAGACAGACACAGCATCAAGAAGAACCTGATCGGAGCACTGCTGTTCGACAGCGGAGAAACAGCAGAAGCAAC<br>AAGACTGAAGAGAACAGCAAGAAGAAGATACACAAGAAGAAAGAACAGAATCTGCTACCTGCAGGAAATCTTCAGCAACGAAATGGC<br>AAAGGTCGACGACAGCTTCTTCCACAGACTGGAAGAAAGCTTCCTGGTCGAAGAAGACAAGAAGCACGAAAGACACCCGATCTTCGG<br>AAACATCGTCGACGAAGTCGCATACCACGAAAAGTACCCGACAATCTACCACCTGAGAAAGAAGCTGGTCGACAGCACAGACAAGGC<br>AGACCTGAGACTGATCTACCTGGCACTGGCACACATGATCAAGTTCAGAGGACACTTCCTGATCGAAGGAGACCTGAACCCGGACAA<br>CAGCGACGTCGACAAGCTGTTCATCCAGCTGGTCCAGACATACAACCAGCTGTTCGAAGAAAACCCGATCAACGCAAGCGGAGTCGA<br>CGCAAAGGCAATCCTGAGCGCAAGACTGAGCAAGAGCAGAAGACTGGAAAACCTGATCGCACAGCTGCCGGGAGAAAAGAAGAACGG<br>ACTGTTCGGAAACCTGATCGCACTGAGCCTGGGACTGACACCGAACTTCAAGAGCAACTTCGACCTGGCAGAAGACGCAAAGCTGCA<br>GCTGAGCAAGGACACATACGACGACGACCTGGACAACCTGCTGGCACAGATCGGAGACCAGTACGCAGACCTGTTCCTGGCAGCAAA<br>GAACCTGAGCGACGCAATCCTGCTGAGCGACATCCTGAGAGTCAACACAGAAATCACAAAGGCACCGCTGAGCGCAAGCATGATCAA<br>GAGATACGACGAACACCACCAGGACCTGACACTGCTGAAGGCACTGGTCAGACAGCAGCTGCCGGAAAAGTACAAGGAAATCTTCTT<br>CGACCAGAGCAAGAACGGATACGCAGGATACATCGACGGAGGAGCAAGCCAGGAAGAATTCTACAAGTTCATCAAGCCGATCCTGGA<br>AAAGATGGACGGAACAGAAGAACTGCTGGTCAAGCTGAACAGAGAAGACCTGCTGAGAAAGCAGAGAACATTCGACAACGGAAGCAT<br>CCCGCACCAGATCCACCTGGGAGAACTGCACGCAATCCTGAGAAGACAGGAAGACTTCTACCCGTTCCTGAAGGACAACAGAGAAAA<br>GATCGAAAAGATCCTGACATTCAGAATCCCGTACTACGTCGGACCGCTGGCAAGAGGAAACAGCAGATTCGCATGGATGACAAGAAA<br>GAGCGAAGAAACAATCACACCGTGGAACTTCGAAGAAGTCGTCGACAAGGGAGCAAGCGCACAGAGCTTCATCGAAAGAATGACAAA<br>CTTCGACAAGAACCTGCCGAACGAAAAGGTCCTGCCGAAGCACAGCCTGCTGTACGAATACTTCACAGTCTACAACGAACTGACAAA<br>GGTCAAGTACGTCACAGAAGGAATGAGAAAGCCGGCATTCCTGAGCGGAGAACAGAAGAAGGCAATCGTCGACCTGCTGTTCAAGAC<br>AAACAGAAAGGTCACAGTCAAGCAGCTGAAGGAAGACTACTTCAAGAAGATCGAATGCTTCGACAGCGTCGAAATCAGCGGAGTCGA<br>AGACAGATTCAACGCAAGCCTGGGAACATACCACGACCTGCTGAAGATCATCAAGGACAAGGACTTCCTGGACAACGAAGAAAACGA<br>AGACATCCTGGAAGACATCGTCCTGACACTGACACTGTTCGAAGACAGAGAAATGATCGAAGAAAGACTGAAGACATACGCACACCT<br>GTTCGACGACAAGGTCATGAAGCAGCTGAAGAGAAGAAGATACACAGGATGGGGAAGACTGAGCAGAAAGCTGATCAACGGAATCAG<br>AGACAAGCAGAGCGGAAAGACAATCCTGGACTTCCTGAAGAGCGACGGATTCGCAAACAGAAACTTCATGCAGCTGATCCACGACGA<br>CAGCCTGACATTCAAGGAAGACATCCAGAAGGCACAGGTCAGCGGACAGGGAGACAGCCTGCACGAACACATCGCAAACCTGGCAGG<br>AAGCCCGGCAATCAAGAAGGGAATCCTGCAGACAGTCAAGGTCGTCGACGAACTGGTCAAGGTCATGGGAAGACACAAGCCGGAAAA<br>CATCGTCATCGAAATGGCAAGAGAAAACCAGACAACACAGAAGGGACAGAAGAACAGCAGAGAAAGAATGAAGAGAATCGAAGAAGG<br>AATCAAGGAACTGGGAAGCCAGATCCTGAAGGAACACCCGGTCGAAAACACACAGCTGCAGAACGAAAAGCTGTACCTGTACTACCT<br>GCAGAACGGAAGAGACATGTACGTCGACCAGGAACTGGACATCAACAGACTGAGCGACTACGACGTCGACCACATCGTCCCGCAGAG<br>CTTCCTGAAGGACGACAGCATCGACAACAAGGTCCTGACAAGAAGCGACAAGAACAGAGGAAAGAGCGACAACGTCCCGAGCGAAGA<br>AGTCGTCAAGAAGATGAAGAACTACTGGAGACAGCTGCTGAACGCAAAGCTGATCACACAGAGAAAGTTCGACAACCTGACAAAGGC<br>AGAGAGAGGAGGACTGAGCGAACTGGACAAGGCAGGATTCATCAAGAGACAGCTGGTCGAAACAAGACAGATCACAAAGCACGTCGC<br>ACAGATCCTGGACAGCAGAATGAACACAAAGTACGACGAAAACGACAAGCTGATCAGAGAAGTCAAGGTCATCACACTGAAGAGCAA<br>GCTGGTCAGCGACTTCAGAAAGGACTTCCAGTTCTACAAGGTCAGAGAAATCAACAACTACCACCACGCACACGACGCATACCTGAA<br>CGCAGTCGTCGGAACAGCACTGATCAAGAAGTACCCGAAGCTGGAAAGCGAATTCGTCTACGGAGACTACAAGGTCTACGACGTCAG<br>AAAGATGATCGCAAAGAGCGAACAGGAAATCGGAAAGGCAACAGCAAAGTACTTCTTCTACAGCAACATCATGAACTTCTTCAAGAC<br>AGAAATCACACTGGCAAACGGAGAAATCAGAAAGAGACCGCTGATCGAAACAAACGGAGAAACAGGAGAAATCGTCTGGGACAAGGG<br>AAGAGACTTCGCAACAGTCAGAAAGGTCCTGAGCATGCCGCAGGTCAACATCGTCAAGAAGACAGAAGTCCAGACAGGAGGATTCAG<br>CAAGGAAAGCATCCTGCCGAAGAGAAACAGCGACAAGCTGATCGCAAGAAAGAAGGACTGGGACCCGAAGAAGTACGGAGGATTCGA<br>CAGCCCGACAGTCGCATACAGCGTCCTGGTCGTCGCAAAGGTCGAAAAGGGAAAGAGCAAGAAGCTGAAGAGCGTCAAGGAACTGCT<br>GGGAATCACAATCATGGAAAGAAGCAGCTTCGAAAAGAACCCGATCGACTTCCTGGAAGCAAAGGGATACAAGGAAGTCAAGAAGGA<br>CCTGATCATCAAGCTGCCGAAGTACAGCCTGTTCGAACTGGAAAACGGAAGAAAGAGAATGCTGGCAAGCGCAGGAGAACTGCAGAA<br>GGGAAACGAACTGGCACTGCCGAGCAAGTACGTCAACTTCCTGTACCTGGCAAGCCACTACGAAAAGCTGAAGGGAAGCCCGGAAGA<br>CAACGAACAGAAGCAGCTGTTCGTCGAACAGCACAAGCACTACCTGGACGAAATCATCGAACAGATCAGCGAATTCAGCAAGAGAGT<br>CATCCTGGCAGACGCAAACCTGGACAAGGTCCTGAGCGCATACAACAAGCACAGAGACAAGCCGATCAGAGAACAGGCAGAAAACAT<br>CATCCACCTGTTCACACTGACAAACCTGGGAGCACCGGCAGCATTCAAGTACTTCGACACAACAATCGACAGAAAGAGATACACAAG<br>CACAAAGGAAGTCCTGGACGCAACACTGATCCACCAGAGCATCACAGGACTGTACGAAACAAGAATCGACCTGAGCCAGCTGGGAGG | 1 |

-continued

| Sequence Table | | |
|---|---|---|
| Description | Sequence | SEQ ID No. |
| | AGACGGAGGAGGAAGCCCGAAGAAGAAGAGAAAGGTCTAGCTAGCCATCACATTTAAAAGCATCTCAGCCTACCATGAGAATAAGAG AAAGAAAATGAAGATCAATAGCTTATTCATCTCTTTTTCTTTTTCGTTGGTGTAAAGCCAACACCCTGTCTAAAAAACATAAATTTC TTTAATCATTTTGCCTCTTTTCTCTGTGCTTCAATTAATAAAAAATGGAAAGAACCTCGAG | |
| G000739 - sgRNA negative control | mG*mA*mU*CACGUCGGCCGUUGGCGGUUUUAGAmGmCmUmAmGmAmAmAmUmAmGmCAAGUUAAAAUAAGGCUAGUCCGUUAUCAm AmCmUmUmGmAmAmAmAmAmGmUmGmGmCmAmCmCmGmAmGmUmCmGmGmUmGmCmU*mU*mU*mU | 2 |
| modified sgRNA sequence (“N” may be any natural or non-natural nucleotide) | mN*mN*mN*NNNNNNNNNNNNNNNNNGUUUUAGAmGmCmUmAmGmAmAmAmUmAmGmCAAGUUAAAAUAAGGCUAGUCCGUUAUCAm AmCmUmUmGmAmAmAmAmAmGmUmGmGmCmAmCmCmGmAmGmUmCmGmGmUmGmCmU*mU*mU*mU | 3 |
| 30/30/39 poly-A sequence | AAAAAAAAAAAAAAAAAAAAAAAAAAAAAAGCGAAAAAAAAAAAAAAAAAAAAAAAAAAAAAACCGAAAAAAAAAAAAAAAAAAAAA AAAAAAAAAAAAAAAAAA | 4 |
| CR003335 gRNA targeting Human TTR (Exon 1) | CUGCUCCUCCUCUGCCUUGC | 5 |
| CR003336 gRNA targeting Human TTR (Exon 1) | CCUCCUCUGCCUUGCUGGAC | 6 |
| CR003337 gRNA targeting Human TTR (Exon 1) | CCAGUCCAGCAAGGCAGAGG | 7 |
| CR003338 gRNA targeting Human TTR (Exon 1) | AUACCAGUCCAGCAAGGCAG | 8 |
| CR003339 gRNA targeting | ACACAAAUACCAGUCCAGCA | 9 |

-continued

Sequence Table

| Description | Sequence | SEQ ID No. |
|---|---|---|
| Human TTR (Exon 1) | | |
| CR003340 gRNA targeting Human TTR (Exon 1) | UGGACUGGUAUUUGUGUCUG | 10 |
| CR003341 gRNA targeting Human TTR (Exon 1) | CUGGUAUUUGUGUCUGAGGC | 11 |
| CR003342 gRNA targeting Human TTR (Exon 2) | CUUCUCUACACCCAGGGCAC | 12 |
| CR003343 gRNA targeting Human TTR (Exon 2) | CAGAGGACACUUGGAUUCAC | 13 |
| CR003344 gRNA targeting Human TTR (Exon 2) | UUUGACCAUCAGAGGACACU | 14 |
| CR003345 gRNA targeting Human TTR (Exon 2) | UCUAGAACUUUGACCAUCAG | 15 |
| CR003346 gRNA targeting Human TTR (Exon 2) | AAAGUUCUAGAUGCUGUCCG | 16 |
| CR003347 gRNA targeting Human TTR | CAUUGAUGGCAGGACUGCCU | 17 |

-continued

| Sequence Table | | |
|---|---|---|
| Description | Sequence | SEQ ID No. |
| (Exon 2) | | |
| CR003348 gRNA targeting Human TTR (Exon 2) | AGGCAGUCCUGCCAUCAAUG | 18 |
| CR003349 gRNA targeting Human TTR (Exon 2) | UGCACGGCCACAUUGAUGGC | 19 |
| CR003350 gRNA targeting Human TTR (Exon 2) | CACAUGCACGGCCACAUUGA | 20 |
| CR003351 gRNA targeting Human TTR (Exon 2) | AGCCUUUCUGAACACAUGCA | 21 |
| CR003352 gRNA targeting Human TTR (Exon 2) | GAAAGGCUGCUGAUGACACC | 22 |
| CR003353 gRNA targeting Human TTR (Exon 2) | AAAGGCUGCUGAUGACACCU | 23 |
| CR003354 gRNA targeting Human TTR (Exon 2) | ACCUGGGAGCCAUUUGCCUC | 24 |
| CR003355 gRNA targeting Human TTR (Exon 2) | CCCAGAGGCAAAUGGCUCCC | 25 |

-continued

Sequence Table

| Description | Sequence | SEQ ID No. |
|---|---|---|
| CR003356 gRNA targeting Human TTR (Exon 2) | GCAACUUACCCAGAGGCAAA | 26 |
| CR003357 gRNA targeting Human TTR (Exon 2) | UUCUUUGGCAACUUACCCAG | 27 |
| CR003358 gRNA targeting Human TTR (Exon 3) | AUGCAGCUCUCCAGACUCAC | 28 |
| CR003359 gRNA targeting Human TTR (Exon 3) | AGUGAGUCUGGAGAGCUGCA | 29 |
| CR003360 gRNA targeting Human TTR (Exon 3) | GUGAGUCUGGAGAGCUGCAU | 30 |
| CR003361 gRNA targeting Human TTR (Exon 3) | GCUGCAUGGGCUCACAACUG | 31 |
| CR003362 gRNA targeting Human TTR (Exon 3) | GCAUGGGCUCACAACUGAGG | 32 |
| CR003363 gRNA targeting Human TTR (Exon 3) | ACUGAGGAGGAAUUUGUAGA | 33 |

-continued

Sequence Table

| Description | Sequence | SEQ ID No. |
|---|---|---|
| CR003364 gRNA targeting Human TTR (Exon 3) | CUGAGGAGGAAUUUGUAGAA | 34 |
| CR003365 gRNA targeting Human TTR (Exon 3) | UGUAGAAGGGAUAUACAAAG | 35 |
| CR003366 gRNA targeting Human TTR (Exon 3) | AAAUAGACACCAAAUCUUAC | 36 |
| CR003367 gRNA targeting Human TTR (Exon 3) | AGACACCAAAUCUUACUGGA | 37 |
| CR003368 gRNA targeting Human TTR (Exon 3) | AAGUGCCUUCCAGUAAGAUU | 38 |
| CR003369 gRNA targeting Human TTR (Exon 3) | CUCUGCAUGCUCAUGGAAUG | 39 |
| CR003370 gRNA targeting Human TTR (Exon 3) | CCUCUGCAUGCUCAUGGAAU | 40 |
| CR003371 gRNA targeting Human TTR (Exon 3) | ACCUCUGCAUGCUCAUGGAA | 41 |
| CR003372 | UACUCACCUCUGCAUGCUCA | 42 |

-continued

Sequence Table

| Description | Sequence | SEQ ID No. |
|---|---|---|
| gRNA targeting Human TTR (Exon 3) | | |
| CR003373 gRNA targeting Human TTR (Exon 4) | GUAUUCACAGCCAACGACUC | 43 |
| CR003374 gRNA targeting Human TTR (Exon 4) | GCGGCGGGGGCCGGAGUCGU | 44 |
| CR003375 gRNA targeting Human TTR (Exon 4) | AAUGGUGUAGCGGCGGGGGC | 45 |
| CR003376 gRNA targeting Human TTR (Exon 4) | CGGCAAUGGUGUAGCGGCGG | 46 |
| CR003377 gRNA targeting Human TTR (Exon 4) | GCGGCAAUGGUGUAGCGGCG | 47 |
| CR003378 gRNA targeting Human TTR (Exon 4) | GGCGGCAAUGGUGUAGCGGC | 48 |
| CR003379 gRNA targeting Human TTR (Exon 4) | GGGCGGCAAUGGUGUAGCGG | 49 |
| CR003380 gRNA | GCAGGGCGGCAAUGGUGUAG | 50 |

-continued

Sequence Table

| Description | Sequence | SEQ ID No. |
|---|---|---|
| targeting Human TTR (Exon 4) | | |
| CR003381 gRNA targeting Human TTR (Exon 4) | GGGGCUCAGCAGGGCGGCAA | 51 |
| CR003382 gRNA targeting Human TTR (Exon 4) | GGAGUAGGGGCUCAGCAGGG | 52 |
| CR003383 gRNA targeting Human TTR (Exon 4) | AUAGGAGUAGGGGCUCAGCA | 53 |
| CR003384 gRNA targeting Human TTR (Exon 4) | AAUAGGAGUAGGGGCUCAGC | 54 |
| CR003385 gRNA targeting Human TTR (Exon 4) | CCCCUACUCCUAUUCCACCA | 55 |
| CR003386 gRNA targeting Human TTR (Exon 4) | CCGUGGUGGAAUAGGAGUAG | 56 |
| CR003387 gRNA targeting Human TTR (Exon 4) | GCCGUGGUGGAAUAGGAGUA | 57 |
| CR003388 gRNA targeting | GACGACAGCCGUGGUGGAAU | 58 |

-continued

| Sequence Table | | |
|---|---|---|
| Description | Sequence | SEQ ID No. |
| Human TTR (Exon 4) | | |
| CR003389 gRNA targeting Human TTR (Exon 4) | AUUGGUGACGACAGCCGUGG | 59 |
| CR003390 gRNA targeting Human TTR (Exon 4) | GGGAUUGGUGACGACAGCCG | 60 |
| CR003391 gRNA targeting Human TTR (Exon 4) | GGCUGUCGUCACCAAUCCCA | 61 |
| CR003392 gRNA targeting Human TTR (Exon 4) | AGUCCCUCAUUCCUUGGGAU | 62 |
| CR005298 gRNA targeting Human TTR (Exon 1) | UCCACUCAUUCUUGGCAGGA | 63 |
| CR005299 gRNA targeting Human TTR (Exon 4) | AGCCGUGGUGGAAUAGGAGU | 64 |
| CR005300 gRNA targeting Human TTR (Exon 1) | UCACAGAAACACUCACCGUA | 65 |
| CR005301 gRNA targeting Human TTR | GUCACAGAAACACUCACCGU | 66 |

-continued

Sequence Table

| Description | Sequence | SEQ ID No. |
|---|---|---|
| (Exon 1) | | |
| CR005302 gRNA targeting Human TTR (Exon 2) | ACGUGUCUUCUCUACACCCA | 67 |
| CR005303 gRNA targeting Human TTR (Exon 2) | UGAAUCCAAGUGUCCUCUGA | 68 |
| CR005304 gRNA targeting Human TTR (Exon 2) | GGCCGUGCAUGUGUUCAGAA | 69 |
| CR005305 gRNA targeting Human TTR (Exon 3) | UAUAGGAAAACCAGUGAGUC | 70 |
| CR005306 gRNA targeting Human TTR (Exon 3) | AAAUCUUACUGGAAGGCACU | 71 |
| CR005307 gRNA targeting Human TTR (Exon 4) | UGUCUGUCUUCUCUCAUAGG | 72 |
| CR000689 gRNA targeting Cyno TTR | ACACAAAUACCAGUCCAGCG | 73 |
| CR005364 gRNA targeting Cyno TTR | AAAGGCUGCUGAUGAGACCU | 74 |
| CR005365 | CAUUGACAGCAGGACUGCCU | 75 |

-continued

| Sequence Table | | |
|---|---|---|
| Description | Sequence | SEQ ID No. |
| gRNA targeting Cyno TTR | | |
| CR005366 gRNA targeting Cyno TTR | AUACCAGUCCAGCGAGGCAG | 76 |
| CR005367 gRNA targeting Cyno TTR | CCAGUCCAGCGAGGCAGAGG | 77 |
| CR005368 gRNA targeting Cyno TTR | CCUCCUCUGCCUCGCUGGAC | 78 |
| CR005369 gRNA targeting Cyno TTR | AAAGUUCUAGAUGCCGUCCG | 79 |
| CR005370 gRNA targeting Cyno TTR | ACUUGUCUUCUCUAUACCCA | 80 |
| CR005371 gRNA targeting Cyno TTR | AAGUGACUUCCAGUAAGAUU | 81 |
| CR005372 gRNA targeting Cyno TTR | AAAAGGCUGCUGAUGAGACC | 82 |
| | Not Used | 83 |
| | Not Used | 84 |
| | Not Used | 85 |
| | Not Used | 86 |
| G000480 sgRNA | mA*mA*mA*GGCUGCUGAUGACACCUGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 87 |

-continued

Sequence Table

| Description | Sequence | SEQ ID No. |
|---|---|---|
| modified sequence targeting Human TTR | | |
| G000481 sgRNA modified sequence targeting Human TTR | mU*mC*mU*AGAACUUUGACCAUCAGGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 88 |
| G000482 sgRNA modified sequence targeting Human TTR | mU*mG*mU*AGAAGGGAUAUACAAAGGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 89 |
| G000483 sgRNA modified sequence targeting Human TTR | mU*mC*mC*ACUCAUUCUUGGCAGGAGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 90 |
| G000484 sgRNA modified sequence targeting Human TTR | mA*mG*mA*CACCAAAUCUUACUGGAGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 91 |
| G000485 sgRNA modified sequence targeting Human TTR | mC*mC*mU*CCUCUGCCUUGCUGGACGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 92 |
| G000486 sgRNA modified sequence targeting Human TTR | mA*mC*mA*CAAAUACCAGUCCAGCAGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 93 |
| G000487 sgRNA | mU*mU*mC*UUUGGCAACUUACCCAGGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 94 |

-continued

Sequence Table

| Description | Sequence | SEQ ID No. |
|---|---|---|
| modified sequence targeting Human TTR | | |
| G000488 sgRNA modified sequence targeting Human TTR | mA*mA*mA*GUUCUAGAUGCUGUCCGGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 95 |
| G000489 sgRNA modified sequence targeting Human TTR | mU*mU*mU*GACCAUCAGAGGACACUGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 96 |
| G000490 sgRNA modified sequence targeting Human TTR | mA*mA*mA*UAGACACCAAAUCUUACGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 97 |
| G000491 sgRNA modified sequence targeting Human TTR | mA*mU*mA*CCAGUCCAGCAAGGCAGGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 98 |
| G000492 sgRNA modified sequence targeting Human TTR | mC*mU*mU*CUCUACACCCAGGGCACGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 99 |
| G000493 sgRNA modified sequence targeting Human TTR | mA*mA*mG*UGCCUUCCAGUAAGAUUGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 100 |
| G000494 sgRNA | mG*mU*mG*AGUCUGGAGAGCUGCAUGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 101 |

-continued

| Sequence Table | | |
|---|---|---|
| Description | Sequence | SEQ ID No. |
| modified sequence targeting Human TTR | | |
| G000495 sgRNA modified sequence targeting Human TTR | mC*mA*mG*AGGACACUUGGAUUCACGUUUUAGAmGmCmUmAmGmAmAmAmUmAmGmCAAGUUAAAAUAAGGCUAGUCCGUUAUCAm AmCmUmUmGmAmAmAmAmAmGmUmGmGmCmAmCmCmGmAmGmUmCmGmGmUmGmCmU*mU*mU*mU | 102 |
| G000496 sgRNA modified sequence targeting Human TTR | mG*mG*mC*CGUGCAUGUGUUCAGAAGUUUUAGAmGmCmUmAmGmAmAmAmUmAmGmCAAGUUAAAAUAAGGCUAGUCCGUUAUCAm AmCmUmUmGmAmAmAmAmAmGmUmGmGmCmAmCmCmGmAmGmUmCmGmGmUmGmCmU*mU*mU*mU | 103 |
| G000497 sgRNA modified sequence targeting Human TTR | mC*mU*mG*CUCCUCCUCUGCCUUGCGUUUUAGAmGmCmUmAmGmAmAmAmUmAmGmCAAGUUAAAAUAAGGCUAGUCCGUUAUCAm AmCmUmUmGmAmAmAmAmAmGmUmGmGmCmAmCmCmGmAmGmUmCmGmGmUmGmCmU*mU*mU*mU | 104 |
| G000498 sgRNA modified sequence targeting Human TTR | mA*mG*mU*GAGUCUGGAGAGCUGCAGUUUUAGAmGmCmUmAmGmAmAmAmUmAmGmCAAGUUAAAAUAAGGCUAGUCCGUUAUCAm AmCmUmUmGmAmAmAmAmAmGmUmGmGmCmAmCmCmGmAmGmUmCmGmGmUmGmCmU*mU*mU*mU | 105 |
| G000499 sgRNA modified sequence targeting Human TTR | mU*mG*mA*AUCCAAGUGUCCUCUGAGUUUUAGAmGmCmUmAmGmAmAmAmUmAmGmCAAGUUAAAAUAAGGCUAGUCCGUUAUCAm AmCmUmUmGmAmAmAmAmAmGmUmGmGmCmAmCmCmGmAmGmUmCmGmGmUmGmCmU*mU*mU*mU | 106 |
| G000500 sgRNA modified sequence targeting Human TTR | mC*mC*mA*GUCCAGCAAGGCAGAGGGUUUUAGAmGmCmUmAmGmAmAmAmUmAmGmCAAGUUAAAAUAAGGCUAGUCCGUUAUCAm AmCmUmUmGmAmAmAmAmAmGmUmGmGmCmAmCmCmGmAmGmUmCmGmGmUmGmCmU*mU*mU*mU | 107 |
| G000501 sgRNA | mU*mC*mA*CAGAAACACUCACCGUAGUUUUAGAmGmCmUmAmGmAmAmAmUmAmGmCAAGUUAAAAUAAGGCUAGUCCGUUAUCAm AmCmUmUmGmAmAmAmAmAmGmUmGmGmCmAmCmCmGmAmGmUmCmGmGmUmGmCmU*mU*mU*mU | 108 |

-continued

| Sequence Table | | |
|---|---|---|
| Description | Sequence | SEQ ID No. |
| modified sequence targeting Human TTR | | |
| G000567 sgRNA modified sequence targeting Human TTR | mG*mA*mA*AGGCUGCUGAUGACACCGUUUUAGAmGmCmUmAmGmAmAmAmUmAmGmCAAGUUAAAAUAAGGCUAGUCCGUUAUCAm AmCmUmUmGmAmAmAmAmAmGmUmGmGmCmAmCmCmGmAmGmUmCmGmGmUmGmCmU*mU*mU*mU | 109 |
| G000568 sgRNA modified sequence targeting Human TTR | mG*mG*mC*UGUCGUCACCAAUCCCAGUUUUAGAmGmCmUmAmGmAmAmAmUmAmGmCAAGUUAAAAUAAGGCUAGUCCGUUAUCAm AmCmUmUmGmAmAmAmAmAmGmUmGmGmCmAmCmCmGmAmGmUmCmGmGmUmGmCmU*mU*mU*mU | 110 |
| G000570 sgRNA modified sequence targeting Human TTR | mC*mA*mU*UGAUGGCAGGACUGCCUGUUUUAGAmGmCmUmAmGmAmAmAmUmAmGmCAAGUUAAAAUAAGGCUAGUCCGUUAUCAm AmCmUmUmGmAmAmAmAmAmGmUmGmGmCmAmCmCmGmAmGmUmCmGmGmUmGmCmU*mU*mU*mU | 111 |
| G000571 sgRNA modified sequence targeting Human TTR | mG*mU*mC*ACAGAAACACUCACCGUGUUUUAGAmGmCmUmAmGmAmAmAmUmAmGmCAAGUUAAAAUAAGGCUAGUCCGUUAUCAm AmCmUmUmGmAmAmAmAmAmGmUmGmGmCmAmCmCmGmAmGmUmCmGmGmUmGmCmU*mU*mU*mU | 112 |
| G000572 sgRNA modified sequence targeting Human TTR | mC*mC*mC*CUACUCCUAUUCCACCAGUUUUAGAmGmCmUmAmGmAmAmAmUmAmGmCAAGUUAAAAUAAGGCUAGUCCGUUAUCAm AmCmUmUmGmAmAmAmAmAmGmUmGmGmCmAmCmCmGmAmGmUmCmGmGmUmGmCmU*mU*mU*mU | 113 |
| G000502 sgRNA modified sequence targeting Cyno TTR | mA*mC*mA*CAAAUACCAGUCCAGCGGUUUUAGAmGmCmUmAmGmAmAmAmUmAmGmCAAGUUAAAAUAAGGCUAGUCCGUUAUCAm AmCmUmUmGmAmAmAmAmAmGmUmGmGmCmAmCmCmGmAmGmUmCmGmGmUmGmCmU*mU*mU*mU | 114 |
| G000503 sgRNA | mA*mA*mA*AGGCUGCUGAUGAGACCGUUUUAGAmGmCmUmAmGmAmAmAmUmAmGmCAAGUUAAAAUAAGGCUAGUCCGUUAUCAm AmCmUmUmGmAmAmAmAmAmGmUmGmGmCmAmCmCmGmAmGmUmCmGmGmUmGmCmU*mU*mU*mU | 115 |

-continued

| Sequence Table | | |
|---|---|---|
| Description | Sequence | SEQ ID No. |
| modified sequence targeting Cyno TTR | | |
| G000504 sgRNA modified sequence targeting Cyno TTR | mA*mA*mA*GGCUGCUGAUGAGACCUGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 116 |
| G000505 sgRNA modified sequence targeting Cyno TTR | mC*mA*mU*UGACAGCAGGACUGCCUGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 117 |
| G000506 sgRNA modified sequence targeting Cyno TTR | mA*mU*mA*CCAGUCCAGCGAGGCAGGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 118 |
| G000507 sgRNA modified sequence targeting Cyno TTR | mC*mC*mA*GUCCAGCGAGGCAGAGGGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 119 |
| G000508 sgRNA modified sequence targeting Cyno TTR | mC*mC*mU*CCUCUGCCUCGCUGGACGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 120 |
| G000509 sgRNA modified sequence targeting Cyno TTR | mA*mA*mA*GUUCUAGAUGCCGUCCGGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 121 |
| G000510 sgRNA | mA*mC*mU*UGUCUUCUCUAUACCCAGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 122 |

-continued

| Sequence Table | | |
|---|---|---|
| Description | Sequence | SEQ ID No. |
| modified sequence targeting Cyno TTR | | |
| G000511 sgRNA modified sequence targeting Cyno TTR | mA*mA*mG*UGACUUCCAGUAAGAUUGUUUUAGAmGmCmUmAmGmAmAmAmUmAmGmCAAGUUAAAAUAAGGCUAGUCCGUUAUCAm<br>AmCmUmUmGmAmAmAmAmAmGmUmGmGmCmAmCmCmGmAmGmUmCmGmGmUmGmCmU*mU*mU*mU | 123 |
| G000282 sgRNA modified sequence targeting Mouse TTR | mU*mU*mA*CAGCCACGUCUACAGCAGUUUUAGAmGmCmUmAmGmAmAmAmUmAmGmCAAGUUAAAAUAAGGCUAGUCCGUUAUCAm<br>AmCmUmUmGmAmAmAmAmAmGmUmGmGmCmAmCmCmGmAmGmUmCmGmGmUmGmCmU*mU*mU*mU | 124 |
| exemplary nucleotide sequence following the 3' end of the Guide Sequence to form a sgRNA | GUUUUAGAGCUAGAAAUAGCAAGUUAAAAUAAGGCUAGUCCGUUAUCAACUUGAAAAAGUGGCACCGAGUCGGUGCUUUU | 125 |
| exemplary nucleotide sequence following the 3' end of the Guide Sequence to form a crRNA | GUUUUAGAGCUAUGCUGUUUUG | 126 |
| | Not used | 127 to 202 |
| Cas9 amino acid sequence | MDKKYSIGLDIGTNSVGWAVITDEYKVPSKKFKVLGNTDRHSIKKNLIGALLFDSGETAEATRLKRTARRRYTRRKNRICYLQEIFS<br>NEMAKVDDSFFHRLEESFLVEEDKKHERHPIFGNIVDEVAYHEKYPTIYHLRKKLVDSTDKADLRLIYLALAHMIKFRGHFLIEGDL<br>NPDNSDVDKLFIQLVQTYNQLFEENPINASGVDAKAILSARLSKSRRLENLIAQLPGEKKNGLFGNLIALSLGLTPNFKSNFDLAED<br>AKLQLSKDTYDDDLDNLLAQIGDQYADLFLAAKNLSDAILLSDILRVNTEITKAPLSASMIKRYDEHHQDLTLLKALVRQQLPEKYK<br>EIFFDQSKNGYAGYIDGGASQEEFYKFIKPILEKMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQSFIERMTNFDKNLPNEKVLPKHSLLYEYFTVYN | 203 |

-continued

Sequence Table

| Description | Sequence | SEQ ID No. |
|---|---|---|
| | ELTKVKYVTEGMRKPAFLSGEQKKAIVDLLFKTNRKVTVKQLKEDYFKKIECFDSVEISGVEDRFNASLGTYHDLLKIIKDKDFLDN<br>EENEDILEDIVLTLTLFEDREMIEERLKTYAHLFDDKVMKQLKRRRYTGWGRLSRKLINGIRDKQSGKTILDFLKSDGFANRNFMQL<br>IHDDSLTFKEDIQKAQVSGQGDSLHEHIANLAGSPAIKKGILQTVKVVDELVKVMGRHKPENIVIEMARENQTTQKGQKNSRERMKR<br>IEEGIKELGSQILKEHPVENTQLQNEKLYLYYLQNGRDMYVDQELDINRLSDYDVDHIVPQSFLKDDSIDNKVLTRSDKNRGKSDNV<br>PSEEVVKKMKNYWRQLLNAKLITQRKFDNLTKAERGGLSELDKAGFIKRQLVETRQITKHVAQILDSRMNTKYDENDKLIREVKVIT<br>LKSKLVSDFRKDFQFYKVREINNYHHAHDAYLNAVVGTALIKKYPKLESEFVYGDYKVYDVRKMIAKSEQEIGKATAKYFFYSNIMN<br>FFKTEITLANGEIRKRPLIETNGETGEIVWDKGRDFATVRKVLSMPQVNIVKKTEVQTGGFSKESILPKRNSDKLIARKKDWDPKKY<br>GGFDSPTVAYSVLVVAKVEKGKSKKLKSVKELLGITIMERSSFEKNPIDFLEAKGYKEVKKDLIIKLPKYSLFELENGRKRMLASAG<br>ELQKGNELALPSKYVNFLYLASHYEKLKGSPEDNEQKQLFVEQHKHYLDEIIEQISEFSKRVILADANLDKVLSAYNKHRDKPIREQ<br>AENIIHLFTLTNLGAPAAFKYFDTTIDRKRYTSTKEVLDATLIHQSITGLYETRIDLSQLGGDGGGSPKKKRKV | |
| Cas9 mRNA open reading frame (ORF) 2 | AUGGACAAGAAGUACAGCAUCGGACUGGACAUCGGAACAAACAGCGUCGGAUGGGCAGUCAUCACAGACGAAUACAAGGUCCCGAGC<br>AAGAAGUUCAAGGUCCUGGGAAACACAGACAGACACAGCAUCAAGAAGAACCUGAUCGGAGCACUGCUGUUCGACAGCGGAGAAACA<br>GCAGAAGCAACAAGACUGAAGAGAACAGCAAGAAGAAGAUACACAAGAAGAAAGAACAGAAUCUGCUACCUGCAGGAAAUCUUCAGC<br>AACGAAAUGGCAAAGGUCGACGACAGCUUCUUCCACAGACUGGAAGAAAGCUUCCUGGUCGAAGAAGACAAGAAGCACGAAAGACAC<br>CCGAUCUUCGGAAACAUCGUCGACGAAGUCGCAUACCACGAAAAGUACCCGACAAUCUACCACCUGAGAAAGAAGCUGGUCGACAGC<br>ACAGACAAGGCAGACCUGAGACUGAUCUACCUGGCACUGGCACACAUGAUCAAGUUCAGAGGACACUUCCUGAUCGAAGGAGACCUG<br>AACCCGGACAACAGCGACGUCGACAAGCUGUUCAUCCAGCUGGUCCAGACAUACAACCAGCUGUUCGAAGAAAACCCGAUCAACGCA<br>AGCGGAGUCGACGCAAAGGCAAUCCUGAGCGCAAGACUGAGCAAGAGCAGAAGACUGGAAAACCUGAUCGCACAGCUGCCGGGAGAA<br>AAGAAGAACGGACUGUUCGGAAACCUGAUCGCACUGAGCCUGGGACUGACACCGAACUUCAAGAGCAACUUCGACCUGGCAGAAGAC<br>GCAAAGCUGCAGCUGAGCAAGGACACAUACGACGACGACCUGGACAACCUGCUGGCACAGAUCGGAGACCAGUACGCAGACCUGUUC<br>CUGGCAGCAAAGAACCUGAGCGACGCAAUCCUGCUGAGCGACAUCCUGAGAGUCAACACAGAAAUCACAAAGGCACCGCUGAGCGCA<br>AGCAUGAUCAAGAGAUACGACGAACACCACCAGGACCUGACACUGCUGAAGGCACUGGUCAGACAGCAGCUGCCGGAAAAGUACAAG<br>GAAAUCUUCUUCGACCAGAGCAAGAACGGAUACGCAGGAUACAUCGACGGAGGAGCAAGCCAGGAAGAAUUCUACAAGUUCAUCAAG<br>CCGAUCCUGGAAAAGAUGGACGGAACAGAAGAACUGCUGGUCAAGCUGAACAGAGAAGACCUGCUGAGAAAGCAGAGAACAUUCGAC<br>AACGGAAGCAUCCCGCACCAGAUCCACCUGGGAGAACUGCACGCAAUCCUGAGAAGACAGGAAGACUUCUACCCGUUCCUGAAGGAC<br>AACAGAGAAAAGAUCGAAAAGAUCCUGACAUUCAGAAUCCCGUACUACGUCGGACCGCUGGCAAGAGGAAACAGCAGAUUCGCAUGG<br>AUGACAAGAAAGAGCGAAGAAACAAUCACACCGUGGAACUUCGAAGAAGUCGUCGACAAGGGAGCAAGCGCACAGAGCUUCAUCGAA<br>AGAAUGACAAACUUCGACAAGAACCUGCCGAACGAAAAGGUCCUGCCGAAGCACAGCCUGCUGUACGAAUACUUCACAGUCUACAAC<br>GAACUGACAAAGGUCAAGUACGUCACAGAAGGAAUGAGAAAGCCGGCAUUCCUGAGCGGAGAACAGAAGAAGGCAAUCGUCGACCUG<br>CUGUUCAAGACAAACAGAAAGGUCACAGUCAAGCAGCUGAAGGAAGACUACUUCAAGAAGAUCGAAUGCUUCGACAGCGUCGAAAUC<br>AGCGGAGUCGAAGACAGAUUCAACGCAAGCCUGGGAACAUACCACGACCUGCUGAAGAUCAUCAAGGACAAGGACUUCCUGGACAAC<br>GAAGAAAACGAAGACAUCCUGGAAGACAUCGUCCUGACACUGACACUGUUCGAAGACAGAGAAAUGAUCGAAGAAAGACUGAAGACA<br>UACGCACACCUGUUCGACGACAAGGUCAUGAAGCAGCUGAAGAGAAGAAGAUACACAGGAUGGGGAAGACUGAGCAGAAAGCUGAUC<br>AACGGAAUCAGAGACAAGCAGAGCGGAAAGACAAUCCUGGACUUCCUGAAGAGCGACGGAUUCGCAAACAGAAACUUCAUGCAGCUG<br>AUCCACGACGACAGCCUGACAUUCAAGGAAGACAUCCAGAAGGCACAGGUCAGCGGACAGGGAGACAGCCUGCACGAACACAUCGCA<br>AACCUGGCAGGAAGCCCGGCAAUCAAGAAGGGAAUCCUGCAGACAGUCAAGGUCGUCGACGAACUGGUCAAGGUCAUGGGAAGACAC<br>AAGCCGGAAAACAUCGUCAUCGAAAUGGCAAGAGAAAACCAGACAACACAGAAGGGACAGAAGAACAGCAGAGAAAGAAUGAAGAGA<br>AUCGAAGAAGGAAUCAAGGAACUGGGAAGCCAGAUCCUGAAGGAACACCCGGUCGAAAACACACAGCUGCAGAACGAAAAGCUGUAC<br>CUGUACUACCUGCAGAACGGAAGAGACAUGUACGUCGACCAGGAACUGGACAUCAACAGACUGAGCGACUACGACGUCGACCACAUC<br>GUCCCGCAGAGCUUCCUGAAGGACGACAGCAUCGACAACAAGGUCCUGACAAGAAGCGACAAGAACAGAGGAAAGAGCGACAACGUC<br>CCGAGCGAAGAAGUCGUCAAGAAGAUGAAGAACUACUGGAGACAGCUGCUGAACGCAAAGCUGAUCACACAGAGAAAGUUCGACAAC<br>CUGACAAAGGCAGAGAGAGGAGGACUGAGCGAACUGGACAAGGCAGGAUUCAUCAAGAGACAGCUGGUCGAAACAAGACAGAUCACA<br>AAGCACGUCGCACAGAUCCUGGACAGCAGAAUGAACACAAAGUACGACGAAAACGACAAGCUGAUCAGAGAAGUCAAGGUCAUCACA<br>CUGAAGAGCAAGCUGGUCAGCGACUUCAGAAAGGACUUCCAGUUCUACAAGGUCAGAGAAAUCAACAACUACCACCACGCACACGAC<br>GCAUACCUGAACGCAGUCGUCGGAACAGCACUGAUCAAGAAGUACCCGAAGCUGGAAAGCGAAUUCGUCUACGGAGACUACAAGGUC<br>UACGACGUCAGAAAGAUGAUCGCAAAGAGCGAACAGGAAAUCGGAAAGGCAACAGCAAAGUACUUCUUCUACAGCAACAUCAUGAAC<br>UUCUUCAAGACAGAAAUCACACUGGCAAACGGAGAAAUCAGAAAGAGACCGCUGAUCGAAACAAACGGAGAAACAGGAGAAAUCGUC<br>UGGGACAAGGGAAGAGACUUCGCAACAGUCAGAAAGGUCCUGAGCAUGCCGCAGGUCAACAUCGUCAAGAAGACAGAAGUCCAGACA | 204 |

-continued

| Sequence Table | | |
|---|---|---|
| Description | Sequence | SEQ ID No. |
| | GGAGGAUUCAGCAAGGAAAGCAUCCUGCCGAAGAGAAACAGCGACAAGCUGAUCGCAAGAAAGAAGGACUGGGACCCGAAGAAGUAC<br>GGAGGAUUCGACAGCCCGACAGUCGCAUACAGCGUCCUGGUCGUCGCAAAGGUCGAAAAGGGAAAGAGCAAGAAGCUGAAGAGCGUC<br>AAGGAACUGCUGGGAAUCACAAUCAUGGAAAGAAGCAGCUUCGAAAAGAACCCGAUCGACUUCCUGGAAGCAAAGGGAUACAAGGAA<br>GUCAAGAAGGACCUGAUCAUCAAGCUGCCGAAGUACAGCCUGUUCGAACUGGAAAACGGAAGAAAGAGAAUGCUGGCAAGCGCAGGA<br>GAACUGCAGAAGGGAAACGAACUGGCACUGCCGAGCAAGUACGUCAACUUCCUGUACCUGGCAAGCCACUACGAAAAGCUGAAGGGA<br>AGCCCGGAAGACAACGAACAGAAGCAGCUGUUCGUCGAACAGCACAAGCACUACCUGGACGAAAUCAUCGAACAGAUCAGCGAAUUC<br>AGCAAGAGAGUCAUCCUGGCAGACGCAAACCUGGACAAGGUCCUGAGCGCAUACAACAAGCACAGAGACAAGCCGAUCAGAGAACAG<br>GCAGAAAACAUCAUCCACCUGUUCACACUGACAAACCUGGGAGCACCGGCAGCAUUCAAGUACUUCGACACAACAAUCGACAGAAAG<br>AGAUACACAAGCACAAAGGAAGUCCUGGACGCAACACUGAUCCACCAGAGCAUCACAGGACUGUACGAAACAAGAAUCGACCUGAGC<br>CAGCUGGGAGGAGACGGAGGAGGAAGCCCGAAGAAGAAGAGAAAGGUCUAG | |
| Cas9 mRNA ORF 1 | AUGGAUAAGAAGUACUCAAUCGGGCUGGAUAUCGGAACUAAUUCCGUGGGUUGGGCAGUGAUCACGGAUGAAUACAAAGUGCCGUCC<br>AAGAAGUUCAAGGUCCUGGGGAACACCGAUAGACACAGCAUCAAGAAAAAUCUCAUCGGAGCCCUGCUGUUUGACUCCGGCGAAACC<br>GCAGAAGCGACCCGGCUCAAACGUACCGCGAGGCGACGCUACACCCGGCGGAAGAAUCGCAUCUGCUAUCUGCAAGAGAUCUUUUCG<br>AACGAAAUGGCAAAGGUCGACGACAGCUUCUUCCACCGCCUGGAAGAAUCUUUCCUGGUGGAGGAGGACAAGAAGCAUGAACGGCAU<br>CCUAUCUUUGGAAACAUCGUCGACGAAGUGGCGUACCACGAAAAGUACCCGACCAUCUACCAUCUGCGGAAGAAGUUGGUUGACUCA<br>ACUGACAAGGCCGACCUCAGAUUGAUCUACUUGGCCCUCGCCCAUAUGAUCAAAUUCCGCGGACACUUCCUGAUCGAAGGCGAUCUG<br>AACCCUGAUAACUCCGACGUGGAUAAGCUUUUCAUUCAACUGGUGCAGACCUACAACCAACUGUUCGAAGAAAACCCAAUCAAUGCU<br>AGCGGCGUCGAUGCCAAGGCCAUCCUGUCCGCCCGGCUGUCGAAGUCGCGGCGCCUCGAAAACCUGAUCGCACAGCUGCCGGGAGAG<br>AAAAAGAACGGACUUUUCGGCAACUUGAUCGCUCUCUCACUGGGACUCACUCCCAAUUUCAAGUCCAAUUUUGACCUGGCCGAGGAC<br>GCGAAGCUGCAACUCUCAAAGGACACCUACGACGACGACUUGGACAAUUUGCUGGCACAAAUUGGCGAUCAGUACGCGGAUCUGUUC<br>CUUGCCGCUAAGAACCUUUCGGACGCAAUCUUGCUGUCCGAUAUCCUGCGCGUGAACACCGAAAUAACCAAAGCGCCGCUUAGCGCC<br>UCGAUGAUUAAGCGGUACGACGAGCAUCACCAGGAUCUCACGCUGCUCAAAGCGCUCGUGAGACAGCAACUGCCUGAAAAGUACAAG<br>GAGAUCUUCUUCGACCAGUCCAAGAAUGGGUACGCAGGGUACAUCGAUGGAGGCGCUAGCCAGGAAGAGUUCUAUAAGUUCAUCAAG<br>CCAAUCCUGGAAAAGAUGGACGGAACCGAAGAACUGCUGGUCAAGCUGAACAGGGAGGAUCUGCUCCGGAAACAGAGAACCUUUGAC<br>AACGGAUCCAUUCCCCACCAGAUCCAUCUGGGUGAGCUGCACGCCAUCUUGCGGCGCCAGGAGGACUUUUACCCAUUCCUCAAGGAC<br>AACCGGGAAAAGAUCGAGAAAAUUCUGACGUUCCGCAUCCCGUAUUACGUGGGCCCACUGGCGCGCGGCAAUUCGCGCUUCGCGUGG<br>AUGACUAGAAAAUCAGAGGAAACCAUCACUCCUUGGAAUUUCGAGGAAGUUGUGGAUAAGGGAGCUUCGGCACAAAGCUUCAUCGAA<br>CGAAUGACCAACUUCGACAAGAAUCUCCCAAACGAGAAGGUGCUUCCUAAGCACAGCCUCCUUUACGAAUACUUCACUGUCUACAAC<br>GAACUGACUAAAGUGAAAUACGUUACUGAAGGAAUGAGGAAGCCGGCCUUUCUGUCCGGAGAACAGAAGAAAGCAAUUGUCGAUCUG<br>CUGUUCAAGACCAACCGCAAGGUGACCGUCAAGCAGCUUAAAGAGGACUACUUCAAGAAGAUCGAGUGUUUCGACUCAGUGGAAAUC<br>AGCGGGGUGGAGGACAGAUUCAACGCUUCGCUGGGAACCUAUCAUGAUCUCCUGAAGAUCAUCAAGGACAAGGACUUCCUUGACAAC<br>GAGGAGAACGAGGACAUCCUGGAAGAUAUCGUCCUGACCUUGACCCUUUUCGAGGAUCGCGAGAUGAUCGAGGAGAGGCUUAAGACC<br>UACGCUCAUCUCUUCGACGAUAAGGUCAUGAAACAACUCAAGCGCCGCCGGUACACUGGUUGGGGCCGCCUCUCCCGCAAGCUGAUC<br>AACGGUAUUCGCGAUAAACAGAGCGGUAAAACUAUCCUGGAUUUCCUCAAAUCGGAUGGCUUCGCUAAUCGUAACUUCAUGCAAUUG<br>AUCCACGACGACAGCCUGACCUUUAAGGAGGACAUCCAAAAAGCACAAGUGUCCGGACAGGGAGACUCACUCCAUGAACACAUCGCG<br>AAUCUGGCCGGUUCGCCGGCGAUUAAGAAGGGAAUUCUGCAAACUGUGAAGGUGGUCGACGAGCUGGUGAAGGUCAUGGGACGGCAC<br>AAACCGGAGAAUAUCGUGAUUGAAAUGGCCCGAGAAAACCAGACUACCCAGAAGGGCCAGAAAAACUCCCGCGAAAGGAUGAAGCGG<br>AUCGAAGAAGGAAUCAAGGAGCUGGGCAGCCAGAUCCUGAAAGAGCACCCGGUGGAAAACACGCAGCUGCAGAACGAGAAGCUCUAC<br>CUGUACUAUUUGCAAAAUGGACGGGACAUGUACGUGGACCAAGAGCUGGACAUCAAUCGGUUGUCUGAUUACGACGUGGACCACAUC<br>GUUCCACAGUCCUUUCUGAAGGAUGACUCGAUCGAUAACAAGGUGUUGACUCGCAGCGACAAGAACAGAGGGAAGUCAGAUAAUGUG<br>CCAUCGGAGGAGGUCGUGAAGAAGAUGAAGAAUUACUGGCGGCAGCUCCUGAAUGCGAAGCUGAUUACCCAGAGAAAGUUUGACAAU<br>CUCACUAAAGCCGAGCGCGGCGGACUCUCAGAGCUGGAUAAGGCUGGAUUCAUCAAACGGCAGCUGGUCGAGACUCGGCAGAUUACC<br>AAGCACGUGGCGCAGAUCUUGGACUCCCGCAUGAACACUAAAUACGACGAGAACGAUAAGCUCAUCCGGGAAGUGAAGGUGAUUACC<br>CUGAAAAGCAAACUUGUGUCGGACUUUCGGAAGGACUUUCAGUUUUACAAAGUGAGAGAAAUCAACAACUACCAUCACGCGCAUGAC<br>GCAUACCUCAACGCUGUGGUCGGUACCGCCCUGAUCAAAAAGUACCCUAAACUUGAAUCGGAGUUUGUGUACGGAGACUACAAGGUC<br>UACGACGUGAGGAAGAUGAUAGCCAAGUCCGAACAGGAAAUCGGGAAAGCAACUGCGAAAUACUUCUUUUACUCAAACAUCAUGAAC<br>UUUUUCAAGACUGAAAUUACGCUGGCCAAUGGAGAAAUCAGGAAGAGGCCACUGAUCGAAACUAACGGAGAAACGGGCGAAAUCGUG<br>UGGGACAAGGGCAGGGACUUCGCAACUGUUCGCAAAGUGCUCUCUAUGCCGCAAGUCAAUAUUGUGAAGAAAACCGAAGUGCAAACC | 205 |

-continued

Sequence Table

| Description | Sequence | SEQ ID No. |
|---|---|---|
| | GGCGGAUUUUCAAAGGAAUCGAUCCUCCCAAAGAGAAAUAGCGACAAGCUCAUUGCACGCAAGAAAGACUGGGACCCGAAGAAGUAC<br>GGAGGAUUCGAUUCGCCGACUGUCGCAUACUCCGUCCUCGUGGUGGCCAAGGUGGAGAAGGGAAAGAGCAAAAAGCUCAAAUCCGUC<br>AAAGAGCUGCUGGGGAUUACCAUCAUGGAACGAUCCUCGUUCGAGAAGAACCCGAUUGAUUUCCUCGAGGCGAAGGGUUACAAGGAG<br>GUGAAGAAGGAUCUGAUCAUCAAACUCCCCAAGUACUCACUGUUCGAACUGGAAAAUGGUCGGAAGCGCAUGCUGGCUUCGGCCGGA<br>GAACUCCAAAAAGGAAAUGAGCUGGCCUUGCCUAGCAAGUACGUCAACUUCCUCUAUCUUGCUUCGCACUACGAAAAACUCAAAGGG<br>UCACCGGAAGAUAACGAACAGAAGCAGCUUUUCGUGGAGCAGCACAAGCAUUAUCUGGAUGAAAUCAUCGAACAAAUCUCCGAGUUU<br>UCAAAGCGCGUGAUCCUCGCCGACGCCAACCUCGACAAAGUCCUGUCGGCCUACAAUAAGCAUAGAGAUAAGCCGAUCAGAGAACAG<br>GCCGAGAACAUUAUCCACUUGUUCACCCUGACUAACCUGGGAGCCCCAGCCGCCUUCAAGUACUUCGAUACUACUAUCGAUCGCAAA<br>AGAUACACGUCCACCAAGGAAGUUCUGGACGCGACCCUGAUCCACCAAAGCAUCACUGGACUCUACGAAACUAGGAUCGAUCUGUCG<br>CAGCUGGGUGGCGAUGGCGGUGGAUCUCCGAAAAAGAAGAGAAAGGUGUAAUGA | |
| | Not Used | 206-212 |
| Amino acid sequence of Cas9 (without NLS) | MDKKYSIGLDIGTNSVGWAVITDEYKVPSKKFKVLGNTDRHSIKKNLIGALLFDSGETAEATRLKRTARRRYTRRKNRICYLQEIFS<br>NEMAKVDDSFFHRLEESFLVEEDKKHERHPIFGNIVDEVAYHEKYPTIYHLRKKLVDSTDKADLRLIYLALAHMIKFRGHFLIEGDL<br>NPDNSDVDKLFIQLVQTYNQLFEENPINASGVDAKAILSARLSKSRRLENLIAQLPGEKKNGLFGNLIALSLGLTPNFKSNFDLAED<br>AKLQLSKDTYDDDLDNLLAQIGDQYADLFLAAKNLSDAILLSDILRVNTEITKAPLSASMIKRYDEHHQDLTLLKALVRQQLPEKYK<br>EIFFDQSKNGYAGYIDGGASQEEFYKFIKPILEKMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQSFIERMTNFDKNLPNEKVLPKHSLLYEYFTVYN<br>ELTKVKYVTEGMRKPAFLSGEQKKAIVDLLFKTNRKVTVKQLKEDYFKKIECFDSVEISGVEDRFNASLGTYHDLLKIIKDKDFLDN<br>EENEDILEDIVLTLTLFEDREMIEERLKTYAHLFDDKVMKQLKRRRYTGWGRLSRKLINGIRDKQSGKTILDFLKSDGFANRNFMQL<br>IHDDSLTFKEDIQKAQVSGQGDSLHEHIANLAGSPAIKKGILQTVKVVDELVKVMGRHKPENIVIEMARENQTTQKGQKNSRERMKR<br>IEEGIKELGSQILKEHPVENTQLQNEKLYLYYLQNGRDMYVDQELDINRLSDYDVDHIVPQSFLKDDSIDNKVLTRSDKNRGKSDNV<br>PSEEVVKKMKNYWRQLLNAKLITQRKFDNLTKAERGGLSELDKAGFIKRQLVETRQITKHVAQILDSRMNTKYDENDKLIREVKVIT<br>LKSKLVSDFRKDFQFYKVREINNYHHAHDAYLNAVVGTALIKKYPKLESEFVYGDYKVYDVRKMIAKSEQEIGKATAKYFFYSNIMN<br>FFKTEITLANGEIRKRPLIETNGETGEIVWDKGRDFATVRKVLSMPQVNIVKKTEVQTGGFSKESILPKRNSDKLIARKKDWDPKKY<br>GGFDSPTVAYSVLVVAKVEKGKSKKLKSVKELLGITIMERSSFEKNPIDFLEAKGYKEVKKDLIIKLPKYSLFELENGRKRMLASAG<br>ELQKGNELALPSKYVNFLYLASHYEKLKGSPEDNEQKQLFVEQHKHYLDEIIEQISEFSKRVILADANLDKVLSAYNKHRDKPIREQ<br>AENIIHLFTLTNLGAPAAFKYFDTTIDRKRYTSTKEVLDATLIHQSITGLYETRIDLSQLGGD | 213 |
| | Not Used | 214-221 |
| Amino acid sequence of Cas9 with two nuclear localization signals as the C-terminal amino acids | MDKKYSIGLDIGTNSVGWAVITDEYKVPSKKFKVLGNTDRHSIKKNLIGALLFDSGETAEATRLKRTARRRYTRRKNRICYLQEIFS<br>NEMAKVDDSFFHRLEESFLVEEDKKHERHPIFGNIVDEVAYHEKYPTIYHLRKKLVDSTDKADLRLIYLALAHMIKFRGHFLIEGDL<br>NPDNSDVDKLFIQLVQTYNQLFEENPINASGVDAKAILSARLSKSRRLENLIAQLPGEKKNGLFGNLIALSLGLTPNFKSNFDLAED<br>AKLQLSKDTYDDDLDNLLAQIGDQYADLFLAAKNLSDAILLSDILRVNTEITKAPLSASMIKRYDEHHQDLTLLKALVRQQLPEKYK<br>EIFFDQSKNGYAGYIDGGASQEEFYKFIKPILEKMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQSFIERMTNFDKNLPNEKVLPKHSLLYEYFTVYN<br>ELTKVKYVTEGMRKPAFLSGEQKKAIVDLLFKTNRKVTVKQLKEDYFKKIECFDSVEISGVEDRFNASLGTYHDLLKIIKDKDFLDN<br>EENEDILEDIVLTLTLFEDREMIEERLKTYAHLFDDKVMKQLKRRRYTGWGRLSRKLINGIRDKQSGKTILDFLKSDGFANRNFMQL<br>IHDDSLTFKEDIQKAQVSGQGDSLHEHIANLAGSPAIKKGILQTVKVVDELVKVMGRHKPENIVIEMARENQTTQKGQKNSRERMKR<br>IEEGIKELGSQILKEHPVENTQLQNEKLYLYYLQNGRDMYVDQELDINRLSDYDVDHIVPQSFLKDDSIDNKVLTRSDKNRGKSDNV<br>PSEEVVKKMKNYWRQLLNAKLITQRKFDNLTKAERGGLSELDKAGFIKRQLVETRQITKHVAQILDSRMNTKYDENDKLIREVKVIT<br>LKSKLVSDFRKDFQFYKVREINNYHHAHDAYLNAVVGTALIKKYPKLESEFVYGDYKVYDVRKMIAKSEQEIGKATAKYFFYSNIMN<br>FFKTEITLANGEIRKRPLIETNGETGEIVWDKGRDFATVRKVLSMPQVNIVKKTEVQTGGFSKESILPKRNSDKLIARKKDWDPKKY<br>GGFDSPTVAYSVLVVAKVEKGKSKKLKSVKELLGITIMERSSFEKNPIDFLEAKGYKEVKKDLIIKLPKYSLFELENGRKRMLASAG<br>ELQKGNELALPSKYVNFLYLASHYEKLKGSPEDNEQKQLFVEQHKHYLDEIIEQISEFSKRVILADANLDKVLSAYNKHRDKPIREQ<br>AENIIHLFTLTNLGAPAAFKYFDTTIDRKRYTSTKEVLDATLIHQSITGLYETRIDLSQLGGD<br>GSGSPKKKRKVDGSPKKKRKVDSG | 222 |

-continued

Sequence Table

| Description | Sequence | SEQ ID No. |
|---|---|---|
| | Not Used | 223-230 |
| T7 promoter | TAATACGACTCACTATA | 231 |
| Human beta-globin 5' UTR | ACATTTGCTTCTGACACAACTGTGTTCACTAGCAACCTCAAACAGACACC | 232 |
| Human beta-globin 3' UTR | GCTCGCTTTCTTGCTGTCCAATTTCTATTAAAGGTTCCTTTGTTCCCTAAGTCCAACTACTAAACTGGGGGATATTATGAAGGGCCT TGAGCATCTGGATTCTGCCTAATAAAAAACATTTATTTTCATTGC | 233 |
| Human alpha-globin 5' UTR | CATAAACCCTGGCGCGCTCGCGGCCCGGCACTCTTCTGGTCCCCACAGACTCAGAGAGAACCCACC | 234 |
| Human alpha-globin 3' UTR | GCTGGAGCCTCGGTGGCCATGCTTCTTGCCCCTTGGGCCTCCCCCCAGCCCCTCCTCCCCTTCCTGCACCCGTACCCCCGTGGTCTT TGAATAAAGTCTGAGTGGGCGGC | 235 |
| *Xenopus laevis* beta-globin 5' UTR | AAGCTCAGAATAAACGCTCAACTTTGGCC | 236 |
| *Xenopus laevis* beta-globin 3' UTR | ACCAGCCTCAAGAACACCCGAATGGAGTCTCTAAGCTACATAATACCAACTTACACTTTACAAAATGTTGTCCCCCAAAATGTAGCC ATTCGTATCTGCTCCTAATAAAAAGAAAGTTTCTTCACATTCT | 237 |
| Bovine Growth Hormone 5' UTR | CAGGGTCCTGTGGACAGCTCACCAGCT | 238 |
| Bovine Growth Hormone 3' UTR | TTGCCAGCCATCTGTTGTTTGCCCCTCCCCCGTGCCTTCCTTGACCCTGGAAGGTGCCACTCCCACTGTCCTTTCCTAATAAAATGA GGAAATTGCATCGCA | 239 |
| Mus musculus hemoglobin alpha, adult chain 1 (Hba-a1), | GCTGCCTTCTGCGGGGCTTGCCTTCTGGCCATGCCCTTCTTCTCTCCCTTGCACCTGTACCTCTTGGTCTTTGAATAAAGCCTGAGT AGGAAG | 240 |

-continued

Sequence Table

| Description | Sequence | SEQ ID No. |
|---|---|---|
| 3' UTR | | |
| HSD17B4 5'<br>UTR | TCCCGCAGTCGGCGTCCAGCGGCTCTGCTTGTTCGTGTGTGTGTCGTTGCAGGCCTTATTC | 241 |
| G282 guide<br>RNA<br>targeting<br>TTR | mU*mU*mA*CAGCCACGUCUACAGCAGUUUUAGAmGmCmUmAmGmAmAmAmUmAmGmCAAGUUAAAAUAAGGCUAGUCCGUUAUCAm<br>AmCmUmUmGmAmAmAmAmAmGmUmGmGmCmAmCmCmGmAmGmUmCmGmGmUmGmCmU*mU*mU*mU | 242 |
| Cas9<br>transcript<br>with 5' UTR<br>of HSD, ORF<br>corresponding<br>to SEQ<br>ID NO: 204,<br>Kozak<br>sequence,<br>and 3' UTR<br>of ALB | GGGTCCCGCAGTCGGCGTCCAGCGGCTCTGCTTGTTCGTGTGTGTGTCGTTGCAGGCCTTATTCGGATCCGCCACCATGGACAAGAA<br>GTACAGCATCGGACTGGACATCGGAACAAACAGCGTCGGATGGGCAGTCATCACAGACGAATACAAGGTCCCGAGCAAGAAGTTCAA<br>GGTCCTGGGAAACACAGACAGACACAGCATCAAGAAGAACCTGATCGGAGCACTGCTGTTCGACAGCGGAGAAACAGCAGAAGCAAC<br>AAGACTGAAGAGAACAGCAAGAAGAAGATACACAAGAAGAAAGAACAGAATCTGCTACCTGCAGGAAATCTTCAGCAACGAAATGGC<br>AAAGGTCGACGACAGCTTCTTCCACAGACTGGAAGAAAGCTTCCTGGTCGAAGAAGACAAGAAGCACGAAAGACACCCGATCTTCGG<br>AAACATCGTCGACGAAGTCGCATACCACGAAAAGTACCCGACAATCTACCACCTGAGAAAGAAGCTGGTCGACAGCACAGACAAGGC<br>AGACCTGAGACTGATCTACCTGGCACTGGCACACATGATCAAGTTCAGAGGACACTTCCTGATCGAAGGAGACCTGAACCCGGACAA<br>CAGCGACGTCGACAAGCTGTTCATCCAGCTGGTCCAGACATACAACCAGCTGTTCGAAGAAAACCCGATCAACGCAAGCGGAGTCGA<br>CGCAAAGGCAATCCTGAGCGCAAGACTGAGCAAGAGCAGAAGACTGGAAAACCTGATCGCACAGCTGCCGGGAGAAAAGAAGAACGG<br>ACTGTTCGGAAACCTGATCGCACTGAGCCTGGGACTGACACCGAACTTCAAGAGCAACTTCGACCTGGCAGAAGACGCAAAGCTGCA<br>GCTGAGCAAGGACACATACGACGACGACCTGGACAACCTGCTGGCACAGATCGGAGACCAGTACGCAGACCTGTTCCTGGCAGCAAA<br>GAACCTGAGCGACGCAATCCTGCTGAGCGACATCCTGAGAGTCAACACAGAAATCACAAAGGCACCGCTGAGCGCAAGCATGATCAA<br>GAGATACGACGAACACCACCAGGACCTGACACTGCTGAAGGCACTGGTCAGACAGCAGCTGCCGGAAAAGTACAAGGAAATCTTCTT<br>CGACCAGAGCAAGAACGGATACGCAGGATACATCGACGGAGGAGCAAGCCAGGAAGAATTCTACAAGTTCATCAAGCCGATCCTGGA<br>AAAGATGGACGGAACAGAAGAACTGCTGGTCAAGCTGAACAGAGAAGACCTGCTGAGAAAGCAGAGAACATTCGACAACGGAAGCAT<br>CCCGCACCAGATCCACCTGGGAGAACTGCACGCAATCCTGAGAAGACAGGAAGACTTCTACCCGTTCCTGAAGGACAACAGAGAAAA<br>GATCGAAAAGATCCTGACATTCAGAATCCCGTACTACGTCGGACCGCTGGCAAGAGGAAACAGCAGATTCGCATGGATGACAAGAAA<br>GAGCGAAGAAACAATCACACCGTGGAACTTCGAAGAAGTCGTCGACAAGGGAGCAAGCGCACAGAGCTTCATCGAAAGAATGACAAA<br>CTTCGACAAGAACCTGCCGAACGAAAAGGTCCTGCCGAAGCACAGCCTGCTGTACGAATACTTCACAGTCTACAACGAACTGACAAA<br>GGTCAAGTACGTCACAGAAGGAATGAGAAAGCCGGCATTCCTGAGCGGAGAACAGAAGAAGGCAATCGTCGACCTGCTGTTCAAGAC<br>AAACAGAAAGGTCACAGTCAAGCAGCTGAAGGAAGACTACTTCAAGAAGATCGAATGCTTCGACAGCGTCGAAATCAGCGGAGTCGA<br>AGACAGATTCAACGCAAGCCTGGGAACATACCACGACCTGCTGAAGATCATCAAGGACAAGGACTTCCTGGACAACGAAGAAAACGA<br>AGACATCCTGGAAGACATCGTCCTGACACTGACACTGTTCGAAGACAGAGAAATGATCGAAGAAAGACTGAAGACATACGCACACCT<br>GTTCGACGACAAGGTCATGAAGCAGCTGAAGAGAAGAAGATACACAGGATGGGGAAGACTGAGCAGAAAGCTGATCAACGGAATCAG<br>AGACAAGCAGAGCGGAAAGACAATCCTGGACTTCCTGAAGAGCGACGGATTCGCAAACAGAAACTTCATGCAGCTGATCCACGACGA<br>CAGCCTGACATTCAAGGAAGACATCCAGAAGGCACAGGTCAGCGGACAGGGAGACAGCCTGCACGAACACATCGCAAACCTGGCAGG<br>AAGCCCGGCAATCAAGAAGGGAATCCTGCAGACAGTCAAGGTCGTCGACGAACTGGTCAAGGTCATGGGAAGACACAAGCCGGAAAA<br>CATCGTCATCGAAATGGCAAGAGAAAACCAGACAACACAGAAGGGACAGAAGAACAGCAGAGAAAGAATGAAGAGAATCGAAGAAGG<br>AATCAAGGAACTGGGAAGCCAGATCCTGAAGGAACACCCGGTCGAAAACACACAGCTGCAGAACGAAAAGCTGTACCTGTACTACCT<br>GCAGAACGGAAGAGACATGTACGTCGACCAGGAACTGGACATCAACAGACTGAGCGACTACGACGTCGACCACATCGTCCCGCAGAG<br>CTTCCTGAAGGACGACAGCATCGACAACAAGGTCCTGACAAGAAGCGACAAGAACAGAGGAAAGAGCGACAACGTCCCGAGCGAAGA<br>AGTCGTCAAGAAGATGAAGAACTACTGGAGACAGCTGCTGAACGCAAAGCTGATCACACAGAGAAAGTTCGACAACCTGACAAAGGC<br>AGAGAGAGGAGGACTGAGCGAACTGGACAAGGCAGGATTCATCAAGAGACAGCTGGTCGAAACAAGACAGATCACAAAGCACGTCGC<br>ACAGATCCTGGACAGCAGAATGAACACAAAGTACGACGAAAACGACAAGCTGATCAGAGAAGTCAAGGTCATCACACTGAAGAGCAA<br>GCTGGTCAGCGACTTCAGAAAGGACTTCCAGTTCTACAAGGTCAGAGAAATCAACAACTACCACCACGCACACGACGCATACCTGAA<br>CGCAGTCGTCGGAACAGCACTGATCAAGAAGTACCCGAAGCTGGAAAGCGAATTCGTCTACGGAGACTACAAGGTCTACGACGTCAG<br>AAAGATGATCGCAAAGAGCGAACAGGAAATCGGAAAGGCAACAGCAAAGTACTTCTTCTACAGCAACATCATGAACTTCTTCAAGAC<br>AGAAATCACACTGGCAAACGGAGAAATCAGAAAGAGACCGCTGATCGAAACAAACGGAGAAACAGGAGAAATCGTCTGGGACAAGGG<br>AAGAGACTTCGCAACAGTCAGAAAGGTCCTGAGCATGCCGCAGGTCAACATCGTCAAGAAGACAGAAGTCCAGACAGGAGGATTCAG | 243 |

-continued

Sequence Table

| Description | Sequence | SEQ ID No. |
|---|---|---|
| | CAAGGAAAGCATCCTGCCGAAGAGAAACAGCGACAAGCTGATCGCAAGAAAGAAGGACTGGGACCCGAAGAAGTACGGAGGATTCGA<br>CAGCCCGACAGTCGCATACAGCGTCCTGGTCGTCGCAAAGGTCGAAAAGGGAAAGAGCAAGAAGCTGAAGAGCGTCAAGGAACTGCT<br>GGGAATCACAATCATGGAAAGAAGCAGCTTCGAAAAGAACCCGATCGACTTCCTGGAAGCAAAGGGATACAAGGAAGTCAAGAAGGA<br>CCTGATCATCAAGCTGCCGAAGTACAGCCTGTTCGAACTGGAAAACGGAAGAAAGAGAATGCTGGCAAGCGCAGGAGAACTGCAGAA<br>GGGAAACGAACTGGCACTGCCGAGCAAGTACGTCAACTTCCTGTACCTGGCAAGCCACTACGAAAAGCTGAAGGGAAGCCCGGAAGA<br>CAACGAACAGAAGCAGCTGTTCGTCGAACAGCACAAGCACTACCTGGACGAAATCATCGAACAGATCAGCGAATTCAGCAAGAGAGT<br>CATCCTGGCAGACGCAAACCTGGACAAGGTCCTGAGCGCATACAACAAGCACAGAGACAAGCCGATCAGAGAACAGGCAGAAAACAT<br>CATCCACCTGTTCACACTGACAAACCTGGGAGCACCGGCAGCATTCAAGTACTTCGACACAACAATCGACAGAAAGAGATACACAAG<br>CACAAAGGAAGTCCTGGACGCAACACTGATCCACCAGAGCATCACAGGACTGTACGAAACAAGAATCGACCTGAGCCAGCTGGGAGG<br>AGACGGAGGAGGAAGCCCGAAGAAGAAGAGAAAGGTCTAGCTAGCCATCACATTTAAAAGCATCTCAGCCTACCATGAGAATAAGAG<br>AAAGAAAATGAAGATCAATAGCTTATTCATCTCTTTTTCTTTTTCGTTGGTGTAAAGCCAACACCCTGTCTAAAAAACATAAATTTC<br>TTTAATCATTTTGCCTCTTTTCTCTGTGCTTCAATTAATAAAAAATGGAAAGAACCTCGAG | |
| Cas9 transcript with 5' UTR of HSD, ORF corresponding to SEQ ID NO: 204, and 3' UTR of ALB | GGGTCCCGCAGTCGGCGTCCAGCGGCTCTGCTTGTTCGTGTGTGTGTCGTTGCAGGCCTTATTCGGATCCATGGACAAGAAGTACAG<br>CATCGGACTGGACATCGGAACAAACAGCGTCGGATGGGCAGTCATCACAGACGAATACAAGGTCCCGAGCAAGAAGTTCAAGGTCCT<br>GGGAAACACAGACAGACACAGCATCAAGAAGAACCTGATCGGAGCACTGCTGTTCGACAGCGGAGAAACAGCAGAAGCAACAAGACT<br>GAAGAGAACAGCAAGAAGAAGATACACAAGAAGAAAGAACAGAATCTGCTACCTGCAGGAAATCTTCAGCAACGAAATGGCAAAGGT<br>CGACGACAGCTTCTTCCACAGACTGGAAGAAAGCTTCCTGGTCGAAGAAGACAAGAAGCACGAAAGACACCCGATCTTCGGAAACAT<br>CGTCGACGAAGTCGCATACCACGAAAAGTACCCGACAATCTACCACCTGAGAAAGAAGCTGGTCGACAGCACAGACAAGGCAGACCT<br>GAGACTGATCTACCTGGCACTGGCACACATGATCAAGTTCAGAGGACACTTCCTGATCGAAGGAGACCTGAACCCGGACAACAGCGA<br>CGTCGACAAGCTGTTCATCCAGCTGGTCCAGACATACAACCAGCTGTTCGAAGAAAACCCGATCAACGCAAGCGGAGTCGACGCAAA<br>GGCAATCCTGAGCGCAAGACTGAGCAAGAGCAGAAGACTGGAAAACCTGATCGCACAGCTGCCGGGAGAAAAGAAGAACGGACTGTT<br>CGGAAACCTGATCGCACTGAGCCTGGGACTGACACCGAACTTCAAGAGCAACTTCGACCTGGCAGAAGACGCAAAGCTGCAGCTGAG<br>CAAGGACACATACGACGACGACCTGGACAACCTGCTGGCACAGATCGGAGACCAGTACGCAGACCTGTTCCTGGCAGCAAAGAACCT<br>GAGCGACGCAATCCTGCTGAGCGACATCCTGAGAGTCAACACAGAAATCACAAAGGCACCGCTGAGCGCAAGCATGATCAAGAGATA<br>CGACGAACACCACCAGGACCTGACACTGCTGAAGGCACTGGTCAGACAGCAGCTGCCGGAAAAGTACAAGGAAATCTTCTTCGACCA<br>GAGCAAGAACGGATACGCAGGATACATCGACGGAGGAGCAAGCCAGGAAGAATTCTACAAGTTCATCAAGCCGATCCTGGAAAAGAT<br>GGACGGAACAGAAGAACTGCTGGTCAAGCTGAACAGAGAAGACCTGCTGAGAAAGCAGAGAACATTCGACAACGGAAGCATCCCGCA<br>CCAGATCCACCTGGGAGAACTGCACGCAATCCTGAGAAGACAGGAAGACTTCTACCCGTTCCTGAAGGACAACAGAGAAAAGATCGA<br>AAAGATCCTGACATTCAGAATCCCGTACTACGTCGGACCGCTGGCAAGAGGAAACAGCAGATTCGCATGGATGACAAGAAAGAGCGA<br>AGAAACAATCACACCGTGGAACTTCGAAGAAGTCGTCGACAAGGGAGCAAGCGCACAGAGCTTCATCGAAAGAATGACAAACTTCGA<br>CAAGAACCTGCCGAACGAAAAGGTCCTGCCGAAGCACAGCCTGCTGTACGAATACTTCACAGTCTACAACGAACTGACAAAGGTCAA<br>GTACGTCACAGAAGGAATGAGAAAGCCGGCATTCCTGAGCGGAGAACAGAAGAAGGCAATCGTCGACCTGCTGTTCAAGACAAACAG<br>AAAGGTCACAGTCAAGCAGCTGAAGGAAGACTACTTCAAGAAGATCGAATGCTTCGACAGCGTCGAAATCAGCGGAGTCGAAGACAG<br>ATTCAACGCAAGCCTGGGAACATACCACGACCTGCTGAAGATCATCAAGGACAAGGACTTCCTGGACAACGAAGAAAACGAAGACAT<br>CCTGGAAGACATCGTCCTGACACTGACACTGTTCGAAGACAGAGAAATGATCGAAGAAAGACTGAAGACATACGCACACCTGTTCGA<br>CGACAAGGTCATGAAGCAGCTGAAGAGAAGAAGATACACAGGATGGGGAAGACTGAGCAGAAAGCTGATCAACGGAATCAGAGACAA<br>GCAGAGCGGAAAGACAATCCTGGACTTCCTGAAGAGCGACGGATTCGCAAACAGAAACTTCATGCAGCTGATCCACGACGACAGCCT<br>GACATTCAAGGAAGACATCCAGAAGGCACAGGTCAGCGGACAGGGAGACAGCCTGCACGAACACATCGCAAACCTGGCAGGAAGCCC<br>GGCAATCAAGAAGGGAATCCTGCAGACAGTCAAGGTCGTCGACGAACTGGTCAAGGTCATGGGAAGACACAAGCCGGAAAACATCGT<br>CATCGAAATGGCAAGAGAAAACCAGACAACACAGAAGGGACAGAAGAACAGCAGAGAAAGAATGAAGAGAATCGAAGAAGGAATCAA<br>GGAACTGGGAAGCCAGATCCTGAAGGAACACCCGGTCGAAAACACACAGCTGCAGAACGAAAAGCTGTACCTGTACTACCTGCAGAA<br>CGGAAGAGACATGTACGTCGACCAGGAACTGGACATCAACAGACTGAGCGACTACGACGTCGACCACATCGTCCCGCAGAGCTTCCT<br>GAAGGACGACAGCATCGACAACAAGGTCCTGACAAGAAGCGACAAGAACAGAGGAAAGAGCGACAACGTCCCGAGCGAAGAAGTCGT<br>CAAGAAGATGAAGAACTACTGGAGACAGCTGCTGAACGCAAAGCTGATCACACAGAGAAAGTTCGACAACCTGACAAAGGCAGAGAG<br>AGGAGGACTGAGCGAACTGGACAAGGCAGGATTCATCAAGAGACAGCTGGTCGAAACAAGACAGATCACAAAGCACGTCGCACAGAT<br>CCTGGACAGCAGAATGAACACAAAGTACGACGAAAACGACAAGCTGATCAGAGAAGTCAAGGTCATCACACTGAAGAGCAAGCTGGT<br>CAGCGACTTCAGAAAGGACTTCCAGTTCTACAAGGTCAGAGAAATCAACAACTACCACCACGCACACGACGCATACCTGAACGCAGT<br>CGTCGGAACAGCACTGATCAAGAAGTACCCGAAGCTGGAAAGCGAATTCGTCTACGGAGACTACAAGGTCTACGACGTCAGAAAGAT | 244 |

-continued

Sequence Table

| Description | Sequence | SEQ ID No. |
|---|---|---|
| | GATCGCAAAGAGCGAACAGGAAATCGGAAAGGCAACAGCAAAGTACTTCTTCTACAGCAACATCATGAACTTCTTCAAGACAGAAAT<br>CACACTGGCAAACGGAGAAATCAGAAAGAGACCGCTGATCGAAACAAACGGAGAAACAGGAGAAATCGTCTGGGACAAGGGAAGAGA<br>CTTCGCAACAGTCAGAAAGGTCCTGAGCATGCCGCAGGTCAACATCGTCAAGAAGACAGAAGTCCAGACAGGAGGATTCAGCAAGGA<br>AAGCATCCTGCCGAAGAGAAACAGCGACAAGCTGATCGCAAGAAAGAAGGACTGGGACCCGAAGAAGTACGGAGGATTCGACAGCCC<br>GACAGTCGCATACAGCGTCCTGGTCGTCGCAAAGGTCGAAAAGGGAAAGAGCAAGAAGCTGAAGAGCGTCAAGGAACTGCTGGGAAT<br>CACAATCATGGAAAGAAGCAGCTTCGAAAAGAACCCGATCGACTTCCTGGAAGCAAAGGGATACAAGGAAGTCAAGAAGGACCTGAT<br>CATCAAGCTGCCGAAGTACAGCCTGTTCGAACTGGAAAACGGAAGAAAGAGAATGCTGGCAAGCGCAGGAGAACTGCAGAAGGGAAA<br>CGAACTGGCACTGCCGAGCAAGTACGTCAACTTCCTGTACCTGGCAAGCCACTACGAAAAGCTGAAGGGAAGCCCGGAAGACAACGA<br>ACAGAAGCAGCTGTTCGTCGAACAGCACAAGCACTACCTGGACGAAATCATCGAACAGATCAGCGAATTCAGCAAGAGAGTCATCCT<br>GGCAGACGCAAACCTGGACAAGGTCCTGAGCGCATACAACAAGCACAGAGACAAGCCGATCAGAGAACAGGCAGAAAACATCATCCA<br>CCTGTTCACACTGACAAACCTGGGAGCACCGGCAGCATTCAAGTACTTCGACACAACAATCGACAGAAAGAGATACACAAGCACAAA<br>GGAAGTCCTGGACGCAACACTGATCCACCAGAGCATCACAGGACTGTACGAAACAAGAATCGACCTGAGCCAGCTGGGAGGAGACGG<br>AGGAGGAAGCCCGAAGAAGAAGAGAAAGGTCTAGCTAGCCATCACATTTAAAAGCATCTCAGCCTACCATGAGAATAAGAGAAAGAA<br>AATGAAGATCAATAGCTTATTCATCTCTTTTTCTTTTTCGTTGGTGTAAAGCCAACACCCTGTCTAAAAAACATAAATTTCTTTAAT<br>CATTTTGCCTCTTTTCTCTGTGCTTCAATTAATAAAAAATGGAAAGAACCTCGAG | |
| | Not Used | 245 |
| Cas9<br>transcript<br>with 5' UTR<br>of HSD, ORF<br>corresponding<br>to SEQ<br>ID NO: 245,<br>Kozak<br>sequence,<br>and 3' UTR<br>of ALB | GGGTCCCGCAGTCGGCGTCCAGCGGCTCTGCTTGTTCGTGTGTGTGTCGTTGCAGGCCTTATTCGGATCTGCCACCATGGATAAGAA<br>GTACTCGATCGGGCTGGATATCGGAACTAATTCCGTGGGTTGGGCAGTGATCACGGATGAATACAAAGTGCCGTCCAAGAAGTTCAA<br>GGTCCTGGGGAACACCGATAGACACAGCATCAAGAAGAATCTCATCGGAGCCCTGCTGTTTGACTCCGGCGAAACCGCAGAAGCGAC<br>CCGGCTCAAACGTACCGCGAGGCGACGCTACACCCGGCGGAAGAATCGCATCTGCTATCTGCAAGAAATCTTTTCGAACGAAATGGC<br>AAAGGTGGACGACAGCTTCTTCCACCGCCTGGAAGAATCTTTCCTGGTGGAGGAGGACAAGAAGCATGAACGGCATCCTATCTTTGG<br>AAACATCGTGGACGAAGTGGCGTACCACGAAAAGTACCCGACCATCTACCATCTGCGGAAGAAGTTGGTTGACTCAACTGACAAGGC<br>CGACCTCAGATTGATCTACTTGGCCCTCGCCCATATGATCAAATTCCGCGGACACTTCCTGATCGAAGGCGATCTGAACCCTGATAA<br>CTCCGACGTGGATAAGCTGTTCATTCAACTGGTGCAGACCTACAACCAACTGTTCGAAGAAAACCCAATCAATGCCAGCGGCGTCGA<br>TGCCAAGGCCATCCTGTCCGCCCGGCTGTCGAAGTCGCGGCGCCTCGAAAACCTGATCGCACAGCTGCCGGGAGAGAAGAAGAACGG<br>ACTTTTCGGCAACTTGATCGCTCTCTCACTGGGACTCACTCCCAATTTCAAGTCCAATTTTGACCTGGCCGAGGACGCGAAGCTGCA<br>ACTCTCAAAGGACACCTACGACGACGACTTGGACAATTTGCTGGCACAAATTGGCGATCAGTACGCGGATCTGTTCCTTGCCGCTAA<br>GAACCTTTCGGACGCAATCTTGCTGTCCGATATCCTGCGCGTGAACACCGAAATAACCAAAGCGCCGCTTAGCGCCTCGATGATTAA<br>GCGGTACGACGAGCATCACCAGGATCTCACGCTGCTCAAAGCGCTCGTGAGACAGCAACTGCCTGAAAAGTACAAGGAGATTTTCTT<br>CGACCAGTCCAAGAATGGGTACGCAGGGTACATCGATGGAGGCGCCAGCCAGGAAGAGTTCTATAAGTTCATCAAGCCAATCCTGGA<br>AAAGATGGACGGAACCGAAGAACTGCTGGTCAAGCTGAACAGGGAGGATCTGCTCCGCAAACAGAGAACCTTTGACAACGGAAGCAT<br>TCCACACCAGATCCATCTGGGTGAGCTGCACGCCATCTTGCGGCGCCAGGAGGACTTTTACCCATTCCTCAAGGACAACCGGGAAAA<br>GATCGAGAAAATTCTGACGTTCCGCATCCCGTATTACGTGGGCCCACTGGCGCGCGGCAATTCGCGCTTCGCGTGGATGACTAGAAA<br>ATCAGAGGAAACCATCACTCCTTGGAATTTCGAGGAAGTTGTGGATAAGGGAGCTTCGGCACAATCCTTCATCGAACGAATGACCAA<br>CTTCGACAAGAATCTCCCAAACGAGAAGGTGCTTCCTAAGCACAGCCTCCTTTACGAATACTTCACTGTCTACAACGAACTGACTAA<br>AGTGAAATACGTTACTGAAGGAATGAGGAAGCCGGCCTTTCTGAGCGGAGAACAGAAGAAAGCGATTGTCGATCTGCTGTTCAAGAC<br>CAACCGCAAGGTGACCGTCAAGCAGCTTAAAGAGGACTACTTCAAGAAGATCGAGTGTTTCGACTCAGTGGAAATCAGCGGAGTGGA<br>GGACAGATTCAACGCTTCGCTGGGAACCTATCATGATCTCCTGAAGATCATCAAGGACAAGGACTTCCTTGACAACGAGGAGAACGA<br>GGACATCCTGGAAGATATCGTCCTGACCTTGACCCTTTTCGAGGATCGCGAGATGATCGAGGAGAGGCTTAAGACCTACGCTCATCT<br>CTTCGACGATAAGGTCATGAAACAACTCAAGCGCCGCCGGTACACTGGTTGGGGCCGCCTCTCCCGCAAGCTGATCAACGGTATTCG<br>CGATAAACAGAGCGGTAAAACTATCCTGGATTTCCTCAAATCGGATGGCTTCGCTAATCGTAACTTCATGCAGTTGATCCACGACGA<br>CAGCCTGACCTTTAAGGAGGACATCCAGAAAGCACAAGTGAGCGGACAGGGAGACTCACTCCATGAACACATCGCGAATCTGGCCGG<br>TTCGCCGGCGATTAAGAAGGGAATCCTGCAAACTGTGAAGGTGGTGGACGAGCTGGTGAAGGTCATGGGACGGCACAAACCGGAGAA<br>TATCGTGATTGAAATGGCCCGAGAAAACCAGACTACCCAGAAGGGCCAGAAGAACTCCCGCGAAAGGATGAAGCGGATCGAAGAAGG<br>AATCAAGGAGCTGGGCAGCCAGATCCTGAAAGAGCACCCGGTGGAAAACACGCAGCTGCAGAACGAGAAGCTCTACCTGTACTATTT<br>GCAAAATGGACGGGACATGTACGTGGACCAAGAGCTGGACATCAATCGGTTGTCTGATTACGACGTGGACCACATCGTTCCACAGTC<br>CTTTCTGAAGGATGACTCCATCGATAACAAGGTGTTGACTCGCAGCGACAAGAACAGAGGGAAGTCAGATAATGTGCCATCGGAGGA | 246 |

-continued

Sequence Table

| Description | Sequence | SEQ ID No. |
|---|---|---|
| | GGTCGTGAAGAAGATGAAGAATTACTGGCGGCAGCTCCTGAATGCGAAGCTGATTACCCAGAGAAAGTTTGACAATCTCACTAAAGC<br>CGAGCGCGGCGGACTCTCAGAGCTGGATAAGGCTGGATTCATCAAACGGCAGCTGGTCGAGACTCGGCAGATTACCAAGCACGTGGC<br>GCAGATCCTGGACTCCCGCATGAACACTAAATACGACGAGAACGATAAGCTCATCCGGGAAGTGAAGGTGATTACCCTGAAAAGCAA<br>ACTTGTGTCGGACTTTCGGAAGGACTTTCAGTTTTACAAAGTGAGAGAAATCAACAACTACCATCACGCGCATGACGCATACCTCAA<br>CGCTGTGGTCGGCACCGCCCTGATCAAGAAGTACCCTAAACTTGAATCGGAGTTTGTGTACGGAGACTACAAGGTCTACGACGTGAG<br>GAAGATGATAGCCAAGTCCGAACAGGAAATCGGGAAAGCAACTGCGAAATACTTCTTTTACTCAAACATCATGAACTTCTTCAAGAC<br>TGAAATTACGCTGGCCAATGGAGAAATCAGGAAGAGGCCACTGATCGAAACTAACGGAGAAACGGGCGAAATCGTGTGGGACAAGGG<br>CAGGGACTTCGCAACTGTTCGCAAAGTGCTCTCTATGCCGCAAGTCAATATTGTGAAGAAAACCGAAGTGCAAACCGGCGGATTTTC<br>AAAGGAATCGATCCTCCCAAAGAGAAATAGCGACAAGCTCATTGCACGCAAGAAAGACTGGGACCCGAAGAAGTACGGAGGATTCGA<br>TTCGCCGACTGTCGCATACTCCGTCCTCGTGGTGGCCAAGGTGGAGAAGGGAAAGAGCAAGAAGCTCAAATCCGTCAAAGAGCTGCT<br>GGGGATTACCATCATGGAACGATCCTCGTTCGAGAAGAACCCGATTGATTTCCTGGAGGCGAAGGGTTACAAGGAGGTGAAGAAGGA<br>TCTGATCATCAAACTGCCCAAGTACTCACTGTTCGAACTGGAAAATGGTCGGAAGCGCATGCTGGCTTCGGCCGGAGAACTCCAGAA<br>AGGAAATGAGCTGGCCTTGCCTAGCAAGTACGTCAACTTCCTCTATCTTGCTTCGCACTACGAGAAACTCAAAGGGTCACCGGAAGA<br>TAACGAACAGAAGCAGCTTTTCGTGGAGCAGCACAAGCATTATCTGGATGAAATCATCGAACAAATCTCCGAGTTTTCAAAGCGCGT<br>GATCCTCGCCGACGCCAACCTCGACAAAGTCCTGTCGGCCTACAATAAGCATAGAGATAAGCCGATCAGAGAACAGGCCGAGAACAT<br>TATCCACTTGTTCACCCTGACTAACCTGGGAGCTCCAGCCGCCTTCAAGTACTTCGATACTACTATCGACCGCAAAAGATACACGTC<br>CACCAAGGAAGTTCTGGACGCGACCCTGATCCACCAAAGCATCACTGGACTCTACGAAACTAGGATCGATCTGTCGCAGCTGGGTGG<br>CGATGGTGGCGGTGGATCCTACCCATACGACGTGCCTGACTACGCCTCCGGAGGTGGTGGCCCCAAGAAGAAACGGAAGGTGTGATA<br>GCTAGCCATCACATTTAAAAGCATCTCAGCCTACCATGAGAATAAGAGAAAGAAAATGAAGATCAATAGCTTATTCATCTCTTTTTC<br>TTTTTCGTTGGTGTAAAGCCAACACCCTGTCTAAAAAACATAAATTTCTTTAATCATTTTGCCTCTTTTCTCTGTGCTTCAATTAAT<br>AAAAAATGGAAAGAACCTCGAG | |
| Cas9 transcript with 5' UTR of HSD, ORF corresponding to SEQ ID NO: 245, and 3' UTR of ALB | GGGTCCCGCAGTCGGCGTCCAGCGGCTCTGCTTGTTCGTGTGTGTGTCGTTGCAGGCCTTATTCGGATCTATGGATAAGAAGTACTC<br>GATCGGGCTGGATATCGGAACTAATTCCGTGGGTTGGGCAGTGATCACGGATGAATACAAAGTGCCGTCCAAGAAGTTCAAGGTCCT<br>GGGGAACACCGATAGACACAGCATCAAGAAGAATCTCATCGGAGCCCTGCTGTTTGACTCCGGCGAAACCGCAGAAGCGACCCGGCT<br>CAAACGTACCGCGAGGCGACGCTACACCCGGCGGAAGAATCGCATCTGCTATCTGCAAGAAATCTTTTCGAACGAAATGGCAAAGGT<br>GGACGACAGCTTCTTCCACCGCCTGGAAGAATCTTTCCTGGTGGAGGAGGACAAGAAGCATGAACGGCATCCTATCTTTGGAAACAT<br>CGTGGACGAAGTGGCGTACCACGAAAAGTACCCGACCATCTACCATCTGCGGAAGAAGTTGGTTGACTCAACTGACAAGGCCGACCT<br>CAGATTGATCTACTTGGCCCTCGCCCATATGATCAAATTCCGCGGACACTTCCTGATCGAAGGCGATCTGAACCCTGATAACTCCGA<br>CGTGGATAAGCTGTTCATTCAACTGGTGCAGACCTACAACCAACTGTTCGAAGAAAACCCAATCAATGCCAGCGGCGTCGATGCCAA<br>GGCCATCCTGTCCGCCCGGCTGTCGAAGTCGCGGCGCCTCGAAAACCTGATCGCACAGCTGCCGGGAGAGAAGAAGAACGGACTTTT<br>CGGCAACTTGATCGCTCTCTCACTGGGACTCACTCCCAATTTCAAGTCCAATTTTGACCTGGCCGAGGACGCGAAGCTGCAACTCTC<br>AAAGGACACCTACGACGACGACTTGGACAATTTGCTGGCACAAATTGGCGATCAGTACGCGGATCTGTTCCTTGCCGCTAAGAACCT<br>TTCGGACGCAATCTTGCTGTCCGATATCCTGCGCGTGAACACCGAAATAACCAAAGCGCCGCTTAGCGCCTCGATGATTAAGCGGTA<br>CGACGAGCATCACCAGGATCTCACGCTGCTCAAAGCGCTCGTGAGACAGCAACTGCCTGAAAAGTACAAGGAGATTTTCTTCGACCA<br>GTCCAAGAATGGGTACGCAGGGTACATCGATGGAGGCGCCAGCCAGGAAGAGTTCTATAAGTTCATCAAGCCAATCCTGGAAAAGAT<br>GGACGGAACCGAAGAACTGCTGGTCAAGCTGAACAGGGAGGATCTGCTCCGCAAACAGAGAACCTTTGACAACGGAAGCATTCCACA<br>CCAGATCCATCTGGGTGAGCTGCACGCCATCTTGCGGCGCCAGGAGGACTTTTACCCATTCCTCAAGGACAACCGGGAAAAGATCGA<br>GAAAATTCTGACGTTCCGCATCCCGTATTACGTGGGCCCACTGGCGCGCGGCAATTCGCGCTTCGCGTGGATGACTAGAAAATCAGA<br>GGAAACCATCACTCCTTGGAATTTCGAGGAAGTTGTGGATAAGGGAGCTTCGGCACAATCCTTCATCGAACGAATGACCAACTTCGA<br>CAAGAATCTCCCAAACGAGAAGGTGCTTCCTAAGCACAGCCTCCTTTACGAATACTTCACTGTCTACAACGAACTGACTAAAGTGAA<br>ATACGTTACTGAAGGAATGAGGAAGCCGGCCTTTCTGAGCGGAGAACAGAAGAAAGCGATTGTCGATCTGCTGTTCAAGACCAACCG<br>CAAGGTGACCGTCAAGCAGCTTAAAGAGGACTACTTCAAGAAGATCGAGTGTTTCGACTCAGTGGAAATCAGCGGAGTGGAGGACAG<br>ATTCAACGCTTCGCTGGGAACCTATCATGATCTCCTGAAGATCATCAAGGACAAGGACTTCCTTGACAACGAGGAGAACGAGGACAT<br>CCTGGAAGATATCGTCCTGACCTTGACCCTTTTCGAGGATCGCGAGATGATCGAGGAGAGGCTTAAGACCTACGCTCATCTCTTCGA<br>CGATAAGGTCATGAAACAACTCAAGCGCCGCCGGTACACTGGTTGGGGCCGCCTCTCCCGCAAGCTGATCAACGGTATTCGCGATAA<br>ACAGAGCGGTAAAACTATCCTGGATTTCCTCAAATCGGATGGCTTCGCTAATCGTAACTTCATGCAGTTGATCCACGACGACAGCCT<br>GACCTTTAAGGAGGACATCCAGAAAGCACAAGTGAGCGGACAGGGAGACTCACTCCATGAACACATCGCGAATCTGGCCGGTTCGCC<br>GGCGATTAAGAAGGGAATCCTGCAAACTGTGAAGGTGGTGGACGAGCTGGTGAAGGTCATGGGACGGCACAAACCGGAGAATATCGT | 247 |

-continued

Sequence Table

| Description | Sequence | SEQ ID No. |
|---|---|---|
| | GATTGAAATGGCCCGAGAAAACCAGACTACCCAGAAGGGCCAGAAGAACTCCCGCGAAAGGATGAAGCGGATCGAAGAAGGAATCAA<br>GGAGCTGGGCAGCCAGATCCTGAAAGAGCACCCGGTGGAAAACACGCAGCTGCAGAACGAGAAGCTCTACCTGTACTATTTGCAAAA<br>TGGACGGGACATGTACGTGGACCAAGAGCTGGACATCAATCGGTTGTCTGATTACGACGTGGACCACATCGTTCCACAGTCCTTTCT<br>GAAGGATGACTCCATCGATAACAAGGTGTTGACTCGCAGCGACAAGAACAGAGGGAAGTCAGATAATGTGCCATCGGAGGAGGTCGT<br>GAAGAAGATGAAGAATTACTGGCGGCAGCTCCTGAATGCGAAGCTGATTACCCAGAGAAAGTTTGACAATCTCACTAAAGCCGAGCG<br>CGGCGGACTCTCAGAGCTGGATAAGGCTGGATTCATCAAACGGCAGCTGGTCGAGACTCGGCAGATTACCAAGCACGTGGCGCAGAT<br>CCTGGACTCCCGCATGAACACTAAATACGACGAGAACGATAAGCTCATCCGGGAAGTGAAGGTGATTACCCTGAAAAGCAAACTTGT<br>GTCGGACTTTCGGAAGGACTTTCAGTTTTACAAAGTGAGAGAAATCAACAACTACCATCACGCGCATGACGCATACCTCAACGCTGT<br>GGTCGGCACCGCCCTGATCAAGAAGTACCCTAAACTTGAATCGGAGTTTGTGTACGGAGACTACAAGGTCTACGACGTGAGGAAGAT<br>GATAGCCAAGTCCGAACAGGAAATCGGGAAAGCAACTGCGAAATACTTCTTTTACTCAAACATCATGAACTTCTTCAAGACTGAAAT<br>TACGCTGGCCAATGGAGAAATCAGGAAGAGGCCACTGATCGAAACTAACGGAGAAACGGGCGAAATCGTGTGGGACAAGGGCAGGGA<br>CTTCGCAACTGTTCGCAAAGTGCTCTCTATGCCGCAAGTCAATATTGTGAAGAAAACCGAAGTGCAAACCGGCGGATTTTCAAAGGA<br>ATCGATCCTCCCAAAGAGAAATAGCGACAAGCTCATTGCACGCAAGAAAGACTGGGACCCGAAGAAGTACGGAGGATTCGATTCGCC<br>GACTGTCGCATACTCCGTCCTCGTGGTGGCCAAGGTGGAGAAGGGAAAGAGCAAGAAGCTCAAATCCGTCAAAGAGCTGCTGGGGAT<br>TACCATCATGGAACGATCCTCGTTCGAGAAGAACCCGATTGATTTCCTGGAGGCGAAGGGTTACAAGGAGGTGAAGAAGGATCTGAT<br>CATCAAACTGCCCAAGTACTCACTGTTCGAACTGGAAAATGGTCGGAAGCGCATGCTGGCTTCGGCCGGAGAACTCCAGAAAGGAAA<br>TGAGCTGGCCTTGCCTAGCAAGTACGTCAACTTCCTCTATCTTGCTTCGCACTACGAGAAACTCAAAGGGTCACCGGAAGATAACGA<br>ACAGAAGCAGCTTTTCGTGGAGCAGCACAAGCATTATCTGGATGAAATCATCGAACAAATCTCCGAGTTTTCAAAGCGCGTGATCCT<br>CGCCGACGCCAACCTCGACAAAGTCCTGTCGGCCTACAATAAGCATAGAGATAAGCCGATCAGAGAACAGGCCGAGAACATTATCCA<br>CTTGTTCACCCTGACTAACCTGGGAGCTCCAGCCGCCTTCAAGTACTTCGATACTACTATCGACCGCAAAAGATACACGTCCACCAA<br>GGAAGTTCTGGACGCGACCCTGATCCACCAAAGCATCACTGGACTCTACGAAACTAGGATCGATCTGTCGCAGCTGGGTGGCGATGG<br>TGGCGGTGGATCCTACCCATACGACGTGCCTGACTACGCCTCCGGAGGTGGTGGCCCCAAGAAGAAACGGAAGGTGTGATAGCTAGC<br>CATCACATTTAAAAGCATCTCAGCCTACCATGAGAATAAGAGAAAGAAAATGAAGATCAATAGCTTATTCATCTCTTTTTCTTTTTC<br>GTTGGTGTAAAGCCAACACCCTGTCTAAAAAACATAAATTTCTTTAATCATTTTGCCTCTTTTCTCTGTGCTTCAATTAATAAAAAA<br>TGGAAAGAACCTCGAG | |
| | Not Used | 248-251 |
| Cas9 ORF with minimal uridine codons frequently used in humans in general; 12.75% U content | ATGGACAAGAAGTACAGCATCGGCCTGGACATCGGCACCAACAGCGTGGGCTGGGCCGTGATCACCGACGAGTACAAGGTGCCCAGC<br>AAGAAGTTCAAGGTGCTGGGCAACACCGACAGACACAGCATCAAGAAGAACCTGATCGGCGCCCTGCTGTTCGACAGCGGCGAGACC<br>GCCGAGGCCACCAGACTGAAGAGAACCGCCAGAAGAAGATACACCAGAAGAAAGAACAGAATCTGCTACCTGCAGGAGATCTTCAGC<br>AACGAGATGGCCAAGGTGGACGACAGCTTCTTCCACAGACTGGAGGAGAGCTTCCTGGTGGAGGAGGACAAGAAGCACGAGAGACAC<br>CCCATCTTCGGCAACATCGTGGACGAGGTGGCCTACCACGAGAAGTACCCCACCATCTACCACCTGAGAAAGAAGCTGGTGGACAGC<br>ACCGACAAGGCCGACCTGAGACTGATCTACCTGGCCCTGGCCCACATGATCAAGTTCAGAGGCCACTTCCTGATCGAGGGCGACCTG<br>AACCCCGACAACAGCGACGTGGACAAGCTGTTCATCCAGCTGGTGCAGACCTACAACCAGCTGTTCGAGGAGAACCCCATCAACGCC<br>AGCGGCGTGGACGCCAAGGCCATCCTGAGCGCCAGACTGAGCAAGAGCAGAAGACTGGAGAACCTGATCGCCCAGCTGCCCGGCGAG<br>AAGAAGAACGGCCTGTTCGGCAACCTGATCGCCCTGAGCCTGGGCCTGACCCCCAACTTCAAGAGCAACTTCGACCTGGCCGAGGAC<br>GCCAAGCTGCAGCTGAGCAAGGACACCTACGACGACGACCTGGACAACCTGCTGGCCCAGATCGGCGACCAGTACGCCGACCTGTTC<br>CTGGCCGCCAAGAACCTGAGCGACGCCATCCTGCTGAGCGACATCCTGAGAGTGAACACCGAGATCACCAAGGCCCCCCTGAGCGCC<br>AGCATGATCAAGAGATACGACGAGCACCACCAGGACCTGACCCTGCTGAAGGCCCTGGTGAGACAGCAGCTGCCCGAGAAGTACAAG<br>GAGATCTTCTTCGACCAGAGCAAGAACGGCTACGCCGGCTACATCGACGGCGGCGCCAGCCAGGAGGAGTTCTACAAGTTCATCAAG<br>CCCATCCTGGAGAAGATGGACGGCACCGAGGAGCTGCTGGTGAAGCTGAACAGAGAGGACCTGCTGAGAAAGCAGAGAACCTTCGAC<br>AACGGCAGCATCCCCCACCAGATCCACCTGGGCGAGCTGCACGCCATCCTGAGAAGACAGGAGGACTTCTACCCCTTCCTGAAGGAC<br>AACAGAGAGAAGATCGAGAAGATCCTGACCTTCAGAATCCCCTACTACGTGGGCCCCCTGGCCAGAGGCAACAGCAGATTCGCCTGG<br>ATGACCAGAAAGAGCGAGGAGACCATCACCCCCTGGAACTTCGAGGAGGTGGTGGACAAGGGCGCCAGCGCCCAGAGCTTCATCGAG<br>AGAATGACCAACTTCGACAAGAACCTGCCCAACGAGAAGGTGCTGCCCAAGCACAGCCTGCTGTACGAGTACTTCACCGTGTACAAC<br>GAGCTGACCAAGGTGAAGTACGTGACCGAGGGCATGAGAAAGCCCGCCTTCCTGAGCGGCGAGCAGAAGAAGGCCATCGTGGACCTG<br>CTGTTCAAGACCAACAGAAAGGTGACCGTGAAGCAGCTGAAGGAGGACTACTTCAAGAAGATCGAGTGCTTCGACAGCGTGGAGATC<br>AGCGGCGTGGAGGACAGATTCAACGCCAGCCTGGGCACCTACCACGACCTGCTGAAGATCATCAAGGACAAGGACTTCCTGGACAAC | 252 |

-continued

Sequence Table

| Description | Sequence | SEQ ID No. |
|---|---|---|
| | GAGGAGAACGAGGACATCCTGGAGGACATCGTGCTGACCCTGACCCTGTTCGAGGACAGAGAGATGATCGAGGAGAGACTGAAGACC<br>TACGCCCACCTGTTCGACGACAAGGTGATGAAGCAGCTGAAGAGAAGAAGATACACCGGCTGGGGCAGACTGAGCAGAAAGCTGATC<br>AACGGCATCAGAGACAAGCAGAGCGGCAAGACCATCCTGGACTTCCTGAAGAGCGACGGCTTCGCCAACAGAAACTTCATGCAGCTG<br>ATCCACGACGACAGCCTGACCTTCAAGGAGGACATCCAGAAGGCCCAGGTGAGCGGCCAGGGCGACAGCCTGCACGAGCACATCGCC<br>AACCTGGCCGGCAGCCCCGCCATCAAGAAGGGCATCCTGCAGACCGTGAAGGTGGTGGACGAGCTGGTGAAGGTGATGGGCAGACAC<br>AAGCCCGAGAACATCGTGATCGAGATGGCCAGAGAGAACCAGACCACCCAGAAGGGCCAGAAGAACAGCAGAGAGAGAATGAAGAGA<br>ATCGAGGAGGGCATCAAGGAGCTGGGCAGCCAGATCCTGAAGGAGCACCCCGTGGAGAACACCCAGCTGCAGAACGAGAAGCTGTAC<br>CTGTACTACCTGCAGAACGGCAGAGACATGTACGTGGACCAGGAGCTGGACATCAACAGACTGAGCGACTACGACGTGGACCACATC<br>GTGCCCCAGAGCTTCCTGAAGGACGACAGCATCGACAACAAGGTGCTGACCAGAAGCGACAAGAACAGAGGCAAGAGCGACAACGTG<br>CCCAGCGAGGAGGTGGTGAAGAAGATGAAGAACTACTGGAGACAGCTGCTGAACGCCAAGCTGATCACCCAGAGAAAGTTCGACAAC<br>CTGACCAAGGCCGAGAGAGGCGGCCTGAGCGAGCTGGACAAGGCCGGCTTCATCAAGAGACAGCTGGTGGAGACCAGACAGATCACC<br>AAGCACGTGGCCCAGATCCTGGACAGCAGAATGAACACCAAGTACGACGAGAACGACAAGCTGATCAGAGAGGTGAAGGTGATCACC<br>CTGAAGAGCAAGCTGGTGAGCGACTTCAGAAAGGACTTCCAGTTCTACAAGGTGAGAGAGATCAACAACTACCACCACGCCCACGAC<br>GCCTACCTGAACGCCGTGGTGGGCACCGCCCTGATCAAGAAGTACCCCAAGCTGGAGAGCGAGTTCGTGTACGGCGACTACAAGGTG<br>TACGACGTGAGAAAGATGATCGCCAAGAGCGAGCAGGAGATCGGCAAGGCCACCGCCAAGTACTTCTTCTACAGCAACATCATGAAC<br>TTCTTCAAGACCGAGATCACCCTGGCCAACGGCGAGATCAGAAAGAGACCCCTGATCGAGACCAACGGCGAGACCGGCGAGATCGTG<br>TGGGACAAGGGCAGAGACTTCGCCACCGTGAGAAAGGTGCTGAGCATGCCCCAGGTGAACATCGTGAAGAAGACCGAGGTGCAGACC<br>GGCGGCTTCAGCAAGGAGAGCATCCTGCCCAAGAGAAACAGCGACAAGCTGATCGCCAGAAAGAAGGACTGGGACCCCAAGAAGTAC<br>GGCGGCTTCGACAGCCCCACCGTGGCCTACAGCGTGCTGGTGGTGGCCAAGGTGGAGAAGGGCAAGAGCAAGAAGCTGAAGAGCGTG<br>AAGGAGCTGCTGGGCATCACCATCATGGAGAGAAGCAGCTTCGAGAAGAACCCCATCGACTTCCTGGAGGCCAAGGGCTACAAGGAG<br>GTGAAGAAGGACCTGATCATCAAGCTGCCCAAGTACAGCCTGTTCGAGCTGGAGAACGGCAGAAAGAGAATGCTGGCCAGCGCCGGC<br>GAGCTGCAGAAGGGCAACGAGCTGGCCCTGCCCAGCAAGTACGTGAACTTCCTGTACCTGGCCAGCCACTACGAGAAGCTGAAGGGC<br>AGCCCCGAGGACAACGAGCAGAAGCAGCTGTTCGTGGAGCAGCACAAGCACTACCTGGACGAGATCATCGAGCAGATCAGCGAGTTC<br>AGCAAGAGAGTGATCCTGGCCGACGCCAACCTGGACAAGGTGCTGAGCGCCTACAACAAGCACAGAGACAAGCCCATCAGAGAGCAG<br>GCCGAGAACATCATCCACCTGTTCACCCTGACCAACCTGGGCGCCCCCGCCGCCTTCAAGTACTTCGACACCACCATCGACAGAAAG<br>AGATACACCAGCACCAAGGAGGTGCTGGACGCCACCCTGATCCACCAGAGCATCACCGGCCTGTACGAGACCAGAATCGACCTGAGC<br>CAGCTGGGCGGCGACGGCGGCGGCAGCCCCAAGAAGAAGAGAAAGGTGTGA | |
| Cas9<br>transcript<br>with 5' UTR<br>of HSD, ORF<br>corresponding<br>to SEQ<br>ID NO: 252,<br>Kozak<br>sequence,<br>and 3' UTR<br>of ALB | GGGTCCCGCAGTCGGCGTCCAGCGGCTCTGCTTGTTCGTGTGTGTGTCGTTGCAGGCCTTATTCGGATCCGCCACCATGGACAAGAA<br>GTACAGCATCGGCCTGGACATCGGCACCAACAGCGTGGGCTGGGCCGTGATCACCGACGAGTACAAGGTGCCCAGCAAGAAGTTCAA<br>GGTGCTGGGCAACACCGACAGACACAGCATCAAGAAGAACCTGATCGGCGCCCTGCTGTTCGACAGCGGCGAGACCGCCGAGGCCAC<br>CAGACTGAAGAGAACCGCCAGAAGAAGATACACCAGAAGAAAGAACAGAATCTGCTACCTGCAGGAGATCTTCAGCAACGAGATGGC<br>CAAGGTGGACGACAGCTTCTTCCACAGACTGGAGGAGAGCTTCCTGGTGGAGGAGGACAAGAAGCACGAGAGACACCCCATCTTCGG<br>CAACATCGTGGACGAGGTGGCCTACCACGAGAAGTACCCCACCATCTACCACCTGAGAAAGAAGCTGGTGGACAGCACCGACAAGGC<br>CGACCTGAGACTGATCTACCTGGCCCTGGCCCACATGATCAAGTTCAGAGGCCACTTCCTGATCGAGGGCGACCTGAACCCCGACAA<br>CAGCGACGTGGACAAGCTGTTCATCCAGCTGGTGCAGACCTACAACCAGCTGTTCGAGGAGAACCCCATCAACGCCAGCGGCGTGGA<br>CGCCAAGGCCATCCTGAGCGCCAGACTGAGCAAGAGCAGAAGACTGGAGAACCTGATCGCCCAGCTGCCCGGCGAGAAGAAGAACGG<br>CCTGTTCGGCAACCTGATCGCCCTGAGCCTGGGCCTGACCCCCAACTTCAAGAGCAACTTCGACCTGGCCGAGGACGCCAAGCTGCA<br>GCTGAGCAAGGACACCTACGACGACGACCTGGACAACCTGCTGGCCCAGATCGGCGACCAGTACGCCGACCTGTTCCTGGCCGCCAA<br>GAACCTGAGCGACGCCATCCTGCTGAGCGACATCCTGAGAGTGAACACCGAGATCACCAAGGCCCCCCTGAGCGCCAGCATGATCAA<br>GAGATACGACGAGCACCACCAGGACCTGACCCTGCTGAAGGCCCTGGTGAGACAGCAGCTGCCCGAGAAGTACAAGGAGATCTTCTT<br>CGACCAGAGCAAGAACGGCTACGCCGGCTACATCGACGGCGGCGCCAGCCAGGAGGAGTTCTACAAGTTCATCAAGCCCATCCTGGA<br>GAAGATGGACGGCACCGAGGAGCTGCTGGTGAAGCTGAACAGAGAGGACCTGCTGAGAAAGCAGAGAACCTTCGACAACGGCAGCAT<br>CCCCCACCAGATCCACCTGGGCGAGCTGCACGCCATCCTGAGAAGACAGGAGGACTTCTACCCCTTCCTGAAGGACAACAGAGAGAA<br>GATCGAGAAGATCCTGACCTTCAGAATCCCCTACTACGTGGGCCCCCTGGCCAGAGGCAACAGCAGATTCGCCTGGATGACCAGAAA<br>GAGCGAGGAGACCATCACCCCCTGGAACTTCGAGGAGGTGGTGGACAAGGGCGCCAGCGCCCAGAGCTTCATCGAGAGAATGACCAA<br>CTTCGACAAGAACCTGCCCAACGAGAAGGTGCTGCCCAAGCACAGCCTGCTGTACGAGTACTTCACCGTGTACAACGAGCTGACCAA<br>GGTGAAGTACGTGACCGAGGGCATGAGAAAGCCCGCCTTCCTGAGCGGCGAGCAGAAGAAGGCCATCGTGGACCTGCTGTTCAAGAC<br>CAACAGAAAGGTGACCGTGAAGCAGCTGAAGGAGGACTACTTCAAGAAGATCGAGTGCTTCGACAGCGTGGAGATCAGCGGCGTGGA | 253 |

-continued

Sequence Table

| Description | Sequence | SEQ ID No. |
|---|---|---|
| | GGACAGATTCAACGCCAGCCTGGGCACCTACCACGACCTGCTGAAGATCATCAAGGACAAGGACTTCCTGGACAACGAGGAGAACGA<br>GGACATCCTGGAGGACATCGTGCTGACCCTGACCCTGTTCGAGGACAGAGAGATGATCGAGGAGAGACTGAAGACCTACGCCCACCT<br>GTTCGACGACAAGGTGATGAAGCAGCTGAAGAGAAGAAGATACACCGGCTGGGGCAGACTGAGCAGAAAGCTGATCAACGGCATCAG<br>AGACAAGCAGAGCGGCAAGACCATCCTGGACTTCCTGAAGAGCGACGGCTTCGCCAACAGAAACTTCATGCAGCTGATCCACGACGA<br>CAGCCTGACCTTCAAGGAGGACATCCAGAAGGCCCAGGTGAGCGGCCAGGGCGACAGCCTGCACGAGCACATCGCCAACCTGGCCGG<br>CAGCCCCGCCATCAAGAAGGGCATCCTGCAGACCGTGAAGGTGGTGGACGAGCTGGTGAAGGTGATGGGCAGACACAAGCCCGAGAA<br>CATCGTGATCGAGATGGCCAGAGAGAACCAGACCACCCAGAAGGGCCAGAAGAACAGCAGAGAGAGAATGAAGAGAATCGAGGAGGG<br>CATCAAGGAGCTGGGCAGCCAGATCCTGAAGGAGCACCCCGTGGAGAACACCCAGCTGCAGAACGAGAAGCTGTACCTGTACTACCT<br>GCAGAACGGCAGAGACATGTACGTGGACCAGGAGCTGGACATCAACAGACTGAGCGACTACGACGTGGACCACATCGTGCCCCAGAG<br>CTTCCTGAAGGACGACAGCATCGACAACAAGGTGCTGACCAGAAGCGACAAGAACAGAGGCAAGAGCGACAACGTGCCCAGCGAGGA<br>GGTGGTGAAGAAGATGAAGAACTACTGGAGACAGCTGCTGAACGCCAAGCTGATCACCCAGAGAAAGTTCGACAACCTGACCAAGGC<br>CGAGAGAGGCGGCCTGAGCGAGCTGGACAAGGCCGGCTTCATCAAGAGACAGCTGGTGGAGACCAGACAGATCACCAAGCACGTGGC<br>CCAGATCCTGGACAGCAGAATGAACACCAAGTACGACGAGAACGACAAGCTGATCAGAGAGGTGAAGGTGATCACCCTGAAGAGCAA<br>GCTGGTGAGCGACTTCAGAAAGGACTTCCAGTTCTACAAGGTGAGAGAGATCAACAACTACCACCACGCCCACGACGCCTACCTGAA<br>CGCCGTGGTGGGCACCGCCCTGATCAAGAAGTACCCCAAGCTGGAGAGCGAGTTCGTGTACGGCGACTACAAGGTGTACGACGTGAG<br>AAAGATGATCGCCAAGAGCGAGCAGGAGATCGGCAAGGCCACCGCCAAGTACTTCTTCTACAGCAACATCATGAACTTCTTCAAGAC<br>CGAGATCACCCTGGCCAACGGCGAGATCAGAAAGAGACCCCTGATCGAGACCAACGGCGAGACCGGCGAGATCGTGTGGGACAAGGG<br>CAGAGACTTCGCCACCGTGAGAAAGGTGCTGAGCATGCCCCAGGTGAACATCGTGAAGAAGACCGAGGTGCAGACCGGCGGCTTCAG<br>CAAGGAGAGCATCCTGCCCAAGAGAAACAGCGACAAGCTGATCGCCAGAAAGAAGGACTGGGACCCCAAGAAGTACGGCGGCTTCGA<br>CAGCCCCACCGTGGCCTACAGCGTGCTGGTGGTGGCCAAGGTGGAGAAGGGCAAGAGCAAGAAGCTGAAGAGCGTGAAGGAGCTGCT<br>GGGCATCACCATCATGGAGAGAAGCAGCTTCGAGAAGAACCCCATCGACTTCCTGGAGGCCAAGGGCTACAAGGAGGTGAAGAAGGA<br>CCTGATCATCAAGCTGCCCAAGTACAGCCTGTTCGAGCTGGAGAACGGCAGAAAGAGAATGCTGGCCAGCGCCGGCGAGCTGCAGAA<br>GGGCAACGAGCTGGCCCTGCCCAGCAAGTACGTGAACTTCCTGTACCTGGCCAGCCACTACGAGAAGCTGAAGGGCAGCCCCGAGGA<br>CAACGAGCAGAAGCAGCTGTTCGTGGAGCAGCACAAGCACTACCTGGACGAGATCATCGAGCAGATCAGCGAGTTCAGCAAGAGAGT<br>GATCCTGGCCGACGCCAACCTGGACAAGGTGCTGAGCGCCTACAACAAGCACAGAGACAAGCCCATCAGAGAGCAGGCCGAGAACAT<br>CATCCACCTGTTCACCCTGACCAACCTGGGCGCCCCCGCCGCCTTCAAGTACTTCGACACCACCATCGACAGAAAGAGATACACCAG<br>CACCAAGGAGGTGCTGGACGCCACCCTGATCCACCAGAGCATCACCGGCCTGTACGAGACCAGAATCGACCTGAGCCAGCTGGGCGG<br>CGACGGCGGCGGCAGCCCCAAGAAGAAGAGAAAGGTGTGACTAGCCATCACATTTAAAAGCATCTCAGCCTACCATGAGAATAAGAG<br>AAAGAAAATGAAGATCAATAGCTTATTCATCTCTTTTTCTTTTTCGTTGGTGTAAAGCCAACACCCTGTCTAAAAAACATAAATTTC<br>TTTAATCATTTTGCCTCTTTTCTCTGTGCTTCAATTAATAAAAAATGGAAAGAACCTCGAG | |
| | Not Used | 254-255 |
| Cas9 transcript with AGG as first three nucleotides for use with CleanCap ™, 5' UTR of HSD, ORF corresponding to SEQ ID NO: 204, Kozak sequence, and 3' UTR | AGGTCCCGCAGTCGGCGTCCAGCGGCTCTGCTTGTTCGTGTGTGTGTCGTTGCAGGCCTTATTCGGATCCGCCACCATGGACAAGAA<br>GTACAGCATCGGACTGGACATCGGAACAAACAGCGTCGGATGGGCAGTCATCACAGACGAATACAAGGTCCCGAGCAAGAAGTTCAA<br>GGTCCTGGGAAACACAGACAGACACAGCATCAAGAAGAACCTGATCGGAGCACTGCTGTTCGACAGCGGAGAAACAGCAGAAGCAAC<br>AAGACTGAAGAGAACAGCAAGAAGAAGATACACAAGAAGAAAGAACAGAATCTGCTACCTGCAGGAAATCTTCAGCAACGAAATGGC<br>AAAGGTCGACGACAGCTTCTTCCACAGACTGGAAGAAAGCTTCCTGGTCGAAGAAGACAAGAAGCACGAAAGACACCCGATCTTCGG<br>AAACATCGTCGACGAAGTCGCATACCACGAAAAGTACCCGACAATCTACCACCTGAGAAAGAAGCTGGTCGACAGCACAGACAAGGC<br>AGACCTGAGACTGATCTACCTGGCACTGGCACACATGATCAAGTTCAGAGGACACTTCCTGATCGAAGGAGACCTGAACCCGGACAA<br>CAGCGACGTCGACAAGCTGTTCATCCAGCTGGTCCAGACATACAACCAGCTGTTCGAAGAAAACCCGATCAACGCAAGCGGAGTCGA<br>CGCAAAGGCAATCCTGAGCGCAAGACTGAGCAAGAGCAGAAGACTGGAAAACCTGATCGCACAGCTGCCGGGAGAAAAGAAGAACGG<br>ACTGTTCGGAAACCTGATCGCACTGAGCCTGGGACTGACACCGAACTTCAAGAGCAACTTCGACCTGGCAGAAGACGCAAAGCTGCA<br>GCTGAGCAAGGACACATACGACGACGACCTGGACAACCTGCTGGCACAGATCGGAGACCAGTACGCAGACCTGTTCCTGGCAGCAAA<br>GAACCTGAGCGACGCAATCCTGCTGAGCGACATCCTGAGAGTCAACACAGAAATCACAAAGGCACCGCTGAGCGCAAGCATGATCAA<br>GAGATACGACGAACACCACCAGGACCTGACACTGCTGAAGGCACTGGTCAGACAGCAGCTGCCGGAAAAGTACAAGGAAATCTTCTT<br>CGACCAGAGCAAGAACGGATACGCAGGATACATCGACGGAGGAGCAAGCCAGGAAGAATTCTACAAGTTCATCAAGCCGATCCTGGA<br>AAAGATGGACGGAACAGAAGAACTGCTGGTCAAGCTGAACAGAGAAGACCTGCTGAGAAAGCAGAGAACATTCGACAACGGAAGCAT<br>CCCGCACCAGATCCACCTGGGAGAACTGCACGCAATCCTGAGAAGACAGGAAGACTTCTACCCGTTCCTGAAGGACAACAGAGAAAA | 256 |

-continued

Sequence Table

| Description | Sequence | SEQ ID No. |
|---|---|---|
| of ALB | GATCGAAAAGATCCTGACATTCAGAATCCCGTACTACGTCGGACCGCTGGCAAGAGGAAACAGCAGATTCGCATGGATGACAAGAAA<br>GAGCGAAGAAACAATCACACCGTGGAACTTCGAAGAAGTCGTCGACAAGGGAGCAAGCGCACAGAGCTTCATCGAAAGAATGACAAA<br>CTTCGACAAGAACCTGCCGAACGAAAAGGTCCTGCCGAAGCACAGCCTGCTGTACGAATACTTCACAGTCTACAACGAACTGACAAA<br>GGTCAAGTACGTCACAGAAGGAATGAGAAAGCCGGCATTCCTGAGCGGAGAACAGAAGAAGGCAATCGTCGACCTGCTGTTCAAGAC<br>AAACAGAAAGGTCACAGTCAAGCAGCTGAAGGAAGACTACTTCAAGAAGATCGAATGCTTCGACAGCGTCGAAATCAGCGGAGTCGA<br>AGACAGATTCAACGCAAGCCTGGGAACATACCACGACCTGCTGAAGATCATCAAGGACAAGGACTTCCTGGACAACGAAGAAAACGA<br>AGACATCCTGGAAGACATCGTCCTGACACTGACACTGTTCGAAGACAGAGAAATGATCGAAGAAAGACTGAAGACATACGCACACCT<br>GTTCGACGACAAGGTCATGAAGCAGCTGAAGAGAAGAAGATACACAGGATGGGGAAGACTGAGCAGAAAGCTGATCAACGGAATCAG<br>AGACAAGCAGAGCGGAAAGACAATCCTGGACTTCCTGAAGAGCGACGGATTCGCAAACAGAAACTTCATGCAGCTGATCCACGACGA<br>CAGCCTGACATTCAAGGAAGACATCCAGAAGGCACAGGTCAGCGGACAGGGAGACAGCCTGCACGAACACATCGCAAACCTGGCAGG<br>AAGCCCGGCAATCAAGAAGGGAATCCTGCAGACAGTCAAGGTCGTCGACGAACTGGTCAAGGTCATGGGAAGACACAAGCCGGAAAA<br>CATCGTCATCGAAATGGCAAGAGAAAACCAGACAACACAGAAGGGACAGAAGAACAGCAGAGAAAGAATGAAGAGAATCGAAGAAGG<br>AATCAAGGAACTGGGAAGCCAGATCCTGAAGGAACACCCGGTCGAAAACACACAGCTGCAGAACGAAAAGCTGTACCTGTACTACCT<br>GCAGAACGGAAGAGACATGTACGTCGACCAGGAACTGGACATCAACAGACTGAGCGACTACGACGTCGACCACATCGTCCCGCAGAG<br>CTTCCTGAAGGACGACAGCATCGACAACAAGGTCCTGACAAGAAGCGACAAGAACAGAGGAAAGAGCGACAACGTCCCGAGCGAAGA<br>AGTCGTCAAGAAGATGAAGAACTACTGGAGACAGCTGCTGAACGCAAAGCTGATCACACAGAGAAAGTTCGACAACCTGACAAAGGC<br>AGAGAGAGGAGGACTGAGCGAACTGGACAAGGCAGGATTCATCAAGAGACAGCTGGTCGAAACAAGACAGATCACAAAGCACGTCGC<br>ACAGATCCTGGACAGCAGAATGAACACAAAGTACGACGAAAACGACAAGCTGATCAGAGAAGTCAAGGTCATCACACTGAAGAGCAA<br>GCTGGTCAGCGACTTCAGAAAGGACTTCCAGTTCTACAAGGTCAGAGAAATCAACAACTACCACCACGCACACGACGCATACCTGAA<br>CGCAGTCGTCGGAACAGCACTGATCAAGAAGTACCCGAAGCTGGAAAGCGAATTCGTCTACGGAGACTACAAGGTCTACGACGTCAG<br>AAAGATGATCGCAAAGAGCGAACAGGAAATCGGAAAGGCAACAGCAAAGTACTTCTTCTACAGCAACATCATGAACTTCTTCAAGAC<br>AGAAATCACACTGGCAAACGGAGAAATCAGAAAGAGACCGCTGATCGAAACAAACGGAGAAACAGGAGAAATCGTCTGGGACAAGGG<br>AAGAGACTTCGCAACAGTCAGAAAGGTCCTGAGCATGCCGCAGGTCAACATCGTCAAGAAGACAGAAGTCCAGACAGGAGGATTCAG<br>CAAGGAAAGCATCCTGCCGAAGAGAAACAGCGACAAGCTGATCGCAAGAAAGAAGGACTGGGACCCGAAGAAGTACGGAGGATTCGA<br>CAGCCCGACAGTCGCATACAGCGTCCTGGTCGTCGCAAAGGTCGAAAAGGGAAAGAGCAAGAAGCTGAAGAGCGTCAAGGAACTGCT<br>GGGAATCACAATCATGGAAAGAAGCAGCTTCGAAAAGAACCCGATCGACTTCCTGGAAGCAAAGGGATACAAGGAAGTCAAGAAGGA<br>CCTGATCATCAAGCTGCCGAAGTACAGCCTGTTCGAACTGGAAAACGGAAGAAAGAGAATGCTGGCAAGCGCAGGAGAACTGCAGAA<br>GGGAAACGAACTGGCACTGCCGAGCAAGTACGTCAACTTCCTGTACCTGGCAAGCCACTACGAAAAGCTGAAGGGAAGCCCGGAAGA<br>CAACGAACAGAAGCAGCTGTTCGTCGAACAGCACAAGCACTACCTGGACGAAATCATCGAACAGATCAGCGAATTCAGCAAGAGAGT<br>CATCCTGGCAGACGCAAACCTGGACAAGGTCCTGAGCGCATACAACAAGCACAGAGACAAGCCGATCAGAGAACAGGCAGAAAACAT<br>CATCCACCTGTTCACACTGACAAACCTGGGAGCACCGGCAGCATTCAAGTACTTCGACACAACAATCGACAGAAAGAGATACACAAG<br>CACAAAGGAAGTCCTGGACGCAACACTGATCCACCAGAGCATCACAGGACTGTACGAAACAAGAATCGACCTGAGCCAGCTGGGAGG<br>AGACGGAGGAGGAAGCCCGAAGAAGAAGAGAAAGGTCTAGCTAGCCATCACATTTAAAAGCATCTCAGCCTACCATGAGAATAAGAG<br>AAAGAAAATGAAGATCAATAGCTTATTCATCTCTTTTTCTTTTTCGTTGGTGTAAAGCCAACACCCTGTCTAAAAAACATAAATTTC<br>TTTAATCATTTTGCCTCTTTTCTCTGTGCTTCAATTAATAAAAAATGGAAAGAACCTCGAG | |
| Cas9 transcript with 5' UTR from CMV, ORF corresponding to SEQ ID NO: 204, Kozak sequence, and 3' UTR of ALB | GGGCAGATCGCCTGGAGACGCCATCCACGCTGTTTTGACCTCCATAGAAGACACCGGGACCGATCCAGCCTCCGCGGCCGGGAACGG<br>TGCATTGGAACGCGGATTCCCCGTGCCAAGAGTGACTCACCGTCCTTGACACGGCCACCATGGACAAGAAGTACAGCATCGGACTGG<br>ACATCGGAACAAACAGCGTCGGATGGGCAGTCATCACAGACGAATACAAGGTCCCGAGCAAGAAGTTCAAGGTCCTGGGAAACACAG<br>ACAGACACAGCATCAAGAAGAACCTGATCGGAGCACTGCTGTTCGACAGCGGAGAAACAGCAGAAGCAACAAGACTGAAGAGAACAG<br>CAAGAAGAAGATACACAAGAAGAAAGAACAGAATCTGCTACCTGCAGGAAATCTTCAGCAACGAAATGGCAAAGGTCGACGACAGCT<br>TCTTCCACAGACTGGAAGAAAGCTTCCTGGTCGAAGAAGACAAGAAGCACGAAAGACACCCGATCTTCGGAAACATCGTCGACGAAG<br>TCGCATACCACGAAAAGTACCCGACAATCTACCACCTGAGAAAGAAGCTGGTCGACAGCACAGACAAGGCAGACCTGAGACTGATCT<br>ACCTGGCACTGGCACACATGATCAAGTTCAGAGGACACTTCCTGATCGAAGGAGACCTGAACCCGGACAACAGCGACGTCGACAAGC<br>TGTTCATCCAGCTGGTCCAGACATACAACCAGCTGTTCGAAGAAAACCCGATCAACGCAAGCGGAGTCGACGCAAAGGCAATCCTGA<br>GCGCAAGACTGAGCAAGAGCAGAAGACTGGAAAACCTGATCGCACAGCTGCCGGGAGAAAAGAAGAACGGACTGTTCGGAAACCTGA<br>TCGCACTGAGCCTGGGACTGACACCGAACTTCAAGAGCAACTTCGACCTGGCAGAAGACGCAAAGCTGCAGCTGAGCAAGGACACAT<br>ACGACGACGACCTGGACAACCTGCTGGCACAGATCGGAGACCAGTACGCAGACCTGTTCCTGGCAGCAAAGAACCTGAGCGACGCAA<br>TCCTGCTGAGCGACATCCTGAGAGTCAACACAGAAATCACAAAGGCACCGCTGAGCGCAAGCATGATCAAGAGATACGACGAACACC | 257 |

-continued

Sequence Table

| Description | Sequence | SEQ ID No. |
|---|---|---|
| | ACCAGGACCTGACACTGCTGAAGGCACTGGTCAGACAGCAGCTGCCGGAAAAGTACAAGGAAATCTTCTTCGACCAGAGCAAGAACG<br>GATACGCAGGATACATCGACGGAGGAGCAAGCCAGGAAGAATTCTACAAGTTCATCAAGCCGATCCTGGAAAAGATGGACGGAACAG<br>AAGAACTGCTGGTCAAGCTGAACAGAGAAGACCTGCTGAGAAAGCAGAGAACATTCGACAACGGAAGCATCCCGCACCAGATCCACC<br>TGGGAGAACTGCACGCAATCCTGAGAAGACAGGAAGACTTCTACCCGTTCCTGAAGGACAACAGAGAAAAGATCGAAAAGATCCTGA<br>CATTCAGAATCCCGTACTACGTCGGACCGCTGGCAAGAGGAAACAGCAGATTCGCATGGATGACAAGAAAGAGCGAAGAAACAATCA<br>CACCGTGGAACTTCGAAGAAGTCGTCGACAAGGGAGCAAGCGCACAGAGCTTCATCGAAAGAATGACAAACTTCGACAAGAACCTGC<br>CGAACGAAAAGGTCCTGCCGAAGCACAGCCTGCTGTACGAATACTTCACAGTCTACAACGAACTGACAAAGGTCAAGTACGTCACAG<br>AAGGAATGAGAAAGCCGGCATTCCTGAGCGGAGAACAGAAGAAGGCAATCGTCGACCTGCTGTTCAAGACAAACAGAAAGGTCACAG<br>TCAAGCAGCTGAAGGAAGACTACTTCAAGAAGATCGAATGCTTCGACAGCGTCGAAATCAGCGGAGTCGAAGACAGATTCAACGCAA<br>GCCTGGGAACATACCACGACCTGCTGAAGATCATCAAGGACAAGGACTTCCTGGACAACGAAGAAAACGAAGACATCCTGGAAGACA<br>TCGTCCTGACACTGACACTGTTCGAAGACAGAGAAATGATCGAAGAAAGACTGAAGACATACGCACACCTGTTCGACGACAAGGTCA<br>TGAAGCAGCTGAAGAGAAGAAGATACACAGGATGGGGAAGACTGAGCAGAAAGCTGATCAACGGAATCAGAGACAAGCAGAGCGGAA<br>AGACAATCCTGGACTTCCTGAAGAGCGACGGATTCGCAAACAGAAACTTCATGCAGCTGATCCACGACGACAGCCTGACATTCAAGG<br>AAGACATCCAGAAGGCACAGGTCAGCGGACAGGGAGACAGCCTGCACGAACACATCGCAAACCTGGCAGGAAGCCCGGCAATCAAGA<br>AGGGAATCCTGCAGACAGTCAAGGTCGTCGACGAACTGGTCAAGGTCATGGGAAGACACAAGCCGGAAAACATCGTCATCGAAATGG<br>CAAGAGAAAACCAGACAACACAGAAGGGACAGAAGAACAGCAGAGAAAGAATGAAGAGAATCGAAGAAGGAATCAAGGAACTGGGAA<br>GCCAGATCCTGAAGGAACACCCGGTCGAAAACACACAGCTGCAGAACGAAAAGCTGTACCTGTACTACCTGCAGAACGGAAGAGACA<br>TGTACGTCGACCAGGAACTGGACATCAACAGACTGAGCGACTACGACGTCGACCACATCGTCCCGCAGAGCTTCCTGAAGGACGACA<br>GCATCGACAACAAGGTCCTGACAAGAAGCGACAAGAACAGAGGAAAGAGCGACAACGTCCCGAGCGAAGAAGTCGTCAAGAAGATGA<br>AGAACTACTGGAGACAGCTGCTGAACGCAAAGCTGATCACACAGAGAAAGTTCGACAACCTGACAAAGGCAGAGAGAGGAGGACTGA<br>GCGAACTGGACAAGGCAGGATTCATCAAGAGACAGCTGGTCGAAACAAGACAGATCACAAAGCACGTCGCACAGATCCTGGACAGCA<br>GAATGAACACAAAGTACGACGAAAACGACAAGCTGATCAGAGAAGTCAAGGTCATCACACTGAAGAGCAAGCTGGTCAGCGACTTCA<br>GAAAGGACTTCCAGTTCTACAAGGTCAGAGAAATCAACAACTACCACCACGCACACGACGCATACCTGAACGCAGTCGTCGGAACAG<br>CACTGATCAAGAAGTACCCGAAGCTGGAAAGCGAATTCGTCTACGGAGACTACAAGGTCTACGACGTCAGAAAGATGATCGCAAAGA<br>GCGAACAGGAAATCGGAAAGGCAACAGCAAAGTACTTCTTCTACAGCAACATCATGAACTTCTTCAAGACAGAAATCACACTGGCAA<br>ACGGAGAAATCAGAAAGAGACCGCTGATCGAAACAAACGGAGAAACAGGAGAAATCGTCTGGGACAAGGGAAGAGACTTCGCAACAG<br>TCAGAAAGGTCCTGAGCATGCCGCAGGTCAACATCGTCAAGAAGACAGAAGTCCAGACAGGAGGATTCAGCAAGGAAAGCATCCTGC<br>CGAAGAGAAACAGCGACAAGCTGATCGCAAGAAAGAAGGACTGGGACCCGAAGAAGTACGGAGGATTCGACAGCCCGACAGTCGCAT<br>ACAGCGTCCTGGTCGTCGCAAAGGTCGAAAAGGGAAAGAGCAAGAAGCTGAAGAGCGTCAAGGAACTGCTGGGAATCACAATCATGG<br>AAAGAAGCAGCTTCGAAAAGAACCCGATCGACTTCCTGGAAGCAAAGGGATACAAGGAAGTCAAGAAGGACCTGATCATCAAGCTGC<br>CGAAGTACAGCCTGTTCGAACTGGAAAACGGAAGAAAGAGAATGCTGGCAAGCGCAGGAGAACTGCAGAAGGGAAACGAACTGGCAC<br>TGCCGAGCAAGTACGTCAACTTCCTGTACCTGGCAAGCCACTACGAAAAGCTGAAGGGAAGCCCGGAAGACAACGAACAGAAGCAGC<br>TGTTCGTCGAACAGCACAAGCACTACCTGGACGAAATCATCGAACAGATCAGCGAATTCAGCAAGAGAGTCATCCTGGCAGACGCAA<br>ACCTGGACAAGGTCCTGAGCGCATACAACAAGCACAGAGACAAGCCGATCAGAGAACAGGCAGAAAACATCATCCACCTGTTCACAC<br>TGACAAACCTGGGAGCACCGGCAGCATTCAAGTACTTCGACACAACAATCGACAGAAAGAGATACACAAGCACAAAGGAAGTCCTGG<br>ACGCAACACTGATCCACCAGAGCATCACAGGACTGTACGAAACAAGAATCGACCTGAGCCAGCTGGGAGGAGACGGAGGAGGAAGCC<br>CGAAGAAGAAGAGAAAGGTCTAGCTAGCCATCACATTTAAAAGCATCTCAGCCTACCATGAGAATAAGAGAAAGAAAATGAAGATCA<br>ATAGCTTATTCATCTCTTTTTCTTTTTCGTTGGTGTAAAGCCAACACCCTGTCTAAAAAACATAAATTTCTTTAATCATTTTGCCTC<br>TTTTCTCTGTGCTTCAATTAATAAAAAATGGAAAGAACCTCGAG | |
| Cas9 transcript with 5' UTR from HBB, ORF corresponding to SEQ ID NO: 204, Kozak | GGGacatttgcttctgacacaactgtgttcactagcaacctcaaacagacaccggatctgccaccATGGACAAGAAGTACAGCATCG<br>GACTGGACATCGGAACAAACAGCGTCGGATGGGCAGTCATCACAGACGAATACAAGGTCCCGAGCAAGAAGTTCAAGGTCCTGGGAA<br>ACACAGACAGACACAGCATCAAGAAGAACCTGATCGGAGCACTGCTGTTCGACAGCGGAGAAACAGCAGAAGCAACAAGACTGAAGA<br>GAACAGCAAGAAGAAGATACACAAGAAGAAAGAACAGAATCTGCTACCTGCAGGAAATCTTCAGCAACGAAATGGCAAAGGTCGACG<br>ACAGCTTCTTCCACAGACTGGAAGAAAGCTTCCTGGTCGAAGAAGACAAGAAGCACGAAAGACACCCGATCTTCGGAAACATCGTCG<br>ACGAAGTCGCATACCACGAAAAGTACCCGACAATCTACCACCTGAGAAAGAAGCTGGTCGACAGCACAGACAAGGCAGACCTGAGAC<br>TGATCTACCTGGCACTGGCACACATGATCAAGTTCAGAGGACACTTCCTGATCGAAGGAGACCTGAACCCGGACAACAGCGACGTCG<br>ACAAGCTGTTCATCCAGCTGGTCCAGACATACAACCAGCTGTTCGAAGAAAACCCGATCAACGCAAGCGGAGTCGACGCAAAGGCAA<br>TCCTGAGCGCAAGACTGAGCAAGAGCAGAAGACTGGAAAACCTGATCGCACAGCTGCCGGGAGAAAAGAAGAACGGACTGTTCGGAA | 258 |

-continued

Sequence Table

| Description | Sequence | SEQ ID No. |
|---|---|---|
| sequence, | ACCTGATCGCACTGAGCCTGGGACTGACACCGAACTTCAAGAGCAACTTCGACCTGGCAGAAGACGCAAAGCTGCAGCTGAGCAAGG | |
| and 3' UTR | ACACATACGACGACGACCTGGACAACCTGCTGGCACAGATCGGAGACCAGTACGCAGACCTGTTCCTGGCAGCAAAGAACCTGAGCG | |
| of HBB | ACGCAATCCTGCTGAGCGACATCCTGAGAGTCAACACAGAAATCACAAAGGCACCGCTGAGCGCAAGCATGATCAAGAGATACGACG | |
| | AACACCACCAGGACCTGACACTGCTGAAGGCACTGGTCAGACAGCAGCTGCCGGAAAAGTACAAGGAAATCTTCTTCGACCAGAGCA | |
| | AGAACGGATACGCAGGATACATCGACGGAGGAGCAAGCCAGGAAGAATTCTACAAGTTCATCAAGCCGATCCTGGAAAAGATGGACG | |
| | GAACAGAAGAACTGCTGGTCAAGCTGAACAGAGAAGACCTGCTGAGAAAGCAGAGAACATTCGACAACGGAAGCATCCCGCACCAGA | |
| | TCCACCTGGGAGAACTGCACGCAATCCTGAGAAGACAGGAAGACTTCTACCCGTTCCTGAAGGACAACAGAGAAAAGATCGAAAAGA | |
| | TCCTGACATTCAGAATCCCGTACTACGTCGGACCGCTGGCAAGAGGAAACAGCAGATTCGCATGGATGACAAGAAAGAGCGAAGAAA | |
| | CAATCACACCGTGGAACTTCGAAGAAGTCGTCGACAAGGGAGCAAGCGCACAGAGCTTCATCGAAAGAATGACAAACTTCGACAAGA | |
| | ACCTGCCGAACGAAAAGGTCCTGCCGAAGCACAGCCTGCTGTACGAATACTTCACAGTCTACAACGAACTGACAAAGGTCAAGTACG | |
| | TCACAGAAGGAATGAGAAAGCCGGCATTCCTGAGCGGAGAACAGAAGAAGGCAATCGTCGACCTGCTGTTCAAGACAAACAGAAAGG | |
| | TCACAGTCAAGCAGCTGAAGGAAGACTACTTCAAGAAGATCGAATGCTTCGACAGCGTCGAAATCAGCGGAGTCGAAGACAGATTCA | |
| | ACGCAAGCCTGGGAACATACCACGACCTGCTGAAGATCATCAAGGACAAGGACTTCCTGGACAACGAAGAAAACGAAGACATCCTGG | |
| | AAGACATCGTCCTGACACTGACACTGTTCGAAGACAGAGAAATGATCGAAGAAAGACTGAAGACATACGCACACCTGTTCGACGACA | |
| | AGGTCATGAAGCAGCTGAAGAGAAGAAGATACACAGGATGGGGAAGACTGAGCAGAAAGCTGATCAACGGAATCAGAGACAAGCAGA | |
| | GCGGAAAGACAATCCTGGACTTCCTGAAGAGCGACGGATTCGCAAACAGAAACTTCATGCAGCTGATCCACGACGACAGCCTGACAT | |
| | TCAAGGAAGACATCCAGAAGGCACAGGTCAGCGGACAGGGAGACAGCCTGCACGAACACATCGCAAACCTGGCAGGAAGCCCGGCAA | |
| | TCAAGAAGGGAATCCTGCAGACAGTCAAGGTCGTCGACGAACTGGTCAAGGTCATGGGAAGACACAAGCCGGAAAACATCGTCATCG | |
| | AAATGGCAAGAGAAAACCAGACAACACAGAAGGGACAGAAGAACAGCAGAGAAAGAATGAAGAGAATCGAAGAAGGAATCAAGGAAC | |
| | TGGGAAGCCAGATCCTGAAGGAACACCCGGTCGAAAACACACAGCTGCAGAACGAAAAGCTGTACCTGTACTACCTGCAGAACGGAA | |
| | GAGACATGTACGTCGACCAGGAACTGGACATCAACAGACTGAGCGACTACGACGTCGACCACATCGTCCCGCAGAGCTTCCTGAAGG | |
| | ACGACAGCATCGACAACAAGGTCCTGACAAGAAGCGACAAGAACAGAGGAAAGAGCGACAACGTCCCGAGCGAAGAAGTCGTCAAGA | |
| | AGATGAAGAACTACTGGAGACAGCTGCTGAACGCAAAGCTGATCACACAGAGAAAGTTCGACAACCTGACAAAGGCAGAGAGAGGAG | |
| | GACTGAGCGAACTGGACAAGGCAGGATTCATCAAGAGACAGCTGGTCGAAACAAGACAGATCACAAAGCACGTCGCACAGATCCTGG | |
| | ACAGCAGAATGAACACAAAGTACGACGAAAACGACAAGCTGATCAGAGAAGTCAAGGTCATCACACTGAAGAGCAAGCTGGTCAGCG | |
| | ACTTCAGAAAGGACTTCCAGTTCTACAAGGTCAGAGAAATCAACAACTACCACCACGCACACGACGCATACCTGAACGCAGTCGTCG | |
| | GAACAGCACTGATCAAGAAGTACCCGAAGCTGGAAAGCGAATTCGTCTACGGAGACTACAAGGTCTACGACGTCAGAAAGATGATCG | |
| | CAAAGAGCGAACAGGAAATCGGAAAGGCAACAGCAAAGTACTTCTTCTACAGCAACATCATGAACTTCTTCAAGACAGAAATCACAC | |
| | TGGCAAACGGAGAAATCAGAAAGAGACCGCTGATCGAAACAAACGGAGAAACAGGAGAAATCGTCTGGGACAAGGGAAGAGACTTCG | |
| | CAACAGTCAGAAAGGTCCTGAGCATGCCGCAGGTCAACATCGTCAAGAAGACAGAAGTCCAGACAGGAGGATTCAGCAAGGAAAGCA | |
| | TCCTGCCGAAGAGAAACAGCGACAAGCTGATCGCAAGAAAGAAGGACTGGGACCCGAAGAAGTACGGAGGATTCGACAGCCCGACAG | |
| | TCGCATACAGCGTCCTGGTCGTCGCAAAGGTCGAAAAGGGAAAGAGCAAGAAGCTGAAGAGCGTCAAGGAACTGCTGGGAATCACAA | |
| | TCATGGAAAGAAGCAGCTTCGAAAAGAACCCGATCGACTTCCTGGAAGCAAAGGGATACAAGGAAGTCAAGAAGGACCTGATCATCA | |
| | AGCTGCCGAAGTACAGCCTGTTCGAACTGGAAAACGGAAGAAAGAGAATGCTGGCAAGCGCAGGAGAACTGCAGAAGGGAAACGAAC | |
| | TGGCACTGCCGAGCAAGTACGTCAACTTCCTGTACCTGGCAAGCCACTACGAAAAGCTGAAGGGAAGCCCGGAAGACAACGAACAGA | |
| | AGCAGCTGTTCGTCGAACAGCACAAGCACTACCTGGACGAAATCATCGAACAGATCAGCGAATTCAGCAAGAGAGTCATCCTGGCAG | |
| | ACGCAAACCTGGACAAGGTCCTGAGCGCATACAACAAGCACAGAGACAAGCCGATCAGAGAACAGGCAGAAAACATCATCCACCTGT | |
| | TCACACTGACAAACCTGGGAGCACCGGCAGCATTCAAGTACTTCGACACAACAATCGACAGAAAGAGATACACAAGCACAAAGGAAG | |
| | TCCTGGACGCAACACTGATCCACCAGAGCATCACAGGACTGTACGAAACAAGAATCGACCTGAGCCAGCTGGGAGGAGACGGAGGAG | |
| | GAAGCCCGAAGAAGAAGAGAAAGGTCTAGctagcgctcgctttcttgctgtccaatttctattaaaggttcctttgttccctaagtc | |
| | caactactaaactgggggatattatgaagggccttgagcatctggattctgcctaataaaaaacatttattttcattgcctcgag | |
| Cas9 | GGGaagctcagaataaacgctcaactttggccggatctgccacCATGGACAAGAAGTACAGCATCGGACTGGACATCGGAACAAACA | 259 |
| transcript | GCGTCGGATGGGCAGTCATCACAGACGAATACAAGGTCCCGAGCAAGAAGTTCAAGGTCCTGGGAAACACAGACAGACACAGCATCA | |
| with 5' UTR | AGAAGAACCTGATCGGAGCACTGCTGTTCGACAGCGGAGAAACAGCAGAAGCAACAAGACTGAAGAGAACAGCAAGAAGAAGATACA | |
| from XBG, | CAAGAAGAAAGAACAGAATCTGCTACCTGCAGGAAATCTTCAGCAACGAAATGGCAAAGGTCGACGACAGCTTCTTCCACAGACTGG | |
| ORF | AAGAAAGCTTCCTGGTCGAAGAAGACAAGAAGCACGAAAGACACCCGATCTTCGGAAACATCGTCGACGAAGTCGCATACCACGAAA | |
| corresponding | AGTACCCGACAATCTACCACCTGAGAAAGAAGCTGGTCGACAGCACAGACAAGGCAGACCTGAGACTGATCTACCTGGCACTGGCAC | |
| to SEQ | ACATGATCAAGTTCAGAGGACACTTCCTGATCGAAGGAGACCTGAACCCGGACAACAGCGACGTCGACAAGCTGTTCATCCAGCTGG | |

-continued

Sequence Table

| Description | Sequence | SEQ ID No. |
|---|---|---|
| ID NO: 204, Kozak sequence, and 3' UTR of XBG | TCCAGACATACAACCAGCTGTTCGAAGAAAACCCGATCAACGCAAGCGGAGTCGACGCAAAGGCAATCCTGAGCGCAAGACTGAGCA AGAGCAGAAGACTGGAAAACCTGATCGCACAGCTGCCGGGAGAAAAGAAGAACGGACTGTTCGGAAACCTGATCGCACTGAGCCTGG GACTGACACCGAACTTCAAGAGCAACTTCGACCTGGCAGAAGACGCAAAGCTGCAGCTGAGCAAGGACACATACGACGACGACCTGG ACAACCTGCTGGCACAGATCGGAGACCAGTACGCAGACCTGTTCCTGGCAGCAAAGAACCTGAGCGACGCAATCCTGCTGAGCGACA TCCTGAGAGTCAACACAGAAATCACAAAGGCACCGCTGAGCGCAAGCATGATCAAGAGATACGACGAACACCACCAGGACCTGACAC TGCTGAAGGCACTGGTCAGACAGCAGCTGCCGGAAAAGTACAAGGAAATCTTCTTCGACCAGAGCAAGAACGGATACGCAGGATACA TCGACGGAGGAGCAAGCCAGGAAGAATTCTACAAGTTCATCAAGCCGATCCTGGAAAAGATGGACGGAACAGAAGAACTGCTGGTCA AGCTGAACAGAGAAGACCTGCTGAGAAAGCAGAGAACATTCGACAACGGAAGCATCCCGCACCAGATCCACCTGGGAGAACTGCACG CAATCCTGAGAAGACAGGAAGACTTCTACCCGTTCCTGAAGGACAACAGAGAAAAGATCGAAAAGATCCTGACATTCAGAATCCCGT ACTACGTCGGACCGCTGGCAAGAGGAAACAGCAGATTCGCATGGATGACAAGAAAGAGCGAAGAAACAATCACACCGTGGAACTTCG AAGAAGTCGTCGACAAGGGAGCAAGCGCACAGAGCTTCATCGAAAGAATGACAAACTTCGACAAGAACCTGCCGAACGAAAAGGTCC TGCCGAAGCACAGCCTGCTGTACGAATACTTCACAGTCTACAACGAACTGACAAAGGTCAAGTACGTCACAGAAGGAATGAGAAAGC CGGCATTCCTGAGCGGAGAACAGAAGAAGGCAATCGTCGACCTGCTGTTCAAGACAAACAGAAAGGTCACAGTCAAGCAGCTGAAGG AAGACTACTTCAAGAAGATCGAATGCTTCGACAGCGTCGAAATCAGCGGAGTCGAAGACAGATTCAACGCAAGCCTGGGAACATACC ACGACCTGCTGAAGATCATCAAGGACAAGGACTTCCTGGACAACGAAGAAAACGAAGACATCCTGGAAGACATCGTCCTGACACTGA CACTGTTCGAAGACAGAGAAATGATCGAAGAAAGACTGAAGACATACGCACACCTGTTCGACGACAAGGTCATGAAGCAGCTGAAGA GAAGAAGATACACAGGATGGGGAAGACTGAGCAGAAAGCTGATCAACGGAATCAGAGACAAGCAGAGCGGAAAGACAATCCTGGACT TCCTGAAGAGCGACGGATTCGCAAACAGAAACTTCATGCAGCTGATCCACGACGACAGCCTGACATTCAAGGAAGACATCCAGAAGG CACAGGTCAGCGGACAGGGAGACAGCCTGCACGAACACATCGCAAACCTGGCAGGAAGCCCGGCAATCAAGAAGGGAATCCTGCAGA CAGTCAAGGTCGTCGACGAACTGGTCAAGGTCATGGGAAGACACAAGCCGGAAAACATCGTCATCGAAATGGCAAGAGAAAACCAGA CAACACAGAAGGGACAGAAGAACAGCAGAGAAAGAATGAAGAGAATCGAAGAAGGAATCAAGGAACTGGGAAGCCAGATCCTGAAGG AACACCCGGTCGAAAACACACAGCTGCAGAACGAAAAGCTGTACCTGTACTACCTGCAGAACGGAAGAGACATGTACGTCGACCAGG AACTGGACATCAACAGACTGAGCGACTACGACGTCGACCACATCGTCCCGCAGAGCTTCCTGAAGGACGACAGCATCGACAACAAGG TCCTGACAAGAAGCGACAAGAACAGAGGAAAGAGCGACAACGTCCCGAGCGAAGAAGTCGTCAAGAAGATGAAGAACTACTGGAGAC AGCTGCTGAACGCAAAGCTGATCACACAGAGAAAGTTCGACAACCTGACAAAGGCAGAGAGAGGAGGACTGAGCGAACTGGACAAGG CAGGATTCATCAAGAGACAGCTGGTCGAAACAAGACAGATCACAAAGCACGTCGCACAGATCCTGGACAGCAGAATGAACACAAAGT ACGACGAAAACGACAAGCTGATCAGAGAAGTCAAGGTCATCACACTGAAGAGCAAGCTGGTCAGCGACTTCAGAAAGGACTTCCAGT TCTACAAGGTCAGAGAAATCAACAACTACCACCACGCACACGACGCATACCTGAACGCAGTCGTCGGAACAGCACTGATCAAGAAGT ACCCGAAGCTGGAAAGCGAATTCGTCTACGGAGACTACAAGGTCTACGACGTCAGAAAGATGATCGCAAAGAGCGAACAGGAAATCG GAAAGGCAACAGCAAAGTACTTCTTCTACAGCAACATCATGAACTTCTTCAAGACAGAAATCACACTGGCAAACGGAGAAATCAGAA AGAGACCGCTGATCGAAACAAACGGAGAAACAGGAGAAATCGTCTGGGACAAGGGAAGAGACTTCGCAACAGTCAGAAAGGTCCTGA GCATGCCGCAGGTCAACATCGTCAAGAAGACAGAAGTCCAGACAGGAGGATTCAGCAAGGAAAGCATCCTGCCGAAGAGAAACAGCG ACAAGCTGATCGCAAGAAAGAAGGACTGGGACCCGAAGAAGTACGGAGGATTCGACAGCCCGACAGTCGCATACAGCGTCCTGGTCG TCGCAAAGGTCGAAAAGGGAAAGAGCAAGAAGCTGAAGAGCGTCAAGGAACTGCTGGGAATCACAATCATGGAAAGAAGCAGCTTCG AAAAGAACCCGATCGACTTCCTGGAAGCAAAGGGATACAAGGAAGTCAAGAAGGACCTGATCATCAAGCTGCCGAAGTACAGCCTGT TCGAACTGGAAAACGGAAGAAAGAGAATGCTGGCAAGCGCAGGAGAACTGCAGAAGGGAAACGAACTGGCACTGCCGAGCAAGTACG TCAACTTCCTGTACCTGGCAAGCCACTACGAAAAGCTGAAGGGAAGCCCGGAAGACAACGAACAGAAGCAGCTGTTCGTCGAACAGC ACAAGCACTACCTGGACGAAATCATCGAACAGATCAGCGAATTCAGCAAGAGAGTCATCCTGGCAGACGCAAACCTGGACAAGGTCC TGAGCGCATACAACAAGCACAGAGACAAGCCGATCAGAGAACAGGCAGAAAACATCATCCACCTGTTCACACTGACAAACCTGGGAG CACCGGCAGCATTCAAGTACTTCGACACAACAATCGACAGAAAGAGATACACAAGCACAAAGGAAGTCCTGGACGCAACACTGATCC ACCAGAGCATCACAGGACTGTACGAAACAAGAATCGACCTGAGCCAGCTGGGAGGAGACGGAGGAGGAAGCCCGAAGAAGAAGAGAA AGGTCTAGctagcaccagcctcaagaacacccgaatggagtctctaagctacataataccaacttacactttacaaaatgttgtccc ccaaaatgtagccattcgtatctgctcctaataaaaagaaagtttcttcacattctctcgag | |
| Cas9 transcript with AGG as first three nucleotides | AGGaagctcagaataaacgctcaactttggccggatctgccacCATGGACAAGAAGTACAGCATCGGACTGGACATCGGAACAAACA GCGTCGGATGGGCAGTCATCACAGACGAATACAAGGTCCCGAGCAAGAAGTTCAAGGTCCTGGGAAACACAGACAGACACAGCATCA AGAAGAACCTGATCGGAGCACTGCTGTTCGACAGCGGAGAAACAGCAGAAGCAACAAGACTGAAGAGAACAGCAAGAAGAAGATACA CAAGAAGAAAGAACAGAATCTGCTACCTGCAGGAAATCTTCAGCAACGAAATGGCAAAGGTCGACGACAGCTTCTTCCACAGACTGG AAGAAAGCTTCCTGGTCGAAGAAGACAAGAAGCACGAAAGACACCCGATCTTCGGAAACATCGTCGACGAAGTCGCATACCACGAAA | 260 |

-continued

Sequence Table

| Description | Sequence | SEQ ID No. |
|---|---|---|
| for use with CleanCap ™, 5' UTR from XBG, ORF corresponding to SEQ ID NO: 204, Kozak sequence, and 3' UTR of XBG | AGTACCCGACAATCTACCACCTGAGAAAGAAGCTGGTCGACAGCACAGACAAGGCAGACCTGAGACTGATCTACCTGGCACTGGCAC ACATGATCAAGTTCAGAGGACACTTCCTGATCGAAGGAGACCTGAACCCGGACAACAGCGACGTCGACAAGCTGTTCATCCAGCTGG TCCAGACATACAACCAGCTGTTCGAAGAAAACCCGATCAACGCAAGCGGAGTCGACGCAAAGGCAATCCTGAGCGCAAGACTGAGCA AGAGCAGAAGACTGGAAAACCTGATCGCACAGCTGCCGGGAGAAAAGAAGAACGGACTGTTCGGAAACCTGATCGCACTGAGCCTGG GACTGACACCGAACTTCAAGAGCAACTTCGACCTGGCAGAAGACGCAAAGCTGCAGCTGAGCAAGGACACATACGACGACGACCTGG ACAACCTGCTGGCACAGATCGGAGACCAGTACGCAGACCTGTTCCTGGCAGCAAAGAACCTGAGCGACGCAATCCTGCTGAGCGACA TCCTGAGAGTCAACACAGAAATCACAAAGGCACCGCTGAGCGCAAGCATGATCAAGAGATACGACGAACACCACCAGGACCTGACAC TGCTGAAGGCACTGGTCAGACAGCAGCTGCCGGAAAAGTACAAGGAAATCTTCTTCGACCAGAGCAAGAACGGATACGCAGGATACA TCGACGGAGGAGCAAGCCAGGAAGAATTCTACAAGTTCATCAAGCCGATCCTGGAAAAGATGGACGGAACAGAAGAACTGCTGGTCA AGCTGAACAGAGAAGACCTGCTGAGAAAGCAGAGAACATTCGACAACGGAAGCATCCCGCACCAGATCCACCTGGGAGAACTGCACG CAATCCTGAGAAGACAGGAAGACTTCTACCCGTTCCTGAAGGACAACAGAGAAAAGATCGAAAAGATCCTGACATTCAGAATCCCGT ACTACGTCGGACCGCTGGCAAGAGGAAACAGCAGATTCGCATGGATGACAAGAAAGAGCGAAGAAACAATCACACCGTGGAACTTCG AAGAAGTCGTCGACAAGGGAGCAAGCGCACAGAGCTTCATCGAAAGAATGACAAACTTCGACAAGAACCTGCCGAACGAAAAGGTCC TGCCGAAGCACAGCCTGCTGTACGAATACTTCACAGTCTACAACGAACTGACAAAGGTCAAGTACGTCACAGAAGGAATGAGAAAGC CGGCATTCCTGAGCGGAGAACAGAAGAAGGCAATCGTCGACCTGCTGTTCAAGACAAACAGAAAGGTCACAGTCAAGCAGCTGAAGG AAGACTACTTCAAGAAGATCGAATGCTTCGACAGCGTCGAAATCAGCGGAGTCGAAGACAGATTCAACGCAAGCCTGGGAACATACC ACGACCTGCTGAAGATCATCAAGGACAAGGACTTCCTGGACAACGAAGAAAACGAAGACATCCTGGAAGACATCGTCCTGACACTGA CACTGTTCGAAGACAGAGAAATGATCGAAGAAAGACTGAAGACATACGCACACCTGTTCGACGACAAGGTCATGAAGCAGCTGAAGA GAAGAAGATACACAGGATGGGGAAGACTGAGCAGAAAGCTGATCAACGGAATCAGAGACAAGCAGAGCGGAAAGACAATCCTGGACT TCCTGAAGAGCGACGGATTCGCAAACAGAAACTTCATGCAGCTGATCCACGACGACAGCCTGACATTCAAGGAAGACATCCAGAAGG CACAGGTCAGCGGACAGGGAGACAGCCTGCACGAACACATCGCAAACCTGGCAGGAAGCCCGGCAATCAAGAAGGGAATCCTGCAGA CAGTCAAGGTCGTCGACGAACTGGTCAAGGTCATGGGAAGACACAAGCCGGAAAACATCGTCATCGAAATGGCAAGAGAAAACCAGA CAACACAGAAGGGACAGAAGAACAGCAGAGAAAGAATGAAGAGAATCGAAGAAGGAATCAAGGAACTGGGAAGCCAGATCCTGAAGG AACACCCGGTCGAAAACACACAGCTGCAGAACGAAAAGCTGTACCTGTACTACCTGCAGAACGGAAGAGACATGTACGTCGACCAGG AACTGGACATCAACAGACTGAGCGACTACGACGTCGACCACATCGTCCCGCAGAGCTTCCTGAAGGACGACAGCATCGACAACAAGG TCCTGACAAGAAGCGACAAGAACAGAGGAAAGAGCGACAACGTCCCGAGCGAAGAAGTCGTCAAGAAGATGAAGAACTACTGGAGAC AGCTGCTGAACGCAAAGCTGATCACACAGAGAAAGTTCGACAACCTGACAAAGGCAGAGAGAGGAGGACTGAGCGAACTGGACAAGG CAGGATTCATCAAGAGACAGCTGGTCGAPACAAGACAGATCACAAAGCACGTCGCACAGATCCTGGACAGCAGAATGAACACAAAGT ACGACGAAAACGACAAGCTGATCAGAGAAGTCAAGGTCATCACACTGAAGAGCAAGCTGGTCAGCGACTTCAGAAAGGACTTCCAGT TCTACAAGGTCAGAGAAATCAACAACTACCACCACGCACACGACGCATACCTGAACGCAGTCGTCGGAACAGCACTGATCAAGAAGT ACCCGAAGCTGGAAAGCGAATTCGTCTACGGAGACTACAAGGTCTACGACGTCAGAAAGATGATCGCAAAGAGCGAACAGGAAATCG GAAAGGCAACAGCAAAGTACTTCTTCTACAGCAACATCATGAACTTCTTCAAGACAGAAATCACACTGGCAAACGGAGAAATCAGAA AGAGACCGCTGATCGAAACAAACGGAGAAACAGGAGAAATCGTCTGGGACAAGGGAAGAGACTTCGCAACAGTCAGAAAGGTCCTGA GCATGCCGCAGGTCAACATCGTCAAGAAGACAGAAGTCCAGACAGGAGGATTCAGCAAGGAAAGCATCCTGCCGAAGAGAAACAGCG ACAAGCTGATCGCAAGAAAGAAGGACTGGGACCCGAAGAAGTACGGAGGATTCGACAGCCCGACAGTCGCATACAGCGTCCTGGTCG TCGCAAAGGTCGAAAAGGGAAAGAGCAAGAAGCTGAAGAGCGTCAAGGAACTGCTGGGAATCACAATCATGGAAAGAAGCAGCTTCG AAAAGAACCCGATCGACTTCCTGGAAGCAAAGGGATACAAGGAAGTCAAGAAGGACCTGATCATCAAGCTGCCGAAGTACAGCCTGT TCGAACTGGAAAACGGAAGAAAGAGAATGCTGGCAAGCGCAGGAGAACTGCAGAAGGGAAACGAACTGGCACTGCCGAGCAAGTACG TCAACTTCCTGTACCTGGCAAGCCACTACGAAAAGCTGAAGGGAAGCCCGGAAGACAACGAACAGAAGCAGCTGTTCGTCGAACAGC ACAAGCACTACCTGGACGAAATCATCGAACAGATCAGCGAATTCAGCAAGAGAGTCATCCTGGCAGACGCAAACCTGGACAAGGTCC TGAGCGCATACAACAAGCACAGAGACAAGCCGATCAGAGAACAGGCAGAAAACATCATCCACCTGTTCACACTGACAAACCTGGGAG CACCGGCAGCATTCAAGTACTTCGACACAACAATCGACAGAAAGAGATACACAAGCACAAAGGAAGTCCTGGACGCAACACTGATCC ACCAGAGCATCACAGGACTGTACGAAACAAGAATCGACCTGAGCCAGCTGGGAGGAGACGGAGGAGGAAGCCCGAAGAAGAAGAGAA AGGTCTAGctagcaccagcctcaagaacacccgaatggagtctctaagctacataataccaacttacactttacaaaatgttgtccc ccaaaatgtagccattcgtatctgctcctaataaaaagaaagtttcttcacattctctcgag | |
| Cas9 transcript with AGG as | AGGTCCCGCAGTCGGCGTCCAGCGGCTCTGCTTGTTCGTGTGTGTGTCGTTGCAGGCCTTATTCGGATCCGCCACCATGGACAAGAA GTACAGCATCGGACTGGACATCGGAACAAACAGCGTCGGATGGGCAGTCATCACAGACGAATACAAGGTCCCGAGCAAGAAGTTCAA GGTCCTGGGAAACACAGACAGACACAGCATCAAGAAGAACCTGATCGGAGCACTGCTGTTCGACAGCGGAGAAACAGCAGAAGCAAC | 261 |

-continued

Sequence Table

| Description | Sequence | SEQ ID No. |
|---|---|---|
| first three nucleotides for use with CleanCap ™, 5' UTR from HSD, ORF corresponding to SEQ ID NO: 204, Kozak sequence, and 3' UTR of ALB | AAGACTGAAGAGAACAGCAAGAAGAAGATACACAAGAAGAAAGAACAGAATCTGCTACCTGCAGGAAATCTTCAGCAACGAAATGGC<br>AAAGGTCGACGACAGCTTCTTCCACAGACTGGAAGAAAGCTTCCTGGTCGAAGAAGACAAGAAGCACGAAAGACACCCGATCTTCGG<br>AAACATCGTCGACGAAGTCGCATACCACGAAAAGTACCCGACAATCTACCACCTGAGAAAGAAGCTGGTCGACAGCACAGACAAGGC<br>AGACCTGAGACTGATCTACCTGGCACTGGCACACATGATCAAGTTCAGAGGACACTTCCTGATCGAAGGAGACCTGAACCCGGACAA<br>CAGCGACGTCGACAAGCTGTTCATCCAGCTGGTCCAGACATACAACCAGCTGTTCGAAGAAAACCCGATCAACGCAAGCGGAGTCGA<br>CGCAAAGGCAATCCTGAGCGCAAGACTGAGCAAGAGCAGAAGACTGGAAAACCTGATCGCACAGCTGCCGGGAGAAAAGAAGAACGG<br>ACTGTTCGGAAACCTGATCGCACTGAGCCTGGGACTGACACCGAACTTCAAGAGCAACTTCGACCTGGCAGAAGACGCAAAGCTGCA<br>GCTGAGCAAGGACACATACGACGACGACCTGGACAACCTGCTGGCACAGATCGGAGACCAGTACGCAGACCTGTTCCTGGCAGCAAA<br>GAACCTGAGCGACGCAATCCTGCTGAGCGACATCCTGAGAGTCAACACAGAAATCACAAAGGCACCGCTGAGCGCAAGCATGATCAA<br>GAGATACGACGAACACCACCAGGACCTGACACTGCTGAAGGCACTGGTCAGACAGCAGCTGCCGGAAAAGTACAAGGAAATCTTCTT<br>CGACCAGAGCAAGAACGGATACGCAGGATACATCGACGGAGGAGCAAGCCAGGAAGAATTCTACAAGTTCATCAAGCCGATCCTGGA<br>AAAGATGGACGGAACAGAAGAACTGCTGGTCAAGCTGAACAGAGAAGACCTGCTGAGAAAGCAGAGAACATTCGACAACGGAAGCAT<br>CCCGCACCAGATCCACCTGGGAGAACTGCACGCAATCCTGAGAAGACAGGAAGACTTCTACCCGTTCCTGAAGGACAACAGAGAAAA<br>GATCGAAAAGATCCTGACATTCAGAATCCCGTACTACGTCGGACCGCTGGCAAGAGGAAACAGCAGATTCGCATGGATGACAAGAAA<br>GAGCGAAGAAACAATCACACCGTGGAACTTCGAAGAAGTCGTCGACAAGGGAGCAAGCGCACAGAGCTTCATCGAAAGAATGACAAA<br>CTTCGACAAGAACCTGCCGAACGAAAAGGTCCTGCCGAAGCACAGCCTGCTGTACGAATACTTCACAGTCTACAACGAACTGACAAA<br>GGTCAAGTACGTCACAGAAGGAATGAGAAAGCCGGCATTCCTGAGCGGAGAACAGAAGAAGGCAATCGTCGACCTGCTGTTCAAGAC<br>AAACAGAAAGGTCACAGTCAAGCAGCTGAAGGAAGACTACTTCAAGAAGATCGAATGCTTCGACAGCGTCGAAATCAGCGGAGTCGA<br>AGACAGATTCAACGCAAGCCTGGGAACATACCACGACCTGCTGAAGATCATCAAGGACAAGGACTTCCTGGACAACGAAGAAAACGA<br>AGACATCCTGGAAGACATCGTCCTGACACTGACACTGTTCGAAGACAGAGAAATGATCGAAGAAAGACTGAAGACATACGCACACCT<br>GTTCGACGACAAGGTCATGAAGCAGCTGAAGAGAAGAAGATACACAGGATGGGGAAGACTGAGCAGAAAGCTGATCAACGGAATCAG<br>AGACAAGCAGAGCGGAAAGACAATCCTGGACTTCCTGAAGAGCGACGGATTCGCAAACAGAAACTTCATGCAGCTGATCCACGACGA<br>CAGCCTGACATTCAAGGAAGACATCCAGAAGGCACAGGTCAGCGGACAGGGAGACAGCCTGCACGAACACATCGCAAACCTGGCAGG<br>AAGCCCGGCAATCAAGAAGGGAATCCTGCAGACAGTCAAGGTCGTCGACGAACTGGTCAAGGTCATGGGAAGACACAAGCCGGAAAA<br>CATCGTCATCGAAATGGCAAGAGAAAACCAGACAACACAGAAGGGACAGAAGAACAGCAGAGAAAGAATGAAGAGAATCGAAGAAGG<br>AATCAAGGAACTGGGAAGCCAGATCCTGAAGGAACACCCGGTCGAAAACACACAGCTGCAGAACGAAAAGCTGTACCTGTACTACCT<br>GCAGAACGGAAGAGACATGTACGTCGACCAGGAACTGGACATCAACAGACTGAGCGACTACGACGTCGACCACATCGTCCCGCAGAG<br>CTTCCTGAAGGACGACAGCATCGACAACAAGGTCCTGACAAGAAGCGACAAGAACAGAGGAAAGAGCGACAACGTCCCGAGCGAAGA<br>AGTCGTCAAGAAGATGAAGAACTACTGGAGACAGCTGCTGAACGCAAAGCTGATCACACAGAGAAAGTTCGACAACCTGACAAAGGC<br>AGAGAGAGGAGGACTGAGCGAACTGGACAAGGCAGGATTCATCAAGAGACAGCTGGTCGAAACAAGACAGATCACAAAGCACGTCGC<br>ACAGATCCTGGACAGCAGAATGAACACAAAGTACGACGAAAACGACAAGCTGATCAGAGAAGTCAAGGTCATCACACTGAAGAGCAA<br>GCTGGTCAGCGACTTCAGAAAGGACTTCCAGTTCTACAAGGTCAGAGAAATCAACAACTACCACCACGCACACGACGCATACCTGAA<br>CGCAGTCGTCGGAACAGCACTGATCAAGAAGTACCCGAAGCTGGAAAGCGAATTCGTCTACGGAGACTACAAGGTCTACGACGTCAG<br>AAAGATGATCGCAAAGAGCGAACAGGAAATCGGAAAGGCAACAGCAAAGTACTTCTTCTACAGCAACATCATGAACTTCTTCAAGAC<br>AGAAATCACACTGGCAAACGGAGAAATCAGAAAGAGACCGCTGATCGAAACAAACGGAGAAACAGGAGAAATCGTCTGGGACAAGGG<br>AAGAGACTTCGCAACAGTCAGAAAGGTCCTGAGCATGCCGCAGGTCAACATCGTCAAGAAGACAGAAGTCCAGACAGGAGGATTCAG<br>CAAGGAAAGCATCCTGCCGAAGAGAAACAGCGACAAGCTGATCGCAAGAAAGAAGGACTGGGACCCGAAGAAGTACGGAGGATTCGA<br>CAGCCCGACAGTCGCATACAGCGTCCTGGTCGTCGCAAAGGTCGAAAAGGGAAAGAGCAAGAAGCTGAAGAGCGTCAAGGAACTGCT<br>GGGAATCACAATCATGGAAAGAAGCAGCTTCGAAAAGAACCCGATCGACTTCCTGGAAGCAAAGGGATACAAGGAAGTCAAGAAGGA<br>CCTGATCATCAAGCTGCCGAAGTACAGCCTGTTCGAACTGGAAAACGGAAGAAAGAGAATGCTGGCAAGCGCAGGAGAACTGCAGAA<br>GGGAAACGAACTGGCACTGCCGAGCAAGTACGTCAACTTCCTGTACCTGGCAAGCCACTACGAAAAGCTGAAGGGAAGCCCGGAAGA<br>CAACGAACAGAAGCAGCTGTTCGTCGAACAGCACAAGCACTACCTGGACGAAATCATCGAACAGATCAGCGAATTCAGCAAGAGAGT<br>CATCCTGGCAGACGCAAACCTGGACAAGGTCCTGAGCGCATACAACAAGCACAGAGACAAGCCGATCAGAGAACAGGCAGAAAACAT<br>CATCCACCTGTTCACACTGACAAACCTGGGAGCACCGGCAGCATTCAAGTACTTCGACACAACAATCGACAGAAAGAGATACACAAG<br>CACAAAGGAAGTCCTGGACGCAACACTGATCCACCAGAGCATCACAGGACTGTACGAAACAAGAATCGACCTGAGCCAGCTGGGAGG<br>AGACGGAGGAGGAAGCCCGAAGAAGAAGAGAAAGGTCTAGCTAGCCATCACATTTAAAAGCATCTCAGCCTACCATGAGAATAAGAG<br>AAAGAAAATGAAGATCAATAGCTTATTCATCTCTTTTTCTTTTTCGTTGGTGTAAAGCCAACACCCTGTCTAAAAAACATAAATTTC<br>TTTAATCATTTTGCCTCTTTTCTCTGTGCTTCAATTAATAAAAAATGGAAAGAACCTCGAG | |

-continued

| Sequence Table | | |
|---|---|---|
| Description | Sequence | SEQ ID No. |
| 30/30/39 poly-A sequence | AAAAAAAAAAAAAAAAAAAAAAAAAAAAAAGCGAAAAAAAAAAAAAAAAAAAAAAAAAAAAAACCGAAAAAAAAAAAAAAAAAAAAA AAAAAAAAAAAAAAAAAA | 262 |
| poly-A 100 sequence | AAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAA AAAAAA | 263 |
| G209 guide RNA | mC*mC*mA*GUCCAGCGAGGCAAAGGGUUUUAGAGCUAGAAAUAGCAAGUUAAAAUAAGGCUAGUCCGUUAUCAACUUGAAAAAGUG GCACCGAGUCGGUGCmU*mU*mU*U | 264 |
| | Not Used | 265-267 |
| Amino acid sequence of *Neisseria meningitidis* Cas9 | MAAFKPNSINYILGLDIGIASVGWAMVEIDEEENPIRLIDLGVRVFERAEVPKTGDSLAMARRLARSVRRLTRRRAHRLLRTRRLLK REGVLQAANFDENGLIKSLPNTPWQLRAAALDRKLTPLEWSAVLLHLIKHRGYLSQRKNEGETADKELGALLKGVAGNAHALQTGDF RTPAELALNKFEKESGHIRNQRSDYSHTFSRKDLQAELILLFEKQKEFGNPHVSGGLKEGIETLLMTQRPALSGDAVQKMLGHCTFE PAEPKAAKNTYTAERFIWLTKLNNLRILEQGSERPLTDTERATLMDEPYRKSKLTYAQARKLLGLEDTAFFKGLRYGKDNAEASTLM EMKAYHAISRALEKEGLKDKKSPLNLSPELQDEIGTAFSLFKTDEDITGRLKDRIQPEILEALLKHISFDKFVQISLKALRRIVPLM EQGKRYDEACAEIYGDHYGKKNTEEKIYLPPIPADEIRNPVVLRALSQARKVINGVVRRYGSPARIHIETAREVGKSFKDRKEIEKR QEENRKDREKAAAKFREYFPNFVGEPKSKDILKLRLYEQQHGKCLYSGKEINLGRLNEKGYVEIDHALPFSRTWDDSFNNKVLVLGS ENQNKGNQTPYEYFNGKDNSREWQEFKARVETSRFPRSKKQRILLQKFDEDGFKERNLNDTRYVNRFLCQFVADRMRLTGKGKKRVF ASNGQITNLLRGFWGLRKVRAENDRHHALDAVVVACSTVAMQQKITRFVRYKEMNAFDGKTIDKETGEVLHQKTHFPQPWEFFAQEV MIRVFGKPDGKPEFEEADTLEKLRTLLAEKLSSRPEAVHEYVTPLFVSRAPNRKMSGQGHMETVKSAKRLDEGVSVLRVPLTQLKLK DLEKMVNREREPKLYEALKARLEAHKDDPAKAFAEPFYKYDKAGNRTQQVKAVRVEQVQKTGVWVRNHNGIADNATMVRVDVFEKGD KYYLVPIYSWQVAKGILPDRAVVQGKDEEDWQLIDDSFNFKFSLHPNDLVEVITKKARMFGYFASCHRGTGNINIRIHDLDHKIGKN GILEGIGVKTALSFQKYQIDELGKEIRPCRLKKRPPVRSGKRTADGSEFESPKKKRKVE | 268 |
| | Not Used | 269 |
| G502 guide RNA | mA*mC*mA*CAAAUACCAGUCCAGCGGUUUUAGAmGmCmUmAmGmAmAmAmUmAmGmCAAGUUAAAAUAAGGCUAGUCCGUUAUCAm AmCmUmUmGmAmAmAmAmAmGmUmGmGmCmAmCmCmGmAmGmUmCmGmGmUmGmCmU*mU*mU*mU | 270 |
| | Not Used | 271 |
| | Not Used | 272 |
| DNA coding sequence of eGFP | TCGCGCGTTTCGGTGATGACGGTGAAAACCTCTGACACATGCAGCTCCCGGAGACGGTCACAGCTTGTCTGTAAGCGGATGCCGGGA GCAGACAAGCCCGTCAGGGCGCGTCAGCGGGTGTTGGCGGGTGTCGGGGCTGGCTTAACTATGCGGCATCAGAGCAGATTGTACTGA GAGTGCACCATATGCGGTGTGAAATACCGCACAGATGCGTAAGGAGAAAATACCGCATCAGGCGCCATTCGCCATTCAGGCTGCGCA ACTGTTGGGAAGGGCGATCGGTGCGGGCCTCTTCGCTATTACGCCAGCTGGCGAAAGGGGGATGTGCTGCAAGGCGATTAAGTTGGG TAACGCCAGGGTTTTCCCAGTCACGACGTTGTAAAACGACGGCCAGTGAATTCTAATACGACTCACTATAGGGTCCCGCAGTCGGCG TCCAGCGGCTCTGCTTGTTCGTGTGTGTGTGTCGTTGCAGGCCTTATTCGGATCCATGGTGAGCAAGGGCGAGGAGCTGTTCACCGGGG TGGTGCCCATCCTGGTCGAGCTGGACGGCGACGTAAACGGCCACAAGTTCAGCGTGTCCGGCGAGGGCGAGGGCGATGCCACCTACG GCAAGCTGACCCTGAAGTTCATCTGCACCACCGGCAAGCTGCCCGTGCCCTGGCCCACCCTCGTGACCACCCTGACCTACGGCGTGC AGTGCTTCAGCCGCTACCCCGACCACATGAAGCAGCACGACTTCTTCAAGTCCGCCATGCCCGAAGGCTACGTCCAGGAGCGCACCA TCTTCTTCAAGGACGACGGCAACTACAAGACCCGCGCCGAGGTGAAGTTCGAGGGCGACACCCTGGTGAACCGCATCGAGCTGAAGG GCATCGACTTCAAGGAGGACGGCAACATCCTGGGGCACAAGCTGGAGTACAACTACAACAGCCACAACGTCTATATCATGGCCGACA AGCAGAAGAACGGCATCAAGGTGAACTTCAAGATCCGCCACAACATCGAGGACGGCAGCGTGCAGCTCGCCGACCACTACCAGCAGA ACACCCCCATCGGCGACGGCCCCGTGCTGCTGCCCGACAACCACTACCTGAGCACCCAGTCCGCCCTGAGCAAAGACCCCAACGAGA AGCGCGATCACATGGTCCTGCTGGAGTTCGTGACCGCCGCCGGGATCACTCTCGGCATGGACGAGCTGTACAAGTAATAGGAATTAT | 273 |

-continued

| Sequence Table | | |
|---|---|---|
| Description | Sequence | SEQ ID No. |
| | GCAGTCTAGCCATCACATTTAAAAGCATCTCAGCCTACCATGAGAATAAGAGAAAGAAAATGAAGATCAATAGCTTATTCATCTCTT<br>TTTCTTTTTCGTTGGTGTAAAGCCAACACCCTGTCTAAAAAACATAAATTTCTTTAATCATTTTGCCTCTTTTCTCTGTGCTTCAAT<br>TAATAAAAAATGGAAAGAACCTCGAGAAAAAAAAAAAAAAAAAAAAAAAAAAAAAAAAAAAAAAAAAAAAAAAAAAAAAAAAAAAAA<br>AAAAAAAAAAAAAAAAAAAAAAAAAAAAAAAAAAAAAAATCTAGACTTAAGCTTGATGAGCTCTAGCTTGGCGTAATCATGGTCATA<br>GCTGTTTCCTGTGTGAAATTGTTATCCGCTCACAATTCCACACAACATACGAGCCGGAAGCATAAAGTGTAAAGCCTGGGGTGCCTA<br>ATGAGTGAGCTAACTCACATTAATTGCGTTGCGCTCACTGCCCGCTTTCCAGTCGGGAAACCTGTCGTGCCAGCTGCATTAATGAAT<br>CGGCCAACGCGCGGGGAGAGGCGGTTTGCGTATTGGGCGCTCTTCCGCTTCCTCGCTCACTGACTCGCTGCGCTCGGTCGTTCGGCT<br>GCGGCGAGCGGTATCAGCTCACTCAAAGGCGGTAATACGGTTATCCACAGAATCAGGGGATAACGCAGGAAAGAACATGTGAGCAAA<br>AGGCCAGCAAAAGGCCAGGAACCGTAAAAAGGCCGCGTTGCTGGCGTTTTTCCATAGGCTCCGCCCCCCTGACGAGCATCACAAAAA<br>TCGACGCTCAAGTCAGAGGTGGCGAAACCCGACAGGACTATAAAGATACCAGGCGTTTCCCCCTGGAAGCTCCCTCGTGCGCTCTCC<br>TGTTCCGACCCTGCCGCTTACCGGATACCTGTCCGCCTTTCTCCCTTCGGGAAGCGTGGCGCTTTCTCATAGCTCACGCTGTAGGTA<br>TCTCAGTTCGGTGTAGGTCGTTCGCTCCAAGCTGGGCTGTGTGCACGAACCCCCCGTTCAGCCCGACCGCTGCGCCTTATCCGGTAA<br>CTATCGTCTTGAGTCCAACCCGGTAAGACACGACTTATCGCCACTGGCAGCAGCCACTGGTAACAGGATTAGCAGAGCGAGGTATGT<br>AGGCGGTGCTACAGAGTTCTTGAAGTGGTGGCCTAACTACGGCTACACTAGAAGAACAGTATTTGGTATCTGCGCTCTGCTGAAGCC<br>AGTTACCTTCGGAAAAAGAGTTGGTAGCTCTTGATCCGGCAAACAAACCACCGCTGGTAGCGGTGGTTTTTTTGTTTGCAAGCAGCA<br>GATTACGCGCAGAAAAAAAGGATCTCAAGAAGATCCTTTGATCTTTTCTACGGGGTCTGACGCTCAGTGGAACGAAAACTCACGTTA<br>AGGGATTTTGGTCATGAGATTATCAAAAAGGATCTTCACCTAGATCCTTTTAAATTAAAAATGAAGTTTTAAATCAATCTAAAGTAT<br>ATATGAGTAAACTTGGTCTGACAGTTACCAATGCTTAATCAGTGAGGCACCTATCTCAGCGATCTGTCTATTTCGTTCATCCATAGT<br>TGCCTGACTCCCCGTCGTGTAGATAACTACGATACGGGAGGGCTTACCATCTGGCCCCAGTGCTGCAATGATACCGCGAGACCCACG<br>CTCACCGGCTCCAGATTTATCAGCAATAAACCAGCCAGCCGGAAGGGCCGAGCGCAGAAGTGGTCCTGCAACTTTATCCGCCTCCAT<br>CCAGTCTATTAATTGTTGCCGGGAAGCTAGAGTAAGTAGTTCGCCAGTTAATAGTTTGCGCAACGTTGTTGCCATTGCTACAGGCAT<br>CGTGGTGTCACGCTCGTCGTTTGGTATGGCTTCATTCAGCTCCGGTTCCCAACGATCAAGGCGAGTTACATGATCCCCCATGTTGTG<br>CAAAAAAGCGGTTAGCTCCTTCGGTCCTCCGATCGTTGTCAGAAGTAAGTTGGCCGCAGTGTTATCACTCATGGTTATGGCAGCACT<br>GCATAATTCTCTTACTGTCATGCCATCCGTAAGATGCTTTTCTGTGACTGGTGAGTACTCAACCAAGTCATTCTGAGAATAGTGTAT<br>GCGGCGACCGAGTTGCTCTTGCCCGGCGTCAATACGGGATAATACCGCGCCACATAGCAGAACTTTAAAAGTGCTCATCATTGGAAA<br>ACGTTCTTCGGGGCGAAAACTCTCAAGGATCTTACCGCTGTTGAGATCCAGTTCGATGTAACCCACTCGTGCACCCAACTGATCTTC<br>AGCATCTTTTACTTTCACCAGCGTTTCTGGGTGAGCAAAAACAGGAAGGCAAAATGCCGCAAAAAAGGGAATAAGGGCGACACGGAA<br>ATGTTGAATACTCATACTCTTCCTTTTTCAATATTATTGAAGCATTTATCAGGGTTATTGTCTCATGAGCGGATACATATTTGAATG<br>TATTTAGAAAAATAAACAAATAGGGGTTCCGCGCACATTTCCCCGAAAAGTGCCACCTGACGTCTAAGAAACCATTATTATCATGAC<br>ATTAACCTATAAAAATAGGCGTATCACGAGGCCCTTTCGTCG | |
| Modified sgRNA pattern, where N are nucleotides encoding a guide sequence | mN*mN*mN*NNNNNNNNNNNNNNNNNGUUUUAG<br>AmGmCmUmAmGmAmAmAmUmAmGmCAAGUUAAA<br>AUAAGGCUAGUCCGUUAUCAmAmCmUmUmGmAm<br>AmAmAmAmGmUmGmGmCmAmCmCmGmAmGmUmC<br>mGmGmUmGmCmU*mU*mU*mU | 274 |
| CMV-1 5' UTR | CAGATCGCCTGGAGACGCCATCCACGCTGTTTTGACCTCCAT | 275 |
| CMV-2 5' UTR | AGAAGACACCGGGACCGATCCAGCCTCCGCGGCCGGGAACGG | 276 |
| CMV-3 5' UTR | TGCATTGGAACGCGGATTCCCCGTGCCAAGAGTGACTCACCG | 277 |

-continued

| Sequence Table | | |
|---|---|---|
| Description | Sequence | SEQ ID No. |
| SV40 NLS | PKKKRKV | 278 |
| Exemplary NLS 1 | LAAKRSRTT | 279 |
| Exemplary NLS 2 | QAAKRSRTT | 280 |
| Exemplary NLS 3 | PAPAKRERTT | 281 |
| Exemplary NLS 4 | QAAKRPRTT | 282 |
| Exemplary NLS 5 | RAAKRPRTT | 283 |
| Exemplary NLS 6 | AAAKRSWSMAA | 284 |
| Exemplary NLS 7 | AAAKRVWSMAF | 285 |
| Exemplary NLS 8 | AAAKRSWSMAF | 286 |
| Exemplary NLS 9 | AAAKRKYFAA | 287 |
| Exemplary NLS 10 | RAAKRKAFAA | 288 |
| Exemplary NLS 11 | RAAKRKYFAV | 289 |
| Alternate SV40 NLS | PKKKRRV | 290 |
| Nucleoplasm in NLS | KRPAATKKAGQAKKKK | 291 |
| Exemplary coding sequence for SV40 NLS | CCGAAGAAGAAGAGAAAGGTC | 292 |
| Exemplary coding | CTGGCAGCAAAGAGAAGCAGAACAACA | 293 |

-continued

Sequence Table

| Description | Sequence | SEQ ID No. |
|---|---|---|
| sequence for NLS1 | | |
| Exemplary coding sequence for NLS2 | CAGGCAGCAAAGAGAAGCAGAACAACA | 294 |
| Exemplary coding sequence for NLS3 | CCGGCACCGGCAAAGAGAGAAAGAACAACA | 295 |
| Exemplary coding sequence for NLS4 | CAGGCAGCAAAGAGACCGAGAACAACA | 296 |
| Exemplary coding sequence for NLS5 | AGAGCAGCAAAGAGACCGAGAACAACA | 297 |
| Exemplary coding sequence for NLS6 | GCAGCAGCAAAGAGAAGCTGGAGCATGGCAGCA | 298 |
| Exemplary coding sequence for NLS7 | GCAGCAGCAAAGAGAGTCTGGAGCATGGCATTC | 299 |
| Exemplary coding sequence for NLS8 | GCAGCAGCAAAGAGAAGCTGGAGCATGGCATTC | 300 |
| Exemplary coding sequence for NLS9 | GCAGCAGCAAAGAGAAAGTACTTCGCAGCA | 301 |
| Exemplary coding sequence for NLS10 | AGAGCAGCAAAGAGAAAGGCATTCGCAGCA | 302 |
| Exemplary | AGAGCAGCAAAGAGAAAGTACTTCGCAGTC | 303 |

-continued

Sequence Table

| Description | Sequence | SEQ ID No. |
|---|---|---|
| coding sequence for NLS11 | | |
| Exemplary coding sequence for alternate SV40 NLS | CCGAAGAAGAAGAGAAGAGTC | 304 |
| exemplary Kozak sequence | gccgccRccAUGG | 305 |
| | Not Used | 306-310 |
| Cas9 ORF using low A codons of Table 5, with start and stop codons | ATGGACAAGAAGTACTCCATCGGCCTGGACATCGGCACCAACTCCGTGGGCTGGGCCGTGATCACCGACGAGTACAAGGTGCCCTCC<br>AAGAAGTTCAAGGTGCTGGGCAACACCGACCGGCACTCCATCAAGAAGAACCTGATCGGCGCCCTGCTGTTCGACTCCGGCGAGACC<br>GCCGAGGCCACCCGGCTGAAGCGGACCGCCCGGCGGCGGTACACCCGGCGGAAGAACCGGATCTGCTACCTGCAGGAGATCTTCTCC<br>AACGAGATGGCCAAGGTGGACGACTCCTTCTTCCACCGGCTGGAGGAGTCCTTCCTGGTGGAGGAGGACAAGAAGCACGAGCGGCAC<br>CCCATCTTCGGCAACATCGTGGACGAGGTGGCCTACCACGAGAAGTACCCCACCATCTACCACCTGCGGAAGAAGCTGGTGGACTCC<br>ACCGACAAGGCCGACCTGCGGCTGATCTACCTGGCCCTGGCCCACATGATCAAGTTCCGGGGCCACTTCCTGATCGAGGGCGACCTG<br>AACCCCGACAACTCCGACGTGGACAAGCTGTTCATCCAGCTGGTGCAGACCTACAACCAGCTGTTCGAGGAGAACCCCATCAACGCC<br>TCCGGCGTGGACGCCAAGGCCATCCTGTCCGCCCGGCTGTCCAAGTCCCGGCGGCTGGAGAACCTGATCGCCCAGCTGCCCGGCGAG<br>AAGAAGAACGGCCTGTTCGGCAACCTGATCGCCCTGTCCCTGGGCCTGACCCCCAACTTCAAGTCCAACTTCGACCTGGCCGAGGAC<br>GCCAAGCTGCAGCTGTCCAAGGACACCTACGACGACGACCTGGACAACCTGCTGGCCCAGATCGGCGACCAGTACGCCGACCTGTTC<br>CTGGCCGCCAAGAACCTGTCCGACGCCATCCTGCTGTCCGACATCCTGCGGGTGAACACCGAGATCACCAAGGCCCCCCTGTCCGCC<br>TCCATGATCAAGCGGTACGACGAGCACCACCAGGACCTGACCCTGCTGAAGGCCCTGGTGCGGCAGCAGCTGCCCGAGAAGTACAAG<br>GAGATCTTCTTCGACCAGTCCAAGAACGGCTACGCCGGCTACATCGACGGCGGCGCCTCCCAGGAGGAGTTCTACAAGTTCATCAAG<br>CCCATCCTGGAGAAGATGGACGGCACCGAGGAGCTGCTGGTGAAGCTGAACCGGGAGGACCTGCTGCGGAAGCAGCGGACCTTCGAC<br>AACGGCTCCATCCCCCACCAGATCCACCTGGGCGAGCTGCACGCCATCCTGCGGCGGCAGGAGGACTTCTACCCCTTCCTGAAGGAC<br>AACCGGGAGAAGATCGAGAAGATCCTGACCTTCCGGATCCCCTACTACGTGGGCCCCCTGGCCCGGGGCAACTCCCGGTTCGCCTGG<br>ATGACCCGGAAGTCCGAGGAGACCATCACCCCCTGGAACTTCGAGGAGGTGGTGGACAAGGGCGCCTCCGCCCAGTCCTTCATCGAG<br>CGGATGACCAACTTCGACAAGAACCTGCCCAACGAGAAGGTGCTGCCCAAGCACTCCCTGCTGTACGAGTACTTCACCGTGTACAAC<br>GAGCTGACCAAGGTGAAGTACGTGACCGAGGGCATGCGGAAGCCCGCCTTCCTGTCCGGCGAGCAGAAGAAGGCCATCGTGGACCTG<br>CTGTTCAAGACCAACCGGAAGGTGACCGTGAAGCAGCTGAAGGAGGACTACTTCAAGAAGATCGAGTGCTTCGACTCCGTGGAGATC<br>TCCGGCGTGGAGGACCGGTTCAACGCCTCCCTGGGCACCTACCACGACCTGCTGAAGATCATCAAGGACAAGGACTTCCTGGACAAC<br>GAGGAGAACGAGGACATCCTGGAGGACATCGTGCTGACCCTGACCCTGTTCGAGGACCGGGAGATGATCGAGGAGCGGCTGAAGACC<br>TACGCCCACCTGTTCGACGACAAGGTGATGAAGCAGCTGAAGCGGCGGCGGTACACCGGCTGGGGCCGGCTGTCCCGGAAGCTGATC<br>AACGGCATCCGGGACAAGCAGTCCGGCAAGACCATCCTGGACTTCCTGAAGTCCGACGGCTTCGCCAACCGGAACTTCATGCAGCTG<br>ATCCACGACGACTCCCTGACCTTCAAGGAGGACATCCAGAAGGCCCAGGTGTCCGGCCAGGGCGACTCCCTGCACGAGCACATCGCC<br>AACCTGGCCGGCTCCCCCGCCATCAAGAAGGGCATCCTGCAGACCGTGAAGGTGGTGGACGAGCTGGTGAAGGTGATGGGCCGGCAC<br>AAGCCCGAGAACATCGTGATCGAGATGGCCCGGGAGAACCAGACCACCCAGAAGGGCCAGAAGAACTCCCGGGAGCGGATGAAGCGG<br>ATCGAGGAGGGCATCAAGGAGCTGGGCTCCCAGATCCTGAAGGAGCACCCCGTGGAGAACACCCAGCTGCAGAACGAGAAGCTGTAC<br>CTGTACTACCTGCAGAACGGCCGGGACATGTACGTGGACCAGGAGCTGGACATCAACCGGCTGTCCGACTACGACGTGGACCACATC<br>GTGCCCCAGTCCTTCCTGAAGGACGACTCCATCGACAACAAGGTGCTGACCCGGTCCGACAAGAACCGGGGCAAGTCCGACAACGTG<br>CCCTCCGAGGAGGTGGTGAAGAAGATGAAGAACTACTGGCGGCAGCTGCTGAACGCCAAGCTGATCACCCAGCGGAAGTTCGACAAC<br>CTGACCAAGGCCGAGCGGGGCGGCCTGTCCGAGCTGGACAAGGCCGGCTTCATCAAGCGGCAGCTGGTGGAGACCCGGCAGATCACC | 311 |

-continued

Sequence Table

| Description | Sequence | SEQ ID No. |
|---|---|---|
| | AAGCACGTGGCCCAGATCCTGGACTCCCGGATGAACACCAAGTACGACGAGAACGACAAGCTGATCCGGGAGGTGAAGGTGATCACC<br>CTGAAGTCCAAGCTGGTGTCCGACTTCCGGAAGGACTTCCAGTTCTACAAGGTGCGGGAGATCAACAACTACCACCACGCCCACGAC<br>GCCTACCTGAACGCCGTGGTGGGCACCGCCCTGATCAAGAAGTACCCCAAGCTGGAGTCCGAGTTCGTGTACGGCGACTACAAGGTG<br>TACGACGTGCGGAAGATGATCGCCAAGTCCGAGCAGGAGATCGGCAAGGCCACCGCCAAGTACTTCTTCTACTCCAACATCATGAAC<br>TTCTTCAAGACCGAGATCACCCTGGCCAACGGCGAGATCCGGAAGCGGCCCCTGATCGAGACCAACGGCGAGACCGGCGAGATCGTG<br>TGGGACAAGGGCCGGGACTTCGCCACCGTGCGGAAGGTGCTGTCCATGCCCCAGGTGAACATCGTGAAGAAGACCGAGGTGCAGACC<br>GGCGGCTTCTCCAAGGAGTCCATCCTGCCCAAGCGGAACTCCGACAAGCTGATCGCCCGGAAGAAGGACTGGGACCCCAAGAAGTAC<br>GGCGGCTTCGACTCCCCCACCGTGGCCTACTCCGTGCTGGTGGTGGCCAAGGTGGAGAAGGGCAAGTCCAAGAAGCTGAAGTCCGTG<br>AAGGAGCTGCTGGGCATCACCATCATGGAGCGGTCCTCCTTCGAGAAGAACCCCATCGACTTCCTGGAGGCCAAGGGCTACAAGGAG<br>GTGAAGAAGGACCTGATCATCAAGCTGCCCAAGTACTCCCTGTTCGAGCTGGAGAACGGCCGGAAGCGGATGCTGGCCTCCGCCGGC<br>GAGCTGCAGAAGGGCAACGAGCTGGCCCTGCCCTCCAAGTACGTGAACTTCCTGTACCTGGCCTCCCACTACGAGAAGCTGAAGGGC<br>TCCCCCGAGGACAACGAGCAGAAGCAGCTGTTCGTGGAGCAGCACAAGCACTACCTGGACGAGATCATCGAGCAGATCTCCGAGTTC<br>TCCAAGCGGGTGATCCTGGCCGACGCCAACCTGGACAAGGTGCTGTCCGCCTACAACAAGCACCGGGACAAGCCCATCCGGGAGCAG<br>GCCGAGAACATCATCCACCTGTTCACCCTGACCAACCTGGGCGCCCCCGCCGCCTTCAAGTACTTCGACACCACCATCGACCGGAAG<br>CGGTACACCTCCACCAAGGAGGTGCTGGACGCCACCCTGATCCACCAGTCCATCACCGGCCTGTACGAGACCCGGATCGACCTGTCC<br>CAGCTGGGCGGCGACGGCGGCGGCTCCCCCAAGAAGAAGCGGAAGGTGTGA | |
| Cas9 ORF using low A/U codons of Table 5, with start and stop codons | ATGGACAAGAAGTACAGCATCGGCCTGGACATCGGCACCAACAGCGTGGGCTGGGCCGTGATCACCGACGAGTACAAGGTGCCCAGC<br>AAGAAGTTCAAGGTGCTGGGCAACACCGACCGGCACAGCATCAAGAAGAACCTGATCGGCGCCCTGCTGTTCGACAGCGGCGAGACC<br>GCCGAGGCCACCCGGCTGAAGCGGACCGCCCGGCGGCGGTACACCCGGCGGAAGAACCGGATCTGCTACCTGCAGGAGATCTTCAGC<br>AACGAGATGGCCAAGGTGGACGACAGCTTCTTCCACCGGCTGGAGGAGAGCTTCCTGGTGGAGGAGGACAAGAAGCACGAGCGGCAC<br>CCCATCTTCGGCAACATCGTGGACGAGGTGGCCTACCACGAGAAGTACCCCACCATCTACCACCTGCGGAAGAAGCTGGTGGACAGC<br>ACCGACAAGGCCGACCTGCGGCTGATCTACCTGGCCCTGGCCCACATGATCAAGTTCCGGGGCCACTTCCTGATCGAGGGCGACCTG<br>AACCCCGACAACAGCGACGTGGACAAGCTGTTCATCCAGCTGGTGCAGACCTACAACCAGCTGTTCGAGGAGAACCCCATCAACGCC<br>AGCGGCGTGGACGCCAAGGCCATCCTGAGCGCCCGGCTGAGCAAGAGCCGGCGGCTGGAGAACCTGATCGCCCAGCTGCCCGGCGAG<br>AAGAAGAACGGCCTGTTCGGCAACCTGATCGCCCTGAGCCTGGGCCTGACCCCCAACTTCAAGAGCAACTTCGACCTGGCCGAGGAC<br>GCCAAGCTGCAGCTGAGCAAGGACACCTACGACGACGACCTGGACAACCTGCTGGCCCAGATCGGCGACCAGTACGCCGACCTGTTC<br>CTGGCCGCCAAGAACCTGAGCGACGCCATCCTGCTGAGCGACATCCTGCGGGTGAACACCGAGATCACCAAGGCCCCCCTGAGCGCC<br>AGCATGATCAAGCGGTACGACGAGCACCACCAGGACCTGACCCTGCTGAAGGCCCTGGTGCGGCAGCAGCTGCCCGAGAAGTACAAG<br>GAGATCTTCTTCGACCAGAGCAAGAACGGCTACGCCGGCTACATCGACGGCGGCGCCAGCCAGGAGGAGTTCTACAAGTTCATCAAG<br>CCCATCCTGGAGAAGATGGACGGCACCGAGGAGCTGCTGGTGAAGCTGAACCGGGAGGACCTGCTGCGGAAGCAGCGGACCTTCGAC<br>AACGGCAGCATCCCCCACCAGATCCACCTGGGCGAGCTGCACGCCATCCTGCGGCGGCAGGAGGACTTCTACCCCTTCCTGAAGGAC<br>AACCGGGAGAAGATCGAGAAGATCCTGACCTTCCGGATCCCCTACTACGTGGGCCCCCTGGCCCGGGGCAACAGCCGGTTCGCCTGG<br>ATGACCCGGAAGAGCGAGGAGACCATCACCCCCTGGAACTTCGAGGAGGTGGTGGACAAGGGCGCCAGCGCCCAGAGCTTCATCGAG<br>CGGATGACCAACTTCGACAAGAACCTGCCCAACGAGAAGGTGCTGCCCAAGCACAGCCTGCTGTACGAGTACTTCACCGTGTACAAC<br>GAGCTGACCAAGGTGAAGTACGTGACCGAGGGCATGCGGAAGCCCGCCTTCCTGAGCGGCGAGCAGAAGAAGGCCATCGTGGACCTG<br>CTGTTCAAGACCAACCGGAAGGTGACCGTGAAGCAGCTGAAGGAGGACTACTTCAAGAAGATCGAGTGCTTCGACAGCGTGGAGATC<br>AGCGGCGTGGAGGACCGGTTCAACGCCAGCCTGGGCACCTACCACGACCTGCTGAAGATCATCAAGGACAAGGACTTCCTGGACAAC<br>GAGGAGAACGAGGACATCCTGGAGGACATCGTGCTGACCCTGACCCTGTTCGAGGACCGGGAGATGATCGAGGAGCGGCTGAAGACC<br>TACGCCCACCTGTTCGACGACAAGGTGATGAAGCAGCTGAAGCGGCGGCGGTACACCGGCTGGGGCCGGCTGAGCCGGAAGCTGATC<br>AACGGCATCCGGGACAAGCAGAGCGGCAAGACCATCCTGGACTTCCTGAAGAGCGACGGCTTCGCCAACCGGAACTTCATGCAGCTG<br>ATCCACGACGACAGCCTGACCTTCAAGGAGGACATCCAGAAGGCCCAGGTGAGCGGCCAGGGCGACAGCCTGCACGAGCACATCGCC<br>AACCTGGCCGGCAGCCCCGCCATCAAGAAGGGCATCCTGCAGACCGTGAAGGTGGTGGACGAGCTGGTGAAGGTGATGGGCCGGCAC<br>AAGCCCGAGAACATCGTGATCGAGATGGCCCGGGAGAACCAGACCACCCAGAAGGGCCAGAAGAACAGCCGGGAGCGGATGAAGCGG<br>ATCGAGGAGGGCATCAAGGAGCTGGGCAGCCAGATCCTGAAGGAGCACCCCGTGGAGAACACCCAGCTGCAGAACGAGAAGCTGTAC<br>CTGTACTACCTGCAGAACGGCCGGGACATGTACGTGGACCAGGAGCTGGACATCAACCGGCTGAGCGACTACGACGTGGACCACATC<br>GTGCCCCAGAGCTTCCTGAAGGACGACAGCATCGACAACAAGGTGCTGACCCGGAGCGACAAGAACCGGGGCAAGAGCGACAACGTG<br>CCCAGCGAGGAGGTGGTGAAGAAGATGAAGAACTACTGGCGGCAGCTGCTGAACGCCAAGCTGATCACCCAGCGGAAGTTCGACAAC<br>CTGACCAAGGCCGAGCGGGGCGGCCTGAGCGAGCTGGACAAGGCCGGCTTCATCAAGCGGCAGCTGGTGGAGACCCGGCAGATCACC | 312 |

-continued

Sequence Table

| Description | Sequence | SEQ ID No. |
|---|---|---|
| | AAGCACGTGGCCCAGATCCTGGACAGCCGGATGAACACCAAGTACGACGAGAACGACAAGCTGATCCGGGAGGTGAAGGTGATCACC<br>CTGAAGAGCAAGCTGGTGAGCGACTTCCGGAAGGACTTCCAGTTCTACAAGGTGCGGGAGATCAACAACTACCACCACGCCCACGAC<br>GCCTACCTGAACGCCGTGGTGGGCACCGCCCTGATCAAGAAGTACCCCAAGCTGGAGAGCGAGTTCGTGTACGGCGACTACAAGGTG<br>TACGACGTGCGGAAGATGATCGCCAAGAGCGAGCAGGAGATCGGCAAGGCCACCGCCAAGTACTTCTTCTACAGCAACATCATGAAC<br>TTCTTCAAGACCGAGATCACCCTGGCCAACGGCGAGATCCGGAAGCGGCCCCTGATCGAGACCAACGGCGAGACCGGCGAGATCGTG<br>TGGGACAAGGGCCGGGACTTCGCCACCGTGCGGAAGGTGCTGAGCATGCCCCAGGTGAACATCGTGAAGAAGACCGAGGTGCAGACC<br>GGCGGCTTCAGCAAGGAGAGCATCCTGCCCAAGCGGAACAGCGACAAGCTGATCGCCCGGAAGAAGGACTGGGACCCCAAGAAGTAC<br>GGCGGCTTCGACAGCCCCACCGTGGCCTACAGCGTGCTGGTGGTGGCCAAGGTGGAGAAGGGCAAGAGCAAGAAGCTGAAGAGCGTG<br>AAGGAGCTGCTGGGCATCACCATCATGGAGCGGAGCAGCTTCGAGAAGAACCCCATCGACTTCCTGGAGGCCAAGGGCTACAAGGAG<br>GTGAAGAAGGACCTGATCATCAAGCTGCCCAAGTACAGCCTGTTCGAGCTGGAGAACGGCCGGAAGCGGATGCTGGCCAGCGCCGGC<br>GAGCTGCAGAAGGGCAACGAGCTGGCCCTGCCCAGCAAGTACGTGAACTTCCTGTACCTGGCCAGCCACTACGAGAAGCTGAAGGGC<br>AGCCCCGAGGACAACGAGCAGAAGCAGCTGTTCGTGGAGCAGCACAAGCACTACCTGGACGAGATCATCGAGCAGATCAGCGAGTTC<br>AGCAAGCGGGTGATCCTGGCCGACGCCAACCTGGACAAGGTGCTGAGCGCCTACAACAAGCACCGGGACAAGCCCATCCGGGAGCAG<br>GCCGAGAACATCATCCACCTGTTCACCCTGACCAACCTGGGCGCCCCCGCCGCCTTCAAGTACTTCGACACCACCATCGACCGGAAG<br>CGGTACACCAGCACCAAGGAGGTGCTGGACGCCACCCTGATCCACCAGAGCATCACCGGCCTGTACGAGACCCGGATCGACCTGAGC<br>CAGCTGGGCGGCGACGGCGGCGGCAGCCCCAAGAAGAAGCGGAAGGTGTGA | |
| Cas9 ORF using low A codons of Table 5, with two C-terminal NLS sequences and start and stop codons | ATGGACAAGAAGTACTCCATCGGCCTGGACATCGGCACCAACTCCGTGGGCTGGGCCGTGATCACCGACGAGTACAAGGTGCCCTCC<br>AAGAAGTTCAAGGTGCTGGGCAACACCGACCGGCACTCCATCAAGAAGAACCTGATCGGCGCCCTGCTGTTCGACTCCGGCGAGACC<br>GCCGAGGCCACCCGGCTGAAGCGGACCGCCCGGCGGCGGTACACCCGGCGGAAGAACCGGATCTGCTACCTGCAGGAGATCTTCTCC<br>AACGAGATGGCCAAGGTGGACGACTCCTTCTTCCACCGGCTGGAGGAGTCCTTCCTGGTGGAGGAGGACAAGAAGCACGAGCGGCAC<br>CCCATCTTCGGCAACATCGTGGACGAGGTGGCCTACCACGAGAAGTACCCCACCATCTACCACCTGCGGAAGAAGCTGGTGGACTCC<br>ACCGACAAGGCCGACCTGCGGCTGATCTACCTGGCCCTGGCCCACATGATCAAGTTCCGGGGCCACTTCCTGATCGAGGGCGACCTG<br>AACCCCGACAACTCCGACGTGGACAAGCTGTTCATCCAGCTGGTGCAGACCTACAACCAGCTGTTCGAGGAGAACCCCATCAACGCC<br>TCCGGCGTGGACGCCAAGGCCATCCTGTCCGCCCGGCTGTCCAAGTCCCGGCGGCTGGAGAACCTGATCGCCCAGCTGCCCGGCGAG<br>AAGAAGAACGGCCTGTTCGGCAACCTGATCGCCCTGTCCCTGGGCCTGACCCCCAACTTCAAGTCCAACTTCGACCTGGCCGAGGAC<br>GCCAAGCTGCAGCTGTCCAAGGACACCTACGACGACGACCTGGACAACCTGCTGGCCCAGATCGGCGACCAGTACGCCGACCTGTTC<br>CTGGCCGCCAAGAACCTGTCCGACGCCATCCTGCTGTCCGACATCCTGCGGGTGAACACCGAGATCACCAAGGCCCCCCTGTCCGCC<br>TCCATGATCAAGCGGTACGACGAGCACCACCAGGACCTGACCCTGCTGAAGGCCCTGGTGCGGCAGCAGCTGCCCGAGAAGTACAAG<br>GAGATCTTCTTCGACCAGTCCAAGAACGGCTACGCCGGCTACATCGACGGCGGCGCCTCCCAGGAGGAGTTCTACAAGTTCATCAAG<br>CCCATCCTGGAGAAGATGGACGGCACCGAGGAGCTGCTGGTGAAGCTGAACCGGGAGGACCTGCTGCGGAAGCAGCGGACCTTCGAC<br>AACGGCTCCATCCCCCACCAGATCCACCTGGGCGAGCTGCACGCCATCCTGCGGCGGCAGGAGGACTTCTACCCCTTCCTGAAGGAC<br>AACCGGGAGAAGATCGAGAAGATCCTGACCTTCCGGATCCCCTACTACGTGGGCCCCCTGGCCCGGGGCAACTCCCGGTTCGCCTGG<br>ATGACCCGGAAGTCCGAGGAGACCATCACCCCCTGGAACTTCGAGGAGGTGGTGGACAAGGGCGCCTCCGCCCAGTCCTTCATCGAG<br>CGGATGACCAACTTCGACAAGAACCTGCCCAACGAGAAGGTGCTGCCCAAGCACTCCCTGCTGTACGAGTACTTCACCGTGTACAAC<br>GAGCTGACCAAGGTGAAGTACGTGACCGAGGGCATGCGGAAGCCCGCCTTCCTGTCCGGCGAGCAGAAGAAGGCCATCGTGGACCTG<br>CTGTTCAAGACCAACCGGAAGGTGACCGTGAAGCAGCTGAAGGAGGACTACTTCAAGAAGATCGAGTGCTTCGACTCCGTGGAGATC<br>TCCGGCGTGGAGGACCGGTTCAACGCCTCCCTGGGCACCTACCACGACCTGCTGAAGATCATCAAGGACAAGGACTTCCTGGACAAC<br>GAGGAGAACGAGGACATCCTGGAGGACATCGTGCTGACCCTGACCCTGTTCGAGGACCGGGAGATGATCGAGGAGCGGCTGAAGACC<br>TACGCCCACCTGTTCGACGACAAGGTGATGAAGCAGCTGAAGCGGCGGCGGTACACCGGCTGGGGCCGGCTGTCCCGGAAGCTGATC<br>AACGGCATCCGGGACAAGCAGTCCGGCAAGACCATCCTGGACTTCCTGAAGTCCGACGGCTTCGCCAACCGGAACTTCATGCAGCTG<br>ATCCACGACGACTCCCTGACCTTCAAGGAGGACATCCAGAAGGCCCAGGTGTCCGGCCAGGGCGACTCCCTGCACGAGCACATCGCC<br>AACCTGGCCGGCTCCCCCGCCATCAAGAAGGGCATCCTGCAGACCGTGAAGGTGGTGGACGAGCTGGTGAAGGTGATGGGCCGGCAC<br>AAGCCCGAGAACATCGTGATCGAGATGGCCCGGGAGAACCAGACCACCCAGAAGGGCCAGAAGAACTCCCGGGAGCGGATGAAGCGG<br>ATCGAGGAGGGCATCAAGGAGCTGGGCTCCCAGATCCTGAAGGAGCACCCCGTGGAGAACACCCAGCTGCAGAACGAGAAGCTGTAC<br>CTGTACTACCTGCAGAACGGCCGGGACATGTACGTGGACCAGGAGCTGGACATCAACCGGCTGTCCGACTACGACGTGGACCACATC<br>GTGCCCCAGTCCTTCCTGAAGGACGACTCCATCGACAACAAGGTGCTGACCCGGTCCGACAAGAACCGGGGCAAGTCCGACAACGTG<br>CCCTCCGAGGAGGTGGTGAAGAAGATGAAGAACTACTGGCGGCAGCTGCTGAACGCCAAGCTGATCACCCAGCGGAAGTTCGACAAC<br>CTGACCAAGGCCGAGCGGGGCGGCCTGTCCGAGCTGGACAAGGCCGGCTTCATCAAGCGGCAGCTGGTGGAGACCCGGCAGATCACC | 313 |

-continued

| Sequence Table | | |
|---|---|---|
| Description | Sequence | SEQ ID No. |
| | AAGCACGTGGCCCAGATCCTGGACTCCCGGATGAACACCAAGTACGACGAGAACGACAAGCTGATCCGGGAGGTGAAGGTGATCACC<br>CTGAAGTCCAAGCTGGTGTCCGACTTCCGGAAGGACTTCCAGTTCTACAAGGTGCGGGAGATCAACAACTACCACCACGCCCACGAC<br>GCCTACCTGAACGCCGTGGTGGGCACCGCCCTGATCAAGAAGTACCCCAAGCTGGAGTCCGAGTTCGTGTACGGCGACTACAAGGTG<br>TACGACGTGCGGAAGATGATCGCCAAGTCCGAGCAGGAGATCGGCAAGGCCACCGCCAAGTACTTCTTCTACTCCAACATCATGAAC<br>TTCTTCAAGACCGAGATCACCCTGGCCAACGGCGAGATCCGGAAGCGGCCCCTGATCGAGACCAACGGCGAGACCGGCGAGATCGTG<br>TGGGACAAGGGCCGGGACTTCGCCACCGTGCGGAAGGTGCTGTCCATGCCCCAGGTGAACATCGTGAAGAAGACCGAGGTGCAGACC<br>GGCGGCTTCTCCAAGGAGTCCATCCTGCCCAAGCGGAACTCCGACAAGCTGATCGCCCGGAAGAAGGACTGGGACCCCAAGAAGTAC<br>GGCGGCTTCGACTCCCCCACCGTGGCCTACTCCGTGCTGGTGGTGGCCAAGGTGGAGAAGGGCAAGTCCAAGAAGCTGAAGTCCGTG<br>AAGGAGCTGCTGGGCATCACCATCATGGAGCGGTCCTCCTTCGAGAAGAACCCCATCGACTTCCTGGAGGCCAAGGGCTACAAGGAG<br>GTGAAGAAGGACCTGATCATCAAGCTGCCCAAGTACTCCCTGTTCGAGCTGGAGAACGGCCGGAAGCGGATGCTGGCCTCCGCCGGC<br>GAGCTGCAGAAGGGCAACGAGCTGGCCCTGCCCTCCAAGTACGTGAACTTCCTGTACCTGGCCTCCCACTACGAGAAGCTGAAGGGC<br>TCCCCCGAGGACAACGAGCAGAAGCAGCTGTTCGTGGAGCAGCACAAGCACTACCTGGACGAGATCATCGAGCAGATCTCCGAGTTC<br>TCCAAGCGGGTGATCCTGGCCGACGCCAACCTGGACAAGGTGCTGTCCGCCTACAACAAGCACCGGGACAAGCCCATCCGGGAGCAG<br>GCCGAGAACATCATCCACCTGTTCACCCTGACCAACCTGGGCGCCCCCGCCGCCTTCAAGTACTTCGACACCACCATCGACCGGAAG<br>CGGTACACCTCCACCAAGGAGGTGCTGGACGCCACCCTGATCCACCAGTCCATCACCGGCCTGTACGAGACCCGGATCGACCTGTCC<br>CAGCTGGGCGGCGACGGCTCCGGCTCCCCCAAGAAGAAGCGGAAGGTGGACGGCTCCCCCAAGAAGAAGCGGAAGGTGGACTCCGGC<br>TGA | |
| | Not Used | 314-328 |
| Nme Cas9 ORF using low A codons of Table 5, with start and stop codons | ATGGCCGCCTTCAAGCCCAACTCCATCAACTACATCCTGGGCCTGGACATCGGCATCGCCTCCGTGGGCTGGGCCATGGTGGAGATC<br>GACGAGGAGGAGAACCCCATCCGGCTGATCGACCTGGGCGTGCGGGTGTTCGAGCGGGCCGAGGTGCCCAAGACCGGCGACTCCCTG<br>GCCATGGCCCGGCGGCTGGCCCGGTCCGTGCGGCGGCTGACCCGGCGGCGGGCCCACCGGCTGCTGCGGACCCGGCGGCTGCTGAAG<br>CGGGAGGGCGTGCTGCAGGCCGCCAACTTCGACGAGAACGGCCTGATCAAGTCCCTGCCCAACACCCCCTGGCAGCTGCGGGCCGCC<br>GCCCTGGACCGGAAGCTGACCCCCCTGGAGTGGTCCGCCGTGCTGCTGCACCTGATCAAGCACCGGGGCTACCTGTCCCAGCGGAAG<br>AACGAGGGCGAGACCGCCGACAAGGAGCTGGGCGCCCTGCTGAAGGGCGTGGCCGGCAACGCCCACGCCCTGCAGACCGGCGACTTC<br>CGGACCCCCGCCGAGCTGGCCCTGAACAAGTTCGAGAAGGAGTCCGGCCACATCCGGAACCAGCGGTCCGACTACTCCCACACCTTC<br>TCCCGGAAGGACCTGCAGGCCGAGCTGATCCTGCTGTTCGAGAAGCAGAAGGAGTTCGGCAACCCCCACGTGTCCGGCGGCCTGAAG<br>GAGGGCATCGAGACCCTGCTGATGACCCAGCGGCCCGCCCTGTCCGGCGACGCCGTGCAGAAGATGCTGGGCCACTGCACCTTCGAG<br>CCCGCCGAGCCCAAGGCCGCCAAGAACACCTACACCGCCGAGCGGTTCATCTGGCTGACCAAGCTGAACAACCTGCGGATCCTGGAG<br>CAGGGCTCCGAGCGGCCCCTGACCGACACCGAGCGGGCCACCCTGATGGACGAGCCCTACCGGAAGTCCAAGCTGACCTACGCCCAG<br>GCCCGGAAGCTGCTGGGCCTGGAGGACACCGCCTTCTTCAAGGGCCTGCGGTACGGCAAGGACAACGCCGAGGCCTCCACCCTGATG<br>GAGATGAAGGCCTACCACGCCATCTCCCGGGCCCTGGAGAAGGAGGGCCTGAAGGACAAGAAGTCCCCCCTGAACCTGTCCCCCGAG<br>CTGCAGGACGAGATCGGCACCGCCTTCTCCCTGTTCAAGACCGACGAGGACATCACCGGCCGGCTGAAGGACCGGATCCAGCCCGAG<br>ATCCTGGAGGCCCTGCTGAAGCACATCTCCTTCGACAAGTTCGTGCAGATCTCCCTGAAGGCCCTGCGGCGGATCGTGCCCCTGATG<br>GAGCAGGGCAAGCGGTACGACGAGGCCTGCGCCGAGATCTACGGCGACCACTACGGCAAGAAGAACACCGAGGAGAAGATCTACCTG<br>CCCCCCATCCCCGCCGACGAGATCCGGAACCCCGTGGTGCTGCGGGCCCTGTCCCAGGCCCGGAAGGTGATCAACGGCGTGGTGCGG<br>CGGTACGGCTCCCCCGCCCGGATCCACATCGAGACCGCCCGGGAGGTGGGCAAGTCCTTCAAGGACCGGAAGGAGATCGAGAAGCGG<br>CAGGAGGAGAACCGGAAGGACCGGGAGAAGGCCGCCGCCAAGTTCCGGGAGTACTTCCCCAACTTCGTGGGCGAGCCCAAGTCCAAG<br>GACATCCTGAAGCTGCGGCTGTACGAGCAGCAGCACGGCAAGTGCCTGTACTCCGGCAAGGAGATCAACCTGGGCCGGCTGAACGAG<br>AAGGGCTACGTGGAGATCGACCACGCCCTGCCCTTCTCCCGGACCTGGGACGACTCCTTCAACAACAAGGTGCTGGTGCTGGGCTCC<br>GAGAACCAGAACAAGGGCAACCAGACCCCCTACGAGTACTTCAACGGCAAGGACAACTCCCGGGAGTGGCAGGAGTTCAAGGCCCGG<br>GTGGAGACCTCCCGGTTCCCCCGGTCCAAGAAGCAGCGGATCCTGCTGCAGAAGTTCGACGAGGACGGCTTCAAGGAGCGGAACCTG<br>AACGACACCCGGTACGTGAACCGGTTCCTGTGCCAGTTCGTGGCCGACCGGATGCGGCTGACCGGCAAGGGCAAGAAGCGGGTGTTC<br>GCCTCCAACGGCCAGATCACCAACCTGCTGCGGGGCTTCTGGGGCCTGCGGAAGGTGCGGGCCGAGAACGACCGGCACCACGCCCTG<br>GACGCCGTGGTGGTGGCCTGCTCCACCGTGGCCATGCAGCAGAAGATCACCCGGTTCGTGCGGTACAAGGAGATGAACGCCTTCGAC<br>GGCAAGACCATCGACAAGGAGACCGGCGAGGTGCTGCACCAGAAGACCCACTTCCCCCAGCCCTGGGAGTTCTTCGCCCAGGAGGTG<br>ATGATCCGGGTGTTCGGCAAGCCCGACGGCAAGCCCGAGTTCGAGGAGGCCGACACCCTGGAGAAGCTGCGGACCCTGCTGGCCGAG<br>AAGCTGTCCTCCCGGCCCGAGGCCGTGCACGAGTACGTGACCCCCCTGTTCGTGTCCCGGGCCCCCAACCGGAAGATGTCCGGCCAG | 328 |

-continued

| Sequence Table | | |
|---|---|---|
| Description | Sequence | SEQ ID No. |
| | GGCCACATGGAGACCGTGAAGTCCGCCAAGCGGCTGGACGAGGGCGTGTCCGTGCTGCGGGTGCCCCTGACCCAGCTGAAGCTGAAG<br>GACCTGGAGAAGATGGTGAACCGGGAGCGGGAGCCCAAGCTGTACGAGGCCCTGAAGGCCCGGCTGGAGGCCCACAAGGACGACCCC<br>GCCAAGGCCTTCGCCGAGCCCTTCTACAAGTACGACAAGGCCGGCAACCGGACCCAGCAGGTGAAGGCCGTGCGGGTGGAGCAGGTG<br>CAGAAGACCGGCGTGTGGGTGCGGAACCACAACGGCATCGCCGACAACGCCACCATGGTGCGGGTGGACGTGTTCGAGAAGGGCGAC<br>AAGTACTACCTGGTGCCCATCTACTCCTGGCAGGTGGCCAAGGGCATCCTGCCCGACCGGGCCGTGGTGCAGGGCAAGGACGAGGAG<br>GACTGGCAGCTGATCGACGACTCCTTCAACTTCAAGTTCTCCCTGCACCCCAACGACCTGGTGGAGGTGATCACCAAGAAGGCCCGG<br>ATGTTCGGCTACTTCGCCTCCTGCCACCGGGGCACCGGCAACATCAACATCCGGATCCACGACCTGGACCACAAGATCGGCAAGAAC<br>GGCATCCTGGAGGGCATCGGCGTGAAGACCGCCCTGTCCTTCCAGAAGTACCAGATCGACGAGCTGGGCAAGGAGATCCGGCCCTGC<br>CGGCTGAAGAAGCGGCCCCCCGTGCGGTCCGGCAAGCGGACCGCCGACGGCTCCGAGTTCGAGTCCCCCAAGAAGAAGCGGAAGGTG<br>GAGTGA | |
| Nme Cas9 ORF using low A/U codons of Table 5, with start and stop codons | ATGGCCGCCTTCAAGCCCAACAGCATCAACTACATCCTGGGCCTGGACATCGGCATCGCCAGCGTGGGCTGGGCCATGGTGGAGATC<br>GACGAGGAGGAGAACCCCATCCGGCTGATCGACCTGGGCGTGCGGGTGTTCGAGCGGGCCGAGGTGCCCAAGACCGGCGACAGCCTG<br>GCCATGGCCCGGCGGCTGGCCCGGAGCGTGCGGCGGCTGACCCGGCGGCGGGCCCACCGGCTGCTGCGGACCCGGCGGCTGCTGAAG<br>CGGGAGGGCGTGCTGCAGGCCGCCAACTTCGACGAGAACGGCCTGATCAAGAGCCTGCCCAACACCCCCTGGCAGCTGCGGGCCGCC<br>GCCCTGGACCGGAAGCTGACCCCCCTGGAGTGGAGCGCCGTGCTGCTGCACCTGATCAAGCACCGGGGCTACCTGAGCCAGCGGAAG<br>AACGAGGGCGAGACCGCCGACAAGGAGCTGGGCGCCCTGCTGAAGGGCGTGGCCGGCAACGCCCACGCCCTGCAGACCGGCGACTTC<br>CGGACCCCCGCCGAGCTGGCCCTGAACAAGTTCGAGAAGGAGAGCGGCCACATCCGGAACCAGCGGAGCGACTACAGCCACACCTTC<br>AGCCGGAAGGACCTGCAGGCCGAGCTGATCCTGCTGTTCGAGAAGCAGAAGGAGTTCGGCAACCCCCACGTGAGCGGCGGCCTGAAG<br>GAGGGCATCGAGACCCTGCTGATGACCCAGCGGCCCGCCCTGAGCGGCGACGCCGTGCAGAAGATGCTGGGCCACTGCACCTTCGAG<br>CCCGCCGAGCCCAAGGCCGCCAAGAACACCTACACCGCCGAGCGGTTCATCTGGCTGACCAAGCTGAACAACCTGCGGATCCTGGAG<br>CAGGGCAGCGAGCGGCCCCTGACCGACACCGAGCGGGCCACCCTGATGGACGAGCCCTACCGGAAGAGCAAGCTGACCTACGCCCAG<br>GCCCGGAAGCTGCTGGGCCTGGAGGACACCGCCTTCTTCAAGGGCCTGCGGTACGGCAAGGACAACGCCGAGGCCAGCACCCTGATG<br>GAGATGAAGGCCTACCACGCCATCAGCCGGGCCCTGGAGAAGGAGGGCCTGAAGGACAAGAAGAGCCCCCTGAACCTGAGCCCCGAG<br>CTGCAGGACGAGATCGGCACCGCCTTCAGCCTGTTCAAGACCGACGAGGACATCACCGGCCGGCTGAAGGACCGGATCCAGCCCGAG<br>ATCCTGGAGGCCCTGCTGAAGCACATCAGCTTCGACAAGTTCGTGCAGATCAGCCTGAAGGCCCTGCGGCGGATCGTGCCCCTGATG<br>GAGCAGGGCAAGCGGTACGACGAGGCCTGCGCCGAGATCTACGGCGACCACTACGGCAAGAAGAACACCGAGGAGAAGATCTACCTG<br>CCCCCCATCCCCGCCGACGAGATCCGGAACCCCGTGGTGCTGCGGGCCCTGAGCCAGGCCCGGAAGGTGATCAACGGCGTGGTGCGG<br>CGGTACGGCAGCCCCGCCCGGATCCACATCGAGACCGCCCGGGAGGTGGGCAAGAGCTTCAAGGACCGGAAGGAGATCGAGAAGCGG<br>CAGGAGGAGAACCGGAAGGACCGGGAGAAGGCCGCCGCCAAGTTCCGGGAGTACTTCCCCAACTTCGTGGGCGAGCCCAAGAGCAAG<br>GACATCCTGAAGCTGCGGCTGTACGAGCAGCAGCACGGCAAGTGCCTGTACAGCGGCAAGGAGATCAACCTGGGCCGGCTGAACGAG<br>AAGGGCTACGTGGAGATCGACCACGCCCTGCCCTTCAGCCGGACCTGGGACGACAGCTTCAACAACAAGGTGCTGGTGCTGGGCAGC<br>GAGAACCAGAACAAGGGCAACCAGACCCCCTACGAGTACTTCAACGGCAAGGACAACAGCCGGGAGTGGCAGGAGTTCAAGGCCCGG<br>GTGGAGACCAGCCGGTTCCCCCGGAGCAAGAAGCAGCGGATCCTGCTGCAGAAGTTCGACGAGGACGGCTTCAAGGAGCGGAACCTG<br>AACGACACCCGGTACGTGAACCGGTTCCTGTGCCAGTTCGTGGCCGACCGGATGCGGCTGACCGGCAAGGGCAAGAAGCGGGTGTTC<br>GCCAGCAACGGCCAGATCACCAACCTGCTGCGGGGCTTCTGGGGCCTGCGGAAGGTGCGGGCCGAGAACGACCGGCACCACGCCCTG<br>GACGCCGTGGTGGTGGCCTGCAGCACCGTGGCCATGCAGCAGAAGATCACCCGGTTCGTGCGGTACAAGGAGATGAACGCCTTCGAC<br>GGCAAGACCATCGACAAGGAGACCGGCGAGGTGCTGCACCAGAAGACCCACTTCCCCCAGCCCTGGGAGTTCTTCGCCCAGGAGGTG<br>ATGATCCGGGTGTTCGGCAAGCCCGACGGCAAGCCCGAGTTCGAGGAGGCCGACACCCTGGAGAAGCTGCGGACCCTGCTGGCCGAG<br>AAGCTGAGCAGCCGGCCCGAGGCCGTGCACGAGTACGTGACCCCCCTGTTCGTGAGCCGGGCCCCCAACCGGAAGATGAGCGGCCAG<br>GGCCACATGGAGACCGTGAAGAGCGCCAAGCGGCTGGACGAGGGCGTGAGCGTGCTGCGGGTGCCCCTGACCCAGCTGAAGCTGAAG<br>GACCTGGAGAAGATGGTGAACCGGGAGCGGGAGCCCAAGCTGTACGAGGCCCTGAAGGCCCGGCTGGAGGCCCACAAGGACGACCCC<br>GCCAAGGCCTTCGCCGAGCCCTTCTACAAGTACGACAAGGCCGGCAACCGGACCCAGCAGGTGAAGGCCGTGCGGGTGGAGCAGGTG<br>CAGAAGACCGGCGTGTGGGTGCGGAACCACAACGGCATCGCCGACAACGCCACCATGGTGCGGGTGGACGTGTTCGAGAAGGGCGAC<br>AAGTACTACCTGGTGCCCATCTACAGCTGGCAGGTGGCCAAGGGCATCCTGCCCGACCGGGCCGTGGTGCAGGGCAAGGACGAGGAG<br>GACTGGCAGCTGATCGACGACAGCTTCAACTTCAAGTTCAGCCTGCACCCCAACGACCTGGTGGAGGTGATCACCAAGAAGGCCCGG<br>ATGTTCGGCTACTTCGCCAGCTGCCACCGGGGCACCGGCAACATCAACATCCGGATCCACGACCTGGACCACAAGATCGGCAAGAAC<br>GGCATCCTGGAGGGCATCGGCGTGAAGACCGCCCTGAGCTTCCAGAAGTACCAGATCGACGAGCTGGGCAAGGAGATCCGGCCCTGC<br>CGGCTGAAGAAGCGGCCCCCCGTGCGGAGCGGCAAGCGGACCGCCGACGGCAGCGAGTTCGAGAGCCCCAAGAAGAAGCGGAAGGTG | 329 |

-continued

| Sequence Table | | |
|---|---|---|
| Description | Sequence | SEQ ID No. |
| | GAGTGA | |
| | Not Used | 330-345 |
| Cas9 ORF using low A codons of Table 5 (no start or stop codons; suitable for inclusion in fusion protein coding sequence) | GACAAGAAGTACTCCATCGGCCTGGACATCGGCACCAACTCCGTGGGCTGGGCCGTGATCACCGACGAGTACAAGGTGCCCTCCAAG<br>AAGTTCAAGGTGCTGGGCAACACCGACCGGCACTCCATCAAGAAGAACCTGATCGGCGCCCTGCTGTTCGACTCCGGCGAGACCGCC<br>GAGGCCACCCGGCTGAAGCGGACCGCCCGGCGGCGGTACACCCGGCGGAAGAACCGGATCTGCTACCTGCAGGAGATCTTCTCCAAC<br>GAGATGGCCAAGGTGGACGACTCCTTCTTCCACCGGCTGGAGGAGTCCTTCCTGGTGGAGGAGGACAAGAAGCACGAGCGGCACCCC<br>ATCTTCGGCAACATCGTGGACGAGGTGGCCTACCACGAGAAGTACCCCACCATCTACCACCTGCGGAAGAAGCTGGTGGACTCCACC<br>GACAAGGCCGACCTGCGGCTGATCTACCTGGCCCTGGCCCACATGATCAAGTTCCGGGGCCACTTCCTGATCGAGGGCGACCTGAAC<br>CCCGACAACTCCGACGTGGACAAGCTGTTCATCCAGCTGGTGCAGACCTACAACCAGCTGTTCGAGGAGAACCCCATCAACGCCTCC<br>GGCGTGGACGCCAAGGCCATCCTGTCCGCCCGGCTGTCCAAGTCCCGGCGGCTGGAGAACCTGATCGCCCAGCTGCCCGGCGAGAAG<br>AAGAACGGCCTGTTCGGCAACCTGATCGCCCTGTCCCTGGGCCTGACCCCCAACTTCAAGTCCAACTTCGACCTGGCCGAGGACGCC<br>AAGCTGCAGCTGTCCAAGGACACCTACGACGACGACCTGGACAACCTGCTGGCCCAGATCGGCGACCAGTACGCCGACCTGTTCCTG<br>GCCGCCAAGAACCTGTCCGACGCCATCCTGCTGTCCGACATCCTGCGGGTGAACACCGAGATCACCAAGGCCCCCCTGTCCGCCTCC<br>ATGATCAAGCGGTACGACGAGCACCACCAGGACCTGACCCTGCTGAAGGCCCTGGTGCGGCAGCAGCTGCCCGAGAAGTACAAGGAG<br>ATCTTCTTCGACCAGTCCAAGAACGGCTACGCCGGCTACATCGACGGCGGCGCCTCCCAGGAGGAGTTCTACAAGTTCATCAAGCCC<br>ATCCTGGAGAAGATGGACGGCACCGAGGAGCTGCTGGTGAAGCTGAACCGGGAGGACCTGCTGCGGAAGCAGCGGACCTTCGACAAC<br>GGCTCCATCCCCCACCAGATCCACCTGGGCGAGCTGCACGCCATCCTGCGGCGGCAGGAGGACTTCTACCCCTTCCTGAAGGACAAC<br>CGGGAGAAGATCGAGAAGATCCTGACCTTCCGGATCCCCTACTACGTGGGCCCCCTGGCCCGGGGCAACTCCCGGTTCGCCTGGATG<br>ACCCGGAAGTCCGAGGAGACCATCACCCCCTGGAACTTCGAGGAGGTGGTGGACAAGGGCGCCTCCGCCCAGTCCTTCATCGAGCGG<br>ATGACCAACTTCGACAAGAACCTGCCCAACGAGAAGGTGCTGCCCAAGCACTCCCTGCTGTACGAGTACTTCACCGTGTACAACGAG<br>CTGACCAAGGTGAAGTACGTGACCGAGGGCATGCGGAAGCCCGCCTTCCTGTCCGGCGAGCAGAAGAAGGCCATCGTGGACCTGCTG<br>TTCAAGACCAACCGGAAGGTGACCGTGAAGCAGCTGAAGGAGGACTACTTCAAGAAGATCGAGTGCTTCGACTCCGTGGAGATCTCC<br>GGCGTGGAGGACCGGTTCAACGCCTCCCTGGGCACCTACCACGACCTGCTGAAGATCATCAAGGACAAGGACTTCCTGGACAACGAG<br>GAGAACGAGGACATCCTGGAGGACATCGTGCTGACCCTGACCCTGTTCGAGGACCGGGAGATGATCGAGGAGCGGCTGAAGACCTAC<br>GCCCACCTGTTCGACGACAAGGTGATGAAGCAGCTGAAGCGGCGGCGGTACACCGGCTGGGGCCGGCTGTCCCGGAAGCTGATCAAC<br>GGCATCCGGGACAAGCAGTCCGGCAAGACCATCCTGGACTTCCTGAAGTCCGACGGCTTCGCCAACCGGAACTTCATGCAGCTGATC<br>CACGACGACTCCCTGACCTTCAAGGAGGACATCCAGAAGGCCCAGGTGTCCGGCCAGGGCGACTCCCTGCACGAGCACATCGCCAAC<br>CTGGCCGGCTCCCCCGCCATCAAGAAGGGCATCCTGCAGACCGTGAAGGTGGTGGACGAGCTGGTGAAGGTGATGGGCCGGCACAAG<br>CCCGAGAACATCGTGATCGAGATGGCCCGGGAGAACCAGACCACCCAGAAGGGCCAGAAGAACTCCCGGGAGCGGATGAAGCGGATC<br>GAGGAGGGCATCAAGGAGCTGGGCTCCCAGATCCTGAAGGAGCACCCCGTGGAGAACACCCAGCTGCAGAACGAGAAGCTGTACCTG<br>TACTACCTGCAGAACGGCCGGGACATGTACGTGGACCAGGAGCTGGACATCAACCGGCTGTCCGACTACGACGTGGACCACATCGTG<br>CCCCAGTCCTTCCTGAAGGACGACTCCATCGACAACAAGGTGCTGACCCGGTCCGACAAGAACCGGGGCAAGTCCGACAACGTGCCC<br>TCCGAGGAGGTGGTGAAGAAGATGAAGAACTACTGGCGGCAGCTGCTGAACGCCAAGCTGATCACCCAGCGGAAGTTCGACAACCTG<br>ACCAAGGCCGAGCGGGGCGGCCTGTCCGAGCTGGACAAGGCCGGCTTCATCAAGCGGCAGCTGGTGGAGACCCGGCAGATCACCAAG<br>CACGTGGCCCAGATCCTGGACTCCCGGATGAACACCAAGTACGACGAGAACGACAAGCTGATCCGGGAGGTGAAGGTGATCACCCTG<br>AAGTCCAAGCTGGTGTCCGACTTCCGGAAGGACTTCCAGTTCTACAAGGTGCGGGAGATCAACAACTACCACCACGCCCACGACGCC<br>TACCTGAACGCCGTGGTGGGCACCGCCCTGATCAAGAAGTACCCCAAGCTGGAGTCCGAGTTCGTGTACGGCGACTACAAGGTGTAC<br>GACGTGCGGAAGATGATCGCCAAGTCCGAGCAGGAGATCGGCAAGGCCACCGCCAAGTACTTCTTCTACTCCAACATCATGAACTTC<br>TTCAAGACCGAGATCACCCTGGCCAACGGCGAGATCCGGAAGCGGCCCCTGATCGAGACCAACGGCGAGACCGGCGAGATCGTGTGG<br>GACAAGGGCCGGGACTTCGCCACCGTGCGGAAGGTGCTGTCCATGCCCCAGGTGAACATCGTGAAGAAGACCGAGGTGCAGACCGGC<br>GGCTTCTCCAAGGAGTCCATCCTGCCCAAGCGGAACTCCGACAAGCTGATCGCCCGGAAGAAGGACTGGGACCCCAAGAAGTACGGC<br>GGCTTCGACTCCCCCACCGTGGCCTACTCCGTGCTGGTGGTGGCCAAGGTGGAGAAGGGCAAGTCCAAGAAGCTGAAGTCCGTGAAG<br>GAGCTGCTGGGCATCACCATCATGGAGCGGTCCTCCTTCGAGAAGAACCCCATCGACTTCCTGGAGGCCAAGGGCTACAAGGAGGTG<br>AAGAAGGACCTGATCATCAAGCTGCCCAAGTACTCCCTGTTCGAGCTGGAGAACGGCCGGAAGCGGATGCTGGCCTCCGCCGGCGAG<br>CTGCAGAAGGGCAACGAGCTGGCCCTGCCCTCCAAGTACGTGAACTTCCTGTACCTGGCCTCCCACTACGAGAAGCTGAAGGGCTCC<br>CCCGAGGACAACGAGCAGAAGCAGCTGTTCGTGGAGCAGCACAAGCACTACCTGGACGAGATCATCGAGCAGATCTCCGAGTTCTCC<br>AAGCGGGTGATCCTGGCCGACGCCAACCTGGACAAGGTGCTGTCCGCCTACAACAAGCACCGGGACAAGCCCATCCGGGAGCAGGCC | 346 |

-continued

Sequence Table

| Description | Sequence | SEQ ID No. |
|---|---|---|
| | GAGAACATCATCCACCTGTTCACCCTGACCAACCTGGGCGCCCCCGCCGCCTTCAAGTACTTCGACACCACCATCGACCGGAAGCGG<br>TACACCTCCACCAAGGAGGTGCTGGACGCCACCCTGATCCACCAGTCCATCACCGGCCTGTACGAGACCCGGATCGACCTGTCCCAG<br>CTGGGCGGCGACGGCGGCGGCTCCCCCAAGAAGAAGCGGAAGGTG | |
| Cas9 ORF using low A/U codons of Table 5 (no start or stop codons; suitable for inclusion in fusion protein coding sequence) | GACAAGAAGTACAGCATCGGCCTGGACATCGGCACCAACAGCGTGGGCTGGGCCGTGATCACCGACGAGTACAAGGTGCCCAGCAAG<br>AAGTTCAAGGTGCTGGGCAACACCGACCGGCACAGCATCAAGAAGAACCTGATCGGCGCCCTGCTGTTCGACAGCGGCGAGACCGCC<br>GAGGCCACCCGGCTGAAGCGGACCGCCCGGCGGCGGTACACCCGGCGGAAGAACCGGATCTGCTACCTGCAGGAGATCTTCAGCAAC<br>GAGATGGCCAAGGTGGACGACAGCTTCTTCCACCGGCTGGAGGAGAGCTTCCTGGTGGAGGAGGACAAGAAGCACGAGCGGCACCCC<br>ATCTTCGGCAACATCGTGGACGAGGTGGCCTACCACGAGAAGTACCCCACCATCTACCACCTGCGGAAGAAGCTGGTGGACAGCACC<br>GACAAGGCCGACCTGCGGCTGATCTACCTGGCCCTGGCCCACATGATCAAGTTCCGGGGCCACTTCCTGATCGAGGGCGACCTGAAC<br>CCCGACAACAGCGACGTGGACAAGCTGTTCATCCAGCTGGTGCAGACCTACAACCAGCTGTTCGAGGAGAACCCCATCAACGCCAGC<br>GGCGTGGACGCCAAGGCCATCCTGAGCGCCCGGCTGAGCAAGAGCCGGCGGCTGGAGAACCTGATCGCCCAGCTGCCCGGCGAGAAG<br>AAGAACGGCCTGTTCGGCAACCTGATCGCCCTGAGCCTGGGCCTGACCCCCAACTTCAAGAGCAACTTCGACCTGGCCGAGGACGCC<br>AAGCTGCAGCTGAGCAAGGACACCTACGACGACGACCTGGACAACCTGCTGGCCCAGATCGGCGACCAGTACGCCGACCTGTTCCTG<br>GCCGCCAAGAACCTGAGCGACGCCATCCTGCTGAGCGACATCCTGCGGGTGAACACCGAGATCACCAAGGCCCCCCTGAGCGCCAGC<br>ATGATCAAGCGGTACGACGAGCACCACCAGGACCTGACCCTGCTGAAGGCCCTGGTGCGGCAGCAGCTGCCCGAGAAGTACAAGGAG<br>ATCTTCTTCGACCAGAGCAAGAACGGCTACGCCGGCTACATCGACGGCGGCGCCAGCCAGGAGGAGTTCTACAAGTTCATCAAGCCC<br>ATCCTGGAGAAGATGGACGGCACCGAGGAGCTGCTGGTGAAGCTGAACCGGGAGGACCTGCTGCGGAAGCAGCGGACCTTCGACAAC<br>GGCAGCATCCCCCACCAGATCCACCTGGGCGAGCTGCACGCCATCCTGCGGCGGCAGGAGGACTTCTACCCCTTCCTGAAGGACAAC<br>CGGGAGAAGATCGAGAAGATCCTGACCTTCCGGATCCCCTACTACGTGGGCCCCCTGGCCCGGGGCAACAGCCGGTTCGCCTGGATG<br>ACCCGGAAGAGCGAGGAGACCATCACCCCCTGGAACTTCGAGGAGGTGGTGGACAAGGGCGCCAGCGCCCAGAGCTTCATCGAGCGG<br>ATGACCAACTTCGACAAGAACCTGCCCAACGAGAAGGTGCTGCCCAAGCACAGCCTGCTGTACGAGTACTTCACCGTGTACAACGAG<br>CTGACCAAGGTGAAGTACGTGACCGAGGGCATGCGGAAGCCCGCCTTCCTGAGCGGCGAGCAGAAGAAGGCCATCGTGGACCTGCTG<br>TTCAAGACCAACCGGAAGGTGACCGTGAAGCAGCTGAAGGAGGACTACTTCAAGAAGATCGAGTGCTTCGACAGCGTGGAGATCAGC<br>GGCGTGGAGGACCGGTTCAACGCCAGCCTGGGCACCTACCACGACCTGCTGAAGATCATCAAGGACAAGGACTTCCTGGACAACGAG<br>GAGAACGAGGACATCCTGGAGGACATCGTGCTGACCCTGACCCTGTTCGAGGACCGGGAGATGATCGAGGAGCGGCTGAAGACCTAC<br>GCCCACCTGTTCGACGACAAGGTGATGAAGCAGCTGAAGCGGCGGCGGTACACCGGCTGGGGCCGGCTGAGCCGGAAGCTGATCAAC<br>GGCATCCGGGACAAGCAGAGCGGCAAGACCATCCTGGACTTCCTGAAGAGCGACGGCTTCGCCAACCGGAACTTCATGCAGCTGATC<br>CACGACGACAGCCTGACCTTCAAGGAGGACATCCAGAAGGCCCAGGTGAGCGGCCAGGGCGACAGCCTGCACGAGCACATCGCCAAC<br>CTGGCCGGCAGCCCCGCCATCAAGAAGGGCATCCTGCAGACCGTGAAGGTGGTGGACGAGCTGGTGAAGGTGATGGGCCGGCACAAG<br>CCCGAGAACATCGTGATCGAGATGGCCCGGGAGAACCAGACCACCCAGAAGGGCCAGAAGAACAGCCGGGAGCGGATGAAGCGGATC<br>GAGGAGGGCATCAAGGAGCTGGGCAGCCAGATCCTGAAGGAGCACCCCGTGGAGAACACCCAGCTGCAGAACGAGAAGCTGTACCTG<br>TACTACCTGCAGAACGGCCGGGACATGTACGTGGACCAGGAGCTGGACATCAACCGGCTGAGCGACTACGACGTGGACCACATCGTG<br>CCCCAGAGCTTCCTGAAGGACGACAGCATCGACAACAAGGTGCTGACCCGGAGCGACAAGAACCGGGGCAAGAGCGACAACGTGCCC<br>AGCGAGGAGGTGGTGAAGAAGATGAAGAACTACTGGCGGCAGCTGCTGAACGCCAAGCTGATCACCCAGCGGAAGTTCGACAACCTG<br>ACCAAGGCCGAGCGGGGCGGCCTGAGCGAGCTGGACAAGGCCGGCTTCATCAAGCGGCAGCTGGTGGAGACCCGGCAGATCACCAAG<br>CACGTGGCCCAGATCCTGGACAGCCGGATGAACACCAAGTACGACGAGAACGACAAGCTGATCCGGGAGGTGAAGGTGATCACCCTG<br>AAGAGCAAGCTGGTGAGCGACTTCCGGAAGGACTTCCAGTTCTACAAGGTGCGGGAGATCAACAACTACCACCACGCCCACGACGCC<br>TACCTGAACGCCGTGGTGGGCACCGCCCTGATCAAGAAGTACCCCAAGCTGGAGAGCGAGTTCGTGTACGGCGACTACAAGGTGTAC<br>GACGTGCGGAAGATGATCGCCAAGAGCGAGCAGGAGATCGGCAAGGCCACCGCCAAGTACTTCTTCTACAGCAACATCATGAACTTC<br>TTCAAGACCGAGATCACCCTGGCCAACGGCGAGATCCGGAAGCGGCCCCTGATCGAGACCAACGGCGAGACCGGCGAGATCGTGTGG<br>GACAAGGGCCGGGACTTCGCCACCGTGCGGAAGGTGCTGAGCATGCCCCAGGTGAACATCGTGAAGAAGACCGAGGTGCAGACCGGC<br>GGCTTCAGCAAGGAGAGCATCCTGCCCAAGCGGAACAGCGACAAGCTGATCGCCCGGAAGAAGGACTGGGACCCCAAGAAGTACGGC<br>GGCTTCGACAGCCCCACCGTGGCCTACAGCGTGCTGGTGGTGGCCAAGGTGGAGAAGGGCAAGAGCAAGAAGCTGAAGAGCGTGAAG<br>GAGCTGCTGGGCATCACCATCATGGAGCGGAGCAGCTTCGAGAAGAACCCCATCGACTTCCTGGAGGCCAAGGGCTACAAGGAGGTG<br>AAGAAGGACCTGATCATCAAGCTGCCCAAGTACAGCCTGTTCGAGCTGGAGAACGGCCGGAAGCGGATGCTGGCCAGCGCCGGCGAG<br>CTGCAGAAGGGCAACGAGCTGGCCCTGCCCAGCAAGTACGTGAACTTCCTGTACCTGGCCAGCCACTACGAGAAGCTGAAGGGCAGC<br>CCCGAGGACAACGAGCAGAAGCAGCTGTTCGTGGAGCAGCACAAGCACTACCTGGACGAGATCATCGAGCAGATCAGCGAGTTCAGC<br>AAGCGGGTGATCCTGGCCGACGCCAACCTGGACAAGGTGCTGAGCGCCTACAACAAGCACCGGGACAAGCCCATCCGGGAGCAGGCC | 347 |

-continued

Sequence Table

| Description | Sequence | SEQ ID No. |
|---|---|---|
| | GAGAACATCATCCACCTGTTCACCCTGACCAACCTGGGCGCCCCCGCCGCCTTCAAGTACTTCGACACCACCATCGACCGGAAGCGG<br>TACACCAGCACCAAGGAGGTGCTGGACGCCACCCTGATCCACCAGAGCATCACCGGCCTGTACGAGACCCGGATCGACCTGAGCCAG<br>CTGGGCGGCGACGGCGGCGGCAGCCCCAAGAAGAAGCGGAAGGTG | |
| Cas9 ORF using low A codons of Table 5, with two C-terminal NLS sequences (no start or stop codons; suitable for inclusion in fusion protein coding sequence) | GACAAGAAGTACTCCATCGGCCTGGACATCGGCACCAACTCCGTGGGCTGGGCCGTGATCACCGACGAGTACAAGGTGCCCTCCAAG<br>AAGTTCAAGGTGCTGGGCAACACCGACCGGCACTCCATCAAGAAGAACCTGATCGGCGCCCTGCTGTTCGACTCCGGCGAGACCGCC<br>GAGGCCACCCGGCTGAAGCGGACCGCCCGGCGGCGGTACACCCGGCGGAAGAACCGGATCTGCTACCTGCAGGAGATCTTCTCCAAC<br>GAGATGGCCAAGGTGGACGACTCCTTCTTCCACCGGCTGGAGGAGTCCTTCCTGGTGGAGGAGGACAAGAAGCACGAGCGGCACCCC<br>ATCTTCGGCAACATCGTGGACGAGGTGGCCTACCACGAGAAGTACCCCACCATCTACCACCTGCGGAAGAAGCTGGTGGACTCCACC<br>GACAAGGCCGACCTGCGGCTGATCTACCTGGCCCTGGCCCACATGATCAAGTTCCGGGGCCACTTCCTGATCGAGGGCGACCTGAAC<br>CCCGACAACTCCGACGTGGACAAGCTGTTCATCCAGCTGGTGCAGACCTACAACCAGCTGTTCGAGGAGAACCCCATCAACGCCTCC<br>GGCGTGGACGCCAAGGCCATCCTGTCCGCCCGGCTGTCCAAGTCCCGGCGGCTGGAGAACCTGATCGCCCAGCTGCCCGGCGAGAAG<br>AAGAACGGCCTGTTCGGCAACCTGATCGCCCTGTCCCTGGGCCTGACCCCCAACTTCAAGTCCAACTTCGACCTGGCCGAGGACGCC<br>AAGCTGCAGCTGTCCAAGGACACCTACGACGACGACCTGGACAACCTGCTGGCCCAGATCGGCGACCAGTACGCCGACCTGTTCCTG<br>GCCGCCAAGAACCTGTCCGACGCCATCCTGCTGTCCGACATCCTGCGGGTGAACACCGAGATCACCAAGGCCCCCCTGTCCGCCTCC<br>ATGATCAAGCGGTACGACGAGCACCACCAGGACCTGACCCTGCTGAAGGCCCTGGTGCGGCAGCAGCTGCCCGAGAAGTACAAGGAG<br>ATCTTCTTCGACCAGTCCAAGAACGGCTACGCCGGCTACATCGACGGCGGCGCCTCCCAGGAGGAGTTCTACAAGTTCATCAAGCCC<br>ATCCTGGAGAAGATGGACGGCACCGAGGAGCTGCTGGTGAAGCTGAACCGGGAGGACCTGCTGCGGAAGCAGCGGACCTTCGACAAC<br>GGCTCCATCCCCCACCAGATCCACCTGGGCGAGCTGCACGCCATCCTGCGGCGGCAGGAGGACTTCTACCCCTTCCTGAAGGACAAC<br>CGGGAGAAGATCGAGAAGATCCTGACCTTCCGGATCCCCTACTACGTGGGCCCCCTGGCCCGGGGCAACTCCCGGTTCGCCTGGATG<br>ACCCGGAAGTCCGAGGAGACCATCACCCCCTGGAACTTCGAGGAGGTGGTGGACAAGGGCGCCTCCGCCCAGTCCTTCATCGAGCGG<br>ATGACCAACTTCGACAAGAACCTGCCCAACGAGAAGGTGCTGCCCAAGCACTCCCTGCTGTACGAGTACTTCACCGTGTACAACGAG<br>CTGACCAAGGTGAAGTACGTGACCGAGGGCATGCGGAAGCCCGCCTTCCTGTCCGGCGAGCAGAAGAAGGCCATCGTGGACCTGCTG<br>TTCAAGACCAACCGGAAGGTGACCGTGAAGCAGCTGAAGGAGGACTACTTCAAGAAGATCGAGTGCTTCGACTCCGTGGAGATCTCC<br>GGCGTGGAGGACCGGTTCAACGCCTCCCTGGGCACCTACCACGACCTGCTGAAGATCATCAAGGACAAGGACTTCCTGGACAACGAG<br>GAGAACGAGGACATCCTGGAGGACATCGTGCTGACCCTGACCCTGTTCGAGGACCGGGAGATGATCGAGGAGCGGCTGAAGACCTAC<br>GCCCACCTGTTCGACGACAAGGTGATGAAGCAGCTGAAGCGGCGGCGGTACACCGGCTGGGGCCGGCTGTCCCGGAAGCTGATCAAC<br>GGCATCCGGGACAAGCAGTCCGGCAAGACCATCCTGGACTTCCTGAAGTCCGACGGCTTCGCCAACCGGAACTTCATGCAGCTGATC<br>CACGACGACTCCCTGACCTTCAAGGAGGACATCCAGAAGGCCCAGGTGTCCGGCCAGGGCGACTCCCTGCACGAGCACATCGCCAAC<br>CTGGCCGGCTCCCCCGCCATCAAGAAGGGCATCCTGCAGACCGTGAAGGTGGTGGACGAGCTGGTGAAGGTGATGGGCCGGCACAAG<br>CCCGAGAACATCGTGATCGAGATGGCCCGGGAGAACCAGACCACCCAGAAGGGCCAGAAGAACTCCCGGGAGCGGATGAAGCGGATC<br>GAGGAGGGCATCAAGGAGCTGGGCTCCCAGATCCTGAAGGAGCACCCCGTGGAGAACACCCAGCTGCAGAACGAGAAGCTGTACCTG<br>TACTACCTGCAGAACGGCCGGGACATGTACGTGGACCAGGAGCTGGACATCAACCGGCTGTCCGACTACGACGTGGACCACATCGTG<br>CCCCAGTCCTTCCTGAAGGACGACTCCATCGACAACAAGGTGCTGACCCGGTCCGACAAGAACCGGGGCAAGTCCGACAACGTGCCC<br>TCCGAGGAGGTGGTGAAGAAGATGAAGAACTACTGGCGGCAGCTGCTGAACGCCAAGCTGATCACCCAGCGGAAGTTCGACAACCTG<br>ACCAAGGCCGAGCGGGGCGGCCTGTCCGAGCTGGACAAGGCCGGCTTCATCAAGCGGCAGCTGGTGGAGACCCGGCAGATCACCAAG<br>CACGTGGCCCAGATCCTGGACTCCCGGATGAACACCAAGTACGACGAGAACGACAAGCTGATCCGGGAGGTGAAGGTGATCACCCTG<br>AAGTCCAAGCTGGTGTCCGACTTCCGGAAGGACTTCCAGTTCTACAAGGTGCGGGAGATCAACAACTACCACCACGCCCACGACGCC<br>TACCTGAACGCCGTGGTGGGCACCGCCCTGATCAAGAAGTACCCCAAGCTGGAGTCCGAGTTCGTGTACGGCGACTACAAGGTGTAC<br>GACGTGCGGAAGATGATCGCCAAGTCCGAGCAGGAGATCGGCAAGGCCACCGCCAAGTACTTCTTCTACTCCAACATCATGAACTTC<br>TTCAAGACCGAGATCACCCTGGCCAACGGCGAGATCCGGAAGCGGCCCCTGATCGAGACCAACGGCGAGACCGGCGAGATCGTGTGG<br>GACAAGGGCCGGGACTTCGCCACCGTGCGGAAGGTGCTGTCCATGCCCCAGGTGAACATCGTGAAGAAGACCGAGGTGCAGACCGGC<br>GGCTTCTCCAAGGAGTCCATCCTGCCCAAGCGGAACTCCGACAAGCTGATCGCCCGGAAGAAGGACTGGGACCCCAAGAAGTACGGC<br>GGCTTCGACTCCCCCACCGTGGCCTACTCCGTGCTGGTGGTGGCCAAGGTGGAGAAGGGCAAGTCCAAGAAGCTGAAGTCCGTGAAG<br>GAGCTGCTGGGCATCACCATCATGGAGCGGTCCTCCTTCGAGAAGAACCCCATCGACTTCCTGGAGGCCAAGGGCTACAAGGAGGTG<br>AAGAAGGACCTGATCATCAAGCTGCCCAAGTACTCCCTGTTCGAGCTGGAGAACGGCCGGAAGCGGATGCTGGCCTCCGCCGGCGAG<br>CTGCAGAAGGGCAACGAGCTGGCCCTGCCCTCCAAGTACGTGAACTTCCTGTACCTGGCCTCCCACTACGAGAAGCTGAAGGGCTCC<br>CCCGAGGACAACGAGCAGAAGCAGCTGTTCGTGGAGCAGCACAAGCACTACCTGGACGAGATCATCGAGCAGATCTCCGAGTTCTCC<br>AAGCGGGTGATCCTGGCCGACGCCAACCTGGACAAGGTGCTGTCCGCCTACAACAAGCACCGGGACAAGCCCATCCGGGAGCAGGCC | 348 |

-continued

Sequence Table

| Description | Sequence | SEQ ID No. |
|---|---|---|
| | GAGAACATCATCCACCTGTTCACCCTGACCAACCTGGGCGCCCCCGCCGCCTTCAAGTACTTCGACACCACCATCGACCGGAAGCGG | |
| | TACACCTCCACCAAGGAGGTGCTGGACGCCACCCTGATCCACCAGTCCATCACCGGCCTGTACGAGACCCGGATCGACCTGTCCCAG | |
| | CTGGGCGGCGACGGCTCCGGCTCCCCCAAGAAGAAGCGGAAGGTGGACGGCTCCCCCAAGAAGAAGCGGAAGGTGGACTCCGGC | |
| | Not Used | 349-355 |
| Cas9 ORF | GACAAGAAGTACAGCATCGGCCTGGACATCGGCACCAACAGCGTGGGCTGGGCCGTGATCACCGACGAGTACAAGGTGCCCAGCAAG | 355 |
| using low | AAGTTCAAGGTGCTGGGCAACACCGACCGGCACAGCATCAAGAAGAACCTGATCGGCGCCCTGCTGTTCGACAGCGGCGAGACCGCC | |
| A/U codons | GAGGCCACCCGGCTGAAGCGGACCGCCCGGCGGCGGTACACCCGGCGGAAGAACCGGATCTGCTACCTGCAGGAGATCTTCAGCAAC | |
| of Table 4, | GAGATGGCCAAGGTGGACGACAGCTTCTTCCACCGGCTGGAGGAGAGCTTCCTGGTGGAGGAGGACAAGAAGCACGAGCGGCACCCC | |
| with two C- | ATCTTCGGCAACATCGTGGACGAGGTGGCCTACCACGAGAAGTACCCCACCATCTACCACCTGCGGAAGAAGCTGGTGGACAGCACC | |
| terminal | GACAAGGCCGACCTGCGGCTGATCTACCTGGCCCTGGCCCACATGATCAAGTTCCGGGGCCACTTCCTGATCGAGGGCGACCTGAAC | |
| NLS | CCCGACAACAGCGACGTGGACAAGCTGTTCATCCAGCTGGTGCAGACCTACAACCAGCTGTTCGAGGAGAACCCCATCAACGCCAGC | |
| sequences | GGCGTGGACGCCAAGGCCATCCTGAGCGCCCGGCTGAGCAAGAGCCGGCGGCTGGAGAACCTGATCGCCCAGCTGCCCGGCGAGAAG | |
| (no start | AAGAACGGCCTGTTCGGCAACCTGATCGCCCTGAGCCTGGGCCTGACCCCCAACTTCAAGAGCAACTTCGACCTGGCCGAGGACGCC | |
| or stop | AAGCTGCAGCTGAGCAAGGACACCTACGACGACGACCTGGACAACCTGCTGGCCCAGATCGGCGACCAGTACGCCGACCTGTTCCTG | |
| codons; | GCCGCCAAGAACCTGAGCGACGCCATCCTGCTGAGCGACATCCTGCGGGTGAACACCGAGATCACCAAGGCCCCCCTGAGCGCCAGC | |
| suitable | ATGATCAAGCGGTACGACGAGCACCACCAGGACCTGACCCTGCTGAAGGCCCTGGTGCGGCAGCAGCTGCCCGAGAAGTACAAGGAG | |
| for | ATCTTCTTCGACCAGAGCAAGAACGGCTACGCCGGCTACATCGACGGCGGCGCCAGCCAGGAGGAGTTCTACAAGTTCATCAAGCCC | |
| inclusion | ATCCTGGAGAAGATGGACGGCACCGAGGAGCTGCTGGTGAAGCTGAACCGGGAGGACCTGCTGCGGAAGCAGCGGACCTTCGACAAC | |
| in fusion | GGCAGCATCCCCCACCAGATCCACCTGGGCGAGCTGCACGCCATCCTGCGGCGGCAGGAGGACTTCTACCCCTTCCTGAAGGACAAC | |
| protein | CGGGAGAAGATCGAGAAGATCCTGACCTTCCGGATCCCCTACTACGTGGGCCCCCTGGCCCGGGGCAACAGCCGGTTCGCCTGGATG | |
| coding | ACCCGGAAGAGCGAGGAGACCATCACCCCCTGGAACTTCGAGGAGGTGGTGGACAAGGGCGCCAGCGCCCAGAGCTTCATCGAGCGG | |
| sequence) | ATGACCAACTTCGACAAGAACCTGCCCAACGAGAAGGTGCTGCCCAAGCACAGCCTGCTGTACGAGTACTTCACCGTGTACAACGAG | |
| | CTGACCAAGGTGAAGTACGTGACCGAGGGCATGCGGAAGCCCGCCTTCCTGAGCGGCGAGCAGAAGAAGGCCATCGTGGACCTGCTG | |
| | TTCAAGACCAACCGGAAGGTGACCGTGAAGCAGCTGAAGGAGGACTACTTCAAGAAGATCGAGTGCTTCGACAGCGTGGAGATCAGC | |
| | GGCGTGGAGGACCGGTTCAACGCCAGCCTGGGCACCTACCACGACCTGCTGAAGATCATCAAGGACAAGGACTTCCTGGACAACGAG | |
| | GAGAACGAGGACATCCTGGAGGACATCGTGCTGACCCTGACCCTGTTCGAGGACCGGGAGATGATCGAGGAGCGGCTGAAGACCTAC | |
| | GCCCACCTGTTCGACGACAAGGTGATGAAGCAGCTGAAGCGGCGGCGGTACACCGGCTGGGGCCGGCTGAGCCGGAAGCTGATCAAC | |
| | GGCATCCGGGACAAGCAGAGCGGCAAGACCATCCTGGACTTCCTGAAGAGCGACGGCTTCGCCAACCGGAACTTCATGCAGCTGATC | |
| | CACGACGACAGCCTGACCTTCAAGGAGGACATCCAGAAGGCCCAGGTGAGCGGCCAGGGCGACAGCCTGCACGAGCACATCGCCAAC | |
| | CTGGCCGGCAGCCCCGCCATCAAGAAGGGCATCCTGCAGACCGTGAAGGTGGTGGACGAGCTGGTGAAGGTGATGGGCCGGCACAAG | |
| | CCCGAGAACATCGTGATCGAGATGGCCCGGGAGAACCAGACCACCCAGAAGGGCCAGAAGAACAGCCGGGAGCGGATGAAGCGGATC | |
| | GAGGAGGGCATCAAGGAGCTGGGCAGCCAGATCCTGAAGGAGCACCCCGTGGAGAACACCCAGCTGCAGAACGAGAAGCTGTACCTG | |
| | TACTACCTGCAGAACGGCCGGGACATGTACGTGGACCAGGAGCTGGACATCAACCGGCTGAGCGACTACGACGTGGACCACATCGTG | |
| | CCCCAGAGCTTCCTGAAGGACGACAGCATCGACAACAAGGTGCTGACCCGGAGCGACAAGAACCGGGGCAAGAGCGACAACGTGCCC | |
| | AGCGAGGAGGTGGTGAAGAAGATGAAGAACTACTGGCGGCAGCTGCTGAACGCCAAGCTGATCACCCAGCGGAAGTTCGACAACCTG | |
| | ACCAAGGCCGAGCGGGGCGGCCTGAGCGAGCTGGACAAGGCCGGCTTCATCAAGCGGCAGCTGGTGGAGACCCGGCAGATCACCAAG | |
| | CACGTGGCCCAGATCCTGGACAGCCGGATGAACACCAAGTACGACGAGAACGACAAGCTGATCCGGGAGGTGAAGGTGATCACCCTG | |
| | AAGAGCAAGCTGGTGAGCGACTTCCGGAAGGACTTCCAGTTCTACAAGGTGCGGGAGATCAACAACTACCACCACGCCCACGACGCC | |
| | TACCTGAACGCCGTGGTGGGCACCGCCCTGATCAAGAAGTACCCCAAGCTGGAGAGCGAGTTCGTGTACGGCGACTACAAGGTGTAC | |
| | GACGTGCGGAAGATGATCGCCAAGAGCGAGCAGGAGATCGGCAAGGCCACCGCCAAGTACTTCTTCTACAGCAACATCATGAACTTC | |
| | TTCAAGACCGAGATCACCCTGGCCAACGGCGAGATCCGGAAGCGGCCCCTGATCGAGACCAACGGCGAGACCGGCGAGATCGTGTGG | |
| | GACAAGGGCCGGGACTTCGCCACCGTGCGGAAGGTGCTGAGCATGCCCCAGGTGAACATCGTGAAGAAGACCGAGGTGCAGACCGGC | |
| | GGCTTCAGCAAGGAGAGCATCCTGCCCAAGCGGAACAGCGACAAGCTGATCGCCCGGAAGAAGGACTGGGACCCCAAGAAGTACGGC | |
| | GGCTTCGACAGCCCCACCGTGGCCTACAGCGTGCTGGTGGTGGCCAAGGTGGAGAAGGGCAAGAGCAAGAAGCTGAAGAGCGTGAAG | |
| | GAGCTGCTGGGCATCACCATCATGGAGCGGAGCAGCTTCGAGAAGAACCCCATCGACTTCCTGGAGGCCAAGGGCTACAAGGAGGTG | |
| | AAGAAGGACCTGATCATCAAGCTGCCCAAGTACAGCCTGTTCGAGCTGGAGAACGGCCGGAAGCGGATGCTGGCCAGCGCCGGCGAG | |
| | CTGCAGAAGGGCAACGAGCTGGCCCTGCCCAGCAAGTACGTGAACTTCCTGTACCTGGCCAGCCACTACGAGAAGCTGAAGGGCAGC | |

-continued

Sequence Table

| Description | Sequence | SEQ ID No. |
|---|---|---|
| | CCCGAGGACAACGAGCAGAAGCAGCTGTTCGTGGAGCAGCACAAGCACTACCTGGACGAGATCATCGAGCAGATCAGCGAGTTCAGC<br>AAGCGGGTGATCCTGGCCGACGCCAACCTGGACAAGGTGCTGAGCGCCTACAACAAGCACCGGGACAAGCCCATCCGGGAGCAGGCC<br>GAGAACATCATCCACCTGTTCACCCTGACCAACCTGGGCGCCCCCGCCGCCTTCAAGTACTTCGACACCACCATCGACCGGAAGCGG<br>TACACCAGCACCAAGGAGGTGCTGGACGCCACCCTGATCCACCAGAGCATCACCGGCCTGTACGAGACCCGGATCGACCTGAGCCAG<br>CTGGGCGGCGACGGCAGCGGCAGCCCCAAGAAGAAGCGGAAGGTGGACGGCAGCCCCAAGAAGAAGCGGAAGGTGGACAGCGGC | |
| Cas9 ORF using low A/U codons of Table 4 (no NLS and no start or stop codons; suitable for inclusion in fusion protein coding sequence) | GACAAGAAGTACAGCATCGGCCTGGACATCGGCACCAACAGCGTGGGCTGGGCCGTGATCACCGACGAGTACAAGGTGCCCAGCAAG<br>AAGTTCAAGGTGCTGGGCAACACCGACCGGCACAGCATCAAGAAGAACCTGATCGGCGCCCTGCTGTTCGACAGCGGCGAGACCGCC<br>GAGGCCACCCGGCTGAAGCGGACCGCCCGGCGGCGGTACACCCGGCGGAAGAACCGGATCTGCTACCTGCAGGAGATCTTCAGCAAC<br>GAGATGGCCAAGGTGGACGACAGCTTCTTCCACCGGCTGGAGGAGAGCTTCCTGGTGGAGGAGGACAAGAAGCACGAGCGGCACCCC<br>ATCTTCGGCAACATCGTGGACGAGGTGGCCTACCACGAGAAGTACCCCACCATCTACCACCTGCGGAAGAAGCTGGTGGACAGCACC<br>GACAAGGCCGACCTGCGGCTGATCTACCTGGCCCTGGCCCACATGATCAAGTTCCGGGGCCACTTCCTGATCGAGGGCGACCTGAAC<br>CCCGACAACAGCGACGTGGACAAGCTGTTCATCCAGCTGGTGCAGACCTACAACCAGCTGTTCGAGGAGAACCCCATCAACGCCAGC<br>GGCGTGGACGCCAAGGCCATCCTGAGCGCCCGGCTGAGCAAGAGCCGGCGGCTGGAGAACCTGATCGCCCAGCTGCCCGGCGAGAAG<br>AAGAACGGCCTGTTCGGCAACCTGATCGCCCTGAGCCTGGGCCTGACCCCCAACTTCAAGAGCAACTTCGACCTGGCCGAGGACGCC<br>AAGCTGCAGCTGAGCAAGGACACCTACGACGACGACCTGGACAACCTGCTGGCCCAGATCGGCGACCAGTACGCCGACCTGTTCCTG<br>GCCGCCAAGAACCTGAGCGACGCCATCCTGCTGAGCGACATCCTGCGGGTGAACACCGAGATCACCAAGGCCCCCCTGAGCGCCAGC<br>ATGATCAAGCGGTACGACGAGCACCACCAGGACCTGACCCTGCTGAAGGCCCTGGTGCGGCAGCAGCTGCCCGAGAAGTACAAGGAG<br>ATCTTCTTCGACCAGAGCAAGAACGGCTACGCCGGCTACATCGACGGCGGCGCCAGCCAGGAGGAGTTCTACAAGTTCATCAAGCCC<br>ATCCTGGAGAAGATGGACGGCACCGAGGAGCTGCTGGTGAAGCTGAACCGGGAGGACCTGCTGCGGAAGCAGCGGACCTTCGACAAC<br>GGCAGCATCCCCCACCAGATCCACCTGGGCGAGCTGCACGCCATCCTGCGGCGGCAGGAGGACTTCTACCCCTTCCTGAAGGACAAC<br>CGGGAGAAGATCGAGAAGATCCTGACCTTCCGGATCCCCTACTACGTGGGCCCCCTGGCCCGGGGCAACAGCCGGTTCGCCTGGATG<br>ACCCGGAAGAGCGAGGAGACCATCACCCCCTGGAACTTCGAGGAGGTGGTGGACAAGGGCGCCAGCGCCCAGAGCTTCATCGAGCGG<br>ATGACCAACTTCGACAAGAACCTGCCCAACGAGAAGGTGCTGCCCAAGCACAGCCTGCTGTACGAGTACTTCACCGTGTACAACGAG<br>CTGACCAAGGTGAAGTACGTGACCGAGGGCATGCGGAAGCCCGCCTTCCTGAGCGGCGAGCAGAAGAAGGCCATCGTGGACCTGCTG<br>TTCAAGACCAACCGGAAGGTGACCGTGAAGCAGCTGAAGGAGGACTACTTCAAGAAGATCGAGTGCTTCGACAGCGTGGAGATCAGC<br>GGCGTGGAGGACCGGTTCAACGCCAGCCTGGGCACCTACCACGACCTGCTGAAGATCATCAAGGACAAGGACTTCCTGGACAACGAG<br>GAGAACGAGGACATCCTGGAGGACATCGTGCTGACCCTGACCCTGTTCGAGGACCGGGAGATGATCGAGGAGCGGCTGAAGACCTAC<br>GCCCACCTGTTCGACGACAAGGTGATGAAGCAGCTGAAGCGGCGGCGGTACACCGGCTGGGGCCGGCTGAGCCGGAAGCTGATCAAC<br>GGCATCCGGGACAAGCAGAGCGGCAAGACCATCCTGGACTTCCTGAAGAGCGACGGCTTCGCCAACCGGAACTTCATGCAGCTGATC<br>CACGACGACAGCCTGACCTTCAAGGAGGACATCCAGAAGGCCCAGGTGAGCGGCCAGGGCGACAGCCTGCACGAGCACATCGCCAAC<br>CTGGCCGGCAGCCCCGCCATCAAGAAGGGCATCCTGCAGACCGTGAAGGTGGTGGACGAGCTGGTGAAGGTGATGGGCCGGCACAAG<br>CCCGAGAACATCGTGATCGAGATGGCCCGGGAGAACCAGACCACCCAGAAGGGCCAGAAGAACAGCCGGGAGCGGATGAAGCGGATC<br>GAGGAGGGCATCAAGGAGCTGGGCAGCCAGATCCTGAAGGAGCACCCCGTGGAGAACACCCAGCTGCAGAACGAGAAGCTGTACCTG<br>TACTACCTGCAGAACGGCCGGGACATGTACGTGGACCAGGAGCTGGACATCAACCGGCTGAGCGACTACGACGTGGACCACATCGTG<br>CCCCAGAGCTTCCTGAAGGACGACAGCATCGACAACAAGGTGCTGACCCGGAGCGACAAGAACCGGGGCAAGAGCGACAACGTGCCC<br>AGCGAGGAGGTGGTGAAGAAGATGAAGAACTACTGGCGGCAGCTGCTGAACGCCAAGCTGATCACCCAGCGGAAGTTCGACAACCTG<br>ACCAAGGCCGAGCGGGGCGGCCTGAGCGAGCTGGACAAGGCCGGCTTCATCAAGCGGCAGCTGGTGGAGACCCGGCAGATCACCAAG<br>CACGTGGCCCAGATCCTGGACAGCCGGATGAACACCAAGTACGACGAGAACGACAAGCTGATCCGGGAGGTGAAGGTGATCACCCTG<br>AAGAGCAAGCTGGTGAGCGACTTCCGGAAGGACTTCCAGTTCTACAAGGTGCGGGAGATCAACAACTACCACCACGCCCACGACGCC<br>TACCTGAACGCCGTGGTGGGCACCGCCCTGATCAAGAAGTACCCCAAGCTGGAGAGCGAGTTCGTGTACGGCGACTACAAGGTGTAC<br>GACGTGCGGAAGATGATCGCCAAGAGCGAGCAGGAGATCGGCAAGGCCACCGCCAAGTACTTCTTCTACAGCAACATCATGAACTTC<br>TTCAAGACCGAGATCACCCTGGCCAACGGCGAGATCCGGAAGCGGCCCCTGATCGAGACCAACGGCGAGACCGGCGAGATCGTGTGG<br>GACAAGGGCCGGGACTTCGCCACCGTGCGGAAGGTGCTGAGCATGCCCCAGGTGAACATCGTGAAGAAGACCGAGGTGCAGACCGGC<br>GGCTTCAGCAAGGAGAGCATCCTGCCCAAGCGGAACAGCGACAAGCTGATCGCCCGGAAGAAGGACTGGGACCCCAAGAAGTACGGC<br>GGCTTCGACAGCCCCACCGTGGCCTACAGCGTGCTGGTGGTGGCCAAGGTGGAGAAGGGCAAGAGCAAGAAGCTGAAGAGCGTGAAG<br>GAGCTGCTGGGCATCACCATCATGGAGCGGAGCAGCTTCGAGAAGAACCCCATCGACTTCCTGGAGGCCAAGGGCTACAAGGAGGTG<br>AAGAAGGACCTGATCATCAAGCTGCCCAAGTACAGCCTGTTCGAGCTGGAGAACGGCCGGAAGCGGATGCTGGCCAGCGCCGGCGAG<br>CTGCAGAAGGGCAACGAGCTGGCCCTGCCCAGCAAGTACGTGAACTTCCTGTACCTGGCCAGCCACTACGAGAAGCTGAAGGGCAGC | 356 |

-continued

| Sequence Table | | |
|---|---|---|
| Description | Sequence | SEQ ID No. |
| | CCCGAGGACAACGAGCAGAAGCAGCTGTTCGTGGAGCAGCACAAGCACTACCTGGACGAGATCATCGAGCAGATCAGCGAGTTCAGC<br>AAGCGGGTGATCCTGGCCGACGCCAACCTGGACAAGGTGCTGAGCGCCTACAACAAGCACCGGGACAAGCCCATCCGGGAGCAGGCC<br>GAGAACATCATCCACCTGTTCACCCTGACCAACCTGGGCGCCCCCGCCGCCTTCAAGTACTTCGACACCACCATCGACCGGAAGCGG<br>TACACCAGCACCAAGGAGGTGCTGGACGCCACCCTGATCCACCAGAGCATCACCGGCCTGTACGAGACCCGGATCGACCTGAGCCAG<br>CTGGGCGGCGAC | |
| | Not Used | 357-362 |
| Nme Cas9 ORF using low A codons of Table 5 (no start or stop codons; suitable for inclusion in fusion protein coding sequence) | GCCGCCTTCAAGCCCAACTCCATCAACTACATCCTGGGCCTGGACATCGGCATCGCCTCCGTGGGCTGGGCCATGGTGGAGATCGAC<br>GAGGAGGAGAACCCCATCCGGCTGATCGACCTGGGCGTGCGGGTGTTCGAGCGGGCCGAGGTGCCCAAGACCGGCGACTCCCTGGCC<br>ATGGCCCGGCGGCTGGCCCGGTCCGTGCGGCGGCTGACCCGGCGGCGGGCCCACCGGCTGCTGCGGACCCGGCGGCTGCTGAAGCGG<br>GAGGGCGTGCTGCAGGCCGCCAACTTCGACGAGAACGGCCTGATCAAGTCCCTGCCCAACACCCCCTGGCAGCTGCGGGCCGCCGCC<br>CTGGACCGGAAGCTGACCCCCCTGGAGTGGTCCGCCGTGCTGCTGCACCTGATCAAGCACCGGGGCTACCTGTCCCAGCGGAAGAAC<br>GAGGGCGAGACCGCCGACAAGGAGCTGGGCGCCCTGCTGAAGGGCGTGGCCGGCAACGCCCACGCCCTGCAGACCGGCGACTTCCGG<br>ACCCCCGCCGAGCTGGCCCTGAACAAGTTCGAGAAGGAGTCCGGCCACATCCGGAACCAGCGGTCCGACTACTCCCACACCTTCTCC<br>CGGAAGGACCTGCAGGCCGAGCTGATCCTGCTGTTCGAGAAGCAGAAGGAGTTCGGCAACCCCCACGTGTCCGGCGGCCTGAAGGAG<br>GGCATCGAGACCCTGCTGATGACCCAGCGGCCCGCCCTGTCCGGCGACGCCGTGCAGAAGATGCTGGGCCACTGCACCTTCGAGCCC<br>GCCGAGCCCAAGGCCGCCAAGAACACCTACACCGCCGAGCGGTTCATCTGGCTGACCAAGCTGAACAACCTGCGGATCCTGGAGCAG<br>GGCTCCGAGCGGCCCCTGACCGACACCGAGCGGGCCACCCTGATGGACGAGCCCTACCGGAAGTCCAAGCTGACCTACGCCCAGGCC<br>CGGAAGCTGCTGGGCCTGGAGGACACCGCCTTCTTCAAGGGCCTGCGGTACGGCAAGGACAACGCCGAGGCCTCCACCCTGATGGAG<br>ATGAAGGCCTACCACGCCATCTCCCGGGCCCTGGAGAAGGAGGGCCTGAAGGACAAGAAGTCCCCCCTGAACCTGTCCCCCGAGCTG<br>CAGGACGAGATCGGCACCGCCTTCTCCCTGTTCAAGACCGACGAGGACATCACCGGCCGGCTGAAGGACCGGATCCAGCCCGAGATC<br>CTGGAGGCCCTGCTGAAGCACATCTCCTTCGACAAGTTCGTGCAGATCTCCCTGAAGGCCCTGCGGCGGATCGTGCCCCTGATGGAG<br>CAGGGCAAGCGGTACGACGAGGCCTGCGCCGAGATCTACGGCGACCACTACGGCAAGAAGAACACCGAGGAGAAGATCTACCTGCCC<br>CCCATCCCCGCCGACGAGATCCGGAACCCCGTGGTGCTGCGGGCCCTGTCCCAGGCCCGGAAGGTGATCAACGGCGTGGTGCGGCGG<br>TACGGCTCCCCCGCCCGGATCCACATCGAGACCGCCCGGGAGGTGGGCAAGTCCTTCAAGGACCGGAAGGAGATCGAGAAGCGGCAG<br>GAGGAGAACCGGAAGGACCGGGAGAAGGCCGCCGCCAAGTTCCGGGAGTACTTCCCCAACTTCGTGGGCGAGCCCAAGTCCAAGGAC<br>ATCCTGAAGCTGCGGCTGTACGAGCAGCAGCACGGCAAGTGCCTGTACTCCGGCAAGGAGATCAACCTGGGCCGGCTGAACGAGAAG<br>GGCTACGTGGAGATCGACCACGCCCTGCCCTTCTCCCGGACCTGGGACGACTCCTTCAACAACAAGGTGCTGGTGCTGGGCTCCGAG<br>AACCAGAACAAGGGCAACCAGACCCCCTACGAGTACTTCAACGGCAAGGACAACTCCCGGGAGTGGCAGGAGTTCAAGGCCCGGGTG<br>GAGACCTCCCGGTTCCCCCGGTCCAAGAAGCAGCGGATCCTGCTGCAGAAGTTCGACGAGGACGGCTTCAAGGAGCGGAACCTGAAC<br>GACACCCGGTACGTGAACCGGTTCCTGTGCCAGTTCGTGGCCGACCGGATGCGGCTGACCGGCAAGGGCAAGAAGCGGGTGTTCGCC<br>TCCAACGGCCAGATCACCAACCTGCTGCGGGGCTTCTGGGGCCTGCGGAAGGTGCGGGCCGAGAACGACCGGCACCACGCCCTGGAC<br>GCCGTGGTGGTGGCCTGCTCCACCGTGGCCATGCAGCAGAAGATCACCCGGTTCGTGCGGTACAAGGAGATGAACGCCTTCGACGGC<br>AAGACCATCGACAAGGAGACCGGCGAGGTGCTGCACCAGAAGACCCACTTCCCCCAGCCCTGGGAGTTCTTCGCCCAGGAGGTGATG<br>ATCCGGGTGTTCGGCAAGCCCGACGGCAAGCCCGAGTTCGAGGAGGCCGACACCCTGGAGAAGCTGCGGACCCTGCTGGCCGAGAAG<br>CTGTCCTCCCGGCCCGAGGCCGTGCACGAGTACGTGACCCCCCTGTTCGTGTCCCGGGCCCCCAACCGGAAGATGTCCGGCCAGGGC<br>CACATGGAGACCGTGAAGTCCGCCAAGCGGCTGGACGAGGGCGTGTCCGTGCTGCGGGTGCCCCTGACCCAGCTGAAGCTGAAGGAC<br>CTGGAGAAGATGGTGAACCGGGAGCGGGAGCCCAAGCTGTACGAGGCCCTGAAGGCCCGGCTGGAGGCCCACAAGGACGACCCCGCC<br>AAGGCCTTCGCCGAGCCCTTCTACAAGTACGACAAGGCCGGCAACCGGACCCAGCAGGTGAAGGCCGTGCGGGTGGAGCAGGTGCAG<br>AAGACCGGCGTGTGGGTGCGGAACCACAACGGCATCGCCGACAACGCCACCATGGTGCGGGTGGACGTGTTCGAGAAGGGCGACAAG<br>TACTACCTGGTGCCCATCTACTCCTGGCAGGTGGCCAAGGGCATCCTGCCCGACCGGGCCGTGGTGCAGGGCAAGGACGAGGAGGAC<br>TGGCAGCTGATCGACGACTCCTTCAACTTCAAGTTCTCCCTGCACCCCAACGACCTGGTGGAGGTGATCACCAAGAAGGCCCGGATG<br>TTCGGCTACTTCGCCTCCTGCCACCGGGGCACCGGCAACATCAACATCCGGATCCACGACCTGGACCACAAGATCGGCAAGAACGGC<br>ATCCTGGAGGGCATCGGCGTGAAGACCGCCCTGTCCTTCCAGAAGTACCAGATCGACGAGCTGGGCAAGGAGATCCGGCCCTGCCGG<br>CTGAAGAAGCGGCCCCCCGTGCGGTCCGGCAAGCGGACCGCCGACGGCTCCGAGTTCGAGTCCCCCAAGAAGAAGCGGAAGGTGGAG | 363 |
| Nme Cas9 ORF using | GCCGCCTTCAAGCCCAACAGCATCAACTACATCCTGGGCCTGGACATCGGCATCGCCAGCGTGGGCTGGGCCATGGTGGAGATCGAC<br>GAGGAGGAGAACCCCATCCGGCTGATCGACCTGGGCGTGCGGGTGTTCGAGCGGGCCGAGGTGCCCAAGACCGGCGACAGCCTGGCC | 364 |

-continued

| Description | Sequence | SEQ ID No. |
|---|---|---|
| low A/U codons of Table 5 (no start or stop codons; suitable for inclusion in fusion protein coding sequence) | ATGGCCCGGCGGCTGGCCCGGAGCGTGCGGCGGCTGACCCGGCGGCGGGCCCACCGGCTGCTGCGGACCCGGCGGCTGCTGAAGCGG<br>GAGGGCGTGCTGCAGGCCGCCAACTTCGACGAGAACGGCCTGATCAAGAGCCTGCCCAACACCCCCTGGCAGCTGCGGGCCGCCGCC<br>CTGGACCGGAAGCTGACCCCCCTGGAGTGGAGCGCCGTGCTGCTGCACCTGATCAAGCACCGGGGCTACCTGAGCCAGCGGAAGAAC<br>GAGGGCGAGACCGCCGACAAGGAGCTGGGCGCCCTGCTGAAGGGCGTGGCCGGCAACGCCCACGCCCTGCAGACCGGCGACTTCCGG<br>ACCCCCGCCGAGCTGGCCCTGAACAAGTTCGAGAAGGAGAGCGGCCACATCCGGAACCAGCGGAGCGACTACAGCCACACCTTCAGC<br>CGGAAGGACCTGCAGGCCGAGCTGATCCTGCTGTTCGAGAAGCAGAAGGAGTTCGGCAACCCCCACGTGAGCGGCGGCCTGAAGGAG<br>GGCATCGAGACCCTGCTGATGACCCAGCGGCCCGCCCTGAGCGGCGACGCCGTGCAGAAGATGCTGGGCCACTGCACCTTCGAGCCC<br>GCCGAGCCCAAGGCCGCCAAGAACACCTACACCGCCGAGCGGTTCATCTGGCTGACCAAGCTGAACAACCTGCGGATCCTGGAGCAG<br>GGCAGCGAGCGGCCCCTGACCGACACCGAGCGGGCCACCCTGATGGACGAGCCCTACCGGAAGAGCAAGCTGACCTACGCCCAGGCC<br>CGGAAGCTGCTGGGCCTGGAGGACACCGCCTTCTTCAAGGGCCTGCGGTACGGCAAGGACAACGCCGAGGCCAGCACCCTGATGGAG<br>ATGAAGGCCTACCACGCCATCAGCCGGGCCCTGGAGAAGGAGGGCCTGAAGGACAAGAAGAGCCCCCTGAACCTGAGCCCCGAGCTG<br>CAGGACGAGATCGGCACCGCCTTCAGCCTGTTCAAGACCGACGAGGACATCACCGGCCGGCTGAAGGACCGGATCCAGCCCGAGATC<br>CTGGAGGCCCTGCTGAAGCACATCAGCTTCGACAAGTTCGTGCAGATCAGCCTGAAGGCCCTGCGGCGGATCGTGCCCCTGATGGAG<br>CAGGGCAAGCGGTACGACGAGGCCTGCGCCGAGATCTACGGCGACCACTACGGCAAGAAGAACACCGAGGAGAAGATCTACCTGCCC<br>CCCATCCCCGCCGACGAGATCCGGAACCCCGTGGTGCTGCGGGCCCTGAGCCAGGCCCGGAAGGTGATCAACGGCGTGGTGCGGCGG<br>TACGGCAGCCCCGCCCGGATCCACATCGAGACCGCCCGGGAGGTGGGCAAGAGCTTCAAGGACCGGAAGGAGATCGAGAAGCGGCAG<br>GAGGAGAACCGGAAGGACCGGGAGAAGGCCGCCGCCAAGTTCCGGGAGTACTTCCCCAACTTCGTGGGCGAGCCCAAGAGCAAGGAC<br>ATCCTGAAGCTGCGGCTGTACGAGCAGCAGCACGGCAAGTGCCTGTACAGCGGCAAGGAGATCAACCTGGGCCGGCTGAACGAGAAG<br>GGCTACGTGGAGATCGACCACGCCCTGCCCTTCAGCCGGACCTGGGACGACAGCTTCAACAACAAGGTGCTGGTGCTGGGCAGCGAG<br>AACCAGAACAAGGGCAACCAGACCCCCTACGAGTACTTCAACGGCAAGGACAACAGCCGGGAGTGGCAGGAGTTCAAGGCCCGGGTG<br>GAGACCAGCCGGTTCCCCCGGAGCAAGAAGCAGCGGATCCTGCTGCAGAAGTTCGACGAGGACGGCTTCAAGGAGCGGAACCTGAAC<br>GACACCCGGTACGTGAACCGGTTCCTGTGCCAGTTCGTGGCCGACCGGATGCGGCTGACCGGCAAGGGCAAGAAGCGGGTGTTCGCC<br>AGCAACGGCCAGATCACCAACCTGCTGCGGGGCTTCTGGGGCCTGCGGAAGGTGCGGGCCGAGAACGACCGGCACCACGCCCTGGAC<br>GCCGTGGTGGTGGCCTGCAGCACCGTGGCCATGCAGCAGAAGATCACCCGGTTCGTGCGGTACAAGGAGATGAACGCCTTCGACGGC<br>AAGACCATCGACAAGGAGACCGGCGAGGTGCTGCACCAGAAGACCCACTTCCCCCAGCCCTGGGAGTTCTTCGCCCAGGAGGTGATG<br>ATCCGGGTGTTCGGCAAGCCCGACGGCAAGCCCGAGTTCGAGGAGGCCGACACCCTGGAGAAGCTGCGGACCCTGCTGGCCGAGAAG<br>CTGAGCAGCCGGCCCGAGGCCGTGCACGAGTACGTGACCCCCCTGTTCGTGAGCCGGGCCCCCAACCGGAAGATGAGCGGCCAGGGC<br>CACATGGAGACCGTGAAGAGCGCCAAGCGGCTGGACGAGGGCGTGAGCGTGCTGCGGGTGCCCCTGACCCAGCTGAAGCTGAAGGAC<br>CTGGAGAAGATGGTGAACCGGGAGCGGGAGCCCAAGCTGTACGAGGCCCTGAAGGCCCGGCTGGAGGCCCACAAGGACGACCCCGCC<br>AAGGCCTTCGCCGAGCCCTTCTACAAGTACGACAAGGCCGGCAACCGGACCCAGCAGGTGAAGGCCGTGCGGGTGGAGCAGGTGCAG<br>AAGACCGGCGTGTGGGTGCGGAACCACAACGGCATCGCCGACAACGCCACCATGGTGCGGGTGGACGTGTTCGAGAAGGGCGACAAG<br>TACTACCTGGTGCCCATCTACAGCTGGCAGGTGGCCAAGGGCATCCTGCCCGACCGGGCCGTGGTGCAGGGCAAGGACGAGGAGGAC<br>TGGCAGCTGATCGACGACAGCTTCAACTTCAAGTTCAGCCTGCACCCCAACGACCTGGTGGAGGTGATCACCAAGAAGGCCCGGATG<br>TTCGGCTACTTCGCCAGCTGCCACCGGGGCACCGGCAACATCAACATCCGGATCCACGACCTGGACCACAAGATCGGCAAGAACGGC<br>ATCCTGGAGGGCATCGGCGTGAAGACCGCCCTGAGCTTCCAGAAGTACCAGATCGACGAGCTGGGCAAGGAGATCCGGCCCTGCCGG<br>CTGAAGAAGCGGCCCCCCGTGCGGAGCGGCAAGCGGACCGCCGACGGCAGCGAGTTCGAGAGCCCCAAGAAGAAGCGGAAGGTGGAG | |
| | Not Used | 365-375 |
| mRNA transcript with XBG UTRs and Cas9 ORF | GGGAAGCUCAGAAUAAACGCUCAACUUUGGCCGGAUCUGCCACCAUGGACAAGAAGUACAGCAUCGGCCUGGACAUCGGCACCAACA<br>GCGUGGGCUGGGCCGUGAUCACCGACGAGUACAAGGUGCCCAGCAAGAAGUUCAAGGUGCUGGGCAACACCGACAGACACAGCAUCA<br>AGAAGAACCUGAUCGGCGCCCUGCUGUUCGACAGCGGCGAGACCGCCGAGGCCACCAGACUGAAGAGAACCGCCAGAAGAAGAUACA<br>CCAGAAGAAAGAACAGAAUCUGCUACCUGCAGGAGAUCUUCAGCAACGAGAUGGCCAAGGUGGACGACAGCUUCUUCCACAGACUGG<br>AGGAGAGCUUCCUGGUGGAGGAGGACAAGAAGCACGAGAGACACCCCAUCUUCGGCAACAUCGUGGACGAGGUGGCCUACCACGAGA<br>AGUACCCCACCAUCUACCACCUGAGAAAGAAGCUGGUGGACAGCACCGACAAGGCCGACCUGAGACUGAUCUACCUGGCCCUGGCCC<br>ACAUGAUCAAGUUCAGAGGCCACUUCCUGAUCGAGGGCGACCUGAACCCCGACAACAGCGACGUGGACAAGCUGUUCAUCCAGCUGG<br>UGCAGACCUACAACCAGCUGUUCGAGGAGAACCCCAUCAACGCCAGCGGCGUGGACGCCAAGGCCAUCCUGAGCGCCAGACUGAGCA<br>AGAGCAGAAGACUGGAGAACCUGAUCGCCCAGCUGCCCGGCGAGAAGAAGAACGGCCUGUUCGGCAACCUGAUCGCCCUGAGCCUGG<br>GCCUGACCCCCAACUUCAAGAGCAACUUCGACCUGGCCGAGGACGCCAAGCUGCAGCUGAGCAAGGACACCUACGACGACGACCUGG | 376 |

-continued

Sequence Table

| Description | Sequence | SEQ ID No. |
|---|---|---|
| | ACAACCUGCUGGCCCAGAUCGGCGACCAGUACGCCGACCUGUUCCUGGCCGCCAAGAACCUGAGCGACGCCAUCCUGCUGAGCGACA<br>UCCUGAGAGUGAACACCGAGAUCACCAAGGCCCCCCUGAGCGCCAGCAUGAUCAAGAGAUACGACGAGCACCACCAGGACCUGACCC<br>UGCUGAAGGCCCUGGUGAGACAGCAGCUGCCCGAGAAGUACAAGGAGAUCUUCUUCGACCAGAGCAAGAACGGCUACGCCGGCUACA<br>UCGACGGCGGCGCCAGCCAGGAGGAGUUCUACAAGUUCAUCAAGCCCAUCCUGGAGAAGAUGGACGGCACCGAGGAGCUGCUGGUGA<br>AGCUGAACAGAGAGGACCUGCUGAGAAAGCAGAGAACCUUCGACAACGGCAGCAUCCCCCACCAGAUCCACCUGGGCGAGCUGCACG<br>CCAUCCUGAGAAGACAGGAGGACUUCUACCCCUUCCUGAAGGACAACAGAGAGAAGAUCGAGAAGAUCCUGACCUUCAGAAUCCCCU<br>ACUACGUGGGCCCCCUGGCCAGAGGCAACAGCAGAUUCGCCUGGAUGACCAGAAAGAGCGAGGAGACCAUCACCCCCUGGAACUUCG<br>AGGAGGUGGUGGACAAGGGCGCCAGCGCCCAGAGCUUCAUCGAGAGAAUGACCAACUUCGACAAGAACCUGCCCAACGAGAAGGUGC<br>UGCCCAAGCACAGCCUGCUGUACGAGUACUUCACCGUGUACAACGAGCUGACCAAGGUGAAGUACGUGACCGAGGGCAUGAGAAAGC<br>CCGCCUUCCUGAGCGGCGAGCAGAAGAAGGCCAUCGUGGACCUGCUGUUCAAGACCAACAGAAAGGUGACCGUGAAGCAGCUGAAGG<br>AGGACUACUUCAAGAAGAUCGAGUGCUUCGACAGCGUGGAGAUCAGCGGCGUGGAGGACAGAUUCAACGCCAGCCUGGGCACCUACC<br>ACGACCUGCUGAAGAUCAUCAAGGACAAGGACUUCCUGGACAACGAGGAGAACGAGGACAUCCUGGAGGACAUCGUGCUGACCCUGA<br>CCCUGUUCGAGGACAGAGAGAUGAUCGAGGAGAGACUGAAGACCUACGCCCACCUGUUCGACGACAAGGUGAUGAAGCAGCUGAAGA<br>GAAGAAGAUACACCGGCUGGGGCAGACUGAGCAGAAAGCUGAUCAACGGCAUCAGAGACAAGCAGAGCGGCAAGACCAUCCUGGACU<br>UCCUGAAGAGCGACGGCUUCGCCAACAGAAACUUCAUGCAGCUGAUCCACGACGACAGCCUGACCUUCAAGGAGGACAUCCAGAAGG<br>CCCAGGUGAGCGGCCAGGGCGACAGCCUGCACGAGCACAUCGCCAACCUGGCCGGCAGCCCCGCCAUCAAGAAGGGCAUCCUGCAGA<br>CCGUGAAGGUGGUGGACGAGCUGGUGAAGGUGAUGGGCAGACACAAGCCCGAGAACAUCGUGAUCGAGAUGGCCAGAGAGAACCAGA<br>CCACCCAGAAGGGCCAGAAGAACAGCAGAGAGAGAAUGAAGAGAAUCGAGGAGGGCAUCAAGGAGCUGGGCAGCCAGAUCCUGAAGG<br>AGCACCCCGUGGAGAACACCCAGCUGCAGAACGAGAAGCUGUACCUGUACUACCUGCAGAACGGCAGAGACAUGUACGUGGACCAGG<br>AGCUGGACAUCAACAGACUGAGCGACUACGACGUGGACCACAUCGUGCCCCAGAGCUUCCUGAAGGACGACAGCAUCGACAACAAGG<br>UGCUGACCAGAAGCGACAAGAACAGAGGCAAGAGCGACAACGUGCCCAGCGAGGAGGUGGUGAAGAAGAUGAAGAACUACUGGAGAC<br>AGCUGCUGAACGCCAAGCUGAUCACCCAGAGAAAGUUCGACAACCUGACCAAGGCCGAGAGAGGCGGCCUGAGCGAGCUGGACAAGG<br>CCGGCUUCAUCAAGAGACAGCUGGUGGAGACCAGACAGAUCACCAAGCACGUGGCCCAGAUCCUGGACAGCAGAAUGAACACCAAGU<br>ACGACGAGAACGACAAGCUGAUCAGAGAGGUGAAGGUGAUCACCCUGAAGAGCAAGCUGGUGAGCGACUUCAGAAAGGACUUCCAGU<br>UCUACAAGGUGAGAGAGAUCAACAACUACCACCACGCCCACGACGCCUACCUGAACGCCGUGGUGGGCACCGCCCUGAUCAAGAAGU<br>ACCCCAAGCUGGAGAGCGAGUUCGUGUACGGCGACUACAAGGUGUACGACGUGAGAAAGAUGAUCGCCAAGAGCGAGCAGGAGAUCG<br>GCAAGGCCACCGCCAAGUACUUCUUCUACAGCAACAUCAUGAACUUCUUCAAGACCGAGAUCACCCUGGCCAACGGCGAGAUCAGAA<br>AGAGACCCCUGAUCGAGACCAACGGCGAGACCGGCGAGAUCGUGUGGGACAAGGGCAGAGACUUCGCCACCGUGAGAAAGGUGCUGA<br>GCAUGCCCCAGGUGAACAUCGUGAAGAAGACCGAGGUGCAGACCGGCGGCUUCAGCAAGGAGAGCAUCCUGCCCAAGAGAAACAGCG<br>ACAAGCUGAUCGCCAGAAAGAAGGACUGGGACCCCAAGAAGUACGGCGGCUUCGACAGCCCCACCGUGGCCUACAGCGUGCUGGUGG<br>UGGCCAAGGUGGAGAAGGGCAAGAGCAAGAAGCUGAAGAGCGUGAAGGAGCUGCUGGGCAUCACCAUCAUGGAGAGAAGCAGCUUCG<br>AGAAGAACCCCAUCGACUUCCUGGAGGCCAAGGGCUACAAGGAGGUGAAGAAGGACCUGAUCAUCAAGCUGCCCAAGUACAGCCUGU<br>UCGAGCUGGAGAACGGCAGAAAGAGAAUGCUGGCCAGCGCCGGCGAGCUGCAGAAGGGCAACGAGCUGGCCCUGCCCAGCAAGUACG<br>UGAACUUCCUGUACCUGGCCAGCCACUACGAGAAGCUGAAGGGCAGCCCCGAGGACAACGAGCAGAAGCAGCUGUUCGUGGAGCAGC<br>ACAAGCACUACCUGGACGAGAUCAUCGAGCAGAUCAGCGAGUUCAGCAAGAGAGUGAUCCUGGCCGACGCCAACCUGGACAAGGUGC<br>UGAGCGCCUACAACAAGCACAGAGACAAGCCCAUCAGAGAGCAGGCCGAGAACAUCAUCCACCUGUUCACCCUGACCAACCUGGGCG<br>CCCCCGCCGCCUUCAAGUACUUCGACACCACCAUCGACAGAAAGAGAUACACCAGCACCAAGGAGGUGCUGGACGCCACCCUGAUCC<br>ACCAGAGCAUCACCGGCCUGUACGAGACCAGAAUCGACCUGAGCCAGCUGGGCGGCGACGGCGGCGGCAGCCCCAAGAAGAAGAGAA<br>AGGUGUGACUAGCACCAGCCUCAAGAACACCCGAAUGGAGUCUCUAAGCUACAUAAUACCAACUUACACUUUACAAAAUGUUGUCCC<br>CCAAAAUGUAGCCAUUCGUAUCUGCUCCUAAUAAAAAGAAAGUUUCUUCACAUUCUCUCGAGAAAAAAAAAAAAAAAAAAAAAAAAA<br>AAAAAAAAAAAAAAAAAAAAAAAAAAAAAAAAAAAAAAAAAAAAAAAAAAA | |
| mRNA transcript with XBG UTRs and Cas9 ORF with low A codons of | GGGAAGCUCAGAAUAAACGCUCAACUUUGGCCGGAUCUGCCACCAUGGACAAGAAGUACUCCAUCGGCCUGGACAUCGGCACCAACU<br>CCGUGGGCUGGGCCGUGAUCACCGACGAGUACAAGGUGCCCUCCAAGAAGUUCAAGGUGCUGGGCAACACCGACCGGCACUCCAUCA<br>AGAAGAACCUGAUCGGCGCCCUGCUGUUCGACUCCGGCGAGACCGCCGAGGCCACCCGGCUGAAGCGGACCGCCCGGCGGCGGUACA<br>CCCGGCGGAAGAACCGGAUCUGCUACCUGCAGGAGAUCUUCUCCAACGAGAUGGCCAAGGUGGACGACUCCUUCUUCCACCGGCUGG<br>AGGAGUCCUUCCUGGUGGAGGAGGACAAGAAGCACGAGCGGCACCCCAUCUUCGGCAACAUCGUGGACGAGGUGGCCUACCACGAGA<br>AGUACCCCACCAUCUACCACCUGCGGAAGAAGCUGGUGGACUCCACCGACAAGGCCGACCUGCGGCUGAUCUACCUGGCCCUGGCCC<br>ACAUGAUCAAGUUCCGGGGCCACUUCCUGAUCGAGGGCGACCUGAACCCCGACAACUCCGACGUGGACAAGCUGUUCAUCCAGCUGG | 377 |

-continued

| Sequence Table | | |
|---|---|---|
| Description | Sequence | SEQ ID No. |
| Table 5 | UGCAGACCUACAACCAGCUGUUCGAGGAGAACCCCAUCAACGCCUCCGGCGUGGACGCCAAGGCCAUCCUGUCCGCCCGGCUGUCCA<br>AGUCCCGGCGGCUGGAGAACCUGAUCGCCCAGCUGCCCGGCGAGAAGAAGAACGGCCUGUUCGGCAACCUGAUCGCCCUGUCCCUGG<br>GCCUGACCCCCAACUUCAAGUCCAACUUCGACCUGGCCGAGGACGCCAAGCUGCAGCUGUCCAAGGACACCUACGACGACGACCUGG<br>ACAACCUGCUGGCCCAGAUCGGCGACCAGUACGCCGACCUGUUCCUGGCCGCCAAGAACCUGUCCGACGCCAUCCUGCUGUCCGACA<br>UCCUGCGGGUGAACACCGAGAUCACCAAGGCCCCCCUGUCCGCCUCCAUGAUCAAGCGGUACGACGAGCACCACCAGGACCUGACCC<br>UGCUGAAGGCCCUGGUGCGGCAGCAGCUGCCCGAGAAGUACAAGGAGAUCUUCUUCGACCAGUCCAAGAACGGCUACGCCGGCUACA<br>UCGACGGCGGCGCCUCCCAGGAGGAGUUCUACAAGUUCAUCAAGCCCAUCCUGGAGAAGAUGGACGGCACCGAGGAGCUGCUGGUGA<br>AGCUGAACCGGGAGGACCUGCUGCGGAAGCAGCGGACCUUCGACAACGGCUCCAUCCCCCACCAGAUCCACCUGGGCGAGCUGCACG<br>CCAUCCUGCGGCGGCAGGAGGACUUCUACCCCUUCCUGAAGGACAACCGGGAGAAGAUCGAGAAGAUCCUGACCUUCCGGAUCCCCU<br>ACUACGUGGGCCCCCUGGCCCGGGGCAACUCCCGGUUCGCCUGGAUGACCCGGAAGUCCGAGGAGACCAUCACCCCCUGGAACUUCG<br>AGGAGGUGGUGGACAAGGGCGCCUCCGCCCAGUCCUUCAUCGAGCGGAUGACCAACUUCGACAAGAACCUGCCCAACGAGAAGGUGC<br>UGCCCAAGCACUCCCUGCUGUACGAGUACUUCACCGUGUACAACGAGCUGACCAAGGUGAAGUACGUGACCGAGGGCAUGCGGAAGC<br>CCGCCUUCCUGUCCGGCGAGCAGAAGAAGGCCAUCGUGGACCUGCUGUUCAAGACCAACCGGAAGGUGACCGUGAAGCAGCUGAAGG<br>AGGACUACUUCAAGAAGAUCGAGUGCUUCGACUCCGUGGAGAUCUCCGGCGUGGAGGACCGGUUCAACGCCUCCCUGGGCACCUACC<br>ACGACCUGCUGAAGAUCAUCAAGGACAAGGACUUCCUGGACAACGAGGAGAACGAGGACAUCCUGGAGGACAUCGUGCUGACCCUGA<br>CCCUGUUCGAGGACCGGGAGAUGAUCGAGGAGCGGCUGAAGACCUACGCCCACCUGUUCGACGACAAGGUGAUGAAGCAGCUGAAGC<br>GGCGGCGGUACACCGGCUGGGGCCGGCUGUCCCGGAAGCUGAUCAACGGCAUCCGGGACAAGCAGUCCGGCAAGACCAUCCUGGACU<br>UCCUGAAGUCCGACGGCUUCGCCAACCGGAACUUCAUGCAGCUGAUCCACGACGACUCCCUGACCUUCAAGGAGGACAUCCAGAAGG<br>CCCAGGUGUCCGGCCAGGGCGACUCCCUGCACGAGCACAUCGCCAACCUGGCCGGCUCCCCCGCCAUCAAGAAGGGCAUCCUGCAGA<br>CCGUGAAGGUGGUGGACGAGCUGGUGAAGGUGAUGGGCCGGCACAAGCCCGAGAACAUCGUGAUCGAGAUGGCCCGGGAGAACCAGA<br>CCACCCAGAAGGGCCAGAAGAACUCCCGGGAGCGGAUGAAGCGGAUCGAGGAGGGCAUCAAGGAGCUGGGCUCCCAGAUCCUGAAGG<br>AGCACCCCGUGGAGAACACCCAGCUGCAGAACGAGAAGCUGUACCUGUACUACCUGCAGAACGGCCGGGACAUGUACGUGGACCAGG<br>AGCUGGACAUCAACCGGCUGUCCGACUACGACGUGGACCACAUCGUGCCCCAGUCCUUCCUGAAGGACGACUCCAUCGACAACAAGG<br>UGCUGACCCGGUCCGACAAGAACCGGGGCAAGUCCGACAACGUGCCCUCCGAGGAGGUGGUGAAGAAGAUGAAGAACUACUGGCGGC<br>AGCUGCUGAACGCCAAGCUGAUCACCCAGCGGAAGUUCGACAACCUGACCAAGGCCGAGCGGGGCGGCCUGUCCGAGCUGGACAAGG<br>CCGGCUUCAUCAAGCGGCAGCUGGUGGAGACCCGGCAGAUCACCAAGCACGUGGCCCAGAUCCUGGACUCCCGGAUGAACACCAAGU<br>ACGACGAGAACGACAAGCUGAUCCGGGAGGUGAAGGUGAUCACCCUGAAGUCCAAGCUGGUGUCCGACUUCCGGAAGGACUUCCAGU<br>UCUACAAGGUGCGGGAGAUCAACAACUACCACCACGCCCACGACGCCUACCUGAACGCCGUGGUGGGCACCGCCCUGAUCAAGAAGU<br>ACCCCAAGCUGGAGUCCGAGUUCGUGUACGGCGACUACAAGGUGUACGACGUGCGGAAGAUGAUCGCCAAGUCCGAGCAGGAGAUCG<br>GCAAGGCCACCGCCAAGUACUUCUUCUACUCCAACAUCAUGAACUUCUUCAAGACCGAGAUCACCCUGGCCAACGGCGAGAUCCGGA<br>AGCGGCCCCUGAUCGAGACCAACGGCGAGACCGGCGAGAUCGUGUGGGACAAGGGCCGGGACUUCGCCACCGUGCGGAAGGUGCUGU<br>CCAUGCCCCAGGUGAACAUCGUGAAGAAGACCGAGGUGCAGACCGGCGGCUUCUCCAAGGAGUCCAUCCUGCCCAAGCGGAACUCCG<br>ACAAGCUGAUCGCCCGGAAGAAGGACUGGGACCCCAAGAAGUACGGCGGCUUCGACUCCCCCACCGUGGCCUACUCCGUGCUGGUGG<br>UGGCCAAGGUGGAGAAGGGCAAGUCCAAGAAGCUGAAGUCCGUGAAGGAGCUGCUGGGCAUCACCAUCAUGGAGCGGUCCUCCUUCG<br>AGAAGAACCCCAUCGACUUCCUGGAGGCCAAGGGCUACAAGGAGGUGAAGAAGGACCUGAUCAUCAAGCUGCCCAAGUACUCCCUGU<br>UCGAGCUGGAGAACGGCCGGAAGCGGAUGCUGGCCUCCGCCGGCGAGCUGCAGAAGGGCAACGAGCUGGCCCUGCCCUCCAAGUACG<br>UGAACUUCCUGUACCUGGCCUCCCACUACGAGAAGCUGAAGGGCUCCCCCGAGGACAACGAGCAGAAGCAGCUGUUCGUGGAGCAGC<br>ACAAGCACUACCUGGACGAGAUCAUCGAGCAGAUCUCCGAGUUCUCCAAGCGGGUGAUCCUGGCCGACGCCAACCUGGACAAGGUGC<br>UGUCCGCCUACAACAAGCACCGGGACAAGCCCAUCCGGGAGCAGGCCGAGAACAUCAUCCACCUGUUCACCCUGACCAACCUGGGCG<br>CCCCCGCCGCCUUCAAGUACUUCGACACCACCAUCGACCGGAAGCGGUACACCUCCACCAAGGAGGUGCUGGACGCCACCCUGAUCC<br>ACCAGUCCAUCACCGGCCUGUACGAGACCCGGAUCGACCUGUCCCAGCUGGGCGGCGACGGCGGCGGCUCCCCCAAGAAGAAGCGGA<br>AGGUGUGACUAGCACCAGCCUCAAGAACACCCGAAUGGAGUCUCUAAGCUACAUAAUACCAACUUACACUUUACAAAAUGUUGUCCC<br>CCAAAAUGUAGCCAUUCGUAUCUGCUCCUAAUAAAAAGAAAGUUUCUUCACAUUCUCUCGAGAAAAAAAAAAAAAAAAAAAAAAAAAAAAAAAAAAAAAA<br>AAAAAAAAAAAAAAAAAAAAAAAAAAAAAAAAAAAAAAAAAAAAAAAAAAAAAAAAAAAAAAA | |
| mRNA transcript with XBG UTRs and | GGGAAGCUCAGAAUAAACGCUCAACUUUGGCCGGAUCUGCCACCAUGGACAAGAAGUACAGCAUCGGCCUGGACAUCGGCACCAACA<br>GCGUGGGCUGGGCCGUGAUCACCGACGAGUACAAGGUGCCCAGCAAGAAGUUCAAGGUGCUGGGCAACACCGACCGGCACAGCAUCA<br>AGAAGAACCUGAUCGGCGCCCUGCUGUUCGACAGCGGCGAGACCGCCGAGGCCACCCGGCUGAAGCGGACCGCCCGGCGGCGGUACA<br>CCCGGCGGAAGAACCGGAUCUGCUACCUGCAGGAGAUCUUCAGCAACGAGAUGGCCAAGGUGGACGACAGCUUCUUCCACCGGCUGG | 378 |

-continued

| Sequence Table | | |
|---|---|---|
| Description | Sequence | SEQ ID No. |
| Cas9 ORF with low U/A codons of Table 5 | AGGAGAGCUUCCUGGUGGAGGAGGACAAGAAGCACGAGCGGCACCCCAUCUUCGGCAACAUCGUGGACGAGGUGGCCUACCACGAGA<br>AGUACCCCACCAUCUACCACCUGCGGAAGAAGCUGGUGGACAGCACCGACAAGGCCGACCUGCGGCUGAUCUACCUGGCCCUGGCCC<br>ACAUGAUCAAGUUCCGGGGCCACUUCCUGAUCGAGGGCGACCUGAACCCCGACAACAGCGACGUGGACAAGCUGUUCAUCCAGCUGG<br>UGCAGACCUACAACCAGCUGUUCGAGGAGAACCCCAUCAACGCCAGCGGCGUGGACGCCAAGGCCAUCCUGAGCGCCCGGCUGAGCA<br>AGAGCCGGCGGCUGGAGAACCUGAUCGCCCAGCUGCCCGGCGAGAAGAAGAACGGCCUGUUCGGCAACCUGAUCGCCCUGAGCCUGG<br>GCCUGACCCCCAACUUCAAGAGCAACUUCGACCUGGCCGAGGACGCCAAGCUGCAGCUGAGCAAGGACACCUACGACGACGACCUGG<br>ACAACCUGCUGGCCCAGAUCGGCGACCAGUACGCCGACCUGUUCCUGGCCGCCAAGAACCUGAGCGACGCCAUCCUGCUGAGCGACA<br>UCCUGCGGGUGAACACCGAGAUCACCAAGGCCCCCCUGAGCGCCAGCAUGAUCAAGCGGUACGACGAGCACCACCAGGACCUGACCC<br>UGCUGAAGGCCCUGGUGCGGCAGCAGCUGCCCGAGAAGUACAAGGAGAUCUUCUUCGACCAGAGCAAGAACGGCUACGCCGGCUACA<br>UCGACGGCGGCGCCAGCCAGGAGGAGUUCUACAAGUUCAUCAAGCCCAUCCUGGAGAAGAUGGACGGCACCGAGGAGCUGCUGGUGA<br>AGCUGAACCGGGAGGACCUGCUGCGGAAGCAGCGGACCUUCGACAACGGCAGCAUCCCCCACCAGAUCCACCUGGGCGAGCUGCACG<br>CCAUCCUGCGGCGGCAGGAGGACUUCUACCCCUUCCUGAAGGACAACCGGGAGAAGAUCGAGAAGAUCCUGACCUUCCGGAUCCCCU<br>ACUACGUGGGCCCCCUGGCCCGGGGCAACAGCCGGUUCGCCUGGAUGACCCGGAAGAGCGAGGAGACCAUCACCCCCUGGAACUUCG<br>AGGAGGUGGUGGACAAGGGCGCCAGCGCCCAGAGCUUCAUCGAGCGGAUGACCAACUUCGACAAGAACCUGCCCAACGAGAAGGUGC<br>UGCCCAAGCACAGCCUGCUGUACGAGUACUUCACCGUGUACAACGAGCUGACCAAGGUGAAGUACGUGACCGAGGGCAUGCGGAAGC<br>CCGCCUUCCUGAGCGGCGAGCAGAAGAAGGCCAUCGUGGACCUGCUGUUCAAGACCAACCGGAAGGUGACCGUGAAGCAGCUGAAGG<br>AGGACUACUUCAAGAAGAUCGAGUGCUUCGACAGCGUGGAGAUCAGCGGCGUGGAGGACCGGUUCAACGCCAGCCUGGGCACCUACC<br>ACGACCUGCUGAAGAUCAUCAAGGACAAGGACUUCCUGGACAACGAGGAGAACGAGGACAUCCUGGAGGACAUCGUGCUGACCCUGA<br>CCCUGUUCGAGGACCGGGAGAUGAUCGAGGAGCGGCUGAAGACCUACGCCCACCUGUUCGACGACAAGGUGAUGAAGCAGCUGAAGC<br>GGCGGCGGUACACCGGCUGGGGCCGGCUGAGCCGGAAGCUGAUCAACGGCAUCCGGGACAAGCAGAGCGGCAAGACCAUCCUGGACU<br>UCCUGAAGAGCGACGGCUUCGCCAACCGGAACUUCAUGCAGCUGAUCCACGACGACAGCCUGACCUUCAAGGAGGACAUCCAGAAGG<br>CCCAGGUGAGCGGCCAGGGCGACAGCCUGCACGAGCACAUCGCCAACCUGGCCGGCAGCCCCGCCAUCAAGAAGGGCAUCCUGCAGA<br>CCGUGAAGGUGGUGGACGAGCUGGUGAAGGUGAUGGGCCGGCACAAGCCCGAGAACAUCGUGAUCGAGAUGGCCCGGGAGAACCAGA<br>CCACCCAGAAGGGCCAGAAGAACAGCCGGGAGCGGAUGAAGCGGAUCGAGGAGGGCAUCAAGGAGCUGGGCAGCCAGAUCCUGAAGG<br>AGCACCCCGUGGAGAACACCCAGCUGCAGAACGAGAAGCUGUACCUGUACUACCUGCAGAACGGCCGGGACAUGUACGUGGACCAGG<br>AGCUGGACAUCAACCGGCUGAGCGACUACGACGUGGACCACAUCGUGCCCCAGAGCUUCCUGAAGGACGACAGCAUCGACAACAAGG<br>UGCUGACCCGGAGCGACAAGAACCGGGGCAAGAGCGACAACGUGCCCAGCGAGGAGGUGGUGAAGAAGAUGAAGAACUACUGGCGGC<br>AGCUGCUGAACGCCAAGCUGAUCACCCAGCGGAAGUUCGACAACCUGACCAAGGCCGAGCGGGGCGGCCUGAGCGAGCUGGACAAGG<br>CCGGCUUCAUCAAGCGGCAGCUGGUGGAGACCCGGCAGAUCACCAAGCACGUGGCCCAGAUCCUGGACAGCCGGAUGAACACCAAGU<br>ACGACGAGAACGACAAGCUGAUCCGGGAGGUGAAGGUGAUCACCCUGAAGAGCAAGCUGGUGAGCGACUUCCGGAAGGACUUCCAGU<br>UCUACAAGGUGCGGGAGAUCAACAACUACCACCACGCCCACGACGCCUACCUGAACGCCGUGGUGGGCACCGCCCUGAUCAAGAAGU<br>ACCCCAAGCUGGAGAGCGAGUUCGUGUACGGCGACUACAAGGUGUACGACGUGCGGAAGAUGAUCGCCAAGAGCGAGCAGGAGAUCG<br>GCAAGGCCACCGCCAAGUACUUCUUCUACAGCAACAUCAUGAACUUCUUCAAGACCGAGAUCACCCUGGCCAACGGCGAGAUCCGGA<br>AGCGGCCCCUGAUCGAGACCAACGGCGAGACCGGCGAGAUCGUGUGGGACAAGGGCCGGGACUUCGCCACCGUGCGGAAGGUGCUGA<br>GCAUGCCCCAGGUGAACAUCGUGAAGAAGACCGAGGUGCAGACCGGCGGCUUCAGCAAGGAGAGCAUCCUGCCCAAGCGGAACAGCG<br>ACAAGCUGAUCGCCCGGAAGAAGGACUGGGACCCCAAGAAGUACGGCGGCUUCGACAGCCCCACCGUGGCCUACAGCGUGCUGGUGG<br>UGGCCAAGGUGGAGAAGGGCAAGAGCAAGAAGCUGAAGAGCGUGAAGGAGCUGCUGGGCAUCACCAUCAUGGAGCGGAGCAGCUUCG<br>AGAAGAACCCCAUCGACUUCCUGGAGGCCAAGGGCUACAAGGAGGUGAAGAAGGACCUGAUCAUCAAGCUGCCCAAGUACAGCCUGU<br>UCGAGCUGGAGAACGGCCGGAAGCGGAUGCUGGCCAGCGCCGGCGAGCUGCAGAAGGGCAACGAGCUGGCCCUGCCCAGCAAGUACG<br>UGAACUUCCUGUACCUGGCCAGCCACUACGAGAAGCUGAAGGGCAGCCCCGAGGACAACGAGCAGAAGCAGCUGUUCGUGGAGCAGC<br>ACAAGCACUACCUGGACGAGAUCAUCGAGCAGAUCAGCGAGUUCAGCAAGCGGGUGAUCCUGGCCGACGCCAACCUGGACAAGGUGC<br>UGAGCGCCUACAACAAGCACCGGGACAAGCCCAUCCGGGAGCAGGCCGAGAACAUCAUCCACCUGUUCACCCUGACCAACCUGGGCG<br>CCCCCGCCGCCUUCAAGUACUUCGACACCACCAUCGACCGGAAGCGGUACACCAGCACCAAGGAGGUGCUGGACGCCACCCUGAUCC<br>ACCAGAGCAUCACCGGCCUGUACGAGACCCGGAUCGACCUGAGCCAGCUGGGCGGCGACGGCGGCGGCAGCCCCAAGAAGAAGCGGA<br>AGGUGUGACUAGCACCAGCCUCAAGAACACCCGAAUGGAGUCUCUAAGCUACAUAAUACCAACUUACACUUUACAAAAUGUUGUCCC<br>CCAAAAUGUAGCCAUUCGUAUCUGCUCCUAAUAAAAAGAAAGUUUCUUCACAUUCUCUCGAGAAAAAAAAAAAAAAAAAAAAAAAAA<br>AAAAAAAAAAAAAAAAAAAAAAAAAAAAAAAAAAAAAAAAAAAAAAAAAAAAAAA | |
| mRNA | GGGTCCCGCAGTCGGCGTCCAGCGGCTCTGCTTGTTCGTGTGTGTGTCGTTGCAGGCCTTATTCGGATCCGCCACCATGGACAAGAA | 379 |

-continued

Sequence Table

| Description | Sequence | SEQ ID No. |
|---|---|---|
| transcript | GTACAGCATCGGACTGGACATCGGAACAAACAGCGTCGGATGGGCAGTCATCACAGACGAATACAAGGTCCCGAGCAAGAAGTTCAA | |
| with ORF | GGTCCTGGGAAACACAGACAGACACAGCATCAAGAAGAACCTGATCGGAGCACTGCTGTTCGACAGCGGAGAAACAGCAGAAGCAAC | |
| encoding | AAGACTGAAGAGAACAGCAAGAAGAAGATACACAAGAAGAAAGAACAGAATCTGCTACCTGCAGGAAATCTTCAGCAACGAAATGGC | |
| Cas9 with | AAAGGTCGACGACAGCTTCTTCCACAGACTGGAAGAAAGCTTCCTGGTCGAAGAAGACAAGAAGCACGAAAGACACCCGATCTTCGG | |
| HiBiT tag, | AAACATCGTCGACGAAGTCGCATACCACGAAAAGTACCCGACAATCTACCACCTGAGAAAGAAGCTGGTCGACAGCACAGACAAGGC | |
| HSD 5' UTR | AGACCTGAGACTGATCTACCTGGCACTGGCACACATGATCAAGTTCAGAGGACACTTCCTGATCGAAGGAGACCTGAACCCGGACAA | |
| and human | CAGCGACGTCGACAAGCTGTTCATCCAGCTGGTCCAGACATACAACCAGCTGTTCGAAGAAAACCCGATCAACGCAAGCGGAGTCGA | |
| ALB 3' UTR | CGCAAAGGCAATCCTGAGCGCAAGACTGAGCAAGAGCAGAAGACTGGAAAACCTGATCGCACAGCTGCCGGGAGAAAAGAAGAACGG | |
| | ACTGTTCGGAAACCTGATCGCACTGAGCCTGGGACTGACACCGAACTTCAAGAGCAACTTCGACCTGGCAGAAGACGCAAAGCTGCA | |
| | GCTGAGCAAGGACACATACGACGACGACCTGGACAACCTGCTGGCACAGATCGGAGACCAGTACGCAGACCTGTTCCTGGCAGCAAA | |
| | GAACCTGAGCGACGCAATCCTGCTGAGCGACATCCTGAGAGTCAACACAGAAATCACAAAGGCACCGCTGAGCGCAAGCATGATCAA | |
| | GAGATACGACGAACACCACCAGGACCTGACACTGCTGAAGGCACTGGTCAGACAGCAGCTGCCGGAAAAGTACAAGGAAATCTTCTT | |
| | CGACCAGAGCAAGAACGGATACGCAGGATACATCGACGGAGGAGCAAGCCAGGAAGAATTCTACAAGTTCATCAAGCCGATCCTGGA | |
| | AAAGATGGACGGAACAGAAGAACTGCTGGTCAAGCTGAACAGAGAAGACCTGCTGAGAAAGCAGAGAACATTCGACAACGGAAGCAT | |
| | CCCGCACCAGATCCACCTGGGAGAACTGCACGCAATCCTGAGAAGACAGGAAGACTTCTACCCGTTCCTGAAGGACAACAGAGAAAA | |
| | GATCGAAAAGATCCTGACATTCAGAATCCCGTACTACGTCGGACCGCTGGCAAGAGGAAACAGCAGATTCGCATGGATGACAAGAAA | |
| | GAGCGAAGAAACAATCACACCGTGGAACTTCGAAGAAGTCGTCGACAAGGGAGCAAGCGCACAGAGCTTCATCGAAAGAATGACAAA | |
| | CTTCGACAAGAACCTGCCGAACGAAAAGGTCCTGCCGAAGCACAGCCTGCTGTACGAATACTTCACAGTCTACAACGAACTGACAAA | |
| | GGTCAAGTACGTCACAGAAGGAATGAGAAAGCCGGCATTCCTGAGCGGAGAACAGAAGAAGGCAATCGTCGACCTGCTGTTCAAGAC | |
| | AAACAGAAAGGTCACAGTCAAGCAGCTGAAGGAAGACTACTTCAAGAAGATCGAATGCTTCGACAGCGTCGAAATCAGCGGAGTCGA | |
| | AGACAGATTCAACGCAAGCCTGGGAACATACCACGACCTGCTGAAGATCATCAAGGACAAGGACTTCCTGGACAACGAAGAAAACGA | |
| | AGACATCCTGGAAGACATCGTCCTGACACTGACACTGTTCGAAGACAGAGAAATGATCGAAGAAAGACTGAAGACATACGCACACCT | |
| | GTTCGACGACAAGGTCATGAAGCAGCTGAAGAGAAGAAGATACACAGGATGGGGAAGACTGAGCAGAAAGCTGATCAACGGAATCAG | |
| | AGACAAGCAGAGCGGAAAGACAATCCTGGACTTCCTGAAGAGCGACGGATTCGCAAACAGAAACTTCATGCAGCTGATCCACGACGA | |
| | CAGCCTGACATTCAAGGAAGACATCCAGAAGGCACAGGTCAGCGGACAGGGAGACAGCCTGCACGAACACATCGCAAACCTGGCAGG | |
| | AAGCCCGGCAATCAAGAAGGGAATCCTGCAGACAGTCAAGGTCGTCGACGAACTGGTCAAGGTCATGGGAAGACACAAGCCGGAAAA | |
| | CATCGTCATCGAAATGGCAAGAGAAAACCAGACAACACAGAAGGGACAGAAGAACAGCAGAGAAAGAATGAAGAGAATCGAAGAAGG | |
| | AATCAAGGAACTGGGAAGCCAGATCCTGAAGGAACACCCGGTCGAAAACACACAGCTGCAGAACGAAAAGCTGTACCTGTACTACCT | |
| | GCAGAACGGAAGAGACATGTACGTCGACCAGGAACTGGACATCAACAGACTGAGCGACTACGACGTCGACCACATCGTCCCGCAGAG | |
| | CTTCCTGAAGGACGACAGCATCGACAACAAGGTCCTGACAAGAAGCGACAAGAACAGAGGAAAGAGCGACAACGTCCCGAGCGAAGA | |
| | AGTCGTCAAGAAGATGAAGAACTACTGGAGACAGCTGCTGAACGCAAAGCTGATCACACAGAGAAAGTTCGACAACCTGACAAAGGC | |
| | AGAGAGAGGAGGACTGAGCGAACTGGACAAGGCAGGATTCATCAAGAGACAGCTGGTCGAAACAAGACAGATCACAAAGCACGTCGC | |
| | ACAGATCCTGGACAGCAGAATGAACACAAAGTACGACGAAAACGACAAGCTGATCAGAGAAGTCAAGGTCATCACACTGAAGAGCAA | |
| | GCTGGTCAGCGACTTCAGAAAGGACTTCCAGTTCTACAAGGTCAGAGAAATCAACAACTACCACCACGCACACGACGCATACCTGAA | |
| | CGCAGTCGTCGGAACAGCACTGATCAAGAAGTACCCGAAGCTGGAAAGCGAATTCGTCTACGGAGACTACAAGGTCTACGACGTCAG | |
| | AAAGATGATCGCAAAGAGCGAACAGGAAATCGGAAAGGCAACAGCAAAGTACTTCTTCTACAGCAACATCATGAACTTCTTCAAGAC | |
| | AGAAATCACACTGGCAAACGGAGAAATCAGAAAGAGACCGCTGATCGAAACAAACGGAGAAACAGGAGAAATCGTCTGGGACAAGGG | |
| | AAGAGACTTCGCAACAGTCAGAAAGGTCCTGAGCATGCCGCAGGTCAACATCGTCAAGAAGACAGAAGTCCAGACAGGAGGATTCAG | |
| | CAAGGAAAGCATCCTGCCGAAGAGAAACAGCGACAAGCTGATCGCAAGAAAGAAGGACTGGGACCCGAAGAAGTACGGAGGATTCGA | |
| | CAGCCCGACAGTCGCATACAGCGTCCTGGTCGTCGCAAAGGTCGAAAAGGGAAAGAGCAAGAAGCTGAAGAGCGTCAAGGAACTGCT | |
| | GGGAATCACAATCATGGAAAGAAGCAGCTTCGAAAAGAACCCGATCGACTTCCTGGAAGCAAAGGGATACAAGGAAGTCAAGAAGGA | |
| | CCTGATCATCAAGCTGCCGAAGTACAGCCTGTTCGAACTGGAAAACGGAAGAAAGAGAATGCTGGCAAGCGCAGGAGAACTGCAGAA | |
| | GGGAAACGAACTGGCACTGCCGAGCAAGTACGTCAACTTCCTGTACCTGGCAAGCCACTACGAAAAGCTGAAGGGAAGCCCGGAAGA | |
| | CAACGAACAGAAGCAGCTGTTCGTCGAACAGCACAAGCACTACCTGGACGAAATCATCGAACAGATCAGCGAATTCAGCAAGAGAGT | |
| | CATCCTGGCAGACGCAAACCTGGACAAGGTCCTGAGCGCATACAACAAGCACAGAGACAAGCCGATCAGAGAACAGGCAGAAAACAT | |
| | CATCCACCTGTTCACACTGACAAACCTGGGAGCACCGGCAGCATTCAAGTACTTCGACACAACAATCGACAGAAAGAGATACACAAG | |
| | CACAAAGGAAGTCCTGGACGCAACACTGATCCACCAGAGCATCACAGGACTGTACGAAACAAGAATCGACCTGAGCCAGCTGGGAGG | |
| | AGACGGAGGAGGAAGCCCGAAGAAGAAGAGAAAGGTCAGCGAAAGCGCAACACCGGAAAGCGTCAGCGGATGGAGACTGTTCAAGAA | |
| | GATCAGCTAGCTAGCCATCACATTTAAAAGCATCTCAGCCTACCATGAGAATAAGAGAAAGAAAATGAAGATCAATAGCTTATTCAT | |

-continued

Sequence Table

| Description | Sequence | SEQ ID No. |
|---|---|---|
| | CTCTTTTTCTTTTTCGTTGGTGTAAAGCCAACACCCTGTCTAAAAAACATAAATTTCTTTAATCATTTTGCCTCTTTTCTCTGTGCT<br>TCAATTAATAAAAAATGGAAAGAACCTCGAGAAAAAAAAAAAAAAAAAAAAAAAAAAAAAAAAAAAAAAAAAAAAAAAAAAAAAAAAA<br>AAAAAAAAAAAAAAAAAAAAAAAA | |
| mRNA transcript with ORF encoding Cas9 with HiBiT tag, CMV-1 5' UTR and human ALB 3' UTR | GGGCAGATCGCCTGGAGACGCCATCCACGCTGTTTTGACCTCCATCGCCACCATGGACAAGAAGTACAGCATCGGACTGGACATCGG<br>AACAAACAGCGTCGGATGGGCAGTCATCACAGACGAATACAAGGTCCCGAGCAAGAAGTTCAAGGTCCTGGGAPACACAGACAGACA<br>CAGCATCAAGAAGAACCTGATCGGAGCACTGCTGTTCGACAGCGGAGAAACAGCAGAAGCAACAAGACTGAAGAGAACAGCAAGAAG<br>AAGATACACAAGAAGAAAGAACAGAATCTGCTACCTGCAGGAAATCTTCAGCAACGAAATGGCAAAGGTCGACGACAGCTTCTTCCA<br>CAGACTGGAAGAAAGCTTCCTGGTCGAAGAAGACAAGAAGCACGAAAGACACCCGATCTTCGGAAACATCGTCGACGAAGTCGCATA<br>CCACGAAAAGTACCCGACAATCTACCACCTGAGAAAGAAGCTGGTCGACAGCACAGACAAGGCAGACCTGAGACTGATCTACCTGGC<br>ACTGGCACACATGATCAAGTTCAGAGGACACTTCCTGATCGAAGGAGACCTGAACCCGGACAACAGCGACGTCGACAAGCTGTTCAT<br>CCAGCTGGTCCAGACATACAACCAGCTGTTCGAAGAAAACCCGATCAACGCAAGCGGAGTCGACGCAAAGGCAATCCTGAGCGCAAG<br>ACTGAGCAAGAGCAGAAGACTGGAAAACCTGATCGCACAGCTGCCGGGAGAAAAGAAGAACGGACTGTTCGGAAACCTGATCGCACT<br>GAGCCTGGGACTGACACCGAACTTCAAGAGCAACTTCGACCTGGCAGAAGACGCAAAGCTGCAGCTGAGCAAGGACACATACGACGA<br>CGACCTGGACAACCTGCTGGCACAGATCGGAGACCAGTACGCAGACCTGTTCCTGGCAGCAAAGAACCTGAGCGACGCAATCCTGCT<br>GAGCGACATCCTGAGAGTCAACACAGAAATCACAAAGGCACCGCTGAGCGCAAGCATGATCAAGAGATACGACGAACACCACCAGGA<br>CCTGACACTGCTGAAGGCACTGGTCAGACAGCAGCTGCCGGAAAAGTACAAGGAAATCTTCTTCGACCAGAGCAAGAACGGATACGC<br>AGGATACATCGACGGAGGAGCAAGCCAGGAAGAATTCTACAAGTTCATCAAGCCGATCCTGGAAAAGATGGACGGAACAGAAGAACT<br>GCTGGTCAAGCTGAACAGAGAAGACCTGCTGAGAAAGCAGAGAACATTCGACAACGGAAGCATCCCGCACCAGATCCACCTGGGAGA<br>ACTGCACGCAATCCTGAGAAGACAGGAAGACTTCTACCCGTTCCTGAAGGACAACAGAGAAAAGATCGAAAAGATCCTGACATTCAG<br>AATCCCGTACTACGTCGGACCGCTGGCAAGAGGAAACAGCAGATTCGCATGGATGACAAGAAAGAGCGAAGAAACAATCACACCGTG<br>GAACTTCGAAGAAGTCGTCGACAAGGGAGCAAGCGCACAGAGCTTCATCGAAAGAATGACAAACTTCGACAAGAACCTGCCGAACGA<br>AAAGGTCCTGCCGAAGCACAGCCTGCTGTACGAATACTTCACAGTCTACAACGAACTGACAAAGGTCAAGTACGTCACAGAAGGAAT<br>GAGAAAGCCGGCATTCCTGAGCGGAGAACAGAAGAAGGCAATCGTCGACCTGCTGTTCAAGACAAACAGAAAGGTCACAGTCAAGCA<br>GCTGAAGGAAGACTACTTCAAGAAGATCGAATGCTTCGACAGCGTCGAAATCAGCGGAGTCGAAGACAGATTCAACGCAAGCCTGGG<br>AACATACCACGACCTGCTGAAGATCATCAAGGACAAGGACTTCCTGGACAACGAAGAAAACGAAGACATCCTGGAAGACATCGTCCT<br>GACACTGACACTGTTCGAAGACAGAGAAATGATCGAAGAAAGACTGAAGACATACGCACACCTGTTCGACGACAAGGTCATGAAGCA<br>GCTGAAGAGAAGAAGATACACAGGATGGGGAAGACTGAGCAGAAAGCTGATCAACGGAATCAGAGACAAGCAGAGCGGAAAGACAAT<br>CCTGGACTTCCTGAAGAGCGACGGATTCGCAAACAGAAACTTCATGCAGCTGATCCACGACGACAGCCTGACATTCAAGGAAGACAT<br>CCAGAAGGCACAGGTCAGCGGACAGGGAGACAGCCTGCACGAACACATCGCAAACCTGGCAGGAAGCCCGGCAATCAAGAAGGGAAT<br>CCTGCAGACAGTCAAGGTCGTCGACGAACTGGTCAAGGTCATGGGAAGACACAAGCCGGAAAACATCGTCATCGAAATGGCAAGAGA<br>AAACCAGACAACACAGAAGGGACAGAAGAACAGCAGAGAAAGAATGAAGAGAATCGAAGAAGGAATCAAGGAACTGGGAAGCCAGAT<br>CCTGAAGGAACACCCGGTCGAAAACACACAGCTGCAGAACGAAAAGCTGTACCTGTACTACCTGCAGAACGGAAGAGACATGTACGT<br>CGACCAGGAACTGGACATCAACAGACTGAGCGACTACGACGTCGACCACATCGTCCCGCAGAGCTTCCTGAAGGACGACAGCATCGA<br>CAACAAGGTCCTGACAAGAAGCGACAAGAACAGAGGAAAGAGCGACAACGTCCCGAGCGAAGAAGTCGTCAAGAAGATGAAGAACTA<br>CTGGAGACAGCTGCTGAACGCAAAGCTGATCACACAGAGAAAGTTCGACAACCTGACAAAGGCAGAGAGAGGAGGACTGAGCGAACT<br>GGACAAGGCAGGATTCATCAAGAGACAGCTGGTCGAAACAAGACAGATCACAAAGCACGTCGCACAGATCCTGGACAGCAGAATGAA<br>CACAAAGTACGACGAAAACGACAAGCTGATCAGAGAAGTCAAGGTCATCACACTGAAGAGCAAGCTGGTCAGCGACTTCAGAAAGGA<br>CTTCCAGTTCTACAAGGTCAGAGAAATCAACAACTACCACCACGCACACGACGCATACCTGAACGCAGTCGTCGGAACAGCACTGAT<br>CAAGAAGTACCCGAAGCTGGAAAGCGAATTCGTCTACGGAGACTACAAGGTCTACGACGTCAGAAAGATGATCGCAAAGAGCGAACA<br>GGAAATCGGAAAGGCAACAGCAAAGTACTTCTTCTACAGCAACATCATGAACTTCTTCAAGACAGAAATCACACTGGCAAACGGAGA<br>AATCAGAAAGAGACCGCTGATCGAAACAAACGGAGAAACAGGAGAAATCGTCTGGGACAAGGGAAGAGACTTCGCAACAGTCAGAAA<br>GGTCCTGAGCATGCCGCAGGTCAACATCGTCAAGAAGACAGAAGTCCAGACAGGAGGATTCAGCAAGGAAAGCATCCTGCCGAAGAG<br>AAACAGCGACAAGCTGATCGCAAGAAAGAAGGACTGGGACCCGAAGAAGTACGGAGGATTCGACAGCCCGACAGTCGCATACAGCGT<br>CCTGGTCGTCGCAAAGGTCGAAAAGGGAAAGAGCAAGAAGCTGAAGAGCGTCAAGGAACTGCTGGGAATCACAATCATGGAAAGAAG<br>CAGCTTCGAAAAGAACCCGATCGACTTCCTGGAAGCAAAGGGATACAAGGAAGTCAAGAAGGACCTGATCATCAAGCTGCCGAAGTA<br>CAGCCTGTTCGAACTGGAAAACGGAAGAAAGAGAATGCTGGCAAGCGCAGGAGAACTGCAGAAGGGAAACGAACTGGCACTGCCGAG<br>CAAGTACGTCAACTTCCTGTACCTGGCAAGCCACTACGAAAAGCTGAAGGGAAGCCCGGAAGACAACGAACAGAAGCAGCTGTTCGT<br>CGAACAGCACAAGCACTACCTGGACGAAATCATCGAACAGATCAGCGAATTCAGCAAGAGAGTCATCCTGGCAGACGCAAACCTGGA | 380 |

-continued

Sequence Table

| Description | Sequence | SEQ ID No. |
|---|---|---|
| | CAAGGTCCTGAGCGCATACAACAAGCACAGAGACAAGCCGATCAGAGAACAGGCAGAAAACATCATCCACCTGTTCACACTGACAAA | |
| | CCTGGGAGCACCGGCAGCATTCAAGTACTTCGACACAACAATCGACAGAAAGAGATACACAAGCACAAAGGAAGTCCTGGACGCAAC | |
| | ACTGATCCACCAGAGCATCACAGGACTGTACGAAACAAGAATCGACCTGAGCCAGCTGGGAGGAGACGGAGGAGGAAGCCCGAAGAA | |
| | GAAGAGAAAGGTCAGCGAAAGCGCAACACCGGAAAGCGTCAGCGGATGGAGACTGTTCAAGAAGATCAGCTAGCTAGCCATCACATT | |
| | TAAAAGCATCTCAGCCTACCATGAGAATAAGAGAAAGAAAATGAAGATCAATAGCTTATTCATCTCTTTTTCTTTTTCGTTGGTGTA | |
| | AAGCCAACACCCTGTCTAAAAAACATAAATTTCTTTAATCATTTTGCCTCTTTTCTCTGTGCTTCAATTAATAAAAAATGGAAAGAA | |
| | CCTCGAAAAAAAAAAAAAAAAAAAAAAAAAAAAAAAAAAAAAAAAAAAAAAAAAAAAAAAAAAAAAAAAAAAAA | |
| mRNA | GGGAGAAGACACCGGGACCGATCCAGCCTCCGCGGCCGGGAACGGCGCCACCATGGACAAGAAGTACAGCATCGGACTGGACATCGG | 381 |
| transcript | AACAAACAGCGTCGGATGGGCAGTCATCACAGACGAATACAAGGTCCCGAGCAAGAAGTTCAAGGTCCTGGGPAACACAGACAGACA | |
| with ORF | CAGCATCAAGAAGAACCTGATCGGAGCACTGCTGTTCGACAGCGGAGAAACAGCAGAAGCAACAAGACTGAAGAGAACAGCAAGAAG | |
| encoding | AAGATACACAAGAAGAAAGAACAGAATCTGCTACCTGCAGGAAATCTTCAGCAACGAAATGGCAAAGGTCGACGACAGCTTCTTCCA | |
| Cas9 with | CAGACTGGAAGAAAGCTTCCTGGTCGAAGAAGACAAGAAGCACGAAAGACACCCGATCTTCGGAAACATCGTCGACGAAGTCGCATA | |
| HiBiT tag, | CCACGAAAAGTACCCGACAATCTACCACCTGAGAAAGAAGCTGGTCGACAGCACAGACAAGGCAGACCTGAGACTGATCTACCTGGC | |
| CMV-2 5' | ACTGGCACACATGATCAAGTTCAGAGGACACTTCCTGATCGAAGGAGACCTGAACCCGGACAACAGCGACGTCGACAAGCTGTTCAT | |
| UTR and | CCAGCTGGTCCAGACATACAACCAGCTGTTCGAAGAAAACCCGATCAACGCAAGCGGAGTCGACGCAAAGGCAATCCTGAGCGCAAG | |
| human ALB | ACTGAGCAAGAGCAGAAGACTGGAAAACCTGATCGCACAGCTGCCGGGAGAAAAGAAGAACGGACTGTTCGGAAACCTGATCGCACT | |
| 3' UTR | GAGCCTGGGACTGACACCGAACTTCAAGAGCAACTTCGACCTGGCAGAAGACGCAAAGCTGCAGCTGAGCAAGGACACATACGACGA | |
| | CGACCTGGACAACCTGCTGGCACAGATCGGAGACCAGTACGCAGACCTGTTCCTGGCAGCAAAGAACCTGAGCGACGCAATCCTGCT | |
| | GAGCGACATCCTGAGAGTCAACACAGAAATCACAAAGGCACCGCTGAGCGCAAGCATGATCAAGAGATACGACGAACACCACCAGGA | |
| | CCTGACACTGCTGAAGGCACTGGTCAGACAGCAGCTGCCGGAAAAGTACAAGGAAATCTTCTTCGACCAGAGCAAGAACGGATACGC | |
| | AGGATACATCGACGGAGGAGCAAGCCAGGAAGAATTCTACAAGTTCATCAAGCCGATCCTGGAAAAGATGGACGGAACAGAAGAACT | |
| | GCTGGTCAAGCTGAACAGAGAAGACCTGCTGAGAAAGCAGAGAACATTCGACAACGGAAGCATCCCGCACCAGATCCACCTGGGAGA | |
| | ACTGCACGCAATCCTGAGAAGACAGGAAGACTTCTACCCGTTCCTGAAGGACAACAGAGAAAAGATCGAAAAGATCCTGACATTCAG | |
| | AATCCCGTACTACGTCGGACCGCTGGCAAGAGGAAACAGCAGATTCGCATGGATGACAAGAAAGAGCGAAGAAACAATCACACCGTG | |
| | GAACTTCGAAGAAGTCGTCGACAAGGGAGCAAGCGCACAGAGCTTCATCGAAAGAATGACAAACTTCGACAAGAACCTGCCGAACGA | |
| | AAAGGTCCTGCCGAAGCACAGCCTGCTGTACGAATACTTCACAGTCTACAACGAACTGACAAAGGTCAAGTACGTCACAGAAGGAAT | |
| | GAGAAAGCCGGCATTCCTGAGCGGAGAACAGAAGAAGGCAATCGTCGACCTGCTGTTCAAGACAAACAGAAAGGTCACAGTCAAGCA | |
| | GCTGAAGGAAGACTACTTCAAGAAGATCGAATGCTTCGACAGCGTCGAAATCAGCGGAGTCGAAGACAGATTCAACGCAAGCCTGGG | |
| | AACATACCACGACCTGCTGAAGATCATCAAGGACAAGGACTTCCTGGACAACGAAGAAAACGAAGACATCCTGGAAGACATCGTCCT | |
| | GACACTGACACTGTTCGAAGACAGAGAAATGATCGAAGAAAGACTGAAGACATACGCACACCTGTTCGACGACAAGGTCATGAAGCA | |
| | GCTGAAGAGAAGAAGATACACAGGATGGGGAAGACTGAGCAGAAAGCTGATCAACGGAATCAGAGACAAGCAGAGCGGAAAGACAAT | |
| | CCTGGACTTCCTGAAGAGCGACGGATTCGCAAACAGAAACTTCATGCAGCTGATCCACGACGACAGCCTGACATTCAAGGAAGACAT | |
| | CCAGAAGGCACAGGTCAGCGGACAGGGAGACAGCCTGCACGAACACATCGCAAACCTGGCAGGAAGCCCGGCAATCAAGAAGGGAAT | |
| | CCTGCAGACAGTCAAGGTCGTCGACGAACTGGTCAAGGTCATGGGAAGACACAAGCCGGAAAACATCGTCATCGAAATGGCAAGAGA | |
| | AAACCAGACAACACAGAAGGGACAGAAGAACAGCAGAGAAAGAATGAAGAGAATCGAAGAAGGAATCAAGGAACTGGGAAGCCAGAT | |
| | CCTGAAGGAACACCCGGTCGAAAACACACAGCTGCAGAACGAAAAGCTGTACCTGTACTACCTGCAGAACGGAAGAGACATGTACGT | |
| | CGACCAGGAACTGGACATCAACAGACTGAGCGACTACGACGTCGACCACATCGTCCCGCAGAGCTTCCTGAAGGACGACAGCATCGA | |
| | CAACAAGGTCCTGACAAGAAGCGACAAGAACAGAGGAAAGAGCGACAACGTCCCGAGCGAAGAAGTCGTCAAGAAGATGAAGAACTA | |
| | CTGGAGACAGCTGCTGAACGCAAAGCTGATCACACAGAGAAAGTTCGACAACCTGACAAAGGCAGAGAGAGGAGGACTGAGCGAACT | |
| | GGACAAGGCAGGATTCATCAAGAGACAGCTGGTCGAAACAAGACAGATCACAAAGCACGTCGCACAGATCCTGGACAGCAGAATGAA | |
| | CACAAAGTACGACGAAAACGACAAGCTGATCAGAGAAGTCAAGGTCATCACACTGAAGAGCAAGCTGGTCAGCGACTTCAGAAAGGA | |
| | CTTCCAGTTCTACAAGGTCAGAGAAATCAACAACTACCACCACGCACACGACGCATACCTGAACGCAGTCGTCGGAACAGCACTGAT | |
| | CAAGAAGTACCCGAAGCTGGAAAGCGAATTCGTCTACGGAGACTACAAGGTCTACGACGTCAGAAAGATGATCGCAAAGAGCGAACA | |
| | GGAAATCGGAAAGGCAACAGCAAAGTACTTCTTCTACAGCAACATCATGAACTTCTTCAAGACAGAAATCACACTGGCAAACGGAGA | |
| | AATCAGAAAGAGACCGCTGATCGAAACAAACGGAGAAACAGGAGAAATCGTCTGGGACAAGGGAAGAGACTTCGCAACAGTCAGAAA | |
| | GGTCCTGAGCATGCCGCAGGTCAACATCGTCAAGAAGACAGAAGTCCAGACAGGAGGATTCAGCAAGGAAAGCATCCTGCCGAAGAG | |
| | AAACAGCGACAAGCTGATCGCAAGAAAGAAGGACTGGGACCCGAAGAAGTACGGAGGATTCGACAGCCCGACAGTCGCATACAGCGT | |
| | CCTGGTCGTCGCAAAGGTCGAAAAGGGAPAGAGCAAGAAGCTGAAGAGCGTCAAGGAACTGCTGGGAATCACAATCATGGAAAGAAG | |

-continued

Sequence Table

| Description | Sequence | SEQ ID No. |
|---|---|---|
| | CAGCTTCGAAAAGAACCCGATCGACTTCCTGGAAGCAAAGGGATACAAGGAAGTCAAGAAGGACCTGATCATCAAGCTGCCGAAGTA | |
| | CAGCCTGTTCGAACTGGAAAACGGAAGAAAGAGAATGCTGGCAAGCGCAGGAGAACTGCAGAAGGGAAACGAACTGGCACTGCCGAG | |
| | CAAGTACGTCAACTTCCTGTACCTGGCAAGCCACTACGAAAAGCTGAAGGGAAGCCCGGAAGACAACGAACAGAAGCAGCTGTTCGT | |
| | CGAACAGCACAAGCACTACCTGGACGAAATCATCGAACAGATCAGCGAATTCAGCAAGAGAGTCATCCTGGCAGACGCAAACCTGGA | |
| | CAAGGTCCTGAGCGCATACAACAAGCACAGAGACAAGCCGATCAGAGAACAGGCAGAAAACATCATCCACCTGTTCACACTGACAAA | |
| | CCTGGGAGCACCGGCAGCATTCAAGTACTTCGACACAACAATCGACAGAAAGAGATACACAAGCACAAAGGAAGTCCTGGACGCAAC | |
| | ACTGATCCACCAGAGCATCACAGGACTGTACGAAACAAGAATCGACCTGAGCCAGCTGGGAGGAGACGGAGGAGGAAGCCCGAAGAA | |
| | GAAGAGAAAGGTCAGCGAAAGCGCAACACCGGAAAGCGTCAGCGGATGGAGACTGTTCAAGAAGATCAGCTAGCTAGCCATCACATT | |
| | TAAAAGCATCTCAGCCTACCATGAGAATAAGAGAAAGAAAATGAAGATCAATAGCTTATTCATCTCTTTTTCTTTTTCGTTGGTGTA | |
| | AAGCCAACACCCTGTCTAAAAAACATAAATTTCTTTAATCATTTTGCCTCTTTTCTCTGTGCTTCAATTAATAAAAAATGGAAAGAA | |
| | CCTCGAGAAAAAAAAAAAAAAAAAAAAAAAAAAAAAAAAAAAAAAAAAAAAAAAAAAAAAAAAAAAAAAAAAAAAAAAAAAAAAAAA | |
| mRNA | GGGTGCATTGGAACGCGGATTCCCCGTGCCAAGAGTGACTCACCGCGCCACCATGGACAAGAAGTACAGCATCGGACTGGACATCGG | 382 |
| transcript | AACAAACAGCGTCGGATGGGCAGTCATCACAGACGAATACAAGGTCCCGAGCAAGAAGTTCAAGGTCCTGGGPAACACAGACAGACA | |
| with ORF | CAGCATCAAGAAGAACCTGATCGGAGCACTGCTGTTCGACAGCGGAGAAACAGCAGAAGCAACAAGACTGAAGAGAACAGCAAGAAG | |
| encoding | AAGATACACAAGAAGAAAGAACAGAATCTGCTACCTGCAGGAAATCTTCAGCAACGAAATGGCAAAGGTCGACGACAGCTTCTTCCA | |
| Cas9 with | CAGACTGGAAGAAAGCTTCCTGGTCGAAGAAGACAAGAAGCACGAAAGACACCCGATCTTCGGAAACATCGTCGACGAAGTCGCATA | |
| HiBiT tag, | CCACGAAAAGTACCCGACAATCTACCACCTGAGAAAGAAGCTGGTCGACAGCACAGACAAGGCAGACCTGAGACTGATCTACCTGGC | |
| CMV-3 5' | ACTGGCACACATGATCAAGTTCAGAGGACACTTCCTGATCGAAGGAGACCTGAACCCGGACAACAGCGACGTCGACAAGCTGTTCAT | |
| UTR and | CCAGCTGGTCCAGACATACAACCAGCTGTTCGAAGAAAACCCGATCAACGCAAGCGGAGTCGACGCAAAGGCAATCCTGAGCGCAAG | |
| human ALB | ACTGAGCAAGAGCAGAAGACTGGAAAACCTGATCGCACAGCTGCCGGGAGAAAAGAAGAACGGACTGTTCGGAAACCTGATCGCACT | |
| 3' UTR | GAGCCTGGGACTGACACCGAACTTCAAGAGCAACTTCGACCTGGCAGAAGACGCAAAGCTGCAGCTGAGCAAGGACACATACGACGA | |
| | CGACCTGGACAACCTGCTGGCACAGATCGGAGACCAGTACGCAGACCTGTTCCTGGCAGCAAAGAACCTGAGCGACGCAATCCTGCT | |
| | GAGCGACATCCTGAGAGTCAACACAGAAATCACAAAGGCACCGCTGAGCGCAAGCATGATCAAGAGATACGACGAACACCACCAGGA | |
| | CCTGACACTGCTGAAGGCACTGGTCAGACAGCAGCTGCCGGAAAAGTACAAGGAAATCTTCTTCGACCAGAGCAAGAACGGATACGC | |
| | AGGATACATCGACGGAGGAGCAAGCCAGGAAGAATTCTACAAGTTCATCAAGCCGATCCTGGAAAAGATGGACGGAACAGAAGAACT | |
| | GCTGGTCAAGCTGAACAGAGAAGACCTGCTGAGAAAGCAGAGAACATTCGACAACGGAAGCATCCCGCACCAGATCCACCTGGGAGA | |
| | ACTGCACGCAATCCTGAGAAGACAGGAAGACTTCTACCCGTTCCTGAAGGACAACAGAGAAAAGATCGAAAAGATCCTGACATTCAG | |
| | AATCCCGTACTACGTCGGACCGCTGGCAAGAGGAAACAGCAGATTCGCATGGATGACAAGAAAGAGCGAAGAAACAATCACACCGTG | |
| | GAACTTCGAAGAAGTCGTCGACAAGGGAGCAAGCGCACAGAGCTTCATCGAAAGAATGACAAACTTCGACAAGAACCTGCCGAACGA | |
| | AAAGGTCCTGCCGAAGCACAGCCTGCTGTACGAATACTTCACAGTCTACAACGAACTGACAAAGGTCAAGTACGTCACAGAAGGAAT | |
| | GAGAAAGCCGGCATTCCTGAGCGGAGAACAGAAGAAGGCAATCGTCGACCTGCTGTTCAAGACAAACAGAAAGGTCACAGTCAAGCA | |
| | GCTGAAGGAAGACTACTTCAAGAAGATCGAATGCTTCGACAGCGTCGAAATCAGCGGAGTCGAAGACAGATTCAACGCAAGCCTGGG | |
| | AACATACCACGACCTGCTGAAGATCATCAAGGACAAGGACTTCCTGGACAACGAAGAAAACGAAGACATCCTGGAAGACATCGTCCT | |
| | GACACTGACACTGTTCGAAGACAGAGAAATGATCGAAGAAAGACTGAAGACATACGCACACCTGTTCGACGACAAGGTCATGAAGCA | |
| | GCTGAAGAGAAGAAGATACACAGGATGGGGAAGACTGAGCAGAAAGCTGATCAACGGAATCAGAGACAAGCAGAGCGGAAAGACAAT | |
| | CCTGGACTTCCTGAAGAGCGACGGATTCGCAAACAGAAACTTCATGCAGCTGATCCACGACGACAGCCTGACATTCAAGGAAGACAT | |
| | CCAGAAGGCACAGGTCAGCGGACAGGGAGACAGCCTGCACGAACACATCGCAAACCTGGCAGGAAGCCCGGCAATCAAGAAGGGAAT | |
| | CCTGCAGACAGTCAAGGTCGTCGACGAACTGGTCAAGGTCATGGGAAGACACAAGCCGGAAAACATCGTCATCGAAATGGCAAGAGA | |
| | AAACCAGACAACACAGAAGGGACAGAAGAACAGCAGAGAAAGAATGAAGAGAATCGAAGAAGGAATCAAGGAACTGGGAAGCCAGAT | |
| | CCTGAAGGAACACCCGGTCGAAAACACACAGCTGCAGAACGAAAAGCTGTACCTGTACTACCTGCAGAACGGAAGAGACATGTACGT | |
| | CGACCAGGAACTGGACATCAACAGACTGAGCGACTACGACGTCGACCACATCGTCCCGCAGAGCTTCCTGAAGGACGACAGCATCGA | |
| | CAACAAGGTCCTGACAAGAAGCGACAAGAACAGAGGAAAGAGCGACAACGTCCCGAGCGAAGAAGTCGTCAAGAAGATGAAGAACTA | |
| | CTGGAGACAGCTGCTGAACGCAAAGCTGATCACACAGAGAAAGTTCGACAACCTGACAAAGGCAGAGAGAGGAGGACTGAGCGAACT | |
| | GGACAAGGCAGGATTCATCAAGAGACAGCTGGTCGAPACAAGACAGATCACAAAGCACGTCGCACAGATCCTGGACAGCAGAATGAA | |
| | CACAAAGTACGACGAAAACGACAAGCTGATCAGAGAAGTCAAGGTCATCACACTGAAGAGCAAGCTGGTCAGCGACTTCAGAAAGGA | |
| | CTTCCAGTTCTACAAGGTCAGAGAAATCAACAACTACCACCACGCACACGACGCATACCTGAACGCAGTCGTCGGAACAGCACTGAT | |
| | CAAGAAGTACCCGAAGCTGGAAAGCGAATTCGTCTACGGAGACTACAAGGTCTACGACGTCAGAAAGATGATCGCAAAGAGCGAACA | |
| | GGAAATCGGAAAGGCAACAGCAAAGTACTTCTTCTACAGCAACATCATGAACTTCTTCAAGACAGAAATCACACTGGCAAACGGAGA | |

-continued

Sequence Table

| Description | Sequence | SEQ ID No. |
|---|---|---|
| | AATCAGAAAGAGACCGCTGATCGAAACAAACGGAGAAACAGGAGAAATCGTCTGGGACAAGGGAAGAGACTTCGCAACAGTCAGAAA<br>GGTCCTGAGCATGCCGCAGGTCAACATCGTCAAGAAGACAGAAGTCCAGACAGGAGGATTCAGCAAGGAAAGCATCCTGCCGAAGAG<br>AAACAGCGACAAGCTGATCGCAAGAAAGAAGGACTGGGACCCGAAGAAGTACGGAGGATTCGACAGCCCGACAGTCGCATACAGCGT<br>CCTGGTCGTCGCAAAGGTCGAAAAGGGAPAGAGCAAGAAGCTGAAGAGCGTCAAGGAACTGCTGGGAATCACAATCATGGAAAGAAG<br>CAGCTTCGAAAAGAACCCGATCGACTTCCTGGAAGCAAAGGGATACAAGGAAGTCAAGAAGGACCTGATCATCAAGCTGCCGAAGTA<br>CAGCCTGTTCGAACTGGAAAACGGAAGAAAGAGAATGCTGGCAAGCGCAGGAGAACTGCAGAAGGGAAACGAACTGGCACTGCCGAG<br>CAAGTACGTCAACTTCCTGTACCTGGCAAGCCACTACGAAAAGCTGAAGGGAAGCCCGGAAGACAACGAACAGAAGCAGCTGTTCGT<br>CGAACAGCACAAGCACTACCTGGACGAAATCATCGAACAGATCAGCGAATTCAGCAAGAGAGTCATCCTGGCAGACGCAAACCTGGA<br>CAAGGTCCTGAGCGCATACAACAAGCACAGAGACAAGCCGATCAGAGAACAGGCAGAAAACATCATCCACCTGTTCACACTGACAAA<br>CCTGGGAGCACCGGCAGCATTCAAGTACTTCGACACAACAATCGACAGAAAGAGATACACAAGCACAAAGGAAGTCCTGGACGCAAC<br>ACTGATCCACCAGAGCATCACAGGACTGTACGAAACAAGAATCGACCTGAGCCAGCTGGGAGGAGACGGAGGAGGAAGCCCGAAGAA<br>GAAGAGAAAGGTCAGCGAAAGCGCAACACCGGAAAGCGTCAGCGGATGGAGACTGTTCAAGAAGATCAGCTAGCTAGCCATCACATT<br>TAAAAGCATCTCAGCCTACCATGAGAATAAGAGAAAGAAAATGAAGATCAATAGCTTATTCATCTCTTTTTCTTTTTCGTTGGTGTA<br>AAGCCAACACCCTGTCTAAAAAACATAAATTTCTTTAATCATTTTGCCTCTTTTCTCTGTGCTTCAATTAATAAAAAATGGAAAGAA<br>CCTCGAGAAAAAAAAAAAAAAAAAAAAAAAAAAAAAAAAAAAAAAAAAAAAAAAAAAAAAAAAAAAAAAAAAAAAAAAAAAAAAAAAA | |
| mRNA transcript with ORF encoding Cas9 with HiBiT tag, HBA 5' UTR and human ALB 3' UTR | GGGCATAAACCCTGGCGCGCTCGCGGCCCGGCACTCTTCTGGTCCCCACAGACTCAGAGAGAACCCACCCGCCACCATGGACAAGAA<br>GTACAGCATCGGACTGGACATCGGAACAAACAGCGTCGGATGGGCAGTCATCACAGACGAATACAAGGTCCCGAGCAAGAAGTTCAA<br>GGTCCTGGGAAACACAGACAGACACAGCATCAAGAAGAACCTGATCGGAGCACTGCTGTTCGACAGCGGAGAAACAGCAGAAGCAAC<br>AAGACTGAAGAGAACAGCAAGAAGAAGATACACAAGAAGAAAGAACAGAATCTGCTACCTGCAGGAAATCTTCAGCAACGAAATGGC<br>AAAGGTCGACGACAGCTTCTTCCACAGACTGGAAGAAAGCTTCCTGGTCGAAGAAGACAAGAAGCACGAAAGACACCCGATCTTCGG<br>AAACATCGTCGACGAAGTCGCATACCACGAAAAGTACCCGACAATCTACCACCTGAGAAAGAAGCTGGTCGACAGCACAGACAAGGC<br>AGACCTGAGACTGATCTACCTGGCACTGGCACACATGATCAAGTTCAGAGGACACTTCCTGATCGAAGGAGACCTGAACCCGGACAA<br>CAGCGACGTCGACAAGCTGTTCATCCAGCTGGTCCAGACATACAACCAGCTGTTCGAAGAAAACCCGATCAACGCAAGCGGAGTCGA<br>CGCAAAGGCAATCCTGAGCGCAAGACTGAGCAAGAGCAGAAGACTGGAAAACCTGATCGCACAGCTGCCGGGAGAAAAGAAGAACGG<br>ACTGTTCGGAAACCTGATCGCACTGAGCCTGGGACTGACACCGAACTTCAAGAGCAACTTCGACCTGGCAGAAGACGCAAAGCTGCA<br>GCTGAGCAAGGACACATACGACGACGACCTGGACAACCTGCTGGCACAGATCGGAGACCAGTACGCAGACCTGTTCCTGGCAGCAAA<br>GAACCTGAGCGACGCAATCCTGCTGAGCGACATCCTGAGAGTCAACACAGAAATCACAAAGGCACCGCTGAGCGCAAGCATGATCAA<br>GAGATACGACGAACACCACCAGGACCTGACACTGCTGAAGGCACTGGTCAGACAGCAGCTGCCGGAAAAGTACAAGGAAATCTTCTT<br>CGACCAGAGCAAGAACGGATACGCAGGATACATCGACGGAGGAGCAAGCCAGGAAGAATTCTACAAGTTCATCAAGCCGATCCTGGA<br>AAAGATGGACGGAACAGAAGAACTGCTGGTCAAGCTGAACAGAGAAGACCTGCTGAGAAAGCAGAGAACATTCGACAACGGAAGCAT<br>CCCGCACCAGATCCACCTGGGAGAACTGCACGCAATCCTGAGAAGACAGGAAGACTTCTACCCGTTCCTGAAGGACAACAGAGAAAA<br>GATCGAAAAGATCCTGACATTCAGAATCCCGTACTACGTCGGACCGCTGGCAAGAGGAAACAGCAGATTCGCATGGATGACAAGAAA<br>GAGCGAAGAAACAATCACACCGTGGAACTTCGAAGAAGTCGTCGACAAGGGAGCAAGCGCACAGAGCTTCATCGAAAGAATGACAAA<br>CTTCGACAAGAACCTGCCGAACGAAAAGGTCCTGCCGAAGCACAGCCTGCTGTACGAATACTTCACAGTCTACAACGAACTGACAAA<br>GGTCAAGTACGTCACAGAAGGAATGAGAAAGCCGGCATTCCTGAGCGGAGAACAGAAGAAGGCAATCGTCGACCTGCTGTTCAAGAC<br>AAACAGAAAGGTCACAGTCAAGCAGCTGAAGGAAGACTACTTCAAGAAGATCGAATGCTTCGACAGCGTCGAAATCAGCGGAGTCGA<br>AGACAGATTCAACGCAAGCCTGGGAACATACCACGACCTGCTGAAGATCATCAAGGACAAGGACTTCCTGGACAACGAAGAAAACGA<br>AGACATCCTGGAAGACATCGTCCTGACACTGACACTGTTCGAAGACAGAGAAATGATCGAAGAAAGACTGAAGACATACGCACACCT<br>GTTCGACGACAAGGTCATGAAGCAGCTGAAGAGAAGAAGATACACAGGATGGGGAAGACTGAGCAGAAAGCTGATCAACGGAATCAG<br>AGACAAGCAGAGCGGAAAGACAATCCTGGACTTCCTGAAGAGCGACGGATTCGCAAACAGAAACTTCATGCAGCTGATCCACGACGA<br>CAGCCTGACATTCAAGGAAGACATCCAGAAGGCACAGGTCAGCGGACAGGGAGACAGCCTGCACGAACACATCGCAAACCTGGCAGG<br>AAGCCCGGCAATCAAGAAGGGAATCCTGCAGACAGTCAAGGTCGTCGACGAACTGGTCAAGGTCATGGGAAGACACAAGCCGGAAAA<br>CATCGTCATCGAAATGGCAAGAGAAAACCAGACAACACAGAAGGGACAGAAGAACAGCAGAGAAAGAATGAAGAGAATCGAAGAAGG<br>AATCAAGGAACTGGGAAGCCAGATCCTGAAGGAACACCCGGTCGAAAACACACAGCTGCAGAACGAAAAGCTGTACCTGTACTACCT<br>GCAGAACGGAAGAGACATGTACGTCGACCAGGAACTGGACATCAACAGACTGAGCGACTACGACGTCGACCACATCGTCCCGCAGAG<br>CTTCCTGAAGGACGACAGCATCGACAACAAGGTCCTGACAAGAAGCGACAAGAACAGAGGAAAGAGCGACAACGTCCCGAGCGAAGA<br>AGTCGTCAAGAAGATGAAGAACTACTGGAGACAGCTGCTGAACGCAAAGCTGATCACACAGAGAAAGTTCGACAACCTGACAAAGGC<br>AGAGAGAGGAGGACTGAGCGAACTGGACAAGGCAGGATTCATCAAGAGACAGCTGGTCGAAACAAGACAGATCACAAAGCACGTCGC | 383 |

-continued

Sequence Table

| Description | Sequence | SEQ ID No. |
|---|---|---|
| | ACAGATCCTGGACAGCAGAATGAACACAAAGTACGACGAAAACGACAAGCTGATCAGAGAAGTCAAGGTCATCACACTGAAGAGCAA<br>GCTGGTCAGCGACTTCAGAAAGGACTTCCAGTTCTACAAGGTCAGAGAAATCAACAACTACCACCACGCACACGACGCATACCTGAA<br>CGCAGTCGTCGGAACAGCACTGATCAAGAAGTACCCGAAGCTGGAAAGCGAATTCGTCTACGGAGACTACAAGGTCTACGACGTCAG<br>AAAGATGATCGCAAAGAGCGAACAGGAAATCGGAAAGGCAACAGCAAAGTACTTCTTCTACAGCAACATCATGAACTTCTTCAAGAC<br>AGAAATCACACTGGCAAACGGAGAAATCAGAAAGAGACCGCTGATCGAAACAAACGGAGAAACAGGAGAAATCGTCTGGGACAAGGG<br>AAGAGACTTCGCAACAGTCAGAAAGGTCCTGAGCATGCCGCAGGTCAACATCGTCAAGAAGACAGAAGTCCAGACAGGAGGATTCAG<br>CAAGGAAAGCATCCTGCCGAAGAGAAACAGCGACAAGCTGATCGCAAGAAAGAAGGACTGGGACCCGAAGAAGTACGGAGGATTCGA<br>CAGCCCGACAGTCGCATACAGCGTCCTGGTCGTCGCAAAGGTCGAAAAGGGAAAGAGCAAGAAGCTGAAGAGCGTCAAGGAACTGCT<br>GGGAATCACAATCATGGAAAGAAGCAGCTTCGAAAAGAACCCGATCGACTTCCTGGAAGCAAAGGGATACAAGGAAGTCAAGAAGGA<br>CCTGATCATCAAGCTGCCGAAGTACAGCCTGTTCGAACTGGAAAACGGAAGAAAGAGAATGCTGGCAAGCGCAGGAGAACTGCAGAA<br>GGGAAACGAACTGGCACTGCCGAGCAAGTACGTCAACTTCCTGTACCTGGCAAGCCACTACGAAAAGCTGAAGGGAAGCCCGGAAGA<br>CAACGAACAGAAGCAGCTGTTCGTCGAACAGCACAAGCACTACCTGGACGAAATCATCGAACAGATCAGCGAATTCAGCAAGAGAGT<br>CATCCTGGCAGACGCAAACCTGGACAAGGTCCTGAGCGCATACAACAAGCACAGAGACAAGCCGATCAGAGAACAGGCAGAAAACAT<br>CATCCACCTGTTCACACTGACAAACCTGGGAGCACCGGCAGCATTCAAGTACTTCGACACAACAATCGACAGAAAGAGATACACAAG<br>CACAAAGGAAGTCCTGGACGCAACACTGATCCACCAGAGCATCACAGGACTGTACGAAACAAGAATCGACCTGAGCCAGCTGGGAGG<br>AGACGGAGGAGGAAGCCCGAAGAAGAAGAGAAAGGTCAGCGAAAGCGCAACACCGGAAAGCGTCAGCGGATGGAGACTGTTCAAGAA<br>GATCAGCTAGCTAGCCATCACATTTAAAAGCATCTCAGCCTACCATGAGAATAAGAGAAAGAAAATGAAGATCAATAGCTTATTCAT<br>CTCTTTTTCTTTTTCGTTGGTGTAAAGCCAACACCCTGTCTAAAAAACATAAATTTCTTTAATCATTTTGCCTCTTTTCTCTGTGCT<br>TCAATTAATAAAAAATGGAAAGAACCTCGAGAAAAAAAAAAAAAAAAAAAAAAAAAAAAAAAAAAAAAAAAAAAAAAAAAAAAAAAA<br>AAAAAAAAAAAAAAAAAAAAAAAA | |
| mRNA transcript with ORF encoding Cas9 with HiBiT tag, HBB 5' UTR and human ALB 3' UTR | GGGACATTTGCTTCTGACACAACTGTGTTCACTAGCAACCTCAAACAGACACCGGATCTCGCCACCATGGACAAGAAGTACAGCATC<br>GGACTGGACATCGGAACAAACAGCGTCGGATGGGCAGTCATCACAGACGAATACAAGGTCCCGAGCAAGAAGTTCAAGGTCCTGGGA<br>AACACAGACAGACACAGCATCAAGAAGAACCTGATCGGAGCACTGCTGTTCGACAGCGGAGAAACAGCAGAAGCAACAAGACTGAAG<br>AGAACAGCAAGAAGAAGATACACAAGAAGAAAGAACAGAATCTGCTACCTGCAGGAAATCTTCAGCAACGAAATGGCAAAGGTCGAC<br>GACAGCTTCTTCCACAGACTGGAAGAAAGCTTCCTGGTCGAAGAAGACAAGAAGCACGAAAGACACCCGATCTTCGGAAACATCGTC<br>GACGAAGTCGCATACCACGAAAAGTACCCGACAATCTACCACCTGAGAAAGAAGCTGGTCGACAGCACAGACAAGGCAGACCTGAGA<br>CTGATCTACCTGGCACTGGCACACATGATCAAGTTCAGAGGACACTTCCTGATCGAAGGAGACCTGAACCCGGACAACAGCGACGTC<br>GACAAGCTGTTCATCCAGCTGGTCCAGACATACAACCAGCTGTTCGAAGAAAACCCGATCAACGCAAGCGGAGTCGACGCAAAGGCA<br>ATCCTGAGCGCAAGACTGAGCAAGAGCAGAAGACTGGAAAACCTGATCGCACAGCTGCCGGGAGAAAAGAAGAACGGACTGTTCGGA<br>AACCTGATCGCACTGAGCCTGGGACTGACACCGAACTTCAAGAGCAACTTCGACCTGGCAGAAGACGCAAAGCTGCAGCTGAGCAAG<br>GACACATACGACGACGACCTGGACAACCTGCTGGCACAGATCGGAGACCAGTACGCAGACCTGTTCCTGGCAGCAAAGAACCTGAGC<br>GACGCAATCCTGCTGAGCGACATCCTGAGAGTCAACACAGAAATCACAAAGGCACCGCTGAGCGCAAGCATGATCAAGAGATACGAC<br>GAACACCACCAGGACCTGACACTGCTGAAGGCACTGGTCAGACAGCAGCTGCCGGAAAAGTACAAGGAAATCTTCTTCGACCAGAGC<br>AAGAACGGATACGCAGGATACATCGACGGAGGAGCAAGCCAGGAAGAATTCTACAAGTTCATCAAGCCGATCCTGGAAAAGATGGAC<br>GGAACAGAAGAACTGCTGGTCAAGCTGAACAGAGAAGACCTGCTGAGAAAGCAGAGAACATTCGACAACGGAAGCATCCCGCACCAG<br>ATCCACCTGGGAGAACTGCACGCAATCCTGAGAAGACAGGAAGACTTCTACCCGTTCCTGAAGGACAACAGAGAAAAGATCGAAAAG<br>ATCCTGACATTCAGAATCCCGTACTACGTCGGACCGCTGGCAAGAGGAAACAGCAGATTCGCATGGATGACAAGAAAGAGCGAAGAA<br>ACAATCACACCGTGGAACTTCGAAGAAGTCGTCGACAAGGGAGCAAGCGCACAGAGCTTCATCGAAAGAATGACAAACTTCGACAAG<br>AACCTGCCGAACGAAAAGGTCCTGCCGAAGCACAGCCTGCTGTACGAATACTTCACAGTCTACAACGAACTGACAAAGGTCAAGTAC<br>GTCACAGAAGGAATGAGAAAGCCGGCATTCCTGAGCGGAGAACAGAAGAAGGCAATCGTCGACCTGCTGTTCAAGACAAACAGAAAG<br>GTCACAGTCAAGCAGCTGAAGGAAGACTACTTCAAGAAGATCGAATGCTTCGACAGCGTCGAAATCAGCGGAGTCGAAGACAGATTC<br>AACGCAAGCCTGGGAACATACCACGACCTGCTGAAGATCATCAAGGACAAGGACTTCCTGGACAACGAAGAAAACGAAGACATCCTG<br>GAAGACATCGTCCTGACACTGACACTGTTCGAAGACAGAGAAATGATCGAAGAAAGACTGAAGACATACGCACACCTGTTCGACGAC<br>AAGGTCATGAAGCAGCTGAAGAGAAGAAGATACACAGGATGGGGAAGACTGAGCAGAAAGCTGATCAACGGAATCAGAGACAAGCAG<br>AGCGGAAAGACAATCCTGGACTTCCTGAAGAGCGACGGATTCGCAAACAGAAACTTCATGCAGCTGATCCACGACGACAGCCTGACA<br>TTCAAGGAAGACATCCAGAAGGCACAGGTCAGCGGACAGGGAGACAGCCTGCACGAACACATCGCAAACCTGGCAGGAAGCCCGGCA<br>ATCAAGAAGGGAATCCTGCAGACAGTCAAGGTCGTCGACGAACTGGTCAAGGTCATGGGAAGACACAAGCCGGAAAACATCGTCATC<br>GAAATGGCAAGAGAAAACCAGACAACACAGAAGGGACAGAAGAACAGCAGAGAAAGAATGAAGAGAATCGAAGAAGGAATCAAGGAA | 384 |

-continued

Sequence Table

| Description | Sequence | SEQ ID No. |
|---|---|---|
| | CTGGGAAGCCAGATCCTGAAGGAACACCCGGTCGAAAACACACAGCTGCAGAACGAAAAGCTGTACCTGTACTACCTGCAGAACGGA<br>AGAGACATGTACGTCGACCAGGAACTGGACATCAACAGACTGAGCGACTACGACGTCGACCACATCGTCCCGCAGAGCTTCCTGAAG<br>GACGACAGCATCGACAACAAGGTCCTGACAAGAAGCGACAAGAACAGAGGAAAGAGCGACAACGTCCCGAGCGAAGAAGTCGTCAAG<br>AAGATGAAGAACTACTGGAGACAGCTGCTGAACGCAAAGCTGATCACACAGAGAAAGTTCGACAACCTGACAAAGGCAGAGAGAGGA<br>GGACTGAGCGAACTGGACAAGGCAGGATTCATCAAGAGACAGCTGGTCGAAACAAGACAGATCACAAAGCACGTCGCACAGATCCTG<br>GACAGCAGAATGAACACAAAGTACGACGAAAACGACAAGCTGATCAGAGAAGTCAAGGTCATCACACTGAAGAGCAAGCTGGTCAGC<br>GACTTCAGAAAGGACTTCCAGTTCTACAAGGTCAGAGAAATCAACAACTACCACCACGCACACGACGCATACCTGAACGCAGTCGTC<br>GGAACAGCACTGATCAAGAAGTACCCGAAGCTGGAAAGCGAATTCGTCTACGGAGACTACAAGGTCTACGACGTCAGAAAGATGATC<br>GCAAAGAGCGAACAGGAAATCGGAAAGGCAACAGCAAAGTACTTCTTCTACAGCAACATCATGAACTTCTTCAAGACAGAAATCACA<br>CTGGCAAACGGAGAAATCAGAAAGAGACCGCTGATCGAAACAAACGGAGAAACAGGAGAAATCGTCTGGGACAAGGGAAGAGACTTC<br>GCAACAGTCAGAAAGGTCCTGAGCATGCCGCAGGTCAACATCGTCAAGAAGACAGAAGTCCAGACAGGAGGATTCAGCAAGGAAAGC<br>ATCCTGCCGAAGAGAAACAGCGACAAGCTGATCGCAAGAAAGAAGGACTGGGACCCGAAGAAGTACGGAGGATTCGACAGCCCGACA<br>GTCGCATACAGCGTCCTGGTCGTCGCAAAGGTCGAAAAGGGAAAGAGCAAGAAGCTGAAGAGCGTCAAGGAACTGCTGGGAATCACA<br>ATCATGGAAAGAAGCAGCTTCGAAAAGAACCCGATCGACTTCCTGGAAGCAAAGGGATACAAGGAAGTCAAGAAGGACCTGATCATC<br>AAGCTGCCGAAGTACAGCCTGTTCGAACTGGAAAACGGAAGAAAGAGAATGCTGGCAAGCGCAGGAGAACTGCAGAAGGGAAACGAA<br>CTGGCACTGCCGAGCAAGTACGTCAACTTCCTGTACCTGGCAAGCCACTACGAAAAGCTGAAGGGAAGCCCGGAAGACAACGAACAG<br>AAGCAGCTGTTCGTCGAACAGCACAAGCACTACCTGGACGAAATCATCGAACAGATCAGCGAATTCAGCAAGAGAGTCATCCTGGCA<br>GACGCAAACCTGGACAAGGTCCTGAGCGCATACAACAAGCACAGAGACAAGCCGATCAGAGAACAGGCAGAAAACATCATCCACCTG<br>TTCACACTGACAAACCTGGGAGCACCGGCAGCATTCAAGTACTTCGACACAACAATCGACAGAAAGAGATACACAAGCACAAAGGAA<br>GTCCTGGACGCAACACTGATCCACCAGAGCATCACAGGACTGTACGAAACAAGAATCGACCTGAGCCAGCTGGGAGGAGACGGAGGA<br>GGAAGCCCGAAGAAGAAGAGAAAGGTCAGCGAAAGCGCAACACCGGAAAGCGTCAGCGGATGGAGACTGTTCAAGAAGATCAGCTAG<br>CTAGCCATCACATTTAAAAGCATCTCAGCCTACCATGAGAATAAGAGAAAGAAAATGAAGATCAATAGCTTATTCATCTCTTTTTCT<br>TTTTCGTTGGTGTAAAGCCAACACCCTGTCTAAAAAACATAAATTTCTTTAATCATTTTGCCTCTTTTCTCTGTGCTTCAATTAATA<br>AAAAATGGAAAGAACCTCGAGAAAAAAAAAAAAAAAAAAAAAAAAAAAAAAAAAAAAAAAAAAAAAAAAAAAAAAAAAAAAAAAAAA<br>AAAAAAAAAAAAAA | |
| mRNA transcript with ORF encoding Cas9 with HiBiT tag, XBG 5' UTR and human ALB 3' UTR | GGGAAGCTCAGAATAAACGCTCAACTTTGGCCGGATCTCGCCACCATGGACAAGAAGTACAGCATCGGACTGGACATCGGAACAAAC<br>AGCGTCGGATGGGCAGTCATCACAGACGAATACAAGGTCCCGAGCAAGAAGTTCAAGGTCCTGGGAAACACAGACAGACACAGCATC<br>AAGAAGAACCTGATCGGAGCACTGCTGTTCGACAGCGGAGAAACAGCAGAAGCAACAAGACTGAAGAGAACAGCAAGAAGAAGATAC<br>ACAAGAAGAAAGAACAGAATCTGCTACCTGCAGGAAATCTTCAGCAACGAAATGGCAAAGGTCGACGACAGCTTCTTCCACAGACTG<br>GAAGAAAGCTTCCTGGTCGAAGAAGACAAGAAGCACGAAAGACACCCGATCTTCGGAAACATCGTCGACGAAGTCGCATACCACGAA<br>AAGTACCCGACAATCTACCACCTGAGAAAGAAGCTGGTCGACAGCACAGACAAGGCAGACCTGAGACTGATCTACCTGGCACTGGCA<br>CACATGATCAAGTTCAGAGGACACTTCCTGATCGAAGGAGACCTGAACCCGGACAACAGCGACGTCGACAAGCTGTTCATCCAGCTG<br>GTCCAGACATACAACCAGCTGTTCGAAGAAAACCCGATCAACGCAAGCGGAGTCGACGCAAAGGCAATCCTGAGCGCAAGACTGAGC<br>AAGAGCAGAAGACTGGAAAACCTGATCGCACAGCTGCCGGGAGAAAAGAAGAACGGACTGTTCGGAAACCTGATCGCACTGAGCCTG<br>GGACTGACACCGAACTTCAAGAGCAACTTCGACCTGGCAGAAGACGCAAAGCTGCAGCTGAGCAAGGACACATACGACGACGACCTG<br>GACAACCTGCTGGCACAGATCGGAGACCAGTACGCAGACCTGTTCCTGGCAGCAAAGAACCTGAGCGACGCAATCCTGCTGAGCGAC<br>ATCCTGAGAGTCAACACAGAAATCACAAAGGCACCGCTGAGCGCAAGCATGATCAAGAGATACGACGAACACCACCAGGACCTGACA<br>CTGCTGAAGGCACTGGTCAGACAGCAGCTGCCGGAAAAGTACAAGGAAATCTTCTTCGACCAGAGCAAGAACGGATACGCAGGATAC<br>ATCGACGGAGGAGCAAGCCAGGAAGAATTCTACAAGTTCATCAAGCCGATCCTGGAAAAGATGGACGGAACAGAAGAACTGCTGGTC<br>AAGCTGAACAGAGAAGACCTGCTGAGAAAGCAGAGAACATTCGACAACGGAAGCATCCCGCACCAGATCCACCTGGGAGAACTGCAC<br>GCAATCCTGAGAAGACAGGAAGACTTCTACCCGTTCCTGAAGGACAACAGAGAAAAGATCGAAAAGATCCTGACATTCAGAATCCCG<br>TACTACGTCGGACCGCTGGCAAGAGGAAACAGCAGATTCGCATGGATGACAAGAAAGAGCGAAGAAACAATCACACCGTGGAACTTC<br>GAAGAAGTCGTCGACAAGGGAGCAAGCGCACAGAGCTTCATCGAAAGAATGACAAACTTCGACAAGAACCTGCCGAACGAAAAGGTC<br>CTGCCGAAGCACAGCCTGCTGTACGAATACTTCACAGTCTACAACGAACTGACAAAGGTCAAGTACGTCACAGAAGGAATGAGAAAG<br>CCGGCATTCCTGAGCGGAGAACAGAAGAAGGCAATCGTCGACCTGCTGTTCAAGACAAACAGAAAGGTCACAGTCAAGCAGCTGAAG<br>GAAGACTACTTCAAGAAGATCGAATGCTTCGACAGCGTCGAAATCAGCGGAGTCGAAGACAGATTCAACGCAAGCCTGGGAACATAC<br>CACGACCTGCTGAAGATCATCAAGGACAAGGACTTCCTGGACAACGAAGAAAACGAAGACATCCTGGAAGACATCGTCCTGACACTG<br>ACACTGTTCGAAGACAGAGAAATGATCGAAGAAAGACTGAAGACATACGCACACCTGTTCGACGACAAGGTCATGAAGCAGCTGAAG | 385 |

-continued

Sequence Table

| Description | Sequence | SEQ ID No. |
|---|---|---|
| | AGAAGAAGATACACAGGATGGGGAAGACTGAGCAGAAAGCTGATCAACGGAATCAGAGACAAGCAGAGCGGAAAGACAATCCTGGAC<br>TTCCTGAAGAGCGACGGATTCGCAAACAGAAACTTCATGCAGCTGATCCACGACGACAGCCTGACATTCAAGGAAGACATCCAGAAG<br>GCACAGGTCAGCGGACAGGGAGACAGCCTGCACGAACACATCGCAAACCTGGCAGGAAGCCCGGCAATCAAGAAGGGAATCCTGCAG<br>ACAGTCAAGGTCGTCGACGAACTGGTCAAGGTCATGGGAAGACACAAGCCGGAAAACATCGTCATCGAAATGGCAAGAGAAAACCAG<br>ACAACACAGAAGGGACAGAAGAACAGCAGAGAAAGAATGAAGAGAATCGAAGAAGGAATCAAGGAACTGGGAAGCCAGATCCTGAAG<br>GAACACCCGGTCGAAAACACACAGCTGCAGAACGAAAAGCTGTACCTGTACTACCTGCAGAACGGAAGAGACATGTACGTCGACCAG<br>GAACTGGACATCAACAGACTGAGCGACTACGACGTCGACCACATCGTCCCGCAGAGCTTCCTGAAGGACGACAGCATCGACAACAAG<br>GTCCTGACAAGAAGCGACAAGAACAGAGGAAAGAGCGACAACGTCCCGAGCGAAGAAGTCGTCAAGAAGATGAAGAACTACTGGAGA<br>CAGCTGCTGAACGCAAAGCTGATCACACAGAGAAAGTTCGACAACCTGACAAAGGCAGAGAGAGGAGGACTGAGCGAACTGGACAAG<br>GCAGGATTCATCAAGAGACAGCTGGTCGAAACAAGACAGATCACAAAGCACGTCGCACAGATCCTGGACAGCAGAATGAACACAAAG<br>TACGACGAAAACGACAAGCTGATCAGAGAAGTCAAGGTCATCACACTGAAGAGCAAGCTGGTCAGCGACTTCAGAAAGGACTTCCAG<br>TTCTACAAGGTCAGAGAAATCAACAACTACCACCACGCACACGACGCATACCTGAACGCAGTCGTCGGAACAGCACTGATCAAGAAG<br>TACCCGAAGCTGGAAAGCGAATTCGTCTACGGAGACTACAAGGTCTACGACGTCAGAAAGATGATCGCAAAGAGCGAACAGGAAATC<br>GGAAAGGCAACAGCAAAGTACTTCTTCTACAGCAACATCATGAACTTCTTCAAGACAGAAATCACACTGGCAAACGGAGAAATCAGA<br>AAGAGACCGCTGATCGAAACAAACGGAGAAACAGGAGAAATCGTCTGGGACAAGGGAAGAGACTTCGCAACAGTCAGAAAGGTCCTG<br>AGCATGCCGCAGGTCAACATCGTCAAGAAGACAGAAGTCCAGACAGGAGGATTCAGCAAGGAAAGCATCCTGCCGAAGAGAAACAGC<br>GACAAGCTGATCGCAAGAAAGAAGGACTGGGACCCGAAGAAGTACGGAGGATTCGACAGCCCGACAGTCGCATACAGCGTCCTGGTC<br>GTCGCAAAGGTCGAAAAGGGAAAGAGCAAGAAGCTGAAGAGCGTCAAGGAACTGCTGGGAATCACAATCATGGAAAGAAGCAGCTTC<br>GAAAAGAACCCGATCGACTTCCTGGAAGCAAAGGGATACAAGGAAGTCAAGAAGGACCTGATCATCAAGCTGCCGAAGTACAGCCTG<br>TTCGAACTGGAAAACGGAAGAAAGAGAATGCTGGCAAGCGCAGGAGAACTGCAGAAGGGAAACGAACTGGCACTGCCGAGCAAGTAC<br>GTCAACTTCCTGTACCTGGCAAGCCACTACGAAAAGCTGAAGGGAAGCCCGGAAGACAACGAACAGAAGCAGCTGTTCGTCGAACAG<br>CACAAGCACTACCTGGACGAAATCATCGAACAGATCAGCGAATTCAGCAAGAGAGTCATCCTGGCAGACGCAAACCTGGACAAGGTC<br>CTGAGCGCATACAACAAGCACAGAGACAAGCCGATCAGAGAACAGGCAGAAAACATCATCCACCTGTTCACACTGACAAACCTGGGA<br>GCACCGGCAGCATTCAAGTACTTCGACACAACAATCGACAGAAAGAGATACACAAGCACAAAGGAAGTCCTGGACGCAACACTGATC<br>CACCAGAGCATCACAGGACTGTACGAAACAAGAATCGACCTGAGCCAGCTGGGAGGAGACGGAGGAGGAAGCCCGAAGAAGAAGAGA<br>AAGGTCAGCGAAAGCGCAACACCGGAAAGCGTCAGCGGATGGAGACTGTTCAAGAAGATCAGCTAGCTAGCCATCACATTTAAAAGC<br>ATCTCAGCCTACCATGAGAATAAGAGAAAGAAAATGAAGATCAATAGCTTATTCATCTCTTTTTCTTTTTCGTTGGTGTAAAGCCAA<br>CACCCTGTCTAAAAAACATAAATTTCTTTAATCATTTTGCCTCTTTTCTCTGTGCTTCAATTAATAAAAAATGGAAAGAACCTCGAG<br>AAAAAAAAAAAAAAAAAAAAAAAAAAAAAAAAAAAAAAAAAAAAAAAAAAAAAAAAAAAAAAAAAAAAAAAAAAA | |
| Amino acid sequence for Cas9 with NLS1 | MDKKYSIGLDIGTNSVGWAVITDEYKVPSKKFKVLGNTDRHSIKKNLIGALLFDSGETAEATRLKRTARRYTRRKNRICYLQEIFS<br>NEMAKVDDSFFHRLEESFLVEEDKKHERHPIFGNIVDEVAYHEKYPTIYHLRKKLVDSTDKADLRLIYLALAHMIKFRGHFLIEGDL<br>NPDNSDVDKLFIQLVQTYNQLFEENPINASGVDAKAILSARLSKSRRLENLIAQLPGEKKNGLFGNLIALSLGLTPNFKSNFDLAED<br>AKLQLSKDTYDDDLDNLLAQIGDQYADLFLAAKNLSDAILLSDILRVNTEITKAPLSASMIKRYDEHHQDLTLLKALVRQQLPEKYK<br>EIFFDQSKNGYAGYIDGGASQEEFYKFIKPILEKMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQSFIERMTNFDKNLPNEKVLPKHSLLYEYFTVYN<br>ELTKVKYVTEGMRKPAFLSGEQKKAIVDLLFKTNRKVTVKQLKEDYFKKIECFDSVEISGVEDRFNASLGTYHDLLKIIKDKDFLDN<br>EENEDILEDIVLTLTLFEDREMIEERLKTYAHLFDDKVMKQLKRRRYTGWGRLSRKLINGIRDKQSGKTILDFLKSDGFANRNFMQL<br>IHDDSLTFKEDIQKAQVSGQGDSLHEHIANLAGSPAIKKGILQTVKVVDELVKVMGRHKPENIVIEMARENQTTQKGQKNSRERMKR<br>IEEGIKELGSQILKEHPVENTQLQNEKLYLYYLQNGRDMYVDQELDINRLSDYDVDHIVPQSFLKDDSIDNKVLTRSDKNRGKSDNV<br>PSEEVVKKMKNYWRQLLNAKLITQRKFDNLTKAERGGLSELDKAGFIKRQLVETRQITKHVAQILDSRMNTKYDENDKLIREVKVIT<br>LKSKLVSDFRKDFQFYKVREINNYHHAHDAYLNAVVGTALIKKYPKLESEFVYGDYKVYDVRKMIAKSEQEIGKATAKYFFYSNIMN<br>FFKTEITLANGEIRKRPLIETNGETGEIVWDKGRDFATVRKVLSMPQVNIVKKTEVQTGGFSKESILPKRNSDKLIARKKDWDPKKY<br>GGFDSPTVAYSVLVVAKVEKGKSKKLKSVKELLGITIMERSSFEKNPIDFLEAKGYKEVKKDLIIKLPKYSLFELENGRKRMLASAG<br>ELQKGNELALPSKYVNFLYLASHYEKLKGSPEDNEQKQLFVEQHKHYLDEIIEQISEFSKRVILADANLDKVLSAYNKHRDKPIREQ<br>AENIIHLFTLTNLGAPAAFKYFDTTIDRKRYTSTKEVLDATLIHQSITGLYETRIDLSQLGGDGGGSLAAKRSRTT | 386 |
| Amino acid sequence | MDKKYSIGLDIGTNSVGWAVITDEYKVPSKKFKVLGNTDRHSIKKNLIGALLFDSGETAEATRLKRTARRYTRRKNRICYLQEIFS<br>NEMAKVDDSFFHRLEESFLVEEDKKHERHPIFGNIVDEVAYHEKYPTIYHLRKKLVDSTDKADLRLIYLALAHMIKFRGHFLIEGDL | 387 |

-continued

Sequence Table

| Description | Sequence | SEQ ID No. |
|---|---|---|
| for Cas9<br>with NLS2 | NPDNSDVDKLFIQLVQTYNQLFEENPINASGVDAKAILSARLSKSRRLENLIAQLPGEKKNGLFGNLIALSLGLTPNFKSNFDLAED<br>AKLQLSKDTYDDDLDNLLAQIGDQYADLFLAAKNLSDAILLSDILRVNTEITKAPLSASMIKRYDEHHQDLTLLKALVRQQLPEKYK<br>EIFFDQSKNGYAGYIDGGASQEEFYKFIKPILEKMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQSFIERMTNFDKNLPNEKVLPKHSLLYEYFTVYN<br>ELTKVKYVTEGMRKPAFLSGEQKKAIVDLLFKTNRKVTVKQLKEDYFKKIECFDSVEISGVEDRFNASLGTYHDLLKIIKDKDFLDN<br>EENEDILEDIVLTLTLFEDREMIEERLKTYAHLFDDKVMKQLKRRRYTGWGRLSRKLINGIRDKQSGKTILDFLKSDGFANRNFMQL<br>IHDDSLTFKEDIQKAQVSGQGDSLHEHIANLAGSPAIKKGILQTVKVVDELVKVMGRHKPENIVIEMARENQTTQKGQKNSRERMKR<br>IEEGIKELGSQILKEHPVENTQLQNEKLYLYYLQNGRDMYVDQELDINRLSDYDVDHIVPQSFLKDDSIDNKVLTRSDKNRGKSDNV<br>PSEEVVKKMKNYWRQLLNAKLITQRKFDNLTKAERGGLSELDKAGFIKRQLVETRQITKHVAQILDSRMNTKYDENDKLIREVKVIT<br>LKSKLVSDFRKDFQFYKVREINNYHHAHDAYLNAVVGTALIKKYPKLESEFVYGDYKVYDVRKMIAKSEQEIGKATAKYFFYSNIMN<br>FFKTEITLANGEIRKRPLIETNGETGEIVWDKGRDFATVRKVLSMPQVNIVKKTEVQTGGFSKESILPKRNSDKLIARKKDWDPKKY<br>GGFDSPTVAYSVLVVAKVEKGKSKKLKSVKELLGITIMERSSFEKNPIDFLEAKGYKEVKKDLIIKLPKYSLFELENGRKRMLASAG<br>ELQKGNELALPSKYVNFLYLASHYEKLKGSPEDNEQKQLFVEQHKHYLDEIIEQISEFSKRVILADANLDKVLSAYNKHRDKPIREQ<br>AENIIHLFTLTNLGAPAAFKYFDTTIDRKRYTSTKEVLDATLIHQSITGLYETRIDLSQLGGDGGGSQAAKRSRTT | |
| Amino acid<br>sequence<br>for Cas9<br>with NLS3 | MDKKYSIGLDIGTNSVGWAVITDEYKVPSKKFKVLGNTDRHSIKKNLIGALLFDSGETAEATRLKRTARRRYTRRKNRICYLQEIFS<br>NEMAKVDDSFFHRLEESFLVEEDKKHERHPIFGNIVDEVAYHEKYPTIYHLRKKLVDSTDKADLRLIYLALAHMIKFRGHFLIEGDL<br>NPDNSDVDKLFIQLVQTYNQLFEENPINASGVDAKAILSARLSKSRRLENLIAQLPGEKKNGLFGNLIALSLGLTPNFKSNFDLAED<br>AKLQLSKDTYDDDLDNLLAQIGDQYADLFLAAKNLSDAILLSDILRVNTEITKAPLSASMIKRYDEHHQDLTLLKALVRQQLPEKYK<br>EIFFDQSKNGYAGYIDGGASQEEFYKFIKPILEKMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQSFIERMTNFDKNLPNEKVLPKHSLLYEYFTVYN<br>ELTKVKYVTEGMRKPAFLSGEQKKAIVDLLFKTNRKVTVKQLKEDYFKKIECFDSVEISGVEDRFNASLGTYHDLLKIIKDKDFLDN<br>EENEDILEDIVLTLTLFEDREMIEERLKTYAHLFDDKVMKQLKRRRYTGWGRLSRKLINGIRDKQSGKTILDFLKSDGFANRNFMQL<br>IHDDSLTFKEDIQKAQVSGQGDSLHEHIANLAGSPAIKKGILQTVKVVDELVKVMGRHKPENIVIEMARENQTTQKGQKNSRERMKR<br>IEEGIKELGSQILKEHPVENTQLQNEKLYLYYLQNGRDMYVDQELDINRLSDYDVDHIVPQSFLKDDSIDNKVLTRSDKNRGKSDNV<br>PSEEVVKKMKNYWRQLLNAKLITQRKFDNLTKAERGGLSELDKAGFIKRQLVETRQITKHVAQILDSRMNTKYDENDKLIREVKVIT<br>LKSKLVSDFRKDFQFYKVREINNYHHAHDAYLNAVVGTALIKKYPKLESEFVYGDYKVYDVRKMIAKSEQEIGKATAKYFFYSNIMN<br>FFKTEITLANGEIRKRPLIETNGETGEIVWDKGRDFATVRKVLSMPQVNIVKKTEVQTGGFSKESILPKRNSDKLIARKKDWDPKKY<br>GGFDSPTVAYSVLVVAKVEKGKSKKLKSVKELLGITIMERSSFEKNPIDFLEAKGYKEVKKDLIIKLPKYSLFELENGRKRMLASAG<br>ELQKGNELALPSKYVNFLYLASHYEKLKGSPEDNEQKQLFVEQHKHYLDEIIEQISEFSKRVILADANLDKVLSAYNKHRDKPIREQ<br>AENIIHLFTLTNLGAPAAFKYFDTTIDRKRYTSTKEVLDATLIHQSITGLYETRIDLSQLGGDGGGSPAPAKRERTT | 388 |
| Amino acid<br>sequence<br>for Cas9<br>with NLS4 | MDKKYSIGLDIGTNSVGWAVITDEYKVPSKKFKVLGNTDRHSIKKNLIGALLFDSGETAEATRLKRTARRRYTRRKNRICYLQEIFS<br>NEMAKVDDSFFHRLEESFLVEEDKKHERHPIFGNIVDEVAYHEKYPTIYHLRKKLVDSTDKADLRLIYLALAHMIKFRGHFLIEGDL<br>NPDNSDVDKLFIQLVQTYNQLFEENPINASGVDAKAILSARLSKSRRLENLIAQLPGEKKNGLFGNLIALSLGLTPNFKSNFDLAED<br>AKLQLSKDTYDDDLDNLLAQIGDQYADLFLAAKNLSDAILLSDILRVNTEITKAPLSASMIKRYDEHHQDLTLLKALVRQQLPEKYK<br>EIFFDQSKNGYAGYIDGGASQEEFYKFIKPILEKMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQSFIERMTNFDKNLPNEKVLPKHSLLYEYFTVYN<br>ELTKVKYVTEGMRKPAFLSGEQKKAIVDLLFKTNRKVTVKQLKEDYFKKIECFDSVEISGVEDRFNASLGTYHDLLKIIKDKDFLDN<br>EENEDILEDIVLTLTLFEDREMIEERLKTYAHLFDDKVMKQLKRRRYTGWGRLSRKLINGIRDKQSGKTILDFLKSDGFANRNFMQL<br>IHDDSLTFKEDIQKAQVSGQGDSLHEHIANLAGSPAIKKGILQTVKVVDELVKVMGRHKPENIVIEMARENQTTQKGQKNSRERMKR<br>IEEGIKELGSQILKEHPVENTQLQNEKLYLYYLQNGRDMYVDQELDINRLSDYDVDHIVPQSFLKDDSIDNKVLTRSDKNRGKSDNV<br>PSEEVVKKMKNYWRQLLNAKLITQRKFDNLTKAERGGLSELDKAGFIKRQLVETRQITKHVAQILDSRMNTKYDENDKLIREVKVIT<br>LKSKLVSDFRKDFQFYKVREINNYHHAHDAYLNAVVGTALIKKYPKLESEFVYGDYKVYDVRKMIAKSEQEIGKATAKYFFYSNIMN<br>FFKTEITLANGEIRKRPLIETNGETGEIVWDKGRDFATVRKVLSMPQVNIVKKTEVQTGGFSKESILPKRNSDKLIARKKDWDPKKY<br>GGFDSPTVAYSVLVVAKVEKGKSKKLKSVKELLGITIMERSSFEKNPIDFLEAKGYKEVKKDLIIKLPKYSLFELENGRKRMLASAG<br>ELQKGNELALPSKYVNFLYLASHYEKLKGSPEDNEQKQLFVEQHKHYLDEIIEQISEFSKRVILADANLDKVLSAYNKHRDKPIREQ<br>AENIIHLFTLTNLGAPAAFKYFDTTIDRKRYTSTKEVLDATLIHQSITGLYETRIDLSQLGGDGGGSQAAKRPRTT | 389 |

-continued

Sequence Table

| Description | Sequence | SEQ ID No. |
|---|---|---|
| Amino acid sequence for Cas9 with NLS5 | MDKKYSIGLDIGTNSVGWAVITDEYKVPSKKFKVLGNTDRHSIKKNLIGALLFDSGETAEATRLKRTARRRYTRRKNRICYLQEIFS<br>NEMAKVDDSFFHRLEESFLVEEDKKHERHPIFGNIVDEVAYHEKYPTIYHLRKKLVDSTDKADLRLIYLALAHMIKFRGHFLIEGDL<br>NPDNSDVDKLFIQLVQTYNQLFEENPINASGVDAKAILSARLSKSRRLENLIAQLPGEKKNGLFGNLIALSLGLTPNFKSNFDLAED<br>AKLQLSKDTYDDDLDNLLAQIGDQYADLFLAAKNLSDAILLSDILRVNTEITKAPLSASMIKRYDEHHQDLTLLKALVRQQLPEKYK<br>EIFFDQSKNGYAGYIDGGASQEEFYKFIKPILEKMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQSFIERMTNFDKNLPNEKVLPKHSLLYEYFTVYN<br>ELTKVKYVTEGMRKPAFLSGEQKKAIVDLLFKTNRKVTVKQLKEDYFKKIECFDSVEISGVEDRFNASLGTYHDLLKIIKDKDFLDN<br>EENEDILEDIVLTLTLFEDREMIEERLKTYAHLFDDKVMKQLKRRRYTGWGRLSRKLINGIRDKQSGKTILDFLKSDGFANRNFMQL<br>IHDDSLTFKEDIQKAQVSGQGDSLHEHIANLAGSPAIKKGILQTVKVVDELVKVMGRHKPENIVIEMARENQTTQKGQKNSRERMKR<br>IEEGIKELGSQILKEHPVENTQLQNEKLYLYYLQNGRDMYVDQELDINRLSDYDVDHIVPQSFLKDDSIDNKVLTRSDKNRGKSDNV<br>PSEEVVKKMKNYWRQLLNAKLITQRKFDNLTKAERGGLSELDKAGFIKRQLVETRQITKHVAQILDSRMNTKYDENDKLIREVKVIT<br>LKSKLVSDFRKDFQFYKVREINNYHHAHDAYLNAVVGTALIKKYPKLESEFVYGDYKVYDVRKMIAKSEQEIGKATAKYFFYSNIMN<br>FFKTEITLANGEIRKRPLIETNGETGEIVWDKGRDFATVRKVLSMPQVNIVKKTEVQTGGFSKESILPKRNSDKLIARKKDWDPKKY<br>GGFDSPTVAYSVLVVAKVEKGKSKKLKSVKELLGITIMERSSFEKNPIDFLEAKGYKEVKKDLIIKLPKYSLFELENGRKRMLASAG<br>ELQKGNELALPSKYVNFLYLASHYEKLKGSPEDNEQKQLFVEQHKHYLDEIIEQISEFSKRVILADANLDKVLSAYNKHRDKPIREQ<br>AENIIHLFTLTNLGAPAAFKYFDTTIDRKRYTSTKEVLDATLIHQSITGLYETRIDLSQLGGDGGGSRAAKRPRTT | 390 |
| Amino acid sequence for Cas9 with NLS6 | MDKKYSIGLDIGTNSVGWAVITDEYKVPSKKFKVLGNTDRHSIKKNLIGALLFDSGETAEATRLKRTARRRYTRRKNRICYLQEIFS<br>NEMAKVDDSFFHRLEESFLVEEDKKHERHPIFGNIVDEVAYHEKYPTIYHLRKKLVDSTDKADLRLIYLALAHMIKFRGHFLIEGDL<br>NPDNSDVDKLFIQLVQTYNQLFEENPINASGVDAKAILSARLSKSRRLENLIAQLPGEKKNGLFGNLIALSLGLTPNFKSNFDLAED<br>AKLQLSKDTYDDDLDNLLAQIGDQYADLFLAAKNLSDAILLSDILRVNTEITKAPLSASMIKRYDEHHQDLTLLKALVRQQLPEKYK<br>EIFFDQSKNGYAGYIDGGASQEEFYKFIKPILEKMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQSFIERMTNFDKNLPNEKVLPKHSLLYEYFTVYN<br>ELTKVKYVTEGMRKPAFLSGEQKKAIVDLLFKTNRKVTVKQLKEDYFKKIECFDSVEISGVEDRFNASLGTYHDLLKIIKDKDFLDN<br>EENEDILEDIVLTLTLFEDREMIEERLKTYAHLFDDKVMKQLKRRRYTGWGRLSRKLINGIRDKQSGKTILDFLKSDGFANRNFMQL<br>IHDDSLTFKEDIQKAQVSGQGDSLHEHIANLAGSPAIKKGILQTVKVVDELVKVMGRHKPENIVIEMARENQTTQKGQKNSRERMKR<br>IEEGIKELGSQILKEHPVENTQLQNEKLYLYYLQNGRDMYVDQELDINRLSDYDVDHIVPQSFLKDDSIDNKVLTRSDKNRGKSDNV<br>PSEEVVKKMKNYWRQLLNAKLITQRKFDNLTKAERGGLSELDKAGFIKRQLVETRQITKHVAQILDSRMNTKYDENDKLIREVKVIT<br>LKSKLVSDFRKDFQFYKVREINNYHHAHDAYLNAVVGTALIKKYPKLESEFVYGDYKVYDVRKMIAKSEQEIGKATAKYFFYSNIMN<br>FFKTEITLANGEIRKRPLIETNGETGEIVWDKGRDFATVRKVLSMPQVNIVKKTEVQTGGFSKESILPKRNSDKLIARKKDWDPKKY<br>GGFDSPTVAYSVLVVAKVEKGKSKKLKSVKELLGITIMERSSFEKNPIDFLEAKGYKEVKKDLIIKLPKYSLFELENGRKRMLASAG<br>ELQKGNELALPSKYVNFLYLASHYEKLKGSPEDNEQKQLFVEQHKHYLDEIIEQISEFSKRVILADANLDKVLSAYNKHRDKPIREQ<br>AENIIHLFTLTNLGAPAAFKYFDTTIDRKRYTSTKEVLDATLIHQSITGLYETRIDLSQLGGDGGGSAAAKRSWSMAA | 391 |
| Amino acid sequence for Cas9 with NLS7 | MDKKYSIGLDIGTNSVGWAVITDEYKVPSKKFKVLGNTDRHSIKKNLIGALLFDSGETAEATRLKRTARRRYTRRKNRICYLQEIFS<br>NEMAKVDDSFFHRLEESFLVEEDKKHERHPIFGNIVDEVAYHEKYPTIYHLRKKLVDSTDKADLRLIYLALAHMIKFRGHFLIEGDL<br>NPDNSDVDKLFIQLVQTYNQLFEENPINASGVDAKAILSARLSKSRRLENLIAQLPGEKKNGLFGNLIALSLGLTPNFKSNFDLAED<br>AKLQLSKDTYDDDLDNLLAQIGDQYADLFLAAKNLSDAILLSDILRVNTEITKAPLSASMIKRYDEHHQDLTLLKALVRQQLPEKYK<br>EIFFDQSKNGYAGYIDGGASQEEFYKFIKPILEKMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQSFIERMTNFDKNLPNEKVLPKHSLLYEYFTVYN<br>ELTKVKYVTEGMRKPAFLSGEQKKAIVDLLFKTNRKVTVKQLKEDYFKKIECFDSVEISGVEDRFNASLGTYHDLLKIIKDKDFLDN<br>EENEDILEDIVLTLTLFEDREMIEERLKTYAHLFDDKVMKQLKRRRYTGWGRLSRKLINGIRDKQSGKTILDFLKSDGFANRNFMQL<br>IHDDSLTFKEDIQKAQVSGQGDSLHEHIANLAGSPAIKKGILQTVKVVDELVKVMGRHKPENIVIEMARENQTTQKGQKNSRERMKR<br>IEEGIKELGSQILKEHPVENTQLQNEKLYLYYLQNGRDMYVDQELDINRLSDYDVDHIVPQSFLKDDSIDNKVLTRSDKNRGKSDNV<br>PSEEVVKKMKNYWRQLLNAKLITQRKFDNLTKAERGGLSELDKAGFIKRQLVETRQITKHVAQILDSRMNTKYDENDKLIREVKVIT<br>LKSKLVSDFRKDFQFYKVREINNYHHAHDAYLNAVVGTALIKKYPKLESEFVYGDYKVYDVRKMIAKSEQEIGKATAKYFFYSNIMN<br>FFKTEITLANGEIRKRPLIETNGETGEIVWDKGRDFATVRKVLSMPQVNIVKKTEVQTGGFSKESILPKRNSDKLIARKKDWDPKKY<br>GGFDSPTVAYSVLVVAKVEKGKSKKLKSVKELLGITIMERSSFEKNPIDFLEAKGYKEVKKDLIIKLPKYSLFELENGRKRMLASAG<br>ELQKGNELALPSKYVNFLYLASHYEKLKGSPEDNEQKQLFVEQHKHYLDEIIEQISEFSKRVILADANLDKVLSAYNKHRDKPIREQ | 392 |

-continued

Sequence Table

| Description | Sequence | SEQ ID No. |
|---|---|---|
| | AENIIHLFTLTNLGAPAAFKYFDTTIDRKRYTSTKEVLDATLIHQSITGLYETRIDLSQLGGDGGGSAAAKRVWSMAF | |
| Amino acid sequence for Cas9 with NLS8 | MDKKYSIGLDIGTNSVGWAVITDEYKVPSKKFKVLGNTDRHSIKKNLIGALLFDSGETAEATRLKRTARRRYTRRKNRICYLQEIFS<br>NEMAKVDDSFFHRLEESFLVEEDKKHERHPIFGNIVDEVAYHEKYPTIYHLRKKLVDSTDKADLRLIYLALAHMIKFRGHFLIEGDL<br>NPDNSDVDKLFIQLVQTYNQLFEENPINASGVDAKAILSARLSKSRRLENLIAQLPGEKKNGLFGNLIALSLGLTPNFKSNFDLAED<br>AKLQLSKDTYDDDLDNLLAQIGDQYADLFLAAKNLSDAILLSDILRVNTEITKAPLSASMIKRYDEHHQDLTLLKALVRQQLPEKYK<br>EIFFDQSKNGYAGYIDGGASQEEFYKFIKPILEKMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQSFIERMTNFDKNLPNEKVLPKHSLLYEYFTVYN<br>ELTKVKYVTEGMRKPAFLSGEQKKAIVDLLFKTNRKVTVKQLKEDYFKKIECFDSVEISGVEDRFNASLGTYHDLLKIIKDKDFLDN<br>EENEDILEDIVLTLTLFEDREMIEERLKTYAHLFDDKVMKQLKRRRYTGWGRLSRKLINGIRDKQSGKTILDFLKSDGFANRNFMQL<br>IHDDSLTFKEDIQKAQVSGQGDSLHEHIANLAGSPAIKKGILQTVKVVDELVKVMGRHKPENIVIEMARENQTTQKGQKNSRERMKR<br>IEEGIKELGSQILKEHPVENTQLQNEKLYLYYLQNGRDMYVDQELDINRLSDYDVDHIVPQSFLKDDSIDNKVLTRSDKNRGKSDNV<br>PSEEVVKKMKNYWRQLLNAKLITQRKFDNLTKAERGGLSELDKAGFIKRQLVETRQITKHVAQILDSRMNTKYDENDKLIREVKVIT<br>LKSKLVSDFRKDFQFYKVREINNYHHAHDAYLNAVVGTALIKKYPKLESEFVYGDYKVYDVRKMIAKSEQEIGKATAKYFFYSNIMN<br>FFKTEITLANGEIRKRPLIETNGETGEIVWDKGRDFATVRKVLSMPQVNIVKKTEVQTGGFSKESILPKRNSDKLIARKKDWDPKKY<br>GGFDSPTVAYSVLVVAKVEKGKSKKLKSVKELLGITIMERSSFEKNPIDFLEAKGYKEVKKDLIIKLPKYSLFELENGRKRMLASAG<br>ELQKGNELALPSKYVNFLYLASHYEKLKGSPEDNEQKQLFVEQHKHYLDEIIEQISEFSKRVILADANLDKVLSAYNKHRDKPIREQ<br>AENIIHLFTLTNLGAPAAFKYFDTTIDRKRYTSTKEVLDATLIHQSITGLYETRIDLSQLGGDGGGSAAAKRSWSMAF | 393 |
| Amino acid sequence for Cas9 with NLS9 | MDKKYSIGLDIGTNSVGWAVITDEYKVPSKKFKVLGNTDRHSIKKNLIGALLFDSGETAEATRLKRTARRRYTRRKNRICYLQEIFS<br>NEMAKVDDSFFHRLEESFLVEEDKKHERHPIFGNIVDEVAYHEKYPTIYHLRKKLVDSTDKADLRLIYLALAHMIKFRGHFLIEGDL<br>NPDNSDVDKLFIQLVQTYNQLFEENPINASGVDAKAILSARLSKSRRLENLIAQLPGEKKNGLFGNLIALSLGLTPNFKSNFDLAED<br>AKLQLSKDTYDDDLDNLLAQIGDQYADLFLAAKNLSDAILLSDILRVNTEITKAPLSASMIKRYDEHHQDLTLLKALVRQQLPEKYK<br>EIFFDQSKNGYAGYIDGGASQEEFYKFIKPILEKMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQSFIERMTNFDKNLPNEKVLPKHSLLYEYFTVYN<br>ELTKVKYVTEGMRKPAFLSGEQKKAIVDLLFKTNRKVTVKQLKEDYFKKIECFDSVEISGVEDRFNASLGTYHDLLKIIKDKDFLDN<br>EENEDILEDIVLTLTLFEDREMIEERLKTYAHLFDDKVMKQLKRRRYTGWGRLSRKLINGIRDKQSGKTILDFLKSDGFANRNFMQL<br>IHDDSLTFKEDIQKAQVSGQGDSLHEHIANLAGSPAIKKGILQTVKVVDELVKVMGRHKPENIVIEMARENQTTQKGQKNSRERMKR<br>IEEGIKELGSQILKEHPVENTQLQNEKLYLYYLQNGRDMYVDQELDINRLSDYDVDHIVPQSFLKDDSIDNKVLTRSDKNRGKSDNV<br>PSEEVVKKMKNYWRQLLNAKLITQRKFDNLTKAERGGLSELDKAGFIKRQLVETRQITKHVAQILDSRMNTKYDENDKLIREVKVIT<br>LKSKLVSDFRKDFQFYKVREINNYHHAHDAYLNAVVGTALIKKYPKLESEFVYGDYKVYDVRKMIAKSEQEIGKATAKYFFYSNIMN<br>FFKTEITLANGEIRKRPLIETNGETGEIVWDKGRDFATVRKVLSMPQVNIVKKTEVQTGGFSKESILPKRNSDKLIARKKDWDPKKY<br>GGFDSPTVAYSVLVVAKVEKGKSKKLKSVKELLGITIMERSSFEKNPIDFLEAKGYKEVKKDLIIKLPKYSLFELENGRKRMLASAG<br>ELQKGNELALPSKYVNFLYLASHYEKLKGSPEDNEQKQLFVEQHKHYLDEIIEQISEFSKRVILADANLDKVLSAYNKHRDKPIREQ<br>AENIIHLFTLTNLGAPAAFKYFDTTIDRKRYTSTKEVLDATLIHQSITGLYETRIDLSQLGGDGGGSAAAKRKYFAA | 394 |
| Amino acid sequence for Cas9 with NLS10 | MDKKYSIGLDIGTNSVGWAVITDEYKVPSKKFKVLGNTDRHSIKKNLIGALLFDSGETAEATRLKRTARRRYTRRKNRICYLQEIFS<br>NEMAKVDDSFFHRLEESFLVEEDKKHERHPIFGNIVDEVAYHEKYPTIYHLRKKLVDSTDKADLRLIYLALAHMIKFRGHFLIEGDL<br>NPDNSDVDKLFIQLVQTYNQLFEENPINASGVDAKAILSARLSKSRRLENLIAQLPGEKKNGLFGNLIALSLGLTPNFKSNFDLAED<br>AKLQLSKDTYDDDLDNLLAQIGDQYADLFLAAKNLSDAILLSDILRVNTEITKAPLSASMIKRYDEHHQDLTLLKALVRQQLPEKYK<br>EIFFDQSKNGYAGYIDGGASQEEFYKFIKPILEKMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQSFIERMTNFDKNLPNEKVLPKHSLLYEYFTVYN<br>ELTKVKYVTEGMRKPAFLSGEQKKAIVDLLFKTNRKVTVKQLKEDYFKKIECFDSVEISGVEDRFNASLGTYHDLLKIIKDKDFLDN<br>EENEDILEDIVLTLTLFEDREMIEERLKTYAHLFDDKVMKQLKRRRYTGWGRLSRKLINGIRDKQSGKTILDFLKSDGFANRNFMQL<br>IHDDSLTFKEDIQKAQVSGQGDSLHEHIANLAGSPAIKKGILQTVKVVDELVKVMGRHKPENIVIEMARENQTTQKGQKNSRERMKR<br>IEEGIKELGSQILKEHPVENTQLQNEKLYLYYLQNGRDMYVDQELDINRLSDYDVDHIVPQSFLKDDSIDNKVLTRSDKNRGKSDNV<br>PSEEVVKKMKNYWRQLLNAKLITQRKFDNLTKAERGGLSELDKAGFIKRQLVETRQITKHVAQILDSRMNTKYDENDKLIREVKVIT<br>LKSKLVSDFRKDFQFYKVREINNYHHAHDAYLNAVVGTALIKKYPKLESEFVYGDYKVYDVRKMIAKSEQEIGKATAKYFFYSNIMN<br>FFKTEITLANGEIRKRPLIETNGETGEIVWDKGRDFATVRKVLSMPQVNIVKKTEVQTGGFSKESILPKRNSDKLIARKKDWDPKKY | 395 |

-continued

Sequence Table

| Description | Sequence | SEQ ID No. |
|---|---|---|
| | GGFDSPTVAYSVLVVAKVEKGKSKKLKSVKELLGITIMERSSFEKNPIDFLEAKGYKEVKKDLIIKLPKYSLFELENGRKRMLASAG<br>ELQKGNELALPSKYVNFLYLASHYEKLKGSPEDNEQKQLFVEQHKHYLDEIIEQISEFSKRVILADANLDKVLSAYNKHRDKPIREQ<br>AENIIHLFTLTNLGAPAAFKYFDTTIDRKRYTSTKEVLDATLIHQSITGLYETRIDLSQLGGDGGGSRAAKRKAFAA | |
| Amino acid sequence for Cas9 with NLS11 | MDKKYSIGLDIGTNSVGWAVITDEYKVPSKKFKVLGNTDRHSIKKNLIGALLFDSGETAEATRLKRTARRRYTRRKNRICYLQEIFS<br>NEMAKVDDSFFHRLEESFLVEEDKKHERHPIFGNIVDEVAYHEKYPTIYHLRKKLVDSTDKADLRLIYLALAHMIKFRGHFLIEGDL<br>NPDNSDVDKLFIQLVQTYNQLFEENPINASGVDAKAILSARLSKSRRLENLIAQLPGEKKNGLFGNLIALSLGLTPNFKSNFDLAED<br>AKLQLSKDTYDDDLDNLLAQIGDQYADLFLAAKNLSDAILLSDILRVNTEITKAPLSASMIKRYDEHHQDLTLLKALVRQQLPEKYK<br>EIFFDQSKNGYAGYIDGGASQEEFYKFIKPILEKMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQSFIERMTNFDKNLPNEKVLPKHSLLYEYFTVYN<br>ELTKVKYVTEGMRKPAFLSGEQKKAIVDLLFKTNRKVTVKQLKEDYFKKIECFDSVEISGVEDRFNASLGTYHDLLKIIKDKDFLDN<br>EENEDILEDIVLTLTLFEDREMIEERLKTYAHLFDDKVMKQLKRRRYTGWGRLSRKLINGIRDKQSGKTILDFLKSDGFANRNFMQL<br>IHDDSLTFKEDIQKAQVSGQGDSLHEHIANLAGSPAIKKGILQTVKVVDELVKVMGRHKPENIVIEMARENQTTQKGQKNSRERMKR<br>IEEGIKELGSQILKEHPVENTQLQNEKLYLYYLQNGRDMYVDQELDINRLSDYDVDHIVPQSFLKDDSIDNKVLTRSDKNRGKSDNV<br>PSEEVVKKMKNYWRQLLNAKLITQRKFDNLTKAERGGLSELDKAGFIKRQLVETRQITKHVAQILDSRMNTKYDENDKLIREVKVIT<br>LKSKLVSDFRKDFQFYKVREINNYHHAHDAYLNAVVGTALIKKYPKLESEFVYGDYKVYDVRKMIAKSEQEIGKATAKYFFYSNIMN<br>FFKTEITLANGEIRKRPLIETNGETGEIVWDKGRDFATVRKVLSMPQVNIVKKTEVQTGGFSKESILPKRNSDKLIARKKDWDPKKY<br>GGFDSPTVAYSVLVVAKVEKGKSKKLKSVKELLGITIMERSSFEKNPIDFLEAKGYKEVKKDLIIKLPKYSLFELENGRKRMLASAG<br>ELQKGNELALPSKYVNFLYLASHYEKLKGSPEDNEQKQLFVEQHKHYLDEIIEQISEFSKRVILADANLDKVLSAYNKHRDKPIREQ<br>AENIIHLFTLTNLGAPAAFKYFDTTIDRKRYTSTKEVLDATLIHQSITGLYETRIDLSQLGGDGGGSRAAKRKYFAV | 396 |

* = PS linkage;
'm' = 2'-O-Me nucleotide

SEQUENCE LISTING

```
Sequence total quantity: 396
SEQ ID NO: 1           moltype = DNA  length = 4411
FEATURE                Location/Qualifiers
misc_feature           1..4411
                       note = Synthetic: Cas9 transcript with 5 UTR of HSD, ORF
                        corresponding to SEQ ID NO: 204, Kozak sequence, and 3 UTR
                        of ALB
source                 1..4411
                       mol_type = other DNA
                       organism = synthetic construct
SEQUENCE: 1
gggtcccgca gtcggcgtcc agcggctctg cttgttcgtg tgtgtgtcgt tgcaggcctt  60
attcggatcc gccaccatgg acaagaagta cagcatcgga ctggacatcg gaacaaacag  120
cgtcggatgg gcagtcatca cagacgaata caaggtcccg agcaagaagt tcaaggtcct  180
gggaaacaca gacagacaca gcatcaagaa gaacctgatc ggagcactgc tgttcgacag  240
cggagaaaca gcagaagcaa caagactgaa gagaacagca agaagaagat acacaagaag  300
aaagaacaga atctgctacc tgcaggaaat cttcagcaac gaaatggcaa aggtcgacga  360
cagcttcttc cacagactgg aagaaagctt cctggtcgaa gaagacaaga agcacgaaag  420
acacccgatc ttcggaaaca tcgtcgacga agtcgcatac cacgaaaagt acccgacaat  480
ctaccacctg agaaagaagc tggtcgacag cacagacaag gcagacctga gactgatcta  540
cctggcactg gcacacatga tcaagttcag aggacacttc ctgatcgaag gagacctgaa  600
cccggacaac agcgacgtcg acaagctgtt catccagctg gtccagacat acaaccagct  660
gttcgaagaa aacccgatca acgcaagcgg agtcgacgca aaggcaatcc tgagcgcaag  720
actgagcaag agcagaagac tggaaaacct gatcgcacag ctgccgggag aaaagaagaa  780
cggactgttc ggaaacctga tcgcactgag cctgggactg acaccgaact tcaagagcaa  840
cttcgacctg gcagaagacg caaagctgca gctgagcaag gacacatacg acgacgacct  900
ggacaacctg ctggcacaga tcggagacca gtacgcagac ctgttcctgg cagcaaagaa  960
cctgagcgac gcaatcctgc tgagcgacat cctgagagtc aacacagaaa tcacaaaggc  1020
accgctgagc gcaagcatga tcaagagata cgacgaacac caccaggacc tgacactgct  1080
gaaggcactg gtcagacagc agctgccgga aaagtacaag gaaatcttct tcgaccagag  1140
caagaacgga tacgcaggat acatcgacgg aggagcaagc caggaagaat tctacaagtt  1200
catcaagccg atcctggaaa agatggacgg aacagaagaa ctgctggtca agctgaacag  1260
agaagacctg ctgagaaagc agagaacatt cgacaacgga agcatcccgc accagatcca  1320
cctgggagaa ctgcacgcaa tcctgagaag acaggaagac ttctacccgt tcctgaagga  1380
caacagagaa aagatcgaaa agatcctgac attcagaatc ccgtactacg tcggaccgct  1440
ggcaagagga aacagcagat tcgcatggat gacaagaaag agcgaagaaa caatcacacc  1500
gtggaacttc gaagaagtcg tcgacaaggg agcaagcgca cagagcttca tcgaaagaat  1560
gacaaacttc gacaagaacc tgccgaacga aaaggtcctg ccgaagcaca gcctgctgta  1620
cgaatacttc acagtctaca acgaactgac aaaggtcaag tacgtcacag aaggaatgag  1680
aaagccggca ttcctgagcg gagaacagaa gaaggcaatc gtcgacctgc tgttcaagac  1740
aaacagaaag gtcacagtca agcagctgaa ggaagactac ttcaagaaga tcgaatgctt  1800
cgacagcgtc gaaatcagcg gagtcgaaga cagattcaac gcaagcctgg gaacatacca  1860
cgacctgctg aagatcatca aggacaagga cttcctggac aacgaagaaa acgaagacat  1920
cctggaagac atcgtcctga cactgacact gttcgaagac agagaaatga tcgaagaaag  1980
actgaagaca tacgcacacc tgttcgacga caaggtcatg aagcagctga agagaagaag  2040
atacacagga tggggaagac tgagcagaaa gctgatcaac ggaatcagag acaagcagag  2100
cggaaagaca atcctggact tcctgaagag cgacggattc gcaaacagaa acttcatgca  2160
gctgatccac gacgacagcc tgacattcaa ggaagacatc cagaaggcac aggtcagcgg  2220
acagggagac agcctgcacg aacacatcgc aaacctggca ggaagcccgg caatcaagaa  2280
gggaatcctg cagacagtca aggtcgtcga cgaactggtc aaggtcatgg gaagacacaa  2340
gccggaaaac atcgtcatcg aaatggcaag agaaaaccag acaacacaga agggacagaa  2400
gaacagcaga gaaagaatga agagaatcga agaaggaatc aaggaactgg gaagccagat  2460
cctgaaggaa cacccggtcg aaaacacaca gctgcagaac gaaaagctgt acctgtacta  2520
cctgcagaac ggaagagaca tgtacgtcga ccaggaactg gacatcaaca gactgagcga  2580
ctacgacgtc gaccacatcg tcccgcagag cttcctgaag gacgacagca tcgacaacaa  2640
ggtcctgaca agaagcgaca agaacagagg aaagagcgac aacgtcccga gcgaagaagt  2700
cgtcaagaag atgaagaact actggagaca gctgctgaac gcaaagctga tcacacagag  2760
aaagttcgac aacctgacaa aggcagagag aggaggactg agcgaactgg acaaggcagg  2820
attcatcaag agacagctgg tcgaaacaag acagatcaca aagcacgtcg cacagatcct  2880
ggacagcaga atgaacacaa agtacgacga aaacgacaag ctgatcagag aagtcaaggt  2940
catcacactg aagagcaagc tggtcagcga cttcagaaag gacttccagt tctacaaggt  3000
cagagaaatc aacaactacc accacgcaca cgacgcatac ctgaacgcag tcgtcggaac  3060
agcactgatc aagaagtacc cgaagctgga aagcgaattc gtctacggag actacaaggt  3120
ctacgacgtc agaaagatga tcgcaaagag cgaacaggaa atcggaaagg caacagcaaa  3180
gtacttcttc tacagcaaca tcatgaactt cttcaagaca gaaatcacac tggcaaacgg  3240
agaaatcaga aagagaccgc tgatcgaaac aaacggagaa acaggagaaa tcgtctggga  3300
caagggaaga gacttcgcaa cagtcagaaa ggtcctgagc atgccgcagg tcaacatcgt  3360
caagaagaca gaagtccaga caggaggatt cagcaaggaa agcatcctgc cgaagagaaa  3420
cagcgacaag ctgatcgcaa gaaagaagga ctgggacccg aagaagtacg gaggattcga  3480
cagcccgaca gtcgcataca gcgtcctggt cgtcgcaaag gtcgaaaagg gaaagagcaa  3540
gaagctgaag agcgtcaagg aactgctggg aatcacaatc atggaaagaa gcagcttcga  3600
aaagaacccg atcgacttcc tggaagcaaa gggatacaag gaagtcaaga aggacctgat  3660
catcaagctg ccgaagtaca gcctgttcga actggaaaac ggaagaaaga gaatgctggc  3720
aagcgcagga gaactgcaga agggaaacga actggcactg ccgagcaagt acgtcaactt  3780
cctgtacctg gcaagccact acgaaaagct gaagggaagc ccggaagaca acgaacagaa  3840
gcagctgttc gtcgaacagc acaagcacta cctggacgaa atcatcgaac agatcagcga  3900
attcagcaag agagtcatcc tggcagacgc aaacctggac aaggtcctga gcgcatacaa  3960
caagcacaga gacaagccga tcagagaaca ggcagaaaac atcatccacc tgttcacact  4020
```

-continued

```
gacaaacctg ggagcaccgg cagcattcaa gtacttcgac acaacaatcg acagaaagag  4080
atacacaagc acaaaggaag tcctggacgc aacactgatc caccagagca tcacaggact  4140
gtacgaaaca agaatcgacc tgagccagct gggaggagac ggaggaggaa gcccgaagaa  4200
gaagagaaag gtctagctag ccatcacatt taaaagcatc tcagcctacc atgagaataa  4260
gagaaagaaa atgaagatca atagcttatt catctctttt tctttttcgt tggtgtaaag  4320
ccaacaccct gtctaaaaaa cataaatttc tttaatcatt ttgcctcttt tctctgtgct  4380
tcaattaata aaaaatggaa agaacctcga g                                 4411

SEQ ID NO: 2           moltype = RNA  length = 100
FEATURE                Location/Qualifiers
misc_feature           1..100
                       note = Synthetic: G000739 - sgRNA negative control
modified_base          1..3
                       mod_base = OTHER
                       note = 2'-O-methylation
modified_base          1..4
                       mod_base = OTHER
                       note = Phosphorothioate internucleoside linkage
modified_base          29..40
                       mod_base = OTHER
                       note = 2'-O-methylation
modified_base          69..100
                       mod_base = OTHER
                       note = 2'-O-methylation
modified_base          97..100
                       mod_base = OTHER
                       note = Phosphorothioate internucleoside linkage
source                 1..100
                       mol_type = other RNA
                       organism = synthetic construct
SEQUENCE: 2
gatcacgtcg gccgttggcg gttttagagc tagaaatagc aagttaaaat aaggctagtc  60
cgttatcaac ttgaaaaagt ggcaccgagt cggtgctttt                       100

SEQ ID NO: 3           moltype = RNA  length = 100
FEATURE                Location/Qualifiers
misc_feature           1..100
                       note = Synthetic: modified sgRNA sequence (N may be any
                        natural or non-natural nucleotide)
variation              1..20
                       note = n is a, c, g, or u
modified_base          1..3
                       mod_base = OTHER
                       note = 2'-O-methylation
modified_base          1..4
                       mod_base = OTHER
                       note = Phosphorothioate internucleoside linkage
modified_base          29..40
                       mod_base = OTHER
                       note = 2'-O-methylation
modified_base          69..100
                       mod_base = OTHER
                       note = 2'-O-methylation
modified_base          97..100
                       mod_base = OTHER
                       note = Phosphorothioate internucleoside linkage
source                 1..100
                       mol_type = other RNA
                       organism = synthetic construct
SEQUENCE: 3
nnnnnnnnnn nnnnnnnnnn gttttagagc tagaaatagc aagttaaaat aaggctagtc  60
cgttatcaac ttgaaaaagt ggcaccgagt cggtgctttt                       100

SEQ ID NO: 4           moltype = RNA  length = 105
FEATURE                Location/Qualifiers
misc_feature           1..105
                       note = Synthetic: 30/30/39 poly-A sequence
source                 1..105
                       mol_type = other RNA
                       organism = synthetic construct
SEQUENCE: 4
aaaaaaaaaa aaaaaaaaaa aaaaaaaaaa gcgaaaaaaa aaaaaaaaaa aaaaaaaaaa  60
aaaccgaaaa aaaaaaaaaa aaaaaaaaaa aaaaaaaaaa aaaaa                 105

SEQ ID NO: 5           moltype = RNA  length = 20
FEATURE                Location/Qualifiers
misc_feature           1..20
                       note = Synthetic: CR003335 gRNA targeting Human TTR (Exon 1)
source                 1..20
```

-continued

```
                        mol_type = other RNA
                        organism = synthetic construct
SEQUENCE: 5
ctgctcctcc tctgccttgc                                              20

SEQ ID NO: 6            moltype = RNA  length = 20
FEATURE                 Location/Qualifiers
misc_feature            1..20
                        note = Synthetic: CR003336 gRNA targeting Human TTR (Exon 1)
source                  1..20
                        mol_type = other RNA
                        organism = synthetic construct
SEQUENCE: 6
cctcctctgc cttgctggac                                              20

SEQ ID NO: 7            moltype = RNA  length = 20
FEATURE                 Location/Qualifiers
misc_feature            1..20
                        note = Synthetic: CR003337 gRNA targeting Human TTR (Exon 1)
source                  1..20
                        mol_type = other RNA
                        organism = synthetic construct
SEQUENCE: 7
ccagtccagc aaggcagagg                                              20

SEQ ID NO: 8            moltype = RNA  length = 20
FEATURE                 Location/Qualifiers
misc_feature            1..20
                        note = Synthetic: CR003338 gRNA targeting Human TTR (Exon 1)
source                  1..20
                        mol_type = other RNA
                        organism = synthetic construct
SEQUENCE: 8
ataccagtcc agcaaggcag                                              20

SEQ ID NO: 9            moltype = RNA  length = 20
FEATURE                 Location/Qualifiers
misc_feature            1..20
                        note = Synthetic: CR003339 gRNA targeting Human TTR (Exon 1)
source                  1..20
                        mol_type = other RNA
                        organism = synthetic construct
SEQUENCE: 9
acacaaatac cagtccagca                                              20

SEQ ID NO: 10           moltype = RNA  length = 20
FEATURE                 Location/Qualifiers
misc_feature            1..20
                        note = Synthetic: CR003340 gRNA targeting Human TTR (Exon 1)
source                  1..20
                        mol_type = other RNA
                        organism = synthetic construct
SEQUENCE: 10
tggactggta tttgtgtctg                                              20

SEQ ID NO: 11           moltype = RNA  length = 20
FEATURE                 Location/Qualifiers
misc_feature            1..20
                        note = Synthetic: CR003341 gRNA targeting Human TTR (Exon 1)
source                  1..20
                        mol_type = other RNA
                        organism = synthetic construct
SEQUENCE: 11
ctggtatttg tgtctgaggc                                              20

SEQ ID NO: 12           moltype = RNA  length = 20
FEATURE                 Location/Qualifiers
misc_feature            1..20
                        note = Synthetic: CR003342 gRNA targeting Human TTR (Exon 2)
source                  1..20
                        mol_type = other RNA
                        organism = synthetic construct
SEQUENCE: 12
cttctctaca cccagggcac                                              20

SEQ ID NO: 13           moltype = RNA  length = 20
FEATURE                 Location/Qualifiers
misc_feature            1..20
                        note = Synthetic: CR003343 gRNA targeting Human TTR (Exon 2)
```

-continued

```
source                 1..20
                       mol_type = other RNA
                       organism = synthetic construct
SEQUENCE: 13
cagaggacac ttggattcac                                              20

SEQ ID NO: 14          moltype = RNA  length = 20
FEATURE                Location/Qualifiers
misc_feature           1..20
                       note = Synthetic: CR003344 gRNA targeting Human TTR (Exon 2)
source                 1..20
                       mol_type = other RNA
                       organism = synthetic construct
SEQUENCE: 14
tttgaccatc agaggacact                                              20

SEQ ID NO: 15          moltype = RNA  length = 20
FEATURE                Location/Qualifiers
misc_feature           1..20
                       note = Synthetic: CR003345 gRNA targeting Human TTR (Exon 2)
source                 1..20
                       mol_type = other RNA
                       organism = synthetic construct
SEQUENCE: 15
tctagaactt tgaccatcag                                              20

SEQ ID NO: 16          moltype = RNA  length = 20
FEATURE                Location/Qualifiers
misc_feature           1..20
                       note = Synthetic: CR003346 gRNA targeting Human TTR (Exon 2)
source                 1..20
                       mol_type = other RNA
                       organism = synthetic construct
SEQUENCE: 16
aaagttctag atgctgtccg                                              20

SEQ ID NO: 17          moltype = RNA  length = 20
FEATURE                Location/Qualifiers
misc_feature           1..20
                       note = Synthetic: CR003347 gRNA targeting Human TTR (Exon 2)
source                 1..20
                       mol_type = other RNA
                       organism = synthetic construct
SEQUENCE: 17
cattgatggc aggactgcct                                              20

SEQ ID NO: 18          moltype = RNA  length = 20
FEATURE                Location/Qualifiers
misc_feature           1..20
                       note = Synthetic: CR003348 gRNA targeting Human TTR (Exon 2)
source                 1..20
                       mol_type = other RNA
                       organism = synthetic construct
SEQUENCE: 18
aggcagtcct gccatcaatg                                              20

SEQ ID NO: 19          moltype = RNA  length = 20
FEATURE                Location/Qualifiers
misc_feature           1..20
                       note = Synthetic: CR003349 gRNA targeting Human TTR (Exon 2)
source                 1..20
                       mol_type = other RNA
                       organism = synthetic construct
SEQUENCE: 19
tgcacggcca cattgatggc                                              20

SEQ ID NO: 20          moltype = RNA  length = 20
FEATURE                Location/Qualifiers
misc_feature           1..20
                       note = Synthetic: CR003350 gRNA targeting Human TTR (Exon 2)
source                 1..20
                       mol_type = other RNA
                       organism = synthetic construct
SEQUENCE: 20
cacatgcacg gccacattga                                              20

SEQ ID NO: 21          moltype = RNA  length = 20
FEATURE                Location/Qualifiers
misc_feature           1..20
```

```
                        note = Synthetic: CR003351 gRNA targeting Human TTR (Exon 2)
source                  1..20
                        mol_type = other RNA
                        organism = synthetic construct
SEQUENCE: 21
agcctttctg aacacatgca                                                20

SEQ ID NO: 22           moltype = RNA  length = 20
FEATURE                 Location/Qualifiers
misc_feature            1..20
                        note = Synthetic: CR003352 gRNA targeting Human TTR (Exon 2)
source                  1..20
                        mol_type = other RNA
                        organism = synthetic construct
SEQUENCE: 22
gaaaggctgc tgatgacacc                                                20

SEQ ID NO: 23           moltype = RNA  length = 20
FEATURE                 Location/Qualifiers
misc_feature            1..20
                        note = Synthetic: CR003353 gRNA targeting Human TTR (Exon 2)
source                  1..20
                        mol_type = other RNA
                        organism = synthetic construct
SEQUENCE: 23
aaaggctgct gatgacacct                                                20

SEQ ID NO: 24           moltype = RNA  length = 20
FEATURE                 Location/Qualifiers
misc_feature            1..20
                        note = Synthetic: CR003354 gRNA targeting Human TTR (Exon 2)
source                  1..20
                        mol_type = other RNA
                        organism = synthetic construct
SEQUENCE: 24
acctgggagc catttgcctc                                                20

SEQ ID NO: 25           moltype = RNA  length = 20
FEATURE                 Location/Qualifiers
misc_feature            1..20
                        note = Synthetic: CR003355 gRNA targeting Human TTR (Exon 2)
source                  1..20
                        mol_type = other RNA
                        organism = synthetic construct
SEQUENCE: 25
cccagaggca aatggctccc                                                20

SEQ ID NO: 26           moltype = RNA  length = 20
FEATURE                 Location/Qualifiers
misc_feature            1..20
                        note = Synthetic: CR003356 gRNA targeting Human TTR (Exon 2)
source                  1..20
                        mol_type = other RNA
                        organism = synthetic construct
SEQUENCE: 26
gcaacttacc cagaggcaaa                                                20

SEQ ID NO: 27           moltype = RNA  length = 20
FEATURE                 Location/Qualifiers
misc_feature            1..20
                        note = Synthetic: CR003357 gRNA targeting Human TTR (Exon 2)
source                  1..20
                        mol_type = other RNA
                        organism = synthetic construct
SEQUENCE: 27
ttctttggca acttacccag                                                20

SEQ ID NO: 28           moltype = RNA  length = 20
FEATURE                 Location/Qualifiers
misc_feature            1..20
                        note = Synthetic: CR003358 gRNA targeting Human TTR (Exon 3)
source                  1..20
                        mol_type = other RNA
                        organism = synthetic construct
SEQUENCE: 28
atgcagctct ccagactcac                                                20

SEQ ID NO: 29           moltype = RNA  length = 20
FEATURE                 Location/Qualifiers
```

-continued

```
misc_feature            1..20
                        note = Synthetic: CR003359 gRNA targeting Human TTR (Exon 3)
source                  1..20
                        mol_type = other RNA
                        organism = synthetic construct
SEQUENCE: 29
agtgagtctg gagagctgca                                               20

SEQ ID NO: 30           moltype = RNA  length = 20
FEATURE                 Location/Qualifiers
misc_feature            1..20
                        note = Synthetic: CR003360 gRNA targeting Human TTR (Exon 3)
source                  1..20
                        mol_type = other RNA
                        organism = synthetic construct
SEQUENCE: 30
gtgagtctgg agagctgcat                                               20

SEQ ID NO: 31           moltype = RNA  length = 20
FEATURE                 Location/Qualifiers
misc_feature            1..20
                        note = Synthetic: CR003361 gRNA targeting Human TTR (Exon 3)
source                  1..20
                        mol_type = other RNA
                        organism = synthetic construct
SEQUENCE: 31
gctgcatggg ctcacaactg                                               20

SEQ ID NO: 32           moltype = RNA  length = 20
FEATURE                 Location/Qualifiers
misc_feature            1..20
                        note = Synthetic: CR003362 gRNA targeting Human TTR (Exon 3)
source                  1..20
                        mol_type = other RNA
                        organism = synthetic construct
SEQUENCE: 32
gcatgggctc acaactgagg                                               20

SEQ ID NO: 33           moltype = RNA  length = 20
FEATURE                 Location/Qualifiers
misc_feature            1..20
                        note = Synthetic: CR003363 gRNA targeting Human TTR (Exon 3)
source                  1..20
                        mol_type = other RNA
                        organism = synthetic construct
SEQUENCE: 33
actgaggagg aatttgtaga                                               20

SEQ ID NO: 34           moltype = RNA  length = 20
FEATURE                 Location/Qualifiers
misc_feature            1..20
                        note = Synthetic: CR003364 gRNA targeting Human TTR (Exon 3)
source                  1..20
                        mol_type = other RNA
                        organism = synthetic construct
SEQUENCE: 34
ctgaggagga atttgtagaa                                               20

SEQ ID NO: 35           moltype = RNA  length = 20
FEATURE                 Location/Qualifiers
misc_feature            1..20
                        note = Synthetic: CR003365 gRNA targeting Human TTR (Exon 3)
source                  1..20
                        mol_type = other RNA
                        organism = synthetic construct
SEQUENCE: 35
tgtagaaggg atatacaaag                                               20

SEQ ID NO: 36           moltype = RNA  length = 20
FEATURE                 Location/Qualifiers
misc_feature            1..20
                        note = Synthetic: CR003366 gRNA targeting Human TTR (Exon 3)
source                  1..20
                        mol_type = other RNA
                        organism = synthetic construct
SEQUENCE: 36
aaatagacac caaatcttac                                               20

SEQ ID NO: 37           moltype = RNA  length = 20
```

```
FEATURE                Location/Qualifiers
misc_feature           1..20
                       note = Synthetic: CR003367 gRNA targeting Human TTR (Exon 3)
source                 1..20
                       mol_type = other RNA
                       organism = synthetic construct
SEQUENCE: 37
agacaccaaa tcttactgga                                              20

SEQ ID NO: 38          moltype = RNA  length = 20
FEATURE                Location/Qualifiers
misc_feature           1..20
                       note = Synthetic: CR003368 gRNA targeting Human TTR (Exon 3)
source                 1..20
                       mol_type = other RNA
                       organism = synthetic construct
SEQUENCE: 38
aagtgccttc cagtaagatt                                              20

SEQ ID NO: 39          moltype = RNA  length = 20
FEATURE                Location/Qualifiers
misc_feature           1..20
                       note = Synthetic: CR003369 gRNA targeting Human TTR (Exon 3)
source                 1..20
                       mol_type = other RNA
                       organism = synthetic construct
SEQUENCE: 39
ctctgcatgc tcatggaatg                                              20

SEQ ID NO: 40          moltype = RNA  length = 20
FEATURE                Location/Qualifiers
misc_feature           1..20
                       note = Synthetic: CR003370 gRNA targeting Human TTR (Exon 3)
source                 1..20
                       mol_type = other RNA
                       organism = synthetic construct
SEQUENCE: 40
cctctgcatg ctcatggaat                                              20

SEQ ID NO: 41          moltype = RNA  length = 20
FEATURE                Location/Qualifiers
misc_feature           1..20
                       note = Synthetic: CR003371 gRNA targeting Human TTR (Exon 3)
source                 1..20
                       mol_type = other RNA
                       organism = synthetic construct
SEQUENCE: 41
acctctgcat gctcatggaa                                              20

SEQ ID NO: 42          moltype = RNA  length = 20
FEATURE                Location/Qualifiers
misc_feature           1..20
                       note = Synthetic: CR003372 gRNA targeting Human TTR (Exon 3)
source                 1..20
                       mol_type = other RNA
                       organism = synthetic construct
SEQUENCE: 42
tactcacctc tgcatgctca                                              20

SEQ ID NO: 43          moltype = RNA  length = 20
FEATURE                Location/Qualifiers
misc_feature           1..20
                       note = Synthetic: CR003373 gRNA targeting Human TTR (Exon 4)
source                 1..20
                       mol_type = other RNA
                       organism = synthetic construct
SEQUENCE: 43
gtattcacag ccaacgactc                                              20

SEQ ID NO: 44          moltype = RNA  length = 20
FEATURE                Location/Qualifiers
misc_feature           1..20
                       note = Synthetic: CR003374 gRNA targeting Human TTR (Exon 4)
source                 1..20
                       mol_type = other RNA
                       organism = synthetic construct
SEQUENCE: 44
gcggcggggg ccggagtcgt                                              20
```

-continued

```
SEQ ID NO: 45           moltype = RNA  length = 20
FEATURE                 Location/Qualifiers
misc_feature            1..20
                        note = Synthetic: CR003375 gRNA targeting Human TTR (Exon 4)
source                  1..20
                        mol_type = other RNA
                        organism = synthetic construct
SEQUENCE: 45
aatggtgtag cggcgggggc                                              20

SEQ ID NO: 46           moltype = RNA  length = 20
FEATURE                 Location/Qualifiers
misc_feature            1..20
                        note = Synthetic: CR003376 gRNA targeting Human TTR (Exon 4)
source                  1..20
                        mol_type = other RNA
                        organism = synthetic construct
SEQUENCE: 46
cggcaatggt gtagcggcgg                                              20

SEQ ID NO: 47           moltype = RNA  length = 20
FEATURE                 Location/Qualifiers
misc_feature            1..20
                        note = Synthetic: CR003377 gRNA targeting Human TTR (Exon 4)
source                  1..20
                        mol_type = other RNA
                        organism = synthetic construct
SEQUENCE: 47
gcggcaatgg tgtagcggcg                                              20

SEQ ID NO: 48           moltype = RNA  length = 20
FEATURE                 Location/Qualifiers
misc_feature            1..20
                        note = Synthetic: CR003378 gRNA targeting Human TTR (Exon 4)
source                  1..20
                        mol_type = other RNA
                        organism = synthetic construct
SEQUENCE: 48
ggcggcaatg gtgtagcggc                                              20

SEQ ID NO: 49           moltype = RNA  length = 20
FEATURE                 Location/Qualifiers
misc_feature            1..20
                        note = Synthetic: CR003379 gRNA targeting Human TTR (Exon 4)
source                  1..20
                        mol_type = other RNA
                        organism = synthetic construct
SEQUENCE: 49
gggcggcaat ggtgtagcgg                                              20

SEQ ID NO: 50           moltype = RNA  length = 20
FEATURE                 Location/Qualifiers
misc_feature            1..20
                        note = Synthetic: CR003380 gRNA targeting Human TTR (Exon 4)
source                  1..20
                        mol_type = other RNA
                        organism = synthetic construct
SEQUENCE: 50
gcagggcggc aatggtgtag                                              20

SEQ ID NO: 51           moltype = RNA  length = 20
FEATURE                 Location/Qualifiers
misc_feature            1..20
                        note = Synthetic: CR003381 gRNA targeting Human TTR (Exon 4)
source                  1..20
                        mol_type = other RNA
                        organism = synthetic construct
SEQUENCE: 51
ggggctcagc agggcggcaa                                              20

SEQ ID NO: 52           moltype = RNA  length = 20
FEATURE                 Location/Qualifiers
misc_feature            1..20
                        note = Synthetic: CR003382 gRNA targeting Human TTR (Exon 4)
source                  1..20
                        mol_type = other RNA
                        organism = synthetic construct
SEQUENCE: 52
ggagtagggg ctcagcaggg                                              20
```

```
SEQ ID NO: 53          moltype = RNA  length = 20
FEATURE                Location/Qualifiers
misc_feature           1..20
                       note = Synthetic: CR003383 gRNA targeting Human TTR (Exon 4)
source                 1..20
                       mol_type = other RNA
                       organism = synthetic construct
SEQUENCE: 53
ataggagtag gggctcagca                                                20

SEQ ID NO: 54          moltype = RNA  length = 20
FEATURE                Location/Qualifiers
misc_feature           1..20
                       note = Synthetic: CR003384 gRNA targeting Human TTR (Exon 4)
source                 1..20
                       mol_type = other RNA
                       organism = synthetic construct
SEQUENCE: 54
aataggagta ggggctcagc                                                20

SEQ ID NO: 55          moltype = RNA  length = 20
FEATURE                Location/Qualifiers
misc_feature           1..20
                       note = Synthetic: CR003385 gRNA targeting Human TTR (Exon 4)
source                 1..20
                       mol_type = other RNA
                       organism = synthetic construct
SEQUENCE: 55
cccctactcc tattccacca                                                20

SEQ ID NO: 56          moltype = RNA  length = 20
FEATURE                Location/Qualifiers
misc_feature           1..20
                       note = Synthetic: CR003386 gRNA targeting Human TTR (Exon 4)
source                 1..20
                       mol_type = other RNA
                       organism = synthetic construct
SEQUENCE: 56
ccgtggtgga ataggagtag                                                20

SEQ ID NO: 57          moltype = RNA  length = 20
FEATURE                Location/Qualifiers
misc_feature           1..20
                       note = Synthetic: CR003387 gRNA targeting Human TTR (Exon 4)
source                 1..20
                       mol_type = other RNA
                       organism = synthetic construct
SEQUENCE: 57
gccgtggtgg aataggagta                                                20

SEQ ID NO: 58          moltype = RNA  length = 20
FEATURE                Location/Qualifiers
misc_feature           1..20
                       note = Synthetic: CR003388 gRNA targeting Human TTR (Exon 4)
source                 1..20
                       mol_type = other RNA
                       organism = synthetic construct
SEQUENCE: 58
gacgacagcc gtggtggaat                                                20

SEQ ID NO: 59          moltype = RNA  length = 20
FEATURE                Location/Qualifiers
misc_feature           1..20
                       note = Synthetic: CR003389 gRNA targeting Human TTR (Exon 4)
source                 1..20
                       mol_type = other RNA
                       organism = synthetic construct
SEQUENCE: 59
attggtgacg acagccgtgg                                                20

SEQ ID NO: 60          moltype = RNA  length = 20
FEATURE                Location/Qualifiers
misc_feature           1..20
                       note = Synthetic: CR003390 gRNA targeting Human TTR (Exon 4)
source                 1..20
                       mol_type = other RNA
                       organism = synthetic construct
SEQUENCE: 60
```

-continued

```
gggattggtg acgacagccg                                              20

SEQ ID NO: 61          moltype = RNA  length = 20
FEATURE                Location/Qualifiers
misc_feature           1..20
                       note = Synthetic: CR003391 gRNA targeting Human TTR (Exon 4)
source                 1..20
                       mol_type = other RNA
                       organism = synthetic construct
SEQUENCE: 61
ggctgtcgtc accaatccca                                              20

SEQ ID NO: 62          moltype = RNA  length = 20
FEATURE                Location/Qualifiers
misc_feature           1..20
                       note = Synthetic: CR003392 gRNA targeting Human TTR (Exon 4)
source                 1..20
                       mol_type = other RNA
                       organism = synthetic construct
SEQUENCE: 62
agtccctcat tccttgggat                                              20

SEQ ID NO: 63          moltype = RNA  length = 20
FEATURE                Location/Qualifiers
misc_feature           1..20
                       note = Synthetic: CR005298 gRNA targeting Human TTR (Exon 1)
source                 1..20
                       mol_type = other RNA
                       organism = synthetic construct
SEQUENCE: 63
tccactcatt cttggcagga                                              20

SEQ ID NO: 64          moltype = RNA  length = 20
FEATURE                Location/Qualifiers
misc_feature           1..20
                       note = Synthetic: CR005299 gRNA targeting Human TTR (Exon 4)
source                 1..20
                       mol_type = other RNA
                       organism = synthetic construct
SEQUENCE: 64
agccgtggtg gaataggagt                                              20

SEQ ID NO: 65          moltype = RNA  length = 20
FEATURE                Location/Qualifiers
misc_feature           1..20
                       note = Synthetic: CR005300 gRNA targeting Human TTR (Exon 1)
source                 1..20
                       mol_type = other RNA
                       organism = synthetic construct
SEQUENCE: 65
tcacagaaac actcaccgta                                              20

SEQ ID NO: 66          moltype = RNA  length = 20
FEATURE                Location/Qualifiers
misc_feature           1..20
                       note = Synthetic: CR005301 gRNA targeting Human TTR (Exon 1)
source                 1..20
                       mol_type = other RNA
                       organism = synthetic construct
SEQUENCE: 66
gtcacagaaa cactcaccgt                                              20

SEQ ID NO: 67          moltype = RNA  length = 20
FEATURE                Location/Qualifiers
misc_feature           1..20
                       note = Synthetic: CR005302 gRNA targeting Human TTR (Exon 2)
source                 1..20
                       mol_type = other RNA
                       organism = synthetic construct
SEQUENCE: 67
acgtgtcttc tctacaccca                                              20

SEQ ID NO: 68          moltype = RNA  length = 20
FEATURE                Location/Qualifiers
misc_feature           1..20
                       note = Synthetic: CR005303 gRNA targeting Human TTR (Exon 2)
source                 1..20
                       mol_type = other RNA
                       organism = synthetic construct
```

```
SEQUENCE: 68
tgaatccaag tgtcctctga                                              20

SEQ ID NO: 69          moltype = RNA  length = 20
FEATURE                Location/Qualifiers
misc_feature           1..20
                       note = Synthetic: CR005304 gRNA targeting Human TTR (Exon 2)
source                 1..20
                       mol_type = other RNA
                       organism = synthetic construct
SEQUENCE: 69
ggccgtgcat gtgttcagaa                                              20

SEQ ID NO: 70          moltype = RNA  length = 20
FEATURE                Location/Qualifiers
misc_feature           1..20
                       note = Synthetic: CR005305 gRNA targeting Human TTR (Exon 3)
source                 1..20
                       mol_type = other RNA
                       organism = synthetic construct
SEQUENCE: 70
tataggaaaa ccagtgagtc                                              20

SEQ ID NO: 71          moltype = RNA  length = 20
FEATURE                Location/Qualifiers
misc_feature           1..20
                       note = Synthetic: CR005306 gRNA targeting Human TTR (Exon 3)
source                 1..20
                       mol_type = other RNA
                       organism = synthetic construct
SEQUENCE: 71
aaatcttact ggaaggcact                                              20

SEQ ID NO: 72          moltype = RNA  length = 20
FEATURE                Location/Qualifiers
misc_feature           1..20
                       note = Synthetic: CR005307 gRNA targeting Human TTR (Exon 4)
source                 1..20
                       mol_type = other RNA
                       organism = synthetic construct
SEQUENCE: 72
tgtctgtctt ctctcatagg                                              20

SEQ ID NO: 73          moltype = RNA  length = 20
FEATURE                Location/Qualifiers
misc_feature           1..20
                       note = Synthetic: CR000689 gRNA targeting Cyno TTR
source                 1..20
                       mol_type = other RNA
                       organism = synthetic construct
SEQUENCE: 73
acacaaatac cagtccagcg                                              20

SEQ ID NO: 74          moltype = RNA  length = 20
FEATURE                Location/Qualifiers
misc_feature           1..20
                       note = Synthetic: CR005364 gRNA targeting Cyno TTR
source                 1..20
                       mol_type = other RNA
                       organism = synthetic construct
SEQUENCE: 74
aaaggctgct gatgagacct                                              20

SEQ ID NO: 75          moltype = RNA  length = 20
FEATURE                Location/Qualifiers
misc_feature           1..20
                       note = Synthetic: CR005365 gRNA targeting Cyno TTR
source                 1..20
                       mol_type = other RNA
                       organism = synthetic construct
SEQUENCE: 75
cattgacagc aggactgcct                                              20

SEQ ID NO: 76          moltype = RNA  length = 20
FEATURE                Location/Qualifiers
misc_feature           1..20
                       note = Synthetic: CR005366 gRNA targeting Cyno TTR
source                 1..20
                       mol_type = other RNA
```

-continued

```
                        organism = synthetic construct
SEQUENCE: 76
ataccagtcc agcgaggcag                                              20

SEQ ID NO: 77           moltype = RNA  length = 20
FEATURE                 Location/Qualifiers
misc_feature            1..20
                        note = Synthetic: CR005367 gRNA targeting Cyno TTR
source                  1..20
                        mol_type = other RNA
                        organism = synthetic construct
SEQUENCE: 77
ccagtccagc gaggcagagg                                              20

SEQ ID NO: 78           moltype = RNA  length = 20
FEATURE                 Location/Qualifiers
misc_feature            1..20
                        note = Synthetic: CR005368 gRNA targeting Cyno TTR
source                  1..20
                        mol_type = other RNA
                        organism = synthetic construct
SEQUENCE: 78
cctcctctgc ctcgctggac                                              20

SEQ ID NO: 79           moltype = RNA  length = 20
FEATURE                 Location/Qualifiers
misc_feature            1..20
                        note = Synthetic: CR005369 gRNA targeting Cyno TTR
source                  1..20
                        mol_type = other RNA
                        organism = synthetic construct
SEQUENCE: 79
aaagttctag atgccgtccg                                              20

SEQ ID NO: 80           moltype = RNA  length = 20
FEATURE                 Location/Qualifiers
misc_feature            1..20
                        note = Synthetic: CR005370 gRNA targeting Cyno TTR
source                  1..20
                        mol_type = other RNA
                        organism = synthetic construct
SEQUENCE: 80
acttgtcttc tctataccca                                              20

SEQ ID NO: 81           moltype = RNA  length = 20
FEATURE                 Location/Qualifiers
misc_feature            1..20
                        note = Synthetic: CR005371 gRNA targeting Cyno TTR
source                  1..20
                        mol_type = other RNA
                        organism = synthetic construct
SEQUENCE: 81
aagtgacttc cagtaagatt                                              20

SEQ ID NO: 82           moltype = RNA  length = 20
FEATURE                 Location/Qualifiers
misc_feature            1..20
                        note = Synthetic: CR005372 gRNA targeting Cyno TTR
source                  1..20
                        mol_type = other RNA
                        organism = synthetic construct
SEQUENCE: 82
aaaaggctgc tgatgagacc                                              20

SEQ ID NO: 83           moltype =   length =
SEQUENCE: 83
000

SEQ ID NO: 84           moltype =   length =
SEQUENCE: 84
000

SEQ ID NO: 85           moltype =   length =
SEQUENCE: 85
000

SEQ ID NO: 86           moltype =   length =
SEQUENCE: 86
000
```

```
SEQ ID NO: 87          moltype = RNA  length = 100
FEATURE                Location/Qualifiers
misc_feature           1..100
                       note = Synthetic: G000480 sgRNA modified sequence targeting
                        Human TTR
modified_base          1..3
                       mod_base = OTHER
                       note = 2'-O-methylation
modified_base          1..4
                       mod_base = OTHER
                       note = Phosphorothioate internucleoside linkage
modified_base          29..40
                       mod_base = OTHER
                       note = 2'-O-methylation
modified_base          69..100
                       mod_base = OTHER
                       note = 2'-O-methylation
modified_base          97..100
                       mod_base = OTHER
                       note = Phosphorothioate internucleoside linkage
source                 1..100
                       mol_type = other RNA
                       organism = synthetic construct
SEQUENCE: 87
aaaggctgct gatgacacct gttttagagc tagaaatagc aagttaaaat aaggctagtc  60
cgttatcaac ttgaaaaagt ggcaccgagt cggtgctttt                        100

SEQ ID NO: 88          moltype = RNA  length = 100
FEATURE                Location/Qualifiers
misc_feature           1..100
                       note = Synthetic: G000481 sgRNA modified sequence targeting
                        Human TTR
modified_base          1..3
                       mod_base = OTHER
                       note = 2'-O-methylation
modified_base          1..4
                       mod_base = OTHER
                       note = Phosphorothioate internucleoside linkage
modified_base          29..40
                       mod_base = OTHER
                       note = 2'-O-methylation
modified_base          69..100
                       mod_base = OTHER
                       note = 2'-O-methylation
modified_base          97..100
                       mod_base = OTHER
                       note = Phosphorothioate internucleoside linkage
source                 1..100
                       mol_type = other RNA
                       organism = synthetic construct
SEQUENCE: 88
tctagaactt tgaccatcag gttttagagc tagaaatagc aagttaaaat aaggctagtc  60
cgttatcaac ttgaaaaagt ggcaccgagt cggtgctttt                        100

SEQ ID NO: 89          moltype = RNA  length = 100
FEATURE                Location/Qualifiers
misc_feature           1..100
                       note = Synthetic: G000482 sgRNA modified sequence targeting
                        Human TTR
modified_base          1..3
                       mod_base = OTHER
                       note = 2'-O-methylation
modified_base          1..4
                       mod_base = OTHER
                       note = Phosphorothioate internucleoside linkage
modified_base          29..40
                       mod_base = OTHER
                       note = 2'-O-methylation
modified_base          69..100
                       mod_base = OTHER
                       note = 2'-O-methylation
modified_base          97..100
                       mod_base = OTHER
                       note = Phosphorothioate internucleoside linkage
source                 1..100
                       mol_type = other RNA
                       organism = synthetic construct
SEQUENCE: 89
```

-continued

```
tgtagaaggg atatacaaag gttttagagc tagaaatagc aagttaaaat aaggctagtc  60
cgttatcaac ttgaaaaagt ggcaccgagt cggtgctttt                       100

SEQ ID NO: 90          moltype = RNA  length = 100
FEATURE                Location/Qualifiers
misc_feature           1..100
                       note = Synthetic: G000483 sgRNA modified sequence targeting
                        Human TTR
modified_base          1..3
                       mod_base = OTHER
                       note = 2'-O-methylation
modified_base          1..4
                       mod_base = OTHER
                       note = Phosphorothioate internucleoside linkage
modified_base          29..40
                       mod_base = OTHER
                       note = 2'-O-methylation
modified_base          69..100
                       mod_base = OTHER
                       note = 2'-O-methylation
modified_base          97..100
                       mod_base = OTHER
                       note = Phosphorothioate internucleoside linkage
source                 1..100
                       mol_type = other RNA
                       organism = synthetic construct
SEQUENCE: 90
tccactcatt cttggcagga gttttagagc tagaaatagc aagttaaaat aaggctagtc  60
cgttatcaac ttgaaaaagt ggcaccgagt cggtgctttt                       100

SEQ ID NO: 91          moltype = RNA  length = 100
FEATURE                Location/Qualifiers
misc_feature           1..100
                       note = Synthetic: G000484 sgRNA modified sequence targeting
                        Human TTR
modified_base          1..3
                       mod_base = OTHER
                       note = 2'-O-methylation
modified_base          1..4
                       mod_base = OTHER
                       note = Phosphorothioate internucleoside linkage
modified_base          29..40
                       mod_base = OTHER
                       note = 2'-O-methylation
modified_base          69..100
                       mod_base = OTHER
                       note = 2'-O-methylation
modified_base          97..100
                       mod_base = OTHER
                       note = Phosphorothioate internucleoside linkage
source                 1..100
                       mol_type = other RNA
                       organism = synthetic construct
SEQUENCE: 91
agacaccaaa tcttactgga gttttagagc tagaaatagc aagttaaaat aaggctagtc  60
cgttatcaac ttgaaaaagt ggcaccgagt cggtgctttt                       100

SEQ ID NO: 92          moltype = RNA  length = 100
FEATURE                Location/Qualifiers
misc_feature           1..100
                       note = Synthetic: G000485 sgRNA modified sequence targeting
                        Human TTR
modified_base          1..3
                       mod_base = OTHER
                       note = 2'-O-methylation
modified_base          1..4
                       mod_base = OTHER
                       note = Phosphorothioate internucleoside linkage
modified_base          29..40
                       mod_base = OTHER
                       note = 2'-O-methylation
modified_base          69..100
                       mod_base = OTHER
                       note = 2'-O-methylation
modified_base          97..100
                       mod_base = OTHER
                       note = Phosphorothioate internucleoside linkage
source                 1..100
                       mol_type = other RNA
```

```
                        organism = synthetic construct
SEQUENCE: 92
cctcctctgc cttgctggac gttttagagc tagaaatagc aagttaaaat aaggctagtc  60
cgttatcaac ttgaaaaagt ggcaccgagt cggtgctttt                        100

SEQ ID NO: 93           moltype = RNA  length = 100
FEATURE                 Location/Qualifiers
misc_feature            1..100
                        note = Synthetic: G000486 sgRNA modified sequence targeting
                         Human TTR
modified_base           1..3
                        mod_base = OTHER
                        note = 2'-O-methylation
modified_base           1..4
                        mod_base = OTHER
                        note = Phosphorothioate internucleoside linkage
modified_base           29..40
                        mod_base = OTHER
                        note = 2'-O-methylation
modified_base           69..100
                        mod_base = OTHER
                        note = 2'-O-methylation
modified_base           97..100
                        mod_base = OTHER
                        note = Phosphorothioate internucleoside linkage
source                  1..100
                        mol_type = other RNA
                        organism = synthetic construct
SEQUENCE: 93
acacaaatac cagtccagca gttttagagc tagaaatagc aagttaaaat aaggctagtc  60
cgttatcaac ttgaaaaagt ggcaccgagt cggtgctttt                        100

SEQ ID NO: 94           moltype = RNA  length = 100
FEATURE                 Location/Qualifiers
misc_feature            1..100
                        note = Synthetic: G000487 sgRNA modified sequence targeting
                         Human TTR
modified_base           1..3
                        mod_base = OTHER
                        note = 2'-O-methylation
modified_base           1..4
                        mod_base = OTHER
                        note = Phosphorothioate internucleoside linkage
modified_base           29..40
                        mod_base = OTHER
                        note = 2'-O-methylation
modified_base           69..100
                        mod_base = OTHER
                        note = 2'-O-methylation
modified_base           97..100
                        mod_base = OTHER
                        note = Phosphorothioate internucleoside linkage
source                  1..100
                        mol_type = other RNA
                        organism = synthetic construct
SEQUENCE: 94
ttctttggca acttacccag gttttagagc tagaaatagc aagttaaaat aaggctagtc  60
cgttatcaac ttgaaaaagt ggcaccgagt cggtgctttt                        100

SEQ ID NO: 95           moltype = RNA  length = 100
FEATURE                 Location/Qualifiers
misc_feature            1..100
                        note = Synthetic: G000488 sgRNA modified sequence targeting
                         Human TTR
modified_base           1..3
                        mod_base = OTHER
                        note = 2'-O-methylation
modified_base           1..4
                        mod_base = OTHER
                        note = Phosphorothioate internucleoside linkage
modified_base           29..40
                        mod_base = OTHER
                        note = 2'-O-methylation
modified_base           69..100
                        mod_base = OTHER
                        note = 2'-O-methylation
modified_base           97..100
                        mod_base = OTHER
                        note = Phosphorothioate internucleoside linkage
```

```
source                  1..100
                        mol_type = other RNA
                        organism = synthetic construct
SEQUENCE: 95
aaagttctag atgctgtccg gttttagagc tagaaatagc aagttaaaat aaggctagtc  60
cgttatcaac ttgaaaaagt ggcaccgagt cggtgctttt                        100

SEQ ID NO: 96           moltype = RNA  length = 100
FEATURE                 Location/Qualifiers
misc_feature            1..100
                        note = Synthetic: G000489 sgRNA modified sequence targeting
                         Human TTR
modified_base           1..3
                        mod_base = OTHER
                        note = 2'-O-methylation
modified_base           1..4
                        mod_base = OTHER
                        note = Phosphorothioate internucleoside linkage
modified_base           29..40
                        mod_base = OTHER
                        note = 2'-O-methylation
modified_base           69..100
                        mod_base = OTHER
                        note = 2'-O-methylation
modified_base           97..100
                        mod_base = OTHER
                        note = Phosphorothioate internucleoside linkage
source                  1..100
                        mol_type = other RNA
                        organism = synthetic construct
SEQUENCE: 96
tttgaccatc agaggacact gttttagagc tagaaatagc aagttaaaat aaggctagtc  60
cgttatcaac ttgaaaaagt ggcaccgagt cggtgctttt                        100

SEQ ID NO: 97           moltype = RNA  length = 100
FEATURE                 Location/Qualifiers
misc_feature            1..100
                        note = Synthetic: G000490 sgRNA modified sequence targeting
                         Human TTR
modified_base           1..3
                        mod_base = OTHER
                        note = 2'-O-methylation
modified_base           1..4
                        mod_base = OTHER
                        note = Phosphorothioate internucleoside linkage
modified_base           29..40
                        mod_base = OTHER
                        note = 2'-O-methylation
modified_base           69..100
                        mod_base = OTHER
                        note = 2'-O-methylation
modified_base           97..100
                        mod_base = OTHER
                        note = Phosphorothioate internucleoside linkage
source                  1..100
                        mol_type = other RNA
                        organism = synthetic construct
SEQUENCE: 97
aaatagacac caaatcttac gttttagagc tagaaatagc aagttaaaat aaggctagtc  60
cgttatcaac ttgaaaaagt ggcaccgagt cggtgctttt                        100

SEQ ID NO: 98           moltype = RNA  length = 100
FEATURE                 Location/Qualifiers
misc_feature            1..100
                        note = Synthetic: G000491 sgRNA modified sequence targeting
                         Human TTR
modified_base           1..3
                        mod_base = OTHER
                        note = 2'-O-methylation
modified_base           1..4
                        mod_base = OTHER
                        note = Phosphorothioate internucleoside linkage
modified_base           29..40
                        mod_base = OTHER
                        note = 2'-O-methylation
modified_base           69..100
                        mod_base = OTHER
                        note = 2'-O-methylation
modified_base           97..100
```

```
                      mod_base = OTHER
                      note = Phosphorothioate internucleoside linkage
source                1..100
                      mol_type = other RNA
                      organism = synthetic construct
SEQUENCE: 98
ataccagtcc agcaaggcag gttttagagc tagaaatagc aagttaaaat aaggctagtc  60
cgttatcaac ttgaaaaagt ggcaccgagt cggtgctttt                       100

SEQ ID NO: 99         moltype = RNA  length = 100
FEATURE               Location/Qualifiers
misc_feature          1..100
                      note = Synthetic: G000492 sgRNA modified sequence targeting
                       Human TTR
modified_base         1..3
                      mod_base = OTHER
                      note = 2'-O-methylation
modified_base         1..4
                      mod_base = OTHER
                      note = Phosphorothioate internucleoside linkage
modified_base         29..40
                      mod_base = OTHER
                      note = 2'-O-methylation
modified_base         69..100
                      mod_base = OTHER
                      note = 2'-O-methylation
modified_base         97..100
                      mod_base = OTHER
                      note = Phosphorothioate internucleoside linkage
source                1..100
                      mol_type = other RNA
                      organism = synthetic construct
SEQUENCE: 99
cttctctaca cccagggcac gttttagagc tagaaatagc aagttaaaat aaggctagtc  60
cgttatcaac ttgaaaaagt ggcaccgagt cggtgctttt                       100

SEQ ID NO: 100        moltype = RNA  length = 100
FEATURE               Location/Qualifiers
misc_feature          1..100
                      note = Synthetic: G000493 sgRNA modified sequence targeting
                       Human TTR
modified_base         1..3
                      mod_base = OTHER
                      note = 2'-O-methylation
modified_base         1..4
                      mod_base = OTHER
                      note = Phosphorothioate internucleoside linkage
modified_base         29..40
                      mod_base = OTHER
                      note = 2'-O-methylation
modified_base         69..100
                      mod_base = OTHER
                      note = 2'-O-methylation
modified_base         97..100
                      mod_base = OTHER
                      note = Phosphorothioate internucleoside linkage
source                1..100
                      mol_type = other RNA
                      organism = synthetic construct
SEQUENCE: 100
aagtgccttc cagtaagatt gttttagagc tagaaatagc aagttaaaat aaggctagtc  60
cgttatcaac ttgaaaaagt ggcaccgagt cggtgctttt                       100

SEQ ID NO: 101        moltype = RNA  length = 100
FEATURE               Location/Qualifiers
misc_feature          1..100
                      note = Synthetic: G000494 sgRNA modified sequence targeting
                       Human TTR
modified_base         1..3
                      mod_base = OTHER
                      note = 2'-O-methylation
modified_base         1..4
                      mod_base = OTHER
                      note = Phosphorothioate internucleoside linkage
modified_base         29..40
                      mod_base = OTHER
                      note = 2'-O-methylation
modified_base         69..100
                      mod_base = OTHER
```

```
                        note = 2'-O-methylation
modified_base           97..100
                        mod_base = OTHER
                        note = Phosphorothioate internucleoside linkage
source                  1..100
                        mol_type = other RNA
                        organism = synthetic construct
SEQUENCE: 101
gtgagtctgg agagctgcat gttttagagc tagaaatagc aagttaaaat aaggctagtc  60
cgttatcaac ttgaaaaagt ggcaccgagt cggtgctttt                        100

SEQ ID NO: 102          moltype = RNA  length = 100
FEATURE                 Location/Qualifiers
misc_feature            1..100
                        note = Synthetic: G000495 sgRNA modified sequence targeting
                         Human TTR
modified_base           1..3
                        mod_base = OTHER
                        note = 2'-O-methylation
modified_base           1..4
                        mod_base = OTHER
                        note = Phosphorothioate internucleoside linkage
modified_base           29..40
                        mod_base = OTHER
                        note = 2'-O-methylation
modified_base           69..100
                        mod_base = OTHER
                        note = 2'-O-methylation
modified_base           97..100
                        mod_base = OTHER
                        note = Phosphorothioate internucleoside linkage
source                  1..100
                        mol_type = other RNA
                        organism = synthetic construct
SEQUENCE: 102
cagaggacac ttggattcac gttttagagc tagaaatagc aagttaaaat aaggctagtc  60
cgttatcaac ttgaaaaagt ggcaccgagt cggtgctttt                        100

SEQ ID NO: 103          moltype = RNA  length = 100
FEATURE                 Location/Qualifiers
misc_feature            1..100
                        note = Synthetic: G000496 sgRNA modified sequence targeting
                         Human TTR
modified_base           1..3
                        mod_base = OTHER
                        note = 2'-O-methylation
modified_base           1..4
                        mod_base = OTHER
                        note = Phosphorothioate internucleoside linkage
modified_base           29..40
                        mod_base = OTHER
                        note = 2'-O-methylation
modified_base           69..100
                        mod_base = OTHER
                        note = 2'-O-methylation
modified_base           97..100
                        mod_base = OTHER
                        note = Phosphorothioate internucleoside linkage
source                  1..100
                        mol_type = other RNA
                        organism = synthetic construct
SEQUENCE: 103
ggccgtgcat gtgttcagaa gttttagagc tagaaatagc aagttaaaat aaggctagtc  60
cgttatcaac ttgaaaaagt ggcaccgagt cggtgctttt                        100

SEQ ID NO: 104          moltype = RNA  length = 100
FEATURE                 Location/Qualifiers
misc_feature            1..100
                        note = Synthetic: G000497 sgRNA modified sequence targeting
                         Human TTR
modified_base           1..3
                        mod_base = OTHER
                        note = 2'-O-methylation
modified_base           1..4
                        mod_base = OTHER
                        note = Phosphorothioate internucleoside linkage
modified_base           29..40
                        mod_base = OTHER
                        note = 2'-O-methylation
```

```
modified_base          69..100
                       mod_base = OTHER
                       note = 2'-O-methylation
modified_base          97..100
                       mod_base = OTHER
                       note = Phosphorothioate internucleoside linkage
source                 1..100
                       mol_type = other RNA
                       organism = synthetic construct
SEQUENCE: 104
ctgctcctcc tctgccttgc gttttagagc tagaaatagc aagttaaaat aaggctagtc  60
cgttatcaac ttgaaaaagt ggcaccgagt cggtgctttt                        100

SEQ ID NO: 105         moltype = RNA  length = 100
FEATURE                Location/Qualifiers
misc_feature           1..100
                       note = Synthetic: G000498 sgRNA modified sequence targeting
                        Human TTR
modified_base          1..3
                       mod_base = OTHER
                       note = 2'-O-methylation
modified_base          1..4
                       mod_base = OTHER
                       note = Phosphorothioate internucleoside linkage
modified_base          29..40
                       mod_base = OTHER
                       note = 2'-O-methylation
modified_base          69..100
                       mod_base = OTHER
                       note = 2'-O-methylation
modified_base          97..100
                       mod_base = OTHER
                       note = Phosphorothioate internucleoside linkage
source                 1..100
                       mol_type = other RNA
                       organism = synthetic construct
SEQUENCE: 105
agtgagtctg gagagctgca gttttagagc tagaaatagc aagttaaaat aaggctagtc  60
cgttatcaac ttgaaaaagt ggcaccgagt cggtgctttt                        100

SEQ ID NO: 106         moltype = RNA  length = 100
FEATURE                Location/Qualifiers
misc_feature           1..100
                       note = Synthetic: G000499 sgRNA modified sequence targeting
                        Human TTR
modified_base          1..3
                       mod_base = OTHER
                       note = 2'-O-methylation
modified_base          1..4
                       mod_base = OTHER
                       note = Phosphorothioate internucleoside linkage
modified_base          29..40
                       mod_base = OTHER
                       note = 2'-O-methylation
modified_base          69..100
                       mod_base = OTHER
                       note = 2'-O-methylation
modified_base          97..100
                       mod_base = OTHER
                       note = Phosphorothioate internucleoside linkage
source                 1..100
                       mol_type = other RNA
                       organism = synthetic construct
SEQUENCE: 106
tgaatccaag tgtcctctga gttttagagc tagaaatagc aagttaaaat aaggctagtc  60
cgttatcaac ttgaaaaagt ggcaccgagt cggtgctttt                        100

SEQ ID NO: 107         moltype = RNA  length = 100
FEATURE                Location/Qualifiers
misc_feature           1..100
                       note = Synthetic: G000500 sgRNA modified sequence targeting
                        Human TTR
modified_base          1..3
                       mod_base = OTHER
                       note = 2'-O-methylation
modified_base          1..4
                       mod_base = OTHER
                       note = Phosphorothioate internucleoside linkage
modified_base          29..40
```

```
                         mod_base = OTHER
                         note = 2'-O-methylation
modified_base            69..100
                         mod_base = OTHER
                         note = 2'-O-methylation
modified_base            97..100
                         mod_base = OTHER
                         note = Phosphorothioate internucleoside linkage
source                   1..100
                         mol_type = other RNA
                         organism = synthetic construct
SEQUENCE: 107
ccagtccagc aaggcagagg gttttagagc tagaaatagc aagttaaaat aaggctagtc  60
cgttatcaac ttgaaaaagt ggcaccgagt cggtgctttt                        100

SEQ ID NO: 108           moltype = RNA  length = 100
FEATURE                  Location/Qualifiers
misc_feature             1..100
                         note = Synthetic: G000501 sgRNA modified sequence targeting
                          Human TTR
modified_base            1..3
                         mod_base = OTHER
                         note = 2'-O-methylation
modified_base            1..4
                         mod_base = OTHER
                         note = Phosphorothioate internucleoside linkage
modified_base            29..40
                         mod_base = OTHER
                         note = 2'-O-methylation
modified_base            69..100
                         mod_base = OTHER
                         note = 2'-O-methylation
modified_base            97..100
                         mod_base = OTHER
                         note = Phosphorothioate internucleoside linkage
source                   1..100
                         mol_type = other RNA
                         organism = synthetic construct
SEQUENCE: 108
tcacagaaac actcaccgta gttttagagc tagaaatagc aagttaaaat aaggctagtc  60
cgttatcaac ttgaaaaagt ggcaccgagt cggtgctttt                        100

SEQ ID NO: 109           moltype = RNA  length = 100
FEATURE                  Location/Qualifiers
misc_feature             1..100
                         note = Synthetic: G000567 sgRNA modified sequence targeting
                          Human TTR
modified_base            1..3
                         mod_base = OTHER
                         note = 2'-O-methylation
modified_base            1..4
                         mod_base = OTHER
                         note = Phosphorothioate internucleoside linkage
modified_base            29..40
                         mod_base = OTHER
                         note = 2'-O-methylation
modified_base            69..100
                         mod_base = OTHER
                         note = 2'-O-methylation
modified_base            97..100
                         mod_base = OTHER
                         note = Phosphorothioate internucleoside linkage
source                   1..100
                         mol_type = other RNA
                         organism = synthetic construct
SEQUENCE: 109
gaaaggctgc tgatgacacc gttttagagc tagaaatagc aagttaaaat aaggctagtc  60
cgttatcaac ttgaaaaagt ggcaccgagt cggtgctttt                        100

SEQ ID NO: 110           moltype = RNA  length = 100
FEATURE                  Location/Qualifiers
misc_feature             1..100
                         note = Synthetic: G000568 sgRNA modified sequence targeting
                          Human TTR
modified_base            1..3
                         mod_base = OTHER
                         note = 2'-O-methylation
modified_base            1..4
                         mod_base = OTHER
```

```
                        note = Phosphorothioate internucleoside linkage
modified_base           29..40
                        mod_base = OTHER
                        note = 2'-O-methylation
modified_base           69..100
                        mod_base = OTHER
                        note = 2'-O-methylation
modified_base           97..100
                        mod_base = OTHER
                        note = Phosphorothioate internucleoside linkage
source                  1..100
                        mol_type = other RNA
                        organism = synthetic construct
SEQUENCE: 110
ggctgtcgtc accaatccca gttttagagc tagaaatagc aagttaaaat aaggctagtc  60
cgttatcaac ttgaaaaagt ggcaccgagt cggtgctttt                        100

SEQ ID NO: 111          moltype = RNA  length = 100
FEATURE                 Location/Qualifiers
misc_feature            1..100
                        note = Synthetic: G000570 sgRNA modified sequence targeting
                         Human TTR
modified_base           1..3
                        mod_base = OTHER
                        note = 2'-O-methylation
modified_base           1..4
                        mod_base = OTHER
                        note = Phosphorothioate internucleoside linkage
modified_base           29..40
                        mod_base = OTHER
                        note = 2'-O-methylation
modified_base           69..100
                        mod_base = OTHER
                        note = 2'-O-methylation
modified_base           97..100
                        mod_base = OTHER
                        note = Phosphorothioate internucleoside linkage
source                  1..100
                        mol_type = other RNA
                        organism = synthetic construct
SEQUENCE: 111
cattgatggc aggactgcct gttttagagc tagaaatagc aagttaaaat aaggctagtc  60
cgttatcaac ttgaaaaagt ggcaccgagt cggtgctttt                        100

SEQ ID NO: 112          moltype = RNA  length = 100
FEATURE                 Location/Qualifiers
misc_feature            1..100
                        note = Synthetic: G000571 sgRNA modified sequence targeting
                         Human TTR
modified_base           1..3
                        mod_base = OTHER
                        note = 2'-O-methylation
modified_base           1..4
                        mod_base = OTHER
                        note = Phosphorothioate internucleoside linkage
modified_base           29..40
                        mod_base = OTHER
                        note = 2'-O-methylation
modified_base           69..100
                        mod_base = OTHER
                        note = 2'-O-methylation
modified_base           97..100
                        mod_base = OTHER
                        note = Phosphorothioate internucleoside linkage
source                  1..100
                        mol_type = other RNA
                        organism = synthetic construct
SEQUENCE: 112
gtcacagaaa cactcaccgt gttttagagc tagaaatagc aagttaaaat aaggctagtc  60
cgttatcaac ttgaaaaagt ggcaccgagt cggtgctttt                        100

SEQ ID NO: 113          moltype = RNA  length = 100
FEATURE                 Location/Qualifiers
misc_feature            1..100
                        note = Synthetic: G000572 sgRNA modified sequence targeting
                         Human TTR
modified_base           1..3
                        mod_base = OTHER
                        note = 2'-O-methylation
```

```
modified_base          1..4
                       mod_base = OTHER
                       note = Phosphorothioate internucleoside linkage
modified_base          29..40
                       mod_base = OTHER
                       note = 2'-O-methylation
modified_base          69..100
                       mod_base = OTHER
                       note = 2'-O-methylation
modified_base          97..100
                       mod_base = OTHER
                       note = Phosphorothioate internucleoside linkage
source                 1..100
                       mol_type = other RNA
                       organism = synthetic construct
SEQUENCE: 113
cccctactcc tattccacca gttttagagc tagaaatagc aagttaaaat aaggctagtc  60
cgttatcaac ttgaaaaagt ggcaccgagt cggtgctttt                        100

SEQ ID NO: 114         moltype = RNA  length = 100
FEATURE                Location/Qualifiers
misc_feature           1..100
                       note = Synthetic: G000502 sgRNA modified sequence targeting
                        Cyno TTR
modified_base          1..3
                       mod_base = OTHER
                       note = 2'-O-methylation
modified_base          1..4
                       mod_base = OTHER
                       note = Phosphorothioate internucleoside linkage
modified_base          29..40
                       mod_base = OTHER
                       note = 2'-O-methylation
modified_base          69..100
                       mod_base = OTHER
                       note = 2'-O-methylation
modified_base          97..100
                       mod_base = OTHER
                       note = Phosphorothioate internucleoside linkage
source                 1..100
                       mol_type = other RNA
                       organism = synthetic construct
SEQUENCE: 114
acacaaatac cagtccagcg gttttagagc tagaaatagc aagttaaaat aaggctagtc  60
cgttatcaac ttgaaaaagt ggcaccgagt cggtgctttt                        100

SEQ ID NO: 115         moltype = RNA  length = 100
FEATURE                Location/Qualifiers
misc_feature           1..100
                       note = Synthetic: G000503 sgRNA modified sequence targeting
                        Cyno TTR
modified_base          1..3
                       mod_base = OTHER
                       note = 2'-O-methylation
modified_base          1..4
                       mod_base = OTHER
                       note = Phosphorothioate internucleoside linkage
modified_base          29..40
                       mod_base = OTHER
                       note = 2'-O-methylation
modified_base          69..100
                       mod_base = OTHER
                       note = 2'-O-methylation
modified_base          97..100
                       mod_base = OTHER
                       note = Phosphorothioate internucleoside linkage
source                 1..100
                       mol_type = other RNA
                       organism = synthetic construct
SEQUENCE: 115
aaaaggctgc tgatgagacc gttttagagc tagaaatagc aagttaaaat aaggctagtc  60
cgttatcaac ttgaaaaagt ggcaccgagt cggtgctttt                        100

SEQ ID NO: 116         moltype = RNA  length = 100
FEATURE                Location/Qualifiers
misc_feature           1..100
                       note = Synthetic: G000504 sgRNA modified sequence targeting
                        Cyno TTR
modified_base          1..3
```

-continued

```
                         mod_base = OTHER
                         note = 2'-O-methylation
modified_base            1..4
                         mod_base = OTHER
                         note = Phosphorothioate internucleoside linkage
modified_base            29..40
                         mod_base = OTHER
                         note = 2'-O-methylation
modified_base            69..100
                         mod_base = OTHER
                         note = 2'-O-methylation
modified_base            97..100
                         mod_base = OTHER
                         note = Phosphorothioate internucleoside linkage
source                   1..100
                         mol_type = other RNA
                         organism = synthetic construct
SEQUENCE: 116
aaaggctgct gatgagacct gttttagagc tagaaatagc aagttaaaat aaggctagtc  60
cgttatcaac ttgaaaaagt ggcaccgagt cggtgctttt                        100

SEQ ID NO: 117           moltype = RNA  length = 100
FEATURE                  Location/Qualifiers
misc_feature             1..100
                         note = Synthetic: G000505 sgRNA modified sequence targeting
                          Cyno TTR
modified_base            1..3
                         mod_base = OTHER
                         note = 2'-O-methylation
modified_base            1..4
                         mod_base = OTHER
                         note = Phosphorothioate internucleoside linkage
modified_base            29..40
                         mod_base = OTHER
                         note = 2'-O-methylation
modified_base            69..100
                         mod_base = OTHER
                         note = 2'-O-methylation
modified_base            97..100
                         mod_base = OTHER
                         note = Phosphorothioate internucleoside linkage
source                   1..100
                         mol_type = other RNA
                         organism = synthetic construct
SEQUENCE: 117
cattgacagc aggactgcct gttttagagc tagaaatagc aagttaaaat aaggctagtc  60
cgttatcaac ttgaaaaagt ggcaccgagt cggtgctttt                        100

SEQ ID NO: 118           moltype = RNA  length = 100
FEATURE                  Location/Qualifiers
misc_feature             1..100
                         note = Synthetic: G000506 sgRNA modified sequence targeting
                          Cyno TTR
modified_base            1..3
                         mod_base = OTHER
                         note = 2'-O-methylation
modified_base            1..4
                         mod_base = OTHER
                         note = Phosphorothioate internucleoside linkage
modified_base            29..40
                         mod_base = OTHER
                         note = 2'-O-methylation
modified_base            69..100
                         mod_base = OTHER
                         note = 2'-O-methylation
modified_base            97..100
                         mod_base = OTHER
                         note = Phosphorothioate internucleoside linkage
source                   1..100
                         mol_type = other RNA
                         organism = synthetic construct
SEQUENCE: 118
ataccagtcc agcgaggcag gttttagagc tagaaatagc aagttaaaat aaggctagtc  60
cgttatcaac ttgaaaaagt ggcaccgagt cggtgctttt                        100

SEQ ID NO: 119           moltype = RNA  length = 100
FEATURE                  Location/Qualifiers
misc_feature             1..100
                         note = Synthetic: G000507 sgRNA modified sequence targeting
```

```
                         Cyno TTR
modified_base           1..3
                        mod_base = OTHER
                        note = 2'-O-methylation
modified_base           1..4
                        mod_base = OTHER
                        note = Phosphorothioate internucleoside linkage
modified_base           29..40
                        mod_base = OTHER
                        note = 2'-O-methylation
modified_base           69..100
                        mod_base = OTHER
                        note = 2'-O-methylation
modified_base           97..100
                        mod_base = OTHER
                        note = Phosphorothioate internucleoside linkage
source                  1..100
                        mol_type = other RNA
                        organism = synthetic construct
SEQUENCE: 119
ccagtccagc gaggcagagg gttttagagc tagaaatagc aagttaaaat aaggctagtc  60
cgttatcaac ttgaaaaagt ggcaccgagt cggtgctttt                        100

SEQ ID NO: 120          moltype = RNA  length = 100
FEATURE                 Location/Qualifiers
misc_feature            1..100
                        note = Synthetic: G000508 sgRNA modified sequence targeting
                         Cyno TTR
modified_base           1..3
                        mod_base = OTHER
                        note = 2'-O-methylation
modified_base           1..4
                        mod_base = OTHER
                        note = Phosphorothioate internucleoside linkage
modified_base           29..40
                        mod_base = OTHER
                        note = 2'-O-methylation
modified_base           69..100
                        mod_base = OTHER
                        note = 2'-O-methylation
modified_base           97..100
                        mod_base = OTHER
                        note = Phosphorothioate internucleoside linkage
source                  1..100
                        mol_type = other RNA
                        organism = synthetic construct
SEQUENCE: 120
cctcctctgc ctcgctggac gttttagagc tagaaatagc aagttaaaat aaggctagtc  60
cgttatcaac ttgaaaaagt ggcaccgagt cggtgctttt                        100

SEQ ID NO: 121          moltype = RNA  length = 100
FEATURE                 Location/Qualifiers
misc_feature            1..100
                        note = Synthetic: G000509 sgRNA modified sequence targeting
                         Cyno TTR
modified_base           1..3
                        mod_base = OTHER
                        note = 2'-O-methylation
modified_base           1..4
                        mod_base = OTHER
                        note = Phosphorothioate internucleoside linkage
modified_base           29..40
                        mod_base = OTHER
                        note = 2'-O-methylation
modified_base           69..100
                        mod_base = OTHER
                        note = 2'-O-methylation
modified_base           97..100
                        mod_base = OTHER
                        note = Phosphorothioate internucleoside linkage
source                  1..100
                        mol_type = other RNA
                        organism = synthetic construct
SEQUENCE: 121
aaagttctag atgccgtccg gttttagagc tagaaatagc aagttaaaat aaggctagtc  60
cgttatcaac ttgaaaaagt ggcaccgagt cggtgctttt                        100

SEQ ID NO: 122          moltype = RNA  length = 100
FEATURE                 Location/Qualifiers
```

-continued

```
misc_feature            1..100
                        note = Synthetic: G000510 sgRNA modified sequence targeting
                         Cyno TTR
modified_base           1..3
                        mod_base = OTHER
                        note = 2'-O-methylation
modified_base           1..4
                        mod_base = OTHER
                        note = Phosphorothioate internucleoside linkage
modified_base           29..40
                        mod_base = OTHER
                        note = 2'-O-methylation
modified_base           69..100
                        mod_base = OTHER
                        note = 2'-O-methylation
modified_base           97..100
                        mod_base = OTHER
                        note = Phosphorothioate internucleoside linkage
source                  1..100
                        mol_type = other RNA
                        organism = synthetic construct
SEQUENCE: 122
acttgtcttc tctataccca gttttagagc tagaaatagc aagttaaaat aaggctagtc  60
cgttatcaac ttgaaaaagt ggcaccgagt cggtgctttt                        100

SEQ ID NO: 123          moltype = RNA  length = 100
FEATURE                 Location/Qualifiers
misc_feature            1..100
                        note = Synthetic: G000511 sgRNA modified sequence targeting
                         Cyno TTR
modified_base           1..3
                        mod_base = OTHER
                        note = 2'-O-methylation
modified_base           1..4
                        mod_base = OTHER
                        note = Phosphorothioate internucleoside linkage
modified_base           29..40
                        mod_base = OTHER
                        note = 2'-O-methylation
modified_base           69..100
                        mod_base = OTHER
                        note = 2'-O-methylation
modified_base           97..100
                        mod_base = OTHER
                        note = Phosphorothioate internucleoside linkage
source                  1..100
                        mol_type = other RNA
                        organism = synthetic construct
SEQUENCE: 123
aagtgacttc cagtaagatt gttttagagc tagaaatagc aagttaaaat aaggctagtc  60
cgttatcaac ttgaaaaagt ggcaccgagt cggtgctttt                        100

SEQ ID NO: 124          moltype = RNA  length = 100
FEATURE                 Location/Qualifiers
misc_feature            1..100
                        note = Synthetic: G000282 sgRNA modified sequence targeting
                         Mouse TTR
modified_base           1..3
                        mod_base = OTHER
                        note = 2'-O-methylation
modified_base           1..4
                        mod_base = OTHER
                        note = Phosphorothioate internucleoside linkage
modified_base           29..40
                        mod_base = OTHER
                        note = 2'-O-methylation
modified_base           69..100
                        mod_base = OTHER
                        note = 2'-O-methylation
modified_base           97..100
                        mod_base = OTHER
                        note = Phosphorothioate internucleoside linkage
source                  1..100
                        mol_type = other RNA
                        organism = synthetic construct
SEQUENCE: 124
ttacagccac gtctacagca gttttagagc tagaaatagc aagttaaaat aaggctagtc  60
cgttatcaac ttgaaaaagt ggcaccgagt cggtgctttt                        100
```

-continued

```
SEQ ID NO: 125         moltype = RNA  length = 80
FEATURE                Location/Qualifiers
misc_feature           1..80
                       note = Synthetic: exemplary nucleotide sequence
source                 1..80
                       mol_type = other RNA
                       organism = synthetic construct
SEQUENCE: 125
gttttagagc tagaaatagc aagttaaaat aaggctagtc cgttatcaac ttgaaaaagt  60
ggcaccgagt cggtgctttt                                              80

SEQ ID NO: 126         moltype = RNA  length = 22
FEATURE                Location/Qualifiers
misc_feature           1..22
                       note = Synthetic: exemplary nucleotide sequence
source                 1..22
                       mol_type = other RNA
                       organism = synthetic construct
SEQUENCE: 126
gttttagagc tatgctgttt tg                                           22

SEQ ID NO: 127         moltype =   length =
SEQUENCE: 127
000

SEQ ID NO: 128         moltype =   length =
SEQUENCE: 128
000

SEQ ID NO: 129         moltype =   length =
SEQUENCE: 129
000

SEQ ID NO: 130         moltype =   length =
SEQUENCE: 130
000

SEQ ID NO: 131         moltype =   length =
SEQUENCE: 131
000

SEQ ID NO: 132         moltype =   length =
SEQUENCE: 132
000

SEQ ID NO: 133         moltype =   length =
SEQUENCE: 133
000

SEQ ID NO: 134         moltype =   length =
SEQUENCE: 134
000

SEQ ID NO: 135         moltype =   length =
SEQUENCE: 135
000

SEQ ID NO: 136         moltype =   length =
SEQUENCE: 136
000

SEQ ID NO: 137         moltype =   length =
SEQUENCE: 137
000

SEQ ID NO: 138         moltype =   length =
SEQUENCE: 138
000

SEQ ID NO: 139         moltype =   length =
SEQUENCE: 139
000

SEQ ID NO: 140         moltype =   length =
SEQUENCE: 140
000

SEQ ID NO: 141         moltype =   length =
SEQUENCE: 141
```

000

SEQ ID NO: 142 moltype = length =
SEQUENCE: 142
000

SEQ ID NO: 143 moltype = length =
SEQUENCE: 143
000

SEQ ID NO: 144 moltype = length =
SEQUENCE: 144
000

SEQ ID NO: 145 moltype = length =
SEQUENCE: 145
000

SEQ ID NO: 146 moltype = length =
SEQUENCE: 146
000

SEQ ID NO: 147 moltype = length =
SEQUENCE: 147
000

SEQ ID NO: 148 moltype = length =
SEQUENCE: 148
000

SEQ ID NO: 149 moltype = length =
SEQUENCE: 149
000

SEQ ID NO: 150 moltype = length =
SEQUENCE: 150
000

SEQ ID NO: 151 moltype = length =
SEQUENCE: 151
000

SEQ ID NO: 152 moltype = length =
SEQUENCE: 152
000

SEQ ID NO: 153 moltype = length =
SEQUENCE: 153
000

SEQ ID NO: 154 moltype = length =
SEQUENCE: 154
000

SEQ ID NO: 155 moltype = length =
SEQUENCE: 155
000

SEQ ID NO: 156 moltype = length =
SEQUENCE: 156
000

SEQ ID NO: 157 moltype = length =
SEQUENCE: 157
000

SEQ ID NO: 158 moltype = length =
SEQUENCE: 158
000

SEQ ID NO: 159 moltype = length =
SEQUENCE: 159
000

SEQ ID NO: 160 moltype = length =
SEQUENCE: 160
000

SEQ ID NO: 161 moltype = length =

SEQUENCE: 161
000

SEQ ID NO: 162 moltype = length =
SEQUENCE: 162
000

SEQ ID NO: 163 moltype = length =
SEQUENCE: 163
000

SEQ ID NO: 164 moltype = length =
SEQUENCE: 164
000

SEQ ID NO: 165 moltype = length =
SEQUENCE: 165
000

SEQ ID NO: 166 moltype = length =
SEQUENCE: 166
000

SEQ ID NO: 167 moltype = length =
SEQUENCE: 167
000

SEQ ID NO: 168 moltype = length =
SEQUENCE: 168
000

SEQ ID NO: 169 moltype = length =
SEQUENCE: 169
000

SEQ ID NO: 170 moltype = length =
SEQUENCE: 170
000

SEQ ID NO: 171 moltype = length =
SEQUENCE: 171
000

SEQ ID NO: 172 moltype = length =
SEQUENCE: 172
000

SEQ ID NO: 173 moltype = length =
SEQUENCE: 173
000

SEQ ID NO: 174 moltype = length =
SEQUENCE: 174
000

SEQ ID NO: 175 moltype = length =
SEQUENCE: 175
000

SEQ ID NO: 176 moltype = length =
SEQUENCE: 176
000

SEQ ID NO: 177 moltype = length =
SEQUENCE: 177
000

SEQ ID NO: 178 moltype = length =
SEQUENCE: 178
000

SEQ ID NO: 179 moltype = length =
SEQUENCE: 179
000

SEQ ID NO: 180 moltype = length =
SEQUENCE: 180
000

SEQ ID NO: 181 moltype = length =
SEQUENCE: 181
000

SEQ ID NO: 182 moltype = length =
SEQUENCE: 182
000

SEQ ID NO: 183 moltype = length =
SEQUENCE: 183
000

SEQ ID NO: 184 moltype = length =
SEQUENCE: 184
000

SEQ ID NO: 185 moltype = length =
SEQUENCE: 185
000

SEQ ID NO: 186 moltype = length =
SEQUENCE: 186
000

SEQ ID NO: 187 moltype = length =
SEQUENCE: 187
000

SEQ ID NO: 188 moltype = length =
SEQUENCE: 188
000

SEQ ID NO: 189 moltype = length =
SEQUENCE: 189
000

SEQ ID NO: 190 moltype = length =
SEQUENCE: 190
000

SEQ ID NO: 191 moltype = length =
SEQUENCE: 191
000

SEQ ID NO: 192 moltype = length =
SEQUENCE: 192
000

SEQ ID NO: 193 moltype = length =
SEQUENCE: 193
000

SEQ ID NO: 194 moltype = length =
SEQUENCE: 194
000

SEQ ID NO: 195 moltype = length =
SEQUENCE: 195
000

SEQ ID NO: 196 moltype = length =
SEQUENCE: 196
000

SEQ ID NO: 197 moltype = length =
SEQUENCE: 197
000

SEQ ID NO: 198 moltype = length =
SEQUENCE: 198
000

SEQ ID NO: 199 moltype = length =
SEQUENCE: 199
000

SEQ ID NO: 200 moltype = length =
SEQUENCE: 200
000

SEQ ID NO: 201 moltype = length =
SEQUENCE: 201
000

SEQ ID NO: 202 moltype = length =
SEQUENCE: 202
000

SEQ ID NO: 203 moltype = AA length = 1379
FEATURE Location/Qualifiers
REGION 1..1379
note = Synthetic: Cas9 amino acid sequence
source 1..1379
mol_type = protein
organism = synthetic construct
SEQUENCE: 203
MDKKYSIGLD IGTNSVGWAV ITDEYKVPSK KFKVLGNTDR HSIKKNLIGA LLFDSGETAE 60
ATRLKRTARR RYTRRKNRIC YLQEIFSNEM AKVDDSFFHR LEESFLVEED KKHERHPIFG 120
NIVDEVAYHE KYPTIYHLRK KLVDSTDKAD LRLIYLALAH MIKFRGHFLI EGDLNPDNSD 180
VDKLFIQLVQ TYNQLFEENP INASGVDAKA ILSARLSKSR RLENLIAQLP GEKKNGLFGN 240
LIALSLGLTP NFKSNFDLAE DAKLQLSKDT YDDDLDNLLA QIGDQYADLF LAAKNLSDAI 300
LLSDILRVNT EITKAPLSAS MIKRYDEHHQ DLTLLKALVR QQLPEKYKEI FFDQSKNGYA 360
GYIDGGASQE EFYKFIKPIL EKMDGTEELL VKLNREDLLR KQRTFDNGSI PHQIHLGELH 420
AILRRQEDFY PFLKDNREKI EKILTFRIPY YVGPLARGNS RFAWMTRKSE ETITPWNFEE 480
VVDKGASAQS FIERMTNFDK NLPNEKVLPK HSLLYEYFTV YNELTKVKYV TEGMRKPAFL 540
SGEQKKAIVD LLFKTNRKVT VKQLKEDYFK KIECFDSVEI SGVEDRFNAS LGTYHDLLKI 600
IKDKDFLDNE ENEDILEDIV LTLTLFEDRE MIEERLKTYA HLFDDKVMKQ LKRRRYTGWG 660
RLSRKLINGI RDKQSGKTIL DFLKSDGFAN RNFMQLIHDD SLTFKEDIQK AQVSGQGDSL 720
HEHIANLAGS PAIKKGILQT VKVVDELVKV MGRHKPENIV IEMARENQTT QKGQKNSRER 780
MKRIEEGIKE LGSQILKEHP VENTQLQNEK LYLYYLQNGR DMYVDQELDI NRLSDYDVDH 840
IVPQSFLKDD SIDNKVLTRS DKNRGKSDNV PSEEVVKKMK NYWRQLLNAK LITQRKFDNL 900
TKAERGGLSE LDKAGFIKRQ LVETRQITKH VAQILDSRMN TKYDENDKLI REVKVITLKS 960
KLVSDFRKDF QFYKVREINN YHHAHDAYLN AVVGTALIKK YPKLESEFVY GDYKVYDVRK 1020
MIAKSEQEIG KATAKYFFYS NIMNFFKTEI TLANGEIRKR PLIETNGETG EIVWDKGRDF 1080
ATVRKVLSMP QVNIVKKTEV QTGGFSKESI LPKRNSDKLI ARKKDWDPKK YGGFDSPTVA 1140
YSVLVVAKVE KGKSKKLKSV KELLGITIME RSSFEKNPID FLEAKGYKEV KKDLIIKLPK 1200
YSLFELENGR KRMLASAGEL QKGNELALPS KYVNFLYLAS HYEKLKGSPE DNEQKQLFVE 1260
QHKHYLDEII EQISEFSKRV ILADANLDKV LSAYNKHRDK PIREQAENII HLFTLTNLGA 1320
PAAFKYFDTT IDRKRYTSTK EVLDATLIHQ SITGLYETRI DLSQLGGDGG GSPKKKRKV 1379

SEQ ID NO: 204 moltype = RNA length = 4140
FEATURE Location/Qualifiers
misc_feature 1..4140
note = Synthetic: Cas9 mRNA open reading frame (ORF) 2
source 1..4140
mol_type = other RNA
organism = synthetic construct
SEQUENCE: 204
atggacaaga agtacagcat cggactggac atcggaacaa acagcgtcgg atgggcagtc 60
atcacagacg aatacaaggt cccgagcaag aagttcaagg tcctgggaaa cacagacaga 120
cacagcatca agaagaacct gatcggagca ctgctgttcg acagcggaga aacagcagaa 180
gcaacaagac tgaagagaac agcaagaaga agatacacaa gaagaaagaa cagaatctgc 240
tacctgcagg aaatcttcag caacgaaatg gcaaaggtcg acgacagctt cttccacaga 300
ctggaagaaa gcttcctggt cgaagaagac aagaagcacg aaagacaccc gatcttcgga 360
aacatcgtcg acgaagtcgc ataccacgaa aagtacccga caatctacca cctgagaaag 420
aagctggtcg acagcacaga caaggcagac ctgagactga tctacctggc actggcacac 480
atgatcaagt tcagaggaca cttcctgatc gaaggagacc tgaacccgga caacagcgac 540
gtcgacaagc tgttcatcca gctggtccag acatacaacc agctgttcga agaaaacccg 600
atcaacgcaa gcggagtcga cgcaaaggca atcctgagcg caagactgag caagagcaga 660
agactggaaa acctgatcgc acagctgccg ggagaaaaga agaacggact gttcggaaac 720
ctgatcgcac tgagcctggg actgacaccg aacttcaaga gcaacttcga cctggcagaa 780
gacgcaaagc tgcagctgag caaggacaca tacgacgacg acctggacaa cctgctggca 840
cagatcggag accagtacgc agacctgttc ctggcagcaa agaacctgag cgacgcaatc 900
ctgctgagcg acatcctgag agtcaacaca gaaatcacaa aggcaccgct gagcgcaagc 960
atgatcaaga gatacgacga acaccaccag gacctgacac tgctgaaggc actggtcaga 1020
cagcagctgc cggaaaagta caaggaaatc ttcttcgacc agagcaagaa cggatacgca 1080
ggatacatcg acggaggagc aagccaggaa gaattctaca agttcatcaa gccgatcctg 1140
gaaaagatgg acggaacaga agaactgctg gtcaagctga acagagaaga cctgctgaga 1200
aagcagagaa cattcgacaa cggaagcatc ccgcaccaga tccacctggg agaactgcac 1260
gcaatcctga gaagacagga agacttctac ccgttcctga aggacaacag agaaaagatc 1320
gaaaagatcc tgacattcag aatcccgtac tacgtcggac cgctggcaag aggaaacagc 1380
agattcgcat ggatgacaag aaagagcgaa gaaacaatca caccgtggaa cttcgaagaa 1440
gtcgtcgaca agggagcaag cgcacagagc ttcatcgaaa gaatgacaaa cttcgacaag 1500
aacctgccga acgaaaaggt cctgccgaag cacagcctgc tgtacgaata cttcacagtc 1560
tacaacgaac tgacaaaggt caagtacgtc acagaaggaa tgagaaagcc ggcattcctg 1620
agcggagaac agaagaaggc aatcgtcgac ctgctgttca agacaaacag aaaggtcaca 1680
gtcaagcagc tgaaggaaga ctacttcaag aagatcgaat gcttcgacag cgtcgaaatc 1740
agcggagtcg aagacagatt caacgcaagc ctgggaacat accacgacct gctgaagatc 1800

-continued

```
atcaaggaca aggacttcct ggacaacgaa gaaaacgaag acatcctgga agacatcgtc  1860
ctgacactga cactgttcga agacagagaa atgatcgaag aaagactgaa gacatacgca  1920
cacctgttcg acgacaaggt catgaagcag ctgaagagaa gaagatacac aggatgggga  1980
agactgagca gaaagctgat caacggaatc agagacaagc agagcggaaa gacaatcctg  2040
gacttcctga agagcgacgg attcgcaaac agaaacttca tgcagctgat ccacgacgac  2100
agcctgacat tcaaggaaga catccagaag gcacaggtca gcggacaggg agacagcctg  2160
cacgaacaca tcgcaaacct ggcaggaagc ccggcaatca agaagggaat cctgcagaca  2220
gtcaaggtcg tcgacgaact ggtcaaggtc atgggaagac acaagccgga aaacatcgtc  2280
atcgaaatgg caagagaaaa ccagacaaca cagaagggac agaagaacag cagagaaaga  2340
atgaagagaa tcgaagaagg aatcaaggaa ctgggaagcc agatcctgaa ggaacacccg  2400
gtcgaaaaca cacagctgca gaacgaaaag ctgtacctgt actacctgca gaacggaaga  2460
gacatgtacg tcgaccagga actggacatc aacagactga gcgactacga cgtcgaccac  2520
atcgtcccgc agagcttcct gaaggacgac agcatcgaca acaaggtcct gacaagaagc  2580
gacaagaaca gaggaaagag cgacaacgtc ccgagcgaag aagtcgtcaa gaagatgaag  2640
aactactgga gacagctgct gaacgcaaag ctgatcacac agagaaagtt cgacaacctg  2700
acaaaggcag agagaggagg actgagcgaa ctggacaagg caggattcat caagagacag  2760
ctggtcgaaa caagacagat cacaaagcac gtcgcacaga tcctggacag cagaatgaac  2820
acaaagtacg acgaaaacga caagctgatc agagaagtca aggtcatcac actgaagagc  2880
aagctggtca gcgacttcag aaaggacttc cagttctaca aggtcagaga aatcaacaac  2940
taccaccacg cacacgacgc atacctgaac gcagtcgtcg gaacagcact gatcaagaag  3000
tacccgaagc tggaaagcga attcgtctac ggagactaca aggtctacga cgtcagaaag  3060
atgatcgcaa agagcgaaca ggaaatcgga aaggcaacag caaagtactt cttctacagc  3120
aacatcatga acttcttcaa gacagaaatc acactggcaa acggagaaat cagaaagaga  3180
ccgctgatcg aaacaaacgg agaaacagga gaaatcgtct gggacaaggg aagagacttc  3240
gcaacagtca gaaaggtcct gagcatgccg caggtcaaca tcgtcaagaa gacagaagtc  3300
cagacaggag gattcagcaa ggaaagcatc ctgccgaaga gaaacagcga caagctgatc  3360
gcaagaaaga aggactggga cccgaagaag tacggaggat tcgacagccc gacagtcgca  3420
tacagcgtcc tggtcgtcgc aaaggtcgaa aagggaaaga gcaagaagct gaagagcgtc  3480
aaggaactgc tgggaatcac aatcatggaa agaagcagct tcgaaaagaa cccgatcgac  3540
ttcctggaag caaagggata caaggaagtc aagaaggacc tgatcatcaa gctgccgaag  3600
tacagcctgt tcgaactgga aaacggaaga aagagaatgc tggcaagcgc aggagaactg  3660
cagaagggaa acgaactggc actgccgagc aagtacgtca acttcctgta cctggcaagc  3720
cactacgaaa agctgaaggg aagcccggaa gacaacgaac agaagcagct gttcgtcgaa  3780
cagcacaagc actacctgga cgaaatcatc gaacagatca gcgaattcag caagagagtc  3840
atcctggcag acgcaaacct ggacaaggtc ctgagcgcat acaacaagca cagagacaag  3900
ccgatcagag aacaggcaga aaacatcatc cacctgttca cactgacaaa cctgggagca  3960
ccggcagcat tcaagtactt cgacacaaca atcgacagaa agagatacac aagcacaaag  4020
gaagtcctgg acgcaacact gatccaccag agcatcacag gactgtacga aacaagaatc  4080
gacctgagcc agctgggagg agacggagga ggaagcccga agaagaagag aaaggtctag  4140
```

```
SEQ ID NO: 205          moltype = RNA  length = 4143
FEATURE                 Location/Qualifiers
misc_feature            1..4143
                        note = Synthetic: Cas9 mRNA ORF 1
source                  1..4143
                        mol_type = other RNA
                        organism = synthetic construct
SEQUENCE: 205
atggataaga agtactcaat cgggctggat atcggaacta attccgtggg ttgggcagtg  60
atcacggatg aatacaaagt gccgtccaag aagttcaagg tcctggggaa caccgataga  120
cacagcatca agaaaaatct catcggagcc ctgctgtttg actccggcga aaccgcagaa  180
gcgacccggc tcaaacgtac cgcgaggcga cgctacaccc ggcggaagaa tcgcatctgc  240
tatctgcaag agatcttttc gaacgaaatg gcaaaggtcg acgacagctt cttccaccgc  300
ctggaagaat ctttcctggt ggaggaggac aagaagcatg aacggcatcc tatctttgga  360
aacatcgtcg acgaagtggc gtaccacgaa aagtacccga ccatctacca tctgcggaag  420
aagttggttg actcaactga caaggccgac ctcagattga tctacttggc cctcgcccat  480
atgatcaaat tccgcggaca cttcctgatc gaaggcgatc tgaaccctga taactccgac  540
gtggataagc ttttcattca actggtgcag acctacaacc aactgttcga agaaaaccca  600
atcaatgcta gcggcgtcga tgccaaggcc atcctgtccg cccggctgtc gaagtcgcgg  660
cgcctcgaaa acctgatcgc acagctgccg ggagagaaaa agaacggact tttcggcaac  720
ttgatcgctc tctcactggg actcactccc aatttcaagt ccaattttga cctggccgag  780
gacgcgaagc tgcaactctc aaaggacacc tacgacgacg acttggacaa tttgctggca  840
caaattggcg atcagtacgc ggatctgttc cttgccgcta agaacctttc ggacgcaatc  900
ttgctgtccg atatcctgcg cgtgaacacc gaaataacca aagcgccgct tagcgcctcg  960
atgattaagc ggtacgacga gcatcaccag gatctcacgc tgctcaaagc gctcgtgaga  1020
cagcaactgc ctgaaaagta caaggagatc ttcttcgacc agtccaagaa tgggtacgca  1080
gggtacatcg atggaggcgc tagccaggaa gagttctata agttcatcaa gccaatcctg  1140
gaaaagatgg acggaaccga agaactgctg gtcaagctga acagggagga tctgctccgg  1200
aaacagagaa cctttgacaa cggatccatt ccccaccaga tccatctggg tgagctgcac  1260
gccatcttgc ggcgccagga ggacttttac ccattcctca aggacaaccg ggaaaagatc  1320
gagaaaattc tgacgttccg catcccgtat tacgtgggcc cactggcgcg cggcaattcg  1380
cgcttcgcgt ggatgactag aaaatcagag gaaaccatca ctccttggaa tttcgaggaa  1440
gttgtggata agggagcttc ggcacaaagc ttcatcgaac gaatgaccaa cttcgacaag  1500
aatctcccaa acgagaaggt gcttcctaag cacagcctcc tttacgaata cttcactgtc  1560
tacaacgaac tgactaaagt gaaatacgtt actgaaggaa tgaggaagcc ggcctttctg  1620
tccggagaac agaagaaagc aattgtcgat ctgctgttca agaccaaccg caaggtgacc  1680
gtcaagcagc ttaaagagga ctacttcaag aagatcgagt gtttcgactc agtggaaatc  1740
agcggggtgg aggacagatt caacgcttcg ctgggaacct atcatgatct cctgaagatc  1800
atcaaggaca aggacttcct tgacaacgag gagaacgagg acatcctgga agatatcgtc  1860
```

-continued

```
ctgaccttga cccttttcga ggatcgcgag atgatcgagg agaggcttaa gacctacgct  1920
catctcttcg acgataaggt catgaaacaa ctcaagcgcc gccggtacac tggttggggc  1980
cgcctctccc gcaagctgat caacggtatt cgcgataaac agagcggtaa aactatcctg  2040
gatttcctca aatcggatgg cttcgctaat cgtaacttca tgcaattgat ccacgacgac  2100
agcctgacct ttaaggagga catccaaaaa gcacaagtgt ccggacaggg agactcactc  2160
catgaacaca tcgcgaatct ggccggttcg ccggcgatta agaagggaat tctgcaaact  2220
gtgaaggtgg tcgacgagct ggtgaaggtc atgggacggc acaaaccgga gaatatcgtg  2280
attgaaatgg cccgagaaaa ccagactacc cagaagggcc agaaaaactc ccgcgaaagg  2340
atgaagcgga tcgaagaagg aatcaaggag ctgggcagcc agatcctgaa agagcacccg  2400
gtggaaaaca cgcagctgca gaacgagaag ctctacctgt actatttgca aaatggacgg  2460
gacatgtacg tggaccaaga gctggacatc aatcggttgt ctgattacga cgtggaccac  2520
atcgttccac agtcctttct gaaggatgac tcgatcgata acaaggtgtt gactcgcagc  2580
gacaagaaca gagggaagtc agataatgtg ccatcggagg aggtcgtgaa gaagatgaag  2640
aattactggc ggcagctcct gaatgcgaag ctgattaccc agagaaagtt tgacaatctc  2700
actaaagccg agcgcggcgg actctcagag ctggataagg ctggattcat caaacggcag  2760
ctggtcgaga ctcggcagat taccaagcac gtggcgcaga tcttggactc ccgcatgaac  2820
actaaatacg acgagaacga taagctcatc cgggaagtga aggtgattac cctgaaaagc  2880
aaacttgtgt cggactttcg gaaggacttt cagttttaca aagtgagaga aatcaacaac  2940
taccatcacg cgcatgacgc atacctcaac gctgtggtcg gtaccgccct gatcaaaaag  3000
taccctaaac ttgaatcgga gtttgtgtac ggagactaca aggtctacga cgtgaggaag  3060
atgatagcca agtccgaaca ggaaatcggg aaagcaactg cgaaatactt cttttactca  3120
aacatcatga actttttcaa gactgaaatt acgctggcca atggagaaat caggaagagg  3180
ccactgatcg aaactaacgg agaaacgggc gaaatcgtgt gggacaaggg cagggacttc  3240
gcaactgttc gcaaagtgct ctctatgccg caagtcaata ttgtgaagaa aaccgaagtg  3300
caaaccggcg gattttcaaa ggaatcgatc ctcccaaaga gaaatagcga caagctcatt  3360
gcacgcaaga aagactggga cccgaagaag tacggaggat tcgattcgcc gactgtcgca  3420
tactccgtcc tcgtggtggc caaggtggag aagggaaaga gcaaaaagct caaatccgtc  3480
aaagagctgc tggggattac catcatggaa cgatcctcgt tcgagaagaa cccgattgat  3540
ttcctcgagg cgaagggtta caaggaggtg aagaaggatc tgatcatcaa actccccaag  3600
tactcactgt tcgaactgga aaatggtcgg aagcgcatgc tggcttcggc cggagaactc  3660
caaaaaggaa atgagctggc cttgcctagc aagtacgtca acttcctcta tcttgcttcg  3720
cactacgaaa aactcaaagg gtcaccggaa gataacgaac agaagcagct tttcgtggag  3780
cagcacaagc attatctgga tgaaatcatc gaacaaatct ccgagttttc aaagcgcgtg  3840
atcctcgccg acgccaacct cgacaaagtc ctgtcggcct acaataagca tagagataag  3900
ccgatcagag aacaggccga gaacattatc cacttgttca ccctgactaa cctgggagcc  3960
ccagccgcct tcaagtactt cgatactact atcgatcgca aaagatacac gtccaccaag  4020
gaagttctgg acgcgaccct gatccaccaa agcatcactg gactctacga aactaggatc  4080
gatctgtcgc agctgggtgg cgatggcggt ggatctccga aaaagaagag aaaggtgtaa  4140
tga                                                                4143
```

```
SEQ ID NO: 206          moltype =   length =
SEQUENCE: 206
000

SEQ ID NO: 207          moltype =   length =
SEQUENCE: 207
000

SEQ ID NO: 208          moltype =   length =
SEQUENCE: 208
000

SEQ ID NO: 209          moltype =   length =
SEQUENCE: 209
000

SEQ ID NO: 210          moltype =   length =
SEQUENCE: 210
000

SEQ ID NO: 211          moltype =   length =
SEQUENCE: 211
000

SEQ ID NO: 212          moltype =   length =
SEQUENCE: 212
000

SEQ ID NO: 213          moltype = AA  length = 1368
FEATURE                 Location/Qualifiers
REGION                  1..1368
                        note = Synthetic: Amino acid sequence of Cas9 (without NLS)
source                  1..1368
                        mol_type = protein
                        organism = synthetic construct
SEQUENCE: 213
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
```

-continued

```
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368

SEQ ID NO: 214         moltype =   length =
SEQUENCE: 214
000

SEQ ID NO: 215         moltype =   length =
SEQUENCE: 215
000

SEQ ID NO: 216         moltype =   length =
SEQUENCE: 216
000

SEQ ID NO: 217         moltype =   length =
SEQUENCE: 217
000

SEQ ID NO: 218         moltype =   length =
SEQUENCE: 218
000

SEQ ID NO: 219         moltype =   length =
SEQUENCE: 219
000

SEQ ID NO: 220         moltype =   length =
SEQUENCE: 220
000

SEQ ID NO: 221         moltype =   length =
SEQUENCE: 221
000

SEQ ID NO: 222         moltype = AA  length = 1392
FEATURE                Location/Qualifiers
REGION                 1..1392
                       note = Synthetic: Amino acid sequence of Cas9 with two
                        nuclear localization signals as the C-terminal amino acids
source                 1..1392
                       mol_type = protein
                       organism = synthetic construct
SEQUENCE: 222
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
```

-continued

```
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGDGS GSPKKKRKVD  1380
GSPKKKRKVD SG                                                     1392

SEQ ID NO: 223         moltype =   length =
SEQUENCE: 223
000

SEQ ID NO: 224         moltype =   length =
SEQUENCE: 224
000

SEQ ID NO: 225         moltype =   length =
SEQUENCE: 225
000

SEQ ID NO: 226         moltype =   length =
SEQUENCE: 226
000

SEQ ID NO: 227         moltype =   length =
SEQUENCE: 227
000

SEQ ID NO: 228         moltype =   length =
SEQUENCE: 228
000

SEQ ID NO: 229         moltype =   length =
SEQUENCE: 229
000

SEQ ID NO: 230         moltype =   length =
SEQUENCE: 230
000

SEQ ID NO: 231         moltype = DNA  length = 17
FEATURE                Location/Qualifiers
misc_feature           1..17
                       note = Synthetic: T7 promoter
source                 1..17
                       mol_type = other DNA
                       organism = synthetic construct
SEQUENCE: 231
taatacgact cactata                                                17

SEQ ID NO: 232         moltype = DNA  length = 50
FEATURE                Location/Qualifiers
misc_feature           1..50
                       note = Human beta-globin 5 UTR
source                 1..50
                       mol_type = genomic DNA
                       organism = Homo sapiens
SEQUENCE: 232
acatttgctt ctgacacaac tgtgttcact agcaacctca aacagacacc             50

SEQ ID NO: 233         moltype = DNA  length = 132
FEATURE                Location/Qualifiers
misc_feature           1..132
                       note = Human beta-globin 3 UTR
source                 1..132
                       mol_type = genomic DNA
                       organism = Homo sapiens
SEQUENCE: 233
gctcgctttc ttgctgtcca atttctatta aaggttcctt tgttccctaa gtccaactac  60
taaactgggg gatattatga agggccttga gcatctggat tctgcctaat aaaaaacatt  120
tattttcatt gc                                                      132

SEQ ID NO: 234         moltype = DNA  length = 66
FEATURE                Location/Qualifiers
misc_feature           1..66
                       note = Human alpha-globin 5 UTR
source                 1..66
                       mol_type = genomic DNA
                       organism = Homo sapiens
```

```
SEQUENCE: 234
cataaaccct ggcgcgctcg cggcccggca ctcttctggt ccccacagac tcagagagaa  60
cccacc                                                             66

SEQ ID NO: 235         moltype = DNA  length = 110
FEATURE                Location/Qualifiers
misc_feature           1..110
                       note = Human alpha-globin 3 UTR
source                 1..110
                       mol_type = genomic DNA
                       organism = Homo sapiens
SEQUENCE: 235
gctggagcct cggtggccat gcttcttgcc ccttgggcct ccccccagcc cctcctcccc  60
ttcctgcacc cgtacccccg tggtctttga ataaagtctg agtgggcggc             110

SEQ ID NO: 236         moltype = DNA  length = 29
FEATURE                Location/Qualifiers
misc_feature           1..29
                       note = Xenopus laevis beta-globin 5 UTR
source                 1..29
                       mol_type = genomic DNA
                       organism = Xenopus laevis
SEQUENCE: 236
aagctcagaa taaacgctca actttggcc                                    29

SEQ ID NO: 237         moltype = DNA  length = 130
FEATURE                Location/Qualifiers
misc_feature           1..130
                       note = Xenopus laevis beta-globin 3 UTR
source                 1..130
                       mol_type = genomic DNA
                       organism = Xenopus laevis
SEQUENCE: 237
accagcctca agaacacccg aatggagtct ctaagctaca taataccaac ttacacttta  60
caaaatgttg tcccccaaaa tgtagccatt cgtatctgct cctaataaaa agaaagtttc  120
ttcacattct                                                         130

SEQ ID NO: 238         moltype = DNA  length = 27
FEATURE                Location/Qualifiers
misc_feature           1..27
                       note = Bovine Growth Hormone 5 UTR
source                 1..27
                       mol_type = genomic DNA
                       organism = Bos sp.
SEQUENCE: 238
cagggtcctg tggacagctc accagct                                      27

SEQ ID NO: 239         moltype = DNA  length = 102
FEATURE                Location/Qualifiers
misc_feature           1..102
                       note = Bovine Growth Hormone 3 UTR
source                 1..102
                       mol_type = genomic DNA
                       organism = Bos sp.
SEQUENCE: 239
ttgccagcca tctgttgttt gcccctcccc cgtgccttcc ttgaccctgg aaggtgccac  60
tcccactgtc ctttcctaat aaaatgagga aattgcatcg ca                     102

SEQ ID NO: 240         moltype = DNA  length = 93
FEATURE                Location/Qualifiers
misc_feature           1..93
                       note = Mus musculus hemoglobin alpha, adult chain 1
                        (Hba-a1), 3UTR
source                 1..93
                       mol_type = genomic DNA
                       organism = Mus musculus
SEQUENCE: 240
gctgccttct gcggggcttg ccttctggcc atgcccttct tctctccctt gcacctgtac  60
ctcttggtct ttgaataaag cctgagtagg aag                               93

SEQ ID NO: 241         moltype = DNA  length = 61
FEATURE                Location/Qualifiers
misc_feature           1..61
                       note = Synthetic: HSD17B4 5 UTR
source                 1..61
                       mol_type = other DNA
                       organism = synthetic construct
SEQUENCE: 241
tcccgcagtc ggcgtccagc ggctctgctt gttcgtgtgt gtgtcgttgc aggccttatt  60
```

```
c                                                                   61

SEQ ID NO: 242          moltype = RNA  length = 100
FEATURE                 Location/Qualifiers
misc_feature            1..100
                        note = Synthetic: G282 guide RNA targeting TTR
modified_base           1..3
                        mod_base = OTHER
                        note = 2'-O-methylation
modified_base           1..4
                        mod_base = OTHER
                        note = Phosphorothioate internucleoside linkage
modified_base           29..40
                        mod_base = OTHER
                        note = 2'-O-methylation
modified_base           69..100
                        mod_base = OTHER
                        note = 2'-O-methylation
modified_base           97..100
                        mod_base = OTHER
                        note = Phosphorothioate internucleoside linkage
source                  1..100
                        mol_type = other RNA
                        organism = synthetic construct
SEQUENCE: 242
ttacagccac gtctacagca gttttagagc tagaaatagc aagttaaaat aaggctagtc  60
cgttatcaac ttgaaaaagt ggcaccgagt cggtgctttt                        100

SEQ ID NO: 243          moltype = DNA  length = 4411
FEATURE                 Location/Qualifiers
misc_feature            1..4411
                        note = Synthetic: Cas9 transcript with 5 UTR of HSD, ORF
                         corresponding to SEQ ID NO: 204, Kozak sequence, and 3 UTR
                         of ALB
source                  1..4411
                        mol_type = other DNA
                        organism = synthetic construct
SEQUENCE: 243
gggtcccgca gtcggcgtcc agcggctctg cttgttcgtg tgtgtgtcgt tgcaggcctt  60
attcggatcc gccaccatgg acaagaagta cagcatcgga ctggacatcg gaacaaacag  120
cgtcggatgg gcagtcatca cagacgaata caaggtcccg agcaagaagt tcaaggtcct  180
gggaaacaca gacagacaca gcatcaagaa gaacctgatc ggagcactgc tgttcgacag  240
cggagaaaca gcagaagcaa caagactgaa gagaacagca agaagaagat acacaagaag  300
aaagaacaga atctgctacc tgcaggaaat cttcagcaac gaaatggcaa aggtcgacga  360
cagcttcttc cacagactgg aagaaagctt cctggtcgaa gaagacaaga agcacgaaag  420
acacccgatc ttcggaaaca tcgtcgacga agtcgcatac cacgaaaagt acccgacaat  480
ctaccacctg agaaagaagc tggtcgacag cacagacaag gcagacctga gactgatcta  540
cctggcactg gcacacatga tcaagttcag aggacacttc ctgatcgaag gagacctgaa  600
cccggacaac agcgacgtcg acaagctgtt catccagctg gtccagacat acaaccagct  660
gttcgaagaa aacccgatca acgcaagcgg agtcgacgca aaggcaatcc tgagcgcaag  720
actgagcaag agcagaagac tggaaaacct gatcgcacag ctgccgggag aaaagaagaa  780
cggactgttc ggaaacctga tcgcactgag cctgggactg acaccgaact tcaagagcaa  840
cttcgacctg gcagaagacg caaagctgca gctgagcaag gacacatacg acgacgacct  900
ggacaacctg ctggcacaga tcggagacca gtacgcagac ctgttcctgg cagcaaagaa  960
cctgagcgac gcaatcctgc tgagcgacat cctgagagtc aacacagaaa tcacaaaggc  1020
accgctgagc gcaagcatga tcaagagata cgacgaacac caccaggacc tgacactgct  1080
gaaggcactg gtcagacagc agctgccgga aaagtacaag gaaatcttct tcgaccagag  1140
caagaacgga tacgcaggat acatcgacgg aggagcaagc caggaagaat tctacaagtt  1200
catcaagccg atcctggaaa agatggacgg aacagaagaa ctgctggtca agctgaacag  1260
agaagacctg ctgagaaagc agagaacatt cgacaacgga agcatcccgc accagatcca  1320
cctgggagaa ctgcacgcaa tcctgagaag acaggaagac ttctacccgt tcctgaagga  1380
caacagagaa aagatcgaaa agatcctgac attcagaatc ccgtactacg tcggaccgct  1440
ggcaagagga aacagcagat tcgcatggat gacaagaaag agcgaagaaa caatcacacc  1500
gtggaacttc gaagaagtcg tcgacaaggg agcaagcgca cagagcttca tcgaaagaat  1560
gacaaacttc gacaagaacc tgccgaacga aaaggtcctg ccgaagcaca gcctgctgta  1620
cgaatacttc acagtctaca acgaactgac aaaggtcaag tacgtcacag aaggaatgag  1680
aaagccggca ttcctgagcg gagaacagaa gaaggcaatc gtcgacctgc tgttcaagac  1740
aaacagaaag gtcacagtca agcagctgaa ggaagactac ttcaagaaga tcgaatgctt  1800
cgacagcgtc gaaatcagcg gagtcgaaga cagattcaac gcaagcctgg gaacatacca  1860
cgacctgctg aagatcatca aggacaagga cttcctggac aacgaagaaa acgaagacat  1920
cctggaagac atcgtcctga cactgacact gttcgaagac agagaaatga tcgaagaaag  1980
actgaagaca tacgcacacc tgttcgacga caaggtcatg aagcagctga agagaagaag  2040
atacacagga tggggaagac tgagcagaaa gctgatcaac ggaatcagag acaagcagag  2100
cggaaagaca atcctggact tcctgaagag cgacggattc gcaaacagaa acttcatgca  2160
gctgatccac gacgacagcc tgacattcaa ggaagacatc cagaaggcac aggtcagcgg  2220
acagggagac agcctgcacg aacacatcgc aaacctggca ggaagcccgg caatcaagaa  2280
gggaatcctg cagacagtca aggtcgtcga cgaactggtc aaggtcatgg gaagacacaa  2340
gccggaaaac atcgtcatcg aaatggcaag agaaaaccag acaacacaga agggacagaa  2400
gaacagcaga gaaagaatga agagaatcga agaaggaatc aaggaactgg gaagccagat  2460
```

```
cctgaaggaa cacccggtcg aaaacacaca gctgcagaac gaaaagctgt acctgtacta  2520
cctgcagaac ggaagagaca tgtacgtcga ccaggaactg gacatcaaca gactgagcga  2580
ctacgacgtc gaccacatcg tcccgcagag cttcctgaag gacgacagca tcgacaacaa  2640
ggtcctgaca agaagcgaca agaacagagg aaagagcgac aacgtcccga gcgaagaagt  2700
cgtcaagaag atgaagaact actggagaca gctgctgaac gcaaagctga tcacacagag  2760
aaagttcgac aacctgacaa aggcagagag aggaggactg agcgaactgg acaaggcagg  2820
attcatcaag agacagctgg tcgaaacaag acagatcaca aagcacgtcg cacagatcct  2880
ggacagcaga atgaacacaa agtacgacga aaacgacaag ctgatcagag aagtcaaggt  2940
catcacactg aagagcaagc tggtcagcga cttcagaaag gacttccagt tctacaaggt  3000
cagagaaatc aacaactacc accacgcaca cgacgcatac ctgaacgcag tcgtcggaac  3060
agcactgatc aagaagtacc cgaagctgga aagcgaattc gtctacggag actacaaggt  3120
ctacgacgtc agaaagatga tcgcaaagag cgaacaggaa atcggaaagg caacagcaaa  3180
gtacttcttc tacagcaaca tcatgaactt cttcaagaca gaaatcacac tggcaaacgg  3240
agaaatcaga aagagaccgc tgatcgaaac aaacggagaa acaggagaaa tcgtctggga  3300
caagggaaga gacttcgcaa cagtcagaaa ggtcctgagc atgccgcagg tcaacatcgt  3360
caagaagaca gaagtccaga caggaggatt cagcaaggaa agcatcctgc cgaagagaaa  3420
cagcgacaag ctgatcgcaa gaaagaagga ctgggacccg aagaagtacg gaggattcga  3480
cagcccgaca gtcgcataca gcgtcctggt cgtcgcaaag gtcgaaaagg gaaagagcaa  3540
gaagctgaag agcgtcaagg aactgctggg aatcacaatc atggaaagaa gcagcttcga  3600
aaagaacccg atcgacttcc tggaagcaaa gggatacaag gaagtcaaga aggacctgat  3660
catcaagctg ccgaagtaca gcctgttcga actggaaaac ggaagaaaga gaatgctggc  3720
aagcgcagga gaactgcaga agggaaacga actggcactg ccgagcaagt acgtcaactt  3780
cctgtacctg gcaagccact acgaaaagct gaagggaagc ccggaagaca acgaacagaa  3840
gcagctgttc gtcgaacagc acaagcacta cctggacgaa atcatcgaac agatcagcga  3900
attcagcaag agagtcatcc tggcagacgc aaacctggac aaggtcctga gcgcatacaa  3960
caagcacaga gacaagccga tcagagaaca ggcagaaaac atcatccacc tgttcacact  4020
gacaaacctg ggagcaccgg cagcattcaa gtacttcgac acaacaatcg acagaaagag  4080
atacacaagc acaaaggaag tcctggacgc aacactgatc caccagagca tcacaggact  4140
gtacgaaaca agaatcgacc tgagccagct gggaggagac ggaggaggaa gcccgaagaa  4200
gaagagaaag gtctagctag ccatcacatt taaaagcatc tcagcctacc atgagaataa  4260
gagaaagaaa atgaagatca atagcttatt catctctttt tctttttcgt tggtgtaaag  4320
ccaacaccct gtctaaaaaa cataaatttc tttaatcatt ttgcctcttt tctctgtgct  4380
tcaattaata aaaaatggaa agaacctcga g                                 4411
```

```
SEQ ID NO: 244          moltype = DNA  length = 4405
FEATURE                 Location/Qualifiers
misc_feature            1..4405
                        note = Synthetic: Cas9 transcript with 5 UTR of HSD, ORF
                         corresponding to SEQ ID NO: 204, and 3 UTR of ALB
source                  1..4405
                        mol_type = other DNA
                        organism = synthetic construct
SEQUENCE: 244
gggtcccgca gtcggcgtcc agcggctctg cttgttcgtg tgtgtgtcgt tgcaggcctt  60
attcggatcc atggacaaga agtacagcat cggactggac atcggaacaa acagcgtcgg  120
atgggcagtc atcacagacg aatacaaggt cccgagcaag aagttcaagg tcctgggaaa  180
cacagacaga cacagcatca agaagaacct gatcggagca ctgctgttcg acagcggaga  240
aacagcagaa gcaacaagac tgaagagaac agcaagaaga agatacacaa gaagaaagaa  300
cagaatctgc tacctgcagg aaatcttcag caacgaaatg gcaaaggtcg acgacagctt  360
cttccacaga ctggaagaaa gcttcctggt cgaagaagac aagaagcacg aaagacaccc  420
gatcttcgga aacatcgtcg acgaagtcgc ataccacgaa aagtacccga caatctacca  480
cctgagaaag aagctggtcg acagcacaga caaggcagac ctgagactga tctacctggc  540
actggcacac atgatcaagt tcagaggaca cttcctgatc gaaggagacc tgaacccgga  600
caacagcgac gtcgacaagc tgttcatcca gctggtccag acatacaacc agctgttcga  660
agaaaacccg atcaacgcaa gcggagtcga cgcaaaggca atcctgagcg caagactgag  720
caagagcaga agactggaaa acctgatcgc acagctgccg ggagaaaaga agaacggact  780
gttcggaaac ctgatcgcac tgagcctggg actgacaccg aacttcaaga gcaacttcga  840
cctggcagaa gacgcaaagc tgcagctgag caaggacaca tacgacgacg acctggacaa  900
cctgctggca cagatcggag accagtacgc agacctgttc ctggcagcaa agaacctgag  960
cgacgcaatc ctgctgagcg acatcctgag agtcaacaca gaaatcacaa aggcaccgct  1020
gagcgcaagc atgatcaaga gatacgacga acaccaccag gacctgacac tgctgaaggc  1080
actggtcaga cagcagctgc cggaaaagta caaggaaatc ttcttcgacc agagcaagaa  1140
cggatacgca ggatacatcg acggaggagc aagccaggaa gaattctaca agttcatcaa  1200
gccgatcctg gaaaagatgg acggaacaga agaactgctg gtcaagctga acagagaaga  1260
cctgctgaga aagcagagaa cattcgacaa cggaagcatc ccgcaccaga tccacctggg  1320
agaactgcac gcaatcctga gaagacagga agacttctac ccgttcctga aggacaacag  1380
agaaaagatc gaaaagatcc tgacattcag aatcccgtac tacgtcggac cgctggcaag  1440
aggaaacagc agattcgcat ggatgacaag aaagagcgaa gaaacaatca caccgtggaa  1500
cttcgaagaa gtcgtcgaca agggagcaag cgcacagagc ttcatcgaaa gaatgacaaa  1560
cttcgacaag aacctgccga acgaaaaggt cctgccgaag cacagcctgc tgtacgaata  1620
cttcacagtc tacaacgaac tgacaaaggt caagtacgtc acagaaggaa tgagaaagcc  1680
ggcattcctg agcggagaac agaagaaggc aatcgtcgac ctgctgttca agacaaacag  1740
aaaggtcaca gtcaagcagc tgaaggaaga ctacttcaag aagatcgaat gcttcgacag  1800
cgtcgaaatc agcggagtcg aagacagatt caacgcaagc ctgggaacat accacgacct  1860
gctgaagatc atcaaggaca aggacttcct ggacaacgaa gaaaacgaag acatcctgga  1920
agacatcgtc ctgacactga cactgttcga agacagagaa atgatcgaag aaagactgaa  1980
gacatacgca cacctgttcg acgacaaggt catgaagcag ctgaagagaa gaagatacac  2040
aggatgggga agactgagca gaaagctgat caacggaatc agagacaagc agagcggaaa  2100
gacaatcctg gacttcctga agagcgacgg attcgcaaac agaaacttca tgcagctgat  2160
```

```
ccacgacgac agcctgacat tcaaggaaga catccagaag gcacaggtca gcggacaggg  2220
agacagcctg cacgaacaca tcgcaaacct ggcaggaagc ccggcaatca agaagggaat  2280
cctgcagaca gtcaaggtcg tcgacgaact ggtcaaggtc atgggaagac acaagccgga  2340
aaacatcgtc atcgaaatgg caagagaaaa ccagacaaca cagaagggac agaagaacag  2400
cagagaaaga atgaagagaa tcgaagaagg aatcaaggaa ctgggaagcc agatcctgaa  2460
ggaacacccg gtcgaaaaca cacagctgca gaacgaaaag ctgtacctgt actacctgca  2520
gaacggaaga gacatgtacg tcgaccagga actggacatc aacagactga gcgactacga  2580
cgtcgaccac atcgtcccgc agagcttcct gaaggacgac agcatcgaca acaaggtcct  2640
gacaagaagc gacaagaaca gaggaaagag cgacaacgtc ccgagcgaag aagtcgtcaa  2700
gaagatgaag aactactgga gacagctgct gaacgcaaag ctgatcacac agagaaagtt  2760
cgacaacctg acaaaggcag agagaggagg actgagcgaa ctggacaagg caggattcat  2820
caagagacag ctggtcgaaa caagacagat cacaaagcac gtcgcacaga tcctggacag  2880
cagaatgaac acaaagtacg acgaaaacga caagctgatc agagaagtca aggtcatcac  2940
actgaagagc aagctggtca gcgacttcag aaaggacttc cagttctaca aggtcagaga  3000
aatcaacaac taccaccacg cacacgacgc atacctgaac gcagtcgtcg gaacagcact  3060
gatcaagaag tacccgaagc tggaaagcga attcgtctac ggagactaca aggtctacga  3120
cgtcagaaag atgatcgcaa agagcgaaca ggaaatcgga aaggcaacag caaagtactt  3180
cttctacagc aacatcatga acttcttcaa gacagaaatc acactggcaa acggagaaat  3240
cagaaagaga ccgctgatcg aaacaaacgg agaaacagga gaaatcgtct gggacaaggg  3300
aagagacttc gcaacagtca gaaaggtcct gagcatgccg caggtcaaca tcgtcaagaa  3360
gacagaagtc cagacaggag gattcagcaa ggaaagcatc ctgccgaaga gaaacagcga  3420
caagctgatc gcaagaaaga aggactggga cccgaagaag tacggaggat tcgacagccc  3480
gacagtcgca tacagcgtcc tggtcgtcgc aaaggtcgaa aagggaaaga gcaagaaagct  3540
gaagagcgtc aaggaactgc tgggaatcac aatcatggaa agaagcagct tcgaaaagaa  3600
cccgatcgac ttcctggaag caaagggata caaggaagtc aagaaggacc tgatcatcaa  3660
gctgccgaag tacagcctgt tcgaactgga aaacggaaga aagagaatgc tggcaagcgc  3720
aggagaactg cagaagggaa acgaactggc actgccgagc aagtacgtca acttcctgta  3780
cctggcaagc cactacgaaa agctgaaggg aagcccggaa gacaacgaac agaagcagct  3840
gttcgtcgaa cagcacaagc actacctgga cgaaatcatc gaacagatca gcgaattcag  3900
caagagagtc atcctggcag acgcaaacct ggacaaggtc ctgagcgcat acaacaagca  3960
cagagacaag ccgatcagag aacaggcaga aaacatcatc cacctgttca cactgacaaa  4020
cctgggagca ccggcagcat tcaagtactt cgacacaaca atcgacagaa agagatacac  4080
aagcacaaag gaagtcctgg acgcaacact gatccaccag agcatcacag gactgtacga  4140
aacaagaatc gacctgagcc agctgggagg agacggagga ggaagcccga agaagaagag  4200
aaaggtctag ctagccatca catttaaaag catctcagcc taccatgaga ataagagaaa  4260
gaaaatgaag atcaatagct tattcatctc tttttctttt tcgttggtgt aaagccaaca  4320
ccctgtctaa aaaacataaa tttctttaat cattttgcct cttttctctg tgcttcaatt  4380
aataaaaaat ggaaagaacc tcgag                                    4405
```

SEQ ID NO: 245 moltype = length =
SEQUENCE: 245
000

SEQ ID NO: 246 moltype = DNA length = 4459
FEATURE Location/Qualifiers
misc_feature 1..4459
note = Synthetic: Cas9 transcript with 5 UTR of HSD, ORF corresponding to SEQ ID NO: 245, Kozak sequence, and 3 UTR of ALB
source 1..4459
mol_type = other DNA
organism = synthetic construct
SEQUENCE: 246

```
gggtcccgca gtcggcgtcc agcggctctg cttgttcgtg tgtgtgtcgt tgcaggcctt  60
attcggatct gccaccatgg ataagaagta ctcgatcggg ctggatatcg gaactaattc  120
cgtgggttgg gcagtgatca cggatgaata caaagtgccg tccaagaagt tcaaggtcct  180
ggggaacacc gatagacaca gcatcaagaa gaatctcatc ggagccctgc tgtttgactc  240
cggcgaaacc gcagaagcga cccggctcaa acgtaccgcg aggcgacgct acacccggcg  300
gaagaatcgc atctgctatc tgcaagaaat cttttcgaac gaaatggcaa aggtggacga  360
cagcttcttc caccgcctgg aagaatcttt cctggtggag gaggacaaga agcatgaacg  420
gcatcctatc tttggaaaca tcgtggacga agtggcgtac cacgaaaagt acccgaccat  480
ctaccatctg cggaagaagt tggttgactc aactgacaag gccgacctca gattgatcta  540
cttggccctc gcccatatga tcaaattccg cggacacttc ctgatcgaag gcgatctgaa  600
ccctgataac tccgacgtgg ataagctgtt cattcaactg gtgcagacct acaaccaact  660
gttcgaagaa aacccaatca atgccagcgg cgtcgatgcc aaggccatcc tgtccgcccg  720
gctgtcgaag tcgcggcgcc tcgaaaacct gatcgcacag ctgccgggag agaagaagaa  780
cggacttttc ggcaacttga tcgctctctc actgggactc actcccaatt tcaagtccaa  840
ttttgacctg gccgaggacg cgaagctgca actctcaaag gacacctacg acgacgactt  900
ggacaatttg ctggcacaaa ttggcgatca gtacgcggat ctgttccttg ccgctaagaa  960
cctttcggac gcaatcttgc tgtccgatat cctgcgcgtg aacaccgaaa taaccaaagc  1020
gccgcttagc gcctcgatga ttaagcggta cgacgagcat caccaggatc tcacgctgct  1080
caaagcgctc gtgagacagc aactgcctga aaagtacaag gagattttct tcgaccagtc  1140
caagaatggg tacgcagggt acatcgatgg aggcgccagc caggaagagt tctataagtt  1200
catcaagcca atcctggaaa agatggacgg aaccgaagaa ctgctggtca agctgaacag  1260
ggaggatctg ctccgcaaac agagaacctt tgacaacgga agcattccac accagatcca  1320
tctgggtgag ctgcacgcca tcttgcggcg ccaggaggac ttttacccat tcctcaagga  1380
caaccgggaa aagatcgaga aaattctgac gttccgcatc ccgtattacg tgggcccact  1440
ggcgcgcggc aattcgcgct tcgcgtggat gactagaaaa tcagaggaaa ccatcactcc  1500
ttggaatttc gaggaagttg tggataaggg agcttcggca caatccttca tcgaacgaat  1560
```

```
gaccaacttc gacaagaatc tcccaaacga gaaggtgctt cctaagcaca gcctccttta  1620
cgaatacttc actgtctaca acgaactgac taaagtgaaa tacgttactg aaggaatgag  1680
gaagccggcc tttctgagcg gagaacagaa gaaagcgatt gtcgatctgc tgttcaagac  1740
caaccgcaag gtgaccgtca agcagcttaa agaggactac ttcaagaaga tcgagtgttt  1800
cgactcagtg gaaatcagcg gagtggagga cagattcaac gcttcgctgg gaacctatca  1860
tgatctcctg aagatcatca aggacaagga cttccttgac aacgaggaga acgaggacat  1920
cctggaagat atcgtcctga ccttgaccct tttcgaggat cgcgagatga tcgaggagag  1980
gcttaagacc tacgctcatc tcttcgacga taaggtcatg aaacaactca agcgccgccg  2040
gtacactggt tggggccgcc tctcccgcaa gctgatcaac ggtattcgcg ataaacagag  2100
cggtaaaact atcctggatt tcctcaaatc ggatggcttc gctaatcgta acttcatgca  2160
gttgatccac gacgacagcc tgacctttaa ggaggacatc cagaaagcac aagtgagcgg  2220
acagggagac tcactccatg aacacatcgc gaatctggcc ggttcgccgg cgattaagaa  2280
gggaatcctg caaactgtga aggtggtgga cgagctggtg aaggtcatgg gacggcacaa  2340
accggagaat atcgtgattg aaatggcccg agaaaaccag actacccaga agggccagaa  2400
gaactcccgc gaaaggatga agcggatcga agaaggaatc aaggagctgg gcagccagat  2460
cctgaaagag cacccggtgg aaaacacgca gctgcagaac gagaagctct acctgtacta  2520
tttgcaaaat ggacgggaca tgtacgtgga ccaagagctg gacatcaatc ggttgtctga  2580
ttacgacgtg gaccacatcg ttccacagtc ctttctgaag gatgactcca tcgataacaa  2640
ggtgttgact cgcagcgaca agaacagagg gaagtcagat aatgtgccat cggaggaggt  2700
cgtgaagaag atgaagaatt actggcggca gctcctgaat gcgaagctga ttacccagag  2760
aaagtttgac aatctcacta aagccgagcg cggcggactc tcagagctgg ataaggctgg  2820
attcatcaaa cggcagctgg tcgagactcg gcagattacc aagcacgtgg cgcagatcct  2880
ggactcccgc atgaacacta aatacgacga gaacgataag ctcatccggg aagtgaaggt  2940
gattaccctg aaaagcaaac ttgtgtcgga ctttcggaag gactttcagt tttacaaagt  3000
gagagaaatc aacaactacc atcacgcgca tgacgcatac ctcaacgctg tggtcggcac  3060
cgccctgatc aagaagtacc ctaaacttga atcggagttt gtgtacggag actacaaggt  3120
ctacgacgtg aggaagatga tagccaagtc cgaacaggaa atcgggaaag caactgcgaa  3180
atacttcttt tactcaaaca tcatgaactt cttcaagact gaaattacgc tggccaatgg  3240
agaaatcagg aagaggccac tgatcgaaac taacggagaa acgggcgaaa tcgtgtggga  3300
caagggcagg gacttcgcaa ctgttcgcaa agtgctctct atgccgcaag tcaatattgt  3360
gaagaaaacc gaagtgcaaa ccggcggatt ttcaaaggaa tcgatcctcc caaagagaaa  3420
tagcgacaag ctcattgcac gcaagaaaga ctgggacccg aagaagtacg gaggattcga  3480
ttcgccgact gtcgcatact ccgtcctcgt ggtggccaag gtggagaagg gaaagagcaa  3540
gaagctcaaa tccgtcaaag agctgctggg gattaccatc atggaacgat cctcgttcga  3600
gaagaacccg attgatttcc tggaggcgaa gggttacaag gaggtgaaga aggatctgat  3660
catcaaactg cccaagtact cactgttcga actggaaaat ggtcggaagc gcatgctggc  3720
ttcggccgga gaactccaga aaggaaatga gctggccttg cctagcaagt acgtcaactt  3780
cctctatctt gcttcgcact acgagaaact caaagggtca ccggaagata acgaacagaa  3840
gcagcttttc gtggagcagc acaagcatta tctggatgaa atcatcgaac aaatctccga  3900
gttttcaaag cgcgtgatcc tcgccgacgc caacctcgac aaagtcctgt cggcctacaa  3960
taagcataga gataagccga tcagagaaca ggccgagaac attatccact tgttcaccct  4020
gactaacctg ggagctccag ccgccttcaa gtacttcgat actactatcg accgcaaaag  4080
atacacgtcc accaaggaag ttctggacgc gaccctgatc caccaaagca tcactggact  4140
ctacgaaact aggatcgatc tgtcgcagct gggtggcgat ggtggcggtg gatcctaccc  4200
atacgacgtg cctgactacg cctccggagg tggtggcccc aagaagaaac ggaaggtgtg  4260
atagctagcc atcacattta aaagcatctc agcctaccat gagaataaga gaaagaaaat  4320
gaagatcaat agcttattca tctctttttc tttttcgttg gtgtaaagcc aacaccctgt  4380
ctaaaaaaca taaatttctt taatcatttt gcctcttttc tctgtgcttc aattaataaa  4440
aaatggaaag aacctcgag                                                4459
```

```
SEQ ID NO: 247          moltype = DNA  length = 4453
FEATURE                 Location/Qualifiers
misc_feature            1..4453
                        note = Synthetic: Cas9 transcript with 5 UTR of HSD, ORF
                         corresponding to SEQ ID NO: 245, and 3 UTR of ALB
source                  1..4453
                        mol_type = other DNA
                        organism = synthetic construct
SEQUENCE: 247
gggtcccgca gtcggcgtcc agcggctctg cttgttcgtg tgtgtgtcgt tgcaggcctt  60
attcggatct atggataaga agtactcgat cgggctggat atcggaacta attccgtggg  120
ttgggcagtg atcacggatg aatacaaagt gccgtccaag aagttcaagg tcctggggaa  180
caccgataga cacagcatca agaagaatct catcggagcc ctgctgtttg actccggcga  240
aaccgcagaa gcgacccggc tcaaacgtac cgcgaggcga cgctacaccc ggcggaagaa  300
tcgcatctgc tatctgcaag aaatcttttc gaacgaaatg gcaaaggtgg acgacagctt  360
cttccaccgc ctggaagaat ctttcctggt ggaggaggac aagaagcatg aacggcatcc  420
tatctttgga aacatcgtgg acgaagtggc gtaccacgaa aagtacccga ccatctacca  480
tctgcggaag aagttggttg actcaactga caaggccgac ctcagattga tctacttggc  540
cctcgcccat atgatcaaat tccgcggaca cttcctgatc gaaggcgatc tgaaccctga  600
taactccgac gtggataagc tgttcattca actggtgcag acctacaacc aactgttcga  660
agaaaaccca atcaatgcca gcggcgtcga tgccaaggcc atcctgtccg cccggctgtc  720
gaagtcgcgg cgcctcgaaa acctgatcgc acagctgccg ggagagaaga agaacggact  780
tttcggcaac ttgatcgctc tctcactggg actcactccc aatttcaagt ccaattttga  840
cctggccgag gacgcgaagc tgcaactctc aaaggacacc tacgacgacg acttggacaa  900
tttgctggca caaattggcg atcagtacgc ggatctgttc cttgccgcta agaacctttc  960
ggacgcaatc ttgctgtccg atatcctgcg cgtgaacacc gaaataacca aagcgccgct  1020
tagcgcctcg atgattaagc ggtacgacga gcatcaccag gatctcacgc tgctcaaagc  1080
gctcgtgaga cagcaactgc ctgaaaagta caaggagatt ttcttcgacc agtccaagaa  1140
tgggtacgca gggtacatcg atggaggcgc cagccaggaa gagttctata agttcatcaa  1200
```

```
gccaatcctg gaaaagatgg acggaaccga agaactgctg gtcaagctga acagggagga  1260
tctgctccgc aaacagagaa cctttgacaa cggaagcatt ccacaccaga tccatctggg  1320
tgagctgcac gccatcttgc ggcgccagga ggacttttac ccattcctca aggacaaccg  1380
ggaaaagatc gagaaaattc tgacgttccg catcccgtat tacgtgggcc cactggcgcg  1440
cggcaattcg cgcttcgcgt ggatgactag aaaatcagag gaaaccatca ctccttggaa  1500
tttcgaggaa gttgtggata agggagcttc ggcacaatcc ttcatcgaac gaatgaccaa  1560
cttcgacaag aatctcccaa acgagaaggt gcttcctaag cacagcctcc tttacgaata  1620
cttcactgtc tacaacgaac tgactaaagt gaaatacgtt actgaaggaa tgaggaagcc  1680
ggcctttctg agcggagaac agaagaaagc gattgtcgat ctgctgttca agaccaaccg  1740
caaggtgacc gtcaagcagc ttaaagagga ctacttcaag aagatcgagt gtttcgactc  1800
agtggaaatc agcggagtgg aggacagatt caacgcttcg ctgggaacct atcatgatct  1860
cctgaagatc atcaaggaca aggacttcct tgacaacgag gagaacgagg acatcctgga  1920
agatatcgtc ctgaccttga accttttcga ggatcgcgag atgatcgagg agaggcttaa  1980
gacctacgct catctcttcg acgataaggt catgaaacaa ctcaagcgcc gccggtacac  2040
tggttggggc cgcctctccc gcaagctgat caacggtatt cgcgataaac agagcggtaa  2100
aactatcctg gatttcctca aatcggatgg cttcgctaat cgtaacttca tgcagttgat  2160
ccacgacgac agcctgacct ttaaggagga catccagaaa gcacaagtga gcggacaggg  2220
agactcactc catgaacaca tcgcgaatct ggccggttcg ccggcgatta agaagggaat  2280
cctgcaaact gtgaaggtgg tggacgagct ggtgaaggtc atgggacggc acaaaccgga  2340
gaatatcgtg attgaaatgg cccgagaaaa ccagactacc cagaagggcc agaagaactc  2400
ccgcgaaagg atgaagcgga tcgaagaagg aatcaaggag ctgggcagcc agatcctgaa  2460
agagcacccg gtggaaaaca cgcagctgca gaacgagaag ctctacctgt actatttgca  2520
aaatggacgg gacatgtacg tggaccaaga gctggacatc aatcggttgt ctgattacga  2580
cgtggaccac atcgttccac agtcctttct gaaggatgac tccatcgata acaaggtgtt  2640
gactcgcagc gacaagaaca gagggaagtc agataatgtg ccatcggagg aggtcgtgaa  2700
gaagatgaag aattactggc ggcagctcct gaatgcgaag ctgattaccc agagaaagtt  2760
tgacaatctc actaaagccg agcgcggcgg actctcagag ctggataagg ctggattcat  2820
caaacggcag ctggtcgaga ctcggcagat taccaagcac gtggcgcaga tcctggactc  2880
ccgcatgaac actaaatacg acgagaacga taagctcatc cgggaagtga aggtgattac  2940
cctgaaaagc aaacttgtgt cggactttcg gaaggacttt cagttttaca aagtgagaga  3000
aatcaacaac taccatcacg cgcatgacgc atacctcaac gctgtggtcg gcaccgccct  3060
gatcaagaag taccctaaac ttgaatcgga gtttgtgtac ggagactaca aggtctacga  3120
cgtgaggaag atgatagcca agtccgaaca ggaaatcggg aaagcaactg cgaaatactt  3180
cttttactca aacatcatga acttcttcaa gactgaaatt acgctggcca atggagaaat  3240
caggaagagg ccactgatcg aaactaacgg agaaacgggc gaaatcgtgt gggacaaggg  3300
cagggacttc gcaactgttc gcaaagtgct ctctatgccg caagtcaata ttgtgaagaa  3360
aaccgaagtg caaaccggcg gattttcaaa ggaatcgatc ctcccaaaga gaaatagcga  3420
caagctcatt gcacgcaaga aagactggga cccgaagaag tacggaggat tcgattcgcc  3480
gactgtcgca tactccgtcc tcgtggtggc caaggtggag aagggaaaga gcaagaagct  3540
caaatccgtc aaagagctgc tggggattac catcatggaa cgatcctcgt tcgagaagaa  3600
cccgattgat ttcctggagg cgaagggtta caaggaggtg aagaaggatc tgatcatcaa  3660
actgcccaag tactcactgt tcgaactgga aaatggtcgg aagcgcatgc tggcttcggc  3720
cggagaactc cagaaaggaa atgagctggc cttgcctagc aagtacgtca acttcctcta  3780
tcttgcttcg cactacgaga aactcaaagg gtcaccggaa gataacgaac agaagcagct  3840
tttcgtggag cagcacaagc attatctgga tgaaatcatc gaacaaatct ccgagttttc  3900
aaagcgcgtg atcctcgccg acgccaacct cgacaaagtc ctgtcggcct acaataagca  3960
tagagataag ccgatcagag aacaggccga gaacattatc cacttgttca ccctgactaa  4020
cctgggagct ccagccgcct tcaagtactt cgatactact atcgaccgca aaagatacac  4080
gtccaccaag gaagttctgg acgcgaccct gatccaccaa agcatcactg gactctacga  4140
aactaggatc gatctgtcgc agctgggtgg cgatggtggc ggtggatcct acccatacga  4200
cgtgcctgac tacgcctccg gaggtggtgg ccccaagaag aaacggaagg tgtgatagct  4260
agccatcaca tttaaaagca tctcagccta ccatgagaat aagagaaaga aaatgaagat  4320
caatagctta ttcatctctt tttctttttc gttggtgtaa agccaacacc ctgtctaaaa  4380
aacataaatt tctttaatca ttttgcctct tttctctgtg cttcaattaa taaaaaatgg  4440
aaagaacctc gag                                                     4453
```

```
SEQ ID NO: 248         moltype =   length =
SEQUENCE: 248
000

SEQ ID NO: 249         moltype =   length =
SEQUENCE: 249
000

SEQ ID NO: 250         moltype =   length =
SEQUENCE: 250
000

SEQ ID NO: 251         moltype =   length =
SEQUENCE: 251
000

SEQ ID NO: 252         moltype = DNA  length = 4140
FEATURE                Location/Qualifiers
misc_feature           1..4140
                       note = Synthetic: Cas9 ORF with minimal uridine codons
                        frequently used in humans in general; 12.75% U content
source                 1..4140
                       mol_type = other DNA
```

organism = synthetic construct
SEQUENCE: 252
atggacaaga agtacagcat cggcctggac atcggcacca acagcgtggg ctgggccgtg 60
atcaccgacg agtacaaggt gcccagcaag aagttcaagg tgctgggcaa caccgacaga 120
cacagcatca agaagaacct gatcggcgcc ctgctgttcg acagcggcga gaccgccgag 180
gccaccagac tgaagagaac cgccagaaga agatacacca gaagaaagaa cagaatctgc 240
tacctgcagg agatcttcag caacgagatg gccaaggtgg acgacagctt cttccacaga 300
ctggaggaga gcttcctggt ggaggaggac aagaagcacg agagacaccc catcttcggc 360
aacatcgtgg acgaggtggc ctaccacgag aagtacccca ccatctacca cctgagaaag 420
aagctggtgg acagcaccga caaggccgac ctgagactga tctacctggc cctggcccac 480
atgatcaagt tcagaggcca cttcctgatc gagggcgacc tgaaccccga caacagcgac 540
gtggacaagc tgttcatcca gctggtgcag acctacaacc agctgttcga ggagaacccc 600
atcaacgcca gcggcgtgga cgccaaggcc atcctgagcg ccagactgag caagagcaga 660
agactggaga acctgatcgc ccagctgccc ggcgagaaga agaacggcct gttcggcaac 720
ctgatcgccc tgagcctggg cctgaccccc aacttcaaga gcaacttcga cctggccgag 780
gacgccaagc tgcagctgag caaggacacc tacgacgacg acctggacaa cctgctggcc 840
cagatcggcg accagtacgc cgacctgttc ctggccgcca agaacctgag cgacgccatc 900
ctgctgagcg acatcctgag agtgaacacc gagatcacca aggcccccct gagcgccagc 960
atgatcaaga gatacgacga gcaccaccag gacctgaccc tgctgaaggc cctggtgaga 1020
cagcagctgc ccgagaagta caaggagatc ttcttcgacc agagcaagaa cggctacgcc 1080
ggctacatcg acggcggcgc cagccaggag gagttctaca agttcatcaa gcccatcctg 1140
gagaagatgg acggcaccga ggagctgctg gtgaagctga acagagagga cctgctgaga 1200
aagcagagaa ccttcgacaa cggcagcatc ccccaccaga tccacctggg cgagctgcac 1260
gccatcctga gaagacagga ggacttctac cccttcctga aggacaacag agagaagatc 1320
gagaagatcc tgaccttcag aatcccctac tacgtgggcc ccctggccag aggcaacagc 1380
agattcgcct ggatgaccag aaagagcgag gagaccatca cccccctggaa cttcgaggag 1440
gtggtggaca agggcgccag cgcccagagc ttcatcgaga gaatgaccaa cttcgacaag 1500
aacctgccca acgagaaggt gctgcccaag cacagcctgc tgtacgagta cttcaccgtg 1560
tacaacgagc tgaccaaggt gaagtacgtg accgagggca tgagaaagcc cgccttcctg 1620
agcggcgagc agaagaaggc catcgtggac ctgctgttca agaccaacag aaaggtgacc 1680
gtgaagcagc tgaaggagga ctacttcaag aagatcgagt gcttcgacag cgtggagatc 1740
agcggcgtgg aggacagatt caacgccagc ctgggcacct accacgacct gctgaagatc 1800
atcaaggaca aggacttcct ggacaacgag gagaacgagg acatcctgga ggacatcgtg 1860
ctgaccctga ccctgttcga ggacagagag atgatcgagg agagactgaa gacctacgcc 1920
cacctgttcg acgacaaggt gatgaagcag ctgaagagaa gaagatacac cggctggggc 1980
agactgagca gaaagctgat caacggcatc agagacaagc agagcggcaa gaccatcctg 2040
gacttcctga agagcgacgg cttcgccaac agaaacttca tgcagctgat ccacgacgac 2100
agcctgacct tcaaggagga catccagaag gcccaggtga gcggccaggg cgacagcctg 2160
cacgagcaca tcgccaacct ggccggcagc cccgccatca agaagggcat cctgcagacc 2220
gtgaaggtgg tggacgagct ggtgaaggtg atgggcagac acaagcccga gaacatcgtg 2280
atcgagatgg ccagagagaa ccagaccacc cagaagggcc agaagaacag cagagagaga 2340
atgaagagaa tcgaggaggg catcaaggag ctgggcagcc agatcctgaa ggagcacccc 2400
gtggagaaca cccagctgca gaacgagaag ctgtacctgt actacctgca gaacggcaga 2460
gacatgtacg tggaccagga gctggacatc aacagactga gcgactacga cgtggaccac 2520
atcgtgcccc agagcttcct gaaggacgac agcatcgaca acaaggtgct gaccagaagc 2580
gacaagaaca gaggcaagag cgacaacgtg cccagcgagg aggtggtgaa gaagatgaag 2640
aactactgga gacagctgct gaacgccaag ctgatcaccc agagaaagtt cgacaacctg 2700
accaaggccg agagaggcgg cctgagcgag ctggacaagg ccggcttcat caagagacag 2760
ctggtggaga ccagacagat caccaagcac gtggcccaga tcctggacag cagaatgaac 2820
accaagtacg acgagaacga caagctgatc agagaggtga aggtgatcac cctgaagagc 2880
aagctggtga gcgacttcag aaaggacttc cagttctaca aggtgagaga gatcaacaac 2940
taccaccacg cccacgacgc ctacctgaac gccgtggtgg gcaccgccct gatcaagaag 3000
taccccaagc tggagagcga gttcgtgtac ggcgactaca aggtgtacga cgtgagaaag 3060
atgatcgcca agagcgagca ggagatcggc aaggccaccg ccaagtactt cttctacagc 3120
aacatcatga acttcttcaa gaccgagatc accctggcca acggcgagat cagaaagaga 3180
cccctgatcg agaccaacgg cgagaccggc gagatcgtgt gggacaaggg cagagacttc 3240
gccaccgtga gaaaggtgct gagcatgccc caggtgaaca tcgtgaagaa gaccgaggtg 3300
cagaccggcg gcttcagcaa ggagagcatc ctgcccaaga gaaacagcga caagctgatc 3360
gccagaaaga aggactggga ccccaagaag tacggcggct tcgacagccc caccgtggcc 3420
tacagcgtgc tggtggtggc caaggtggag aagggcaaga gcaagaagct gaagagcgtg 3480
aaggagctgc tgggcatcac catcatggag agaagcagct tcgagaagaa ccccatcgac 3540
ttcctggagg ccaagggcta caaggaggtg aagaaggacc tgatcatcaa gctgcccaag 3600
tacagcctgt tcgagctgga gaacggcaga aagagaatgc tggccagcgc cggcgagctg 3660
cagaagggca acgagctggc cctgcccagc aagtacgtga acttcctgta cctggccagc 3720
cactacgaga agctgaaggg cagccccgag gacaacgagc agaagcagct gttcgtggag 3780
cagcacaagc actacctgga cgagatcatc gagcagatca gcgagttcag caagagagtg 3840
atcctggccg acgccaacct ggacaaggtg ctgagcgcct acaacaagca cagagacaag 3900
cccatcagag agcaggccga gaacatcatc cacctgttca ccctgaccaa cctgggcgcc 3960
cccgccgcct tcaagtactt cgacaccacc atcgacagaa agagatacac cagcaccaag 4020
gaggtgctgg acgccaccct gatccaccag agcatcaccg gcctgtacga gaccagaatc 4080
gacctgagcc agctgggcgg cgacggcggc ggcagcccca agaagaagag aaaggtgtga 4140

SEQ ID NO: 253 moltype = DNA length = 4411
FEATURE Location/Qualifiers
misc_feature 1..4411
note = Synthetic: Cas9 transcript with 5 UTR of HSD, ORF corresponding to SEQ ID NO: 252, Kozak sequence, and 3 UTR of ALB
source 1..4411 mol_type = other DNA
organism = synthetic construct

SEQUENCE: 253

```
gggtcccgca gtcggcgtcc agcggctctg cttgttcgtg tgtgtgtcgt tgcaggcctt  60
attcggatcc gccaccatgg acaagaagta cagcatcggc ctggacatcg gcaccaacag  120
cgtgggctgg gccgtgatca ccgacgagta caaggtgccc agcaagaagt tcaaggtgct  180
gggcaacacc gacagacaca gcatcaagaa gaacctgatc ggcgccctgc tgttcgacag  240
cggcgagacc gccgaggcca ccagactgaa gagaaccgcc agaagaagat acaccagaag  300
aaagaacaga atctgctacc tgcaggagat cttcagcaac gagatggcca aggtggacga  360
cagcttcttc cacagactgg aggagagctt cctggtggag gaggacaaga agcacgagag  420
acaccccatc ttcggcaaca tcgtggacga ggtggcctac cacgagaagt accccaccat  480
ctaccacctg agaaagaagc tggtggacag caccgacaag gccgacctga gactgatcta  540
cctggccctg gcccacatga tcaagttcag aggccacttc ctgatcgagg gcgacctgaa  600
ccccgacaac agcgacgtgg acaagctgtt catccagctg gtgcagacct acaaccagct  660
gttcgaggag aaccccatca acgccagcgg cgtggacgcc aaggccatcc tgagcgccag  720
actgagcaag agcagaagac tggagaacct gatcgcccag ctgcccggcg agaagaagaa  780
cggcctgttc ggcaacctga tcgccctgag cctgggcctg acccccaact tcaagagcaa  840
cttcgacctg gccgaggacg ccaagctgca gctgagcaag gacacctacg acgacgacct  900
ggacaacctg ctggcccaga tcggcgacca gtacgccgac ctgttcctgg ccgccaagaa  960
cctgagcgac gccatcctgc tgagcgacat cctgagagtg aacaccgaga tcaccaaggc  1020
ccccctgagc gccagcatga tcaagagata cgacgagcac caccaggacc tgaccctgct  1080
gaaggccctg gtgagacagc agctgcccga gaagtacaag gagatcttct tcgaccagag  1140
caagaacggc tacgccggct acatcgacgg cggcgccagc caggaggagt tctacaagtt  1200
catcaagccc atcctggaga agatggacgg caccgaggag ctgctggtga agctgaacag  1260
agaggacctg ctgagaaagc agagaacctt cgacaacggc agcatccccc accagatcca  1320
cctgggcgag ctgcacgcca tcctgagaag acaggaggac ttctacccct tcctgaagga  1380
caacagagag aagatcgaga agatcctgac cttcagaatc ccctactacg tgggccccct  1440
ggccagaggc aacagcagat tcgcctggat gaccagaaag agcgaggaga ccatcacccc  1500
ctggaacttc gaggaggtgg tggacaaggg cgccagcgcc cagagcttca tcgagagaat  1560
gaccaacttc gacaagaacc tgcccaacga gaaggtgctg cccaagcaca gcctgctgta  1620
cgagtacttc accgtgtaca acgagctgac caaggtgaag tacgtgaccg agggcatgag  1680
aaagcccgcc ttcctgagcg gcgagcagaa gaaggccatc gtggacctgc tgttcaagac  1740
caacagaaag gtgaccgtga agcagctgaa ggaggactac ttcaagaaga tcgagtgctt  1800
cgacagcgtg gagatcagcg gcgtggagga cagattcaac gccagcctgg gcacctacca  1860
cgacctgctg aagatcatca aggacaagga cttcctggac aacgaggaga acgaggacat  1920
cctggaggac atcgtgctga ccctgaccct gttcgaggac agagagatga tcgaggagag  1980
actgaagacc tacgcccacc tgttcgacga caaggtgatg aagcagctga agagaagaag  2040
atacaccggc tggggcagac tgagcagaaa gctgatcaac ggcatcagag acaagcagag  2100
cggcaagacc atcctggact tcctgaagag cgacggcttc gccaacagaa acttcatgca  2160
gctgatccac gacgacagcc tgaccttcaa ggaggacatc cagaaggccc aggtgagcgg  2220
ccagggcgac agcctgcacg agcacatcgc caacctggcc ggcagccccg ccatcaagaa  2280
gggcatcctg cagaccgtga aggtggtgga cgagctggtg aaggtgatgg gcagacacaa  2340
gcccgagaac atcgtgatcg agatggccag agagaaccag accacccaga agggccagaa  2400
gaacagcaga gagagaatga agagaatcga ggagggcatc aaggagctgg gcagccagat  2460
cctgaaggag caccccgtgg agaacaccca gctgcagaac gagaagctgt acctgtacta  2520
cctgcagaac ggcagagaca tgtacgtgga ccaggagctg gacatcaaca gactgagcga  2580
ctacgacgtg gaccacatcg tgccccagag cttcctgaag gacgacagca tcgacaacaa  2640
ggtgctgacc agaagcgaca agaacagagg caagagcgac aacgtgccca gcgaggaggt  2700
ggtgaagaag atgaagaact actggagaca gctgctgaac gccaagctga tcacccagag  2760
aaagttcgac aacctgacca aggccgagag aggcggcctg agcgagctgg acaaggccgg  2820
cttcatcaag agacagctgg tggagaccag acagatcacc aagcacgtgg cccagatcct  2880
ggacagcaga atgaacacca agtacgacga gaacgacaag ctgatcagag aggtgaaggt  2940
gatcaccctg aagagcaagc tggtgagcga cttcagaaag gacttccagt tctacaaggt  3000
gagagagatc aacaactacc accacgccca cgacgcctac ctgaacgccg tggtgggcac  3060
cgccctgatc aagaagtacc ccaagctgga gagcgagttc gtgtacggcg actacaaggt  3120
gtacgacgtg agaaagatga tcgccaagag cgagcaggag atcggcaagg ccaccgccaa  3180
gtacttcttc tacagcaaca tcatgaactt cttcaagacc gagatcaccc tggccaacgg  3240
cgagatcaga aagagacccc tgatcgagac caacggcgag accggcgaga tcgtgtggga  3300
caagggcaga gacttcgcca ccgtgagaaa ggtgctgagc atgccccagg tgaacatcgt  3360
gaagaagacc gaggtgcaga ccggcggctt cagcaaggag agcatcctgc ccaagagaaa  3420
cagcgacaag ctgatcgcca gaaagaagga ctgggacccc aagaagtacg gcggcttcga  3480
cagccccacc gtggcctaca gcgtgctggt ggtggccaag gtggagaagg gcaagagcaa  3540
gaagctgaag agcgtgaagg agctgctggg catcaccatc atggagagaa gcagcttcga  3600
gaagaacccc atcgacttcc tggaggccaa gggctacaag gaggtgaaga aggacctgat  3660
catcaagctg cccaagtaca gcctgttcga gctggagaac ggcagaaaga gaatgctggc  3720
cagcgccggc gagctgcaga agggcaacga gctggccctg cccagcaagt acgtgaactt  3780
cctgtacctg gccagccact acgagaagct gaagggcagc cccgaggaca acgagcagaa  3840
gcagctgttc gtggagcagc acaagcacta cctggacgag atcatcgagc agatcagcga  3900
gttcagcaag agagtgatcc tggccgacgc caacctggac aaggtgctga gcgcctacaa  3960
caagcacaga gacaagccca tcagagagca ggccgagaac atcatccacc tgttcaccct  4020
gaccaacctg ggcgcccccg ccgccttcaa gtacttcgac accaccatcg acagaaagag  4080
atacaccagc accaaggagg tgctggacgc caccctgatc caccagagca tcaccggcct  4140
gtacgagacc agaatcgacc tgagccagct gggcggcgac ggcggcggca gccccaagaa  4200
gaagagaaag gtgtgactag ccatcacatt taaaagcatc tcagcctacc atgagaataa  4260
gagaaagaaa atgaagatca atagcttatt catctctttt tctttttcgt tggtgtaaag  4320
ccaacaccct gtctaaaaaa cataaatttc tttaatcatt ttgcctcttt tctctgtgct  4380
tcaattaata aaaaatggaa agaacctcga g                                4411
```

SEQ ID NO: 254 moltype = length =

-continued

```
SEQUENCE: 254
000

SEQ ID NO: 255         moltype =   length =
SEQUENCE: 255
000

SEQ ID NO: 256         moltype = DNA  length = 4411
FEATURE                Location/Qualifiers
misc_feature           1..4411
                       note = Synthetic: Cas9 transcript with AGG as first three
                        nucleotides for use with CleanCapTM, 5 UTR of HSD, ORF
                        corresponding to SEQ ID NO: 204, Kozak sequence, and 3 UTR
                        of ALB
source                 1..4411
                       mol_type = other DNA
                       organism = synthetic construct
SEQUENCE: 256
aggtcccgca gtcggcgtcc agcggctctg cttgttcgtg tgtgtgtcgt tgcaggcctt  60
attcggatcc gccaccatgg acaagaagta cagcatcgga ctggacatcg gaacaaacag  120
cgtcggatgg gcagtcatca cagacgaata caaggtcccg agcaagaagt tcaaggtcct  180
gggaaacaca gacagacaca gcatcaagaa gaacctgatc ggagcactgc tgttcgacag  240
cggagaaaca gcagaagcaa caagactgaa gagaacagca agaagaagat acacaagaag  300
aaagaacaga atctgctacc tgcaggaaat cttcagcaac gaaatggcaa aggtcgacga  360
cagcttcttc cacagactgg aagaaagctt cctggtcgaa gaagacaaga agcacgaaag  420
acacccgatc ttcggaaaca tcgtcgacga agtcgcatac cacgaaaagt acccgacaat  480
ctaccacctg agaaagaagc tggtcgacag cacagacaag gcagacctga gactgatcta  540
cctggcactg gcacacatga tcaagttcag aggacacttc ctgatcgaag gagacctgaa  600
cccggacaac agcgacgtcg acaagctgtt catccagctg gtccagacat acaaccagct  660
gttcgaagaa aacccgatca acgcaagcgg agtcgacgca aaggcaatcc tgagcgcaag  720
actgagcaag agcagaagac tggaaaacct gatcgcacag ctgccgggag aaaagaagaa  780
cggactgttc ggaaacctga tcgcactgag cctgggactg acaccgaact tcaagagcaa  840
cttcgacctg gcagaagacg caaagctgca gctgagcaag gacacatacg acgacgacct  900
ggacaacctg ctggcacaga tcggagacca gtacgcagac ctgttcctgg cagcaaagaa  960
cctgagcgac gcaatcctgc tgagcgacat cctgagagtc aacacagaaa tcacaaaggc  1020
accgctgagc gcaagcatga tcaagagata cgacgaacac caccaggacc tgacactgct  1080
gaaggcactg gtcagacagc agctgccgga aaagtacaag gaaatcttct tcgaccagag  1140
caagaacgga tacgcaggat acatcgacgg aggagcaagc caggaagaat tctacaagtt  1200
catcaagccg atcctggaaa agatggacgg aacagaagaa ctgctggtca agctgaacag  1260
agaagacctg ctgagaaagc agagaacatt cgacaacgga agcatcccgc accagatcca  1320
cctgggagaa ctgcacgcaa tcctgagaag acaggaagac ttctacccgt tcctgaagga  1380
caacagagaa aagatcgaaa agatcctgac attcagaatc ccgtactacg tcggaccgct  1440
ggcaagagga aacagcagat tcgcatggat gacaagaaag agcgaagaaa caatcacacc  1500
gtggaacttc gaagaagtcg tcgacaaggg agcaagcgca cagagcttca tcgaaagaat  1560
gacaaacttc gacaagaacc tgccgaacga aaaggtcctg ccgaagcaca gcctgctgta  1620
cgaatacttc acagtctaca acgaactgac aaaggtcaag tacgtcacag aaggaatgag  1680
aaagccggca ttcctgagcg gagaacagaa gaaggcaatc gtcgacctgc tgttcaagac  1740
aaacagaaag gtcacagtca agcagctgaa ggaagactac ttcaagaaga tcgaatgctt  1800
cgacagcgtc gaaatcagcg gagtcgaaga cagattcaac gcaagcctgg gaacatacca  1860
cgacctgctg aagatcatca aggacaagga cttcctggac aacgaagaaa acgaagacat  1920
cctggaagac atcgtcctga cactgacact gttcgaagac agagaaatga tcgaagaaag  1980
actgaagaca tacgcacacc tgttcgacga caaggtcatg aagcagctga agagaagaag  2040
atacacagga tggggaagac tgagcagaaa gctgatcaac ggaatcagag acaagcagag  2100
cggaaagaca atcctggact tcctgaagag cgacggattc gcaaacagaa acttcatgca  2160
gctgatccac gacgacagcc tgacattcaa ggaagacatc cagaaggcac aggtcagcgg  2220
acagggagac agcctgcacg aacacatcgc aaacctggca ggaagcccgg caatcaagaa  2280
gggaatcctg cagacagtca aggtcgtcga cgaactggtc aaggtcatgg gaagacacaa  2340
gccggaaaac atcgtcatcg aaatggcaag agaaaaccag acaacacaga agggacagaa  2400
gaacagcaga gaaagaatga agagaatcga agaaggaatc aaggaactgg gaagccagat  2460
cctgaaggaa cacccggtcg aaaacacaca gctgcagaac gaaaagctgt acctgtacta  2520
cctgcagaac ggaagagaca tgtacgtcga ccaggaactg gacatcaaca gactgagcga  2580
ctacgacgtc gaccacatcg tcccgcagag cttcctgaag gacgacagca tcgacaacaa  2640
ggtcctgaca agaagcgaca agaacagagg aaagagcgac aacgtcccga gcgaagaagt  2700
cgtcaagaag atgaagaact actggagaca gctgctgaac gcaaagctga tcacacagag  2760
aaagttcgac aacctgacaa aggcagagag aggaggactg agcgaactgg acaaggcagg  2820
attcatcaag agacagctgg tcgaaacaag acagatcaca aagcacgtcg cacagatcct  2880
ggacagcaga atgaacacaa agtacgacga aaacgacaag ctgatcagag aagtcaaggt  2940
catcacactg aagagcaagc tggtcagcga cttcagaaag gacttccagt tctacaaggt  3000
cagagaaatc aacaactacc accacgcaca cgacgcatac ctgaacgcag tcgtcggaac  3060
agcactgatc aagaagtacc cgaagctgga aagcgaattc gtctacggag actacaaggt  3120
ctacgacgtc agaaagatga tcgcaaagag cgaacaggaa atcggaaagg caacagcaaa  3180
gtacttcttc tacagcaaca tcatgaactt cttcaagaca gaaatcacac tggcaaacgg  3240
agaaatcaga aagagaccgc tgatcgaaac aaacggagaa acaggagaaa tcgtctggga  3300
caagggaaga gacttcgcaa cagtcagaaa ggtcctgagc atgccgcagg tcaacatcgt  3360
caagaagaca gaagtccaga caggaggatt cagcaaggaa agcatcctgc cgaagagaaa  3420
cagcgacaag ctgatcgcaa gaaagaagga ctgggacccg aagaagtacg gaggattcga  3480
cagcccgaca gtcgcataca gcgtcctggt cgtcgcaaag gtcgaaaagg gaaagagcaa  3540
gaagctgaag agcgtcaagg aactgctggg aatcacaatc atggaaagaa gcagcttcga  3600
aaagaacccg atcgacttcc tggaagcaaa gggatacaag gaagtcaaga aggacctgat  3660
```

```
catcaagctg ccgaagtaca gcctgttcga actggaaaac ggaagaaaga gaatgctggc  3720
aagcgcagga gaactgcaga agggaaacga actggcactg ccgagcaagt acgtcaactt  3780
cctgtacctg gcaagccact acgaaaagct gaagggaagc ccggaagaca acgaacagaa  3840
gcagctgttc gtcgaacagc acaagcacta cctggacgaa atcatcgaac agatcagcga  3900
attcagcaag agagtcatcc tggcagacgc aaacctggac aaggtcctga gcgcatacaa  3960
caagcacaga gacaagccga tcagagaaca ggcagaaaac atcatccacc tgttcacact  4020
gacaaacctg ggagcaccgg cagcattcaa gtacttcgac acaacaatcg acagaaagag  4080
atacacaagc acaaaggaag tcctggacgc aacactgatc caccagagca tcacaggact  4140
gtacgaaaca agaatcgacc tgagccagct gggaggagac ggaggaggaa gcccgaagaa  4200
gaagagaaag gtctagctag ccatcacatt taaaagcatc tcagcctacc atgagaataa  4260
gagaaagaaa atgaagatca atagcttatt catctctttt tctttttcgt tggtgtaaag  4320
ccaacaccct gtctaaaaaa cataaatttc tttaatcatt ttgcctcttt tctctgtgct  4380
tcaattaata aaaaatggaa agaacctcga g                                 4411
```

```
SEQ ID NO: 257          moltype = DNA  length = 4481
FEATURE                 Location/Qualifiers
misc_feature            1..4481
                        note = Synthetic: Cas9 transcript with 5 UTR from CMV, ORF
                         corresponding to SEQ ID NO: 204, Kozak sequence, and 3 UTR
                         of ALB
source                  1..4481
                        mol_type = other DNA
                        organism = synthetic construct
SEQUENCE: 257
gggcagatcg cctggagacg ccatccacgc tgttttgacc tccatagaag acaccgggac  60
cgatccagcc tccgcggccg ggaacggtgc attggaacgc ggattccccg tgccaagagt  120
gactcaccgt ccttgacacg gccaccatgg acaagaagta cagcatcgga ctggacatcg  180
gaacaaacag cgtcggatgg gcagtcatca cagacgaata caaggtcccg agcaagaagt  240
tcaaggtcct gggaaacaca gacagacaca gcatcaagaa gaacctgatc ggagcactgc  300
tgttcgacag cggagaaaca gcagaagcaa caagactgaa gagaacagca agaagaagat  360
acacaagaag aaagaacaga atctgctacc tgcaggaaat cttcagcaac gaaatggcaa  420
aggtcgacga cagcttcttc cacagactgg aagaaagctt cctggtcgaa gaagacaaga  480
agcacgaaag acacccgatc ttcggaaaca tcgtcgacga agtcgcatac cacgaaaagt  540
acccgacaat ctaccacctg agaaagaagc tggtcgacag cacagacaag gcagacctga  600
gactgatcta cctggcactg gcacacatga tcaagttcag aggacacttc ctgatcgaag  660
gagacctgaa cccggacaac agcgacgtcg acaagctgtt catccagctg gtccagacat  720
acaaccagct gttcgaagaa aacccgatca acgcaagcgg agtcgacgca aaggcaatcc  780
tgagcgcaag actgagcaag agcagaagac tggaaaacct gatcgcacag ctgccgggag  840
aaaagaagaa cggactgttc ggaaacctga tcgcactgag cctgggactg acaccgaact  900
tcaagagcaa cttcgacctg gcagaagacg caaagctgca gctgagcaag gacacatacg  960
acgacgacct ggacaacctg ctggcacaga tcggagacca gtacgcagac ctgttcctgg  1020
cagcaaagaa cctgagcgac gcaatcctgc tgagcgacat cctgagagtc aacacagaaa  1080
tcacaaaggc accgctgagc gcaagcatga tcaagagata cgacgaacac caccaggacc  1140
tgacactgct gaaggcactg gtcagacagc agctgccgga aaagtacaag gaaatcttct  1200
tcgaccagag caagaacgga tacgcaggat acatcgacgg aggagcaagc caggaagaat  1260
tctacaagtt catcaagccg atcctggaaa agatggacgg aacagaagaa ctgctggtca  1320
agctgaacag agaagacctg ctgagaaagc agagaacatt cgacaacgga agcatcccgc  1380
accagatcca cctgggagaa ctgcacgcaa tcctgagaag acaggaagac ttctacccgt  1440
tcctgaagga caacagagaa aagatcgaaa agatcctgac attcagaatc ccgtactacg  1500
tcggaccgct ggcaagagga aacagcagat tcgcatggat gacaagaaag agcgaagaaa  1560
caatcacacc gtggaacttc gaagaagtcg tcgacaaggg agcaagcgca cagagcttca  1620
tcgaaagaat gacaaacttc gacaagaacc tgccgaacga aaaggtcctg ccgaagcaca  1680
gcctgctgta cgaatacttc acagtctaca acgaactgac aaaggtcaag tacgtcacag  1740
aaggaatgag aaagccggca ttcctgagcg gagaacagaa gaaggcaatc gtcgacctgc  1800
tgttcaagac aaacagaaag gtcacagtca agcagctgaa ggaagactac ttcaagaaga  1860
tcgaatgctt cgacagcgtc gaaatcagcg gagtcgaaga cagattcaac gcaagcctgg  1920
gaacatacca cgacctgctg aagatcatca aggacaagga cttcctggac aacgaagaaa  1980
acgaagacat cctggaagac atcgtcctga cactgacact gttcgaagac agagaaatga  2040
tcgaagaaag actgaagaca tacgcacacc tgttcgacga caaggtcatg aagcagctga  2100
agagaagaag atacacagga tggggaagac tgagcagaaa gctgatcaac ggaatcagag  2160
acaagcagag cggaaagaca atcctggact tcctgaagag cgacggattc gcaaacagaa  2220
acttcatgca gctgatccac gacgacagcc tgacattcaa ggaagacatc cagaaggcac  2280
aggtcagcgg acagggagac agcctgcacg aacacatcgc aaacctggca ggaagcccgg  2340
caatcaagaa gggaatcctg cagacagtca aggtcgtcga cgaactggtc aaggtcatgg  2400
gaagacacaa gccggaaaac atcgtcatcg aaatggcaag agaaaaccag acaacacaga  2460
agggacagaa gaacagcaga gaaagaatga agagaatcga agaaggaatc aaggaactgg  2520
gaagccagat cctgaaggaa cacccggtcg aaaacacaca gctgcagaac gaaaagctgt  2580
acctgtacta cctgcagaac ggaagagaca tgtacgtcga ccaggaactg gacatcaaca  2640
gactgagcga ctacgacgtc gaccacatcg tcccgcagag cttcctgaag gacgacagca  2700
tcgacaacaa ggtcctgaca agaagcgaca agaacagagg aaagagcgac aacgtcccga  2760
gcgaagaagt cgtcaagaag atgaagaact actggagaca gctgctgaac gcaaagctga  2820
tcacacagag aaagttcgac aacctgacaa aggcagagag aggaggactg agcgaactgg  2880
acaaggcagg attcatcaag agacagctgg tcgaaacaag acagatcaca aagcacgtcg  2940
cacagatcct ggacagcaga atgaacacaa agtacgacga aaacgacaag ctgatcagag  3000
aagtcaaggt catcacactg aagagcaagc tggtcagcga cttcagaaag gacttccagt  3060
tctacaaggt cagagaaatc aacaactacc accacgcaca cgacgcatac ctgaacgcag  3120
tcgtcggaac agcactgatc aagaagtacc cgaagctgga aagcgaattc gtctacggag  3180
actacaaggt ctacgacgtc agaaagatga tcgcaaagag cgaacaggaa atcggaaagg  3240
caacagcaaa gtacttcttc tacagcaaca tcatgaactt cttcaagaca gaaatcacac  3300
```

```
tggcaaacgg agaaatcaga aagagaccgc tgatcgaaac aaacggagaa acaggagaaa  3360
tcgtctggga caagggaaga gacttcgcaa cagtcagaaa ggtcctgagc atgccgcagg  3420
tcaacatcgt caagaagaca gaagtccaga caggaggatt cagcaaggaa agcatcctgc  3480
cgaagagaaa cagcgacaag ctgatcgcaa gaaagaagga ctgggacccg aagaagtacg  3540
gaggattcga cagcccgaca gtcgcataca gcgtcctggt cgtcgcaaag gtcgaaaagg  3600
gaaagagcaa gaagctgaag agcgtcaagg aactgctggg aatcacaatc atggaaagaa  3660
gcagcttcga aaagaacccg atcgacttcc tggaagcaaa gggatacaag gaagtcaaga  3720
aggacctgat catcaagctg ccgaagtaca gcctgttcga actggaaaac ggaagaaaga  3780
gaatgctggc aagcgcagga gaactgcaga agggaaacga actggcactg ccgagcaagt  3840
acgtcaactt cctgtacctg gcaagccact acgaaaagct gaagggaagc ccggaagaca  3900
acgaacagaa gcagctgttc gtcgaacagc acaagcacta cctggacgaa atcatcgaac  3960
agatcagcga attcagcaag agagtcatcc tggcagacgc aaacctggac aaggtcctga  4020
gcgcatacaa caagcacaga gacaagccga tcagagaaca ggcagaaaac atcatccacc  4080
tgttcacact gacaaacctg ggagcaccgg cagcattcaa gtacttcgac acaacaatcg  4140
acagaaagag atacacaagc acaaaggaag tcctggacgc aacactgatc caccagagca  4200
tcacaggact gtacgaaaca agaatcgacc tgagccagct gggaggagac ggaggaggaa  4260
gcccgaagaa gaagagaaag gtctagctag ccatcacatt taaaagcatc tcagcctacc  4320
atgagaataa gagaaagaaa atgaagatca atagcttatt catctctttt tctttttcgt  4380
tggtgtaaag ccaacaccct gtctaaaaaa cataaatttc tttaatcatt ttgcctcttt  4440
tctctgtgct tcaattaata aaaaatggaa agaacctcga g                        4481

SEQ ID NO: 258          moltype = DNA  length = 4348
FEATURE                 Location/Qualifiers
misc_feature            1..4348
                        note = Synthetic: Cas9 transcript with 5 UTR from HBB, ORF
                         corresponding to SEQ ID NO: 204, Kozak sequence, and 3 UTR
                         of HBB
source                  1..4348
                        mol_type = other DNA
                        organism = synthetic construct
SEQUENCE: 258
gggacatttg cttctgacac aactgtgttc actagcaacc tcaaacagac accggatctg  60
ccaccatgga caagaagtac agcatcggac tggacatcgg aacaaacagc gtcggatggg  120
cagtcatcac agacgaatac aaggtcccga gcaagaagtt caaggtcctg ggaaacacag  180
acagacacag catcaagaag aacctgatcg gagcactgct gttcgacagc ggagaaacag  240
cagaagcaac aagactgaag agaacagcaa gaagaagata cacaagaaga aagaacagaa  300
tctgctacct gcaggaaatc ttcagcaacg aaatggcaaa ggtcgacgac agcttcttcc  360
acagactgga agaaagcttc ctggtcgaag aagacaagaa gcacgaaaga cacccgatct  420
tcggaaacat cgtcgacgaa gtcgcatacc acgaaaagta cccgacaatc taccacctga  480
gaaagaagct ggtcgacagc acagacaagg cagacctgag actgatctac ctggcactgg  540
cacacatgat caagttcaga ggacacttcc tgatcgaagg agacctgaac ccggacaaca  600
gcgacgtcga caagctgttc atccagctgg tccagacata caaccagctg ttcgaagaaa  660
acccgatcaa cgcaagcgga gtcgacgcaa aggcaatcct gagcgcaaga ctgagcaaga  720
gcagaagact ggaaaacctg atcgcacagc tgccgggaga aaagaagaac ggactgttcg  780
gaaacctgat cgcactgagc ctgggactga caccgaactt caagagcaac ttcgacctgg  840
cagaagacgc aaagctgcag ctgagcaagg acacatacga cgacgacctg gacaacctgc  900
tggcacagat cggagaccag tacgcagacc tgttcctggc agcaaagaac ctgagcgacg  960
caatcctgct gagcgacatc ctgagagtca acacagaaat cacaaaggca ccgctgagcg  1020
caagcatgat caagagatac gacgaacacc accaggacct gacactgctg aaggcactgg  1080
tcagacagca gctgccggaa aagtacaagg aaatcttctt cgaccagagc aagaacggat  1140
acgcaggata catcgacgga ggagcaagcc aggaagaatt ctacaagttc atcaagccga  1200
tcctggaaaa gatggacgga acagaagaac tgctggtcaa gctgaacaga gaagacctgc  1260
tgagaaagca gagaacattc gacaacggaa gcatcccgca ccagatccac ctgggagaac  1320
tgcacgcaat cctgagaaga caggaagact tctacccgtt cctgaaggac aacagagaaa  1380
agatcgaaaa gatcctgaca ttcagaatcc cgtactacgt cggaccgctg gcaagaggaa  1440
acagcagatt cgcatggatg acaagaaaga gcgaagaaac aatcacaccg tggaacttcg  1500
aagaagtcgt cgacaaggga gcaagcgcac agagcttcat cgaaagaatg acaaacttcg  1560
acaagaacct gccgaacgaa aaggtcctgc cgaagcacag cctgctgtac gaatacttca  1620
cagtctacaa cgaactgaca aaggtcaagt acgtcacaga aggaatgaga aagccggcat  1680
tcctgagcgg agaacagaag aaggcaatcg tcgacctgct gttcaagaca aacagaaagg  1740
tcacagtcaa gcagctgaag gaagactact tcaagaagat cgaatgcttc gacagcgtcg  1800
aaatcagcgg agtcgaagac agattcaacg caagcctggg aacataccac gacctgctga  1860
agatcatcaa ggacaaggac ttcctggaca acgaagaaaa cgaagacatc ctggaagaca  1920
tcgtcctgac actgacactg ttcgaagaca gagaaatgat cgaagaaaga ctgaagacat  1980
acgcacacct gttcgacgac aaggtcatga agcagctgaa gagaagaaga tacacaggat  2040
ggggaagact gagcagaaag ctgatcaacg gaatcagaga caagcagagc ggaaagacaa  2100
tcctggactt cctgaagagc gacggattcg caaacagaaa cttcatgcag ctgatccacg  2160
acgacagcct gacattcaag gaagacatcc agaaggcaca ggtcagcgga cagggagaca  2220
gcctgcacga acacatcgca aacctggcag gaagcccggc aatcaagaag ggaatcctgc  2280
agacagtcaa ggtcgtcgac gaactggtca aggtcatggg aagacacaag ccggaaaaca  2340
tcgtcatcga aatggcaaga gaaaaccaga caacacagaa gggacagaag aacagcagag  2400
aaagaatgaa gagaatcgaa gaaggaatca aggaactggg aagccagatc ctgaaggaac  2460
acccggtcga aaacacacag ctgcagaacg aaaagctgta cctgtactac ctgcagaacg  2520
gaagagacat gtacgtcgac caggaactgg acatcaacag actgagcgac tacgacgtcg  2580
accacatcgt cccgcagagc ttcctgaagg acgacagcat cgacaacaag gtcctgacaa  2640
gaagcgacaa gaacagagga aagagcgaca acgtcccgag cgaagaagtc gtcaagaaga  2700
tgaagaacta ctggagacag ctgctgaacg caaagctgat cacacagaga aagttcgaca  2760
acctgacaaa ggcagagaga ggaggactga gcgaactgga caaggcagga ttcatcaaga  2820
gacagctggt cgaaacaaga cagatcacaa agcacgtcgc acagatcctg gacagcagaa  2880
```

```
tgaacacaaa gtacgacgaa aacgacaagc tgatcagaga agtcaaggtc atcacactga  2940
agagcaagct ggtcagcgac ttcagaaagg acttccagtt ctacaaggtc agagaaatca  3000
acaactacca ccacgcacac gacgcatacc tgaacgcagt cgtcggaaca gcactgatca  3060
agaagtaccc gaagctggaa agcgaattcg tctacggaga ctacaaggtc tacgacgtca  3120
gaaagatgat cgcaaagagc gaacaggaaa tcggaaaggc aacagcaaag tacttcttct  3180
acagcaacat catgaacttc ttcaagacag aaatcacact ggcaaacgga gaaatcagaa  3240
agagaccgct gatcgaaaca aacggagaaa caggagaaat cgtctgggac aagggaagag  3300
acttcgcaac agtcagaaag gtcctgagca tgccgcaggt caacatcgtc aagaagacag  3360
aagtccagac aggaggattc agcaaggaaa gcatcctgcc gaagagaaac agcgacaagc  3420
tgatcgcaag aaagaaggac tgggacccga agaagtacgg aggattcgac agcccgacag  3480
tcgcatacag cgtcctggtc gtcgcaaagg tcgaaaaggg aaagagcaag aagctgaaga  3540
gcgtcaagga actgctggga atcacaatca tggaaagaag cagcttcgaa aagaacccga  3600
tcgacttcct ggaagcaaag ggatacaagg aagtcaagaa ggacctgatc atcaagctgc  3660
cgaagtacag cctgttcgaa ctggaaaacg gaagaaagag aatgctggca agcgcaggag  3720
aactgcagaa gggaaacgaa ctggcactgc cgagcaagta cgtcaacttc ctgtacctgg  3780
caagccacta cgaaaagctg aagggaagcc cggaagacaa cgaacagaag cagctgttcg  3840
tcgaacagca caagcactac ctggacgaaa tcatcgaaca gatcagcgaa ttcagcaaga  3900
gagtcatcct ggcagacgca aacctggaca aggtcctgag cgcatacaac aagcacagag  3960
acaagccgat cagagaacag gcagaaaaca tcatccacct gttcacactg acaaacctgg  4020
gagcaccggc agcattcaag tacttcgaca caacaatcga cagaaagaga tacacaagca  4080
caaaggaagt cctggacgca acactgatcc accagagcat cacaggactg tacgaaacaa  4140
gaatcgacct gagccagctg ggaggagacg gaggaggaag cccgaagaag aagagaaagg  4200
tctagctagc gctcgctttc ttgctgtcca atttctatta aaggttcctt tgttccctaa  4260
gtccaactac taaactgggg gatattatga agggccttga gcatctggat tctgcctaat  4320
aaaaaacatt tattttcatt gcctcgag                                      4348
```

```
SEQ ID NO: 259          moltype = DNA  length = 4325
FEATURE                 Location/Qualifiers
misc_feature            1..4325
                        note = Synthetic: Cas9 transcript with 5 UTR from XBG, ORF
                         corresponding to SEQ ID NO: 204, Kozak sequence, and 3 UTR
                         of XBG
source                  1..4325
                        mol_type = other DNA
                        organism = synthetic construct
SEQUENCE: 259
gggaagctca gaataaacgc tcaactttgg ccggatctgc caccatggac aagaagtaca  60
gcatcggact ggacatcgga acaaacagcg tcggatgggc agtcatcaca gacgaataca  120
aggtcccgag caagaagttc aaggtcctgg gaaacacaga cagacacagc atcaagaaga  180
acctgatcgg agcactgctg ttcgacagcg gagaaacagc agaagcaaca agactgaaga  240
gaacagcaag aagaagatac acaagaagaa agaacagaat ctgctacctg caggaaatct  300
tcagcaacga aatggcaaag gtcgacgaca gcttcttcca cagactggaa gaaagcttcc  360
tggtcgaaga agacaagaag cacgaaagac acccgatctt cggaaacatc gtcgacgaag  420
tcgcatacca cgaaaagtac ccgacaatct accacctgag aaagaagctg gtcgacagca  480
cagacaaggc agacctgaga ctgatctacc tggcactggc acacatgatc aagttcagag  540
gacacttcct gatcgaagga gacctgaacc cggacaacag cgacgtcgac aagctgttca  600
tccagctggt ccagacatac aaccagctgt tcgaagaaaa cccgatcaac gcaagcggag  660
tcgacgcaaa ggcaatcctg agcgcaagac tgagcaagag cagaagactg gaaaacctga  720
tcgcacagct gccgggagaa aagaagaacg gactgttcgg aaacctgatc gcactgagcc  780
tgggactgac accgaacttc aagagcaact tcgacctggc agaagacgca aagctgcagc  840
tgagcaagga cacatacgac gacgacctgg acaacctgct ggcacagatc ggagaccagt  900
acgcagacct gttcctggca gcaaagaacc tgagcgacgc aatcctgctg agcgacatcc  960
tgagagtcaa cacagaaatc acaaaggcac cgctgagcgc aagcatgatc aagagatacg  1020
acgaacacca ccaggacctg acactgctga aggcactggt cagacagcag ctgccggaaa  1080
agtacaagga aatcttcttc gaccagagca agaacggata cgcaggatac atcgacggag  1140
gagcaagcca ggaagaattc tacaagttca tcaagccgat cctggaaaag atggacggaa  1200
cagaagaact gctggtcaag ctgaacagag aagacctgct gagaaagcag agaacattcg  1260
acaacggaag catcccgcac cagatccacc tgggagaact gcacgcaatc ctgagaagac  1320
aggaagactt ctacccgttc ctgaaggaca acagagaaaa gatcgaaaag atcctgacat  1380
tcagaatccc gtactacgtc ggaccgctgg caagaggaaa cagcagattc gcatggatga  1440
caagaaagag cgaagaaaca atcacaccgt ggaacttcga agaagtcgtc gacaagggag  1500
caagcgcaca gagcttcatc gaaagaatga caaacttcga caagaacctg ccgaacgaaa  1560
aggtcctgcc gaagcacagc ctgctgtacg aatacttcac agtctacaac gaactgacaa  1620
aggtcaagta cgtcacagaa ggaatgagaa agccggcatt cctgagcgga gaacagaaga  1680
aggcaatcgt cgacctgctg ttcaagacaa acagaaaggt cacagtcaag cagctgaagg  1740
aagactactt caagaagatc gaatgcttcg acagcgtcga aatcagcgga gtcgaagaca  1800
gattcaacgc aagcctggga acataccacg acctgctgaa gatcatcaag gacaaggact  1860
tcctggacaa cgaagaaaac gaagacatcc tggaagacat cgtcctgaca ctgacactgt  1920
tcgaagacag agaaatgatc gaagaaagac tgaagacata cgcacacctg ttcgacgaca  1980
aggtcatgaa gcagctgaag agaagaagat acacaggatg gggaagactg agcagaaagc  2040
tgatcaacgg aatcagagac aagcagagcg gaaagacaat cctggacttc ctgaagagcg  2100
acggattcgc aaacagaaac ttcatgcagc tgatccacga cgacagcctg acattcaagg  2160
aagacatcca gaaggcacag gtcagcggac agggagacag cctgcacgaa cacatcgcaa  2220
acctggcagg aagcccggca atcaagaagg gaatcctgca gacagtcaag gtcgtcgacg  2280
aactggtcaa ggtcatggga agacacaagc cggaaaacat cgtcatcgaa atggcaagag  2340
aaaaccagac aacacagaag ggacagaaga acagcagaga aagaatgaag agaatcgaag  2400
aaggaatcaa ggaactggga agccagatcc tgaaggaaca cccggtcgaa aacacacagc  2460
tgcagaacga aaagctgtac ctgtactacc tgcagaacgg aagagacatg tacgtcgacc  2520
aggaactgga catcaacaga ctgagcgact acgacgtcga ccacatcgtc ccgcagagct  2580
```

-continued

```
tcctgaagga cgacagcatc gacaacaagg tcctgacaag aagcgacaag aacagaggaa  2640
agagcgacaa cgtcccgagc gaagaagtcg tcaagaagat gaagaactac tggagacagc  2700
tgctgaacgc aaagctgatc acacagagaa agttcgacaa cctgacaaag gcagagagag  2760
gaggactgag cgaactggac aaggcaggat tcatcaagag acagctggtc gaaacaagac  2820
agatcacaaa gcacgtcgca cagatcctgg acagcagaat gaacacaaag tacgacgaaa  2880
acgacaagct gatcagagaa gtcaaggtca tcacactgaa gagcaagctg gtcagcgact  2940
tcagaaagga cttccagttc tacaaggtca gagaaatcaa caactaccac cacgcacacg  3000
acgcatacct gaacgcagtc gtcggaacag cactgatcaa gaagtacccg aagctggaaa  3060
gcgaattcgt ctacggagac tacaaggtct acgacgtcag aaagatgatc gcaaagagcg  3120
aacaggaaat cggaaaggca acagcaaagt acttcttcta cagcaacatc atgaacttct  3180
tcaagacaga aatcacactg gcaaacggag aaatcagaaa gagaccgctg atcgaaacaa  3240
acggagaaac aggagaaatc gtctgggaca agggaagaga cttcgcaaca gtcagaaagg  3300
tcctgagcat gccgcaggtc aacatcgtca agaagacaga agtccagaca ggaggattca  3360
gcaaggaaag catcctgccg aagagaaaca gcgacaagct gatcgcaaga aagaaggact  3420
gggacccgaa gaagtacgga ggattcgaca gcccgacagt cgcatacagc gtcctggtcg  3480
tcgcaaaggt cgaaaaggga aagagcaaga agctgaagag cgtcaaggaa ctgctgggaa  3540
tcacaatcat ggaaagaagc agcttcgaaa agaacccgat cgacttcctg gaagcaaagg  3600
gatacaagga agtcaagaag gacctgatca tcaagctgcc gaagtacagc ctgttcgaac  3660
tggaaaacgg aagaaagaga atgctggcaa gcgcaggaga actgcagaag ggaaacgaac  3720
tggcactgcc gagcaagtac gtcaacttcc tgtacctggc aagccactac gaaaagctga  3780
agggaagccc ggaagacaac gaacagaagc agctgttcgt cgaacagcac aagcactacc  3840
tggacgaaat catcgaacag atcagcgaat tcagcaagag agtcatcctg gcagacgcaa  3900
acctggacaa ggtcctgagc gcatacaaca agcacagaga caagccgatc agagaacagg  3960
cagaaaacat catccacctg ttcacactga caaacctggg agcaccggca gcattcaagt  4020
acttcgacac aacaatcgac agaaagagat acacaagcac aaaggaagtc ctggacgcaa  4080
cactgatcca ccagagcatc acaggactgt acgaaacaag aatcgacctg agccagctgg  4140
gaggagacgg aggaggaagc ccgaagaaga agagaaaggt ctagctagca ccagcctcaa  4200
gaacacccga atggagtctc taagctacat aataccaact tacactttac aaaatgttgt  4260
cccccaaaat gtagccattc gtatctgctc ctaataaaaa gaaagtttct tcacattctc  4320
tcgag                                                             4325
```

```
SEQ ID NO: 260          moltype = DNA  length = 4325
FEATURE                 Location/Qualifiers
misc_feature            1..4325
                        note = Synthetic: Cas9 transcript with AGG as first three
                         nucleotides for use with CleanCapTM, 5 UTR from XBG, ORF
                         corresponding to SEQ ID NO: 204, Kozak sequence, and 3 UTR
                         of XBG
source                  1..4325
                        mol_type = other DNA
                        organism = synthetic construct
SEQUENCE: 260
aggaagctca gaataaacgc tcaactttgg ccggatctgc caccatggac aagaagtaca  60
gcatcggact ggacatcgga acaaacagcg tcggatgggc agtcatcaca gacgaataca  120
aggtcccgag caagaagttc aaggtcctgg gaaacacaga cagacacagc atcaagaaga  180
acctgatcgg agcactgctg ttcgacagcg gagaaacagc agaagcaaca agactgaaga  240
gaacagcaag aagaagatac acaagaagaa agaacagaat ctgctacctg caggaaatct  300
tcagcaacga aatggcaaag gtcgacgaca gcttcttcca cagactggaa gaaagcttcc  360
tggtcgaaga agacaagaag cacgaaagac acccgatctt cggaaacatc gtcgacgaag  420
tcgcatacca cgaaaagtac ccgacaatct accacctgag aaagaagctg gtcgacagca  480
cagacaaggc agacctgaga ctgatctacc tggcactggc acacatgatc aagttcagag  540
gacacttcct gatcgaagga gacctgaacc cggacaacag cgacgtcgac aagctgttca  600
tccagctggt ccagacatac aaccagctgt tcgaagaaaa cccgatcaac gcaagcggag  660
tcgacgcaaa ggcaatcctg agcgcaagac tgagcaagag cagaagactg gaaaacctga  720
tcgcacagct gccgggagaa aagaagaacg gactgttcgg aaacctgatc gcactgagcc  780
tgggactgac accgaacttc aagagcaact tcgacctggc agaagacgca aagctgcagc  840
tgagcaagga cacatacgac gacgacctgg acaacctgct ggcacagatc ggagaccagt  900
acgcagacct gttcctggca gcaaagaacc tgagcgacgc aatcctgctg agcgacatcc  960
tgagagtcaa cacagaaatc acaaaggcac cgctgagcgc aagcatgatc aagagatacg  1020
acgaacacca ccaggacctg acactgctga aggcactggt cagacagcag ctgccggaaa  1080
agtacaagga aatcttcttc gaccagagca agaacggata cgcaggatac atcgacggag  1140
gagcaagcca ggaagaattc tacaagttca tcaagccgat cctggaaaag atggacggaa  1200
cagaagaact gctggtcaag ctgaacagag aagacctgct gagaaagcag agaacattcg  1260
acaacggaag catcccgcac cagatccacc tgggagaact gcacgcaatc ctgagaagac  1320
aggaagactt ctacccgttc ctgaaggaca acagagaaaa gatcgaaaag atcctgacat  1380
tcagaatccc gtactacgtc ggaccgctgg caagaggaaa cagcagattc gcatggatga  1440
caagaaagag cgaagaaaca atcacaccgt ggaacttcga agaagtcgtc gacaagggag  1500
caagcgcaca gagcttcatc gaaagaatga caaacttcga caagaacctg ccgaacgaaa  1560
aggtcctgcc gaagcacagc ctgctgtacg aatacttcac agtctacaac gaactgacaa  1620
aggtcaagta cgtcacagaa ggaatgagaa agccggcatt cctgagcgga gaacagaaga  1680
aggcaatcgt cgacctgctg ttcaagacaa acagaaaggt cacagtcaag cagctgaagg  1740
aagactactt caagaagatc gaatgcttcg acagcgtcga aatcagcgga gtcgaagaca  1800
gattcaacgc aagcctggga acataccacg acctgctgaa gatcatcaag gacaaggact  1860
tcctggacaa cgaagaaaac gaagacatcc tggaagacat cgtcctgaca ctgacactgt  1920
tcgaagacag agaaatgatc gaagaaagac tgaagacata cgcacacctg ttcgacgaca  1980
aggtcatgaa gcagctgaag agaagaagat acacaggatg gggaagactg agcagaaagc  2040
tgatcaacgg aatcagagac aagcagagcg gaaagacaat cctggacttc ctgaagagcg  2100
acggattcgc aaacagaaac ttcatgcagc tgatccacga cgacagcctg acattcaagg  2160
aagacatcca gaaggcacag gtcagcggac agggagacag cctgcacgaa cacatcgcaa  2220
```

-continued

```
acctggcagg aagcccggca atcaagaagg gaatcctgca gacagtcaag gtcgtcgacg  2280
aactggtcaa ggtcatggga agacacaagc cggaaaacat cgtcatcgaa atggcaagag  2340
aaaaccagac aacacagaag ggacagaaga acagcagaga aagaatgaag agaatcgaag  2400
aaggaatcaa ggaactggga agccagatcc tgaaggaaca cccggtcgaa aacacacagc  2460
tgcagaacga aaagctgtac ctgtactacc tgcagaacgg aagagacatg tacgtcgacc  2520
aggaactgga catcaacaga ctgagcgact acgacgtcga ccacatcgtc ccgcagagct  2580
tcctgaagga cgacagcatc gacaacaagg tcctgacaag aagcgacaag aacagaggaa  2640
agagcgacaa cgtcccgagc gaagaagtcg tcaagaagat gaagaactac tggagacagc  2700
tgctgaacgc aaagctgatc acacagagaa agttcgacaa cctgacaaag gcagagagag  2760
gaggactgag cgaactggac aaggcaggat tcatcaagag acagctggtc gaaacaagac  2820
agatcacaaa gcacgtcgca cagatcctgg acagcagaat gaacacaaag tacgacgaaa  2880
acgacaagct gatcagagaa gtcaaggtca tcacactgaa gagcaagctg gtcagcgact  2940
tcagaaagga cttccagttc tacaaggtca gagaaatcaa caactaccac cacgcacacg  3000
acgcatacct gaacgcagtc gtcggaacag cactgatcaa gaagtacccg aagctggaaa  3060
gcgaattcgt ctacggagac tacaaggtct acgacgtcag aaagatgatc gcaaagagcg  3120
aacaggaaat cggaaaggca acagcaaagt acttcttcta cagcaacatc atgaacttct  3180
tcaagacaga aatcacactg gcaaacggag aaatcagaaa gagaccgctg atcgaaacaa  3240
acggagaaac aggagaaatc gtctgggaca agggaagaga cttcgcaaca gtcagaaagg  3300
tcctgagcat gccgcaggtc aacatcgtca agaagacaga agtccagaca ggaggattca  3360
gcaaggaaag catcctgccg aagagaaaca gcgacaagct gatcgcaaga aagaaggact  3420
gggacccgaa gaagtacgga ggattcgaca gcccgacagt cgcatacagc gtcctggtcg  3480
tcgcaaaggt cgaaaaggga aagagcaaga agctgaagag cgtcaaggaa ctgctgggaa  3540
tcacaatcat ggaaagaagc agcttcgaaa agaacccgat cgacttcctg gaagcaaagg  3600
gatacaagga agtcaagaag gacctgatca tcaagctgcc gaagtacagc ctgttcgaac  3660
tggaaaacgg aagaaagaga atgctggcaa gcgcaggaga actgcagaag ggaaacgaac  3720
tggcactgcc gagcaagtac gtcaacttcc tgtacctggc aagccactac gaaaagctga  3780
agggaagccc ggaagacaac gaacagaagc agctgttcgt cgaacagcac aagcactacc  3840
tggacgaaat catcgaacag atcagcgaat tcagcaagag agtcatcctg gcagacgcaa  3900
acctggacaa ggtcctgagc gcatacaaca agcacagaga caagccgatc agagaacagg  3960
cagaaaacat catccacctg ttcacactga caaacctggg agcaccggca gcattcaagt  4020
acttcgacac aacaatcgac agaaagagat acacaagcac aaaggaagtc ctggacgcaa  4080
cactgatcca ccagagcatc acaggactgt acgaaacaag aatcgacctg agccagctgg  4140
gaggagacgg aggaggaagc ccgaagaaga agagaaaggt ctagctagca ccagcctcaa  4200
gaacacccga atggagtctc taagctacat aataccaact tacactttac aaaatgttgt  4260
cccccaaaat gtagccattc gtatctgctc ctaataaaaa gaaagtttct tcacattctc  4320
tcgag                                                             4325
```

```
SEQ ID NO: 261         moltype = DNA  length = 4411
FEATURE                Location/Qualifiers
misc_feature           1..4411
                       note = Synthetic: Cas9 transcript with AGG as first three
                        nucleotides for use with CleanCapTM, 5 UTR from HSD, ORF
                        corresponding to SEQ ID NO: 204, Kozak sequence, and 3 UTR
                        of ALB
source                 1..4411
                       mol_type = other DNA
                       organism = synthetic construct
SEQUENCE: 261
aggtcccgca gtcggcgtcc agcggctctg cttgttcgtg tgtgtgtcgt tgcaggcctt  60
attcggatcc gccaccatgg acaagaagta cagcatcgga ctggacatcg gaacaaacag  120
cgtcggatgg gcagtcatca cagacgaata caaggtcccg agcaagaagt tcaaggtcct  180
gggaaacaca gacagacaca gcatcaagaa gaacctgatc ggagcactgc tgttcgacag  240
cggagaaaca gcagaagcaa caagactgaa gagaacagca agaagaagat acacaagaag  300
aaagaacaga atctgctacc tgcaggaaat cttcagcaac gaaatggcaa aggtcgacga  360
cagcttcttc cacagactgg aagaaagctt cctggtcgaa gaagacaaga agcacgaaag  420
acacccgatc ttcggaaaca tcgtcgacga agtcgcatac cacgaaaagt acccgacaat  480
ctaccacctg agaaagaagc tggtcgacag cacagacaag gcagacctga gactgatcta  540
cctggcactg gcacacatga tcaagttcag aggacacttc ctgatcgaag gagacctgaa  600
cccggacaac agcgacgtcg acaagctgtt catccagctg gtccagacat acaaccagct  660
gttcgaagaa aacccgatca acgcaagcgg agtcgacgca aaggcaatcc tgagcgcaag  720
actgagcaag agcagaagac tggaaaacct gatcgcacag ctgccgggag aaaagaagaa  780
cggactgttc ggaaacctga tcgcactgag cctgggactg acaccgaact tcaagagcaa  840
cttcgacctg gcagaagacg caaagctgca gctgagcaag gacacatacg acgacgacct  900
ggacaacctg ctggcacaga tcggagacca gtacgcagac ctgttcctgg cagcaaagaa  960
cctgagcgac gcaatcctgc tgagcgacat cctgagagtc aacacagaaa tcacaaaggc  1020
accgctgagc gcaagcatga tcaagagata cgacgaacac caccaggacc tgacactgct  1080
gaaggcactg gtcagacagc agctgccgga aaagtacaag gaaatcttct tcgaccagag  1140
caagaacgga tacgcaggat acatcgacgg aggagcaagc caggaagaat tctacaagtt  1200
catcaagccg atcctggaaa agatggacgg aacagaagaa ctgctggtca agctgaacag  1260
agaagacctg ctgagaaagc agagaacatt cgacaacgga agcatcccgc accagatcca  1320
cctgggagaa ctgcacgcaa tcctgagaag acaggaagac ttctacccgt tcctgaagga  1380
caacagagaa aagatcgaaa agatcctgac attcagaatc ccgtactacg tcggaccgct  1440
ggcaagagga aacagcagat tcgcatggat gacaagaaag agcgaagaaa caatcacacc  1500
gtggaacttc gaagaagtcg tcgacaaggg agcaagcgca cagagcttca tcgaaagaat  1560
gacaaacttc gacaagaacc tgccgaacga aaaggtcctg ccgaagcaca gcctgctgta  1620
cgaatacttc acagtctaca acgaactgac aaaggtcaag tacgtcacag aaggaatgag  1680
aaagccggca ttcctgagcg gagaacagaa gaaggcaatc gtcgacctgc tgttcaagac  1740
aaacagaaag gtcacagtca agcagctgaa ggaagactac ttcaagaaga tcgaatgctt  1800
cgacagcgtc gaaatcagcg gagtcgaaga cagattcaac gcaagcctgg gaacatacca  1860
```

-continued

```
cgacctgctg aagatcatca aggacaagga cttcctggac aacgaagaaa acgaagacat  1920
cctggaagac atcgtcctga cactgacact gttcgaagac agagaaatga tcgaagaaag  1980
actgaagaca tacgcacacc tgttcgacga caaggtcatg aagcagctga agagaagaag  2040
atacacagga tggggaagac tgagcagaaa gctgatcaac ggaatcagag acaagcagag  2100
cggaaagaca atcctggact tcctgaagag cgacggattc gcaaacagaa acttcatgca  2160
gctgatccac gacgacagcc tgacattcaa ggaagacatc cagaaggcac aggtcagcgg  2220
acagggagac agcctgcacg aacacatcgc aaacctggca ggaagcccgg caatcaagaa  2280
gggaatcctg cagacagtca aggtcgtcga cgaactggtc aaggtcatgg gaagacacaa  2340
gccggaaaac atcgtcatcg aaatggcaag agaaaaccag acaacacaga agggacagaa  2400
gaacagcaga gaaagaatga agagaatcga agaaggaatc aaggaactgg gaagccagat  2460
cctgaaggaa cacccggtcg aaaacacaca gctgcagaac gaaaagctgt acctgtacta  2520
cctgcagaac ggaagagaca tgtacgtcga ccaggaactg gacatcaaca gactgagcga  2580
ctacgacgtc gaccacatcg tcccgcagag cttcctgaag gacgacagca tcgacaacaa  2640
ggtcctgaca agaagcgaca agaacagagg aaagagcgac aacgtcccga gcgaagaagt  2700
cgtcaagaag atgaagaact actggagaca gctgctgaac gcaaagctga tcacacagag  2760
aaagttcgac aacctgacaa aggcagagag aggaggactg agcgaactgg acaaggcagg  2820
attcatcaag agacagctgg tcgaaacaag acagatcaca aagcacgtcg cacagatcct  2880
ggacagcaga atgaacacaa agtacgacga aaacgacaag ctgatcagag aagtcaaggt  2940
catcacactg aagagcaagc tggtcagcga cttcagaaag gacttccagt tctacaaggt  3000
cagagaaatc aacaactacc accacgcaca cgacgcatac ctgaacgcag tcgtcggaac  3060
agcactgatc aagaagtacc cgaagctgga aagcgaattc gtctacggag actacaaggt  3120
ctacgacgtc agaaagatga tcgcaaagag cgaacaggaa atcggaaagg caacagcaaa  3180
gtacttcttc tacagcaaca tcatgaactt cttcaagaca gaaatcacac tggcaaacgg  3240
agaaatcaga aagagaccgc tgatcgaaac aaacggagaa acaggagaaa tcgtctggga  3300
caagggaaga gacttcgcaa cagtcagaaa ggtcctgagc atgccgcagg tcaacatcgt  3360
caagaagaca gaagtccaga caggaggatt cagcaaggaa agcatcctgc cgaagagaaa  3420
cagcgacaag ctgatcgcaa gaaagaagga ctgggacccg aagaagtacg gaggattcga  3480
cagcccgaca gtcgcataca gcgtcctggt cgtcgcaaag gtcgaaaagg gaaagagcaa  3540
gaagctgaag agcgtcaagg aactgctggg aatcacaatc atggaaagaa gcagcttcga  3600
aaagaacccg atcgacttcc tggaagcaaa gggatacaag gaagtcaaga aggacctgat  3660
catcaagctg ccgaagtaca gcctgttcga actggaaaac ggaagaaaga gaatgctggc  3720
aagcgcagga gaactgcaga agggaaacga actggcactg ccgagcaagt acgtcaactt  3780
cctgtacctg gcaagccact acgaaaagct gaagggaagc ccggaagaca acgaacagaa  3840
gcagctgttc gtcgaacagc acaagcacta cctggacgaa atcatcgaac agatcagcga  3900
attcagcaag agagtcatcc tggcagacgc aaacctggac aaggtcctga gcgcatacaa  3960
caagcacaga gacaagccga tcagagaaca ggcagaaaac atcatccacc tgttcacact  4020
gacaaacctg ggagcaccgg cagcattcaa gtacttcgac acaacaatcg acagaaagag  4080
atacacaagc acaaaggaag tcctggacgc aacactgatc caccagagca tcacaggact  4140
gtacgaaaca agaatcgacc tgagccagct gggaggagac ggaggaggaa gcccgaagaa  4200
gaagagaaag gtctagctag ccatcacatt taaaagcatc tcagcctacc atgagaataa  4260
gagaaagaaa atgaagatca atagcttatt catctctttt tctttttcgt tggtgtaaag  4320
ccaacaccct gtctaaaaaa cataaatttc tttaatcatt ttgcctcttt tctctgtgct  4380
tcaattaata aaaaatggaa agaacctcga g                                 4411
```

```
SEQ ID NO: 262         moltype = RNA  length = 105
FEATURE                Location/Qualifiers
misc_feature           1..105
                       note = Synthetic: 30/30/39 poly-A sequence
source                 1..105
                       mol_type = other RNA
                       organism = synthetic construct
SEQUENCE: 262
aaaaaaaaaa aaaaaaaaaa aaaaaaaaaa gcgaaaaaaa aaaaaaaaaa aaaaaaaaaa  60
aaaccgaaaa aaaaaaaaaa aaaaaaaaaa aaaaaaaaaa aaaaa                 105
```

```
SEQ ID NO: 263         moltype = RNA  length = 93
FEATURE                Location/Qualifiers
misc_feature           1..93
                       note = Synthetic: poly-A 100 sequence
source                 1..93
                       mol_type = other RNA
                       organism = synthetic construct
SEQUENCE: 263
aaaaaaaaaa aaaaaaaaaa aaaaaaaaaa aaaaaaaaaa aaaaaaaaaa aaaaaaaaaa  60
aaaaaaaaaa aaaaaaaaaa aaaaaaaaaa aaa                               93
```

```
SEQ ID NO: 264         moltype = RNA  length = 100
FEATURE                Location/Qualifiers
misc_feature           1..100
                       note = Synthetic: G209 guide RNA
modified_base          1..3
                       mod_base = OTHER
                       note = 2'-O-methylation
modified_base          1..4
                       mod_base = OTHER
                       note = Phosphorothioate internucleoside linkage
modified_base          29..40
                       mod_base = OTHER
                       note = 2'-O-methylation
```

```
modified_base          69..100
                       mod_base = OTHER
                       note = 2'-O-methylation
modified_base          97..100
                       mod_base = OTHER
                       note = Phosphorothioate internucleoside linkage
source                 1..100
                       mol_type = other RNA
                       organism = synthetic construct
SEQUENCE: 264
ccagtccagc gaggcaaagg gttttagagc tagaaatagc aagttaaaat aaggctagtc  60
cgttatcaac ttgaaaaagt ggcaccgagt cggtgctttt                        100

SEQ ID NO: 265         moltype =   length =
SEQUENCE: 265
000

SEQ ID NO: 266         moltype =   length =
SEQUENCE: 266
000

SEQ ID NO: 267         moltype =   length =
SEQUENCE: 267
000

SEQ ID NO: 268         moltype = AA  length = 1103
FEATURE                Location/Qualifiers
REGION                 1..1103
                       note = misc_feature - Amino acid sequence of Neisseria
                        meningitidis Cas9
source                 1..1103
                       mol_type = protein
                       organism = Neisseria meningitidis
SEQUENCE: 268
MAAFKPNSIN YILGLDIGIA SVGWAMVEID EEENPIRLID LGVRVFERAE VPKTGDSLAM  60
ARRLARSVRR LTRRRAHRLL RTRRLLKREG VLQAANFDEN GLIKSLPNTP WQLRAAALDR  120
KLTPLEWSAV LLHLIKHRGY LSQRKNEGET ADKELGALLK GVAGNAHALQ TGDFRTPAEL  180
ALNKFEKESG HIRNQRSDYS HTFSRKDLQA ELILLFEKQK EFGNPHVSGG LKEGIETLLM  240
TQRPALSGDA VQKMLGHCTF EPAEPKAAKN TYTAERFIWL TKLNNLRILE QGSERPLTDT  300
ERATLMDEPY RKSKLTYAQA RKLLGLEDTA FFKGLRYGKD NAEASTLMEM KAYHAISRAL  360
EKEGLKDKKS PLNLSPELQD EIGTAFSLFK TDEDITGRLK DRIQPEILEA LLKHISFDKF  420
VQISLKALRR IVPLMEQGKR YDEACAEIYG DHYGKKNTEE KIYLPPIPAD EIRNPVVLRA  480
LSQARKVING VVRRYGSPAR IHIETAREVG KSFKDRKEIE KRQEENRKDR EKAAAKFREY  540
FPNFVGEPKS KDILKLRLYE QQHGKCLYSG KEINLGRLNE KGYVEIDHAL PFSRTWDDSF  600
NNKVLVLGSE NQNKGNQTPY EYFNGKDNSR EWQEFKARVE TSRFPRSKKQ RILLQKFDED  660
GFKERNLNDT RYVNRFLCQF VADRMRLTGK GKKRVFASNG QITNLLRGFW GLRKVRAEND  720
RHHALDAVVV ACSTVAMQQK ITRFVRYKEM NAFDGKTIDK ETGEVLHQKT HFPQPWEFFA  780
QEVMIRVFGK PDGKPEFEEA DTLEKLRTLL AEKLSSRPEA VHEYVTPLFV SRAPNRKMSG  840
QGHMETVKSA KRLDEGVSVL RVPLTQLKLK DLEKMVNRER EPKLYEALKA RLEAHKDDPA  900
KAFAEPFYKY DKAGNRTQQV KAVRVEQVQK TGVWVRNHNG IADNATMVRV DVFEKGDKYY  960
LVPIYSWQVA KGILPDRAVV QGKDEEDWQL IDDSFNFKFS LHPNDLVEVI TKKARMFGYF  1020
ASCHRGTGNI NIRIHDLDHK IGKNGILEGI GVKTALSFQK YQIDELGKEI RPCRLKKRPP  1080
VRSGKRTADG SEFESPKKKR KVE                                          1103

SEQ ID NO: 269         moltype =   length =
SEQUENCE: 269
000

SEQ ID NO: 270         moltype = RNA  length = 100
FEATURE                Location/Qualifiers
misc_feature           1..100
                       note = Synthetic: G502 guide RNA
modified_base          1..3
                       mod_base = OTHER
                       note = 2'-O-methylation
modified_base          1..4
                       mod_base = OTHER
                       note = Phosphorothioate internucleoside linkage
modified_base          29..40
                       mod_base = OTHER
                       note = 2'-O-methylation
modified_base          69..100
                       mod_base = OTHER
                       note = 2'-O-methylation
modified_base          97..100
                       mod_base = OTHER
                       note = Phosphorothioate internucleoside linkage
source                 1..100
                       mol_type = other RNA
```

-continued

```
                        organism = synthetic construct
SEQUENCE: 270
acacaaatac cagtccagcg gttttagagc tagaaatagc aagttaaaat aaggctagtc  60
cgttatcaac ttgaaaaagt ggcaccgagt cggtgctttt                        100

SEQ ID NO: 271          moltype =   length =
SEQUENCE: 271
000

SEQ ID NO: 272          moltype =   length =
SEQUENCE: 272
000

SEQ ID NO: 273          moltype = DNA  length = 3783
FEATURE                 Location/Qualifiers
misc_feature            1..3783
                        note = Synthetic: DNA coding sequence of eGFP
source                  1..3783
                        mol_type = other DNA
                        organism = synthetic construct
SEQUENCE: 273
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcaggcgcc  240
attcgccatt caggctgcgc aactgttggg aagggcgatc ggtgcgggcc tcttcgctat  300
tacgccagct ggcgaaaggg ggatgtgctg caaggcgatt aagttgggta acgccagggt  360
tttcccagtc acgacgttgt aaaacgacgg ccagtgaatt ctaatacgac tcactatagg  420
gtcccgcagt cggcgtccag cggctctgct tgttcgtgtg tgtgtcgttg caggccttat  480
tcggatccat ggtgagcaag ggcgaggagc tgttcaccgg ggtggtgccc atcctggtcg  540
agctggacgg cgacgtaaac ggccacaagt tcagcgtgtc cggcgagggc gagggcgatg  600
ccacctacgg caagctgacc ctgaagttca tctgcaccac cggcaagctg cccgtgccct  660
ggcccaccct cgtgaccacc ctgacctacg gcgtgcagtg cttcagccgc taccccgacc  720
acatgaagca gcacgacttc ttcaagtccg ccatgcccga aggctacgtc caggagcgca  780
ccatcttctt caaggacgac ggcaactaca agacccgcgc cgaggtgaag ttcgagggcg  840
acaccctggt gaaccgcatc gagctgaagg gcatcgactt caaggaggac ggcaacatcc  900
tggggcacaa gctggagtac aactacaaca gccacaacgt ctatatcatg gccgacaagc  960
agaagaacgg catcaaggtg aacttcaaga tccgccacaa catcgaggac ggcagcgtgc  1020
agctcgccga ccactaccag cagaacaccc ccatcggcga cggccccgtg ctgctgcccg  1080
acaaccacta cctgagcacc cagtccgccc tgagcaaaga ccccaacgag aagcgcgatc  1140
acatggtcct gctggagttc gtgaccgccg ccgggatcac tctcggcatg gacgagctgt  1200
acaagtaata ggaattatgc agtctagcca tcacatttaa aagcatctca gcctaccatg  1260
agaataagag aaagaaaatg aagatcaata gcttattcat ctcttttct ttttcgttgg  1320
tgtaaagcca acaccctgtc taaaaaacat aaatttcttt aatcattttg cctcttttct  1380
ctgtgcttca attaataaaa aatggaaaga acctcgagaa aaaaaaaaaa aaaaaaaaaa  1440
aaaaaaaaaa aaaaaaaaaa aaaaaaaaaa aaaaaaaaaa aaaaaaaaaa aaaaaaaaaa  1500
aaaaaaaaaa aaaaaaaatc tagacttaag cttgatgagc tctagcttgg cgtaatcatg  1560
gtcatagctg tttcctgtgt gaaattgtta tccgctcaca attccacaca acatacgagc  1620
cggaagcata aagtgtaaag cctggggtgc ctaatgagtg agctaactca cattaattgc  1680
gttgcgctca ctgcccgctt tccagtcggg aaacctgtcg tgccagctgc attaatgaat  1740
cggccaacgc gcggggagag gcggtttgcg tattgggcgc tcttccgctt cctcgctcac  1800
tgactcgctg cgctcggtcg ttcggctgcg gcgagcggta tcagctcact caaaggcggt  1860
aatacggtta tccacagaat caggggataa cgcaggaaag aacatgtgag caaaaggcca  1920
gcaaaaggcc aggaaccgta aaaaggccgc gttgctggcg tttttccata ggctccgccc  1980
ccctgacgag catcacaaaa atcgacgctc aagtcagagg tggcgaaacc cgacaggact  2040
ataaagatac caggcgtttc cccctggaag ctccctcgtg cgctctcctg ttccgaccct  2100
gccgcttacc ggatacctgt ccgcctttct cccttcggga agcgtggcgc tttctcatag  2160
ctcacgctgt aggtatctca gttcggtgta ggtcgttcgc tccaagctgg gctgtgtgca  2220
cgaacccccc gttcagcccg accgctgcgc cttatccggt aactatcgtc ttgagtccaa  2280
cccggtaaga cacgacttat cgccactggc agcagccact ggtaacagga ttagcagagc  2340
gaggtatgta ggcggtgcta cagagttctt gaagtggtgg cctaactacg gctacactag  2400
aagaacagta tttggtatct gcgctctgct gaagccagtt accttcggaa aaagagttgg  2460
tagctcttga tccggcaaac aaaccaccgc tggtagcggt ggtttttttg tttgcaagca  2520
gcagattacg cgcagaaaaa aaggatctca agaagatcct ttgatctttt ctacggggtc  2580
tgacgctcag tggaacgaaa actcacgtta agggattttg gtcatgagat tatcaaaaag  2640
gatcttcacc tagatccttt taaattaaaa atgaagtttt aaatcaatct aaagtatata  2700
tgagtaaact tggtctgaca gttaccaatg cttaatcagt gaggcaccta tctcagcgat  2760
ctgtctattt cgttcatcca tagttgcctg actccccgtc gtgtagataa ctacgatacg  2820
ggagggctta ccatctggcc ccagtgctgc aatgataccg cgagacccac gctcaccggc  2880
tccagattta tcagcaataa accagccagc cggaagggcc gagcgcagaa gtggtcctgc  2940
aactttatcc gcctccatcc agtctattaa ttgttgccgg gaagctagag taagtagttc  3000
gccagttaat agtttgcgca acgttgttgc cattgctaca ggcatcgtgg tgtcacgctc  3060
gtcgtttggt atggcttcat tcagctccgg ttcccaacga tcaaggcgag ttacatgatc  3120
ccccatgttg tgcaaaaaag cggttagctc cttcggtcct ccgatcgttg tcagaagtaa  3180
gttggccgca gtgttatcac tcatggttat ggcagcactg cataattctc ttactgtcat  3240
gccatccgta agatgctttt ctgtgactgg tgagtactca accaagtcat tctgagaata  3300
gtgtatgcgg cgaccgagtt gctcttgccc ggcgtcaata cgggataata ccgcgccaca  3360
tagcagaact ttaaaagtgc tcatcattgg aaaacgttct tcggggcgaa aactctcaag  3420
gatcttaccg ctgttgagat ccagttcgat gtaacccact cgtgcaccca actgatcttc  3480
```

-continued

```
agcatctttt actttcacca gcgtttctgg gtgagcaaaa acaggaaggc aaaatgccgc  3540
aaaaaaggga ataagggcga cacggaaatg ttgaatactc atactcttcc tttttcaata  3600
ttattgaagc atttatcagg gttattgtct catgagcgga tacatatttg aatgtattta  3660
gaaaaataaa caaatagggg ttccgcgcac atttccccga aaagtgccac ctgacgtcta  3720
agaaaccatt attatcatga cattaaccta taaaaatagg cgtatcacga ggccctttcg  3780
tcg                                                                3783

SEQ ID NO: 274          moltype = RNA  length = 100
FEATURE                 Location/Qualifiers
misc_feature            1..100
                        note = Synthetic: Modified sgRNA pattern, where N are
                         nucleotides encoding a guide sequence
variation               1..20
                        note = n is a, c, g, or u
modified_base           1..3
                        mod_base = OTHER
                        note = 2'-O-methylation
modified_base           1..4
                        mod_base = OTHER
                        note = Phosphorothioate internucleoside linkage
modified_base           29..40
                        mod_base = OTHER
                        note = 2'-O-methylation
modified_base           69..100
                        mod_base = OTHER
                        note = 2'-O-methylation
modified_base           97..100
                        mod_base = OTHER
                        note = Phosphorothioate internucleoside linkage
source                  1..100
                        mol_type = other RNA
                        organism = synthetic construct
SEQUENCE: 274
nnnnnnnnnn nnnnnnnnnn gttttagagc tagaaatagc aagttaaaat aaggctagtc  60
cgttatcaac ttgaaaaagt ggcaccgagt cggtgctttt                        100

SEQ ID NO: 275          moltype = DNA  length = 42
FEATURE                 Location/Qualifiers
misc_feature            1..42
                        note = Synthetic: CMV-1 5 UTR
source                  1..42
                        mol_type = other DNA
                        organism = synthetic construct
SEQUENCE: 275
cagatcgcct ggagacgcca tccacgctgt tttgacctcc at                     42

SEQ ID NO: 276          moltype = DNA  length = 42
FEATURE                 Location/Qualifiers
misc_feature            1..42
                        note = Synthetic: CMV-2 5 UTR
source                  1..42
                        mol_type = other DNA
                        organism = synthetic construct
SEQUENCE: 276
agaagacacc gggaccgatc cagcctccgc ggccgggaac gg                     42

SEQ ID NO: 277          moltype = DNA  length = 42
FEATURE                 Location/Qualifiers
misc_feature            1..42
                        note = Synthetic: CMV-3 5 UTR
source                  1..42
                        mol_type = other DNA
                        organism = synthetic construct
SEQUENCE: 277
tgcattggaa cgcggattcc ccgtgccaag agtgactcac cg                     42

SEQ ID NO: 278          moltype = AA  length = 7
FEATURE                 Location/Qualifiers
REGION                  1..7
                        note = Synthetic: SV40 NLS
source                  1..7
                        mol_type = protein
                        organism = synthetic construct
SEQUENCE: 278
PKKKRKV                                                            7

SEQ ID NO: 279          moltype = AA  length = 9
FEATURE                 Location/Qualifiers
REGION                  1..9
```

```
                        note = Synthetic: Exemplary NLS 1
source                  1..9
                        mol_type = protein
                        organism = synthetic construct
SEQUENCE: 279
LAAKRSRTT                                                        9

SEQ ID NO: 280          moltype = AA  length = 9
FEATURE                 Location/Qualifiers
REGION                  1..9
                        note = Synthetic: Exemplary NLS 2
source                  1..9
                        mol_type = protein
                        organism = synthetic construct
SEQUENCE: 280
QAAKRSRTT                                                        9

SEQ ID NO: 281          moltype = AA  length = 10
FEATURE                 Location/Qualifiers
REGION                  1..10
                        note = Synthetic: Exemplary NLS 3
source                  1..10
                        mol_type = protein
                        organism = synthetic construct
SEQUENCE: 281
PAPAKRERTT                                                       10

SEQ ID NO: 282          moltype = AA  length = 9
FEATURE                 Location/Qualifiers
REGION                  1..9
                        note = Synthetic: Exemplary NLS 4
source                  1..9
                        mol_type = protein
                        organism = synthetic construct
SEQUENCE: 282
QAAKRPRTT                                                        9

SEQ ID NO: 283          moltype = AA  length = 9
FEATURE                 Location/Qualifiers
REGION                  1..9
                        note = Synthetic: Exemplary NLS 5
source                  1..9
                        mol_type = protein
                        organism = synthetic construct
SEQUENCE: 283
RAAKRPRTT                                                        9

SEQ ID NO: 284          moltype = AA  length = 11
FEATURE                 Location/Qualifiers
REGION                  1..11
                        note = Synthetic: Exemplary NLS 6
source                  1..11
                        mol_type = protein
                        organism = synthetic construct
SEQUENCE: 284
AAAKRSWSMA A                                                     11

SEQ ID NO: 285          moltype = AA  length = 11
FEATURE                 Location/Qualifiers
REGION                  1..11
                        note = Synthetic: Exemplary NLS 7
source                  1..11
                        mol_type = protein
                        organism = synthetic construct
SEQUENCE: 285
AAAKRVWSMA F                                                     11

SEQ ID NO: 286          moltype = AA  length = 11
FEATURE                 Location/Qualifiers
REGION                  1..11
                        note = Synthetic: Exemplary NLS 8
source                  1..11
                        mol_type = protein
                        organism = synthetic construct
SEQUENCE: 286
AAAKRSWSMA F                                                     11

SEQ ID NO: 287          moltype = AA  length = 10
FEATURE                 Location/Qualifiers
```

-continued

```
REGION               1..10
                     note = Synthetic: Exemplary NLS 9
source               1..10
                     mol_type = protein
                     organism = synthetic construct
SEQUENCE: 287
AAAKRKYFAA                                                    10

SEQ ID NO: 288       moltype = AA  length = 10
FEATURE              Location/Qualifiers
REGION               1..10
                     note = Synthetic: Exemplary NLS 10
source               1..10
                     mol_type = protein
                     organism = synthetic construct
SEQUENCE: 288
RAAKRKAFAA                                                    10

SEQ ID NO: 289       moltype = AA  length = 10
FEATURE              Location/Qualifiers
REGION               1..10
                     note = Synthetic: Exemplary NLS 11
source               1..10
                     mol_type = protein
                     organism = synthetic construct
SEQUENCE: 289
RAAKRKYFAV                                                    10

SEQ ID NO: 290       moltype = AA  length = 7
FEATURE              Location/Qualifiers
REGION               1..7
                     note = Synthetic: Alternate SV40 NLS
source               1..7
                     mol_type = protein
                     organism = synthetic construct
SEQUENCE: 290
PKKKRRV                                                       7

SEQ ID NO: 291       moltype = AA  length = 16
FEATURE              Location/Qualifiers
REGION               1..16
                     note = Synthetic: Nucleoplasmin NLS
source               1..16
                     mol_type = protein
                     organism = synthetic construct
SEQUENCE: 291
KRPAATKKAG QAKKKK                                             16

SEQ ID NO: 292       moltype = DNA  length = 21
FEATURE              Location/Qualifiers
misc_feature         1..21
                     note = Synthetic: Exemplary coding sequence for SV40 NLS
source               1..21
                     mol_type = other DNA
                     organism = synthetic construct
SEQUENCE: 292
ccgaagaaga agagaaaggt c                                       21

SEQ ID NO: 293       moltype = DNA  length = 27
FEATURE              Location/Qualifiers
misc_feature         1..27
                     note = Synthetic: Exemplary coding sequence for NLS1
source               1..27
                     mol_type = other DNA
                     organism = synthetic construct
SEQUENCE: 293
ctggcagcaa agagaagcag aacaaca                                 27

SEQ ID NO: 294       moltype = DNA  length = 27
FEATURE              Location/Qualifiers
misc_feature         1..27
                     note = Synthetic: Exemplary coding sequence for NLS2
source               1..27
                     mol_type = other DNA
                     organism = synthetic construct
SEQUENCE: 294
caggcagcaa agagaagcag aacaaca                                 27

SEQ ID NO: 295       moltype = DNA  length = 30
```

-continued

```
FEATURE                Location/Qualifiers
misc_feature           1..30
                       note = Synthetic: Exemplary coding sequence for NLS3
source                 1..30
                       mol_type = other DNA
                       organism = synthetic construct
SEQUENCE: 295
ccggcaccgg caaagagaga aagaacaaca                                   30

SEQ ID NO: 296         moltype = DNA  length = 27
FEATURE                Location/Qualifiers
misc_feature           1..27
                       note = Synthetic: Exemplary coding sequence for NLS4
source                 1..27
                       mol_type = other DNA
                       organism = synthetic construct
SEQUENCE: 296
caggcagcaa agagaccgag aacaaca                                      27

SEQ ID NO: 297         moltype = DNA  length = 27
FEATURE                Location/Qualifiers
misc_feature           1..27
                       note = Synthetic: Exemplary coding sequence for NLS5
source                 1..27
                       mol_type = other DNA
                       organism = synthetic construct
SEQUENCE: 297
agagcagcaa agagaccgag aacaaca                                      27

SEQ ID NO: 298         moltype = DNA  length = 33
FEATURE                Location/Qualifiers
misc_feature           1..33
                       note = Synthetic: Exemplary coding sequence for NLS6
source                 1..33
                       mol_type = other DNA
                       organism = synthetic construct
SEQUENCE: 298
gcagcagcaa agagaagctg gagcatggca gca                               33

SEQ ID NO: 299         moltype = DNA  length = 33
FEATURE                Location/Qualifiers
misc_feature           1..33
                       note = Synthetic: Exemplary coding sequence for NLS7
source                 1..33
                       mol_type = other DNA
                       organism = synthetic construct
SEQUENCE: 299
gcagcagcaa agagagtctg gagcatggca ttc                               33

SEQ ID NO: 300         moltype = DNA  length = 33
FEATURE                Location/Qualifiers
misc_feature           1..33
                       note = Synthetic: Exemplary coding sequence for NLS8
source                 1..33
                       mol_type = other DNA
                       organism = synthetic construct
SEQUENCE: 300
gcagcagcaa agagaagctg gagcatggca ttc                               33

SEQ ID NO: 301         moltype = DNA  length = 30
FEATURE                Location/Qualifiers
misc_feature           1..30
                       note = Synthetic: Exemplary coding sequence for NLS9
source                 1..30
                       mol_type = other DNA
                       organism = synthetic construct
SEQUENCE: 301
gcagcagcaa agagaaagta cttcgcagca                                   30

SEQ ID NO: 302         moltype = DNA  length = 30
FEATURE                Location/Qualifiers
misc_feature           1..30
                       note = Synthetic: Exemplary coding sequence for NLS10
source                 1..30
                       mol_type = other DNA
                       organism = synthetic construct
SEQUENCE: 302
agagcagcaa agagaaaggc attcgcagca                                   30
```

```
SEQ ID NO: 303         moltype = DNA  length = 30
FEATURE                Location/Qualifiers
misc_feature           1..30
                       note = Synthetic: Exemplary coding sequence for NLS11
source                 1..30
                       mol_type = other DNA
                       organism = synthetic construct
SEQUENCE: 303
agagcagcaa agagaaagta cttcgcagtc                                   30

SEQ ID NO: 304         moltype = DNA  length = 21
FEATURE                Location/Qualifiers
misc_feature           1..21
                       note = Synthetic: Exemplary coding sequence for alternate
                        SV40 NLS
source                 1..21
                       mol_type = other DNA
                       organism = synthetic construct
SEQUENCE: 304
ccgaagaaga agagaagagt c                                            21

SEQ ID NO: 305         moltype = RNA  length = 13
FEATURE                Location/Qualifiers
misc_feature           1..13
                       note = Synthetic: exemplary Kozak sequence
source                 1..13
                       mol_type = other RNA
                       organism = synthetic construct
SEQUENCE: 305
gccgccrcca tgg                                                     13

SEQ ID NO: 306         moltype =   length =
SEQUENCE: 306
000

SEQ ID NO: 307         moltype =   length =
SEQUENCE: 307
000

SEQ ID NO: 308         moltype =   length =
SEQUENCE: 308
000

SEQ ID NO: 309         moltype =   length =
SEQUENCE: 309
000

SEQ ID NO: 310         moltype =   length =
SEQUENCE: 310
000

SEQ ID NO: 311         moltype = DNA  length = 4140
FEATURE                Location/Qualifiers
misc_feature           1..4140
                       note = Synthetic: Cas9 ORF using low A codons of Table 5,
                        with start and stop codons
source                 1..4140
                       mol_type = other DNA
                       organism = synthetic construct
SEQUENCE: 311
atggacaaga agtactccat cggcctggac atcggcacca actccgtggg ctgggccgtg  60
atcaccgacg agtacaaggt gccctccaag aagttcaagg tgctgggcaa caccgaccgg  120
cactccatca agaagaacct gatcggcgcc ctgctgttcg actccggcga gaccgccgag  180
gccacccggc tgaagcggac cgcccggcgg cggtacaccc ggcggaagaa ccggatctgc  240
tacctgcagg agatcttctc caacgagatg gccaaggtgg acgactcctt cttccaccgg  300
ctggaggagt ccttcctggt ggaggaggac aagaagcacg agcggcaccc catcttcggc  360
aacatcgtgg acgaggtggc ctaccacgag aagtacccca ccatctacca cctgcggaag  420
aagctggtgg actccaccga caaggccgac ctgcggctga tctacctggc cctggcccac  480
atgatcaagt tccggggcca cttcctgatc gagggcgacc tgaaccccga caactccgac  540
gtggacaagc tgttcatcca gctggtgcag acctacaacc agctgttcga ggagaacccc  600
atcaacgcct ccggcgtgga cgccaaggcc atcctgtccg cccggctgtc caagtcccgg  660
cggctggaga acctgatcgc ccagctgccc ggcgagaaga agaacggcct gttcggcaac  720
ctgatcgccc tgtccctggg cctgaccccc aacttcaagt ccaacttcga cctggccgag  780
gacgccaagc tgcagctgtc caaggacacc tacgacgacg acctggacaa cctgctggcc  840
cagatcggcg accagtacgc cgacctgttc ctggccgcca agaacctgtc cgacgccatc  900
ctgctgtccg acatcctgcg ggtgaacacc gagatcacca aggcccccct gtccgcctcc  960
atgatcaagc ggtacgacga gcaccaccag gacctgaccc tgctgaaggc cctggtgcgg  1020
cagcagctgc ccgagaagta caaggagatc ttcttcgacc agtccaagaa cggctacgcc  1080
ggctacatcg acggcggcgc ctcccaggag gagttctaca agttcatcaa gcccatcctg  1140
```

```
gagaagatgg acggcaccga ggagctgctg gtgaagctga accgggagga cctgctgcgg  1200
aagcagcgga ccttcgacaa cggctccatc ccccaccaga tccacctggg cgagctgcac  1260
gccatcctgc ggcggcagga ggacttctac cccttcctga aggacaaccg ggagaagatc  1320
gagaagatcc tgaccttccg gatcccctac tacgtgggcc ccctggcccg gggcaactcc  1380
cggttcgcct ggatgacccg gaagtccgag gagaccatca cccccctggaa cttcgaggag  1440
gtggtggaca agggcgcctc cgcccagtcc ttcatcgagc ggatgaccaa cttcgacaag  1500
aacctgccca acgagaaggt gctgcccaag cactccctgc tgtacgagta cttcaccgtg  1560
tacaacgagc tgaccaaggt gaagtacgtg accgagggca tgcggaagcc cgccttcctg  1620
tccggcgagc agaagaaggc catcgtggac ctgctgttca agaccaaccg gaaggtgacc  1680
gtgaagcagc tgaaggagga ctacttcaag aagatcgagt gcttcgactc cgtggagatc  1740
tccggcgtgg aggaccggtt caacgcctcc ctgggcacct accacgacct gctgaagatc  1800
atcaaggaca aggacttcct ggacaacgag gagaacgagg acatcctgga ggacatcgtg  1860
ctgaccctga ccctgttcga ggaccgggag atgatcgagg agcggctgaa gacctacgcc  1920
cacctgttcg acgacaaggt gatgaagcag ctgaagcggc ggcggtacac cggctggggc  1980
cggctgtccc ggaagctgat caacggcatc cgggacaagc agtccggcaa gaccatcctg  2040
gacttcctga agtccgacgg cttcgccaac cggaacttca tgcagctgat ccacgacgac  2100
tccctgacct tcaaggagga catccagaag gcccaggtgt ccggccaggg cgactccctg  2160
cacgagcaca tcgccaacct ggccggctcc cccgccatca agaagggcat cctgcagacc  2220
gtgaaggtgg tggacgagct ggtgaaggtg atgggccggc acaagcccga gaacatcgtg  2280
atcgagatgg cccgggagaa ccagaccacc cagaagggcc agaagaactc ccgggagcgg  2340
atgaagcgga tcgaggaggg catcaaggag ctgggctccc agatcctgaa ggagcacccc  2400
gtggagaaca cccagctgca gaacgagaag ctgtacctgt actacctgca gaacggccgg  2460
gacatgtacg tggaccagga gctggacatc aaccggctgt ccgactacga cgtggaccac  2520
atcgtgcccc agtccttcct gaaggacgac tccatcgaca acaaggtgct gacccggtcc  2580
gacaagaacc ggggcaagtc cgacaacgtg ccctccgagg aggtggtgaa gaagatgaag  2640
aactactggc ggcagctgct gaacgccaag ctgatcaccc agcggaagtt cgacaacctg  2700
accaaggccg agcggggcgg cctgtccgag ctggacaagg ccggcttcat caagcggcag  2760
ctggtggaga cccggcagat caccaagcac gtggcccaga tcctggactc ccggatgaac  2820
accaagtacg acgagaacga caagctgatc cgggaggtga aggtgatcac cctgaagtcc  2880
aagctggtgt ccgacttccg gaaggacttc cagttctaca aggtgcggga gatcaacaac  2940
taccaccacg cccacgacgc ctacctgaac gccgtggtgg gcaccgccct gatcaagaag  3000
taccccaagc tggagtccga gttcgtgtac ggcgactaca aggtgtacga cgtgcggaag  3060
atgatcgcca agtccgagca ggagatcggc aaggccaccg ccaagtactt cttctactcc  3120
aacatcatga acttcttcaa gaccgagatc accctggcca acggcgagat ccggaagcgg  3180
cccctgatcg agaccaacgg cgagaccggc gagatcgtgt gggacaaggg ccgggacttc  3240
gccaccgtgc ggaaggtgct gtccatgccc caggtgaaca tcgtgaagaa gaccgaggtg  3300
cagaccggcg gcttctccaa ggagtccatc ctgcccaagc ggaactccga caagctgatc  3360
gcccggaaga aggactggga ccccaagaag tacggcggct tcgactcccc caccgtggcc  3420
tactccgtgc tggtggtggc caaggtggag aagggcaagt ccaagaagct gaagtccgtg  3480
aaggagctgc tgggcatcac catcatggag cggtcctcct tcgagaagaa ccccatcgac  3540
ttcctggagg ccaagggcta caaggaggtg aagaaggacc tgatcatcaa gctgcccaag  3600
tactccctgt tcgagctgga gaacggccgg aagcggatgc tggcctccgc cggcgagctg  3660
cagaagggca acgagctggc cctgccctcc aagtacgtga acttcctgta cctggcctcc  3720
cactacgaga agctgaaggg ctcccccgag gacaacgagc agaagcagct gttcgtggag  3780
cagcacaagc actacctgga cgagatcatc gagcagatct ccgagttctc caagcgggtg  3840
atcctggccg acgccaacct ggacaaggtg ctgtccgcct acaacaagca ccgggacaag  3900
cccatccggg agcaggccga gaacatcatc cacctgttca ccctgaccaa cctgggcgcc  3960
cccgccgcct tcaagtactt cgacaccacc atcgaccgga agcggtacac ctccaccaag  4020
gaggtgctgg acgccaccct gatccaccag tccatcaccg gcctgtacga gacccggatc  4080
gacctgtccc agctgggcgg cgacggcggc ggctccccca agaagaagcg gaaggtgtga  4140

SEQ ID NO: 312          moltype = DNA  length = 4140
FEATURE                 Location/Qualifiers
misc_feature            1..4140
                        note = Synthetic: Cas9 ORF using low A/U codons of Table 5,
                         with start and stop codons
source                  1..4140
                        mol_type = other DNA
                        organism = synthetic construct
SEQUENCE: 312
atggacaaga agtacagcat cggcctggac atcggcacca acagcgtggg ctgggccgtg  60
atcaccgacg agtacaaggt gcccagcaag aagttcaagg tgctgggcaa caccgaccgg  120
cacagcatca agaagaacct gatcggcgcc ctgctgttcg acagcggcga gaccgccgag  180
gccacccggc tgaagcggac cgcccggcgg cggtacaccc ggcggaagaa ccggatctgc  240
tacctgcagg agatcttcag caacgagatg gccaaggtgg acgacagctt cttccaccgg  300
ctggaggaga gcttcctggt ggaggaggac aagaagcacg agcggcaccc catcttcggc  360
aacatcgtgg acgaggtggc ctaccacgag aagtacccca ccatctacca cctgcggaag  420
aagctggtgg acagcaccga caaggccgac ctgcggctga tctacctggc cctggcccac  480
atgatcaagt tccggggcca cttcctgatc gagggcgacc tgaaccccga caacagcgac  540
gtggacaagc tgttcatcca gctggtgcag acctacaacc agctgttcga ggagaacccc  600
atcaacgcca gcggcgtgga cgccaaggcc atcctgagcg cccggctgag caagagccgg  660
cggctggaga acctgatcgc ccagctgccc ggcgagaaga agaacggcct gttcggcaac  720
ctgatcgccc tgagcctggg cctgaccccc aacttcaaga gcaacttcga cctggccgag  780
gacgccaagc tgcagctgag caaggacacc tacgacgacg acctggacaa cctgctggcc  840
cagatcggcg accagtacgc cgacctgttc ctggccgcca agaacctgag cgacgccatc  900
ctgctgagcg acatcctgcg ggtgaacacc gagatcacca aggccccccct gagcgccagc  960
atgatcaagc ggtacgacga gcaccaccag gacctgaccc tgctgaaggc cctggtgcgg  1020
cagcagctgc ccgagaagta caaggagatc ttcttcgacc agagcaagaa cggctacgcc  1080
ggctacatcg acggcggcgc cagccaggag gagttctaca agttcatcaa gcccatcctg  1140
```

```
gagaagatgg acggcaccga ggagctgctg gtgaagctga accgggagga cctgctgcgg  1200
aagcagcgga ccttcgacaa cggcagcatc ccccaccaga tccacctggg cgagctgcac  1260
gccatcctgc ggcggcagga ggacttctac cccttcctga aggacaaccg ggagaagatc  1320
gagaagatcc tgaccttccg gatcccctac tacgtgggcc ccctggcccg gggcaacagc  1380
cggttcgcct ggatgacccg gaagagcgag gagaccatca ccccctggaa cttcgaggag  1440
gtggtggaca agggcgccag cgcccagagc ttcatcgagc ggatgaccaa cttcgacaag  1500
aacctgccca acgagaaggt gctgcccaag cacagcctgc tgtacgagta cttcaccgtg  1560
tacaacgagc tgaccaaggt gaagtacgtg accgagggca tgcggaagcc cgccttcctg  1620
agcggcgagc agaagaaggc catcgtggac ctgctgttca agaccaaccg gaaggtgacc  1680
gtgaagcagc tgaaggagga ctacttcaag aagatcgagt gcttcgacag cgtggagatc  1740
agcggcgtgg aggaccggtt caacgccagc ctgggcacct accacgacct gctgaagatc  1800
atcaaggaca aggacttcct ggacaacgag gagaacgagg acatcctgga ggacatcgtg  1860
ctgaccctga ccctgttcga ggaccgggag atgatcgagg agcggctgaa gacctacgcc  1920
cacctgttcg acgacaaggt gatgaagcag ctgaagcggc ggcggtacac cggctggggc  1980
cggctgagcc ggaagctgat caacggcatc cgggacaagc agagcggcaa gaccatcctg  2040
gacttcctga agagcgacgg cttcgccaac cggaacttca tgcagctgat ccacgacgac  2100
agcctgacct tcaaggagga catccagaag gcccaggtga gcggccaggg cgacagcctg  2160
cacgagcaca tcgccaacct ggccggcagc cccgccatca agaagggcat cctgcagacc  2220
gtgaaggtgg tggacgagct ggtgaaggtg atgggccggc acaagcccga gaacatcgtg  2280
atcgagatgg cccgggagaa ccagaccacc cagaagggcc agaagaacag ccgggagcgg  2340
atgaagcgga tcgaggaggg catcaaggag ctgggcagcc agatcctgaa ggagcacccc  2400
gtggagaaca cccagctgca gaacgagaag ctgtacctgt actacctgca gaacggccgg  2460
gacatgtacg tggaccagga gctggacatc aaccggctga gcgactacga cgtggaccac  2520
atcgtgcccc agagcttcct gaaggacgac agcatcgaca acaaggtgct gacccggagc  2580
gacaagaacc ggggcaagag cgacaacgtg cccagcgagg aggtggtgaa gaagatgaag  2640
aactactggc ggcagctgct gaacgccaag ctgatcaccc agcggaagtt cgacaacctg  2700
accaaggccg agcggggcgg cctgagcgag ctggacaagg ccggcttcat caagcggcag  2760
ctggtggaga cccggcagat caccaagcac gtggcccaga tcctggacag ccggatgaac  2820
accaagtacg acgagaacga caagctgatc cgggaggtga aggtgatcac cctgaagagc  2880
aagctggtga gcgacttccg gaaggacttc cagttctaca aggtgcggga gatcaacaac  2940
taccaccacg cccacgacgc ctacctgaac gccgtggtgg gcaccgccct gatcaagaag  3000
taccccaagc tggagagcga gttcgtgtac ggcgactaca aggtgtacga cgtgcggaag  3060
atgatcgcca agagcgagca ggagatcggc aaggccaccg ccaagtactt cttctacagc  3120
aacatcatga acttcttcaa gaccgagatc accctggcca acggcgagat ccggaagcgg  3180
cccctgatcg agaccaacgg cgagaccggc gagatcgtgt gggacaaggg ccgggacttc  3240
gccaccgtgc ggaaggtgct gagcatgccc caggtgaaca tcgtgaagaa gaccgaggtg  3300
cagaccggcg gcttcagcaa ggagagcatc ctgcccaagc ggaacagcga caagctgatc  3360
gcccggaaga aggactggga ccccaagaag tacggcggct tcgacagccc caccgtggcc  3420
tacagcgtgc tggtggtggc caaggtggag aagggcaaga gcaagaagct gaagagcgtg  3480
aaggagctgc tgggcatcac catcatggag cggagcagct tcgagaagaa ccccatcgac  3540
ttcctggagg ccaagggcta caaggaggtg aagaaggacc tgatcatcaa gctgcccaag  3600
tacagcctgt tcgagctgga gaacggccgg aagcggatgc tggccagcgc cggcgagctg  3660
cagaagggca acgagctggc cctgcccagc aagtacgtga acttcctgta cctggccagc  3720
cactacgaga agctgaaggg cagccccgag gacaacgagc agaagcagct gttcgtggag  3780
cagcacaagc actacctgga cgagatcatc gagcagatca gcgagttcag caagcgggtg  3840
atcctggccg acgccaacct ggacaaggtg ctgagcgcct acaacaagca ccgggacaag  3900
cccatccggg agcaggccga gaacatcatc cacctgttca ccctgaccaa cctgggcgcc  3960
cccgccgcct tcaagtactt cgacaccacc atcgaccgga agcggtacac cagcaccaag  4020
gaggtgctgg acgccaccct gatccaccag agcatcaccg gcctgtacga gacccggatc  4080
gacctgagcc agctgggcgg cgacggcggc ggcagcccca agaagaagcg gaaggtgtga  4140
```

```
SEQ ID NO: 313          moltype = DNA  length = 4179
FEATURE                 Location/Qualifiers
misc_feature            1..4179
                        note = Synthetic: Cas9 ORF using low A codons of Table 5,
                         with two C-terminal NLS sequences and start and stop codons
source                  1..4179
                        mol_type = other DNA
                        organism = synthetic construct
SEQUENCE: 313
atggacaaga agtactccat cggcctggac atcggcacca actccgtggg ctgggccgtg  60
atcaccgacg agtacaaggt gccctccaag aagttcaagg tgctgggcaa caccgaccgg  120
cactccatca agaagaacct gatcggcgcc ctgctgttcg actccggcga gaccgccgag  180
gccacccggc tgaagcggac cgcccggcgg cggtacaccc ggcggaagaa ccggatctgc  240
tacctgcagg agatcttctc caacgagatg gccaaggtgg acgactcctt cttccaccgg  300
ctggaggagt ccttcctggt ggaggaggac aagaagcacg agcggcaccc catcttcggc  360
aacatcgtgg acgaggtggc ctaccacgag aagtacccca ccatctacca cctgcggaag  420
aagctggtgg actccaccga caaggccgac ctgcggctga tctacctggc cctggcccac  480
atgatcaagt tccggggcca cttcctgatc gagggcgacc tgaaccccga caactccgac  540
gtggacaagc tgttcatcca gctggtgcag acctacaacc agctgttcga ggagaacccc  600
atcaacgcct ccggcgtgga cgccaaggcc atcctgtccg cccggctgtc caagtcccgg  660
cggctggaga acctgatcgc ccagctgccc ggcgagaaga agaacggcct gttcggcaac  720
ctgatcgccc tgtccctggg cctgaccccc aacttcaagt ccaacttcga cctggccgag  780
gacgccaagc tgcagctgtc caaggacacc tacgacgacg acctggacaa cctgctggcc  840
cagatcggcg accagtacgc cgacctgttc ctggccgcca agaacctgtc cgacgccatc  900
ctgctgtccg acatcctgcg ggtgaacacc gagatcacca aggccccct gtccgcctcc  960
atgatcaagc ggtacgacga gcaccaccag gacctgaccc tgctgaaggc cctggtgcgg  1020
cagcagctgc ccgagaagta caaggagatc ttcttcgacc agtccaagaa cggctacgcc  1080
ggctacatcg acggcggcgc ctcccaggag gagttctaca agttcatcaa gcccatcctg  1140
```

-continued

```
gagaagatgg acggcaccga ggagctgctg gtgaagctga accgggagga cctgctgcgg  1200
aagcagcgga ccttcgacaa cggctccatc ccccaccaga tccacctggg cgagctgcac  1260
gccatcctgc ggcggcagga ggacttctac cccttcctga aggacaaccg ggagaagatc  1320
gagaagatcc tgaccttccg gatcccctac tacgtgggcc ccctggcccg gggcaactcc  1380
cggttcgcct ggatgacccg gaagtccgag gagaccatca ccccctggaa cttcgaggag  1440
gtggtggaca agggcgcctc cgcccagtcc ttcatcgagc ggatgaccaa cttcgacaag  1500
aacctgccca acgagaaggt gctgcccaag cactccctgc tgtacgagta cttcaccgtg  1560
tacaacgagc tgaccaaggt gaagtacgtg accgagggca tgcggaagcc cgccttcctg  1620
tccggcgagc agaagaaggc catcgtggac ctgctgttca agaccaaccg gaaggtgacc  1680
gtgaagcagc tgaaggagga ctacttcaag aagatcgagt gcttcgactc cgtggagatc  1740
tccggcgtgg aggaccggtt caacgcctcc ctgggcacct accacgacct gctgaagatc  1800
atcaaggaca aggacttcct ggacaacgag gagaacgagg acatcctgga ggacatcgtg  1860
ctgaccctga ccctgttcga ggaccgggag atgatcgagg agcggctgaa gacctacgcc  1920
cacctgttcg acgacaaggt gatgaagcag ctgaagcggc ggcggtacac cggctggggc  1980
cggctgtccc ggaagctgat caacggcatc cgggacaagc agtccggcaa gaccatcctg  2040
gacttcctga agtccgacgg cttcgccaac cggaacttca tgcagctgat ccacgacgac  2100
tccctgacct tcaaggagga catccagaag gcccaggtgt ccggccaggg cgactccctg  2160
cacgagcaca tcgccaacct ggccggctcc cccgccatca agaagggcat cctgcagacc  2220
gtgaaggtgg tggacgagct ggtgaaggtg atgggccggc acaagcccga gaacatcgtg  2280
atcgagatgg cccgggagaa ccagaccacc cagaagggcc agaagaactc ccgggagcgg  2340
atgaagcgga tcgaggaggg catcaaggag ctgggctccc agatcctgaa ggagcacccc  2400
gtggagaaca cccagctgca gaacgagaag ctgtacctgt actacctgca gaacggccgg  2460
gacatgtacg tggaccagga gctggacatc aaccggctgt ccgactacga cgtggaccac  2520
atcgtgcccc agtccttcct gaaggacgac tccatcgaca acaaggtgct gacccggtcc  2580
gacaagaacc ggggcaagtc cgacaacgtg ccctccgagg aggtggtgaa gaagatgaag  2640
aactactggc ggcagctgct gaacgccaag ctgatcaccc agcggaagtt cgacaacctg  2700
accaaggccg agcggggcgg cctgtccgag ctggacaagg ccggcttcat caagcggcag  2760
ctggtggaga cccggcagat caccaagcac gtggcccaga tcctggactc ccggatgaac  2820
accaagtacg acgagaacga caagctgatc cgggaggtga aggtgatcac cctgaagtcc  2880
aagctggtgt ccgacttccg gaaggacttc cagttctaca aggtgcggga gatcaacaac  2940
taccaccacg cccacgacgc ctacctgaac gccgtggtgg gcaccgccct gatcaagaag  3000
taccccaagc tggagtccga gttcgtgtac ggcgactaca aggtgtacga cgtgcggaag  3060
atgatcgcca agtccgagca ggagatcggc aaggccaccg ccaagtactt cttctactcc  3120
aacatcatga acttcttcaa gaccgagatc accctggcca acggcgagat ccggaagcgg  3180
cccctgatcg agaccaacgg cgagaccggc gagatcgtgt gggacaaggg ccgggacttc  3240
gccaccgtgc ggaaggtgct gtccatgccc caggtgaaca tcgtgaagaa gaccgaggtg  3300
cagaccggcg gcttctccaa ggagtccatc ctgcccaagc ggaactccga caagctgatc  3360
gcccggaaga aggactggga ccccaagaag tacggcggct tcgactcccc caccgtggcc  3420
tactccgtgc tggtggtggc caaggtggag aagggcaagt ccaagaagct gaagtccgtg  3480
aaggagctgc tgggcatcac catcatggag cggtcctcct tcgagaagaa ccccatcgac  3540
ttcctggagg ccaagggcta caaggaggtg aagaaggacc tgatcatcaa gctgcccaag  3600
tactccctgt tcgagctgga gaacggccgg aagcggatgc tggcctccgc cggcgagctg  3660
cagaagggca acgagctggc cctgccctcc aagtacgtga acttcctgta cctggcctcc  3720
cactacgaga agctgaaggg ctcccccgag gacaacgagc agaagcagct gttcgtggag  3780
cagcacaagc actacctgga cgagatcatc gagcagatct ccgagttctc caagcgggtg  3840
atcctggccg acgccaacct ggacaaggtg ctgtccgcct acaacaagca ccgggacaag  3900
cccatccggg agcaggccga gaacatcatc cacctgttca ccctgaccaa cctgggcgcc  3960
cccgccgcct tcaagtactt cgacaccacc atcgaccgga agcggtacac ctccaccaag  4020
gaggtgctgg acgccaccct gatccaccag tccatcaccg gcctgtacga gacccggatc  4080
gacctgtccc agctgggcgg cgacggctcc ggctccccca agaagaagcg gaaggtggac  4140
ggctccccca agaagaagcg gaaggtggac tccggctga                        4179
```

SEQ ID NO: 314 moltype = length =
SEQUENCE: 314
000

SEQ ID NO: 315 moltype = length =
SEQUENCE: 315
000

SEQ ID NO: 316 moltype = length =
SEQUENCE: 316
000

SEQ ID NO: 317 moltype = length =
SEQUENCE: 317
000

SEQ ID NO: 318 moltype = length =
SEQUENCE: 318
000

SEQ ID NO: 319 moltype = length =
SEQUENCE: 319
000

SEQ ID NO: 320 moltype = length =
SEQUENCE: 320
000

```
SEQ ID NO: 321         moltype =   length =
SEQUENCE: 321
000

SEQ ID NO: 322         moltype =   length =
SEQUENCE: 322
000

SEQ ID NO: 323         moltype =   length =
SEQUENCE: 323
000

SEQ ID NO: 324         moltype =   length =
SEQUENCE: 324
000

SEQ ID NO: 325         moltype =   length =
SEQUENCE: 325
000

SEQ ID NO: 326         moltype =   length =
SEQUENCE: 326
000

SEQ ID NO: 327         moltype =   length =
SEQUENCE: 327
000

SEQ ID NO: 328         moltype = DNA  length = 3312
FEATURE                Location/Qualifiers
misc_feature           1..3312
                       note = Synthetic: Nme Cas9 ORF using low A codons of Table
                        5, with start and stop codons
source                 1..3312
                       mol_type = other DNA
                       organism = synthetic construct
SEQUENCE: 328
atggccgcct tcaagcccaa ctccatcaac tacatcctgg gcctggacat cggcatcgcc  60
tccgtgggct gggccatggt ggagatcgac gaggaggaga accccatccg gctgatcgac  120
ctgggcgtgc gggtgttcga gcgggccgag gtgcccaaga ccggcgactc cctggccatg  180
gcccggcggc tggcccggtc cgtgcggcgg ctgacccggc ggcgggccca ccggctgctg  240
cggacccggc ggctgctgaa gcgggagggc gtgctgcagg ccgccaactt cgacgagaac  300
ggcctgatca agtccctgcc caacaccccc tggcagctgc gggccgccgc cctggaccgg  360
aagctgaccc ccctggagtg gtccgccgtg ctgctgcacc tgatcaagca ccggggctac  420
ctgtcccagc ggaagaacga gggcgagacc gccgacaagg agctgggcgc cctgctgaag  480
ggcgtggccg gcaacgccca cgccctgcag accggcgact tccggacccc cgccgagctg  540
gccctgaaca agttcgagaa ggagtccggc cacatccgga accagcggtc cgactactcc  600
cacaccttct cccggaagga cctgcaggcc gagctgatcc tgctgttcga gaagcagaag  660
gagttcggca acccccacgt gtccggcggc ctgaaggagg gcatcgagac cctgctgatg  720
acccagcggc ccgccctgtc cggcgacgcc gtgcagaaga tgctgggcca ctgcaccttc  780
gagcccgccg agcccaaggc cgccaagaac acctacaccg ccgagcggtt catctggctg  840
accaagctga acaacctgcg gatcctggag cagggctccg agcggcccct gaccgacacc  900
gagcgggcca ccctgatgga cgagccctac cggaagtcca agctgaccta cgcccaggcc  960
cggaagctgc tgggcctgga ggacaccgcc ttcttcaagg gcctgcggta cggcaaggac  1020
aacgccgagg cctccaccct gatggagatg aaggcctacc acgccatctc ccgggccctg  1080
gagaaggagg gcctgaagga caagaagtcc cccctgaacc tgtcccccga gctgcaggac  1140
gagatcggca ccgccttctc cctgttcaag accgacgagg acatcaccgg ccggctgaag  1200
gaccggatcc agcccgagat cctggaggcc ctgctgaagc acatctcctt cgacaagttc  1260
gtgcagatct ccctgaaggc cctgcggcgg atcgtgcccc tgatggagca gggcaagcgg  1320
tacgacgagg cctgcgccga gatctacggc gaccactacg gcaagaagaa caccgaggag  1380
aagatctacc tgccccccat ccccgccgac gagatccgga accccgtggt gctgcgggcc  1440
ctgtcccagg cccggaaggt gatcaacggc gtggtgcggc ggtacggctc ccccgcccgg  1500
atccacatcg agaccgcccg ggaggtgggc aagtccttca aggaccggaa ggagatcgag  1560
aagcggcagg aggagaaccg gaaggaccgg gagaaggccg ccgccaagtt ccgggagtac  1620
ttccccaact tcgtgggcga gcccaagtcc aaggacatcc tgaagctgcg gctgtacgag  1680
cagcagcacg gcaagtgcct gtactccggc aaggagatca acctgggccg gctgaacgag  1740
aagggctacg tggagatcga ccacgccctg cccttctccc ggacctggga cgactccttc  1800
aacaacaagg tgctggtgct gggctccgag aaccagaaca agggcaacca gaccccctac  1860
gagtacttca acggcaagga caactcccgg gagtggcagg agttcaaggc ccgggtggag  1920
acctcccggt tcccccggtc caagaagcag cggatcctgc tgcagaagtt cgacgaggac  1980
ggcttcaagg agcggaacct gaacgacacc cggtacgtga accggttcct gtgccagttc  2040
gtggccgacc ggatgcggct gaccggcaag ggcaagaagc gggtgttcgc ctccaacggc  2100
cagatcacca acctgctgcg gggcttctgg ggcctgcgga aggtgcgggc cgagaacgac  2160
cggcaccacg ccctggacgc cgtggtggtg gcctgctcca ccgtggccat gcagcagaag  2220
atcacccggt tcgtgcggta caaggagatg aacgccttcg acggcaagac catcgacaag  2280
gagaccggcg aggtgctgca ccagaagacc cacttccccc agccctggga gttcttcgcc  2340
caggaggtga tgatccgggt gttcggcaag cccgacggca agcccgagtt cgaggaggcc  2400
gacaccctgg agaagctgcg gaccctgctg gccgagaagc tgtcctcccg gcccgaggcc  2460
```

```
gtgcacgagt acgtgacccc cctgttcgtg tcccgggccc ccaaccggaa gatgtccggc  2520
cagggccaca tggagaccgt gaagtccgcc aagcggctgg acgagggcgt gtccgtgctg  2580
cgggtgcccc tgacccagct gaagctgaag gacctggaga agatggtgaa ccgggagcgg  2640
gagcccaagc tgtacgaggc cctgaaggcc cggctggagg cccacaagga cgacccccgcc  2700
aaggccttcg ccgagccctt ctacaagtac gacaaggccg gcaaccggac ccagcaggtg  2760
aaggccgtgc gggtggagca ggtgcagaag accggcgtgt gggtgcggaa ccacaacggc  2820
atcgccgaca acgccaccat ggtgcgggtg gacgtgttcg agaagggcga caagtactac  2880
ctggtgccca tctactcctg gcaggtggcc aagggcatcc tgcccgaccg ggccgtggtg  2940
cagggcaagg acgaggagga ctggcagctg atcgacgact ccttcaactt caagttctcc  3000
ctgcaccccca acgacctggt ggaggtgatc accaagaagg cccggatgtt cggctacttc  3060
gcctcctgcc accggggcac cggcaacatc aacatccgga tccacgacct ggaccacaag  3120
atcggcaaga acggcatcct ggagggcatc ggcgtgaaga ccgccctgtc cttccagaag  3180
taccagatcg acgagctggg caaggagatc cggccctgcc ggctgaagaa gcggcccccc  3240
gtgcggtccg gcaagcggac cgccgacggc tccgagttcg agtcccccaa gaagaagcgg  3300
aaggtggagt ga                                                      3312

SEQ ID NO: 329          moltype = DNA  length = 3312
FEATURE                 Location/Qualifiers
misc_feature            1..3312
                        note = Synthetic: Nme Cas9 ORF using low A/U codons of
                         Table 5, with start and stop codons
source                  1..3312
                        mol_type = other DNA
                        organism = synthetic construct
SEQUENCE: 329
atggccgcct tcaagcccaa cagcatcaac tacatcctgg gcctggacat cggcatcgcc  60
agcgtgggct gggccatggt ggagatcgac gaggaggaga accccatccg gctgatcgac  120
ctgggcgtgc gggtgttcga gcgggccgag gtgcccaaga ccggcgacag cctggccatg  180
gcccggcggc tggcccggag cgtgcggcgg ctgacccggc ggcgggccca ccggctgctg  240
cggacccggc ggctgctgaa gcgggagggc gtgctgcagg ccgccaactt cgacgagaac  300
ggcctgatca agagcctgcc caacaccccc tggcagctgc gggccgccgc cctggaccgg  360
aagctgaccc ccctggagtg gagcgccgtg ctgctgcacc tgatcaagca ccggggctac  420
ctgagccagc ggaagaacga gggcgagacc gccgacaagg agctgggcgc cctgctgaag  480
ggcgtggccg gcaacgccca cgccctgcag accggcgact tccggacccc cgccgagctg  540
gccctgaaca agttcgagaa ggagagcggc cacatccgga accagcggag cgactacagc  600
cacaccttca gccggaagga cctgcaggcc gagctgatcc tgctgttcga gaagcagaag  660
gagttcggca acccccacgt gagcggcggc ctgaaggagg gcatcgagac cctgctgatg  720
acccagcggc ccgccctgag cggcgacgcc gtgcagaaga tgctgggcca ctgcaccttc  780
gagcccgccg agcccaaggc cgccaagaac acctacaccg ccgagcggtt catctggctg  840
accaagctga acaacctgcg gatcctggag cagggcagcg agcggcccct gaccgacacc  900
gagcgggcca ccctgatgga cgagccctac cggaagagca agctgaccta cgcccaggcc  960
cggaagctgc tgggcctgga ggacaccgcc ttcttcaagg gcctgcggta cggcaaggac  1020
aacgccgagg ccagcaccct gatggagatg aaggcctacc acgccatcag ccgggccctg  1080
gagaaggagg gcctgaagga caagaagagc cccctgaacc tgagccccga gctgcaggac  1140
gagatcggca ccgccttcag cctgttcaag accgacgagg acatcaccgg ccggctgaag  1200
gaccggatcc agcccgagat cctggaggcc ctgctgaagc acatcagctt cgacaagttc  1260
gtgcagatca gcctgaaggc cctgcggcgg atcgtgcccc tgatggagca gggcaagcgg  1320
tacgacgagg cctgcgccga gatctacggc gaccactacg gcaagaagaa caccgaggag  1380
aagatctacc tgccccccat ccccgccgac gagatccgga accccgtggt gctgcgggcc  1440
ctgagccagg cccggaaggt gatcaacggc gtggtgcggc ggtacggcag ccccgcccgg  1500
atccacatcg agaccgcccg ggaggtgggc aagagcttca aggaccggaa ggagatcgag  1560
aagcggcagg aggagaaccg gaaggaccgg gagaaggccg ccgccaagtt ccgggagtac  1620
ttccccaact tcgtgggcga gcccaagagc aaggacatcc tgaagctgcg gctgtacgag  1680
cagcagcacg gcaagtgcct gtacagcggc aaggagatca acctgggccg gctgaacgag  1740
aagggctacg tggagatcga ccacgccctg cccttcagcc ggacctggga cgacagcttc  1800
aacaacaagg tgctggtgct gggcagcgag aaccagaaca agggcaacca gaccccctac  1860
gagtacttca acggcaagga caacagccgg gagtggcagg agttcaaggc ccgggtggag  1920
accagccggt tcccccggag caagaagcag cggatcctgc tgcagaagtt cgacgaggac  1980
ggcttcaagg agcggaacct gaacgacacc cggtacgtga accggttcct gtgccagttc  2040
gtggccgacc ggatgcggct gaccggcaag ggcaagaagc gggtgttcgc cagcaacggc  2100
cagatcacca acctgctgcg gggcttctgg ggcctgcgga aggtgcgggc cgagaacgac  2160
cggcaccacg ccctggacgc cgtggtggtg gcctgcagca ccgtggccat gcagcagaag  2220
atcacccggt tcgtgcggta caaggagatg aacgccttcg acggcaagac catcgacaag  2280
gagaccggcg aggtgctgca ccagaagacc cacttccccc agccctggga gttcttcgcc  2340
caggaggtga tgatccgggt gttcggcaag cccgacggca agcccgagtt cgaggaggcc  2400
gacaccctgg agaagctgcg gaccctgctg gccgagaagc tgagcagccg gcccgaggcc  2460
gtgcacgagt acgtgacccc cctgttcgtg agccgggccc ccaaccggaa gatgagcggc  2520
cagggccaca tggagaccgt gaagagcgcc aagcggctgg acgagggcgt gagcgtgctg  2580
cgggtgcccc tgacccagct gaagctgaag gacctggaga agatggtgaa ccgggagcgg  2640
gagcccaagc tgtacgaggc cctgaaggcc cggctggagg cccacaagga cgacccccgcc  2700
aaggccttcg ccgagccctt ctacaagtac gacaaggccg gcaaccggac ccagcaggtg  2760
aaggccgtgc gggtggagca ggtgcagaag accggcgtgt gggtgcggaa ccacaacggc  2820
atcgccgaca acgccaccat ggtgcgggtg gacgtgttcg agaagggcga caagtactac  2880
ctggtgccca tctacagctg gcaggtggcc aagggcatcc tgcccgaccg ggccgtggtg  2940
cagggcaagg acgaggagga ctggcagctg atcgacgaca gcttcaactt caagttcagc  3000
ctgcaccccca acgacctggt ggaggtgatc accaagaagg cccggatgtt cggctacttc  3060
gccagctgcc accggggcac cggcaacatc aacatccgga tccacgacct ggaccacaag  3120
atcggcaaga acggcatcct ggagggcatc ggcgtgaaga ccgccctgag cttccagaag  3180
taccagatcg acgagctggg caaggagatc cggccctgcc ggctgaagaa gcggcccccc  3240
```

-continued

```
gtgcggagcg gcaagcggac cgccgacggc agcgagttcg agagccccaa gaagaagcgg  3300
aaggtggagt ga                                                       3312

SEQ ID NO: 330          moltype =   length =
SEQUENCE: 330
000

SEQ ID NO: 331          moltype =   length =
SEQUENCE: 331
000

SEQ ID NO: 332          moltype =   length =
SEQUENCE: 332
000

SEQ ID NO: 333          moltype =   length =
SEQUENCE: 333
000

SEQ ID NO: 334          moltype =   length =
SEQUENCE: 334
000

SEQ ID NO: 335          moltype =   length =
SEQUENCE: 335
000

SEQ ID NO: 336          moltype =   length =
SEQUENCE: 336
000

SEQ ID NO: 337          moltype =   length =
SEQUENCE: 337
000

SEQ ID NO: 338          moltype =   length =
SEQUENCE: 338
000

SEQ ID NO: 339          moltype =   length =
SEQUENCE: 339
000

SEQ ID NO: 340          moltype =   length =
SEQUENCE: 340
000

SEQ ID NO: 341          moltype =   length =
SEQUENCE: 341
000

SEQ ID NO: 342          moltype =   length =
SEQUENCE: 342
000

SEQ ID NO: 343          moltype =   length =
SEQUENCE: 343
000

SEQ ID NO: 344          moltype =   length =
SEQUENCE: 344
000

SEQ ID NO: 345          moltype =   length =
SEQUENCE: 345
000

SEQ ID NO: 346          moltype = DNA  length = 4134
FEATURE                 Location/Qualifiers
misc_feature            1..4134
                        note = Synthetic: Cas9 ORF using low A codons of Table 5
                         (no start or stop codons; suitable for inclusion in fusion
                         protein coding sequence)
source                  1..4134
                        mol_type = other DNA
                        organism = synthetic construct
SEQUENCE: 346
gacaagaagt actccatcgg cctggacatc ggcaccaact ccgtgggctg ggccgtgatc  60
accgacgagt acaaggtgcc ctccaagaag ttcaaggtgc tgggcaacac cgaccggcac  120
```

```
tccatcaaga agaacctgat cggcgccctg ctgttcgact ccggcgagac cgccgaggcc  180
acccggctga agcggaccgc ccggcggcgg tacacccggc ggaagaaccg gatctgctac  240
ctgcaggaga tcttctccaa cgagatggcc aaggtggacg actccttctt ccaccggctg  300
gaggagtcct tcctggtgga ggaggacaag aagcacgagc ggcaccccat cttcggcaac  360
atcgtggacg aggtggccta ccacgagaag taccccacca tctaccacct gcggaagaag  420
ctggtggact ccaccgacaa ggccgacctg cggctgatct acctggccct ggcccacatg  480
atcaagttcc ggggccactt cctgatcgag ggcgacctga accccgacaa ctccgacgtg  540
gacaagctgt tcatccagct ggtgcagacc tacaaccagc tgttcgagga gaaccccatc  600
aacgcctccg gcgtggacgc caaggccatc ctgtccgccc ggctgtccaa gtcccggcgg  660
ctggagaacc tgatcgccca gctgcccggc gagaagaaga acggcctgtt cggcaacctg  720
atcgccctgt ccctgggcct gacccccaac ttcaagtcca acttcgacct ggccgaggac  780
gccaagctgc agctgtccaa ggacacctac gacgacgacc tggacaacct gctggcccag  840
atcggcgacc agtacgccga cctgttcctg gccgccaaga acctgtccga cgccatcctg  900
ctgtccgaca tcctgcgggt gaacaccgag atcaccaagg ccccccctgtc cgcctccatg  960
atcaagcggt acgacgagca ccaccaggac ctgaccctgc tgaaggccct ggtgcggcag  1020
cagctgcccg agaagtacaa ggagatcttc ttcgaccagt ccaagaacgg ctacgccggc  1080
tacatcgacg gcggcgcctc ccaggaggag ttctacaagt tcatcaagcc catcctggag  1140
aagatggacg gcaccgagga gctgctggtg aagctgaacc gggaggacct gctgcggaag  1200
cagcggacct tcgacaacgg ctccatcccc caccagatcc acctgggcga gctgcacgcc  1260
atcctgcggc ggcaggagga cttctacccc ttcctgaagg acaaccggga gaagatcgag  1320
aagatcctga ccttccggat cccctactac gtgggccccc tggcccgggg caactcccgg  1380
ttcgcctgga tgacccggaa gtccgaggag accatcaccc cctggaactt cgaggaggtg  1440
gtggacaagg gcgcctccgc ccagtccttc atcgagcgga tgaccaactt cgacaagaac  1500
ctgcccaacg agaaggtgct gcccaagcac tccctgctgt acgagtactt caccgtgtac  1560
aacgagctga ccaaggtgaa gtacgtgacc gagggcatgc ggaagcccgc cttcctgtcc  1620
ggcgagcaga agaaggccat cgtggacctg ctgttcaaga ccaaccggaa ggtgaccgtg  1680
aagcagctga aggaggacta cttcaagaag atcgagtgct tcgactccgt ggagatctcc  1740
ggcgtggagg accggttcaa cgcctccctg ggcacctacc acgacctgct gaagatcatc  1800
aaggacaagg acttcctgga caacgaggag aacgaggaca tcctggagga catcgtgctg  1860
accctgaccc tgttcgagga ccgggagatg atcgaggagc ggctgaagac ctacgcccac  1920
ctgttcgacg acaaggtgat gaagcagctg aagcggcggc ggtacaccgg ctggggccgg  1980
ctgtcccgga agctgatcaa cggcatccgg gacaagcagt ccggcaagac catcctggac  2040
ttcctgaagt ccgacggctt cgccaaccgg aacttcatgc agctgatcca cgacgactcc  2100
ctgaccttca aggaggacat ccagaaggcc caggtgtccg gccagggcga ctccctgcac  2160
gagcacatcg ccaacctggc cggctccccc gccatcaaga agggcatcct gcagaccgtg  2220
aaggtggtgg acgagctggt gaaggtgatg ggccggcaca agcccgagaa catcgtgatc  2280
gagatggccc gggagaacca gaccacccag aagggccaga agaactcccg ggagcggatg  2340
aagcggatcg aggagggcat caaggagctg ggctcccaga tcctgaagga gcaccccgtg  2400
gagaacaccc agctgcagaa cgagaagctg tacctgtact acctgcagaa cggccgggac  2460
atgtacgtgg accaggagct ggacatcaac cggctgtccg actacgacgt ggaccacatc  2520
gtgccccagt ccttcctgaa ggacgactcc atcgacaaca aggtgctgac ccggtccgac  2580
aagaaccggg gcaagtccga caacgtgccc tccgaggagg tggtgaagaa gatgaagaac  2640
tactggcggc agctgctgaa cgccaagctg atcacccagc ggaagttcga caacctgacc  2700
aaggccgagc ggggcggcct gtccgagctg gacaaggccg gcttcatcaa gcggcagctg  2760
gtggagaccc ggcagatcac caagcacgtg gcccagatcc tggactcccg gatgaacacc  2820
aagtacgacg agaacgacaa gctgatccgg gaggtgaagg tgatcaccct gaagtccaag  2880
ctggtgtccg acttccggaa ggacttccag ttctacaagg tgcgggagat caacaactac  2940
caccacgccc acgacgccta cctgaacgcc gtggtgggca ccgccctgat caagaagtac  3000
cccaagctgg agtccgagtt cgtgtacggc gactacaagg tgtacgacgt gcggaagatg  3060
atcgccaagt ccgagcagga gatcggcaag gccaccgcca agtacttctt ctactccaac  3120
atcatgaact tcttcaagac cgagatcacc ctggccaacg gcgagatccg gaagcggccc  3180
ctgatcgaga ccaacggcga gaccggcgag atcgtgtggg acaagggccg ggacttcgcc  3240
accgtgcgga aggtgctgtc catgccccag gtgaacatcg tgaagaagac cgaggtgcag  3300
accggcggct tctccaagga gtccatcctg cccaagcgga actccgacaa gctgatcgcc  3360
cggaagaagg actgggaccc caagaagtac ggcggcttcg actcccccac cgtggcctac  3420
tccgtgctgg tggtggccaa ggtggagaag ggcaagtcca agaagctgaa gtccgtgaag  3480
gagctgctgg gcatcaccat catggagcgg tcctccttcg agaagaaccc catcgacttc  3540
ctggaggcca agggctacaa ggaggtgaag aaggacctga tcatcaagct gcccaagtac  3600
tccctgttcg agctggagaa cggccggaag cggatgctgg cctccgccgg cgagctgcag  3660
aagggcaacg agctggccct gccctccaag tacgtgaact tcctgtacct ggcctcccac  3720
tacgagaagc tgaagggctc ccccgaggac aacgagcaga agcagctgtt cgtggagcag  3780
cacaagcact acctggacga gatcatcgag cagatctccg agttctccaa gcgggtgatc  3840
ctggccgacg ccaacctgga caaggtgctg tccgcctaca acaagcaccg ggacaagccc  3900
atccgggagc aggccgagaa catcatccac ctgttcaccc tgaccaacct gggcgccccc  3960
gccgccttca agtacttcga caccaccatc gaccggaagc ggtacacctc caccaaggag  4020
gtgctggacg ccaccctgat ccaccagtcc atcaccggcc tgtacgagac ccggatcgac  4080
ctgtcccagc tgggcggcga cggcggcggc tcccccaaga agaagcggaa ggtg        4134
```

```
SEQ ID NO: 347         moltype = DNA  length = 4134
FEATURE                Location/Qualifiers
misc_feature           1..4134
                       note = Synthetic: Cas9 ORF using low A/U codons of Table 5
                        (no start or stop codons; suitable for inclusion in fusion
                        protein coding sequence)
source                 1..4134
                       mol_type = other DNA
                       organism = synthetic construct
SEQUENCE: 347
gacaagaagt acagcatcgg cctggacatc ggcaccaaca gcgtgggctg ggccgtgatc  60
```

```
accgacgagt acaaggtgcc cagcaagaag ttcaaggtgc tgggcaacac cgaccggcac  120
agcatcaaga agaacctgat cggcgccctg ctgttcgaca gcggcgagac cgccgaggcc  180
acccggctga agcggaccgc ccggcggcgg tacacccggc ggaagaaccg gatctgctac  240
ctgcaggaga tcttcagcaa cgagatggcc aaggtggacg acagcttctt ccaccggctg  300
gaggagagct tcctggtgga ggaggacaag aagcacgagc ggcaccccat cttcggcaac  360
atcgtggacg aggtggccta ccacgagaag taccccacca tctaccacct gcggaagaag  420
ctggtggaca gcaccgacaa ggccgacctg cggctgatct acctggccct ggcccacatg  480
atcaagttcc ggggccactt cctgatcgag ggcgacctga accccgacaa cagcgacgtg  540
gacaagctgt tcatccagct ggtgcagacc tacaaccagc tgttcgagga gaaccccatc  600
aacgccagcg gcgtggacgc caaggccatc ctgagcgccc ggctgagcaa gagccggcgg  660
ctggagaacc tgatcgccca gctgcccggc gagaagaaga acggcctgtt cggcaacctg  720
atcgccctga gcctgggcct gacccccaac ttcaagagca acttcgacct ggccgaggac  780
gccaagctgc agctgagcaa ggacacctac gacgacgacc tggacaacct gctggcccag  840
atcggcgacc agtacgccga cctgttcctg gccgccaaga acctgagcga cgccatcctg  900
ctgagcgaca tcctgcgggt gaacaccgag atcaccaagg ccccccctgag cgccagcatg  960
atcaagcggt acgacgagca ccaccaggac ctgaccctgc tgaaggccct ggtgcggcag  1020
cagctgcccg agaagtacaa ggagatcttc ttcgaccaga gcaagaacgg ctacgccggc  1080
tacatcgacg gcggcgccag ccaggaggag ttctacaagt tcatcaagcc catcctggag  1140
aagatggacg gcaccgagga gctgctggtg aagctgaacc gggaggacct gctgcggaag  1200
cagcggacct tcgacaacgg cagcatcccc caccagatcc acctgggcga gctgcacgcc  1260
atcctgcggc ggcaggagga cttctacccc ttcctgaagg acaaccggga gaagatcgag  1320
aagatcctga ccttccggat ccccctactac gtgggccccc tggcccgggg caacagccgg  1380
ttcgcctgga tgacccggaa gagcgaggag accatcaccc cctggaactt cgaggaggtg  1440
gtggacaagg gcgccagcgc ccagagcttc atcgagcgga tgaccaactt cgacaagaac  1500
ctgcccaacg agaaggtgct gcccaagcac agcctgctgt acgagtactt caccgtgtac  1560
aacgagctga ccaaggtgaa gtacgtgacc gagggcatgc ggaagcccgc cttcctgagc  1620
ggcgagcaga agaaggccat cgtggacctg ctgttcaaga ccaaccggaa ggtgaccgtg  1680
aagcagctga aggaggacta cttcaagaag atcgagtgct tcgacagcgt ggagatcagc  1740
ggcgtggagg accggttcaa cgccagcctg ggcacctacc acgacctgct gaagatcatc  1800
aaggacaagg acttcctgga caacgaggag aacgaggaca tcctggagga catcgtgctg  1860
accctgaccc tgttcgagga ccgggagatg atcgaggagc ggctgaagac ctacgcccac  1920
ctgttcgacg acaaggtgat gaagcagctg aagcggcggc ggtacaccgg ctggggccgg  1980
ctgagccgga agctgatcaa cggcatccgg gacaagcaga gcggcaagac catcctggac  2040
ttcctgaaga gcgacggctt cgccaaccgg aacttcatgc agctgatcca cgacgacagc  2100
ctgaccttca aggaggacat ccagaaggcc caggtgagcg gccagggcga cagcctgcac  2160
gagcacatcg ccaacctggc cggcagcccc gccatcaaga agggcatcct gcagaccgtg  2220
aaggtggtgg acgagctggt gaaggtgatg ggccggcaca agcccgagaa catcgtgatc  2280
gagatggccc gggagaacca gaccacccag aagggccaga agaacagccg ggagcggatg  2340
aagcggatcg aggagggcat caaggagctg ggcagccaga tcctgaagga gcaccccgtg  2400
gagaacaccc agctgcagaa cgagaagctg tacctgtact acctgcagaa cggccgggac  2460
atgtacgtgg accaggagct ggacatcaac cggctgagcg actacgacgt ggaccacatc  2520
gtgccccaga gcttcctgaa ggacgacagc atcgacaaca aggtgctgac ccggagcgac  2580
aagaaccggg gcaagagcga caacgtgccc agcgaggagg tggtgaagaa gatgaagaac  2640
tactggcggc agctgctgaa cgccaagctg atcacccagc ggaagttcga caacctgacc  2700
aaggccgagc ggggcggcct gagcgagctg gacaaggccg gcttcatcaa gcggcagctg  2760
gtggagaccc ggcagatcac caagcacgtg gcccagatcc tggacagccg gatgaacacc  2820
aagtacgacg agaacgacaa gctgatccgg gaggtgaagg tgatcaccct gaagagcaag  2880
ctggtgagcg acttccggaa ggacttccag ttctacaagg tgcgggagat caacaactac  2940
caccacgccc acgacgccta cctgaacgcc gtggtgggca ccgccctgat caagaagtac  3000
cccaagctgg agagcgagtt cgtgtacggc gactacaagg tgtacgacgt gcggaagatg  3060
atcgccaaga gcgagcagga gatcggcaag gccaccgcca agtacttctt ctacagcaac  3120
atcatgaact tcttcaagac cgagatcacc ctggccaacg gcgagatccg gaagcggccc  3180
ctgatcgaga ccaacggcga gaccggcgag atcgtgtggg acaagggccg ggacttcgcc  3240
accgtgcgga aggtgctgag catgccccag gtgaacatcg tgaagaagac cgaggtgcag  3300
accggcggct tcagcaagga gagcatcctg cccaagcgga acagcgacaa gctgatcgcc  3360
cggaagaagg actgggaccc caagaagtac ggcggcttcg acagccccac cgtggcctac  3420
agcgtgctgg tggtggccaa ggtggagaag ggcaagagca agaagctgaa gagcgtgaag  3480
gagctgctgg gcatcaccat catggagcgg agcagcttcg agaagaaccc catcgacttc  3540
ctggaggcca agggctacaa ggaggtgaag aaggacctga tcatcaagct gcccaagtac  3600
agcctgttcg agctggagaa cggccggaag cggatgctgg ccagcgccgg cgagctgcag  3660
aagggcaacg agctggccct gcccagcaag tacgtgaact tcctgtacct ggccagccac  3720
tacgagaagc tgaagggcag ccccgaggac aacgagcaga agcagctgtt cgtggagcag  3780
cacaagcact acctggacga gatcatcgag cagatcagcg agttcagcaa gcgggtgatc  3840
ctggccgacg ccaacctgga caaggtgctg agcgcctaca acaagcaccg ggacaagccc  3900
atccgggagc aggccgagaa catcatccac ctgttcaccc tgaccaacct gggcgccccc  3960
gccgccttca agtacttcga caccaccatc gaccggaagc ggtacaccag caccaaggag  4020
gtgctggacg ccaccctgat ccaccagagc atcaccggcc tgtacgagac ccggatcgac  4080
ctgagccagc tgggcggcga cggcggcggc agccccaaga agaagcggaa ggtg        4134
```

```
SEQ ID NO: 348         moltype = DNA  length = 4173
FEATURE                Location/Qualifiers
misc_feature           1..4173
                       note = Synthetic: Cas9 ORF using low A codons of Table 5,
                        with two C-terminal NLS sequences (no start or stop
                        codons; suitable for inclusion in fusion protein coding
                        sequence)
source                 1..4173
                       mol_type = other DNA
                       organism = synthetic construct
```

SEQUENCE: 348
gacaagaagt actccatcgg cctggacatc ggcaccaact ccgtgggctg ggccgtgatc 60
accgacgagt acaaggtgcc ctccaagaag ttcaaggtgc tgggcaacac cgaccggcac 120
tccatcaaga agaacctgat cggcgccctg ctgttcgact ccggcgagac cgccgaggcc 180
acccggctga agcggaccgc ccggcggcgg tacacccggc ggaagaaccg gatctgctac 240
ctgcaggaga tcttctccaa cgagatggcc aaggtggacg actccttctt ccaccggctg 300
gaggagtcct tcctggtgga ggaggacaag aagcacgagc ggcaccccat cttcggcaac 360
atcgtggacg aggtggccta ccacgagaag taccccacca tctaccacct gcggaagaag 420
ctggtggact ccaccgacaa ggccgacctg cggctgatct acctggccct ggcccacatg 480
atcaagttcc ggggccactt cctgatcgag ggcgacctga accccgacaa ctccgacgtg 540
gacaagctgt tcatccagct ggtgcagacc tacaaccagc tgttcgagga gaaccccatc 600
aacgcctccg gcgtggacgc caaggccatc ctgtccgccc ggctgtccaa gtcccggcgg 660
ctggagaacc tgatcgccca gctgcccggc gagaagaaga acggcctgtt cggcaacctg 720
atcgccctgt ccctgggcct gacccccaac ttcaagtcca acttcgacct ggccgaggac 780
gccaagctgc agctgtccaa ggacacctac gacgacgacc tggacaacct gctggcccag 840
atcggcgacc agtacgccga cctgttcctg gccgccaaga acctgtccga cgccatcctg 900
ctgtccgaca tcctgcgggt gaacaccgag atcaccaagg ccccctgtc cgcctccatg 960
atcaagcggt acgacgagca ccaccaggac ctgaccctgc tgaaggccct ggtgcggcag 1020
cagctgcccg agaagtacaa ggagatcttc ttcgaccagt ccaagaacgg ctacgccggc 1080
tacatcgacg gcggcgcctc ccaggaggag ttctacaagt tcatcaagcc catcctggag 1140
aagatggacg gcaccgagga gctgctggtg aagctgaacc gggaggacct gctgcggaag 1200
cagcggacct tcgacaacgg ctccatcccc caccagatcc acctgggcga gctgcacgcc 1260
atcctgcggc ggcaggagga cttctacccc ttcctgaagg acaaccggga gaagatcgag 1320
aagatcctga ccttccggat cccctactac gtgggccccc tggcccgggg caactcccgg 1380
ttcgcctgga tgacccggaa gtccgaggag accatcaccc cctggaactt cgaggaggtg 1440
gtggacaagg gcgcctccgc ccagtccttc atcgagcgga tgaccaactt cgacaagaac 1500
ctgcccaacg agaaggtgct gcccaagcac tccctgctgt acgagtactt caccgtgtac 1560
aacgagctga ccaaggtgaa gtacgtgacc gagggcatgc ggaagcccgc cttcctgtcc 1620
ggcgagcaga agaaggccat cgtggacctg ctgttcaaga ccaaccggaa ggtgaccgtg 1680
aagcagctga aggaggacta cttcaagaag atcgagtgct tcgactccgt ggagatctcc 1740
ggcgtggagg accggttcaa cgcctccctg ggcacctacc acgacctgct gaagatcatc 1800
aaggacaagg acttcctgga caacgaggag aacgaggaca tcctggagga catcgtgctg 1860
accctgaccc tgttcgagga ccgggagatg atcgaggagc ggctgaagac ctacgcccac 1920
ctgttcgacg acaaggtgat gaagcagctg aagcggcggc ggtacaccgg ctggggccgg 1980
ctgtcccgga agctgatcaa cggcatccgg gacaagcagt ccggcaagac catcctggac 2040
ttcctgaagt ccgacggctt cgccaaccgg aacttcatgc agctgatcca cgacgactcc 2100
ctgaccttca aggaggacat ccagaaggcc caggtgtccg gccagggcga ctccctgcac 2160
gagcacatcg ccaacctggc cggctccccc gccatcaaga agggcatcct gcagaccgtg 2220
aaggtggtgg acgagctggt gaaggtgatg ggccggcaca agcccgagaa catcgtgatc 2280
gagatggccc gggagaacca gaccacccag aagggccaga agaactcccg ggagcggatg 2340
aagcggatcg aggagggcat caaggagctg ggctcccaga tcctgaagga gcaccccgtg 2400
gagaacaccc agctgcagaa cgagaagctg tacctgtact acctgcagaa cggccgggac 2460
atgtacgtgg accaggagct ggacatcaac cggctgtccg actacgacgt ggaccacatc 2520
gtgccccagt ccttcctgaa ggacgactcc atcgacaaca aggtgctgac ccggtccgac 2580
aagaaccggg gcaagtccga caacgtgccc tccgaggagg tggtgaagaa gatgaagaac 2640
tactggcggc agctgctgaa cgccaagctg atcacccagc ggaagttcga caacctgacc 2700
aaggccgagc ggggcggcct gtccgagctg gacaaggccg gcttcatcaa gcggcagctg 2760
gtggagaccc ggcagatcac caagcacgtg gcccagatcc tggactcccg gatgaacacc 2820
aagtacgacg agaacgacaa gctgatccgg gaggtgaagg tgatcaccct gaagtccaag 2880
ctggtgtccg acttccggaa ggacttccag ttctacaagg tgcgggagat caacaactac 2940
caccacgccc acgacgccta cctgaacgcc gtggtgggca ccgccctgat caagaagtac 3000
cccaagctgg agtccgagtt cgtgtacggc gactacaagg tgtacgacgt gcggaagatg 3060
atcgccaagt ccgagcagga gatcggcaag gccaccgcca agtacttctt ctactccaac 3120
atcatgaact tcttcaagac cgagatcacc ctggccaacg gcgagatccg gaagcggccc 3180
ctgatcgaga ccaacggcga gaccggcgag atcgtgtggg acaagggccg ggacttcgcc 3240
accgtgcgga aggtgctgtc catgccccag gtgaacatcg tgaagaagac cgaggtgcag 3300
accggcggct tctccaagga gtccatcctg cccaagcgga actccgacaa gctgatcgcc 3360
cggaagaagg actgggaccc caagaagtac ggcggcttcg actcccccac cgtggcctac 3420
tccgtgctgg tggtggccaa ggtggagaag ggcaagtcca agaagctgaa gtccgtgaag 3480
gagctgctgg gcatcaccat catggagcgg tcctccttcg agaagaaccc catcgacttc 3540
ctggaggcca agggctacaa ggaggtgaag aaggacctga tcatcaagct gcccaagtac 3600
tccctgttcg agctggagaa cggccggaag cggatgctgg cctccgccgg cgagctgcag 3660
aagggcaacg agctggccct gccctccaag tacgtgaact tcctgtacct ggcctcccac 3720
tacgagaagc tgaagggctc ccccgaggac aacgagcaga agcagctgtt cgtggagcag 3780
cacaagcact acctggacga gatcatcgag cagatctccg agttctccaa gcgggtgatc 3840
ctggccgacg ccaacctgga caaggtgctg tccgcctaca acaagcaccg ggacaagccc 3900
atccgggagc aggccgagaa catcatccac ctgttcaccc tgaccaacct gggcgccccc 3960
gccgccttca agtacttcga caccaccatc gaccggaagc ggtacacctc caccaaggag 4020
gtgctggacg ccaccctgat ccaccagtcc atcaccggcc tgtacgagac ccggatcgac 4080
ctgtcccagc tgggcggcga cggctccggc tcccccaaga agaagcggaa ggtggacggc 4140
tcccccaaga agaagcggaa ggtggactcc ggc 4173

SEQ ID NO: 349 moltype = length =
SEQUENCE: 349
000

SEQ ID NO: 350 moltype = length =
SEQUENCE: 350
000

```
SEQ ID NO: 351         moltype =   length =
SEQUENCE: 351
000

SEQ ID NO: 352         moltype =   length =
SEQUENCE: 352
000

SEQ ID NO: 353         moltype =   length =
SEQUENCE: 353
000

SEQ ID NO: 354         moltype =   length =
SEQUENCE: 354
000

SEQ ID NO: 355         moltype = DNA  length = 4173
FEATURE                Location/Qualifiers
misc_feature           1..4173
                       note = Synthetic: Cas9 ORF using low A/U codons of Table 4,
                        with two C-terminal NLS sequences (no start or stop
                        codons; suitable for inclusion in fusion protein coding
                        sequence)
source                 1..4173
                       mol_type = other DNA
                       organism = synthetic construct
SEQUENCE: 355
gacaagaagt acagcatcgg cctggacatc ggcaccaaca gcgtgggctg ggccgtgatc  60
accgacgagt acaaggtgcc cagcaagaag ttcaaggtgc tgggcaacac cgaccggcac  120
agcatcaaga agaacctgat cggcgccctg ctgttcgaca gcggcgagac cgccgaggcc  180
acccggctga agcggaccgc ccggcggcgg tacacccggc ggaagaaccg gatctgctac  240
ctgcaggaga tcttcagcaa cgagatggcc aaggtggacg acagcttctt ccaccggctg  300
gaggagagct tcctggtgga ggaggacaag aagcacgagc ggcaccccat cttcggcaac  360
atcgtggacg aggtggccta ccacgagaag taccccacca tctaccacct gcggaagaag  420
ctggtggaca gcaccgacaa ggccgacctg cggctgatct acctggccct ggcccacatg  480
atcaagttcc ggggccactt cctgatcgag ggcgacctga accccgacaa cagcgacgtg  540
gacaagctgt tcatccagct ggtgcagacc tacaaccagc tgttcgagga gaaccccatc  600
aacgccagcg gcgtggacgc caaggccatc ctgagcgccc ggctgagcaa gagccggcgg  660
ctggagaacc tgatcgccca gctgcccggc gagaagaaga acggcctgtt cggcaacctg  720
atcgccctga gcctgggcct gacccccaac ttcaagagca acttcgacct ggccgaggac  780
gccaagctgc agctgagcaa ggacacctac gacgacgacc tggacaacct gctggcccag  840
atcggcgacc agtacgccga cctgttcctg gccgccaaga acctgagcga cgccatcctg  900
ctgagcgaca tcctgcgggt gaacaccgag atcaccaagg ccccccctgag cgccagcatg  960
atcaagcggt acgacgagca ccaccaggac ctgaccctgc tgaaggccct ggtgcggcag  1020
cagctgcccg agaagtacaa ggagatcttc ttcgaccaga gcaagaacgg ctacgccggc  1080
tacatcgacg gcggcgccag ccaggaggag ttctacaagt tcatcaagcc catcctggag  1140
aagatggacg gcaccgagga gctgctggtg aagctgaacc gggaggacct gctgcggaag  1200
cagcggacct tcgacaacgg cagcatcccc caccagatcc acctgggcga gctgcacgcc  1260
atcctgcggc ggcaggagga cttctacccc ttcctgaagg acaaccggga gaagatcgag  1320
aagatcctga ccttccggat ccccctactac gtgggccccc tggcccgggg caacagccgg  1380
ttcgcctgga tgacccggaa gagcgaggag accatcaccc cctggaactt cgaggaggtg  1440
gtggacaagg gcgccagcgc ccagagcttc atcgagcgga tgaccaactt cgacaagaac  1500
ctgcccaacg agaaggtgct gcccaagcac agcctgctgt acgagtactt caccgtgtac  1560
aacgagctga ccaaggtgaa gtacgtgacc gagggcatgc ggaagcccgc cttcctgagc  1620
ggcgagcaga agaaggccat cgtggacctg ctgttcaaga ccaaccggaa ggtgaccgtg  1680
aagcagctga aggaggacta cttcaagaag atcgagtgct tcgacagcgt ggagatcagc  1740
ggcgtggagg accggttcaa cgccagcctg ggcacctacc acgacctgct gaagatcatc  1800
aaggacaagg acttcctgga caacgaggag aacgaggaca tcctggagga catcgtgctg  1860
accctgaccc tgttcgagga ccgggagatg atcgaggagc ggctgaagac ctacgcccac  1920
ctgttcgacg acaaggtgat gaagcagctg aagcggcggc ggtacaccgg ctggggccgg  1980
ctgagccgga agctgatcaa cggcatccgg gacaagcaga gcggcaagac catcctggac  2040
ttcctgaaga gcgacggctt cgccaaccgg aacttcatgc agctgatcca cgacgacagc  2100
ctgaccttca aggaggacat ccagaaggcc caggtgagcg gccagggcga cagcctgcac  2160
gagcacatcg ccaacctggc cggcagcccc gccatcaaga agggcatcct gcagaccgtg  2220
aaggtggtgg acgagctggt gaaggtgatg ggccggcaca agcccgagaa catcgtgatc  2280
gagatggccc gggagaacca gaccacccag aagggccaga agaacagccg ggagcggatg  2340
aagcggatcg aggagggcat caaggagctg ggcagccaga tcctgaagga gcaccccgtg  2400
gagaacaccc agctgcagaa cgagaagctg tacctgtact acctgcagaa cggccgggac  2460
atgtacgtgg accaggagct ggacatcaac cggctgagcg actacgacgt ggaccacatc  2520
gtgccccaga gcttcctgaa ggacgacagc atcgacaaca aggtgctgac ccggagcgac  2580
aagaaccggg gcaagagcga caacgtgccc agcgaggagg tggtgaagaa gatgaagaac  2640
tactggcggc agctgctgaa cgccaagctg atcacccagc ggaagttcga caacctgacc  2700
aaggccgagc ggggcggcct gagcgagctg gacaaggccg gcttcatcaa gcggcagctg  2760
gtggagaccc ggcagatcac caagcacgtg gcccagatcc tggacagccg gatgaacacc  2820
aagtacgacg agaacgacaa gctgatccgg gaggtgaagg tgatcaccct gaagagcaag  2880
ctggtgagcg acttccggaa ggacttccag ttctacaagg tgcgggagat caacaactac  2940
caccacgccc acgacgccta cctgaacgcc gtggtgggca ccgccctgat caagaagtac  3000
cccaagctgg agagcgagtt cgtgtacggc gactacaagg tgtacgacgt gcggaagatg  3060
```

```
atcgccaaga gcgagcagga gatcggcaag gccaccgcca agtacttctt ctacagcaac  3120
atcatgaact tcttcaagac cgagatcacc ctggccaacg gcgagatccg gaagcggccc  3180
ctgatcgaga ccaacggcga gaccggcgag atcgtgtggg acaagggccg ggacttcgcc  3240
accgtgcgga aggtgctgag catgccccag gtgaacatcg tgaagaagac cgaggtgcag  3300
accggcggct tcagcaagga gagcatcctg cccaagcgga acagcgacaa gctgatcgcc  3360
cggaagaagg actgggaccc caagaagtac ggcggcttcg acagccccac cgtggcctac  3420
agcgtgctgg tggtggccaa ggtggagaag ggcaagagca agaagctgaa gagcgtgaag  3480
gagctgctgg gcatcaccat catggagcgg agcagcttcg agaagaaccc catcgacttc  3540
ctggaggcca agggctacaa ggaggtgaag aaggacctga tcatcaagct gcccaagtac  3600
agcctgttcg agctggagaa cggccggaag cggatgctgg ccagcgccgg cgagctgcag  3660
aagggcaacg agctggccct gcccagcaag tacgtgaact tcctgtacct ggccagccac  3720
tacgagaagc tgaagggcag ccccgaggac aacgagcaga agcagctgtt cgtggagcag  3780
cacaagcact acctggacga gatcatcgag cagatcagcg agttcagcaa gcgggtgatc  3840
ctggccgacg ccaacctgga caaggtgctg agcgcctaca acaagcaccg ggacaagccc  3900
atccgggagc aggccgagaa catcatccac ctgttcaccc tgaccaacct gggcgccccc  3960
gccgccttca agtacttcga caccaccatc gaccggaagc ggtacaccag caccaaggag  4020
gtgctggacg ccaccctgat ccaccagagc atcaccggcc tgtacgagac ccggatcgac  4080
ctgagccagc tgggcggcga cggcagcggc agccccaaga agaagcggaa ggtggacggc  4140
agccccaaga agaagcggaa ggtggacagc ggc                              4173
```

```
SEQ ID NO: 356          moltype = DNA  length = 4101
FEATURE                 Location/Qualifiers
misc_feature            1..4101
                        note = Synthetic: Cas9 ORF using low A/U codons of Table 4
                         (no NLS and no start or stop codons; suitable for
                         inclusion in fusion protein coding sequence)
source                  1..4101
                        mol_type = other DNA
                        organism = synthetic construct
SEQUENCE: 356
gacaagaagt acagcatcgg cctggacatc ggcaccaaca gcgtgggctg ggccgtgatc  60
accgacgagt acaaggtgcc cagcaagaag ttcaaggtgc tgggcaacac cgaccggcac  120
agcatcaaga agaacctgat cggcgccctg ctgttcgaca gcggcgagac cgccgaggcc  180
acccggctga agcggaccgc ccggcggcgg tacacccggc ggaagaaccg gatctgctac  240
ctgcaggaga tcttcagcaa cgagatggcc aaggtggacg acagcttctt ccaccggctg  300
gaggagagct tcctggtgga ggaggacaag aagcacgagc ggcaccccat cttcggcaac  360
atcgtggacg aggtggccta ccacgagaag taccccacca tctaccacct gcggaagaag  420
ctggtggaca gcaccgacaa ggccgacctg cggctgatct acctggccct ggcccacatg  480
atcaagttcc ggggccactt cctgatcgag ggcgacctga accccgacaa cagcgacgtg  540
gacaagctgt tcatccagct ggtgcagacc tacaaccagc tgttcgagga gaaccccatc  600
aacgccagcg gcgtggacgc caaggccatc ctgagcgccc ggctgagcaa gagccggcgg  660
ctggagaacc tgatcgccca gctgcccggc gagaagaaga acggcctgtt cggcaacctg  720
atcgccctga gcctgggcct gacccccaac ttcaagagca acttcgacct ggccgaggac  780
gccaagctgc agctgagcaa ggacacctac gacgacgacc tggacaacct gctggcccag  840
atcggcgacc agtacgccga cctgttcctg gccgccaaga acctgagcga cgccatcctg  900
ctgagcgaca tcctgcgggt gaacaccgag atcaccaagg ccccccctgag cgccagcatg  960
atcaagcggt acgacgagca ccaccaggac ctgaccctgc tgaaggccct ggtgcggcag  1020
cagctgcccg agaagtacaa ggagatcttc ttcgaccaga gcaagaacgg ctacgccggc  1080
tacatcgacg gcggcgccag ccaggaggag ttctacaagt tcatcaagcc catcctggag  1140
aagatggacg gcaccgagga gctgctggtg aagctgaacc gggaggacct gctgcggaag  1200
cagcggacct tcgacaacgg cagcatcccc caccagatcc acctgggcga gctgcacgcc  1260
atcctgcggc ggcaggagga cttctacccc ttcctgaagg acaaccggga gaagatcgag  1320
aagatcctga ccttccggat cccctactac gtgggccccc tggcccgggg caacagccgg  1380
ttcgcctgga tgacccggaa gagcgaggag accatcaccc cctggaactt cgaggaggtg  1440
gtggacaagg gcgccagcgc ccagagcttc atcgagcgga tgaccaactt cgacaagaac  1500
ctgcccaacg agaaggtgct gcccaagcac agcctgctgt acgagtactt caccgtgtac  1560
aacgagctga ccaaggtgaa gtacgtgacc gagggcatgc ggaagcccgc cttcctgagc  1620
ggcgagcaga agaaggccat cgtggacctg ctgttcaaga ccaaccggaa ggtgaccgtg  1680
aagcagctga aggaggacta cttcaagaag atcgagtgct tcgacagcgt ggagatcagc  1740
ggcgtggagg accggttcaa cgccagcctg ggcacctacc acgacctgct gaagatcatc  1800
aaggacaagg acttcctgga caacgaggag aacgaggaca tcctggagga catcgtgctg  1860
accctgaccc tgttcgagga ccgggagatg atcgaggagc ggctgaagac ctacgcccac  1920
ctgttcgacg acaaggtgat gaagcagctg aagcggcggc ggtacaccgg ctggggccgg  1980
ctgagccgga agctgatcaa cggcatccgg gacaagcaga gcggcaagac catcctggac  2040
ttcctgaaga gcgacggctt cgccaaccgg aacttcatgc agctgatcca cgacgacagc  2100
ctgaccttca aggaggacat ccagaaggcc caggtgagcg gccagggcga cagcctgcac  2160
gagcacatcg ccaacctggc cggcagcccc gccatcaaga agggcatcct gcagaccgtg  2220
aaggtggtgg acgagctggt gaaggtgatg ggccggcaca agcccgagaa catcgtgatc  2280
gagatggccc gggagaacca gaccacccag aagggccaga agaacagccg ggagcggatg  2340
aagcggatcg aggagggcat caaggagctg ggcagccaga tcctgaagga gcaccccgtg  2400
gagaacaccc agctgcagaa cgagaagctg tacctgtact acctgcagaa cggccgggac  2460
atgtacgtgg accaggagct ggacatcaac cggctgagcg actacgacgt ggaccacatc  2520
gtgccccaga gcttcctgaa ggacgacagc atcgacaaca aggtgctgac ccggagcgac  2580
aagaaccggg gcaagagcga caacgtgccc agcgaggagg tggtgaagaa gatgaagaac  2640
tactggcggc agctgctgaa cgccaagctg atcacccagc ggaagttcga caacctgacc  2700
aaggccgagc ggggcggcct gagcgagctg gacaaggccg gcttcatcaa gcggcagctg  2760
gtggagaccc ggcagatcac caagcacgtg gcccagatcc tggacagccg gatgaacacc  2820
aagtacgacg agaacgacaa gctgatccgg gaggtgaagg tgatcaccct gaagagcaag  2880
ctggtgagcg acttccggaa ggacttccag ttctacaagg tgcgggagat caacaactac  2940
```

```
caccacgccc acgacgccta cctgaacgcc gtggtgggca ccgccctgat caagaagtac  3000
cccaagctgg agagcgagtt cgtgtacggc gactacaagg tgtacgacgt gcggaagatg  3060
atcgccaaga gcgagcagga gatcggcaag gccaccgcca agtacttctt ctacagcaac  3120
atcatgaact tcttcaagac cgagatcacc ctggccaacg gcgagatccg gaagcggccc  3180
ctgatcgaga ccaacggcga gaccggcgag atcgtgtggg acaagggccg ggacttcgcc  3240
accgtgcgga aggtgctgag catgccccag gtgaacatcg tgaagaagac cgaggtgcag  3300
accggcggct tcagcaagga gagcatcctg cccaagcgga acagcgacaa gctgatcgcc  3360
cggaagaagg actgggaccc caagaagtac ggcggcttcg acagccccac cgtggcctac  3420
agcgtgctgg tggtggccaa ggtggagaag ggcaagagca agaagctgaa gagcgtgaag  3480
gagctgctgg gcatcaccat catggagcgg agcagcttcg agaagaaccc catcgacttc  3540
ctggaggcca agggctacaa ggaggtgaag aaggacctga tcatcaagct gcccaagtac  3600
agcctgttcg agctggagaa cggccggaag cggatgctgg ccagcgccgg cgagctgcag  3660
aagggcaacg agctggccct gcccagcaag tacgtgaact tcctgtacct ggccagccac  3720
tacgagaagc tgaagggcag ccccgaggac aacgagcaga agcagctgtt cgtggagcag  3780
cacaagcact acctggacga gatcatcgag cagatcagcg agttcagcaa gcgggtgatc  3840
ctggccgacg ccaacctgga caaggtgctg agcgcctaca acaagcaccg ggacaagccc  3900
atccgggagc aggccgagaa catcatccac ctgttcaccc tgaccaacct gggcgccccc  3960
gccgccttca agtacttcga caccaccatc gaccggaagc ggtacaccag caccaaggag  4020
gtgctggacg ccaccctgat ccaccagagc atcaccggcc tgtacgagac ccggatcgac  4080
ctgagccagc tgggcggcga c                                          4101

SEQ ID NO: 357          moltype =   length =
SEQUENCE: 357
000

SEQ ID NO: 358          moltype =   length =
SEQUENCE: 358
000

SEQ ID NO: 359          moltype =   length =
SEQUENCE: 359
000

SEQ ID NO: 360          moltype =   length =
SEQUENCE: 360
000

SEQ ID NO: 361          moltype =   length =
SEQUENCE: 361
000

SEQ ID NO: 362          moltype =   length =
SEQUENCE: 362
000

SEQ ID NO: 363          moltype = DNA  length = 3306
FEATURE                 Location/Qualifiers
misc_feature            1..3306
                        note = Synthetic: Nme Cas9 ORF using low A codons of Table
                         5 (no start or stop codons; suitable for inclusion in
                         fusion protein coding sequence)
source                  1..3306
                        mol_type = other DNA
                        organism = synthetic construct
SEQUENCE: 363
gccgccttca agcccaactc catcaactac atcctgggcc tggacatcgg catcgcctcc  60
gtgggctggg ccatggtgga gatcgacgag gaggagaacc ccatccggct gatcgacctg  120
ggcgtgcggg tgttcgagcg ggccgaggtg cccaagaccg gcgactccct ggccatggcc  180
cggcggctgg cccggtccgt gcggcggctg acccggcggc gggcccaccg gctgctgcgg  240
acccggcggc tgctgaagcg ggagggcgtg ctgcaggccg ccaacttcga cgagaacggc  300
ctgatcaagt ccctgcccaa cacccctgg cagctgcggg ccgccgccct ggaccggaag  360
ctgacccccc tggagtggtc cgccgtgctg ctgcacctga tcaagcaccg gggctacctg  420
tcccagcgga agaacgaggg cgagaccgcc gacaaggagc tgggcgccct gctgaagggc  480
gtggccggca acgcccacgc cctgcagacc ggcgacttcc ggacccccgc cgagctggcc  540
ctgaacaagt tcgagaagga gtccggccac atccggaacc agcggtccga ctactcccac  600
accttctccc ggaaggacct gcaggccgag ctgatcctgc tgttcgagaa gcagaaggag  660
ttcggcaacc cccacgtgtc cggcggcctg aaggagggca tcgagaccct gctgatgacc  720
cagcggcccg ccctgtccgg cgacgccgtg cagaagatgc tgggccactg caccttcgag  780
cccgccgagc ccaaggccgc caagaacacc tacaccgccg agcggttcat ctggctgacc  840
aagctgaaca acctgcggat cctggagcag ggctccgagc ggcccctgac cgacaccgag  900
cgggccaccc tgatggacga gccctaccgg aagtccaagc tgacctacgc ccaggcccgg  960
aagctgctgg gcctggagga caccgccttc ttcaagggcc tgcggtacgg caaggacaac  1020
gccgaggcct ccaccctgat ggagatgaag gcctaccacg ccatctcccg ggccctggag  1080
aaggagggcc tgaaggacaa gaagtccccc ctgaacctgt cccccgagct gcaggacgag  1140
atcggcaccg ccttctccct gttcaagacc gacgaggaca tcaccggccg gctgaaggac  1200
cggatccagc ccgagatcct ggaggccctg ctgaagcaca tctccttcga caagttcgtg  1260
cagatctccc tgaaggccct gcggcggatc gtgcccctga tggagcaggg caagcggtac  1320
gacgaggcct gcgccgagat ctacggcgac cactacggca agaagaacac cgaggagaag  1380
atctacctgc cccccatccc cgccgacgag atccggaacc ccgtggtgct gcgggccctg  1440
```

-continued

```
tcccaggccc ggaaggtgat caacggcgtg gtgcggcggt acggctcccc cgcccggatc  1500
cacatcgaga ccgcccggga ggtgggcaag tccttcaagg accggaagga gatcgagaag  1560
cggcaggagg agaaccggaa ggaccgggag aaggccgccg ccaagttccg ggagtacttc  1620
cccaacttcg tgggcgagcc caagtccaag gacatcctga agctgcggct gtacgagcag  1680
cagcacggca agtgcctgta ctccggcaag gagatcaacc tgggccggct gaacgagaag  1740
ggctacgtgg agatcgacca cgccctgccc ttctcccgga cctgggacga ctccttcaac  1800
aacaaggtgc tggtgctggg ctccgagaac cagaacaagg gcaaccagac cccctacgag  1860
tacttcaacg gcaaggacaa ctcccgggag tggcaggagt tcaaggcccg ggtggagacc  1920
tcccggttcc cccggtccaa gaagcagcgg atcctgctgc agaagttcga cgaggacggc  1980
ttcaaggagc ggaacctgaa cgacacccgg tacgtgaacc ggttcctgtg ccagttcgtg  2040
gccgaccgga tgcggctgac cggcaagggc aagaagcggg tgttcgcctc caacggccag  2100
atcaccaacc tgctgcgggg cttctggggc ctgcggaagg tgcgggccga gaacgaccgg  2160
caccacgccc tggacgccgt ggtggtggcc tgctccaccg tggccatgca gcagaagatc  2220
acccggttcg tgcggtacaa ggagatgaac gccttcgacg gcaagaccat cgacaaggag  2280
accggcgagg tgctgcacca gaagacccac ttcccccagc cctgggagtt cttcgcccag  2340
gaggtgatga tccgggtgtt cggcaagccc gacggcaagc ccgagttcga ggaggccgac  2400
accctggaga agctgcggac cctgctggcc gagaagctgt cctcccggcc cgaggccgtg  2460
cacgagtacg tgaccccccct gttcgtgtcc cgggcccccca accggaagat gtccggccag  2520
ggccacatgg agaccgtgaa gtccgccaag cggctggacg agggcgtgtc cgtgctgcgg  2580
gtgcccctga cccagctgaa gctgaaggac ctggagaaga tggtgaaccg ggagcgggag  2640
cccaagctgt acgaggccct gaaggcccgg ctggaggccc acaaggacga ccccgccaag  2700
gccttcgccg agcccttcta caagtacgac aaggccggca accggaccca gcaggtgaag  2760
gccgtgcggg tggagcaggt gcagaagacc ggcgtgtggg tgcggaacca caacggcatc  2820
gccgacaacg ccaccatggt gcgggtggac gtgttcgaga agggcgacaa gtactacctg  2880
gtgcccatct actcctggca ggtggccaag ggcatcctgc ccgaccgggc cgtggtgcag  2940
ggcaaggacg aggaggactg gcagctgatc gacgactcct tcaacttcaa gttctccctg  3000
caccccaacg acctggtgga ggtgatcacc aagaaggccc ggatgttcgg ctacttcgcc  3060
tcctgccacc ggggcaccgg caacatcaac atccggatcc acgacctgga ccacaagatc  3120
ggcaagaacg gcatcctgga gggcatcggc gtgaagaccg ccctgtcctt ccagaagtac  3180
cagatcgacg agctgggcaa ggagatccgg ccctgccggc tgaagaagcg gccccccgtg  3240
cggtccggca agcggaccgc cgacggctcc gagttcgagt cccccaagaa gaagcggaag  3300
gtggag                                                             3306

SEQ ID NO: 364          moltype = DNA  length = 3306
FEATURE                 Location/Qualifiers
misc_feature            1..3306
                        note = Synthetic: Nme Cas9 ORF using low A/U codons of
                         Table 5 (no start or stop codons; suitable for inclusion
                         in fusion protein coding sequence)
source                  1..3306
                        mol_type = other DNA
                        organism = synthetic construct
SEQUENCE: 364
gccgccttca agcccaacag catcaactac atcctgggcc tggacatcgg catcgccagc  60
gtgggctggg ccatggtgga gatcgacgag gaggagaacc ccatccggct gatcgacctg  120
ggcgtgcggg tgttcgagcg ggccgaggtg cccaagaccg gcgacagcct ggccatggcc  180
cggcggctgg cccggagcgt gcggcggctg acccggcggc gggcccaccg gctgctgcgg  240
acccggcggc tgctgaagcg ggagggcgtg ctgcaggccg ccaacttcga cgagaacggc  300
ctgatcaaga gcctgcccaa cacccccctgg cagctgcggg ccgccgccct ggaccggaag  360
ctgaccccccc tggagtggag cgccgtgctg ctgcacctga tcaagcaccg gggctacctg  420
agccagcgga agaacgaggg cgagaccgcc gacaaggagc tgggcgccct gctgaagggc  480
gtggccggca acgcccacgc cctgcagacc ggcgacttcc ggacccccgc cgagctggcc  540
ctgaacaagt tcgagaagga gagcggccac atccggaacc agcggagcga ctacagccac  600
accttcagcc ggaaggacct gcaggccgag ctgatcctgc tgttcgagaa gcagaaggag  660
ttcggcaacc cccacgtgag cggcggcctg aaggagggca tcgagaccct gctgatgacc  720
cagcggcccg ccctgagcgg cgacgccgtg cagaagatgc tgggccactg caccttcgag  780
cccgccgagc ccaaggccgc caagaacacc tacaccgccg agcggttcat ctggctgacc  840
aagctgaaca acctgcggat cctggagcag ggcagcgagc ggcccctgac cgacaccgag  900
cgggccaccc tgatggacga gccctaccgg aagagcaagc tgacctacgc ccaggcccgg  960
aagctgctgg gcctggagga caccgccttc ttcaagggcc tgcggtacgg caaggacaac  1020
gccgaggcca gcaccctgat ggagatgaag gcctaccacg ccatcagccg ggccctggag  1080
aaggagggcc tgaaggacaa gaagagcccc ctgaacctga gccccgagct gcaggacgag  1140
atcggcaccg ccttcagcct gttcaagacc gacgaggaca tcaccggccg gctgaaggac  1200
cggatccagc ccgagatcct ggaggccctg ctgaagcaca tcagcttcga caagttcgtg  1260
cagatcagcc tgaaggccct gcggcggatc gtgcccctga tggagcaggg caagcggtac  1320
gacgaggcct gcgccgagat ctacggcgac cactacggca agaagaacac cgaggagaag  1380
atctacctgc cccccatccc cgccgacgag atccggaacc ccgtggtgct gcgggccctg  1440
agccaggccc ggaaggtgat caacggcgtg gtgcggcggt acggcagccc cgcccggatc  1500
cacatcgaga ccgcccggga ggtgggcaag agcttcaagg accggaagga gatcgagaag  1560
cggcaggagg agaaccggaa ggaccgggag aaggccgccg ccaagttccg ggagtacttc  1620
cccaacttcg tgggcgagcc caagagcaag gacatcctga agctgcggct gtacgagcag  1680
cagcacggca agtgcctgta cagcggcaag gagatcaacc tgggccggct gaacgagaag  1740
ggctacgtgg agatcgacca cgccctgccc ttcagccgga cctgggacga cagcttcaac  1800
aacaaggtgc tggtgctggg cagcgagaac cagaacaagg gcaaccagac cccctacgag  1860
tacttcaacg gcaaggacaa cagccgggag tggcaggagt tcaaggcccg ggtggagacc  1920
agccggttcc cccggagcaa gaagcagcgg atcctgctgc agaagttcga cgaggacggc  1980
ttcaaggagc ggaacctgaa cgacacccgg tacgtgaacc ggttcctgtg ccagttcgtg  2040
gccgaccgga tgcggctgac cggcaagggc aagaagcggg tgttcgccag caacggccag  2100
atcaccaacc tgctgcgggg cttctggggc ctgcggaagg tgcgggccga gaacgaccgg  2160
```

-continued

```
caccacgccc tggacgccgt ggtggtggcc tgcagcaccg tggccatgca gcagaagatc  2220
acccggttcg tgcggtacaa ggagatgaac gccttcgacg gcaagaccat cgacaaggag  2280
accggcgagg tgctgcacca gaagacccac ttcccccagc cctgggagtt cttcgcccag  2340
gaggtgatga tccgggtgtt cggcaagccc gacggcaagc ccgagttcga ggaggccgac  2400
accctggaga agctgcggac cctgctggcc gagaagctga gcagccggcc cgaggccgtg  2460
cacgagtacg tgaccccccct gttcgtgagc cgggcccccca accggaagat gagcggccag  2520
ggccacatgg agaccgtgaa gagcgccaag cggctggacg agggcgtgag cgtgctgcgg  2580
gtgcccctga cccagctgaa gctgaaggac ctggagaaga tggtgaaccg ggagcgggag  2640
cccaagctgt acgaggccct gaaggcccgg ctggaggccc acaaggacga ccccgccaag  2700
gccttcgccg agcccttcta caagtacgac aaggccggca accggaccca gcaggtgaag  2760
gccgtgcggg tggagcaggt gcagaagacc ggcgtgtggg tgcggaacca caacggcatc  2820
gccgacaacg ccaccatggt gcgggtggac gtgttcgaga agggcgacaa gtactacctg  2880
gtgcccatct acagctggca ggtggccaag ggcatcctgc ccgaccgggc cgtggtgcag  2940
ggcaaggacg aggaggactg gcagctgatc gacgacagct tcaacttcaa gttcagcctg  3000
caccccaacg acctggtgga ggtgatcacc aagaaggccc ggatgttcgg ctacttcgcc  3060
agctgccacc ggggcaccgg caacatcaac atccggatcc acgacctgga ccacaagatc  3120
ggcaagaacg gcatcctgga gggcatcggc gtgaagaccg ccctgagctt ccagaagtac  3180
cagatcgacg agctgggcaa ggagatccgg ccctgccggc tgaagaagcg gccccccgtg  3240
cggagcggca agcggaccgc cgacggcagc gagttcgaga gccccaagaa gaagcggaag  3300
gtggag                                                              3306

SEQ ID NO: 365         moltype =   length =
SEQUENCE: 365
000

SEQ ID NO: 366         moltype =   length =
SEQUENCE: 366
000

SEQ ID NO: 367         moltype =   length =
SEQUENCE: 367
000

SEQ ID NO: 368         moltype =   length =
SEQUENCE: 368
000

SEQ ID NO: 369         moltype =   length =
SEQUENCE: 369
000

SEQ ID NO: 370         moltype =   length =
SEQUENCE: 370
000

SEQ ID NO: 371         moltype =   length =
SEQUENCE: 371
000

SEQ ID NO: 372         moltype =   length =
SEQUENCE: 372
000

SEQ ID NO: 373         moltype =   length =
SEQUENCE: 373
000

SEQ ID NO: 374         moltype =   length =
SEQUENCE: 374
000

SEQ ID NO: 375         moltype =   length =
SEQUENCE: 375
000

SEQ ID NO: 376         moltype = RNA  length = 4405
FEATURE                Location/Qualifiers
misc_feature           1..4405
                       note = Synthetic: mRNA transcript with XBG UTRs and Cas9 ORF
source                 1..4405
                       mol_type = other RNA
                       organism = synthetic construct
SEQUENCE: 376
gggaagctca gaataaacgc tcaactttgg ccggatctgc caccatggac aagaagtaca  60
gcatcggcct ggacatcggc accaacagcg tgggctgggc cgtgatcacc gacgagtaca  120
aggtgcccag caagaagttc aaggtgctgg gcaacaccga cagacacagc atcaagaaga  180
acctgatcgg cgccctgctg ttcgacagcg gcgagaccgc cgaggccacc agactgaaga  240
gaaccgccag aagaagatac accagaagaa agaacagaat ctgctacctg caggagatct  300
tcagcaacga gatggccaag gtggacgaca gcttcttcca cagactggag gagagcttcc  360
```

```
tggtggagga ggacaagaag cacgagagac accccatctt cggcaacatc gtggacgagg  420
tggcctacca cgagaagtac cccaccatct accacctgag aaagaagctg gtggacagca  480
ccgacaaggc cgacctgaga ctgatctacc tggccctggc ccacatgatc aagttcagag  540
gccacttcct gatcgagggc gacctgaacc ccgacaacag cgacgtggac aagctgttca  600
tccagctggt gcagacctac aaccagctgt tcgaggagaa ccccatcaac gccagcggcg  660
tggacgccaa ggccatcctg agcgccagac tgagcaagag cagaagactg gagaacctga  720
tcgcccagct gcccggcgag aagaagaacg gcctgttcgg caacctgatc gccctgagcc  780
tgggcctgac ccccaacttc aagagcaact tcgacctggc cgaggacgcc aagctgcagc  840
tgagcaagga cacctacgac gacgacctgg acaacctgct ggcccagatc ggcgaccagt  900
acgccgacct gttcctggcc gccaagaacc tgagcgacgc catcctgctg agcgacatcc  960
tgagagtgaa caccgagatc accaaggccc ccctgagcgc cagcatgatc aagagatacg  1020
acgagcacca ccaggacctg accctgctga aggccctggt gagacagcag ctgcccgaga  1080
agtacaagga gatcttcttc gaccagagca agaacggcta cgccggctac atcgacggcg  1140
gcgccagcca ggaggagttc tacaagttca tcaagcccat cctggagaag atggacggca  1200
ccgaggagct gctggtgaag ctgaacagag aggacctgct gagaaagcag agaaccttcg  1260
acaacggcag catcccccac cagatccacc tgggcgagct gcacgccatc ctgagaagac  1320
aggaggactt ctacccettc ctgaaggaca acagagagaa gatcgagaag atcctgacct  1380
tcagaatccc ctactacgtg ggccccctgg ccagaggcaa cagcagattc gcctggatga  1440
ccagaaagag cgaggagacc atcacccect ggaacttcga ggaggtggtg gacaagggcg  1500
ccagcgccca gagcttcatc gagagaatga ccaacttcga caagaacctg cccaacgaga  1560
aggtgctgcc caagcacagc ctgctgtacg agtacttcac cgtgtacaac gagctgacca  1620
aggtgaagta cgtgaccgag ggcatgagaa agcccgcctt cctgagcggc gagcagaaga  1680
aggccatcgt ggacctgctg ttcaagacca acagaaaggt gaccgtgaag cagctgaagg  1740
aggactactt caagaagatc gagtgcttcg acagcgtgga gatcagcggc gtggaggaca  1800
gattcaacgc cagcctgggc acctaccacg acctgctgaa gatcatcaag gacaaggact  1860
tcctggacaa cgaggagaac gaggacatcc tggaggacat cgtgctgacc ctgaccctgt  1920
tcgaggacag agagatgatc gaggagagac tgaagaccta cgcccacctg ttcgacgaca  1980
aggtgatgaa gcagctgaag agaagaagat acaccggctg gggcagactg agcagaaagc  2040
tgatcaacgg catcagagac aagcagagcg gcaagaccat cctggacttc ctgaagagcg  2100
acggcttcgc caacagaaac ttcatgcagc tgatccacga cgacagcctg accttcaagg  2160
aggacatcca gaaggcccag gtgagcggcc agggcgacag cctgcacgag cacatcgcca  2220
acctggccgg cagccccgcc atcaagaagg gcatcctgca gaccgtgaag gtggtggacg  2280
agctggtgaa ggtgatgggc agacacaagc ccgagaacat cgtgatcgag atggccagag  2340
agaaccagac cacccagaag ggccagaaga acagcagaga gagaatgaag agaatcgagg  2400
agggcatcaa ggagctgggc agccagatcc tgaaggagca ccccgtggag aacacccagc  2460
tgcagaacga gaagctgtac ctgtactacc tgcagaacgg cagagacatg tacgtggacc  2520
aggagctgga catcaacaga ctgagcgact acgacgtgga ccacatcgtg ccccagagct  2580
tcctgaagga cgacagcatc gacaacaagg tgctgaccag aagcgacaag aacagaggca  2640
agagcgacaa cgtgcccagc gaggaggtgg tgaagaagat gaagaactac tggagacagc  2700
tgctgaacgc caagctgatc acccagagaa agttcgacaa cctgaccaag gccgagagag  2760
gcggcctgag cgagctggac aaggccggct tcatcaagag acagctggtg gagaccagac  2820
agatcaccaa gcacgtggcc cagatcctgg acagcagaat gaacaccaag tacgacgaga  2880
acgacaagct gatcagagag gtgaaggtga tcaccctgaa gagcaagctg gtgagcgact  2940
tcagaaagga cttccagttc tacaaggtga gagagatcaa caactaccac cacgcccacg  3000
acgcctacct gaacgccgtg gtgggcaccg ccctgatcaa gaagtacccc aagctggaga  3060
gcgagttcgt gtacggcgac tacaaggtgt acgacgtgag aaagatgatc gccaagagcg  3120
agcaggagat cggcaaggcc accgccaagt acttcttcta cagcaacatc atgaacttct  3180
tcaagaccga gatcaccctg gccaacggcg agatcagaaa gagacccctg atcgagacca  3240
acggcgagac cggcgagatc gtgtgggaca agggcagaga cttcgccacc gtgagaaagg  3300
tgctgagcat gccccaggtg aacatcgtga agaagaccga ggtgcagacc ggcggcttca  3360
gcaaggagag catcctgccc aagagaaaca gcgacaagct gatcgccaga aagaaggact  3420
gggaccccaa gaagtacggc ggcttcgaca gccccaccgt ggcctacagc gtgctggtgg  3480
tggccaaggt ggagaagggc aagagcaaga agctgaagag cgtgaaggag ctgctgggca  3540
tcaccatcat ggagagaagc agcttcgaga agaaccccat cgacttcctg gaggccaagg  3600
gctacaagga ggtgaagaag gacctgatca tcaagctgcc caagtacagc ctgttcgagc  3660
tggagaacgg cagaaagaga atgctggcca gcgccggcga gctgcagaag ggcaacgagc  3720
tggccctgcc cagcaagtac gtgaacttcc tgtacctggc cagccactac gagaagctga  3780
agggcagccc cgaggacaac gagcagaagc agctgttcgt ggagcagcac aagcactacc  3840
tggacgagat catcgagcag atcagcgagt tcagcaagag agtgatcctg gccgacgcca  3900
acctggacaa ggtgctgagc gcctacaaca agcacagaga caagcccatc agagagcagg  3960
ccgagaacat catccacctg ttcaccctga ccaacctggg cgcccccgcc gccttcaagt  4020
acttcgacac caccatcgac agaaagagat acaccagcac caaggaggtg ctggacgcca  4080
ccctgatcca ccagagcatc accggcctgt acgagaccag aatcgacctg agccagctgg  4140
gcggcgacgg cggcggcagc cccaagaaga agagaaaggt gtgactagca ccagcctcaa  4200
gaacacccga atggagtctc taagctacat aataccaact tacactttac aaaatgttgt  4260
cccccaaaat gtagccattc gtatctgctc ctaataaaaa gaaagtttct tcacattctc  4320
tcgagaaaaa aaaaaaaaaa aaaaaaaaaa aaaaaaaaaa aaaaaaaaaa aaaaaaaaaa  4380
aaaaaaaaaa aaaaaaaaaa aaaaa                                        4405

SEQ ID NO: 377         moltype = RNA  length = 4405
FEATURE                Location/Qualifiers
misc_feature           1..4405
                       note = Synthetic: mRNA transcript with XBG UTRs and Cas9
                        ORF with low A codons of Table 5
source                 1..4405
                       mol_type = other RNA
                       organism = synthetic construct
SEQUENCE: 377
gggaagctca gaataaacgc tcaactttgg ccggatctgc caccatggac aagaagtact  60
```

-continued

```
ccatcggcct ggacatcggc accaactccg tgggctgggc cgtgatcacc gacgagtaca  120
aggtgccctc caagaagttc aaggtgctgg gcaacaccga ccggcactcc atcaagaaga  180
acctgatcgg cgccctgctg ttcgactccg gcgagaccgc cgaggccacc cggctgaagc  240
ggaccgcccg gcggcggtac acccggcgga agaaccggat ctgctacctg caggagatct  300
tctccaacga gatggccaag gtggacgact ccttcttcca ccggctggag gagtccttcc  360
tggtggagga ggacaagaag cacgagcggc accccatctt cggcaacatc gtggacgagg  420
tggcctacca cgagaagtac cccaccatct accacctgcg gaagaagctg gtggactcca  480
ccgacaaggc cgacctgcgg ctgatctacc tggccctggc ccacatgatc aagttccggg  540
gccacttcct gatcgagggc gacctgaacc ccgacaactc cgacgtggac aagctgttca  600
tccagctggt gcagacctac aaccagctgt tcgaggagaa ccccatcaac gcctccggcg  660
tggacgccaa ggccatcctg tccgcccggc tgtccaagtc ccggcggctg gagaacctga  720
tcgcccagct gcccggcgag aagaagaacg gcctgttcgg caacctgatc gccctgtccc  780
tgggcctgac ccccaacttc aagtccaact tcgacctggc cgaggacgcc aagctgcagc  840
tgtccaagga cacctacgac gacgacctgg acaacctgct ggcccagatc ggcgaccagt  900
acgccgacct gttcctggcc gccaagaacc tgtccgacgc catcctgctg tccgacatcc  960
tgcgggtgaa caccgagatc accaaggccc ccctgtccgc ctccatgatc aagcggtacg  1020
acgagcacca ccaggacctg accctgctga aggccctggt gcggcagcag ctgcccgaga  1080
agtacaagga gatcttcttc gaccagtcca agaacggcta cgccggctac atcgacggcg  1140
gcgcctccca ggaggagttc tacaagttca tcaagcccat cctggagaag atggacggca  1200
ccgaggagct gctggtgaag ctgaaccggg aggacctgct gcggaagcag cggaccttcg  1260
acaacggctc catcccccac cagatccacc tgggcgagct gcacgccatc ctgcggcggc  1320
aggaggactt ctaccccttc ctgaaggaca accgggagaa gatcgagaag atcctgacct  1380
tccggatccc ctactacgtg ggccccctgg cccggggcaa ctcccggttc gcctggatga  1440
cccggaagtc cgaggagacc atcacccccct ggaacttcga ggaggtggtg gacaagggcg  1500
cctccgccca gtccttcatc gagcggatga ccaacttcga caagaacctg cccaacgaga  1560
aggtgctgcc caagcactcc ctgctgtacg agtacttcac cgtgtacaac gagctgacca  1620
aggtgaagta cgtgaccgag ggcatgcgga agcccgcctt cctgtccggc gagcagaaga  1680
aggccatcgt ggacctgctg ttcaagacca accggaaggt gaccgtgaag cagctgaagg  1740
aggactactt caagaagatc gagtgcttcg actccgtgga gatctccggc gtggaggacc  1800
ggttcaacgc ctccctgggc acctaccacg acctgctgaa gatcatcaag gacaaggact  1860
tcctggacaa cgaggagaac gaggacatcc tggaggacat cgtgctgacc ctgaccctgt  1920
tcgaggaccg ggagatgatc gaggagcggc tgaagaccta cgcccacctg ttcgacgaca  1980
aggtgatgaa gcagctgaag cggcggcggt acaccggctg gggccggctg tcccggaagc  2040
tgatcaacgg catccgggac aagcagtccg gcaagaccat cctggacttc ctgaagtccg  2100
acggcttcgc caaccggaac ttcatgcagc tgatccacga cgactccctg accttcaagg  2160
aggacatcca gaaggcccag gtgtccggcc agggcgactc cctgcacgag cacatcgcca  2220
acctggccgg ctcccccgcc atcaagaagg gcatcctgca gaccgtgaag gtggtggacg  2280
agctggtgaa ggtgatgggc cggcacaagc ccgagaacat cgtgatcgag atggcccggg  2340
agaaccagac cacccagaag ggccagaaga actcccggga gcggatgaag cggatcgagg  2400
agggcatcaa ggagctgggc tcccagatcc tgaaggagca ccccgtggag aacacccagc  2460
tgcagaacga gaagctgtac ctgtactacc tgcagaacgg ccgggacatg tacgtggacc  2520
aggagctgga catcaaccgg ctgtccgact acgacgtgga ccacatcgtg ccccagtcct  2580
tcctgaagga cgactccatc gacaacaagg tgctgacccg gtccgacaag aaccggggca  2640
agtccgacaa cgtgccctcc gaggaggtgg tgaagaagat gaagaactac tggcggcagc  2700
tgctgaacgc caagctgatc acccagcgga agttcgacaa cctgaccaag gccgagcggg  2760
gcggcctgtc cgagctggac aaggccggct tcatcaagcg gcagctggtg gagacccggc  2820
agatcaccaa gcacgtggcc cagatcctgg actcccggat gaacaccaag tacgacgaga  2880
acgacaagct gatccgggag gtgaaggtga tcaccctgaa gtccaagctg gtgtccgact  2940
tccggaagga cttccagttc tacaaggtgc gggagatcaa caactaccac cacgcccacg  3000
acgcctacct gaacgccgtg gtgggcaccg ccctgatcaa gaagtacccc aagctggagt  3060
ccgagttcgt gtacggcgac tacaaggtgt acgacgtgcg gaagatgatc gccaagtccg  3120
agcaggagat cggcaaggcc accgccaagt acttcttcta ctccaacatc atgaacttct  3180
tcaagaccga gatcaccctg gccaacggcg agatccggaa gcggcccctg atcgagacca  3240
acggcgagac cggcgagatc gtgtgggaca agggccggga cttcgccacc gtgcggaagg  3300
tgctgtccat gccccaggtg aacatcgtga agaagaccga ggtgcagacc ggcggcttct  3360
ccaaggagtc catcctgccc aagcggaact ccgacaagct gatcgcccgg aagaaggact  3420
gggaccccaa gaagtacggc ggcttcgact cccccaccgt ggcctactcc gtgctggtgg  3480
tggccaaggt ggagaagggc aagtccaaga agctgaagtc cgtgaaggag ctgctgggca  3540
tcaccatcat ggagcggtcc tccttcgaga agaaccccat cgacttcctg gaggccaagg  3600
gctacaagga ggtgaagaag gacctgatca tcaagctgcc caagtactcc ctgttcgagc  3660
tggagaacgg ccggaagcgg atgctggcct ccgccggcga gctgcagaag ggcaacgagc  3720
tggccctgcc ctccaagtac gtgaacttcc tgtacctggc ctcccactac gagaagctga  3780
agggctcccc cgaggacaac gagcagaagc agctgttcgt ggagcagcac aagcactacc  3840
tggacgagat catcgagcag atctccgagt tctccaagcg ggtgatcctg gccgacgcca  3900
acctggacaa ggtgctgtcc gcctacaaca agcaccggga caagcccatc cgggagcagg  3960
ccgagaacat catccacctg ttcaccctga ccaacctggg cgcccccgcc gccttcaagt  4020
acttcgacac caccatcgac cggaagcggt acacctccac caaggaggtg ctggacgcca  4080
ccctgatcca ccagtccatc accggcctgt acgagacccg gatcgacctg tcccagctgg  4140
gcggcgacgg cggcggctcc cccaagaaga agcggaaggt gtgactagca ccagcctcaa  4200
gaacacccga atggagtctc taagctacat aataccaact tacactttac aaaatgttgt  4260
cccccaaaat gtagccattc gtatctgctc ctaataaaaa gaaagtttct tcacattctc  4320
tcgagaaaaa aaaaaaaaaa aaaaaaaaaa aaaaaaaaaa aaaaaaaaaa aaaaaaaaaa  4380
aaaaaaaaaa aaaaaaaaaa aaaaa                                       4405
```

```
SEQ ID NO: 378          moltype = RNA  length = 4405
FEATURE                 Location/Qualifiers
misc_feature            1..4405
                        note = Synthetic: mRNA transcript with XBG UTRs and Cas9
                         ORF with low U/A codons of Table 5
```

-continued

```
source                  1..4405
                        mol_type = other RNA
                        organism = synthetic construct
SEQUENCE: 378
gggaagctca gaataaacgc tcaactttgg ccggatctgc caccatggac aagaagtaca  60
gcatcggcct ggacatcggc accaacagcg tgggctgggc cgtgatcacc gacgagtaca  120
aggtgcccag caagaagttc aaggtgctgg gcaacaccga ccggcacagc atcaagaaga  180
acctgatcgg cgccctgctg ttcgacagcg gcgagaccgc cgaggccacc cggctgaagc  240
ggaccgcccg gcggcggtac acccggcgga agaaccggat ctgctacctg caggagatct  300
tcagcaacga gatggccaag gtggacgaca gcttcttcca ccggctggag gagagcttcc  360
tggtggagga ggacaagaag cacgagcggc accccatctt cggcaacatc gtggacgagg  420
tggcctacca cgagaagtac cccaccatct accacctgcg gaagaagctg gtggacagca  480
ccgacaaggc cgacctgcgg ctgatctacc tggccctggc ccacatgatc aagttccggg  540
gccacttcct gatcgagggc gacctgaacc ccgacaacag cgacgtggac aagctgttca  600
tccagctggt gcagacctac aaccagctgt tcgaggagaa ccccatcaac gccagcggcg  660
tggacgccaa ggccatcctg agcgcccggc tgagcaagag ccggcggctg gagaacctga  720
tcgcccagct gcccggcgag aagaagaacg gcctgttcgg caacctgatc gccctgagcc  780
tgggcctgac ccccaacttc aagagcaact tcgacctggc cgaggacgcc aagctgcagc  840
tgagcaagga cacctacgac gacgacctgg acaacctgct ggcccagatc ggcgaccagt  900
acgccgacct gttcctggcc gccaagaacc tgagcgacgc catcctgctg agcgacatcc  960
tgcgggtgaa caccgagatc accaaggccc ccctgagcgc cagcatgatc aagcggtacg  1020
acgagcacca ccaggacctg accctgctga aggccctggt gcggcagcag ctgcccgaga  1080
agtacaagga gatcttcttc gaccagagca agaacggcta cgccggctac atcgacggcg  1140
gcgccagcca ggaggagttc tacaagttca tcaagcccat cctggagaag atggacggca  1200
ccgaggagct gctggtgaag ctgaaccggg aggacctgct gcggaagcag cggaccttcg  1260
acaacggcag catcccccac cagatccacc tgggcgagct gcacgccatc ctgcggcggc  1320
aggaggactt ctaccccttc ctgaaggaca accgggagaa gatcgagaag atcctgacct  1380
tccggatccc ctactacgtg ggccccctgg cccggggcaa cagccggttc gcctggatga  1440
cccggaagag cgaggagacc atcacccccct ggaacttcga ggaggtggtg gacaagggcg  1500
ccagcgccca gagcttcatc gagcggatga ccaacttcga caagaacctg cccaacgaga  1560
aggtgctgcc caagcacagc ctgctgtacg agtacttcac cgtgtacaac gagctgacca  1620
aggtgaagta cgtgaccgag ggcatgcgga agcccgcctt cctgagcggc gagcagaaga  1680
aggccatcgt ggacctgctg ttcaagacca accggaaggt gaccgtgaag cagctgaagg  1740
aggactactt caagaagatc gagtgcttcg acagcgtgga gatcagcggc gtggaggacc  1800
ggttcaacgc cagcctgggc acctaccacg acctgctgaa gatcatcaag gacaaggact  1860
tcctggacaa cgaggagaac gaggacatcc tggaggacat cgtgctgacc ctgaccctgt  1920
tcgaggaccg ggagatgatc gaggagcggc tgaagaccta cgcccacctg ttcgacgaca  1980
aggtgatgaa gcagctgaag cggcggcggt acaccggctg gggccggctg agccggaagc  2040
tgatcaacgg catccgggac aagcagagcg gcaagaccat cctggacttc ctgaagagcg  2100
acggcttcgc caaccggaac ttcatgcagc tgatccacga cgacagcctg accttcaagg  2160
aggacatcca gaaggcccag gtgagcggcc agggcgacag cctgcacgag cacatcgcca  2220
acctggccgg cagccccgcc atcaagaagg gcatcctgca gaccgtgaag gtggtggacg  2280
agctggtgaa ggtgatgggc cggcacaagc ccgagaacat cgtgatcgag atggcccggg  2340
agaaccagac caccagaag ggccagaaga acagccggga gcggatgaag cggatcgagg  2400
agggcatcaa ggagctgggc agccagatcc tgaaggagca ccccgtggag aacacccagc  2460
tgcagaacga gaagctgtac ctgtactacc tgcagaacgg ccgggacatg tacgtggacc  2520
aggagctgga catcaaccgg ctgagcgact acgacgtgga ccacatcgtg ccccagagct  2580
tcctgaagga cgacagcatc gacaacaagg tgctgacccg gagcgacaag aaccggggca  2640
agagcgacaa cgtgcccagc gaggaggtgg tgaagaagat gaagaactac tggcggcagc  2700
tgctgaacgc caagctgatc acccagcgga agttcgacaa cctgaccaag gccgagcggg  2760
gcggcctgag cgagctggac aaggccggct tcatcaagcg gcagctggtg gagacccggc  2820
agatcaccaa gcacgtggcc cagatcctgg acagccggat gaacaccaag tacgacgaga  2880
acgacaagct gatccgggag gtgaaggtga tcaccctgaa gagcaagctg gtgagcgact  2940
tccggaagga cttccagttc tacaaggtgc gggagatcaa caactaccac cacgcccacg  3000
acgcctacct gaacgccgtg gtgggcaccg ccctgatcaa gaagtacccc aagctggaga  3060
gcgagttcgt gtacggcgac tacaaggtgt acgacgtgcg gaagatgatc gccaagagcg  3120
agcaggagat cggcaaggcc accgccaagt acttcttcta cagcaacatc atgaacttct  3180
tcaagaccga gatcaccctg gccaacggcg agatccggaa gcggcccctg atcgagacca  3240
acggcgagac cggcgagatc gtgtgggaca agggccggga cttcgccacc gtgcggaagg  3300
tgctgagcat gccccaggtg aacatcgtga agaagaccga ggtgcagacc ggcggcttca  3360
gcaaggagag catcctgccc aagcggaaca gcgacaagct gatcgcccgg aagaaggact  3420
gggaccccaa gaagtacggc ggcttcgaca gccccaccgt ggcctacagc gtgctggtgg  3480
tggccaaggt ggagaagggc aagagcaaga agctgaagag cgtgaaggag ctgctgggca  3540
tcaccatcat ggagcggagc agcttcgaga agaaccccat cgacttcctg gaggccaagg  3600
gctacaagga ggtgaagaag gacctgatca tcaagctgcc caagtacagc ctgttcgagc  3660
tggagaacgg ccggaagcgg atgctggcca gcgccggcga gctgcagaag ggcaacgagc  3720
tggccctgcc cagcaagtac gtgaacttcc tgtacctggc cagccactac gagaagctga  3780
agggcagccc cgaggacaac gagcagaagc agctgttcgt ggagcagcac aagcactacc  3840
tggacgagat catcgagcag atcagcgagt tcagcaagcg ggtgatcctg gccgacgcca  3900
acctggacaa ggtgctgagc gcctacaaca agcaccggga caagcccatc cgggagcagg  3960
ccgagaacat catccacctg ttcaccctga ccaacctggg cgcccccgcc gccttcaagt  4020
acttcgacac caccatcgac cggaagcggt acaccagcac caaggaggtg ctggacgcca  4080
ccctgatcca ccagagcatc accggcctgt acgagacccg gatcgacctg agccagctgg  4140
gcggcgacgg cggcggcagc cccaagaaga agcggaaggt gtgactagca ccagcctcaa  4200
gaacacccga atggagtctc taagctacat aataccaact tacactttac aaaatgttgt  4260
cccccaaaat gtagccattc gtatctgctc ctaataaaaa gaaagtttct tcacattctc  4320
tcgagaaaaa aaaaaaaaaa aaaaaaaaaa aaaaaaaaaa aaaaaaaaaa aaaaaaaaaa  4380
aaaaaaaaaa aaaaaaaaaa aaaaa                                       4405
```

```
SEQ ID NO: 379          moltype = DNA  length = 4548
FEATURE                 Location/Qualifiers
misc_feature            1..4548
                        note = Synthetic: mRNA transcript with ORF encoding Cas9
                         with HiBiT tag, HSD 5 UTR and human ALB 3 UTR
source                  1..4548
                        mol_type = other DNA
                        organism = synthetic construct
SEQUENCE: 379
gggtcccgca gtcggcgtcc agcggctctg cttgttcgtg tgtgtgtcgt tgcaggcctt  60
attcggatcc gccaccatgg acaagaagta cagcatcgga ctggacatcg gaacaaacag  120
cgtcggatgg gcagtcatca cagacgaata caaggtcccg agcaagaagt tcaaggtcct  180
gggaaacaca gacagacaca gcatcaagaa gaacctgatc ggagcactgc tgttcgacag  240
cggagaaaca gcagaagcaa caagactgaa gagaacagca agaagaagat acacaagaag  300
aaagaacaga atctgctacc tgcaggaaat cttcagcaac gaaatggcaa aggtcgacga  360
cagcttcttc cacagactgg aagaaagctt cctggtcgaa gaagacaaga agcacgaaag  420
acacccgatc ttcggaaaca tcgtcgacga agtcgcatac cacgaaaagt acccgacaat  480
ctaccacctg agaaagaagc tggtcgacag cacagacaag gcagacctga gactgatcta  540
cctggcactg gcacacatga tcaagttcag aggacacttc ctgatcgaag gagacctgaa  600
cccggacaac agcgacgtcg acaagctgtt catccagctg gtccagacat acaaccagct  660
gttcgaagaa aacccgatca acgcaagcgg agtcgacgca aaggcaatcc tgagcgcaag  720
actgagcaag agcagaagac tggaaaacct gatcgcacag ctgccgggag aaaagaagaa  780
cggactgttc ggaaacctga tcgcactgag cctgggactg acaccgaact tcaagagcaa  840
cttcgacctg gcagaagacg caaagctgca gctgagcaag gacacatacg acgacgacct  900
ggacaacctg ctggcacaga tcggagacca gtacgcagac ctgttcctgg cagcaaagaa  960
cctgagcgac gcaatcctgc tgagcgacat cctgagagtc aacacagaaa tcacaaaggc  1020
accgctgagc gcaagcatga tcaagagata cgacgaacac caccaggacc tgacactgct  1080
gaaggcactg gtcagacagc agctgccgga aaagtacaag gaaatcttct tcgaccagag  1140
caagaacgga tacgcaggat acatcgacgg aggagcaagc caggaagaat tctacaagtt  1200
catcaagccg atcctggaaa agatggacgg aacagaagaa ctgctggtca agctgaacag  1260
agaagacctg ctgagaaagc agagaacatt cgacaacgga agcatcccgc accagatcca  1320
cctgggagaa ctgcacgcaa tcctgagaag acaggaagac ttctacccgt tcctgaagga  1380
caacagagaa aagatcgaaa agatcctgac attcagaatc ccgtactacg tcggaccgct  1440
ggcaagagga aacagcagat tcgcatggat gacaagaaag agcgaagaaa caatcacacc  1500
gtggaacttc gaagaagtcg tcgacaaggg agcaagcgca cagagcttca tcgaaagaat  1560
gacaaacttc gacaagaacc tgccgaacga aaaggtcctg ccgaagcaca gcctgctgta  1620
cgaatacttc acagtctaca acgaactgac aaaggtcaag tacgtcacag aaggaatgag  1680
aaagccggca ttcctgagcg gagaacagaa gaaggcaatc gtcgacctgc tgttcaagac  1740
aaacagaaag gtcacagtca agcagctgaa ggaagactac ttcaagaaga tcgaatgctt  1800
cgacagcgtc gaaatcagcg gagtcgaaga cagattcaac gcaagcctgg gaacatacca  1860
cgacctgctg aagatcatca aggacaagga cttcctggac aacgaagaaa acgaagacat  1920
cctggaagac atcgtcctga cactgacact gttcgaagac agagaaatga tcgaagaaag  1980
actgaagaca tacgcacacc tgttcgacga caaggtcatg aagcagctga agagaagaag  2040
atacacagga tggggaagac tgagcagaaa gctgatcaac ggaatcagag acaagcagag  2100
cggaaagaca atcctggact tcctgaagag cgacggattc gcaaacagaa acttcatgca  2160
gctgatccac gacgacagcc tgacattcaa ggaagacatc cagaaggcac aggtcagcgg  2220
acagggagac agcctgcacg aacacatcgc aaacctggca ggaagcccgg caatcaagaa  2280
gggaatcctg cagacagtca aggtcgtcga cgaactggtc aaggtcatgg gaagacacaa  2340
gccggaaaac atcgtcatcg aaatggcaag agaaaaccag acaacacaga agggacagaa  2400
gaacagcaga gaaagaatga agagaatcga agaaggaatc aaggaactgg gaagccagat  2460
cctgaaggaa cacccggtcg aaaacacaca gctgcagaac gaaaagctgt acctgtacta  2520
cctgcagaac ggaagagaca tgtacgtcga ccaggaactg gacatcaaca gactgagcga  2580
ctacgacgtc gaccacatcg tcccgcagag cttcctgaag gacgacagca tcgacaacaa  2640
ggtcctgaca agaagcgaca agaacagagg aaagagcgac aacgtcccga gcgaagaagt  2700
cgtcaagaag atgaagaact actggagaca gctgctgaac gcaaagctga tcacacagag  2760
aaagttcgac aacctgacaa aggcagagag aggaggactg agcgaactgg acaaggcagg  2820
attcatcaag agacagctgg tcgaaacaag acagatcaca aagcacgtcg cacagatcct  2880
ggacagcaga atgaacacaa agtacgacga aaacgacaag ctgatcagag aagtcaaggt  2940
catcacactg aagagcaagc tggtcagcga cttcagaaag gacttccagt tctacaaggt  3000
cagagaaatc aacaactacc accacgcaca cgacgcatac ctgaacgcag tcgtcggaac  3060
agcactgatc aagaagtacc cgaagctgga aagcgaattc gtctacggag actacaaggt  3120
ctacgacgtc agaaagatga tcgcaaagag cgaacaggaa atcggaaagg caacagcaaa  3180
gtacttcttc tacagcaaca tcatgaactt cttcaagaca gaaatcacac tggcaaacgg  3240
agaaatcaga aagagaccgc tgatcgaaac aaacggagaa acaggagaaa tcgtctggga  3300
caagggaaga gacttcgcaa cagtcagaaa ggtcctgagc atgccgcagg tcaacatcgt  3360
caagaagaca gaagtccaga caggaggatt cagcaaggaa agcatcctgc cgaagagaaa  3420
cagcgacaag ctgatcgcaa gaaagaagga ctgggacccg aagaagtacg gaggattcga  3480
cagcccgaca gtcgcataca gcgtcctggt cgtcgcaaag gtcgaaaagg gaaagagcaa  3540
gaagctgaag agcgtcaagg aactgctggg aatcacaatc atggaaagaa gcagcttcga  3600
aaagaacccg atcgacttcc tggaagcaaa gggatacaag gaagtcaaga aggacctgat  3660
catcaagctg ccgaagtaca gcctgttcga actggaaaac ggaagaaaga gaatgctggc  3720
aagcgcagga gaactgcaga agggaaacga actggcactg ccgagcaagt acgtcaactt  3780
cctgtacctg gcaagccact acgaaaagct gaagggaagc ccggaagaca acgaacagaa  3840
gcagctgttc gtcgaacagc acaagcacta cctggacgaa atcatcgaac agatcagcga  3900
attcagcaag agagtcatcc tggcagacgc aaacctggac aaggtcctga gcgcatacaa  3960
caagcacaga gacaagccga tcagagaaca ggcagaaaac atcatccacc tgttcacact  4020
gacaaacctg ggagcaccgg cagcattcaa gtacttcgac acaacaatcg acagaaagag  4080
atacacaagc acaaaggaag tcctggacgc aacactgatc caccagagca tcacaggact  4140
gtacgaaaca agaatcgacc tgagccagct gggaggagac ggaggaggaa gcccgaagaa  4200
```

```
gaagagaaag gtcagcgaaa gcgcaacacc ggaaagcgtc agcggatgga gactgttcaa  4260
gaagatcagc tagctagcca tcacatttaa aagcatctca gcctaccatg agaataagag  4320
aaagaaaatg aagatcaata gcttattcat ctctttttct ttttcgttgg tgtaaagcca  4380
acaccctgtc taaaaaacat aaatttcttt aatcattttg cctcttttct ctgtgcttca  4440
attaataaaa aatggaaaga acctcgagaa aaaaaaaaaa aaaaaaaaaa aaaaaaaaaa  4500
aaaaaaaaaa aaaaaaaaaa aaaaaaaaaa aaaaaaaaaa aaaaaaaa              4548

SEQ ID NO: 380         moltype = DNA  length = 4522
FEATURE                Location/Qualifiers
misc_feature           1..4522
                       note = Synthetic: mRNA transcript with ORF encoding Cas9
                        with HiBiT tag, CMV-1 5 UTR and human ALB 3 UTR
source                 1..4522
                       mol_type = other DNA
                       organism = synthetic construct
SEQUENCE: 380
gggcagatcg cctggagacg ccatccacgc tgttttgacc tccatcgcca ccatggacaa  60
gaagtacagc atcggactgg acatcggaac aaacagcgtc ggatgggcag tcatcacaga  120
cgaatacaag gtcccgagca agaagttcaa ggtcctggga aacacagaca gacacagcat  180
caagaagaac ctgatcggag cactgctgtt cgacagcgga gaaacagcag aagcaacaag  240
actgaagaga acagcaagaa gaagatacac aagaagaaag aacagaatct gctacctgca  300
ggaaatcttc agcaacgaaa tggcaaaggt cgacgacagc ttcttccaca gactggaaga  360
aagcttcctg gtcgaagaag acaagaagca cgaaagacac ccgatcttcg gaaacatcgt  420
cgacgaagtc gcataccacg aaaagtaccc gacaatctac cacctgagaa agaagctggt  480
cgacagcaca gacaaggcag acctgagact gatctacctg gcactggcac acatgatcaa  540
gttcagagga cacttcctga tcgaaggaga cctgaacccg gacaacagcg acgtcgacaa  600
gctgttcatc cagctggtcc agacatacaa ccagctgttc gaagaaaacc cgatcaacgc  660
aagcggagtc gacgcaaagg caatcctgag cgcaagactg agcaagagca gaagactgga  720
aaacctgatc gcacagctgc cgggagaaaa gaagaacgga ctgttcggaa acctgatcgc  780
actgagcctg ggactgacac cgaacttcaa gagcaacttc gacctggcag aagacgcaaa  840
gctgcagctg agcaaggaca catacgacga cgacctggac aacctgctgg cacagatcgg  900
agaccagtac gcagacctgt tcctggcagc aaagaacctg agcgacgcaa tcctgctgag  960
cgacatcctg agagtcaaca cagaaatcac aaaggcaccg ctgagcgcaa gcatgatcaa  1020
gagatacgac gaacaccacc aggacctgac actgctgaag gcactggtca gacagcagct  1080
gccggaaaag tacaaggaaa tcttcttcga ccagagcaag aacggatacg caggatacat  1140
cgacggagga gcaagccagg aagaattcta caagttcatc aagccgatcc tggaaaagat  1200
ggacggaaca gaagaactgc tggtcaagct gaacagagaa gacctgctga gaaagcagag  1260
aacattcgac aacggaagca tcccgcacca gatccacctg ggagaactgc acgcaatcct  1320
gagaagacag gaagacttct acccgttcct gaaggacaac agagaaaaga tcgaaaagat  1380
cctgacattc agaatcccgt actacgtcgg accgctggca agaggaaaca gcagattcgc  1440
atggatgaca agaaagagcg aagaaacaat cacaccgtgg aacttcgaag aagtcgtcga  1500
caagggagca agcgcacaga gcttcatcga aagaatgaca aacttcgaca agaacctgcc  1560
gaacgaaaag gtcctgccga agcacagcct gctgtacgaa tacttcacag tctacaacga  1620
actgacaaag gtcaagtacg tcacagaagg aatgagaaag ccggcattcc tgagcggaga  1680
acagaagaag gcaatcgtcg acctgctgtt caagacaaac agaaaggtca cagtcaagca  1740
gctgaaggaa gactacttca agaagatcga atgcttcgac agcgtcgaaa tcagcggagt  1800
cgaagacaga ttcaacgcaa gcctgggaac ataccacgac ctgctgaaga tcatcaagga  1860
caaggacttc ctggacaacg aagaaaacga agacatcctg gaagacatcg tcctgacact  1920
gacactgttc gaagacagag aaatgatcga agaaagactg aagacatacg cacacctgtt  1980
cgacgacaag gtcatgaagc agctgaagag aagaagatac acaggatggg gaagactgag  2040
cagaaagctg atcaacggaa tcagagacaa gcagagcgga aagacaatcc tggacttcct  2100
gaagagcgac ggattcgcaa acagaaactt catgcagctg atccacgacg acagcctgac  2160
attcaaggaa gacatccaga aggcacaggt cagcggacag ggagacagcc tgcacgaaca  2220
catcgcaaac ctggcaggaa gcccggcaat caagaaggga atcctgcaga cagtcaaggt  2280
cgtcgacgaa ctggtcaagg tcatgggaag acacaagccg gaaaacatcg tcatcgaaat  2340
ggcaagagaa aaccagacaa cacagaaggg acagaagaac agcagagaaa gaatgaagag  2400
aatcgaagaa ggaatcaagg aactgggaag ccagatcctg aaggaacacc cggtcgaaaa  2460
cacacagctg cagaacgaaa agctgtacct gtactacctg cagaacggaa gagacatgta  2520
cgtcgaccag gaactggaca tcaacagact gagcgactac gacgtcgacc acatcgtccc  2580
gcagagcttc ctgaaggacg acagcatcga caacaaggtc ctgacaagaa gcgacaagaa  2640
cagaggaaag agcgacaacg tcccgagcga agaagtcgtc aagaagatga agaactactg  2700
gagacagctg ctgaacgcaa agctgatcac acagagaaag ttcgacaacc tgacaaaggc  2760
agagagagga ggactgagcg aactggacaa ggcaggattc atcaagagac agctggtcga  2820
aacaagacag atcacaaagc acgtcgcaca gatcctggac agcagaatga acacaaagta  2880
cgacgaaaac gacaagctga tcagagaagt caaggtcatc acactgaaga gcaagctggt  2940
cagcgacttc agaaaggact tccagttcta caaggtcaga gaaatcaaca actaccacca  3000
cgcacacgac gcatacctga acgcagtcgt cggaacagca ctgatcaaga agtacccgaa  3060
gctggaaagc gaattcgtct acggagacta caaggtctac gacgtcagaa agatgatcgc  3120
aaagagcgaa caggaaatcg gaaaggcaac agcaaagtac ttcttctaca gcaacatcat  3180
gaacttcttc aagacagaaa tcacactggc aaacggagaa atcagaaaga gaccgctgat  3240
cgaaacaaac ggagaaacag gagaaatcgt ctgggacaag ggaagagact tcgcaacagt  3300
cagaaaggtc ctgagcatgc cgcaggtcaa catcgtcaag aagacagaag tccagacagg  3360
aggattcagc aaggaaagca tcctgccgaa gagaaacagc gacaagctga tcgcaagaaa  3420
gaaggactgg gacccgaaga agtacggagg attcgacagc ccgacagtcg catacagcgt  3480
cctggtcgtc gcaaaggtcg aaaagggaaa gagcaagaag ctgaagagcg tcaaggaact  3540
gctgggaatc acaatcatgg aaagaagcag cttcgaaaag aacccgatcg acttcctgga  3600
agcaaaggga tacaaggaag tcaagaagga cctgatcatc aagctgccga agtacagcct  3660
gttcgaactg gaaaacggaa gaaagagaat gctggcaagc gcaggagaac tgcagaaggg  3720
aaacgaactg gcactgccga gcaagtacgt caacttcctg tacctggcaa gccactacga  3780
```

```
aaagctgaag ggaagcccgg aagacaacga acagaagcag ctgttcgtcg aacagcacaa  3840
gcactacctg gacgaaatca tcgaacagat cagcgaattc agcaagagag tcatcctggc  3900
agacgcaaac ctggacaagg tcctgagcgc atacaacaag cacagagaca agccgatcag  3960
agaacaggca gaaaacatca tccacctgtt cacactgaca aacctgggag caccggcagc  4020
attcaagtac ttcgacacaa caatcgacag aaagagatac acaagcacaa aggaagtcct  4080
ggacgcaaca ctgatccacc agagcatcac aggactgtac gaaacaagaa tcgacctgag  4140
ccagctggga ggagacggag gaggaagccc gaagaagaag agaaaggtca gcgaaagcgc  4200
aacaccggaa agcgtcagcg gatggagact gttcaagaag atcagctagc tagccatcac  4260
atttaaaagc atctcagcct accatgagaa taagagaaag aaaatgaaga tcaatagctt  4320
attcatctct ttttcttttt cgttggtgta aagccaacac cctgtctaaa aaacataaat  4380
ttctttaatc attttgcctc ttttctctgt gcttcaatta ataaaaaatg gaaagaacct  4440
cgaaaaaaaa aaaaaaaaaa aaaaaaaaaa aaaaaaaaaa aaaaaaaaaa aaaaaaaaaa  4500
aaaaaaaaaa aaaaaaaaaa aa                                           4522

SEQ ID NO: 381         moltype = DNA  length = 4524
FEATURE                Location/Qualifiers
misc_feature           1..4524
                       note = Synthetic: mRNA transcript with ORF encoding Cas9
                        with HiBiT tag, CMV-2 5 UTR and human ALB 3 UTR
source                 1..4524
                       mol_type = other DNA
                       organism = synthetic construct
SEQUENCE: 381
gggagaagac accgggaccg atccagcctc cgcggccggg aacggcgcca ccatggacaa  60
gaagtacagc atcggactgg acatcggaac aaacagcgtc ggatgggcag tcatcacaga  120
cgaatacaag gtcccgagca agaagttcaa ggtcctggga aacacagaca gacacagcat  180
caagaagaac ctgatcggag cactgctgtt cgacagcgga gaaacagcag aagcaacaag  240
actgaagaga acagcaagaa gaagatacac aagaagaaag aacagaatct gctacctgca  300
ggaaatcttc agcaacgaaa tggcaaaggt cgacgacagc ttcttccaca gactggaaga  360
aagcttcctg gtcgaagaag acaagaagca cgaaagacac ccgatcttcg gaaacatcgt  420
cgacgaagtc gcataccacg aaaagtaccc gacaatctac cacctgagaa agaagctggt  480
cgacagcaca gacaaggcag acctgagact gatctacctg gcactggcac acatgatcaa  540
gttcagagga cacttcctga tcgaaggaga cctgaacccg gacaacagcg acgtcgacaa  600
gctgttcatc cagctggtcc agacatacaa ccagctgttc gaagaaaacc cgatcaacgc  660
aagcggagtc gacgcaaagg caatcctgag cgcaagactg agcaagagca gaagactgga  720
aaacctgatc gcacagctgc cgggagaaaa gaagaacgga ctgttcggaa acctgatcgc  780
actgagcctg ggactgacac cgaacttcaa gagcaacttc gacctggcag aagacgcaaa  840
gctgcagctg agcaaggaca catacgacga cgacctggac aacctgctgg cacagatcgg  900
agaccagtac gcagacctgt tcctggcagc aaagaacctg agcgacgcaa tcctgctgag  960
cgacatcctg agagtcaaca cagaaatcac aaaggcaccg ctgagcgcaa gcatgatcaa  1020
gagatacgac gaacaccacc aggacctgac actgctgaag gcactggtca gacagcagct  1080
gccggaaaag tacaaggaaa tcttcttcga ccagagcaag aacggatacg caggatacat  1140
cgacggagga gcaagccagg aagaattcta caagttcatc aagccgatcc tggaaaagat  1200
ggacggaaca gaagaactgc tggtcaagct gaacagagaa gacctgctga gaaagcagag  1260
aacattcgac aacggaagca tcccgcacca gatccacctg ggagaactgc acgcaatcct  1320
gagaagacag gaagacttct acccgttcct gaaggacaac agagaaaaga tcgaaaagat  1380
cctgacattc agaatcccgt actacgtcgg accgctggca agaggaaaca gcagattcgc  1440
atggatgaca agaaagagcg aagaaacaat cacaccgtgg aacttcgaag aagtcgtcga  1500
caagggagca agcgcacaga gcttcatcga aagaatgaca aacttcgaca agaacctgcc  1560
gaacgaaaag gtcctgccga agcacagcct gctgtacgaa tacttcacag tctacaacga  1620
actgacaaag gtcaagtacg tcacagaagg aatgagaaag ccggcattcc tgagcggaga  1680
acagaagaag gcaatcgtcg acctgctgtt caagacaaac agaaaggtca cagtcaagca  1740
gctgaaggaa gactacttca agaagatcga atgcttcgac agcgtcgaaa tcagcggagt  1800
cgaagacaga ttcaacgcaa gcctgggaac ataccacgac ctgctgaaga tcatcaagga  1860
caaggacttc ctggacaacg aagaaaacga agacatcctg gaagacatcg tcctgacact  1920
gacactgttc gaagacagag aaatgatcga agaaagactg aagacatacg cacacctgtt  1980
cgacgacaag gtcatgaagc agctgaagag aagaagatac acaggatggg gaagactgag  2040
cagaaagctg atcaacggaa tcagagacaa gcagagcgga aagacaatcc tggacttcct  2100
gaagagcgac ggattcgcaa acagaaactt catgcagctg atccacgacg acagcctgac  2160
attcaaggaa gacatccaga aggcacaggt cagcggacag ggagacagcc tgcacgaaca  2220
catcgcaaac ctggcaggaa gcccggcaat caagaaggga atcctgcaga cagtcaaggt  2280
cgtcgacgaa ctggtcaagg tcatgggaag acacaagccg gaaaacatcg tcatcgaaat  2340
ggcaagagaa aaccagacaa cacagaaggg acagaagaac agcagagaaa gaatgaagag  2400
aatcgaagaa ggaatcaagg aactgggaag ccagatcctg aaggaacacc cggtcgaaaa  2460
cacacagctg cagaacgaaa agctgtacct gtactacctg cagaacggaa gagacatgta  2520
cgtcgaccag gaactggaca tcaacagact gagcgactac gacgtcgacc acatcgtccc  2580
gcagagcttc ctgaaggacg acagcatcga caacaaggtc ctgacaagaa gcgacaagaa  2640
cagaggaaag agcgacaacg tcccgagcga agaagtcgtc aagaagatga agaactactg  2700
gagacagctg ctgaacgcaa agctgatcac acagagaaag ttcgacaacc tgacaaaggc  2760
agagagagga ggactgagcg aactggacaa ggcaggattc atcaagagac agctggtcga  2820
aacaagacag atcacaaagc acgtcgcaca gatcctggac agcagaatga acacaaagta  2880
cgacgaaaac gacaagctga tcagagaagt caaggtcatc acactgaaga gcaagctggt  2940
cagcgacttc agaaaggact tccagttcta caaggtcaga gaaatcaaca actaccacca  3000
cgcacacgac gcatacctga acgcagtcgt cggaacagca ctgatcaaga agtacccgaa  3060
gctggaaagc gaattcgtct acggagacta caaggtctac gacgtcagaa agatgatcgc  3120
aaagagcgaa caggaaatcg gaaaggcaac agcaaagtac ttcttctaca gcaacatcat  3180
gaacttcttc aagacagaaa tcacactggc aaacggagaa atcagaaaga gaccgctgat  3240
cgaaacaaac ggagaaacag gagaaatcgt ctgggacaag ggaagagact tcgcaacagt  3300
cagaaaggtc ctgagcatgc cgcaggtcaa catcgtcaag aagacagaag tccagacagg  3360
```

```
aggattcagc aaggaaagca tcctgccgaa gagaaacagc gacaagctga tcgcaagaaa  3420
gaaggactgg gacccgaaga agtacggagg attcgacagc ccgacagtcg catacagcgt  3480
cctggtcgtc gcaaaggtcg aaaagggaaa gagcaagaag ctgaagagcg tcaaggaact  3540
gctgggaatc acaatcatgg aaagaagcag cttcgaaaag aacccgatcg acttcctgga  3600
agcaaaggga tacaaggaag tcaagaagga cctgatcatc aagctgccga agtacagcct  3660
gttcgaactg gaaaacggaa gaaagagaat gctggcaagc gcaggagaac tgcagaaggg  3720
aaacgaactg gcactgccga gcaagtacgt caacttcctg tacctggcaa gccactacga  3780
aaagctgaag ggaagcccgg aagacaacga acagaagcag ctgttcgtcg aacagcacaa  3840
gcactacctg gacgaaatca tcgaacagat cagcgaattc agcaagagag tcatcctggc  3900
agacgcaaac ctggacaagg tcctgagcgc atacaacaag cacagagaca agccgatcag  3960
agaacaggca gaaaacatca tccacctgtt cacactgaca aacctgggag caccggcagc  4020
attcaagtac ttcgacacaa caatcgacag aaagagatac acaagcacaa aggaagtcct  4080
ggacgcaaca ctgatccacc agagcatcac aggactgtac gaaacaagaa tcgacctgag  4140
ccagctggga ggagacggag gaggaagccc gaagaagaag agaaaggtca gcgaaagcgc  4200
aacaccggaa agcgtcagcg gatggagact gttcaagaag atcagctagc tagccatcac  4260
atttaaaagc atctcagcct accatgagaa taagagaaag aaaatgaaga tcaatagctt  4320
attcatctct tttctttttt cgttggtgta aagccaacac cctgtctaaa aaacataaat  4380
ttctttaatc attttgcctc ttttctctgt gcttcaatta ataaaaaatg gaaagaacct  4440
cgagaaaaaa aaaaaaaaaa aaaaaaaaaa aaaaaaaaaa aaaaaaaaaa aaaaaaaaaa  4500
aaaaaaaaaa aaaaaaaaaa aaaa                                         4524
```

| | |
|---|---|
| SEQ ID NO: 382 | moltype = DNA length = 4524 |
| FEATURE | Location/Qualifiers |
| misc_feature | 1..4524 |
| | note = Synthetic: mRNA transcript with ORF encoding Cas9 with HiBiT tag, CMV-3 5 UTR and human ALB 3 UTR |
| source | 1..4524 |
| | mol_type = other DNA |
| | organism = synthetic construct |

SEQUENCE: 382

```
gggtgcattg gaacgcggat tccccgtgcc aagagtgact caccgcgcca ccatggacaa  60
gaagtacagc atcggactgg acatcggaac aaacagcgtc ggatgggcag tcatcacaga  120
cgaatacaag gtcccgagca agaagttcaa ggtcctggga aacacagaca gacacagcat  180
caagaagaac ctgatcggag cactgctgtt cgacagcgga gaaacagcag aagcaacaag  240
actgaagaga acagcaagaa gaagatacac aagaagaaag aacagaatct gctacctgca  300
ggaaatcttc agcaacgaaa tggcaaaggt cgacgacagc ttcttccaca gactggaaga  360
aagcttcctg gtcgaagaag acaagaagca cgaaagacac ccgatcttcg gaaacatcgt  420
cgacgaagtc gcataccacg aaaagtaccc gacaatctac cacctgagaa agaagctggt  480
cgacagcaca gacaaggcag acctgagact gatctacctg gcactggcac acatgatcaa  540
gttcagagga cacttcctga tcgaaggaga cctgaacccg gacaacagcg acgtcgacaa  600
gctgttcatc cagctggtcc agacatacaa ccagctgttc gaagaaaacc cgatcaacgc  660
aagcggagtc gacgcaaagg caatcctgag cgcaagactg agcaagagca gaagactgga  720
aaacctgatc gcacagctgc cgggagaaaa gaagaacgga ctgttcggaa acctgatcgc  780
actgagcctg ggactgacac cgaacttcaa gagcaacttc gacctggcag aagacgcaaa  840
gctgcagctg agcaaggaca catacgacga cgacctggac aacctgctgg cacagatcgg  900
agaccagtac gcagacctgt tcctggcagc aaagaacctg agcgacgcaa tcctgctgag  960
cgacatcctg agagtcaaca cagaaatcac aaaggcaccg ctgagcgcaa gcatgatcaa  1020
gagatacgac gaacaccacc aggacctgac actgctgaag gcactggtca gacagcagct  1080
gccggaaaag tacaaggaaa tcttcttcga ccagagcaag aacggatacg caggatacat  1140
cgacggagga gcaagccagg aagaattcta caagttcatc aagccgatcc tggaaaagat  1200
ggacggaaca gaagaactgc tggtcaagct gaacagagaa gacctgctga gaaagcagag  1260
aacattcgac aacggaagca tcccgcacca gatccacctg ggagaactgc acgcaatcct  1320
gagaagacag gaagacttct acccgttcct gaaggacaac agagaaaaga tcgaaaagat  1380
cctgacattc agaatcccgt actacgtcgg accgctggca agaggaaaca gcagattcgc  1440
atggatgaca agaaagagcg aagaaacaat cacaccgtgg aacttcgaag aagtcgtcga  1500
caagggagca agcgcacaga gcttcatcga aagaatgaca aacttcgaca agaacctgcc  1560
gaacgaaaag gtcctgccga agcacagcct gctgtacgaa tacttcacag tctacaacga  1620
actgacaaag gtcaagtacg tcacagaagg aatgagaaag ccggcattcc tgagcggaga  1680
acagaagaag gcaatcgtcg acctgctgtt caagacaaac agaaaggtca cagtcaagca  1740
gctgaaggaa gactacttca agaagatcga atgcttcgac agcgtcgaaa tcagcggagt  1800
cgaagacaga ttcaacgcaa gcctgggaac ataccacgac ctgctgaaga tcatcaagga  1860
caaggacttc ctggacaacg aagaaaacga agacatcctg gaagacatcg tcctgacact  1920
gacactgttc gaagacagag aaatgatcga agaaagactg aagacatacg cacacctgtt  1980
cgacgacaag gtcatgaagc agctgaagag aagaagatac acaggatggg gaagactgag  2040
cagaaagctg atcaacggaa tcagagacaa gcagagcgga aagacaatcc tggacttcct  2100
gaagagcgac ggattcgcaa acagaaactt catgcagctg atccacgacg acagcctgac  2160
attcaaggaa gacatccaga aggcacaggt cagcggacag ggagacagcc tgcacgaaca  2220
catcgcaaac ctggcaggaa gcccggcaat caagaaggga atcctgcaga cagtcaaggt  2280
cgtcgacgaa ctggtcaagg tcatgggaag acacaagccg gaaaacatcg tcatcgaaat  2340
ggcaagagaa aaccagacaa cacagaaggg acagaagaac agcagagaaa gaatgaagag  2400
aatcgaagaa ggaatcaagg aactgggaag ccagatcctg aaggaacacc cggtcgaaaa  2460
cacacagctg cagaacgaaa agctgtacct gtactacctg cagaacggaa gagacatgta  2520
cgtcgaccag gaactggaca tcaacagact gagcgactac gacgtcgacc acatcgtccc  2580
gcagagcttc ctgaaggacg acagcatcga caacaaggtc ctgacaagaa gcgacaagaa  2640
cagaggaaag agcgacaacg tcccgagcga agaagtcgtc aagaagatga agaactactg  2700
gagacagctg ctgaacgcaa agctgatcac acagagaaag ttcgacaacc tgacaaaggc  2760
agagagagga ggactgagcg aactggacaa ggcaggattc atcaagagac agctggtcga  2820
aacaagacag atcacaaagc acgtcgcaca gatcctggac agcagaatga acacaaagta  2880
cgacgaaaac gacaagctga tcagagaagt caaggtcatc acactgaaga gcaagctggt  2940
```

```
cagcgacttc agaaaggact tccagttcta caaggtcaga gaaatcaaca actaccacca  3000
cgcacacgac gcatacctga acgcagtcgt cggaacagca ctgatcaaga agtacccgaa  3060
gctggaaagc gaattcgtct acggagacta caaggtctac gacgtcagaa agatgatcgc  3120
aaagagcgaa caggaaatcg gaaaggcaac agcaaagtac ttcttctaca gcaacatcat  3180
gaacttcttc aagacagaaa tcacactggc aaacggagaa atcagaaaga gaccgctgat  3240
cgaaacaaac ggagaaacag gagaaatcgt ctgggacaag ggaagagact tcgcaacagt  3300
cagaaaggtc ctgagcatgc cgcaggtcaa catcgtcaag aagacagaag tccagacagg  3360
aggattcagc aaggaaagca tcctgccgaa gagaaacagc gacaagctga tcgcaagaaa  3420
gaaggactgg gacccgaaga agtacggagg attcgacagc ccgacagtcg catacagcgt  3480
cctggtcgtc gcaaaggtcg aaaagggaaa gagcaagaag ctgaagagcg tcaaggaact  3540
gctgggaatc acaatcatgg aaagaagcag cttcgaaaag aacccgatcg acttcctgga  3600
agcaaaggga tacaaggaag tcaagaagga cctgatcatc aagctgccga agtacagcct  3660
gttcgaactg gaaaacggaa gaaagagaat gctggcaagc gcaggagaac tgcagaaggg  3720
aaacgaactg gcactgccga gcaagtacgt caacttcctg tacctggcaa gccactacga  3780
aaagctgaag ggaagcccgg aagacaacga acagaagcag ctgttcgtcg aacagcacaa  3840
gcactacctg gacgaaatca tcgaacagat cagcgaattc agcaagagag tcatcctggc  3900
agacgcaaac ctggacaagg tcctgagcgc atacaacaag cacagagaca agccgatcag  3960
agaacaggca gaaaacatca tccacctgtt cacactgaca aacctgggag caccggcagc  4020
attcaagtac ttcgacacaa caatcgacag aaagagatac acaagcacaa aggaagtcct  4080
ggacgcaaca ctgatccacc agagcatcac aggactgtac gaaacaagaa tcgacctgag  4140
ccagctggga ggagacggag gaggaagccc gaagaagaag agaaaggtca gcgaaagcgc  4200
aacaccggaa agcgtcagcg gatggagact gttcaagaag atcagctagc tagccatcac  4260
atttaaaagc atctcagcct accatgagaa taagagaaag aaaatgaaga tcaatagctt  4320
attcatctct ttttcttttt cgttggtgta aagccaacac cctgtctaaa aaacataaat  4380
ttctttaatc attttgcctc ttttctctgt gcttcaatta ataaaaaatg gaaagaacct  4440
cgagaaaaaa aaaaaaaaaa aaaaaaaaaa aaaaaaaaaa aaaaaaaaaa aaaaaaaaaa  4500
aaaaaaaaaa aaaaaaaaaa aaaa                                          4524

SEQ ID NO: 383          moltype = DNA  length = 4548
FEATURE                 Location/Qualifiers
misc_feature            1..4548
                        note = Synthetic: mRNA transcript with ORF encoding Cas9
                         with HiBiT tag, HBA 5 UTR and human ALB 3 UTR
source                  1..4548
                        mol_type = other DNA
                        organism = synthetic construct
SEQUENCE: 383
gggcataaac cctggcgcgc tcgcggcccg gcactcttct ggtccccaca gactcagaga  60
gaacccaccc gccaccatgg acaagaagta cagcatcgga ctggacatcg gaacaaacag  120
cgtcggatgg gcagtcatca cagacgaata caaggtcccg agcaagaagt tcaaggtcct  180
gggaaacaca gacagacaca gcatcaagaa gaacctgatc ggagcactgc tgttcgacag  240
cggagaaaca gcagaagcaa caagactgaa gagaacagca agaagaagat acacaagaag  300
aaagaacaga atctgctacc tgcaggaaat cttcagcaac gaaatggcaa aggtcgacga  360
cagcttcttc cacagactgg aagaaagctt cctggtcgaa gaagacaaga agcacgaaag  420
acacccgatc ttcggaaaca tcgtcgacga agtcgcatac cacgaaaagt acccgacaat  480
ctaccacctg agaaagaagc tggtcgacag cacagacaag gcagacctga gactgatcta  540
cctggcactg gcacacatga tcaagttcag aggacacttc ctgatcgaag gagacctgaa  600
cccggacaac agcgacgtcg acaagctgtt catccagctg gtccagacat acaaccagct  660
gttcgaagaa aacccgatca acgcaagcgg agtcgacgca aaggcaatcc tgagcgcaag  720
actgagcaag agcagaagac tggaaaacct gatcgcacag ctgccgggag aaaagaagaa  780
cggactgttc ggaaacctga tcgcactgag cctgggactg acaccgaact tcaagagcaa  840
cttcgacctg gcagaagacg caaagctgca gctgagcaag gacacatacg acgacgacct  900
ggacaacctg ctggcacaga tcggagacca gtacgcagac ctgttcctgg cagcaaagaa  960
cctgagcgac gcaatcctgc tgagcgacat cctgagagtc aacacagaaa tcacaaaggc  1020
accgctgagc gcaagcatga tcaagagata cgacgaacac caccaggacc tgacactgct  1080
gaaggcactg gtcagacagc agctgccgga aaagtacaag gaaatcttct tcgaccagag  1140
caagaacgga tacgcaggat acatcgacgg aggagcaagc caggaagaat tctacaagtt  1200
catcaagccg atcctggaaa agatggacgg aacagaagaa ctgctggtca agctgaacag  1260
agaagacctg ctgagaaagc agagaacatt cgacaacgga agcatcccgc accagatcca  1320
cctgggagaa ctgcacgcaa tcctgagaag acaggaagac ttctacccgt tcctgaagga  1380
caacagagaa aagatcgaaa agatcctgac attcagaatc ccgtactacg tcggaccgct  1440
ggcaagagga aacagcagat tcgcatggat gacaagaaag agcgaagaaa caatcacacc  1500
gtggaacttc gaagaagtcg tcgacaaggg agcaagcgca cagagcttca tcgaaagaat  1560
gacaaacttc gacaagaacc tgccgaacga aaaggtcctg ccgaagcaca gcctgctgta  1620
cgaatacttc acagtctaca acgaactgac aaaggtcaag tacgtcacag aaggaatgag  1680
aaagccggca ttcctgagcg gagaacagaa gaaggcaatc gtcgacctgc tgttcaagac  1740
aaacagaaag gtcacagtca agcagctgaa ggaagactac ttcaagaaga tcgaatgctt  1800
cgacagcgtc gaaatcagcg gagtcgaaga cagattcaac gcaagcctgg gaacatacca  1860
cgacctgctg aagatcatca aggacaagga cttcctggac aacgaagaaa acgaagacat  1920
cctggaagac atcgtcctga cactgacact gttcgaagac agagaaatga tcgaagaaag  1980
actgaagaca tacgcacacc tgttcgacga caaggtcatg aagcagctga agagaagaag  2040
atacacagga tggggaagac tgagcagaaa gctgatcaac ggaatcagag acaagcagag  2100
cggaaagaca atcctggact tcctgaagag cgacggattc gcaaacagaa acttcatgca  2160
gctgatccac gacgacagcc tgacattcaa ggaagacatc cagaaggcac aggtcagcgg  2220
acagggagac agcctgcacg aacacatcgc aaacctggca ggaagcccgg caatcaagaa  2280
gggaatcctg cagacagtca aggtcgtcga cgaactggtc aaggtcatgg gaagacacaa  2340
gccggaaaac atcgtcatcg aaatggcaag agaaaaccag acaacacaga agggacagaa  2400
gaacagcaga gaaagaatga agagaatcga agaaggaatc aaggaactgg gaagccagat  2460
cctgaaggaa cacccggtcg aaaacacaca gctgcagaac gaaaagctgt acctgtacta  2520
```

-continued

```
cctgcagaac ggaagagaca tgtacgtcga ccaggaactg gacatcaaca gactgagcga  2580
ctacgacgtc gaccacatcg tcccgcagag cttcctgaag gacgacagca tcgacaacaa  2640
ggtcctgaca agaagcgaca agaacagagg aaagagcgac aacgtcccga gcgaagaagt  2700
cgtcaagaag atgaagaact actggagaca gctgctgaac gcaaagctga tcacacagag  2760
aaagttcgac aacctgacaa aggcagagag aggaggactg agcgaactgg acaaggcagg  2820
attcatcaag agacagctgg tcgaaacaag acagatcaca aagcacgtcg cacagatcct  2880
ggacagcaga atgaacacaa agtacgacga aaacgacaag ctgatcagag aagtcaaggt  2940
catcacactg aagagcaagc tggtcagcga cttcagaaag gacttccagt tctacaaggt  3000
cagagaaatc aacaactacc accacgcaca cgacgcatac ctgaacgcag tcgtcggaac  3060
agcactgatc aagaagtacc cgaagctgga aagcgaattc gtctacggag actacaaggt  3120
ctacgacgtc agaaagatga tcgcaaagag cgaacaggaa atcggaaagg caacagcaaa  3180
gtacttcttc tacagcaaca tcatgaactt cttcaagaca gaaatcacac tggcaaacgg  3240
agaaatcaga aagagaccgc tgatcgaaac aaacggagaa acaggagaaa tcgtctggga  3300
caagggaaga gacttcgcaa cagtcagaaa ggtcctgagc atgccgcagg tcaacatcgt  3360
caagaagaca gaagtccaga caggaggatt cagcaaggaa agcatcctgc cgaagagaaa  3420
cagcgacaag ctgatcgcaa gaaagaagga ctgggacccg aagaagtacg gaggattcga  3480
cagcccgaca gtcgcataca gcgtcctggt cgtcgcaaag gtcgaaaagg gaaagagcaa  3540
gaagctgaag agcgtcaagg aactgctggg aatcacaatc atggaaagaa gcagcttcga  3600
aaagaacccg atcgacttcc tggaagcaaa gggatacaag gaagtcaaga aggacctgat  3660
catcaagctg ccgaagtaca gcctgttcga actggaaaac ggaagaaaga gaatgctggc  3720
aagcgcagga gaactgcaga agggaaacga actggcactg ccgagcaagt acgtcaactt  3780
cctgtacctg gcaagccact acgaaaagct gaagggaagc ccggaagaca acgaacagaa  3840
gcagctgttc gtcgaacagc acaagcacta cctggacgaa atcatcgaac agatcagcga  3900
attcagcaag agagtcatcc tggcagacgc aaacctggac aaggtcctga gcgcatacaa  3960
caagcacaga gacaagccga tcagagaaca ggcagaaaac atcatccacc tgttcacact  4020
gacaaacctg ggagcaccgg cagcattcaa gtacttcgac acaacaatcg acagaaagag  4080
atacacaagc acaaaggaag tcctggacgc aacactgatc caccagagca tcacaggact  4140
gtacgaaaca agaatcgacc tgagccagct gggaggagac ggaggaggaa gcccgaagaa  4200
gaagagaaag gtcagcgaaa gcgcaacacc ggaaagcgtc agcggatgga gactgttcaa  4260
gaagatcagc tagctagcca tcacatttaa aagcatctca gcctaccatg agaataagag  4320
aaagaaaatg aagatcaata gcttattcat ctctttttct ttttcgttgg tgtaaagcca  4380
acaccctgtc taaaaaacat aaatttcttt aatcattttg cctcttttct ctgtgcttca  4440
attaataaaa aatggaaaga acctcgagaa aaaaaaaaaa aaaaaaaaaa aaaaaaaaaa  4500
aaaaaaaaaa aaaaaaaaaa aaaaaaaaaa aaaaaaaaaa aaaaaaaa              4548
```

```
SEQ ID NO: 384          moltype = DNA  length = 4538
FEATURE                 Location/Qualifiers
misc_feature            1..4538
                        note = Synthetic: mRNA transcript with ORF encoding Cas9
                         with HiBiT tag, HBB 5 UTR and human ALB 3 UTR
source                  1..4538
                        mol_type = other DNA
                        organism = synthetic construct
SEQUENCE: 384
gggacatttg cttctgacac aactgtgttc actagcaacc tcaaacagac accggatctc  60
gccaccatgg acaagaagta cagcatcgga ctggacatcg gaacaaacag cgtcggatgg  120
gcagtcatca cagacgaata caaggtcccg agcaagaagt tcaaggtcct gggaaacaca  180
gacagacaca gcatcaagaa gaacctgatc ggagcactgc tgttcgacag cggagaaaca  240
gcagaagcaa caagactgaa gagaacagca agaagaagat acacaagaag aaagaacaga  300
atctgctacc tgcaggaaat cttcagcaac gaaatggcaa aggtcgacga cagcttcttc  360
cacagactgg aagaaagctt cctggtcgaa gaagacaaga agcacgaaag acacccgatc  420
ttcggaaaca tcgtcgacga agtcgcatac cacgaaaagt acccgacaat ctaccacctg  480
agaaagaagc tggtcgacag cacagacaag gcagacctga gactgatcta cctggcactg  540
gcacacatga tcaagttcag aggacacttc ctgatcgaag gagacctgaa cccggacaac  600
agcgacgtcg acaagctgtt catccagctg gtccagacat acaaccagct gttcgaagaa  660
aacccgatca acgcaagcgg agtcgacgca aaggcaatcc tgagcgcaag actgagcaag  720
agcagaagac tggaaaacct gatcgcacag ctgccgggag aaaagaagaa cggactgttc  780
ggaaacctga tcgcactgag cctgggactg acaccgaact tcaagagcaa cttcgacctg  840
gcagaagacg caaagctgca gctgagcaag gacacatacg acgacgacct ggacaacctg  900
ctggcacaga tcggagacca gtacgcagac ctgttcctgg cagcaaagaa cctgagcgac  960
gcaatcctgc tgagcgacat cctgagagtc aacacagaaa tcacaaaggc accgctgagc  1020
gcaagcatga tcaagagata cgacgaacac caccaggacc tgacactgct gaaggcactg  1080
gtcagacagc agctgccgga aaagtacaag gaaatcttct tcgaccagag caagaacgga  1140
tacgcaggat acatcgacgg aggagcaagc caggaagaat tctacaagtt catcaagccg  1200
atcctggaaa agatggacgg aacagaagaa ctgctggtca agctgaacag agaagacctg  1260
ctgagaaagc agagaacatt cgacaacgga agcatcccgc accagatcca cctgggagaa  1320
ctgcacgcaa tcctgagaag acaggaagac ttctacccgt tcctgaagga caacagagaa  1380
aagatcgaaa agatcctgac attcagaatc ccgtactacg tcggaccgct ggcaagagga  1440
aacagcagat tcgcatggat gacaagaaag agcgaagaaa caatcacacc gtggaacttc  1500
gaagaagtcg tcgacaaggg agcaagcgca cagagcttca tcgaaagaat gacaaacttc  1560
gacaagaacc tgccgaacga aaaggtcctg ccgaagcaca gcctgctgta cgaatacttc  1620
acagtctaca acgaactgac aaaggtcaag tacgtcacag aaggaatgag aaagccggca  1680
ttcctgagcg gagaacagaa gaaggcaatc gtcgacctgc tgttcaagac aaacagaaag  1740
gtcacagtca agcagctgaa ggaagactac ttcaagaaga tcgaatgctt cgacagcgtc  1800
gaaatcagcg gagtcgaaga cagattcaac gcaagcctgg gaacatacca cgacctgctg  1860
aagatcatca aggacaagga cttcctggac aacgaagaaa acgaagacat cctggaagac  1920
atcgtcctga cactgacact gttcgaagac agagaaatga tcgaagaaag actgaagaca  1980
tacgcacacc tgttcgacga caaggtcatg aagcagctga agagaagaag atacacagga  2040
tggggaagac tgagcagaaa gctgatcaac ggaatcagag acaagcagag cggaaagaca  2100
```

-continued

```
atcctggact tcctgaagag cgacggattc gcaaacagaa acttcatgca gctgatccac  2160
gacgacagcc tgacattcaa ggaagacatc cagaaggcac aggtcagcgg acagggagac  2220
agcctgcacg aacacatcgc aaacctggca ggaagcccgg caatcaagaa gggaatcctg  2280
cagacagtca aggtcgtcga cgaactggtc aaggtcatgg gaagacacaa gccggaaaac  2340
atcgtcatcg aaatggcaag agaaaaccag acaacacaga agggacagaa gaacagcaga  2400
gaaagaatga agagaatcga agaaggaatc aaggaactgg gaagccagat cctgaaggaa  2460
caccccggtcg aaaacacaca gctgcagaac gaaaagctgt acctgtacta cctgcagaac  2520
ggaagagaca tgtacgtcga ccaggaactg gacatcaaca gactgagcga ctacgacgtc  2580
gaccacatcg tcccgcagag cttcctgaag gacgacagca tcgacaacaa ggtcctgaca  2640
agaagcgaca agaacagagg aaagagcgac aacgtcccga gcgaagaagt cgtcaagaag  2700
atgaagaact actggagaca gctgctgaac gcaaagctga tcacacagag aaagttcgac  2760
aacctgacaa aggcagagag aggaggactg agcgaactgg acaaggcagg attcatcaag  2820
agacagctgg tcgaaacaag acagatcaca aagcacgtcg cacagatcct ggacagcaga  2880
atgaacacaa agtacgacga aaacgacaag ctgatcagag aagtcaaggt catcacactg  2940
aagagcaagc tggtcagcga cttcagaaag gacttccagt tctacaaggt cagagaaatc  3000
aacaactacc accacgcaca cgacgcatac ctgaacgcag tcgtcggaac agcactgatc  3060
aagaagtacc cgaagctgga aagcgaattc gtctacggag actacaaggt ctacgacgtc  3120
agaaagatga tcgcaaagag cgaacaggaa atcggaaagg caacagcaaa gtacttcttc  3180
tacagcaaca tcatgaactt cttcaagaca gaaatcacac tggcaaacgg agaaatcaga  3240
aagagaccgc tgatcgaaac aaacggagaa acaggagaaa tcgtctggga caagggaaga  3300
gacttcgcaa cagtcagaaa ggtcctgagc atgccgcagg tcaacatcgt caagaagaca  3360
gaagtccaga caggaggatt cagcaaggaa agcatcctgc cgaagagaaa cagcgacaag  3420
ctgatcgcaa gaaagaagga ctgggacccg aagaagtacg gaggattcga cagcccgaca  3480
gtcgcataca gcgtcctggt cgtcgcaaag gtcgaaaagg gaaagagcaa gaagctgaag  3540
agcgtcaagg aactgctggg aatcacaatc atggaaagaa gcagcttcga aaagaacccg  3600
atcgacttcc tggaagcaaa gggatacaag gaagtcaaga aggacctgat catcaagctg  3660
ccgaagtaca gcctgttcga actggaaaac ggaagaaaga gaatgctggc aagcgcagga  3720
gaactgcaga agggaaacga actggcactg ccgagcaagt acgtcaactt cctgtacctg  3780
gcaagccact acgaaaagct gaagggaagc ccggaagaca acgaacagaa gcagctgttc  3840
gtcgaacagc acaagcacta cctggacgaa atcatcgaac agatcagcga attcagcaag  3900
agagtcatcc tggcagacgc aaacctggac aaggtcctga gcgcatacaa caagcacaga  3960
gacaagccga tcagagaaca ggcagaaaac atcatccacc tgttcacact gacaaacctg  4020
ggagcaccgg cagcattcaa gtacttcgac acaacaatcg acagaaagag atacacaagc  4080
acaaaggaag tcctggacgc aacactgatc caccagagca tcacaggact gtacgaaaca  4140
agaatcgacc tgagccagct gggaggagac ggaggaggaa gcccgaagaa gaagagaaag  4200
gtcagcgaaa gcgcaacacc ggaaagcgtc agcggatgga gactgttcaa gaagatcagc  4260
tagctagcca tcacatttaa aagcatctca gcctaccatg agaataagag aaagaaaatg  4320
aagatcaata gcttattcat ctctttttct tttcgttgg tgtaaagcca acaccctgtc  4380
taaaaaacat aaatttcttt aatcattttg cctcttttct ctgtgcttca attaataaaa  4440
aatggaaaga acctcgagaa aaaaaaaaaa aaaaaaaaaa aaaaaaaaaa aaaaaaaaaa  4500
aaaaaaaaaa aaaaaaaaaa aaaaaaaaaa aaaaaaaa                          4538
```

```
SEQ ID NO: 385          moltype = DNA  length = 4517
FEATURE                 Location/Qualifiers
misc_feature            1..4517
                        note = Synthetic: mRNA transcript with ORF encoding Cas9
                         with HiBiT tag, XBG 5 UTR and human ALB 3 UTR
source                  1..4517
                        mol_type = other DNA
                        organism = synthetic construct
SEQUENCE: 385
gggaagctca gaataaacgc tcaactttgg ccggatctcg ccaccatgga caagaagtac  60
agcatcggac tggacatcgg aacaaacagc gtcggatggg cagtcatcac agacgaatac  120
aaggtcccga gcaagaagtt caaggtcctg ggaaacacag acagacacag catcaagaag  180
aacctgatcg gagcactgct gttcgacagc ggagaaacag cagaagcaac aagactgaag  240
agaacagcaa gaagaagata cacaagaaga aagaacagaa tctgctacct gcaggaaatc  300
ttcagcaacg aaatggcaaa ggtcgacgac agcttcttcc acagactgga agaaagcttc  360
ctggtcgaag aagacaagaa gcacgaaaga cacccgatct tcggaaacat cgtcgacgaa  420
gtcgcatacc acgaaaagta cccgacaatc taccacctga gaaagaagct ggtcgacagc  480
acagacaagg cagacctgag actgatctac ctggcactgg cacacatgat caagttcaga  540
ggacacttcc tgatcgaagg agacctgaac ccggacaaca gcgacgtcga caagctgttc  600
atccagctgg tccagacata caaccagctg ttcgaagaaa acccgatcaa cgcaagcgga  660
gtcgacgcaa aggcaatcct gagcgcaaga ctgagcaaga gcagaagact ggaaaacctg  720
atcgcacagc tgccgggaga aaagaagaac ggactgttcg gaaacctgat cgcactgagc  780
ctgggactga caccgaactt caagagcaac ttcgacctgg cagaagacgc aaagctgcag  840
ctgagcaagg acacatacga cgacgacctg gacaacctgc tggcacagat cggagaccag  900
tacgcagacc tgttcctggc agcaaagaac ctgagcgacg caatcctgct gagcgacatc  960
ctgagagtca acacagaaat cacaaaggca ccgctgagcg caagcatgat caagagatac  1020
gacgaacacc accaggacct gacactgctg aaggcactgg tcagacagca gctgccggaa  1080
aagtacaagg aaatcttctt cgaccagagc aagaacggat acgcaggata catcgacgga  1140
ggagcaagcc aggaagaatt ctacaagttc atcaagccga tcctggaaaa gatggacgga  1200
acagaagaac tgctggtcaa gctgaacaga gaagacctgc tgagaaagca gagaacattc  1260
gacaacggaa gcatcccgca ccagatccac ctgggagaac tgcacgcaat cctgagaaga  1320
caggaagact tctacccgtt cctgaaggac aacagagaaa agatcgaaaa gatcctgaca  1380
ttcagaatcc cgtactacgt cggaccgctg gcaagaggaa acagcagatt cgcatggatg  1440
acaagaaaga gcgaagaaac aatcacaccg tggaacttcg aagaagtcgt cgacaaggga  1500
gcaagcgcac agagcttcat cgaaagaatg acaaacttcg acaagaacct gccgaacgaa  1560
aaggtcctgc cgaagcacag cctgctgtac gaatacttca cagtctacaa cgaactgaca  1620
aaggtcaagt acgtcacaga aggaatgaga aagccggcat tcctgagcgg agaacagaag  1680
```

-continued

```
aaggcaatcg tcgacctgct gttcaagaca aacagaaagg tcacagtcaa gcagctgaag  1740
gaagactact tcaagaagat cgaatgcttc gacagcgtcg aaatcagcgg agtcgaagac  1800
agattcaacg caagcctggg aacataccac gacctgctga agatcatcaa ggacaaggac  1860
ttcctggaca acgaagaaaa cgaagacatc ctggaagaca tcgtcctgac actgacactg  1920
ttcgaagaca gagaaatgat cgaagaaaga ctgaagacat acgcacacct gttcgacgac  1980
aaggtcatga agcagctgaa gagaagaaga tacacaggat ggggaagact gagcagaaag  2040
ctgatcaacg gaatcagaga caagcagagc ggaaagacaa tcctggactt cctgaagagc  2100
gacggattcg caaacagaaa cttcatgcag ctgatccacg acgacagcct gacattcaag  2160
gaagacatcc agaaggcaca ggtcagcgga cagggagaca gcctgcacga acacatcgca  2220
aacctggcag gaagcccggc aatcaagaag ggaatcctgc agacagtcaa ggtcgtcgac  2280
gaactggtca aggtcatggg aagacacaag ccggaaaaca tcgtcatcga aatggcaaga  2340
gaaaaccaga caacacagaa gggacagaag aacagcagag aaagaatgaa gagaatcgaa  2400
gaaggaatca aggaactggg aagccagatc ctgaaggaac acccggtcga aaacacacag  2460
ctgcagaacg aaaagctgta cctgtactac ctgcagaacg gaagagacat gtacgtcgac  2520
caggaactgg acatcaacag actgagcgac tacgacgtcg accacatcgt cccgcagagc  2580
ttcctgaagg acgacagcat cgacaacaag gtcctgacaa gaagcgacaa gaacagagga  2640
aagagcgaca acgtcccgag cgaagaagtc gtcaagaaga tgaagaacta ctggagacag  2700
ctgctgaacg caaagctgat cacacagaga aagttcgaca acctgacaaa ggcagagaga  2760
ggaggactga gcgaactgga caaggcagga ttcatcaaga gacagctggt cgaaacaaga  2820
cagatcacaa agcacgtcgc acagatcctg gacagcagaa tgaacacaaa gtacgacgaa  2880
aacgacaagc tgatcagaga agtcaaggtc atcacactga agagcaagct ggtcagcgac  2940
ttcagaaagg acttccagtt ctacaaggtc agagaaatca acaactacca ccacgcacac  3000
gacgcatacc tgaacgcagt cgtcggaaca gcactgatca agaagtaccc gaagctggaa  3060
agcgaattcg tctacggaga ctacaaggtc tacgacgtca gaaagatgat cgcaaagagc  3120
gaacaggaaa tcggaaaggc aacagcaaag tacttcttct acagcaacat catgaacttc  3180
ttcaagacag aaatcacact ggcaaacgga gaaatcagaa agagaccgct gatcgaaaca  3240
aacggagaaa caggagaaat cgtctgggac aagggaagag acttcgcaac agtcagaaag  3300
gtcctgagca tgccgcaggt caacatcgtc aagaagacag aagtccagac aggaggattc  3360
agcaaggaaa gcatcctgcc gaagagaaac agcgacaagc tgatcgcaag aaagaaggac  3420
tgggacccga agaagtacgg aggattcgac agcccgacag tcgcatacag cgtcctggtc  3480
gtcgcaaagg tcgaaaaggg aaagagcaag aagctgaaga gcgtcaagga actgctggga  3540
atcacaatca tggaaagaag cagcttcgaa aagaacccga tcgacttcct ggaagcaaag  3600
ggatacaagg aagtcaagaa ggacctgatc atcaagctgc cgaagtacag cctgttcgaa  3660
ctggaaaacg gaagaaagag aatgctggca agcgcaggag aactgcagaa gggaaacgaa  3720
ctggcactgc cgagcaagta cgtcaacttc ctgtacctgg caagccacta cgaaaagctg  3780
aagggaagcc cggaagacaa cgaacagaag cagctgttcg tcgaacagca caagcactac  3840
ctggacgaaa tcatcgaaca gatcagcgaa ttcagcaaga gagtcatcct ggcagacgca  3900
aacctggaca aggtcctgag cgcatacaac aagcacagag acaagccgat cagagaacag  3960
gcagaaaaca tcatccacct gttcacactg acaaacctgg gagcaccggc agcattcaag  4020
tacttcgaca caacaatcga cagaaagaga tacacaagca caaaggaagt cctggacgca  4080
acactgatcc accagagcat cacaggactg tacgaaacaa gaatcgacct gagccagctg  4140
ggaggagacg gaggaggaag cccgaagaag aagagaaagg tcagcgaaag cgcaacaccg  4200
gaaagcgtca gcggatggag actgttcaag aagatcagct agctagccat cacatttaaa  4260
agcatctcag cctaccatga gaataagaga aagaaaatga agatcaatag cttattcatc  4320
tctttttctt tttcgttggt gtaaagccaa caccctgtct aaaaaacata aatttcttta  4380
atcattttgc ctcttttctc tgtgcttcaa ttaataaaaa atggaaagaa cctcgagaaa  4440
aaaaaaaaaa aaaaaaaaaa aaaaaaaaaa aaaaaaaaaa aaaaaaaaaa aaaaaaaaaa  4500
aaaaaaaaaa aaaaaaa                                                4517

SEQ ID NO: 386          moltype = AA  length = 1381
FEATURE                 Location/Qualifiers
REGION                  1..1381
                        note = Synthetic: Amino acid sequence for Cas9 with NLS1
source                  1..1381
                        mol_type = protein
                        organism = synthetic construct
SEQUENCE: 386
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
```

-continued

```
PAAFKYFDTT IDRKRYTSTK EVLDATLIHQ SITGLYETRI DLSQLGGDGG GSLAAKRSRT  1380
T                                                                  1381

SEQ ID NO: 387          moltype = AA  length = 1381
FEATURE                 Location/Qualifiers
REGION                  1..1381
                        note = Synthetic: Amino acid sequence for Cas9 with NLS2
source                  1..1381
                        mol_type = protein
                        organism = synthetic construct
SEQUENCE: 387
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGDGG GSQAAKRSRT  1380
T                                                                  1381

SEQ ID NO: 388          moltype = AA  length = 1382
FEATURE                 Location/Qualifiers
REGION                  1..1382
                        note = Synthetic: Amino acid sequence for Cas9 with NLS3
source                  1..1382
                        mol_type = protein
                        organism = synthetic construct
SEQUENCE: 388
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGDGG GSPAPAKRER  1380
TT                                                                 1382

SEQ ID NO: 389          moltype = AA  length = 1381
FEATURE                 Location/Qualifiers
REGION                  1..1381
                        note = Synthetic: Amino acid sequence for Cas9 with NLS4
source                  1..1381
                        mol_type = protein
                        organism = synthetic construct
SEQUENCE: 389
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
```

-continued

```
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGDGG GSQAAKRPRT  1380
T                                                                 1381

SEQ ID NO: 390          moltype = AA  length = 1381
FEATURE                 Location/Qualifiers
REGION                  1..1381
                        note = Synthetic: Amino acid sequence for Cas9 with NLS5
source                  1..1381
                        mol_type = protein
                        organism = synthetic construct
SEQUENCE: 390
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGDGG GSRAAKRPRT  1380
T                                                                 1381

SEQ ID NO: 391          moltype = AA  length = 1383
FEATURE                 Location/Qualifiers
REGION                  1..1383
                        note = Synthetic: Amino acid sequence for Cas9 with NLS6
source                  1..1383
                        mol_type = protein
                        organism = synthetic construct
SEQUENCE: 391
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
```

```
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGDGG GSAAAKRSWS  1380
MAA                                                               1383

SEQ ID NO: 392          moltype = AA  length = 1383
FEATURE                 Location/Qualifiers
REGION                  1..1383
                        note = Synthetic: Amino acid sequence for Cas9 with NLS7
source                  1..1383
                        mol_type = protein
                        organism = synthetic construct
SEQUENCE: 392
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGDGG GSAAAKRVWS  1380
MAF                                                               1383

SEQ ID NO: 393          moltype = AA  length = 1383
FEATURE                 Location/Qualifiers
REGION                  1..1383
                        note = Synthetic: Amino acid sequence for Cas9 with NLS8
source                  1..1383
                        mol_type = protein
                        organism = synthetic construct
SEQUENCE: 393
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGDGG GSAAAKRSWS  1380
MAF                                                               1383

SEQ ID NO: 394          moltype = AA  length = 1382
FEATURE                 Location/Qualifiers
REGION                  1..1382
```

```
                        note = Synthetic: Amino acid sequence for Cas9 with NLS9
source                  1..1382
                        mol_type = protein
                        organism = synthetic construct
SEQUENCE: 394
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGDGG GSAAAKRKYF  1380
AA                                                                1382

SEQ ID NO: 395          moltype = AA  length = 1382
FEATURE                 Location/Qualifiers
REGION                  1..1382
                        note = Synthetic: Amino acid sequence for Cas9 with NLS10
source                  1..1382
                        mol_type = protein
                        organism = synthetic construct
SEQUENCE: 395
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGDGG GSRAAKRKAF  1380
AA                                                                1382

SEQ ID NO: 396          moltype = AA  length = 1382
FEATURE                 Location/Qualifiers
REGION                  1..1382
                        note = Synthetic: Amino acid sequence for Cas9 with NLS11
source                  1..1382
                        mol_type = protein
                        organism = synthetic construct
SEQUENCE: 396
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
```

-continued

```
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGDGG GSRAAKRKYF  1380
AV                                                                1382
```

What is claimed is:

1. A method of treating amyloidosis associated with deposition of transthyretin (ATTR) in a subject in need thereof, the method comprising administering to the subject a therapeutically effective amount of a pharmaceutical formulation comprising:

a single guide RNA (sgRNA) comprising the sequence mA*mA*mA*GGCUGCUGAUGACACCUGUUUU AGAmGmCmUmAmGmAmAmAmUmA mGmCAAGUUAAAAUAAGGCUAGUCCGUUAU-CAmAmCmUmUmGmAmAmAmAmAm GmUmGmGmCmAmCmCmGmAmGmUmCmGm GmUmGmCmU*mU*mU*mU (SEQ ID NO: 87), wherein a * indicates a phosphorothioate (PS) linkage and a lower case "m" indicates that the nucleotide is 2'-O-Me modified; and a messenger RNA (mRNA) comprising an open reading frame (ORF) that is at least 98% identical to SEQ ID NO: 311, wherein the ORF encodes a Cas9 and each thymidine in SEQ ID NO: 311 is replaced with a modified or unmodified uridine.

2. The method of claim 1, wherein the ORF comprises SEQ ID NO: 311, wherein each thymidine in SEQ ID NO: 311 is replaced with a modified or unmodified uridine.

3. The method of claim 2, wherein each thymidine in SEQ ID NO: 311 is replaced with N1-methyl-pseudouridine.

4. The method of claim 1, wherein the mRNA comprises:

a 5' UTR with at least 90% identity to any one of SEQ ID NOs: 232, 234, 236, 238, 241, or 275-277, wherein each thymidine in any one of SEQ ID NOs: 232, 234, 236, 238, 241, and 275-277 is replaced with a modified or unmodified uridine; and/or a 3' UTR with at least 90% identity to any one of SEQ ID NOs: 233, 235, 237, 239, or 240, wherein each thymidine in any one of SEQ ID NOs: 233, 235, 237, 239, or 240 is replaced with a modified or unmodified uridine.

5. The method of claim 1, wherein the mRNA comprises a 5' UTR and a 3' UTR from the same source, wherein the source is a constitutively expressed mRNA.

6. The method of claim 1, wherein the mRNA comprises a 5' cap selected from Cap0, Cap1, and Cap2.

7. The method of claim 1, wherein at least 10% of the uridine in the mRNA is modified uridine.

8. The method of claim 7, wherein the modified uridine is one or more of N1-methyl-pseudouridine, pseudouridine, 5-methoxyuridine, or 5-iodouridine.

9. The method of claim 1, wherein the mRNA is at least 95%, 96%, 97%, 98%, 99%, or 99.5% identical to SEQ ID NO: 377, wherein each uridine in SEQ ID NO: 377 is modified or unmodified.

10. The method of claim 9, wherein each uridine in SEQ ID NO: 377 is N1-methyl-pseudouridine.

11. The method of claim 1, wherein the Cas9 comprises a nuclear localization signal (NLS).

12. The method of claim 1, wherein the sgRNA and the mRNA are associated with a lipid nanoparticle (LNP).

13. The method of claim 12, wherein the LNP comprises a CCD lipid, a neutral lipid, a helper lipid, and a stealth lipid.

14. The method of claim 13, wherein the CCD lipid is Lipid A ((9Z,12Z)-3-((4,4-bis(octyloxy)butanoyl)oxy)-2-((((3-(diethylamino)propoxy)carbonyl)oxy)methyl)propyloctadeca-9,12-dienoate, also called 3-((4,4-bis(octyloxy)butanoyl)oxy)-2-((((3-(diethylamino)propoxy)carbonyl)oxy)methyl)propyl (9Z,12Z)-octadeca-9,12-dienoate).

15. The method of claim 14, wherein the neutral lipid is distearoylphosphatidylcholine (DSPC);

the helper lipid is cholesterol; and the stealth lipid is 1,2-dimyristoyl-sn-glycero-3-phosphoethanolamine-N-[methoxy(polyethylene glycol)-2000] (PEG2k-DMG).

16. The method of claim 14, wherein the LNP comprises:

about 50 mol-% Lipid A;

about 9 mol-% distearoylphosphatidylcholine (DSPC);

about 38 mol-% cholesterol; and about 3 mol-% 1,2-dimyristoyl-sn-glycero-3-phosphoethanolamine-N-[methoxy(polyethylene glycol)-2000] (PEG2k-DMG).

17. The method of claim 1, wherein each thymidine in SEQ ID NO: 311 is replaced with N1-methyl-pseudouridine.

18. The method of claim 1, wherein the subject is human and serum transthyretin (TTR) levels in the subject, measured eight weeks after administration of the pharmaceutical formulation, are reduced by at least 50% compared to serum TTR levels before administration of the pharmaceutical formulation to the subject; and/or amyloid deposition in the subject is reduced by between 30 and 35%, 35 and 40%, 40 and 45%, 45 and 50%, 50 and 55%, 55 and 60%, 60 and 65%, 65 and 70%, 70 and 75%, 75 and 80%, 80 and 85%, 85 and 90%, 90 and 95%, or 95 and 99% compared to the amyloid deposition in a negative control or to the level of amyloid deposition in the subject before administration of the pharmaceutical formulation to the subject.

19. The method of claim 1, wherein the ATTR is ATTR familial amyloidosis.

20. The method of claim 1, wherein the ATTR is wild-type ATTR.

21. The method of claim 1, wherein the subject has been diagnosed with familial amyloid cardiomyopathy or exhibits symptoms of restrictive cardiomyopathy or congestive heart failure.

22. The method of claim 1, wherein the subject has been diagnosed with familial amyloid polyneuropathy or exhibits symptoms of sensorimotor neuropathy.

23. A method of treating amyloidosis associated with deposition of transthyretin (ATTR) in a subject in need thereof, the method comprising administering to the subject a therapeutically effective amount of a pharmaceutical formulation comprising:

a single guide RNA (sgRNA) comprising the sequence mA*mA*mA*GGCUGCUGAUGACACCUGUUUU AGAmGmCmUmAmGmAmAmAmUmA mGmCAAGUUAAAAUAAGGCUAGUCCGUUAU-CAmAmCmUmUmGmAmAmAmAmAm GmUmGmGmCmAmCmCmGmAmGmUmCmGm GmUmGmCmU*mU*mU*mU (SEQ ID NO: 87) wherein a * indicates a phosphorothioate (PS) linkage and a lower case "m" indicates that the nucleotide is 2'-O-Me modified; and a messenger RNA (mRNA) comprising SEQ ID NO: 377, wherein each uridine in SEQ ID NO: 377 is modified or unmodified.

24. The method of claim 23, wherein the mRNA further comprises a 5' cap selected from Cap0, Cap1, and Cap2 and each uridine in SEQ ID NO: 377 is modified.

25. The method of claim 23, wherein each uridine in SEQ ID NO:377 is N1-methyl-pseudouridine.

26. The method of claim 23, wherein the subject is human and serum transthyretin (TTR) levels in the subject, measured eight weeks after administration of the pharmaceutical formulation, are reduced by at least 50% compared to serum TTR levels before administration of the pharmaceutical formulation to the subject; and/or amyloid deposition in the subject is reduced by between 30 and 35%, 35 and 40%, 40 and 45%, 45 and 50%, 50 and 55%, 55 and 60%, 60 and 65%, 65 and 70%, 70 and 75%, 75 and 80%, 80 and 85%, 85 and 90%, 90 and 95%, or 95 and 99% compared to the amyloid deposition in a negative control or to the level of amyloid deposition in the subject before administration of the pharmaceutical formulation to the subject.

27. The method of claim 23, wherein the ATTR is ATTR familial amyloidosis.

28. The method of claim 23, wherein the ATTR is wild-type ATTR.

29. The method of claim 23, wherein the subject has been diagnosed with familial amyloid cardiomyopathy or exhibits symptoms of restrictive cardiomyopathy or congestive heart failure.

30. The method of claim 23, wherein the subject has been diagnosed with familial amyloid polyneuropathy or exhibits symptoms of sensorimotor neuropathy.

* * * * *